US012735402B2

(12) United States Patent
Josyula et al.

(10) Patent No.: US 12,735,402 B2
(45) Date of Patent: Sep. 15, 2026

(54) PAI-1 INHIBITORS AND USES THEREOF

(71) Applicant: The Cleveland Clinic Foundation, Cleveland, OH (US)

(72) Inventors: Vara Prasad Josyula, Cleveland, OH (US); Thaddeus Stappenbeck, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 19/309,326

(22) Filed: Aug. 25, 2025

(65) Prior Publication Data

US 2026/0242355 A1 Aug. 20, 2026

Related U.S. Application Data

(60) Provisional application No. 63/759,889, filed on Feb. 18, 2025.

(51) Int. Cl.

*C07D 401/14* (2006.01)
*A61K 31/357* (2006.01)

(Continued)

(52) U.S. Cl.

CPC .......... *C07D 401/14* (2013.01); *A61K 31/357* (2013.01); *A61K 31/4155* (2013.01);

(Continued)

(58) Field of Classification Search

CPC .. C07D 401/14; C07D 213/80; C07D 215/12; C07D 231/12; C07D 231/40; C07D 261/08; C07D 319/16; C07D 401/04; C07D 401/12; C07D 403/10; C07D 403/12; C07D 405/04; C07D 405/12; C07D 405/14; C07D 413/04; C07D 413/10; C07D 413/12; C07D 413/14; C07D 471/04; A61K 31/357; A61K 31/4155; A61K 31/416; A61K 31/4192; A61K 31/422; A61K 31/4245; A61K 31/437; A61K 31/4439; A61K 31/444; A61K 31/454; A61K 31/4545;

(Continued)

(56) References Cited

U.S. PATENT DOCUMENTS 5,731,328 A 3/1998 Berg et al.
5,763,483 A 6/1998 Bischofberger et al.

(Continued)

FOREIGN PATENT DOCUMENTS

AU 2017336363 A1 5/2019
CN 101386619 A 3/2009

(Continued)

OTHER PUBLICATIONS

Cas Registration No. 2248871-73-8 ( filed on Nov. 18, 2018, Chemcats, Chemical Library Supplier (Year: 2018).*

(Continued)

*Primary Examiner* — Taylor V Oh
(74) *Attorney, Agent, or Firm* — Casimir Jones, S.C.; Anne M. Reynolds

(57) ABSTRACT

Disclosed herein are compounds, pharmaceutical compositions comprising the compounds, methods of inhibiting PAI-1 using the compounds, and methods of treating IBDs using the compounds.

8 Claims, 3 Drawing Sheets

(51) Int. Cl.

| | |
|---|---|
| ***A61K 31/4155*** | (2006.01) |
| ***A61K 31/416*** | (2006.01) |
| ***A61K 31/4192*** | (2006.01) |
| ***A61K 31/422*** | (2006.01) |
| ***A61K 31/4245*** | (2006.01) |
| ***A61K 31/437*** | (2006.01) |
| ***A61K 31/4439*** | (2006.01) |
| ***A61K 31/444*** | (2006.01) |
| ***A61K 31/454*** | (2006.01) |
| ***A61K 31/4545*** | (2006.01) |
| ***A61K 31/4709*** | (2006.01) |
| ***A61K 31/497*** | (2006.01) |
| ***A61K 31/501*** | (2006.01) |
| ***A61K 31/506*** | (2006.01) |
| ***A61K 31/513*** | (2006.01) |
| ***A61P 1/00*** | (2006.01) |
| ***C07D 213/80*** | (2006.01) |
| ***C07D 215/12*** | (2006.01) |
| ***C07D 231/12*** | (2006.01) |
| ***C07D 231/40*** | (2006.01) |
| ***C07D 261/08*** | (2006.01) |
| ***C07D 319/16*** | (2006.01) |
| ***C07D 401/04*** | (2006.01) |
| ***C07D 401/12*** | (2006.01) |
| ***C07D 403/10*** | (2006.01) |
| ***C07D 403/12*** | (2006.01) |
| ***C07D 405/04*** | (2006.01) |
| ***C07D 405/12*** | (2006.01) |
| ***C07D 405/14*** | (2006.01) |
| ***C07D 413/04*** | (2006.01) |
| ***C07D 413/10*** | (2006.01) |
| ***C07D 413/12*** | (2006.01) |
| ***C07D 413/14*** | (2006.01) |
| ***C07D 471/04*** | (2006.01) |

(52) U.S. Cl.

CPC ........ *A61K 31/416* (2013.01); *A61K 31/4192* (2013.01); *A61K 31/422* (2013.01); *A61K 31/4245* (2013.01); *A61K 31/437* (2013.01); *A61K 31/4439* (2013.01); *A61K 31/444* (2013.01); *A61K 31/454* (2013.01); *A61K 31/4545* (2013.01); *A61K 31/4709* (2013.01); *A61K 31/497* (2013.01); *A61K 31/501* (2013.01); *A61K 31/506* (2013.01); *A61K 31/513* (2013.01); *A61P 1/00* (2018.01); *C07D 213/80* (2013.01); *C07D 215/12* (2013.01); *C07D 231/12* (2013.01); *C07D 231/40* (2013.01); *C07D 261/08* (2013.01); *C07D 319/16* (2013.01); *C07D 401/04* (2013.01); *C07D 401/12* (2013.01); *C07D 403/10* (2013.01); *C07D 403/12* (2013.01); *C07D 405/04* (2013.01); *C07D 405/12* (2013.01); *C07D 405/14* (2013.01); *C07D 413/04* (2013.01); *C07D 413/10* (2013.01); *C07D 413/12* (2013.01); *C07D 413/14* (2013.01); *C07D 471/04* (2013.01)

(58) Field of Classification Search

CPC .............. A61K 31/4709; A61K 31/497; A61K 31/501; A61K 31/506; A61K 31/513; A61P 1/00

USPC .......................................................... 514/252

See application file for complete search history.

(56) References Cited

U.S. PATENT DOCUMENTS

| | | | | |
|---|---|---|---|---|
| 5,952,375 | A | 9/1999 | Bischofberger et al. | |
| 6,270,766 | B1 | 8/2001 | Feldman et al. | |
| 7,057,086 | B2 | 6/2006 | Vaughan et al. | |
| 7,741,356 | B2 | 6/2010 | Breslin et al. | |
| 7,786,158 | B2 | 8/2010 | Breslin et al. | |
| 7,846,442 | B2 | 12/2010 | Feldmann et al. | |
| 8,344,011 | B2 | 1/2013 | Breslin et al. | |
| 8,609,709 | B2 | 12/2013 | Breslin et al. | |
| 9,387,206 | B2 | 7/2016 | Cohen et al. | |
| 9,427,438 | B2 | 8/2016 | Alam | |
| 9,527,878 | B2 | 12/2016 | Lawrence et al. | |
| 9,845,327 | B2 | 12/2017 | Krainc et al. | |
| 10,092,537 | B2 | 10/2018 | Ando et al. | |
| 11,007,179 | B2 | 5/2021 | Costello et al. | |
| 11,090,291 | B2 | 8/2021 | Costello et al. | |
| 11,160,792 | B2 | 11/2021 | Costello et al. | |
| 11,311,516 | B2 | 4/2022 | Costello et al. | |
| 2008/0188540 | A1 | 8/2008 | Tesconi et al. | |
| 2008/0188543 | A1 | 8/2008 | Thakur et al. | |
| 2009/0042918 | A1* | 2/2009 | Kearney .............. | C07D 333/38<br>514/378 |
| 2011/0105574 | A1 | 5/2011 | Fleenor et al. | |
| 2012/0022080 | A1* | 1/2012 | Miyata ................. | C07D 409/12<br>514/444 |
| 2013/0165473 | A1 | 6/2013 | Duggan | |
| 2013/0289086 | A1 | 10/2013 | Duggan | |
| 2013/0309690 | A1 | 11/2013 | Ringe et al. | |
| 2014/0296256 | A1 | 10/2014 | Miyata et al. | |
| 2015/0361063 | A1 | 12/2015 | Ringe et al. | |
| 2018/0042922 | A1 | 2/2018 | Cheruvu et al. | |
| 2020/0147007 | A1 | 5/2020 | Lawrence et al. | |
| 2020/0165677 | A1 | 5/2020 | Stappenbeck et al. | |
| 2020/0330592 | A1 | 10/2020 | Black | |
| 2022/0340665 | A1 | 10/2022 | Ando et al. | |

FOREIGN PATENT DOCUMENTS

| | | | |
|---|---|---|---|
| EP | 2473166 | A2 | 7/2012 |
| EP | 3752201 | A1 | 12/2020 |
| EP | 3875078 | A1 | 9/2021 |
| JP | H1072413 | A | 3/1998 |
| JP | H11255895 | A | 9/1999 |
| JP | 2001206948 | A | 7/2001 |
| JP | 2002080596 | A | 3/2002 |
| JP | 2020012104 | A | 1/2020 |
| WO | WO-2003006443 | A2 | 1/2003 |
| WO | WO-2004018414 | A2 | 3/2004 |
| WO | WO-2006039356 | A2 | 4/2006 |
| WO | WO-2006062093 | A1 | 6/2006 |
| WO | WO-2009038842 | A2 | 3/2009 |
| WO | WO-2010087430 | A1 | 8/2010 |
| WO | WO-2010113022 | A1 | 10/2010 |
| WO | WO-2010141932 | A1 | 12/2010 |
| WO | WO-2011057110 | A1 | 5/2011 |
| WO | WO-2012008543 | A1 | 1/2012 |
| WO | WO-2014171464 | A1 | 10/2014 |
| WO | WO-2020009016 | A1 | 1/2020 |
| WO | WO-2020056191 | A1 | 3/2020 |
| WO | WO-2020163966 | A1 | 8/2020 |
| WO | WO-2021235532 | A1 | 11/2021 |

OTHER PUBLICATIONS

Cas Registration No. 2921455-78-7 ( filed on Apr. 23, 2023, Chemcats, Chemical Library Supplier (Year: 2023).*

Anderson K.D., et al., “A Controlled Trial of Corticosteroids in Children with Corrosive Injury of the Esophagus”, The New England Journal of Medicine, Sep. 6, 1990, vol. 323, No. 10, pp. 637-640.

Arevalo-Silva C., et al., “Ingestion of Caustic Substances: a 15-year Experience”, The Laryngoscope, Aug. 2006, vol. 116, No. 8, pp. 1422-1426.

(56) References Cited

OTHER PUBLICATIONS

Axon Medchem: "T 1776Na Axon 1769", Retrieved Nov. 12, 2025, 5 pages.
Baddawy H.A., et al., "Synthesis and Reactions of N-Hydroxy-1-phenylnaphthalene-2,3-dicarboximide", Indian Journal of Chemistry, Section B: Organic Chemistry Including Medicinal Chemistry, 1980, vol. 19B, No. 2, pp. 112-114 (5 Pages).
Bio Techne Ltd: "Sk 216", Catalog #: 6187, Retrieved Nov. 25, 2025, 5 pages.
Bio Techne Ltd: "TM5275 Sodium Salt", Catalog #: 5769, Retrieved Nov. 12, 2025. 4 pages.
Borja A.R., et al., "Lye Injuries of the Esophagus Analysis of Ninety Cases of Lye Ingestion", The Journal of Thoracic and Cardiovascular Surgery, Apr. 1969, vol. 57, No. 4, pp. 533-538.
Chen D., et al., "Structure-Based Redesign of an Edema Toxin Inhibitor", Bioorganic & Medicinal Chemistry, Jan. 1, 2012, vol. 20, No. 1, pp. 368-376 (19 Pages).
Cheng H-T., et al., "Profiling of Inflammatory Cytokines in Patients with Caustic Gastrointestinal Tract Injury", PLoS One, Nov. 18, 2021, vol. 16, No. 11, e0260012, pp. 1-12.
Cho W., et al., "Dual Changes in Conformation and Optical Properties of Fluorophores Within a Metal-organic Framework During Framework Construction and Associated Sensing Event", Journal of the American Chemical Society, 2014, vol. 136, No. 35, pp. 12201-12204.
Dalapati R., et al., "A Pyrene-Functionalized Metal-Organic Framework for Nonenzymatic and Ratiometric Detection of Uric Acid in Biological Fluid via Conformational Change", Inorganic Chemistry, 2019, vol. 58, No. 9, pp. 5654-5663. DOI: 10.1021/acs.inorgchem.8b03629.
El-Sayed R.A., et al., "Synthesis and Antimicrobial Activity of some new 4-phenyl-2-(o-, m- and p-carboxyphenyl)-5.6-benso-1:3-Isoindolindione Amino Acid and Peptide Derivatives", Proceedings of the Indian National Science Academy, Part A: Physical Sciences, 1997, vol. 63, No. 4, pp. 337-344 (10 Pages).
Esbriet: "(Pirfenidone) Tablets", Retrieved Nov. 12, 2025, 4 pages.
Grantome: "Preclinical Development of a First in Class Therapeutic for Treating Idiopathic Pulmonary Fibrosis", 2019, Mdi Therapeutics Inc, Retrieved Nov. 12, 2025, 2 pages.
Gummin D.D., et al., "2019 Annual Report of the American Association of Poison Control Centers' National Poison Data System (NPDS): 37th Annual Report", Clinical Toxicology (Phila), Dec. 2020, vol. 58, No. 12, pp. 1360-1541 (183 Pages).
Hamed A.A., et al., "Synthesis of benzo[g]quinazoline-2,4-diones via Lossen Rearrangement of N-(arylsulphonyloxy)naphthalene-2,3-Dicarboximide Derivatives", India Journal of Chemistry, Section B: Organic Chemistry Including Medicinal Chemistry, 1980, vol. 19B, No. 3, pp. 221-223 (5 Pages).
Hosaka S., et al., Inhibition of Plasminogen Activator Inhibitor-1 Activation Suppresses High Fat Diet-Induced Weight Gain via Alleviation of Hypothalamic Leptin Resistance, Front Pharmacology, Jun. 24, 2020, vol. 11, No. 943, pp. 1-12.
Huang W-T., et al., "Therapeutic Value of Small Molecule Inhibitor to Plasminogen Activator Inhibitor-1 for Lung Fibrosis", American Journal of Respiratory Cell and Molecular Biology, Jan. 2012, vol. 46, No. 1, pp. 87-95.
International Search Report and Written Opinion for PCT/US2025/043386, Mailed Nov. 28, 2025, 13 pages.
Kemnitzer W., et al., "Discovery of N-aryl-9-oxo-9H-Fluorene-1-Carboxamides as a New Series of Apoptosis Inducers Using a Cell-and Caspase-based High-throughput Screening Assy. 1. Structure-Activity Relationships of the Carboxamide Group", Bioorganic & Medicinal Chemistry Letters, 2009, vol. 19, No. 11, pp. 3045-3049.
Khalaf N.S., et al., "Synthesis and Antimicrobial activity of some new 4-phenyl-2-(0-, m-, & p-carboxyphenyl)-5:6-benxo-1:3-Isoindolindione Amino Acid and Peptide Derivatives", AL-Azhar Bulletin of Science, 1996, vol. 7, No. 2, pp. 1251-1260 (14 Pages).
Kobak K.A., et al., "Determining the Contributions of Protein Synthesis and Breakdown to Muscle Atrophy Requires Non-steady-state Equations", Journal of Cachexia, Sarcopenia and Muscle, Dec. 2021, vol. 12, vol. 6, pp. 1764-1775.
Kochhar R., et al., "Corrosive Induced Carcinoma of Esophagus: Report of Three Patients and Review of Literature", Journal of Gastroenterology and Hepatology, Apr. 2006, vol. 21, No. 4, pp. 777-780.
Li Y., et al., "Nationwide Estimate of Emergency Department Visits in the United States Related to Caustic Ingestion", Diseases of the Esophagus, Jun. 15, 2020, vol. 33, No. 6, doaa012, pp. 1-9.
MedChemExpress (MCE): "Loureirin B", Master of Bioactive Molecules, Retrieved Nov. 12, 2025, 5 pages.
MedChemExpress (MCE): "Tiplaxtinin (synonyms: PAI-039; Tiplasinin)", Master of Bioactive Molecules,, Retrieved Nov. 12, 2025, 5 pages.
MedChemExpress (MCE): "TM5441", PAI-1 Inhibitor, Master of Bioactive Molecules, Retrieved Nov. 12, 2025, 5 pages.
MedChemExpress (MCE): "Toddalolactone", PAI-1 Inhibitor, Master of Bioactive Molecules, Retrieved Nov. 12, 2025, 4 pages.
MedKoo Biosciences Inc: "MedKoo Cat#319882", Aleplasinin, Retrieved Nov. 12, 2025, 3 pages.
Michigan Medicine: "Fast Forward Medical Innovation", MedigenixBio, University of Michigan Website, Retrieved Nov. 12, 2025, 18 pages.
Ofev (nintedanib)capsules 150mg, Boeringer Ingelheim, Retrieved Nov. 12, 2025, 6 pages.
Okonta K.E., et al., "In Patients with Corrosive Oesophageal Stricture for Surgery, is Oesophagectomy Rather than Bypass Necessary to Reduce the Risk of Oesophageal Malignancy", Interactive Cardio Vascular and Thoracic Surgery (ICVTS), Oct. 2012, vol. 15, No. 4, pp. 713-715.
Park J., et al., "Micro-Crystals of Metal-organic Frameworks Constructed from Pyrene-based Organic Linkers and Lanthanide Ions for Tunable White Light Emission", CrystEngComm, 2016, vol. 18, No. 43, pp. 8372-8376.
Placencio V.R., et al., "Small Molecule Inhibitors of Plasminogen Activator Inhibitor-1 Elicit Anti-Tumorigenic and Anti-Angiogenic Activity", PLoS One, Jul. 24, 2015, vol. 10, No. 7, e0133786, pp. 1-18.
PubChem SID: 479346291, Substance Record Z6291484506, Modify date Apr. 25, 2023, 5 Pages.
Rouch A., et al., "Small Molecules Inhibitors of Plasminogen Activator Inhibitor-1—An Overview", European Journal of Medicinal Chemistry, Mar. 6, 2015, vol. 92, pp. 619-636.
Santa Cruz: "Geodin (CAS 427-63-4)", Santa Cruz Animal Health, Retrieved Nov. 12, 2025, 3 pages.
SciFinder, American Chemical Society (ACS), 2020, 16 pages.
SciFinder, American Chemical Society (ACS), 2020, 5 pages.
Sprogyte L., et al., "Pathogenesis of Alkali Injury-Induced Limbal Stem Cell Deficiency: A Literature Survey of Animal Models", Cells, May 1, 2023, vol. 12, No. 9, 1294, pp. 1-21.
Togo H., et al., "Synthesis of New Photosensitive Polyimides Containing Pendant Proparhyl Ester Groups", Journal of Photopolymer Science and Technology, 1999, vol. 12, No. 2, pp. 223-230 (7 Pages).
Wang Y., et al., "Pan-Transciptome-based Candidate Therapeutic Discovery for Idiopathic Pulmonary Fibrosis", bioRxiv, 10.1101/824367, Jun. 29, 2020, 35 pages.
Yamaoka N., et al., "Identification of Novel Plasminogen Activator Inhibitor-1 Inhibitors with Improved Oral Bioavailability: Structure Optimization of N-acylanthranilic Acid Derivatives", Bioorganic & Medicinal Chemistry Letters, 2018, vol. 28, No. 4, pp. 809-813, DOI: 10.1016/j.bmcl.2017.11.016.

* cited by examiner

PAI-1 INHIBITORS AND USES THEREOF

CROSS-REFERENCE TO RELATED APPLICATIONS

This application claims priority to and the benefit of U.S. Provisional Patent Application No. 63/759,889, filed on Feb. 18, 2025, the disclosure of which is incorporated herein by reference in its entirety.

STATEMENT REGARDING FEDERALLY SPONSORED RESEARCH

This invention was made with government support under W81XWH-22-1-0675 awarded by the Department of Defense. The government has certain rights in the invention.

FIELD

Provided herein are compounds, pharmaceutical compositions comprising the compounds, methods of inhibiting PAI-1 using the compounds, and methods of treating IBDs using the compounds.

BACKGROUND

Plasminogen activator inhibitor 1 (PAI-1), part of the serpin superfamily, makes up about 10% of plasma proteins. Serpins consist of roughly 400 residues with molecular masses ranging from 38 to 70 kDa. They share about 35% amino acid homology and have a similar tertiary structure with three β-pleated sheets, α-helices, and a reactive site loop. The reactive site, 30-40 amino acids from the carboxy terminal, mimics the target protease's substrate. PAI-1 is the most important physiologic regulator of the plasminogen activation system through its inhibition of its target serine proteases, tissue plasminogen activator (tPA), and urokinase plasminogen activator (uPA). PAI-1 exists in four different forms: active, latent, cleaved and target bound form.

A common feature of inflammatory bowel diseases (IBD) including two of its major forms, Crohn's disease (CD) and ulcerative colitis (UC), is inflammation and damage to the inner lining of the intestine (the mucosa). Moderate to severe IBD often is correlated with poor mucosal wound healing. Despite decades of drug development in this disease which has directly targeted inflammation, there is no pharmacologic agent that directly targets wound repair. In the US, over 3.1 million people (1.3%) have IBD. The disease's pathogenesis is complex, involving genetic factors, environmental influences, and microbiome and immune system dysregulation. Despite understanding these components, IBD remains incurable. Chronic inflammation and epithelial damage require constant mucosal repair. Mild to moderate cases are treated with local anti-inflammatory agents and steroids, while moderate to severe cases use biologics like anti-TNF alpha antibodies, anti-IL-12/23 antagonists, and anti-integrins, though these can cause infections. Many patients with moderate to severe disease do not achieve remission due to lack of response, intolerance, or side effects. Non-hematopoietic-derived cells, like intestinal epithelial cells (IECs), are promising targets for new therapies. IECs are crucial in IBD pathogenesis and easily accessible from the gut lumen. Besides serving as a barrier, they modulate interactions with the microbiome and immune system, making them vital for maintaining intestinal homeostasis.

IBD patients have enhanced serum coagulation and an increased risk of thrombosis. PAI-1 is pro-thrombotic as it inhibits fibrinolysis through inhibition of tissue plasminogen activator (tPA). Several lines of evidence suggest the PAI-1 inhibition should be considered for IBD: (i) PAI-1 is elevated in the serum of IBD patients potentially increasing the risk of thrombosis; (ii) PAI-1 expression is highly induced in intestinal epithelial cells in areas of active disease in IBD; (iii) PAI-1 was also a part of a prominent module of transcripts related to thrombosis/coagulation; this category was the highest enriched pathway in areas of active IBD in a retrospective analysis of IBD-related transcriptomes from 1800 intestinal biopsies across 14 independent cohorts. PAI-1 was predicted to potentially link epithelial defects to immune activation by Bayesian analysis; (iv) PAI-1 expression levels correlated with response to anti-TNF biologic therapy; (v) loss of function studies of PAI-1 in animal models promote intestinal repair and decrease inflammation. Mechanistically, PAI-1 expression is induced in the intestinal epithelium and links two closely interacting cellular compartments in IBD: intestinal epithelial and inflammatory myeloid cells. The intestinal epithelium senses injuries/pathogens and separates the luminal microbiota from the immune system to prevent uncontrolled inflammation. Published data show PAI-1 is induced in damaged intestinal epithelial cells in IBD specimens, suggesting that in addition to endothelial cells and platelets, intestinal epithelial cells are a source of PAI-1 in IBD. Mechanistically, PAI-1's main target, tissue plasminogen activation (tPA) is also induced in damaged intestinal epithelial cells, thus showing proximity of these two induced proteins. tPA activity aids in wound repair and inhibits inflammation through activation of plasmin which in turn activates TGF-β.

High PAI-1 levels are linked to various diseases. PAI-1 irreversibly binds to and inhibits tPA, contributing to thromboembolic conditions. Inhibiting PAI-1 may enhance fibrinolysis; animal studies show that PAI-1-inhibiting antibodies boost fibrinolysis significantly. Elevated PAI-1 levels are implicated in acute and chronic illnesses like deep vein thrombosis, atherosclerosis, and type 2 diabetes. Pro-inflammatory cytokines induce PAI-1 expression in endothelial cells, raising PAI-1 levels during inflammation. PAI-1 also influences cell migration, adhesion, senescence, cancer invasion, and tissue remodeling. It serves as a prognostic factor in breast cancer and other cancers, and is a plasma biomarker for nonalcoholic fatty liver disease.

SUMMARY

In one aspect, disclosed herein is a compound of formula (I):

(I)

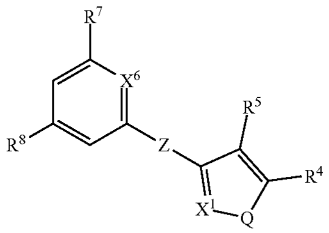

or a pharmaceutically acceptable salt thereof, wherein:

Z is —CONH—, —$CR^aR^bO$—, tetrazolyl, or oxadiazolyl, wherein $R^a$ and $R^b$ are each independently selected from hydrogen and $C_1$-$C_4$ alkyl;

$X^1$ is —$C(R^1)$— or N;

Q is —$C(R^2)$=$X^3$— or —$N(R^c)$—;

$X^3$ is —$C(R^3)$— or N;

$R^c$ is H or $C_1$-$C_4$ alkyl;

$R^1$ is H, halo, or $C_1$-$C_4$ alkyl;

$R^2$ is H, halo, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, or $C_1$-$C_4$ haloalkoxy;

$R^3$ is H, halo, or $C_1$-$C_4$ alkyl;

wherein $R^2$ and $R^3$ are optionally taken together with the carbon atoms to which they are attached to form a 5-or 6-membered ring optionally substituted with 1 or 2 substituents independently selected from $C_1$-$C_4$ alkyl, halo, and oxo;

$R^4$ is H, halo, $C_1$-$C_4$ alkyl, or —COOH;

$R^5$ is —$(CH_2)_m$—X, wherein: m is 0, 1, or 2; X is —C(O)$OR^d$, —C(O)$NHR^e$, —$OR^f$, —C(N—OH)$NH_2$, H, monocyclic heteroaryl, or monocyclic heterocyclyl, wherein the heteroaryl and heterocyclyl are independently unsubstituted or substituted with 1 or 2 substituents independently selected from $C_1$-$C_4$ alkyl, halo, and oxo; $R^d$ is H or $C_1$-$C_4$ alkyl; $R^e$ is H, $C_1$-$C_4$ alkyl, —OH, $C_1$-$C_4$ alkoxy, or —$NH_2$; and $R^f$ is H or $C_1$-$C_4$ alkyl;

$X^6$ is $CR^6$ or N;

$R^6$ is H, halo, or $C_1$-$C_4$ alkyl;

$R^7$ is H, $C_1$-$C_4$ alkyl, $C_2$-$C_4$ alkenyl, $C_2$-$C_4$ alkynyl, aryl, monocyclic heteroaryl, bicyclic heteroaryl, or monocyclic heterocyclyl, wherein the aryl, monocyclic heteroaryl, and bicyclic heteroaryl are independently substituted with 1 or 2 substituents independently selected from $C_1$-$C_4$ alkyl, halo, and monocyclic heterocyclyl, and the monocyclic heterocyclyl is unsubstituted or substituted with 1 or 2 substituents independently selected from $C_1$-$C_4$ alkyl, halo, and oxo; and $R^8$ is monocyclic heteroaryl, bicyclic heteroaryl, or aryl, each of which is independently unsubstituted or substituted with 1, 2, or 3 substituents independently selected from $C_1$-$C_6$ alkyl, $C_2$-$C_6$ alkenyl, $C_2$-$C_6$ alkynyl, $C_3$-$C_6$ cycloalkyl, halo, $C_1$-$C_6$ haloalkyl, —$(CH_2)_n$—Y, and a monocyclic heterocyclyl having 1 or 2 heteroatoms independently selected from 0 and N, wherein the monocyclic heterocyclyl is unsubstituted or substituted with 1 or 2 substituents independently selected from $C_1$-$C_4$ alkyl; wherein n is 1, 2, 3, or 4, and Y is selected from —$COOR_9$ and —$NR^hR^i$, wherein $R^g$, $R^h$, and $R^i$ are each independently selected from H and $C_1$-$C_4$ alkyl.

In some embodiments, Z is:

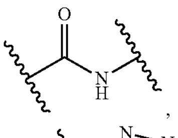,
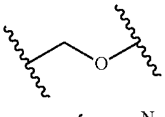,
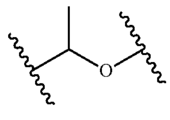,
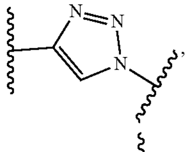,
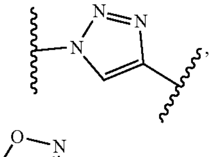, or
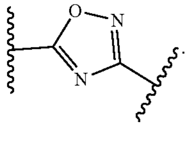.

In some embodiments, $X^1$ is $CR^1$ and $R^1$ is H. In some embodiments, $X^1$ is N.

In some embodiments, Q is —$C(R^2)$=$X^3$—. In some embodiments, $R^2$ is H, halo, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, or $C_1$-$C_4$ haloalkoxy, $X^3$ is —$C(R^3)$—, and $R^3$ is H, halo, or $C_1$-$C_4$ alkyl. In some embodiments, $R^2$ is H, chloro, methyl, ethyl, isopropyl, ethynyl, propargyl, tert-butyl, methoxy, trifluoromethyl, or trifluoromethoxy. In some embodiments, $R^2$ is halo, $C_1$-$C_4$ alkyl, $C_1$-$C_4$ alkoxy, $C_1$-$C_4$ haloalkyl, or $C_1$-$C_4$ haloalkoxy, $X^3$ is —$C(R^3)$—, and $R^3$ is H. In some embodiments, $R^2$ is chloro, methoxy, trifluoromethyl, or trifluoromethoxy, $X^3$ is —$C(R^3)$—, and $R^3$ is H. In some embodiments, $X^3$ is —$C(R^3)$—, and $R^3$ is H or chloro. In some embodiments, $X^3$ is —$C(R^3)$—, and $R^2$ and $R^3$ are taken together with the carbon atoms to which they are attached to form a phenyl ring, a 5-or 6-membered heterocyclyl ring having 1 or 2 oxygen atoms, or a 5-or 6-membered heteroaryl ring having 1 or 2 nitrogen atoms, each of which is independently unsubstituted or substituted with 1 $C_1$-$C_4$ alkyl group. In some embodiments, $X^3$ is N.

In some embodiments, Q is —$N(R^c)$— and $R^c$ is methyl.

In some embodiments, $R^4$ is H or —COOH. In some embodiments, $R^4$ is H.

In some embodiments, $R^5$ is —$(CH_2)_m$—X, wherein: m is 0 or 1; X is —C(O)$OR^d$, —C(O)$NHR^e$, —$OR^f$, —C(N—OH)$NH_2$, H, a monocyclic heteroaryl having 1, 2, 3, or 4 heteroatoms independently selected from N, O, and S, or a monocyclic heterocyclyl having 1, 2 or 3 heteroatoms independently selected from N, O, and S, and wherein the heterocyclyl is optionally substituted with an oxo group; $R^d$ is H or methyl; $R^e$ is H, methyl, —OH, methoxy, or —$NH_2$; and $R^f$ is H. In some embodiments, $R^5$ is —COOH, —$COOCH_3$, —$CONH_2$, —$CONHNH_2$, —$CONHOCH_3$, —CONHOH, —$CH_2OH$, —$CH_2COOH$, —$CH_2COOCH_3$, —$CH_2CONH_2$, —$CH_2CONHNH_2$, —$CH_2NHOCH_3$, —$CH_2CONHOH$, —$CH_2CH_2OH$, 1H-tetrazol-5-yl, 5-oxo-4H-1,2,4-oxadiazol-3-yl, —C(=N—OH)$NH_2$, or H.

In some embodiments, $X^6$ is $CR^6$ and $R^6$ is H. In some embodiments, $X^6$ is N.

In some embodiments, $R^7$ is H, $C_2$-$C_4$ alkynyl, aryl, a 5-or 6-membered monocyclic heteroaryl having 1 or 2 N atoms, a 9-or 10-membered bicyclic heteroaryl having 1 or 2 N atoms, and a 5-or 6-membered monocyclic heterocyclyl having 1 or 2 N atoms, wherein the aryl, monocyclic heteroaryl, and bicyclic heteroaryl are independently unsubstituted or substituted with 1 or 2 substituents independently selected from $C_1$-$C_4$ alkyl, halo, and monocyclic heterocyclyl having 1 heteroatom selected from 0 and N, and wherein the monocyclic heterocyclyl is unsubstituted or substituted with 1 or 2 oxo groups. In some embodiments, $R^7$ is H, —C≡CH, phenyl, pyridyl, pyrazinyl, pyrimidinyl, pyridazinyl, pyrazolyl, imidazopyridinyl, pyrrolopyridinyl, and tetrahydropyrimidinyl, wherein the phenyl, pyridyl, pyrazinyl, pyrimidinyl, pyridazinyl, pyrazolyl, imidazopyridinyl, and pyrrolopyridinyl are independently unsubstituted or substituted with 1 or 2 substituents independently selected from methyl, fluoro, and tetrahydropyranyl, and wherein the tetrahydropyrimidinyl is unsubstituted or substituted with 1 or 2 oxo groups.

In some embodiments, $R^8$ is a 5-or 6-membered monocyclic heteroaryl having 1 or 2 heteroatoms independently selected from N, O, and S; a bicyclic 9-or 10-membered heteroaryl having 1 or 2 heteroatoms independently selected from N, O, and S; and phenyl; each of which is independently unsubstituted or substituted with 1, 2, or 3 substituents independently selected from $C_1$-$C_4$ alkyl, $C_2$-$C_4$ alkynyl, $C_3$-$C_6$ cycloalkyl, halo, $C_1$-$C_4$ haloalkyl, and —$(CH_2)_n$—Y, and a monocyclic 5-or 6-membered heterocyclyl having 1 heteroatom selected from 0 and N, wherein the monocyclic heterocyclyl is unsubstituted or substituted with 1 $C_1$-$C_4$ alkyl group, wherein n is 1 or 2 and Y is —COOR$^g$ or —NR$^h$R$^i$, wherein R$^g$, R$^h$, and R$^i$ are each independently selected from H and methyl. In some embodiments, R$^8$ is pyrazolyl, oxazolyl, quinolinyl, or phenyl, each of which is independently unsubstituted or substituted with 1, 2, or 3 substituents independently selected from methyl, ethyl, isopropyl, cyclopropyl, propargyl, fluoro, chloro, trifluoromethyl, —$CH_2CH_2COOH$, —$CH_2CH_2N(CH_3)_2$, tetrahydropyranyl, and piperidinyl, wherein the piperidinyl is unsubstituted or substituted with a methyl group.

In some embodiments, the compound of formula (I) is a compound of formula (Ia):

(Ia)

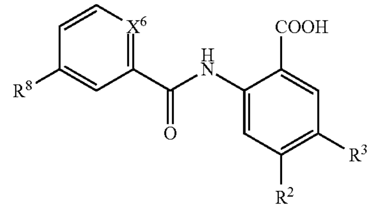

or a pharmaceutically acceptable salt thereof, wherein:

R$^8$ is a 5-membered monocyclic heteroaryl having 1 or 2 heteroatoms independently selected from N, O, and S, which is unsubstituted or substituted with 1, 2, or 3 substituents independently selected from $C_1$-$C_4$ alkyl, $C_2$-$C_4$ alkynyl, $C_3$-$C_6$ cycloalkyl, halo, $C_1$-$C_4$ haloalkyl, and —$(CH_2)_n$—Y.

In some embodiments, R$^8$ is a group of formula:

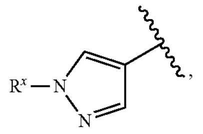

wherein R$^x$ is H, $C_1$-$C_4$ alkyl, $C_2$-$C_4$ alkynyl, $C_3$-$C_6$ cycloalkyl, —$(CH_2)_n$—Y, or a monocyclic heterocyclyl having 1 or 2 heteroatoms independently selected from 0 and N, wherein the monocyclic heterocyclyl is unsubstituted or substituted with 1 $C_1$-$C_4$ alkyl group; wherein n is 1 or 2, and Y is selected from —$COOR_9$ and —NR$^h$R$^i$, wherein R$^g$, R$^h$, and R$^i$ are each independently selected from H and $C_1$-$C_4$ alkyl.

In some embodiments, the compound is selected from the compounds listed in Table 1.

In one aspect, disclosed herein is a pharmaceutical composition comprising a compound of formula (I), or a pharmaceutically acceptable salt thereof, and a pharmaceutically acceptable carrier.

In one aspect, disclosed herein is a method of inhibiting plasminogen activator inhibitor 1 (PAI-1) in a sample, comprising contacting the sample with a compound of formula (I), or a pharmaceutically acceptable salt thereof.

In one aspect, disclosed herein is a method of treating an inflammatory bowel disease in a subject in need thereof, comprising administering to the subject a therapeutically effective amount of a compound of formula (I), or a pharmaceutically acceptable salt thereof. In some embodiments, the inflammatory bowel disease is Crohn's disease. In some embodiments, the inflammatory bowel disease is ulcerative colitis.

BRIEF DESCRIPTION OF THE DRAWINGS

FIG. 1A: experimental design PO delivery. FIGS. 1B, 1C, and 1D: H&E images of the wound bed in distal colon (1B: vehicle, 1C: Example 1 IP, 1D: Example 1 PO), with arrows indicating wound associated epithelial cells covering the ulcer in Example 1 treated mice. FIG. 1E: Comparison of distal colon wound % that was ulcerated, vehicle vs. Example 1 treated group.

FIG. 1F: Comparison of ulcers covered by WAE cells (%) vehicle vs Example 1 treated mice.

FIG. 1G: Colon lengths for vehicle, and Example 1 by PO and IP administration (5 mg/kg).

FIG. 1H: Distal colon wound percentage that was ulcerated for vehicle, and Example 1 by PO and IP administration (5 mg/k). Bars=100 μm. * indicates P<0.05; ** indicates P<0.01 by Student's t-test.

FIG. 2A: Experimental design. FIG. 2B: TNBS-induced severe mucosal damage percentage, vehicle vs. Example 1. FIGS. 2C-2D: Representative images of colon (FIG. 2C: vehicle, arrows-severe ulcers; FIG. 2D: Example 1, arrows WAE cells covering area of injury and crypt loss). N=7 mice/group. Bars=100 μm.

DETAILED DESCRIPTION

Figure 1A:
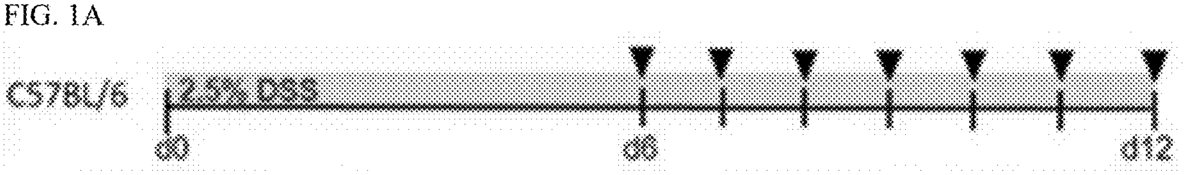
FIGS. 1A-1H show in vivo efficacy data in a DSS-induced mouse model of IBD.

Provided herein are compounds, pharmaceutical compositions comprising the compounds, methods of inhibiting PAI-1 using the compounds, and methods of treating IBDs using the compounds.

Definitions

Unless otherwise defined herein, scientific and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

As used herein and in the appended claims, the singular forms "a", "an", and "the" include plural reference unless the context clearly dictates otherwise.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Definitions of specific functional groups and chemical terms are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Sorrell, Organic Chemistry, $2^{nd}$ edition, University Science Books, Sausalito, 2006; Smith, March's Advanced Organic Chemistry: Reactions, Mechanism, and Structure, $7^{th}$ Edition, John Wiley & Sons, Inc., New York, 2013; Larock, Comprehensive Organic Transformations, $3^{rd}$ Edition, John Wiley & Sons, Inc., New York, 2018; and Carruthers, Some Modern Methods of Organic Synthesis, $3^{rd}$ Edition, Cambridge University Press, Cambridge, 1987; the entire contents of each of which are incorporated herein by reference.

As used herein, the term "alkyl" refers to a radical of a straight or branched saturated hydrocarbon chain. The alkyl chain can include, e.g., from 1 to 24 carbon atoms ($C_1$-$C_{24}$ alkyl), 1 to 16 carbon atoms ($C_1$-$C_{16}$ alkyl), 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_5$ alkyl), 1 to 6 carbon atoms ($C_1$-$C_6$ alkyl), 1 to 4 carbon atoms ($C_1$-$C_4$ alkyl), 1 to 3 carbon atoms ($C_1$-$C_3$ alkyl), or 1 to 2 carbon atoms ($C_1$-$C_2$ alkyl). Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

As used herein, the term "alkenyl" refers to a radical of a straight or branched hydrocarbon chain containing at least one carbon-carbon double bond and no triple bonds. The double bond(s) may be located at any position(s) with the hydrocarbon chain. The alkenyl chain can include, e.g., from 2 to 24 carbon atoms ($C_2$-$C_{24}$ alkenyl), 2 to 16 carbon atoms ($C_2$-$C_{16}$ alkenyl), 2 to 14 carbon atoms ($C_2$-$C_{14}$ alkenyl), 2 to 12 carbon atoms ($C_2$-$C_{12}$ alkenyl), 2 to 10 carbon atoms ($C_2$-$C_{10}$ alkenyl), 2 to 8 carbon atoms ($C_2$-$C_5$ alkenyl), 2 to 6 carbon atoms ($C_2$-$C_6$ alkenyl), 2 to 4 carbon atoms ($C_2$-$C_4$ alkenyl), 2 to 3 carbon atoms ($C_2$-$C_3$ alkenyl), or 2 carbon atoms ($C_2$ alkenyl). Representative examples of alkenyl include, but are not limited to, ethenyl, 1-propenyl, 2-propenyl, 1-butenyl, 2-butenyl, butadienyl, 2-methyl-2-propenyl, 3-butenyl, pentenyl, pentadienyl, hexenyl, heptenyl, octenyl, octatrienyl, and the like.

As used herein, the term "alkynyl" means a radical of a straight or branched hydrocarbon chain containing at least one carbon-carbon triple bond. The alkynyl chain can include, e.g., from 2 to 24 carbon atoms ($C_2$-$C_{24}$ alkynyl), 2 to 16 carbon atoms ($C_2$-$C_{16}$ alkynyl), 2 to 14 carbon atoms ($C_2$-$C_{14}$ alkynyl), 2 to 12 carbon atoms ($C_2$-$C_{12}$ alkynyl), 2 to 10 carbon atoms ($C_2$-$C_{10}$ alkynyl), 2 to 8 carbon atoms ($C_2$-$C_5$ alkynyl), 2 to 6 carbon atoms ($C_2$-$C_6$ alkynyl), 2 to 4 carbon atoms ($C_2$-$C_4$ alkynyl), 2 to 3 carbon atoms ($C_2$-$C_3$ alkynyl), or 2 carbon atoms ($C_2$ alkynyl). The triple bond(s) may be located at any position(s) with the hydrocarbon chain. Representative examples of alkynyl include, but are not limited to, ethynyl, 1-propynyl, 2-propynyl, 1-butynyl, 2-butynyl, and the like.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, and tert-butoxy.

As used herein, the term "aryl" refers to a radical of a monocyclic, bicyclic, or tricyclic 4n+2 aromatic ring system (e.g., having 6, 10, or 14 $\pi$ electrons shared in a cyclic array) having 6-14 ring carbon atoms and zero heteroatoms ("$C_6$-$C_{14}$ aryl"). In some embodiments, an aryl group has six ring carbon atoms ("$C_6$ aryl," i.e., phenyl). In some embodiments, an aryl group has ten ring carbon atoms ("$C_{10}$ aryl," e.g., naphthyl such as 1-naphthyl and 2-naphthyl). In some embodiments, an aryl group has fourteen ring carbon atoms ("$C_{14}$ aryl," e.g., anthracenyl and phenanthrenyl).

As used herein, the term "cycloalkyl" refers to a radical of a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl.

As used herein, the term "halogen" or "halo" refers to F, Cl, Br, or I.

As used herein, the term "haloalkyl" refers to an alkyl group, as defined herein, in which at least one hydrogen atom (e.g., one, two, three, four, five, six, seven or eight hydrogen atoms) is replaced with a halogen. In some embodiments, each hydrogen atom of the alkyl group is replaced with a halogen ("perhaloalkyl"). Representative examples of haloalkyl include, but are not limited to, fluoromethyl, difluoromethyl, trifluoromethyl, 2-fluoroethyl, 2,2,2-trifluoroethyl, and 3,3,3-trifluoropropyl.

As used herein, the term "haloalkoxy" refers to a haloalkyl group, as defined herein, appended to the parent molecular moiety through an oxygen atom. Representative examples of haloalkoxy include, but are not limited to, difluoromethoxy, trifluoromethoxy, and 2,2,2-trifluoroethoxy.

As used herein, the term "heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, and the like) the point of attachment can be on either ring, i.e., either the ring bearing a heteroatom (e.g., 2-indolyl) or the ring that does not contain a heteroatom (e.g., 5-indolyl). Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

As used herein, the term "heterocyclyl" refers to a radical of a 3-to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl (e.g., 2,2,6,6-tetramethylpiperidinyl), tetrahydropyranyl, dihydropyridinyl, pyridinonyl (e.g., 1-methylpyridin-2-onyl), and thianyl. Exemplary 6-membered heterocyclyl groups containing two heteroatoms include, without limitation, piperazinyl, morpholinyl, pyridazinonyl (2-methylpyridazin-3-onyl), pyrimidinonyl (e.g., 1-methylpyrimidin-2-onyl, 3-methylpyrimidin-4-onyl), dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclyl ring) include, without limitation, indolinyl, isoindolinyl, dihydrobenzofuranyl, dihydrobenzothienyl, benzoxazolinonyl, and the like. Exemplary 5-membered heterocyclyl groups fused to a heterocyclyl ring (also referred to herein as a 5,5-bicyclic heterocyclyl ring) include, without limitation, octahydropyrrolopyrrolyl (e.g., octahydropyrrolo[3,4-c]pyrrolyl), and the like. Exemplary 6-membered heterocyclyl groups fused to a heterocyclyl ring (also referred to as a 4,6-membered heterocyclyl ring) include, without limitation, diazaspirononanyl (e.g., 2,7-diazaspiro[3.5]nonanyl). Exemplary 6-membered heterocyclyl groups fused to an aryl ring (also referred to herein as a 6,6-bicyclic heterocyclyl ring) include, without limitation, tetrahydroquinolinyl, tetrahydroisoquinolinyl, and the like. Exemplary 6-membered heterocyclyl groups fused to a cycloalkyl ring (also referred to herein as a 6,7-bicyclic heterocyclyl ring) include, without limitation, azabicyclooctanyl (e.g., (1,5)-8-azabicyclo[3.2.1]octanyl). Exemplary 6-membered heterocyclyl groups fused to a cycloalkyl ring (also referred to herein as a 6,8-bicyclic heterocyclyl ring) include, without limitation, azabicyclononanyl (e.g., 9-azabicyclo[3.3.1]nonanyl).

As used herein, the term "hydroxy" or "hydroxyl" refers to an —OH group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable substituent group known to those of skill in the art (e.g., one or more of the groups recited below), provided that the designated atom's normal valence is not exceeded. Substituent groups include, but are not limited to, alkyl, alkenyl, alkynyl, alkoxy, acyl, amino, amido, amidino, aryl, azido, carbamoyl, carboxyl, carboxyl ester, cyano, cycloalkyl, cycloalkenyl, guanidino, halo, haloalkyl, haloalkoxy, heteroaryl, heterocyclyl, hydroxy, hydrazino, imino, oxo, nitro, phosphate, phosphonate, sulfonic acid, thiol, thione, or combinations thereof.

As used herein, in chemical structures the indication:

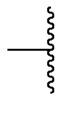

represents a point of attachment of one moiety to another moiety (e.g., a substituent group to the rest of the compound).

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The terms "administer," "administering," or "administration," as used herein refer to implanting, absorbing, ingesting, injecting, inhaling, or otherwise introducing a compound or a pharmaceutical composition.

As used herein, the terms "condition," "disease," and "disorder" are used interchangeably.

An "effective amount" of a compound or composition refers to an amount sufficient to elicit a desired biological response (e.g., treating a condition). As will be appreciated by those skilled in the art, the effective amount of a compound may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of a compound or composition may reduce tumor burden or stop the growth or spread of a tumor.

A "therapeutically effective amount" of a compound or composition is an amount sufficient to provide a therapeutic benefit in the treatment of a condition, or to delay or minimize one or more symptoms associated with the condition. In some embodiments, a therapeutically effective amount is an amount sufficient to provide a therapeutic benefit in the treatment of a condition or to minimize one or more symptoms associated with the condition.

A therapeutically effective amount of a compound means an amount of therapeutic agent, alone or in combination with other therapies, that provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. A "subject" to which administration is contemplated includes, but is not limited to, a human (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys).

As used herein, the terms "treatment," "treat," and "treating" refer to reversing, alleviating, delaying the onset of, or inhibiting the progress of a disease or condition, or one or more signs or symptoms thereof. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

Compounds

Disclosed herein is a compound of formula (I):

(I)

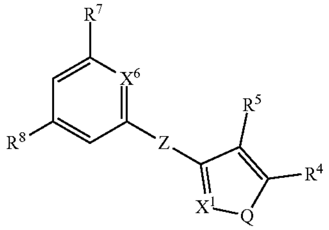

or a pharmaceutically acceptable salt thereof, wherein:

Z is —CONH—, —$CR^aR^bO$—, tetrazolyl, or oxadiazolyl, wherein $R^a$ and $R^b$ are each independently selected from hydrogen and $C_1$-$C_4$ alkyl;

$X^1$ is —C(R')— or N;

Q is —$C(R^2)$=$X^3$— or —$N(R^c)$—;

$X^3$ is —$C(R^3)$— or N;

$R^c$ is H or $C_1$-$C_4$ alkyl;

$R^1$ is H, halo, or $C_1$-$C_4$ alkyl;

$R^2$ is H, halo, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, or $C_1$-$C_4$ haloalkoxy;

$R^3$ is H, halo, or $C_1$-$C_4$ alkyl;

wherein $R^2$ and $R^3$ are optionally taken together with the carbon atoms to which they are attached to form a 5-or 6-membered ring optionally substituted with 1 or 2 substituents independently selected from $C_1$-$C_4$ alkyl, halo, and oxo;

$R^4$ is H, halo, $C_1$-$C_4$ alkyl, or —COOH;

$R^5$ is —$(CH_2)_m$—X, wherein: m is 0, 1, or 2; X is —$C(O)OR^d$, —$C(O)NHR^e$, —$OR^f$, —C(N—OH)$NH_2$, H, monocyclic heteroaryl, or monocyclic heterocyclyl, wherein the heteroaryl and heterocyclyl are independently unsubstituted or substituted with 1 or 2 substituents independently selected from $C_1$-$C_4$ alkyl, halo, and oxo; $R^d$ is H or $C_1$-$C_4$ alkyl; $R^e$ is H, $C_1$-$C_4$ alkyl, —OH, $C_1$-$C_4$ alkoxy, or —$NH_2$; and $R^d$ is H or $C_1$-$C_4$ alkyl;

$X^6$ is $CR^6$ or N;

$R^6$ is H, halo, or $C_1$-$C_4$ alkyl;

$R^7$ is H, $C_1$-$C_4$ alkyl, $C_2$-$C_4$ alkenyl, $C_2$-$C_4$ alkynyl, aryl, monocyclic heteroaryl, bicyclic heteroaryl, or monocyclic heterocyclyl, wherein the aryl, monocyclic heteroaryl, and bicyclic heteroaryl are independently substituted with 1 or 2 substituents independently selected from $C_1$-$C_4$ alkyl, halo, and monocyclic heterocyclyl, and the monocyclic heterocyclyl is unsubstituted or substituted with 1 or 2 substituents independently selected from $C_1$-$C_4$ alkyl, halo, and oxo; and $R^8$ is monocyclic heteroaryl, bicyclic heteroaryl, or aryl, each of which is independently unsubstituted or substituted with 1, 2, or 3 substituents independently selected from $C_1$-$C_6$ alkyl, $C_2$-$C_6$ alkenyl, $C_2$-$C_6$ alkynyl, $C_3$-$C_6$ cycloalkyl, halo, $C_1$-$C_6$ haloalkyl, —$(CH_2)_n$—Y, and a monocyclic heterocyclyl having 1 or 2 heteroatoms independently selected from 0 and N, wherein the monocyclic heterocyclyl is unsubstituted or substituted with 1 or 2 substituents independently selected from $C_1$-$C_4$ alkyl; wherein n is 1, 2, 3, or 4, and Y is selected from —$COOR_9$ and —$NR^hR^i$, wherein $R^g$, $R^h$, and $R^i$ are each independently selected from H and $C_1$-$C_4$ alkyl.

In some embodiments, Z is:

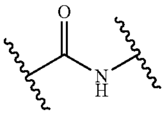,
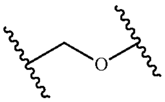,
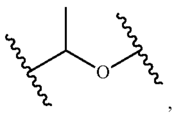,
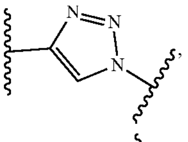,
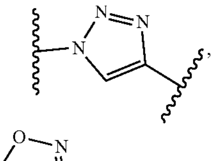, or
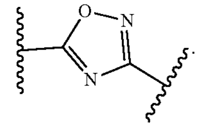.

In some embodiments, Z is:

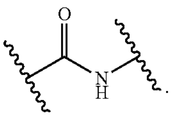 [SMILES: *NC(*)=O].

In some embodiments, Z is:

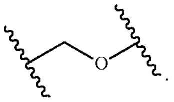 [SMILES: *CO*].

In some embodiments, $X^1$ is $CR^1$ and $R^1$ is H. In some embodiments, $X^1$ is N.

In some embodiments, Q is $—C(R^2)═X^3—$. In some embodiments, $R^2$ is H, halo, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, or $C_1$-$C_4$ haloalkoxy, $X^3$ is $—C(R^3)—$, and $R^3$ is H, halo, or $C_1$-$C_4$ alkyl. In some embodiments, $R^2$ is H, chloro, methyl, ethyl, isopropyl, ethynyl, propargyl, tert-butyl, methoxy, trifluoromethyl, or trifluoromethoxy. In some embodiments, $R^2$ is H.

In some embodiments, $X^3$ is $—C(R^3)—$, and $R^3$ is H or chloro. In some embodiments, $X^3$ is $—C(R^3)—$ and $R^3$ is H. In some embodiments, $X^3$ is $—C(R^3)—$ and $R^3$ is chloro.

In some embodiments, Q is $—C(R^2)═X^3—$ and $X^3$ is $—C(R^3)—$, and $R^2$ and $R^3$ are taken together with the carbon atoms to which they are attached to form a phenyl ring, a 5-or 6-membered heterocyclyl ring having 1 or 2 oxygen atoms, or a 5-or 6-membered heteroaryl ring having 1 or 2 nitrogen atoms, each of which is independently unsubstituted or substituted with 1 $C_1$-$C_4$ alkyl group. In some embodiments, Q is $—C(R^2)═X^3—$ and $X^3$ is $—C(R^3)—$, and $R^2$ and $R^3$ are taken together with the carbon atoms to which they are attached to form a structure selected from:

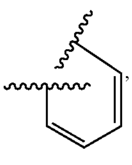,
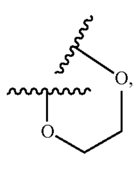,
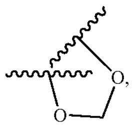,

-continued

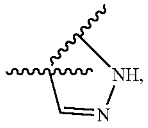 and 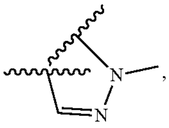, wherein each ~~~ represents a point of attachment to the carbon atoms in group Q.

In some embodiments, Q is $—C(R^2)═X^3—$ and $X^3$ is N.

In some embodiments, Q is $—N(R^e)—$ and $R^c$ is methyl.

In some embodiments, $R^4$ is H or —COOH. In some embodiments, $R^4$ is H.

In some embodiments, $R^5$ is $—(CH_2)_m—X$, wherein: m is 0 or 1; X is $—C(O)OR^d$, $—C(O)NHR^e$, $—OR^f$, —C(N—OH)$NH_2$, H, a monocyclic heteroaryl having 1, 2, 3, or 4 heteroatoms independently selected from N, O, and S, or a monocyclic heterocyclyl having 1, 2 or 3 heteroatoms independently selected from N, O, and S, and wherein the heterocyclyl is optionally substituted with an oxo group; $R^d$ is H or methyl; $R^e$ is H, methyl, —OH, methoxy, or $—NH_2$; and $R^f$ is H. In some embodiments, $R^5$ is —COOH, $—COOCH_3$, $—CONH_2$, $—CONHNH_2$, $—CONHOCH_3$, —CONHOH, $—CH_2OH$, $—CH_2COOH$, $—CH_2COOCH_3$, $—CH_2CONH_2$, $—CH_2CONHNH_2$, $—CH_2NHOCH_3$, $—CH_2CONHOH$, $—CH_2CH_2OH$, 1H-tetrazol-5-yl, 5-oxo-4H-1,2,4-oxadiazol-3-yl, —C(═N—OH)$NH_2$, or H. In some embodiments, $R^5$ is —COOH.

In some embodiments, $X^6$ is $CR^6$ and $R^6$ is H. In some embodiments, $X^6$ is N.

In some embodiments, $R^7$ is H, $C_2$-$C_4$ alkynyl, aryl, a 5-or 6-membered monocyclic heteroaryl having 1 or 2 N atoms, a 9-or 10-membered bicyclic heteroaryl having 1 or 2 N atoms, and a 5-or 6-membered monocyclic heterocyclyl having 1 or 2 N atoms, wherein the aryl, monocyclic heteroaryl, and bicyclic heteroaryl are independently unsubstituted or substituted with 1 or 2 substituents independently selected from $C_1$-$C_4$ alkyl, halo, and monocyclic heterocyclyl having 1 heteroatom selected from 0 and N, and wherein the monocyclic heterocyclyl is unsubstituted or substituted with 1 or 2 oxo groups. In some embodiments, $R^7$ is H, —C≡CH, phenyl, pyridyl, pyrazinyl, pyrimidinyl, pyridazinyl, pyrazolyl, imidazopyridinyl, pyrrolopyridinyl, and tetrahydropyrimidinyl, wherein the phenyl, pyridyl, pyrazinyl, pyrimidinyl, pyridazinyl, pyrazolyl, imidazopyridinyl, and pyrrolopyridinyl are independently unsubstituted or substituted with 1 or 2 substituents independently selected from methyl, fluoro, and tetrahydropyranyl, and wherein the tetrahydropyrimidinyl is unsubstituted or substituted with 1 or 2 oxo groups. In some embodiments, $R^7$ is H. In some embodiments, $R^7$ is pyrazolyl, which is substituted with 1 tetrahydropyranyl group.

In some embodiments, $R^8$ is a 5-or 6-membered monocyclic heteroaryl having 1 or 2 heteroatoms independently selected from N, O, and S; a bicyclic 9-or 10-membered heteroaryl having 1 or 2 heteroatoms independently selected from N, O, and S; or phenyl; each of which is independently unsubstituted or substituted with 1, 2, or 3 substituents independently selected from $C_1$-$C_4$ alkyl, $C_2$-$C_4$ alkynyl, $C_3$-$C_6$ cycloalkyl, halo, $C_1$-$C_4$ haloalkyl, and $—(CH_2)_n—Y$, and a monocyclic 5-or 6-membered heterocyclyl having 1 heteroatom selected from 0 and N, wherein the monocyclic heterocyclyl is unsubstituted or substituted with 1 $C_1$-$C_4$ alkyl group, wherein n is 1 or 2 and Y is $—COOR^g$ or $—NR^hR^i$, wherein $R^g$, $R^h$, and $R^i$ are each independently selected from H and methyl. In some embodiments, $R^8$ is pyrazolyl, oxazolyl, quinolinyl, or phenyl, each of which is independently unsubstituted or substituted with 1, 2, or 3 substituents independently selected from methyl, ethyl, isopropyl, cyclopropyl, propargyl, fluoro, chloro, trifluoromethyl, $—CH_2CH_2COOH$, $—CH_2CH_2N(CH_3)_2$, tetrahydropyranyl, and piperidinyl, wherein the piperidinyl is unsubstituted or substituted with a methyl group. In some embodiments, $R^8$ is pyrazolyl, which is unsubstituted or substituted with 1, 2, or 3 substituents independently selected from methyl, ethyl, isopropyl, cyclopropyl, propargyl, $—CH_2CH_2COOH$, $—CH_2CH_2N(CH_3)_2$, tetrahydropyranyl, and piperidinyl, wherein the piperidinyl is unsubstituted or substituted with a methyl group. In some embodiments, $R^8$ is pyrazolyl, which is unsubstituted or substituted with 1 substituent selected from methyl, ethyl, isopropyl, cyclopropyl, propargyl, $—CH_2CH_2COOH$, $—CH_2CH_2N(CH_3)_2$, tetrahydropyranyl, and piperidinyl, wherein the piperidinyl is unsubstituted or substituted with a methyl group. In some embodiments, $R^8$ is pyrazolyl, which is substituted with 1 tetrahydropyranyl group.

In some embodiments, the compound of formula (I) is a compound of formula (Ia):

(Ia)

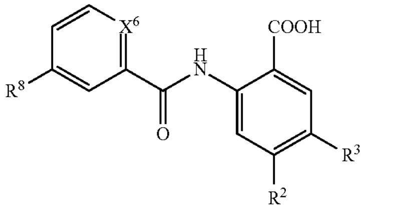

wherein:

$R^8$ is a 5-membered monocyclic heteroaryl having 1 or 2 heteroatoms independently selected from N, O, and S, which is unsubstituted or substituted with 1, 2, or 3 substituents independently selected from $C_1$-$C_4$ alkyl, $C_2$-$C_4$ alkynyl, $C_3$-$C_6$ cycloalkyl, halo, $C_1$-$C_4$ haloalkyl, and $—(CH_2)_n—Y$.

In some embodiments, the compound of formula (I) is a compound of formula (Ib):

(Ib)

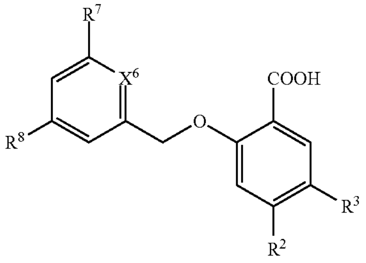

wherein:

$R^7$ is H or a 5-membered monocyclic heteroaryl having 1 or 2 heteroatoms independently selected from N, O, and S, which is unsubstituted or substituted with 1, 2, or 3 substituents independently selected from $C_1$-$C_4$ alkyl, $C_2$-$C_4$ alkynyl, $C_3$-$C_6$ cycloalkyl, halo, $C_1$-$C_4$ haloalkyl, and $—(CH_2)_n—Y$; and $R^8$ is a 5-membered monocyclic heteroaryl having 1 or 2 heteroatoms independently selected from N, O, and S, which is unsubstituted or substituted with 1, 2, or 3 substituents independently selected from $C_1$-$C_4$ alkyl, $C_2$-$C_4$ alkynyl, $C_3$-$C_6$ cycloalkyl, halo, $C_1$-$C_4$ haloalkyl, and $—(CH_2)_n—Y$.

In formula (Ia) and formula (Ib), the groups $R^2$, $R^3$, and $X^6$ are any of the groups defined or described herein above for formula (I). In some embodiments, in formula (Ta) and formula (Tb), $R^8$ is a group of formula:

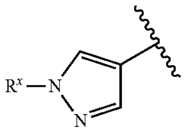

wherein $R^X$ is H, $C_1$-$C_4$ alkyl, $C_2$-$C_4$ alkynyl, $C_3$-$C_6$ cycloalkyl, $—(CH_2)_n—Y$, or a monocyclic heterocyclyl having 1 or 2 heteroatoms independently selected from 0 and N, wherein the monocyclic heterocyclyl is unsubstituted or substituted with 1 $C_1$-$C_4$ alkyl group; wherein n is 1 or 2, and Y is selected from $—COOR^g$ and $—NR^hR^i$, wherein $R^g$, $R^h$, and $R^i$ are each independently selected from H and $C_1$-$C_4$ alkyl.

In some embodiments, the compound of formula (I) is a compound listed in Table 1.

TABLE 1

Compounds of the Disclosure

| Example # | Chemical Name |
|---|---|
| 1 | 4-chloro-2-[[3-(1-tetrahydropyran-4-ylpyrazol-4-yl)benzoyl]amino]benzoic acid |
| 2 | 2-[[3-[1-(2-carboxyethyl)pyrazol-4-yl]benzoyl]amino]-4-chloro-benzoic acid |
| 3 | 2-[[3-(1H-pyrazol-4-yl)benzoyl]amino]benzoic acid |
| 4 | 2-[[3-(1-tetrahydropyran-4-ylpyrazol-3-yl)benzoyl]amino]benzoic acid |
| 5 | 2-[[3-[1-(2-carboxyethyl)pyrazol-4-yl]benzoyl]amino]benzoic acid |
| 6 | 2-[[4-(1-tetrahydropyran-4-ylpyrazol-4-yl)pyridine-2-carbonyl]amino]benzoic acid |
| 7 | 2-[[4-[1-(2-carboxyethyl)pyrazol-4-yl]pyridine-2-carbonyl]amino]benzoic acid |
| 8 | 2-[[3-(8-quinolyl)benzoyl]amino]benzoic acid |
| 9 | 4-methyl-2-[[3-(1H-pyrazol-4-yl)benzoyl]amino]benzoic acid |
| 10 | 4-methyl-2-[[3-(1-tetrahydropyran-4-ylpyrazol-4-yl)benzoyl]amino]benzoic acid |
| 11 | 2-[[3-[1-(2-carboxyethyl)pyrazol-4-yl]benzoyl]amino]-4-methyl-benzoic acid |

TABLE 1-continued

| Compounds of the Disclosure | |
|---|---|
| Example # | Chemical Name |
| 12 | 4-methyl-2-[[4-(1-tetrahydropyran-4-ylpyrazol-4-yl)pyridine-2-carbonyl]amino]benzoic acid |
| 13 | 2-[[4-[1-(2-carboxyethyl)pyrazol-4-yl]pyridine-2-carbonyl]amino]-4-methyl-benzoic acid |
| 14 | 4-methyl-2-[[3-(8-quinolyl)benzoyl]amino]benzoic acid |
| 15 | 2-[[3-(1H-pyrazol-4-yl)benzoyl]amino]-4-(trifluoromethyl)benzoic acid |
| 16 | 2-[[3-(1-tetrahydropyran-4-ylpyrazol-4-yl)benzoyl]amino]-4-(trifluoromethyl)benzoic acid |
| 17 | 2-[[3-[1-(2-carboxyethyl)pyrazol-4-yl]benzoyl]amino]-4-(trifluoromethyl)benzoic acid |
| 18 | 2-[[4-(1-tetrahydropyran-4-ylpyrazol-4-yl)pyridine-2-carbonyl]amino]-4-(trifluoromethyl)benzoic acid |
| 19 | 2-[[4-[1-(2-carboxyethyl)pyrazol-4-yl]pyridine-2-carbonyl]amino]-4-(trifluoromethyl)benzoic acid |
| 20 | 2-[[3-(8-quinolyl)benzoyl]amino]-4-(trifluoromethyl)benzoic acid |
| 21 | 4-isopropyl-2-[[3-(1H-pyrazol-4-yl)benzoyl]amino]benzoic acid |
| 22 | 4-isopropyl-2-[[3-(1-tetrahydropyran-4-ylpyrazol-4-yl)benzoyl]amino]benzoic acid |
| 23 | 2-[[3-[1-(2-carboxyethyl)pyrazol-4-yl]benzoyl]amino]-4-isopropyl-benzoic acid |
| 24 | 4-isopropyl-2-[[4-(1-tetrahydropyran-4-ylpyrazol-4-yl)pyridine-2-carbonyl]amino]benzoic acid |
| 25 | 2-[[4-[1-(2-carboxyethyl)pyrazol-4-yl]pyridine-2-carbonyl]amino]-4-isopropyl-benzoic acid |
| 26 | 4-isopropyl-2-[[3-(8-quinolyl)benzoyl]amino]benzoic acid |
| 27 | 4-tert-butyl-2-[[3-(1H-pyrazol-4-yl)benzoyl]amino]benzoic acid |
| 28 | 4-tert-butyl-2-[3-(1-tetrahydropyran-4-ylpyrazol-3-yl)benzoyl]amino]benzoic acid |
| 29 | 4-tert-butyl-2-[[3-[1-(2-carboxyethyl)pyrazol-4-yl]benzoyl]amino]benzoic acid |
| 30 | 4-tert-butyl-2-[[4-(1-tetrahydropyran-4-ylpyrazol-4-yl)pyridine-2-carbonyl]amino]benzoic acid |
| 31 | 4-tert-butyl-2-[[4-[1-(2-carboxyethyl)pyrazol-4-yl]pyridine-2-carbonyl]amino]benzoic acid |
| 32 | 4-tert-butyl-2-[[3-(8-quinolyl)benzoyl]amino]benzoic acid |
| 33 | 4-methoxy-2-[[3-(1H-pyrazol-4-yl)benzoyl]amino]benzoic acid |
| 34 | 4-methoxy-2-[[3-(1-tetrahydropyran-4-ylpyrazol-4-yl)benzoyl]amino]benzoic acid |
| 35 | 2-[[3-[1-(2-carboxyethyl)pyrazol-4-yl]benzoyl]amino]-4-methoxy-benzoic acid |
| 36 | 4-methoxy-2-[[4-(1-tetrahydropyran-4-ylpyrazol-4-yl)pyridine-2-carbonyl]amino]benzoic acid |
| 37 | 2-[[4-[1-(2-carboxyethyl)pyrazol-4-yl]pyridine-2-carbonyl]amino]-4-methoxy-benzoic acid |
| 38 | 4-methoxy-2-[[3-(8-quinolyl)benzoyl]amino]benzoic acid |
| 39 | 2-[[3-(1H-pyrazol-4-yl)benzoyl]amino]-4-(trifluoromethoxy)benzoic acid |
| 40 | 2-[[3-(1-tetrahydropyran-4-ylpyrazol-4-yl)benzoyl]amino]-4-(trifluoromethoxy)benzoic acid |
| 41 | 2-[[3-[1-(2-carboxyethyl)pyrazol-4-yl]benzoyl]amino]-4-(trifluoromethoxy)benzoic acid |
| 42 | 2-[[4-(1-tetrahydropyran-4-ylpyrazol-4-yl)pyridine-2-carbonyl]amino]-4-(trifluoromethoxy)benzoic acid |
| 43 | 2-[[4-[1-(2-carboxyethyl)pyrazol-4-yl]pyridine-2-carbonyl]amino]-4-(trifluoromethoxy)benzoic acid |
| 44 | 2-[[3-(8-quinolyl)benzoyl]amino]-4-(trifluoromethoxy)benzoic acid |
| 45 | 6-chloro-2-[3-(1H-pyrazol-4-yl)benzoyl]amino]pyridine-3-carboxylic acid |
| 46 | 6-chloro-2-[[3-(1-tetrahydropyran-4-ylpyrazol-4-yl)benzoyl]amino]pyridine-3-carboxylic acid |
| 47 | 2-[[3-[1-(2-carboxyethyl)pyrazol-4-yl]benzoyl]amino]-6-chloro-pyridine-3-carboxylic acid |
| 48 | 6-chloro-2-[[3-(8-quinolyl)benzoyl]amino]pyridine-3-carboxylic acid |
| 49 | 2-methyl-4-[[3-(1H-pyrazol-4-yl)benzoyl]amino]pyrimidine-5-carboxylic acid |
| 50 | 2-methyl-4-[[3-(1-tetrahydropyran-4-ylpyrazol-4-yl)benzoyl]amino]pyrimidine-5-carboxylic acid |
| 51 | 4-[[3-[1-(2-carboxyethyl)pyrazol-4-yl]benzoyl]amino]-2-methyl-pyrimidine-5-carboxylic acid |
| 52 | 2-methyl-4-[[3-(8-quinolyl)benzoyl]amino]pyrimidine-5-carboxylic acid |
| 53 | 6-methoxy-2-[[3-(1H-pyrazol-4-yl)benzoyl]amino]pyridine-3-carboxylic acid |
| 54 | 6-methoxy-2-[[3-(1-tetrahydropyran-4-ylpyrazol-4-yl)benzoyl]amino]pyridine-3-carboxylic acid |
| 55 | 2-[[3-[1-(2-carboxyethyl)pyrazol-4-yl]benzoyl]amino]-6-methoxy-pyridine-3-carboxylic acid |
| 56 | 4,5-dichloro-2-[[3-(1-tetrahydropyran-4-ylpyrazol-4-yl)benzoyl]amino]benzoic acid |
| 57 | 2-[[3-[1-(2-carboxyethyl)pyrazol-4-yl]benzoyl]amino]-4,5-dichloro-benzoic acid |
| 58 | 4,5-dichloro-2-[[3-(1H-pyrazol-4-yl)benzoyl]amino]benzoic acid |
| 59 | 3-[[3-(1-tetrahydropyran-4-ylpyrazol-4-yl)benzoyl]amino]naphthalene-2-carboxylic acid |
| 60 | 3-[[3-[1-(2-carboxyethyl)pyrazol-4-yl]benzoyl]amino]naphthalene-2-carboxylic acid |
| 61 | 3-[[3-(1H-pyrazol-4-yl)benzoyl]amino]naphthalene-2-carboxylic acid |
| 62 | 2-[[3-(1-tetrahydropyran-4-ylpyrazol-4-yl)benzoyl]amino]quinoline-3-carboxylic acid |
| 63 | 2-[[3-[1-(2-carboxyethyl)pyrazol-4-yl]benzoyl]amino]quinoline-3-carboxylic acid |
| 64 | 2-[[3-(1H-pyrazol-4-yl)benzoyl]amino]quinoline-3-carboxylic acid |
| 65 | 6-[[3-(1-tetrahydropyran-4-ylpyrazol-4-yl)benzoyl]amino]-2,3-dihydro-1,4-benzodioxine-7-carboxylic acid |
| 65 | [6-[[3-(1-tetrahydropyran-4-ylpyrazol-4-yl)benzoyl]amino]-2,3-dihydro-1,4-benzodioxine-7-carbonyl]oxysodium |

TABLE 1-continued

| Compounds of the Disclosure | |
|---|---|
| Example # | Chemical Name |
| 66 | 6-[[3-[1-(2-carboxyethyl)pyrazol-4-yl]benzoyl]amino]-2,3-dihydro-1,4-benzodioxine-7-carboxylic acid |
| 67 | 6-[3-(1H-pyrazol-3-yl)benzoyl]amino]-2,3-dihydro-1,4-benzodioxine-7-carboxylic acid |
| 68 | 6-[[3-(1-tetrahydropyran-4-ylpyrazol-4-yl)benzoyl]amino]-1,3-benzodioxole-5-carboxylic acid |
| 69 | 6-[[3-(1H-pyrazol-4-yl)benzoyl]amino]-1,3-benzodioxole-5-carboxylic acid |
| 70 | 5-[[3-(1-tetrahydropyran-4-ylpyrazol-4-yl)benzoyl]amino]-1H-indazole-6-carboxylic acid |
| 71 | 1-methyl-5-[[3-(1-tetrahydropyran-4-ylpyrazol-4-yl)benzoyl]amino]indazole-6-carboxylic acid |
| 72 | 5-[[3-[1-(2-carboxyethyl)pyrazol-4-yl]benzoyl]amino]-1H-indazole-6-carboxylic acid |
| 73 | 5-[[3-[1-(2-carboxyethyl)pyrazol-4-yl]benzoyl]amino]-1-methyl-indazole-6-carboxylic acid |
| 74 | 5-[[3-(1H-pyrazol-4-yl)benzoyl]amino]-1H-indazole-6-carboxylic acid |
| 75 | 1-methyl-5-[[3-(1H-pyrazol-4-yl)benzoyl]amino]indazole-6-carboxylic acid |
| 76 | methyl 4-chloro-2-[3-(1-tetrahydropyran-4-ylpyrazol-4-yl)benzoyl]amino]benzoate |
| 77 | 4-chloro-2-[[3-(1-tetrahydropyran-4-ylpyrazol-4-yl)benzoyl]amino]benzamide |
| 78 | N-[5-chloro-2-(hydrazinecarbonyl)phenyl]-3-(1-tetrahydropyran-4-ylpyrazol-4-yl)benzamide |
| 79 | 4-chloro-N-methoxy-2-[[3-(1-tetrahydropyran-4-ylpyrazol-3-yl)benzoyl]amino]benzamide |
| 80 | N-[5-chloro-2-(hydroxycarbamoyl)phenyl]-3-(1-tetrahydropyran-4-ylpyrazol-3-yl)benzamide |
| 81 | N-[5-chloro-2-(hydroxymethyl)phenyl]-3-(1-tetrahydropyran-4-ylpyrazol-4-yl)benzamide |
| 82 | 2-[4-chloro-2-[3-(1-tetrahydropyran-4-ylpyrazol-4-yl)benzoyl]amino]phenyl]acetic acid |
| 83 | methyl 2-[4-chloro-2-[[3-(1-tetrahydropyran-4-ylpyrazol-4-yl)benzoyl]amino]phenyl]acetate |
| 84 | N-[2-(2-amino-2-oxo-ethyl)-5-chloro-phenyl]-3-(1-tetrahydropyran-4-ylpyrazol-4-yl)benzamide |
| 86 | N-[5-chloro-2-[2-(methoxyamino)-2-oxo-ethyl]phenyl]-3-(1-tetrahydropyran-4-ylpyrazol-4-yl)benzamide |
| 87 | N-[5-chloro-2-[2-(hydroxyamino)-2-oxo-ethyl]phenyl]-3-(1-tetrahydropyran-4-ylpyrazol-4-yl)benzamide |
| 85 | N-[5-chloro-2-(2-hydrazino-2-oxo-ethyl)phenyl]-3-(1-tetrahydropyran-4-ylpyrazol-4-yl)benzamide |
| 88 | N-[5-chloro-2-(2-hydroxyethyl)phenyl]-3-(1-tetrahydropyran-4-ylpyrazol-3-yl)benzamide |
| 89 | 4-chloro-2-[4-[3-(1H-pyrazol-4-yl)phenyl]triazol-1-yl]benzoic acid |
| 90 | 4-chloro-2-(4-(3-(1-(tetrahydro-2H-pyran-4-yl)-1H-pyrazol-4-yl)phenyl)-1H-1,2,3-triazol-1-yl)benzoic acid |
| 91 | 2-[4-[3-[1-(2-carboxyethyl)pyrazol-4-yl]phenyl]triazol-1-yl]-4-chloro-benzoic acid |
| 92 | 4-chloro-2-[1-[3-(1H-pyrazol-4-yl)phenyl]triazol-4-yl]benzoic acid |
| 93 | 2-[1-[3-[1-(2-carboxyethyl)pyrazol-4-yl]phenyl]triazol-4-yl]-4-chloro-benzoic acid |
| 94 | 2-[5-[3-(1H-pyrazol-4-yl)phenyl]-1,2,4-oxadiazol-3-yl]benzoic acid |
| 95 | 2-[[4-(1H-pyrazol-4-yl)pyridine-2-carbonyl]amino]benzoic acid |
| 96 | 2-[[3-(1-tetrahydropyran-4-ylpyrazol-4-yl)benzoyl]amino]pyridine-3-carboxylic acid |
| 97 | 1-methyl-3-[[4-(1H-pyrazol-4-yl)pyridine-2-carbonyl]amino]pyrazole-4-carboxylic acid |
| 98 | 1-methyl-3-[[3-(1-tetrahydropyran-4-ylpyrazol-4-yl)benzoyl]amino]pyrazole-4-carboxylic acid |
| 99 | 2-[[4-(1H-pyrazol-4-yl)pyridine-2-carbonyl]amino]pyridine-3-carboxylic acid |
| 100 | 2-[[4-(1-tetrahydropyran-4-ylpyrazol-4-yl)pyridine-2-carbonyl]amino]pyridine-3-carboxylic acid |
| 101 | 6-methoxy-2-[[4-(1H-pyrazol-4-yl)pyridine-2-carbonyl]amino]pyridine-3-carboxylic acid |
| 102 | 6-methoxy-2-[[4-(1-tetrahydropyran-4-ylpyrazol-4-yl)pyridine-2-carbonyl]amino]pyridine-3-carboxylic acid |
| 103 | 2-[[3-(1,3-dimethylpyrazol-4-yl)benzoyl]amino]benzoic acid |
| 104 | 2-[[3-(1,3,5-trimethylpyrazol-4-yl)benzoyl]amino]benzoic acid |
| 105 | 2-[[3-(1-methylpyrazol-4-yl)benzoyl]amino]benzoic acid |
| 106 | 2-[[3-(1-isopropylpyrazol-4-yl)benzoyl]amino]benzoic acid |
| 107 | 2-[[3-(1-cyclopropylpyrazol-4-yl)benzoyl]amino]benzoic acid |
| 108 | 2-[[3-[1-(2-hydroxyethyl)pyrazol-4-yl]benzoyl]amino]benzoic acid |
| 109 | 2-[[3-[1-[2-(dimethylamino)ethyl]pyrazol-4-yl]benzoyl]amino]benzoic acid |
| 110 | 2-[[3-[1-(4-piperidyl)pyrazol-4-yl]benzoyl]amino]benzoic acid |
| 111 | 2-[[3-[1-(1-methyl-4-piperidyl)pyrazol-4-yl]benzoyl]amino]benzoic acid |
| 112 | 2-[[3-(1,3-dimethylpyrazol-4-yl)benzoyl]amino]-6-methoxy-pyridine-3-carboxylic acid |
| 113 | 6-methoxy-2-[[3-(1,3,5-trimethylpyrazol-4-yl)benzoyl]amino]pyridine-3-carboxylic acid |
| 114 | 6-methoxy-2-[[3-(1-methylpyrazol-4-yl)benzoyl]amino]pyridine-3-carboxylic acid |
| 115 | 2-[[3-(1-isopropylpyrazol-4-yl)benzoyl]amino]-6-methoxy-pyridine-3-carboxylic acid |
| 116 | 2-[3-(1-cyclopropylpyrazol-4-yl)benzoyl]amino]-6-methoxy-pyridine-3-carboxylic acid |
| 117 | 2-[[3-[1-(2-hydroxyethyl)pyrazol-4-yl]benzoyl]amino]-6-methoxy-pyridine-3-carboxylic acid |
| 118 | 2-[[3-[1-[2-(dimethylamino)ethyl]pyrazol-4-yl]benzoyl]amino]-6-methoxy-pyridine-3-carboxylic acid |
| 119 | 6-methoxy-2-[[3-[1-(1-methyl-4-piperidyl)pyrazol-4-yl]benzoyl]amino]pyridine-3-carboxylic acid |
| 120 | 4-chloro-2-[3-phenyl-5-(1-tetrahydropyran-4-ylpyrazol-4-yl)benzoyl]amino]benzoic acid |
| 121 | 4-chloro-2-[[3-(2-pyridyl)-5-(1-tetrahydropyran-4-ylpyrazol-4-yl)benzoyl]amino]benzoic acid |

TABLE 1-continued

| Compounds of the Disclosure | |
|---|---|
| Example # | Chemical Name |
| 122 | 4-chloro-2-[[3-(3-pyridyl)-5-(1-tetrahydropyran-4-ylpyrazol-4-yl)benzoyl]amino]benzoic acid |
| 123 | 4-chloro-2-[[3-pyrazin-2-yl-5-(1-tetrahydropyran-4-ylpyrazol-4-yl)benzoyl]amino]benzoic acid |
| 124 | 4-chloro-2-[[3-pyridazin-3-yl-5-(1-tetrahydropyran-4-ylpyrazol-4-yl)benzoyl]amino]benzoic acid |
| 125 | 4-chloro-2-[[3-(6-methyl-2-pyridyl)-5-(1-tetrahydropyran-4-ylpyrazol-4-yl)benzoyl]amino]benzoic acid |
| 126 | 4-chloro-2-[[3-(2-fluoro-6-methyl-3-pyridyl)-5-(1-tetrahydropyran-4-ylpyrazol-4-yl)benzoyl]amino]benzoic acid |
| 127 | 4-chloro-2-[[3-(6-methylpyrazin-2-yl)-5-(1-tetrahydropyran-4-ylpyrazol-4-yl)benzoyl]amino]benzoic acid |
| 128 | 4-chloro-2-[[3-(6-methyl-3-pyridyl)-5-(1-tetrahydropyran-4-ylpyrazol-4-yl)benzoyl]amino]benzoic acid |
| 129 | 4-chloro-2-[[3-pyrimidin-5-yl-5-(1-tetrahydropyran-4-ylpyrazol-4-yl)benzoyl]amino]benzoic acid |
| 130 | 4-chloro-2-[[3-(2,4-dioxo-1H-pyrimidin-5-yl)-5-(1-tetrahydropyran-4-ylpyrazol-4-yl)benzoyl]amino]benzoic acid |
| 131 | 4-chloro-2-[[3-(4-fluorophenyl)-5-(1-tetrahydropyran-4-ylpyrazol-4-yl)benzoyl]amino]benzoic acid |
| 132 | 4-chloro-2-[[3-(3,4-difluorophenyl)-5-(1-tetrahydropyran-4-ylpyrazol-4-yl)benzoyl]amino]benzoic acid |
| 133 | 4-chloro-2-[[3-(1,5-dihydroimidazo[1,2-a]pyridin-6-yl)-5-(1-tetrahydropyran-4-ylpyrazol-4-yl)benzoyl]amino]benzoic acid |
| 134 | 4-chloro-2-[[3-(1H-pyrrolo[2,3-b]pyridin-6-yl)-5-(1-tetrahydropyran-4-ylpyrazol-4-yl)benzoyl]amino]benzoic acid |
| 135 | 2-[[3,5-bis(1-tetrahydropyran-4-ylpyrazol-4-yl)benzoyl]amino]-4-chloro-benzoic acid |
| 136 | 2-[[3-[1-(2-carboxyethyl)pyrazol-4-yl]-5-(1-tetrahydropyran-4-ylpyrazol-4-yl)benzoyl]amino]-4-chloro-benzoic acid |
| 137 | 4-chloro-2-[[3-(1H-pyrazol-4-yl)-5-(1-tetrahydropyran-4-ylpyrazol-4-yl)benzoyl]amino]benzoic acid |
| 138 | 6-methoxy-2-[[3-phenyl-5-(1H-pyrazol-4-yl)benzoyl]amino]pyridine-3-carboxylic acid |
| 139 | 6-methoxy-2-[[3-(1H-pyrazol-4-yl)-5-(2-pyridyl)benzoyl]amino]pyridine-3-carboxylic acid |
| 140 | 6-methoxy-2-[[3-(1H-pyrazol-3-yl)-5-(3-pyridyl)benzoyl]amino]pyridine-3-carboxylic acid |
| 141 | 6-methoxy-2-[[3-pyrazin-2-yl-5-(1H-pyrazol-4-yl)benzoyl]amino]pyridine-3-carboxylic acid |
| 142 | 6-methoxy-2-[[3-(1H-pyrazol-4-yl)-5-pyridazin-3-yl-benzoyl]amino]pyridine-3-carboxylic acid |
| 143 | 6-methoxy-2-[[3-(6-methyl-2-pyridyl)-5-(1H-pyrazol-4-yl)benzoyl]amino]pyridine-3-carboxylic acid |
| 144 | 2-[[3-(2-fluoro-6-methyl-3-pyridyl)-5-(1H-pyrazol-4-yl)benzoyl]amino]-6-methoxy-pyridine-3-carboxylic acid |
| 145 | 6-methoxy-2-[[3-(6-methylpyrazin-2-yl)-5-(1H-pyrazol-4-yl)benzoyl]amino]pyridine-3-carboxylic acid |
| 146 | 6-methoxy-2-[[3-(6-methyl-3-pyridyl)-5-(1H-pyrazol-4-yl)benzoyl]amino]pyridine-3-carboxylic acid |
| 147 | 6-methoxy-2-[[3-(1H-pyrazol-4-yl)-5-pyrimidin-5-yl-benzoyl]amino]pyridine-3-carboxylic acid |
| 148 | 2-[[3-(2,4-dioxo-1H-pyrimidin-5-yl)-5-(1H-pyrazol-4-yl)benzoyl]amino]-6-methoxy-pyridine-3-carboxylic acid |
| 149 | 2-[[3-(4-fluorophenyl)-5-(1H-pyrazol-4-yl)benzoyl]amino]-6-methoxy-pyridine-3-carboxylic acid |
| 150 | 2-[3-(3,4-difluorophenyl)-5-(1H-pyrazol-3-yl)benzoyl]amino]-6-methoxy-pyridine-3-carboxylic acid |
| 151 | 2-[[3-(1,5-dihydroimidazo[1,2-a]pyridin-6-yl)-5-(1H-pyrazol-4-yl)benzoyl]amino]-6-methoxy-pyridine-3-carboxylic acid |
| 152 | 6-methoxy-2-[[3-(1H-pyrazol-3-yl)-5-(1H-pyrrolo[2,3-b]pyridin-5-yl)benzoyl]amino]pyridine-3-carboxylic acid |
| 153 | 6-methoxy-2-[[3-(1H-pyrazol-4-yl)-5-(1-tetrahydropyran-4-ylpyrazol-4-yl)benzoyl]amino]pyridine-3-carboxylic acid |
| 154 | 2-[[3-[1-(2-carboxyethyl)pyrazol-4-yl]-5-(1H-pyrazol-4-yl)benzoyl]amino]-6-methoxy-pyridine-3-carboxylic acid |
| 155 | 2-[3,5-bis(1H-pyrazol-4-yl)benzoyl]amino]-6-methoxy-pyridine-3-carboxylic acid |
| 156 | 6-[[3-phenyl-5-(1-tetrahydropyran-4-ylpyrazol-4-yl)benzoyl]amino]-2,3-dihydro-1,4-benzodioxine-7-carboxylic acid |
| 157 | 6-[[3-(2-pyridyl)-5-(1-tetrahydropyran-4-ylpyrazol-4-yl)benzoyl]amino]-2,3-dihydro-1,4-benzodioxine-7-carboxylic acid |
| 158 | 6-[[3-(3-pyridyl)-5-(1-tetrahydropyran-4-ylpyrazol-4-yl)benzoyl]amino]-2,3-dihydro-1,4-benzodioxine-7-carboxylic acid |
| 159 | 6-[[3-pyrazin-2-yl-5-(1-tetrahydropyran-4-ylpyrazol-4-yl)benzoyl]amino]-2,3-dihydro-1,4-benzodioxine-7-carboxylic acid |
| 160 | 6-[[3-pyridazin-3-yl-5-(1-tetrahydropyran-4-ylpyrazol-4-yl)benzoyl]amino]-2,3-dihydro-1,4-benzodioxine-7-carboxylic acid |

TABLE 1-continued

Compounds of the Disclosure

| Example # | Chemical Name |
|---|---|
| 161 | 6-[[3-(6-methyl-2-pyridyl)-5-(1-tetrahydropyran-4-ylpyrazol-3-yl)benzoyl]amino]-2,3-dihydro-1,4-benzodioxine-7-carboxylic acid |
| 162 | 6-[[3-(2-fluoro-6-methyl-3-pyridyl)-5-(1-tetrahydropyran-4-ylpyrazol-4-yl)benzoyl]amino]-2,3-dihydro-1,4-benzodioxine-7-carboxylic acid |
| 163 | 6-[[3-(6-methylpyrazin-2-yl)-5-(1-tetrahydropyran-4-ylpyrazol-4-yl)benzoyl]amino]-2,3-dihydro-1,4-benzodioxine-7-carboxylic acid |
| 164 | 6-[[3-(6-methyl-3-pyridyl)-5-(1-tetrahydropyran-4-ylpyrazol-4-yl)benzoyl]amino]-2,3-dihydro-1,4-benzodioxine-7-carboxylic acid |
| 165 | 6-[[3-pyrimidin-5-yl-5-(1-tetrahydropyran-4-ylpyrazol-4-yl)benzoyl]amino]-2,3-dihydro-1,4-benzodioxine-7-carboxylic acid |
| 166 | 6-[[3-(2,4-dioxo-1H-pyrimidin-5-yl)-5-(1-tetrahydropyran-4-ylpyrazol-3-yl)benzoyl]amino]-2,3-dihydro-1,4-benzodioxine-7-carboxylic acid |
| 167 | 6-[[3-(4-fluorophenyl)-5-(1-tetrahydropyran-4-ylpyrazol-4-yl)benzoyl]amino]-2,3-dihydro-1,4-benzodioxine-7-carboxylic acid |
| 168 | 6-[[3-(3,4-difluorophenyl)-5-(1-tetrahydropyran-4-ylpyrazol-4-yl)benzoyl]amino]-2,3-dihydro-1,4-benzodioxine-7-carboxylic acid |
| 169 | 6-[[3-(1,5-dihydroimidazo[1,2-a]pyridin-6-yl)-5-(1-tetrahydropyran-4-ylpyrazol-4-yl)benzoyl]amino]-2,3-dihydro-1,4-benzodioxine-7-carboxylic acid |
| 170 | 6-[[3-(1H-pyrrolo[2,3-b]pyridin-5-yl)-5-(1-tetrahydropyran-4-ylpyrazol-4-yl)benzoyl]amino]-2,3-dihydro-1,4-benzodioxine-7-carboxylic acid |
| 171 | 6-[[3,5-bis(1-tetrahydropyran-4-ylpyrazol-4-yl)benzoyl]amino]-2,3-dihydro-1,4-benzodioxine-7-carboxylic acid |
| 172 | 6-[[3-[1-(2-carboxyethyl)pyrazol-4-yl]-5-(1-tetrahydropyran-4-ylpyrazol-3-yl)benzoyl]amino]-2,3-dihydro-1,4-benzodioxine-7-carboxylic acid |
| 173 | 6-[3-(1H-pyrazol-4-yl)-5-(1-tetrahydropyran-4-ylpyrazol-4-yl)benzoyl]amino]-2,3-dihydro-1,4-benzodioxine-7-carboxylic acid |
| 174 | 4,5-dichloro-2-[3-phenyl-5-(1-tetrahydropyran-4-ylpyrazol-4-yl)benzoyl]amino]benzoic acid |
| 175 | 4,5-dichloro-2-(3-(pyridin-2-yl)-5-(1-(tetrahydro-2H-pyran-4-yl)-1H-pyrazol-4-yl)benzamido)benzoic acid |
| 176 | 4,5-dichloro-2-[[3-(3-pyridyl)-5-(1-tetrahydropyran-4-ylpyrazol-4-yl)benzoyl]amino]benzoic acid |
| 177 | 4,5-dichloro-2-[[3-pyrazin-2-yl-5-(1-tetrahydropyran-4-ylpyrazol-4-yl)benzoyl]amino]benzoic acid |
| 178 | 4,5-dichloro-2-[[3-pyridazin-3-yl-5-(1-tetrahydropyran-4-ylpyrazol-4-yl)benzoyl]amino]benzoic acid |
| 179 | 4,5-dichloro-2-[[3-(6-methyl-2-pyridyl)-5-(1-tetrahydropyran-4-ylpyrazol-4-yl)benzoyl]amino]benzoic acid |
| 180 | 4,5-dichloro-2-[[3-(2-fluoro-6-methyl-3-pyridyl)-5-(1-tetrahydropyran-4-ylpyrazol-4-yl)benzoyl]amino]benzoic acid |
| 181 | 4,5-dichloro-2-[[3-(6-methylpyrazin-2-yl)-5-(1-tetrahydropyran-4-ylpyrazol-4-yl)benzoyl]amino]benzoic acid |
| 182 | 4,5-dichloro-2-[[3-(6-methyl-3-pyridyl)-5-(1-tetrahydropyran-4-ylpyrazol-4-yl)benzoyl]amino]benzoic acid |
| 183 | 4,5-dichloro-2-[[3-pyrimidin-5-yl-5-(1-tetrahydropyran-4-ylpyrazol-4-yl)benzoyl]amino]benzoic acid |
| 184 | 4,5-dichloro-2-[[3-[1-(methylcarbamoylcarbamoyl)vinyl]-5-(1-tetrahydropyran-4-ylpyrazol-3-yl)benzoyl]amino]benzoic acid |
| 185 | 4,5-dichloro-2-[[3-(4-fluorophenyl)-5-(1-tetrahydropyran-4-ylpyrazol-4-yl)benzoyl]amino]benzoic acid |
| 186 | 4,5-dichloro-2-[[3-(3,4-difluorophenyl)-5-(1-tetrahydropyran-4-ylpyrazol-4-yl)benzoyl]amino]benzoic acid |
| 187 | 4,5-dichloro-2-[[3-(1,5-dihydroimidazo[1,2-a]pyridin-6-yl)-5-(1-tetrahydropyran-4-ylpyrazol-4-yl)benzoyl]amino]benzoic acid |
| 188 | 4,5-dichloro-2-[3-(1H-pyrrolo[2,3-b]pyridin-5-yl)-5-(1-tetrahydropyran-4-ylpyrazol-4-yl)benzoyl]amino]benzoic acid |
| 189 | 2-(3,5-bis(1-(tetrahydro-2H-pyran-4-yl)-1H-pyrazol-4-yl)benzamido)-4,5-dichlorobenzoic acid |
| 190 | 2-[[3-[1-(2-carboxyethyl)pyrazol-4-yl]-5-(1-tetrahydropyran-4-ylpyrazol-4-yl)benzoyl]amino]-4,5-dichloro-benzoic acid |
| 191 | 4,5-dichloro-2-[[3-(1H-pyrazol-4-yl)-5-(1-tetrahydropyran-4-ylpyrazol-4-yl)benzoyl]amino]benzoic acid |
| 192 | [4-ethynyl-2-[[3-(1-tetrahydropyran-4-ylpyrazol-3-yl)benzoyl]amino]benzoyl]oxysodium |
| 193 | [4-chloro-2-[[3-ethynyl-5-(1-tetrahydropyran-4-ylpyrazol-4-yl)benzoyl]amino]benzoyl]oxysodium |
| 194 | [6-[[3-ethynyl-5-(1-tetrahydropyran-4-ylpyrazol-4-yl)benzoyl]amino]-2,3-dihydro-1,4-benzodioxine-7-carbonyl]oxysodium |
| 195 | [4-chloro-2-[[3-(1-prop-2-ynylpyrazol-4-yl)benzoyl]amino]benzoyl]oxysodium |
| 196 | [6-[[3-(1-prop-2-ynylpyrazol-4-yl)benzoyl]amino]-2,3-dihydro-1,4-benzodioxine-7-carbonyl]oxysodium |
| 197 | N-[6-methoxy-3-(1H-tetrazol-5-yl)-2-pyridyl]-3-(1H-pyrazol-4-yl)benzamide |
| 198 | N-[5-chloro-2-(5-oxo-4H-1,2,4-oxadiazol-3-yl)phenyl]-3-(1-tetrahydropyran-4-ylpyrazol-4-yl)benzamide |
| 199 | N-[5-chloro-2-(1H-tetrazol-5-yl)phenyl]-3-(1-tetrahydropyran-4-ylpyrazol-4-yl)benzamide |

TABLE 1-continued

| Compounds of the Disclosure | |
|---|---|
| Example # | Chemical Name |
| 200 | N-[7-(5-oxo-4H-1,2,4-oxadiazol-3-yl)-2,3-dihydro-1,4-benzodioxin-6-yl]-3-(1-tetrahydropyran-4-ylpyrazol-4-yl)benzamide |
| 201 | 3-(1-tetrahydropyran-4-ylpyrazol-4-yl)-N-[7-(1H-tetrazol-5-yl)-2,3-dihydro-1,4-benzodioxin-6-yl]benzamide |
| 202 | 5-[2-[4-[3-(1H-pyrazol-4-yl)phenyl]triazol-1-yl]phenyl]-1H-tetrazole |
| 203 | 3-[6-[4-[3-(1H-pyrazol-4-yl)phenyl]triazol-1-yl]-2,3-dihydro-1,4-benzodioxin-7-yl]-4H-1,2,4-oxadiazol-5-one |
| 204 | 4-chloro-2-[[3-(1-tetrahydropyran-4-ylpyrazol-4-yl)phenyl]methoxy]benzoic acid |
| 205 | 4,5-dichloro-2-[3-(1-tetrahydropyran-4-ylpyrazol-4-yl)phenyl]methoxy]benzoic acid |
| 206 | 7-[3-(1-tetrahydropyran-4-ylpyrazol-4-yl)phenyl]methoxy]-2,3-dihydro-1,4-benzodioxine-5-carboxylic acid |
| 207 | 4-methoxy-2-[[3-(1-tetrahydropyran-4-ylpyrazol-4-yl)phenyl]methoxy]benzoic acid |
| 208 | 4-chloro-2-[1-[3-(1-tetrahydropyran-4-ylpyrazol-4-yl)phenyl]ethoxy]benzoic acid |
| 209 | 4-chloro-2-[[4-(1-tetrahydropyran-4-ylpyrazol-4-yl)-2-pyridyl]methoxy]benzoic acid |
| 210 | 4-chloro-2-[[3-(1H-pyrazol-4-yl)phenyl]methoxy]benzoic acid |
| 211 | 4,5-dichloro-2-[[3-(1H-pyrazol-4-yl)phenyl]methoxy]benzoic acid |
| 212 | 4,5-dichloro-2-[[4-(1-tetrahydropyran-4-ylpyrazol-4-yl)-2-pyridyl]methoxy]benzoic acid |
| 213 | 6-[[4-(1-tetrahydropyran-4-ylpyrazol-4-yl)-2-pyridyl]methoxy]-2,3-dihydro-1,4-benzodioxine-7-carboxylic acid |
| 214 | 2-[[4-(1H-pyrazol-4-yl)-2-pyridyl]methoxy]benzoic acid |
| 215 | 4-isopropyl-2-[[4-(1-tetrahydropyran-4-ylpyrazol-4-yl)-2-pyridyl]methoxy]benzoic acid |
| 216 | methyl 2-[4-chloro-2-[[4-(1-tetrahydropyran-4-ylpyrazol-4-yl)-2-pyridyl]methoxy]phenyl]acetate |
| 217 | 2-[4-chloro-2-[[4-(1-tetrahydropyran-4-ylpyrazol-4-yl)-2-pyridyl]methoxy]phenyl]acetic acid |
| 218 | methyl 2-[4-chloro-2-[[3-(1-tetrahydropyran-4-ylpyrazol-4-yl)phenyl]methoxy]phenyl]acetate |
| 219 | 2-[4-chloro-2-[[3-(1-tetrahydropyran-4-ylpyrazol-4-yl)phenyl]methoxy]phenyl]acetic acid |
| 220 | 2-[[3-(1-isopropylpyrazol-4-yl)phenyl]methoxy]-6-methoxy-pyridine-3-carboxylic acid |
| 221 | 3-[4-chloro-2-[[3-(1-tetrahydropyran-4-ylpyrazol-4-yl)phenyl]methoxy]phenyl]-4H-1,2,4-oxadiazol-5-one |
| 222 | 3-[4,5-dichloro-2-[[3-(1-tetrahydropyran-4-ylpyrazol-4-yl)phenyl]methoxy]phenyl]-4H-1,2,4-oxadiazol-5-one |
| 223 | 3-[4-chloro-2-[[4-(1-tetrahydropyran-4-ylpyrazol-4-yl)-2-pyridyl]methoxy]phenyl]-4H-1,2,4-oxadiazol-5-one |
| 224 | 3-[6-[[4-(1-tetrahydropyran-4-ylpyrazol-4-yl)-2-pyridyl]methoxy]-2,3-dihydro-1,4-benzodioxin-7-yl]-4H-1,2,4-oxadiazol-5-one |
| 225 | 2-[[3,5-bis(1-tetrahydropyran-4-ylpyrazol-4-yl)phenyl]methoxy]-4,5-dichloro-benzoic acid |
| 226 | 2-((3,5-bis(1-(tetrahydro-2H-pyran-4-yl)-1H-pyrazol-4-yl)benzyl)oxy)-6-methoxynicotinic acid |
| 227 | 7-((3,5-bis(1-(tetrahydro-2H-pyran-4-yl)-1H-pyrazol-4-yl)benzyl)oxy)-2,3-dihydrobenzo[b][1,4]dioxine-6-carboxylic acid |
| 228 | 2-[3,5-bis(1H-pyrazol-4-yl)phenyl]methoxy]benzoic acid |
| 229 | 6-methoxy-2-(3-(quinolin-8-yl)benzamido)nicotinic acid |
| 230 | 4-chloro-2-[(3-isoxazol-4-ylphenyl)methoxy]benzoic acid |
| 231 | 6-[(3-isoxazol-4-ylphenyl)methoxy]-2,3-dihydro-1,4-benzodioxine-7-carboxylic acid |
| 232 | sodium 2-(4-(1H-pyrazol-4-yl)picolinamido)-4,5-dichlorobenzoate |
| 233 | sodium 4,5-dichloro-2-(4-(1-(tetrahydro-2H-pyran-4-yl)-1H-pyrazol-4-yl)picolinamido)benzoate |
| 234 | sodium 4,5-dichloro-2-(4-(isoxazol-4-yl)picolinamido)benzoate |
| 235 | 4,5-dichloro-2-(3-(isoxazol-4-yl)benzamido)benzoic acid |
| 236 | sodium 4-chloro-2-(3-(isoxazol-4-yl)benzamido)benzoate |
| 237 | sodium 7-(4-(1-(tetrahydro-2H-pyran-4-yl)-1H-pyrazol-4-yl)picolinamido)-2,3-dihydrobenzo[b][1,4]dioxine-6-carboxylate |
| 238 | sodium 7-(4-(1H-pyrazol-4-yl)picolinamido)-2,3-dihydrobenzo[b][1,4]dioxine-6-carboxylate |
| 239 | sodium 7-(4-(isoxazol-4-yl)picolinamido)-2,3-dihydrobenzo[b][1,4]dioxine-6-carboxylate |
| 240 | sodium 6-(4-(1H-pyrazol-4-yl)picolinamido)benzo[d][1,3]dioxole-5-carboxylate |
| 241 | sodium 7-(3-(isoxazol-4-yl)benzamido)-2,3-dihydrobenzo[b][1,4]dioxine-6-carboxylate |
| 242 | sodium 2-([1,1'-biphenyl]-3-carboxamido)-6-methoxynicotinate |
| 243 | sodium 2-(4'-fluoro-[1,1'-biphenyl]-3-carboxamido)-6-methoxynicotinate |
| 244 | sodium 2-(3'-fluoro-[1,1'-biphenyl]-3-carboxamido)-6-methoxynicotinate |
| 245 | sodium 2-(2'-fluoro-[1,1'-biphenyl]-3-carboxamido)-6-methoxynicotinate |
| 246 | sodium 2-(3',4'-difluoro-[1,1'-biphenyl]-3-carboxamido)-6-methoxynicotinate |
| 247 | sodium 6-methoxy-2-(4'-(trifluoromethyl)-[1,1'-biphenyl]-3-carboxamido)nicotinate |
| 248 | sodium 2-(4'-chloro-[1,1'-biphenyl]-3-carboxamido)-6-methoxynicotinate |
| 249 | sodium 7-(3',4'-difluoro-[1,1'-biphenyl]-3-carboxamido)-2,3-dihydrobenzo[b][1,4]dioxine-6-carboxylate |
| 250 | sodium 7-(4'-(trifluoromethyl)-[1,1'-biphenyl]-3-carboxamido)-2,3-dihydrobenzo[b][1,4]dioxine-6-carboxylate |
| 251 | sodium 7-(4'-chloro-[1,1'-biphenyl]-3-carboxamido)-2,3-dihydrobenzo[b][1,4]dioxine-6-carboxylate |
| 252 | sodium 7-(4'-fluoro-[1,1'-biphenyl]-3-carboxamido)-2,3-dihydrobenzo[b][1,4]dioxine-6-carboxylate |

TABLE 1-continued

Compounds of the Disclosure

| Example # | Chemical Name |
|---|---|
| 253 | sodium 7-(3'-fluoro-[1,1'-biphenyl]-3-carboxamido)-2,3-dihydrobenzo[b][1,4]dioxine-6-carboxylate |
| 254 | sodium 7-([1,1'-biphenyl]-3-carboxamido)-2,3-dihydrobenzo[b][1,4]dioxine-6-carboxylate |
| 255 | sodium 2-(3-(isoxazol-4-yl)benzamido)benzoate |
| 256 | sodium 4-chloro-2-((3-(1-(tetrahydro-2H-pyran-4-yl)-1H-pyrazol-4-yl)benzyl)oxy)benzoate |
| 257 | sodium 7-(2'-fluoro-[1,1'-biphenyl]-3-carboxamido)-2,3-dihydrobenzo[b][1,4]dioxine-6-carboxylate |
| 258 | sodium 3-(3-(1-(tetrahydro-2H-pyran-4-yl)-1H-pyrazol-4-yl)benzamido)benzoate |
| 259 | sodium 3-chloro-5-(3-(1-(tetrahydro-2H-pyran-4-yl)-1H-pyrazol-4-yl)benzamido)benzoate |
| 260 | sodium 2-(4-(3-(1H-pyrazol-4-yl)phenyl)-1H-1,2,3-triazol-1-yl)benzoate |
| 261 | sodium 2,3-dichloro-5-(3-(1-(tetrahydro-2H-pyran-4-yl)-1H-pyrazol-4-yl)benzamido)benzoate |
| 262 | sodium 2-(1-(3-(1H-pyrazol-4-yl)phenyl)-1H-1,2,3-triazol-4-yl)benzoate |
| 263 | sodium 2-(4-(3-(1H-pyrazol-4-yl)phenyl)-1H-1,2,3-triazol-1-yl)-4,5-dichlorobenzoate |
| 264 | sodium 7-(4-(3-(1H-pyrazol-4-yl)phenyl)-1H-1,2,3-triazol-1-yl)-2,3-dihydrobenzo[b][1,4]dioxine-6-carboxylate |
| 265 | sodium 2-(4-(3-(1H-pyrazol-4-yl)phenyl)-1H-1,2,3-triazol-1-yl)-5-chlorobenzoate |
| 272 | 2-[[3-(1H-pyrazol-4-yl)benzoyl]amino]pyridine-3-carboxylic acid |
| 275 | 6-[[3-(1H-pyrazol-4-yl)phenyl]methoxy]-2,3-dihydro-1,4-benzodioxine-7-carboxylic acid |
| 276 | 3-[2-[4-[3-(1H-pyrazol-4-yl)phenyl]triazol-1-yl]phenyl]-4H-1,2,4-oxadiazol-5-one |
| 277 | 2-[(3-isoxazol-4-ylphenyl)methoxy]benzoic acid |
| 278 | 6-methoxy-2-[[3-(1-tetrahydropyran-4-ylpyrazol-4-yl)phenyl]methoxy]pyridine-3-carboxylic acid |
| 279 | 3-[4,5-dichloro-2-[[4-(1-tetrahydropyran-4-ylpyrazol-4-yl)-2-pyridyl]methoxy]phenyl]-4H-1,2,4-oxadiazol-5-one |
| 280 | 4,5-dichloro-2-[[3-(3-pyridyl)-5-(1-tetrahydropyran-4-ylpyrazol-4-yl)phenyl]methoxy]benzoic acid |
| 281 | 5-[4,5-dichloro-2-[4-[3-(1H-pyrazol-4-yl)phenyl]triazol-1-yl]phenyl]-2H-tetrazole |
| 282 | 4,5-dichloro-2-[3-(6-methyl-3-pyridyl)-5-(1-tetrahydropyran-4-ylpyrazol-4-yl)phenyl]methoxy]benzoic acid |
| 283 | 3-[4,5-dichloro-2-[4-[3-(1H-pyrazol-4-yl)phenyl]triazol-1-yl]phenyl]-4H-1,2,4-oxadiazol-5-one |

Certain compounds described herein may have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers, in mixtures and as pure or partially purified compounds, are included within the scope of this disclosure.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art. Alternatively, any enantiomer of a compound may be obtained by stereoselective synthesis using optically pure starting materials or reagents of known configuration by methods well known in the art.

Compounds may also possess tautomeric forms, and all tautomers also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}p$, $^{35}S$, $^{18}F$, and $^{36}Cl$, respectively. Substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Compounds disclosed herein can exist in solvated as well as unsolvated forms with pharmaceutically acceptable solvents such as water, ethanol, and the like, and it is intended that the disclosure encompass both solvated and unsolvated forms. In one embodiment, the compound is amorphous. In one embodiment, the compound is a single polymorph. In another embodiment, the compound is a mixture of polymorphs. In another embodiment, the compound is in a crystalline form.

a. Methods of Synthesis

Compounds disclosed herein can be prepared by a variety of methods, including those illustrated in the Examples.

Compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Reactions can be worked up in a conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Standard experimentation, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006).

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization, or enzymatic resolution).

Similarly, when a pure geometric isomer of a compound is required, it can be obtained by carrying out one of the procedures described herein using a pure geometric isomer as a starting material, or by resolution of a mixture of the geometric isomers of the compound or intermediates using a standard procedure such as chromatographic separation.

The synthetic schemes and specific examples as described are illustrative and are not to be read as limiting the scope of the disclosure or the claims. Alternatives, modifications, and equivalents of the synthetic methods and specific examples are contemplated.

b. Pharmaceutically Acceptable Salts

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compound with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. Amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine.

Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Pharmaceutical Compositions

The disclosed compounds may be incorporated into pharmaceutical compositions suitable for administration to a subject (such as a patient, which may be a human or non-human). The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the disclosure are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease or condition, the prophylactically effective amount will be less than the therapeutically effective amount.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their pharmaceutically acceptable salts may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90% by weight of the composition.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10% by weight of the composition.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50% by weight of the composition.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10% by weight of the composition.

Suitable colorants include a colorant such as an FD&C dye. When used, the amount of colorant in a systemic or topical composition is typically about 0.005 to about 0.1% by weight of the composition.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s), when used, in a systemic or topical composition is typically about 0.001 to about 1% by weight of the composition.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5% by weight of the composition.

Suitable preservatives include benzalkonium chloride, methyl paraben, and sodium benzoate. The amount of preservative(s) in a systemic or topical composition is typically about 0.01 to about 5% by weight of the composition.

Suitable glidants include silicon dioxide. The amount of glidant(s) in a systemic or topical composition is typically about 1 to about 5% by weight of the composition.

Suitable solvents include water, isotonic saline, ethyl oleate, glycerin, hydroxylated castor oils, alcohols such as ethanol, and phosphate buffer solutions. The amount of solvent(s) in a systemic or topical composition is typically from about 0 to about 100% by weight of the composition.

Suitable suspending agents include AVICEL RC-591 (from FMC Corporation of Philadelphia, PA) and sodium alginate. The amount of suspending agent(s) in a systemic or topical composition is typically about 1 to about 8% by weight of the composition.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5% by weight of the composition.

Although the amounts of components in the systemic compositions may vary depending on the type of systemic composition prepared, in general, systemic compositions include 0.01% to 50% by weight of an active compound and 50% to 99.99% by weight of one or more carriers. Compositions for parenteral administration typically include 0.1% to 10% by weight of actives and 90% to 99.9% by weight of a carrier including a diluent and a solvent.

Compositions for oral administration can have various dosage forms. For example, solid forms include tablets, capsules, granules, and bulk powders. These oral dosage forms include a safe and effective amount, usually at least about 5% by weight, and more particularly from about 25% to about 50% by weight of actives. The oral dosage compositions include about 50% to about 95% by weight of carriers, and more particularly, from about 50% to about 75% by weight.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I), including compounds of formula (Ia)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this disclosure.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I), such as a compound of formula (Ia)), or a pharmaceutically acceptable salt thereof), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this disclosure are described in the following references: Modem Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95% by weight of the composition.

Suitable propellants include propane, butane, isobutane, dimethyl ether, carbon dioxide, nitrous oxide, and combinations thereof. The amount of propellant(s) in a topical composition is typically about 0% to about 95% by weight of the composition.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95% by weight of the composition.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95% by weight of the composition.

The amount of thickener(s) in a topical composition is typically about 0% to about 95% by weight of the composition.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95% by weight of the composition.

The amount of fragrance in a topical composition is typically about 0% to about 0.5%, particularly, about 0.001% to about 0.1% by weight of the composition.

Suitable pH adjusting additives include HCl or NaOH in amounts sufficient to adjust the pH of a topical pharmaceutical composition.

Methods of Use

As disclosed herein, compounds of formula (I), including compounds of formula (Ia) and specific example compounds described herein, inhibit the activity of PAI-1. As such, the compounds can be used in methods of inhibiting PAI-1 in a sample. As also disclosed herein, compounds of formula (I), including compounds of formula (Ia) and specific example compounds described herein, have activity in mouse models of IBD.

Accordingly, in some embodiments, disclosed herein is a method of inhibiting PAI-1 in a sample, comprising contacting the sample with a compound of formula (I) (including compounds of formula (Ia) and specific example compounds disclosed herein), or a pharmaceutically acceptable salt thereof. In some embodiments, disclosed herein is a method of treating an inflammatory bowel disease in a subject in need thereof, comprising administering to the subject a therapeutically effective amount of a compound of formula (I) (including compounds of formula (Ia) and specific example compounds disclosed herein), or a pharmaceutically acceptable salt thereof. In some embodiments, the inflammatory bowel disease is Crohn's disease. In some embodiments, the inflammatory bowel disease is ulcerative colitis.

In the methods of treatment described herein, a compound or pharmaceutical composition may be administered to the subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; or by implant of a depot, for example, subcutaneously or intramuscularly. In some embodiments, the administration comprises oral administration. Additional modes of administration may include adding the compound and/or a composition comprising the compound to a food or beverage, including a water supply for an animal, to supply the compound as part of the animal's diet.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present disclosure. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100 g to about 250 mg per kilogram body weight of the subject per day.

The compound or composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

When used in methods of treatment disclosed herein, a compound or composition described herein may be used in combination with other known therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

EXAMPLES

All solvents and chemical reagents were obtained from commercial sources and were used without further purification or drying. NMR spectra were recorded on either a Bruker AV400 spectrometer or a Bruker AV500 spectrometer. Chemical shifts are quoted in ppm using residual undeuterated solvent as the internal reference. LC/MS spectra were recorded on a Waters Aquity UPLC using either method A; Waters UPLC® BEHTM C18 2.1×100 mm 1.7 m column at 40° C. eluting with 0.1% formic acid in acetonitrile and 0.1% formic acid in water using a gradient of 5-100% over 1.35 mins at a rate of 0.9 mL/min, or method B; Phenomenex Kinetix-XB C18 2.1×100 mm, 1.7 m column at 40° C. eluting with 0.1% formic acid in acetonitrile and 0.1% formic acid in water using a gradient of 5-100% over 5.8 mins at a rate of 0.6 mL/min. LC/MS purity was assigned using AUC monitoring at 215 nm.

Synthesis of 4-chloro-2-(3-(1-(tetrahydro-2H-pyran-4-yl)-1H-pyrazol-4yl)benzamido)benzoic acid (Example 1) and its sodium salt (Example 1-Na salt)

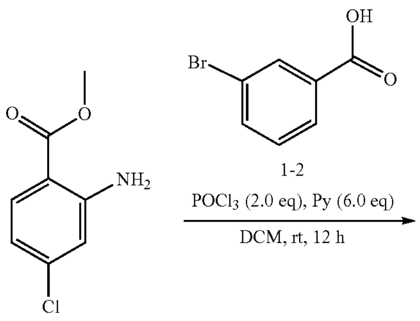

1-1

-continued

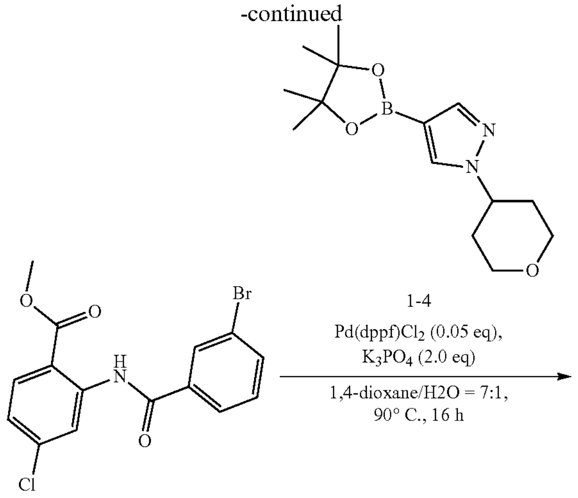

1-3

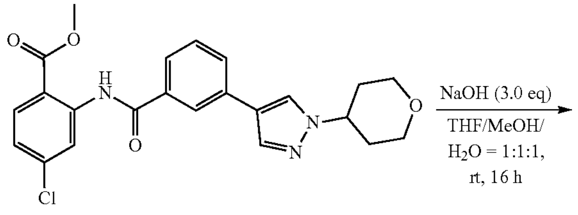

1-5

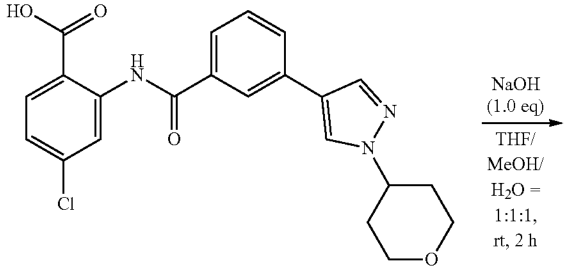

Example 1

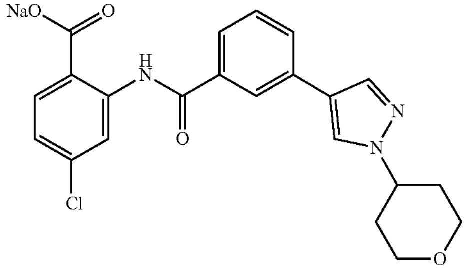

Example 1-Na salt

Preparation of methyl 2-(3-bromobenzamido)-4-chlorobenzoate (compound 1-3). To a solution of 1-1 (20 g, 108 mmol, 1.0 eq) in DCM (200 mL), was added 1-2 (21.6 g, 108 mmol, 1.0 eq), Py (51.2 g, 648 mmol, 6.0 eq), $POCl_3$ (33 g, 216 mmol, 2.0 eq) at 0° C. The mixture was stirred at room temperature for 16 hours. LC/MS showed finished. The mixture was poured into water, extracted with DCM (3×200 mL), the organic phase was dried over $Na_2SO_4$ and concentrated under vacuum. The crude compound was purified by column 0% 9% EA in PE to give a crude (22.5 g, Purity: 69%). The crude was triturated with hexane to afford methyl 2-(3-bromobenzamido)-4-chlorobenzoate (1-3, 14.2 g, Purity: 93%, Yield: 36%) as a yellow solid. (The procedure was repeated several times to obtain 144 g, in total, of 1-3). LC/MS (ESI) m/z: 368 $(M+H)^+$ Preparation of methyl 4-chloro-2-(3-(1-(tetrahydro-2H-pyran-4-yl)-1H-pyrazol-4-yl)benzamido)benzoate (1-5) To a solution of methyl 2-(3-bromobenzamido)-4-chlorobenzoate (1-3, 19.5 g, 53 mmol, 1.0 eq) in dioxane/$H_2O$=7:1 (70 mL:10 mL), was added 1-(tetrahydro-2H-pyran-4-yl)-4-(4,4,5,5-tetramethyl-1,3,2-dioxaborolan-2-yl)-1H-pyrazole (1-4, 14.7 g, 53 mmol, 1.0 eq), Pd(dppf)$Cl_2$ (2.0 g, 2.7 mmol, 0.05 eq), $K_3PO_4$ (22.5 g, 106 mmol, 2.0 eq). The mixture was stirred at 90° C. for 16 hours. LC/MS showed finished. The mixture was concentrated and purified by column 0%-50% EA in PE to give the methyl 4-chloro-2-(3-(1-(tetrahydro-2H-pyran-4-yl)-1H-pyrazol-4-yl)benzamido) benzoate (1-5, 14.7 g, 33.5 mmol, yield 63%) as a yellow solid. (The procedure was repeated several times to obtain 94.8 g, in total, of 1-5). LC/MS (ESI) m/z:440.1 $(M+H)^+$ Preparation of 4-chloro-2-(3-(1-(tetrahydro-2H-pyran-4-yl)-1H-pyrazol-4-yl)benzamido)benzoic acid (Example 1) To a solution of methyl compound 1-5 (25 g, 26.9 mmol, 1.0 eq) in THF:MeOH:$H_2$ O=1:1:1 (600 mL) was added NaOH (6.8 g, 170.8 mmol, 3.0 eq). The reaction mixture was stirred at room temperature for 16 hours. TLC showed finished. The reaction solution was adjusted with 1M hydrochloric acid to pH 3-4, a large amount of precipitate formed. After filtration and drying in vacuum, white solid Example 1 (21.1 g, yield 87%) was obtained. (The procedure was repeated several times to obtain 86 g, in total, of Example 1. LC/MS (ESI) m/z:426 $(M+H)^+$. $^1$H NMR (400 MHz, DMSO-$d_6$) δ 14.11 (s, 1H), 12.29 (s, 1H), 8.83 (d, J=2.1 Hz, 1H), 8.38 (s, 1H), 8.15 (s, 1H), 8.07 (d, J=8.6 Hz, 1H), 7.99 (s, 1H), 7.87 (d, J=7.8 Hz, 1H), 7.75 (d, J=7.8 Hz, 1H), 7.58 (t, J=7.7 Hz, 1H), 7.31-7.25 (m, 1H), 4.50-4.35 (m, 1H), 3.99 (d, J=11.2 Hz, 2H), 3.55-3.44 (m, 2H), 2.11-1.94 (m, 4H).

Preparation of sodium 4-chloro-2-(3-(1-(tetrahydro-2H-pyran-4-yl)-1H-pyrazol-4-yl)benzamido)benzoate (Example 1-Na salt). To a solution of methyl Example 1 (20 g, 46.9 mmol, 1.0 eq) in THF:MeOH:$H_2$ O=1:1:1 (600 mL) was added NaOH (2.0 g, 49.2 mmol, 1.05 eq). The reaction mixture was stirred at room temperature for 12 hours. TLC showed finished. The reaction solution was concentrated in vacuum and lyophilized in vacuum to afford a crude. The crude was triturated with $H_2O$ and dried in vacuum to afford Example 1-Na salt (20.5 g, yield: 97%) as a white solid. (The procedure was repeated several times to obtain 51-5 g, in total, of Example 1-Na salt). LC/MS (ESI) m/z:426 $(M-23+H)^+$. $^1$H NMR (400 MHz, DMSO-$d_6$) δ 15.72 (s, 1H), 8.79 (d, J=1.6 Hz, 1H), 8.35 (s, 1H), 8.23 (s, 1H), 8.07 (d, J=8.4 Hz, 1H), 7.98 (s, 1H), 7.90-7.76 (m, 2H), 7.53 (t, J=7.6 Hz, 1H), 7.11-7.04 (m, 1H), 4.52-4.41 (m, 1H), 3.99 (d, J=11.2 Hz, 2H), 3.56-3.46 (m, 2H), 2.08-1.97 (m, 4H).

Synthesis of Intermediates

Synthesis of substituted 2-amino benzoic acid esters

1. Synthesis of methyl 2-amino-4-isopropylbenzoate (I1-6)

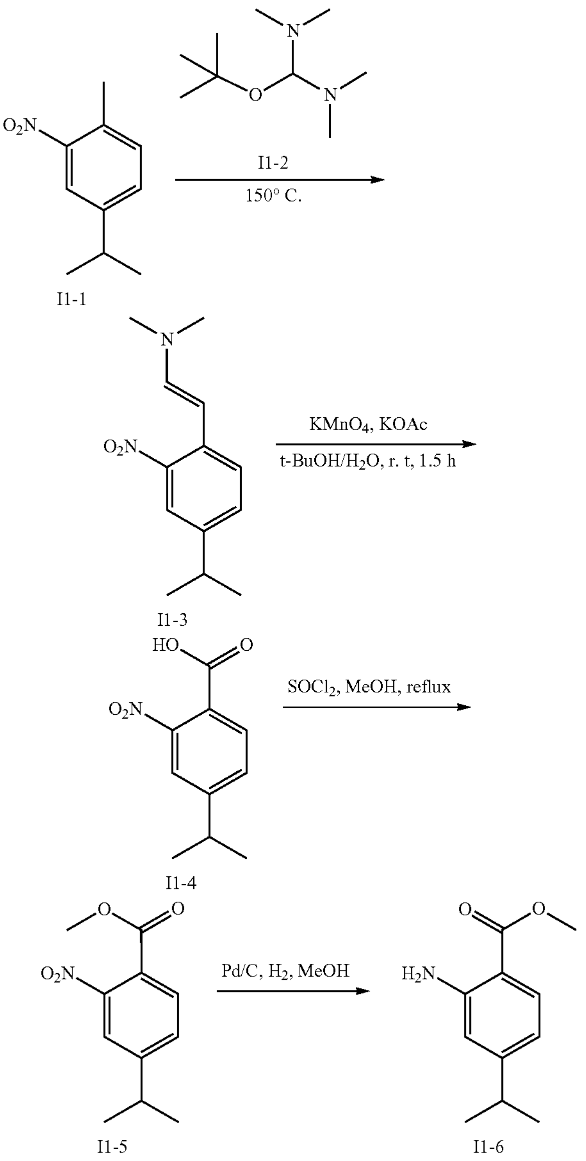

Preparation of (E)-2-(4-isopropyl-2-nitrophenyl)-N,N-dimethylethen-1-amine (I1-3). To a solution of 4-isopropyl-1-methyl-2-nitrobenzene (23-1, 2.0 g, 13.95 mmol, 1.0 eq), 1-tert-butoxy-N,N,N',N'-tetramethylmethanediamine (23-2, 7.3 g, 41.85 mmol, 3.0 eq) was stirred at 110° C. for 10 h. It was concentrated in vacuum to give 23-3 (2.5 g, crude and use for next step directly) as red liquid. $^1$H NMR (400 MHz, $CDCl_3$) δ 7.69 (d, J=1.9 Hz, 1H), 7.37 (d, J=8.4 Hz, 1H), 7.23 (dd, J=8.4, 1.8 Hz, 1H), 6.90-6.84 (m, 1H), 5.83 (d, J=13.5 Hz, 1H), 2.91-2.84 (m, 7H), 1.26-1.21 (m, 6H).

Preparation of 4-isopropyl-2-nitrobenzoic acid (I1-4). To a solution of (E)-2-(4-isopropyl-2-nitrophenyl)-N,N-dimethylethen-1-amine (I1-3, 2.5 g, 10.67 mmol, 1.0 eq), KOAc (12.84 g, 131.02 mmol, 12.28 eq) in t-BuOH/$H_2O$ (150 ml/37.5 ml) was added $KMnO_4$ (12.84 g, 81.27 mmol, 7.62 eq). It was stirred at RT for 3 h. LC/MS shows that it has been completed. It was filtered and washed Filter residue by water (3x30 ml) and MeOH(3x30 ml). It was concentrated in vacuum, partitioned between EA and water. The water phase regulated pH 1-3 then extracted by EA to obtain I1-4 (2.025 g 86% yield) as white solid. LC/MS (ESI) m/z: 208.0 $(M-H)^-$.

Preparation of methyl 4-isopropyl-2-nitrobenzoate (I1-5). To a solution of 4-isopropyl-2-nitrobenzoic acid(I1-4, 4.5 g, 21.51 mmol,1.0 eq), $SOCl_2$ (4.5 ml), DMF (two drops) was stirred at 50 under $N_2$ for 3 h. It was concentrated in vacuum. The residue was added TEA (2.4 g, 23.66 mmol 1.1 eq) and MeOH (40 ml). It was stirred at RT for 1 h and concentrated in vacuum. It was purified by silica gel column chromatography (PE/EA=10/1) to give I1-5 (4.46 g, 92% yield) as white solid. $^1H$ NMR (400 MHz, $CDCl_3$) δ 7.71 (ddd, J=15.9, 8.2, 5.3 Hz, 2H), 7.51 (dd, J=7.9, 1.5 Hz, 1H), 3.93-3.89 (m, 3H), 3.03 (hept, J=6.9 Hz, 1H), 1.28 (dd, J=11.5, 7.1 Hz, 6H).

Preparation of methyl 2-amino-4-isopropylbenzoate (I1-6). To a solution of methyl 4-isopropyl-2-nitrobenzoate (I1-5, 4.98 g, 22.3 mmol, 1.0 eq), Pd/C (1.0 g) in MeOH (40 ml) was stirred at RT under $H_2$ for 16 h. LC/MS shows that it has been completed. It was filtered and purified by silica gel column (PE/EA=20/1) to give I1-6 (4.0 g, 92% yield) as pink solid. LC/MS (ESI) m/z: 194.1 $(M+H)^+$.

2. Synthesis of methyl 2-amino-4-(tert-butyl)benzoate (12-6)

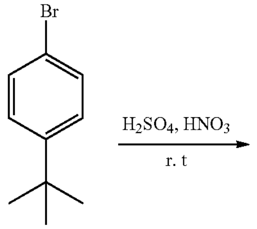

I2-1

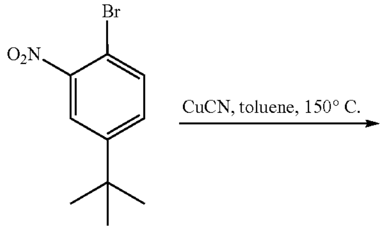

I2-2

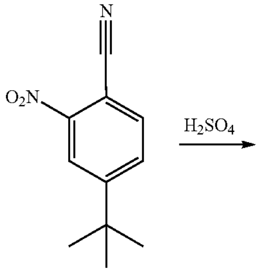

I2-3

-continued

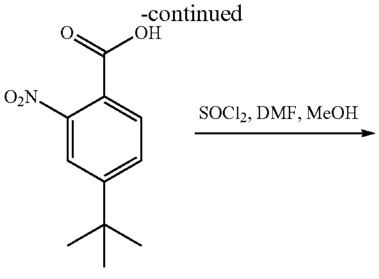

I2-4

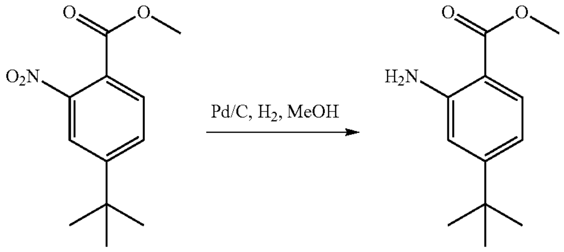

I2-5 I2-6

Preparation of 1-bromo-4-(tert-butyl)-2-nitrobenzene (12-2). To a solution of 1-bromo-4-(tert-butyl)benzene (I2-1, 5.28 ml, 31.0 mmol, 1.0 eq), $HNO_3/H_2SO_4$ (4 ml/5.4 ml) was stirred at 0° C.-RT for 16 h. TLC shows that it has been completed. It was quenched by ice and extracted with EA to obtain I2-2 (8.5 g, 85% purity, 90% yield). $^1H$ NMR (400 MHz, $CDCl_3$) δ 7.83 (t, J=3.1 Hz, 1H), 7.66-7.61 (m, 1H), 7.45 (dd, J=8.5, 2.3 Hz, 1H), 1.34 (s, 9H).

Preparation of 4-(tert-butyl)-2-nitrobenzonitrile (12-3). To a solution of 1-bromo-4-(tert-butyl)-2-nitrobenzene (I2-2, 1.0 g, 3.874 mmol, 1.0 eq), CuCN (347 mg, 3.874 mmol, 1.0 eq) in DMF (1.0 ml) was stirred at 150° C. for 1 h, then it was added toluene(5 ml) and stirred at 130° C. for 3 h. TLC shows that it has been completed. It was filtered and purified by silica gel column chromatography (PE/EA=10/1) to give I2-3 (583 mg, 74% yield). $^1H$ NMR (400 MHz, $CDCl_3$) δ 8.34 (t, J=5.0 Hz, 1H), 7.87-7.77 (m, 2H), 1.40 (s, 9H).

Preparation of 4-(tert-butyl)-2-nitrobenzoic acid (12-4). To a solution of 4-(tert-butyl)-2-nitrobenzonitrile (I2-3, 7.478 g, 36.6 mmol, 1.0 eq) in 70% $H_2SO_4$ (40 mL) was stirred at 120° C. under $N_2$ for 16 h. TLC shows that it has been completed. It was quenched by ice and extracted with EA. The organic phase extracted with saturated sodium bicarbonate aqueous solution, then adjusted $p^H$ to 1-3, extracted with EA to obtain I2-4 (6.411 g, 78% yield). LC/MS (ESI) m/z: 222.1 $(M-H)^-$.

Preparation of methyl 4-(tert-butyl)-2-nitrobenzoate (12-5). To a solution of 4-(tert-butyl)-2-nitrobenzoic acid (I2-4, 6.7 g, 30.0 mmol, 1.0 eq) in DCM (80 ML) was added DMF (two drops) and $SOCl_2$ (7.0 ml). It was stirred at 50° C. under $N_2$ for 3 h. It was concentrated in vacuum. The residue was added MeOH (100 ml) and stirred at RT for 2 h. TLC shows that it has been completed. Concentrated and purified by silica gel column chromatography (PE/EA=10/1) to give I2-5 (6.828 g, 96% yield). $^1H$ NMR (400 MHz, $CDCl_3$) δ 7.86 (d, J=1.6 Hz, 1H), 7.73-7.64 (m, 2H), 3.91 (d, J=5.0 Hz, 3H), 1.37 (d, J=4.9 Hz, 9H).

Preparation of methyl 2-amino-4-(tert-butyl)benzoate (12-6). To a solution of methyl 4-(tert-butyl)-2-nitrobenzoate (I2-5, 6.828 g, 28.78 mmol, 1.0 eq) in MeOH (100 ml) was added Pd/C (1.4 g). It was stirred at RT under $H_2$ for 16 h. LC/MS shows that it has been completed. It was filtered and purified by silica gel column chromatography (PE/EA=10/1) to give I2-6 (5.961 g, 98% yield). LC/MS (ESI) m/z: 208.1 $(M+H)^+$.

3. Synthesis of methyl 2-amino-4-(trifluoromethoxy)benzoate (13-5)

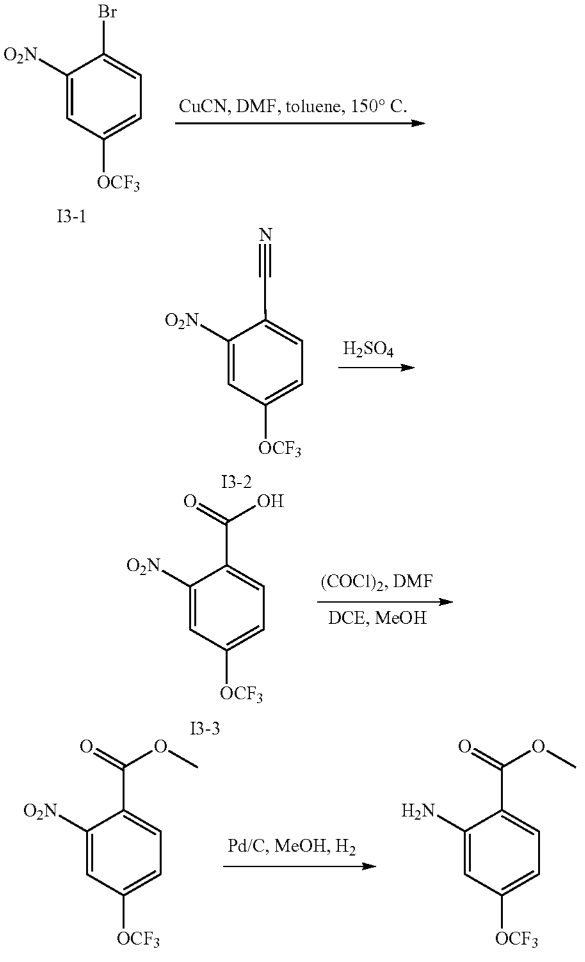

I3-1
I3-2
I3-3
I3-4
I3-5

Preparation of 2-nitro-4-(trifluoromethoxy)benzonitrile (I3-2). To a solution of 1-bromo-2-nitro-4-(trifluoromethoxy)benzene (I3-1, 5.0 g, 17.5 mmol, 1.0 eq), CuCN (1.57 g, 17.5 mmol, 1.0 eq) in DMF (5.0 mL) was stirred at 150° C. for 1 h, then it was added toluene(25 ml) and stirred at 130° C. for 3 h. TLC shows that it has been completed. It was filtered and purified by silica gel column chromatography (PE/EA=10/1) to give I3-2 (2.965 mg, 73% yield). $^1H$ NMR (400 MHz, $CDCl_3$) δ 8.18 (d, J=1.6 Hz, 1H), 8.00 (d, J=8.6 Hz, 1H), 7.67 (dd, J=8.6, 1.2 Hz, 1H).

Preparation of 2-nitro-4-(trifluoromethoxy)benzoic acid (I3-3). To a solution of 2-nitro-4-(trifluoromethoxy)benzonitrile (I3-2, 7.83 g, 33.7 mmol, 1.0 eq) in 70% $H_2SO_4$ (40 ml) was stirred at 120° C. under $N_2$ for 16 h. TLC shows that it has been completed. It was quenched by ice and extracted with EA. The organic phase extracted with saturated sodium bicarbonate aqueous solution, then adjusted $p^H$ to 1-3, extracted with EA to obtain I3-3 (5.487 g, 65% yield). LC/MS (ESI) m/z: 250.0 $(M-H)^-$.

Preparation of methyl 2-nitro-4-(trifluoromethoxy)benzoate (I3-4). To a solution of 2-nitro-4-(trifluoromethoxy) benzoic acid (I3-3, 8.1 g, 32.3 mmol, 1.0 eq) in DCE (50 mL) was added DMF (two drops) and $(COCl)_2$ (3.5 ml). It was stirred at 90° C. under $N_2$ for 2 h. It was concentrated in vacuum. The residue was added TEA (3.6 g, 35.6 mmol, 1.1 eq), DCM(25 ml),MeOH (25 ml) and stirred at RT for 16 h. TLC shows that it has been completed. Concentrated and purified by silica gel column chromatography (PE/EA=10/1) to give I3-4 (8.385 g, 98% yield). $^1H$ NMR (400 MHz, $CDCl_3$) δ 7.85 (d, J=8.5 Hz, 1H), 7.74 (d, J=1.5 Hz, 1H), 7.52 (ddd, J=8.5, 2.3, 1.0 Hz, 1H), 3.94 (s, 3H).

Preparation of methyl 2-amino-4-(tert-butyl)benzoate (compound 13-5). To a solution of methyl 2-nitro-4-(trifluoromethoxy)benzoate (I3-4, 8.358 g, 31.64 mmol, 1.0 eq) in MeOH (100 ml) was added Pd/C (2.0 g). It was stirred at RT under $H_2$ for 16 h. LC/MS shows that it has been completed. It was filtered and purified by silica gel column chromatography (PE/EA=10/1) to give I3-5 (7.178 g, 96% yield). LC/MS (ESI) m/z: 236.0 $(M+H)^+$.

4. Synthesis of methyl 2-amino-6-methoxynicotinate (I4-6)

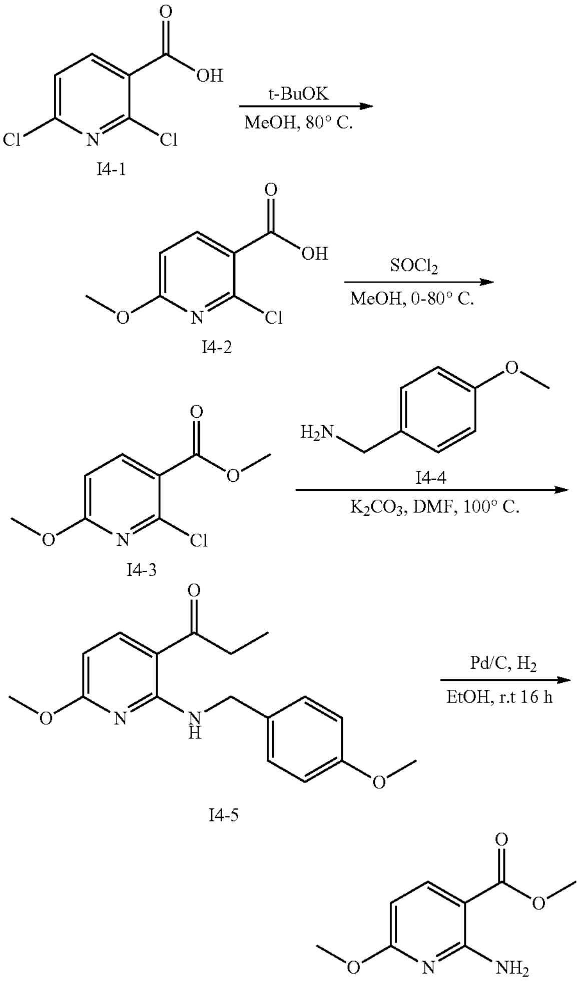

I4-1
I4-2
I4-3
I4-5
I4-6

Preparation of 2-chloro-6-methoxynicotinic acid (I4-2). To a solution of 2,6-dichloronicotinic acid (I4-1, 7.725 g, 40.23 mmol, 1.0 eq) in MeOH (70 ml) was added potassium tert-butoxide (22.529 g, 201.15 mmol, 5.0 eq) at 27° C. The reaction mixture was heated to 80° C. for 16 h. The reaction mixture was concentrated and diluted with water and acidified with 6N HCl (to pH=2-3) until I4-2 (5.95 g, 79% yield) was obtained as white solid. LC/MS (ESI) m/z: 185.9(M−H)$^-$.

Preparation of methyl 2-chloro-6-methoxynicotinate (I4-3). To a solution of 2-chloro-6-methoxynicotinic acid (I4-2, 5.95 g, 31.82 mmol, 1.0 eq) in MeOH (60 ml) was added thionyl chloride (24.226 g, 203.65 mmol, 6.4 eq) at 0° C. The reaction mixture was heated to 80° C. for 16 h. The reaction mixture was quenched with ice-cold water and concentrated. And the mixture was extracted with ethyl acetate. The organic layer was washed with $NaHCO_3$ (20 ml) and concentrated to give I4-3 (5.7 g, 89% yield) as white solid. LC/MS (ESI) m/z: 202.1(M+H)$^+$.

Preparation of methyl 6-methoxy-2-((4-methoxybenzyl) amino)nicotinate (compound 14-5). To a solution of methyl 2-chloro-6-methoxynicotinate (I4-3, 5.7 g, 28.38 mmol, 1.0 eq) in DMF (60 ml) was added (4-methoxyphenyl)methanamine (I4-4, 4.672 g, 34.06 mmol, 1.2 eq) and potassium carbonate (5.875 g, 42.57 mmol, 1.5 eq) at 0° C. The reaction mixture was heated to 100° C. for 16 h. The reaction mixture was added water (30 ml) and extracted with ethyl acetate (40 ml×3). Concentrated and purified by silica gel column chromatography (PE/EA=120:1) to give I4-5 (4.8 g, 57% yield) as off-white solid. LC/MS (ESI) m/z: 303.2(M+H)$^+$.

Preparation of methyl 2-amino-6-methoxynicotinate (I4-6). To a solution of methyl 6-methoxy-2-((4-methoxybenzyl)amino)nicotinate (I4-5, 4.8 g, 16.22 mmol, 1.0 eq) in MeOH (50 ml) was added Pd/C (2.59 g, 8.11 mmol, 0.5 eq) and AcOH (1 ml) at 27° C. The reaction mixture was stirred under $H_2$ at 45° C. for 16 h. The reaction mixture was filtered and concentrated to give crude I4-6 (3 g, 100% yield) as off-white solid. LC/MS (ESI) m/z: 182.2(M+H)$^+$.

5. Synthesis methyl 2-aminoquinoline-3-carboxylate (15-4)

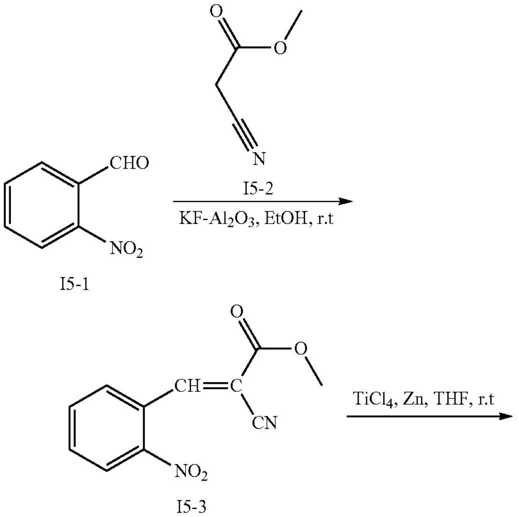

I5-1

I5-3

-continued

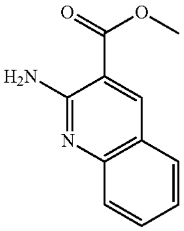

I5-4

Preparation of methyl (E)-2-cyano-3-(2-nitrophenyl)acrylate (15-3). To a solution of 2-nitrobenzaldehyde (I5-1, 2.5 g, 16.56 mmol, 1.0 eq), methyl 2-cyanoacetate (I5-2, 2.2 g, 21.52 mmol, 1.3 eq) in EtOH (9 ml) was added KF—$Al_2O_3$ (332 mg). It was stirred at room temperature under $N_2$ for 3 hrs. LC/MS shows that it has been completed. It was extracted by EA to give I5-3 (1.4 g, 90% yield). $^1H$ NMR (400 MHz, $CDCl_3$) δ 8.74 (d, J=6.0 Hz, 1H), 8.29 (dd, J=8.2, 1.1 Hz, 1H), 7.89-7.69 (m, 3H), 3.98 (s, 3H).

Preparation of methyl 2-aminoquinoline-3-carboxylate (15-4). To a solution of Zinc powder (2.37 g, 36.2 mmol, 6.0 eq) in THF (25 ml) was added slowly $TiCl_4$ (3.433 g, 18.1 mmol, 3.0 eq) at room temperature under $N_2$. It was reflux at 70° C. under $N_2$ for 2 h. It was cooled to room temperature and added solution of methyl (E)-2-cyano-3-(2-nitrophenyl) acrylate (I5-3, 1.4 g, 6.03 mmol, 1.0 eq) in THF (3 ml) slowly at room temperature under $N_2$.It was stirred at room temperature under $N_2$ for 15 min. LC/MS shows that it has been completed. It was quenched by 10% $K_2CO_3$ (50 ml) and extracted by DCM to give I5-4 (400 mg, obtained). LC/MS (ESI) m/z: 203.1 (M+H)$^+$.

6. Synthesis of methyl 7-amino-2,3-dihydrobenzo [b][1,4]dioxine-6-carboxylate (I6-3)

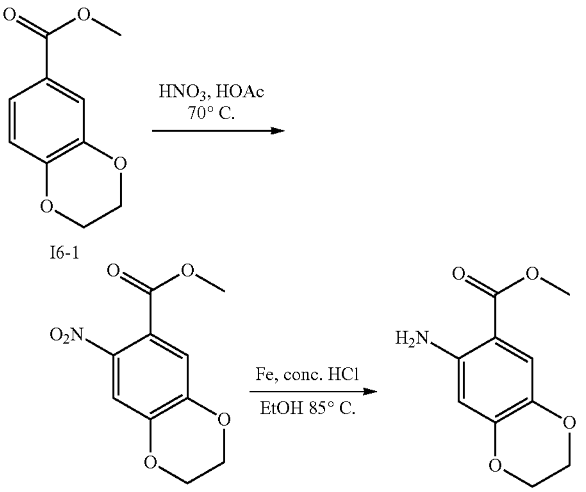

I6-1

I6-2

I6-3

Preparation of methyl 7-nitro-2,3-dihydrobenzo[b][1,4] dioxine-6-carboxylate (16-2). To a solution of methyl 2,3-dihydrobenzo[b][1,4]dioxine-6-carboxylate (I6-1, 10 g, 51.50 mmol, 1.0 eq) in Acetic acid (100 ml) was added Nitric acid (28 ml,70% $HNO_3$) at 27° C. The reaction mixture was heated to 70° C. for 16 h. After cooling to room temperature, the reaction mixture was concentrated under vacuum and acidified with 5% NaOH (to pH=7). Then ethyl acetate (10 ml) was added and the organic phase was washed with water. After dried the organic phase was concentrated and purified by column chromatography on silica-gel column chromatography (PE/EA=5:1) to give I6-2 (11.3 g, 92% yield as yellow solid. LC/MS (ESI) m/z: 240.0(M−H)$^-$.

Preparation of methyl 7-amino-2,3-dihydrobenzo[b][1,4]dioxine-6-carboxylate (16-3). To a solution of methyl 7-nitro-2,3-dihydrobenzo[b][1,4]dioxine-6-carboxylate (I6-2, 1 g, 4.18 mmol, 1.0 eq) in EtOH (15 ml) was heated to 85° C. and Iron powder (1.17 g, 204.85 mmol), concentrated HCl (0.017 ml). The reaction mixture was stirred at 85° C. for 16 h. The reaction mixture was filtered, and filtrate was purified by column chromatography on silica-gel column chromatography (PE/EA=8:1) to give I6-3 (1.14 g, 93% yield) as yellow solid. LC/MS (ESI) m/z: 210.0(M+H)$^+$.

7. Synthesis of methyl 6-aminobenzo[d][1,3]dioxole-5-carboxylate (I7-4)

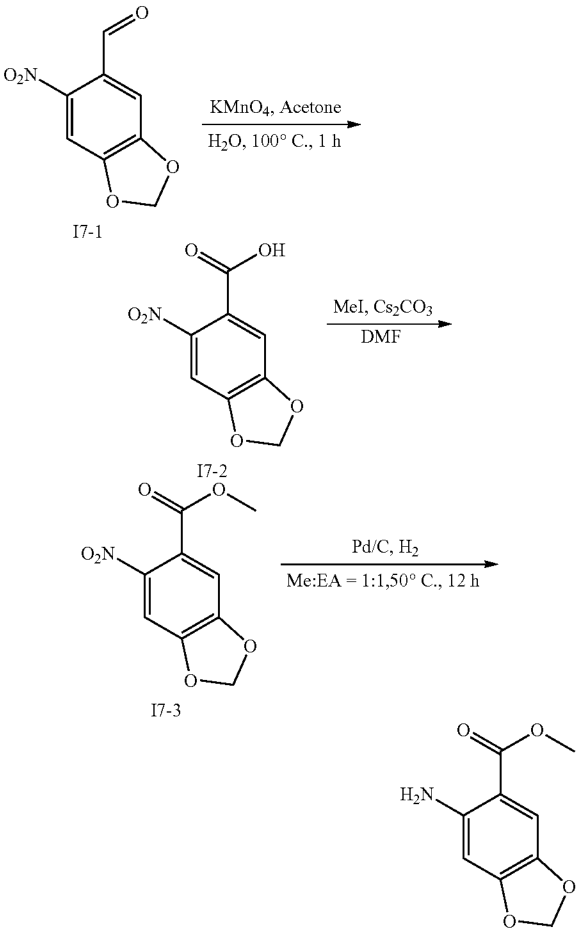

I7-1 I7-2 I7-3 I7-4

Preparation of 6-nitrobenzo[d][1,3]dioxole-5-carboxylic acid (compound 17-2). To a solution of 6-nitrobenzo[d][1,3]dioxole-5-carbaldehyde (I7-1, 5 g, 25.6 mmol, 1.0 eq), $KMnO_4$ (8 g, 50.4 mmol, 1.97 eq) in acetone/$H_2O$ (40 mL/60 mL) was stirred at 100° C. for 1 hours. The mixture evaporated in vacuum to dryness. The mixture precipitated from the water solution by acidification to $p^H$ 1 with concentrated hydrochloric acid. The residual aqueous solution was lyophilized to give I7-2 (3.451 g, 63.4% yield) as yellow solid. LC/MS (ESI) m/z: 212 (M+H)$^+$.

Preparation of methyl 6-nitrobenzo[d][1,3]dioxole-5-carboxylate (compound 17-3). To a solution of 6-nitrobenzo[d][1,3]dioxole-5-carboxylic acid (I7-2, 1.5 g, 6.38 mmol, 1.0 eq) and $Cs_2O_3$ (5.2 g, 15.95 mmol, 2.5 eq)in DMF (20 ml) was added Mel (1.359 g/0.6 ml, 9.57 mmol, 1.5 eq) at 0° C., and the reaction mixture was stirred at room temperature for 16 hours. The mixture was diluted with EA and washed with water, the organic phase was washed by $NH_4Cl$ and dried over $Na_2SO_4$ and concentrated under vacuum. The crude compound was purified by silica gel column chromatography (PE:EA=2:1) to give the I7-3 (1.32 g, 83% yield) as white solid.

Preparation of methyl 6-aminobenzo[d][1,3]dioxole-5-carboxylate (compound 17-4). To a solution of methyl 6-nitrobenzo[d][1,3]dioxole-5-carboxylate (I7-3, 250 mg, 1.1 mmol, 1.0 eq) in MeOH/EA(4 ml/4 ml) was added Pd/C (50 mg). The mixture was stirred at 50° C. for 12 hours under $H_2$. The mixture was filtered by EA, the liquid was concentrated under vacuum to give the I7-4 (217 mg, 100% yield) as a yellow solid. LC/MS (ESI) m/z:196 (M+H)$^+$ 8. Synthesis of methyl 5-amino-1H-indazole-6-carboxylate (I8-3)

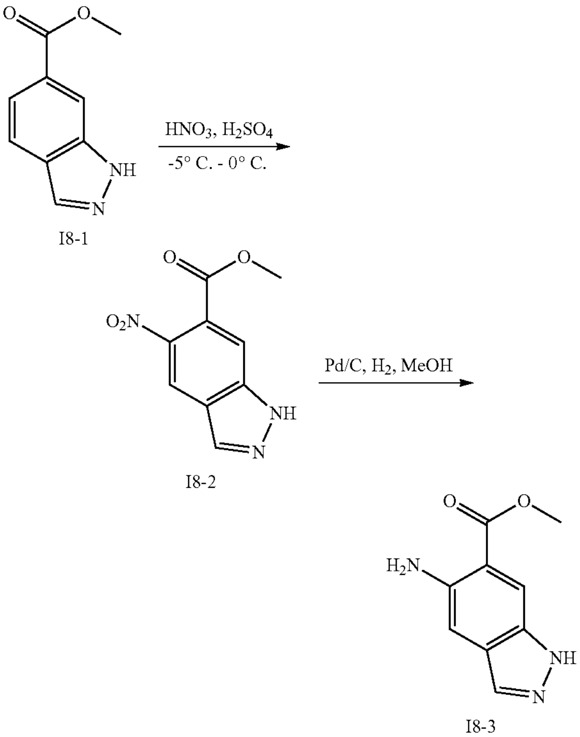

I8-1 I8-2 I8-3

Preparation of methyl 5-nitro-1H-indazole-6-carboxylate (18-2). To a solution of methyl 1H-indazole-6-carboxylate (I8-1, 1 g, 5.68 mmol, 1.0 eq) in $H_2SO_4$ (4 ml) was added a solution of Nitric acid (1 ml,70% $HNO_3$) and $H_2SO_4$ (1 ml) at 0° C. The reaction mixture was stirred at 0° C. for 1 h. After cooling to room temperature, the reaction mixture was poured into ice water (30 ml) and filtered. Then filter cake was washed with water and lyophilized to give I8-2 (1.2 g, 92% yield) as yellow solid. LC/MS (ESI) m/z: 222.1(M−H)$^-$.

Preparation of methyl 5-amino-1H-indazole-6-carboxylate (18-3). To a solution of methyl 5-nitro-1H-indazole-6-carboxylate (I8-2, 400 mg, 1.81 mmol, 1.0 eq) in MeOH/THF (4 ml/4 ml) was added Palladium carbon (80 mg), acetic acid (0.05 ml). The reaction mixture was stirred at room temperature under $H_2$ for 16 h. The reaction mixture was filtered, and filtrate was purified by column chromatography on silica-gel (PE/EA=3:1) to give I8-3 (269 mg, 78% yield) as yellow solid. LC/MS (ESI) m/z: 192.1$(M+H)^+$.

9. Synthesis of methyl 5-amino-1-methyl-1H-indazole-6-carboxylate (I8-3)

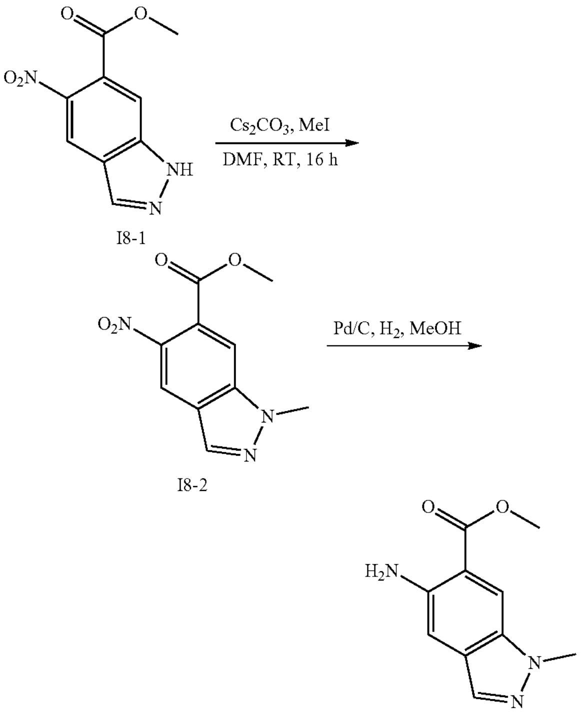

I8-1

I8-2

I8-3

Preparation of methyl 1-methyl-5-nitro-1H-indazole-6-carboxylate (18-2). To a solution of methyl 5-nitro-1H-indazole-6-carboxylate (I8-1, 3 g, 13.57 mmol, 1.0 eq) and $Cs_2O_3$ (11.058 g, 33.92 mmol, 2.5 eq) in DMF (30 ml) was added MeI (2.891 g/1.27 ml, 20.36 mmol, 1.5 eq). The reaction mixture was stirred at 0° C. for 16 hours. The mixture was diluted with EA and washed with water, the organic phase was washed by $NH_4Cl$ and dried over $Na_2SO_4$ and concentrated under vacuum. The crude compound was purified by silica gel column chromatography (PE:EA=1:1) to give the I8-2 (989 mg, 31% yield) as yellow solid. LC/MS (ESI) m/z: 236 $(M+H)^+$.

Preparation of methyl 5-amino-1-methyl-1H-indazole-6-carboxylate (18-3). To a solution of methyl 1-methyl-5-nitro-1H-indazole-6-carboxylate (18-2, 739 mg, 3.14 mmol, 1.0 eq) in MeOH(24 ml) was added Pd/C (150 mg). The mixture was stirred at room temperature for 16 hours under $H_2$. The mixture was filtered by EA, the liquid was concentrated under vacuum to give the I8-3 (616 mg, 95% yield) as a yellow solid. LC/MS (ESI) m/z:206 $(M+H)^+$ 9. Synthesis of methyl 2-amino-6-methoxynicotinate (I9-6)

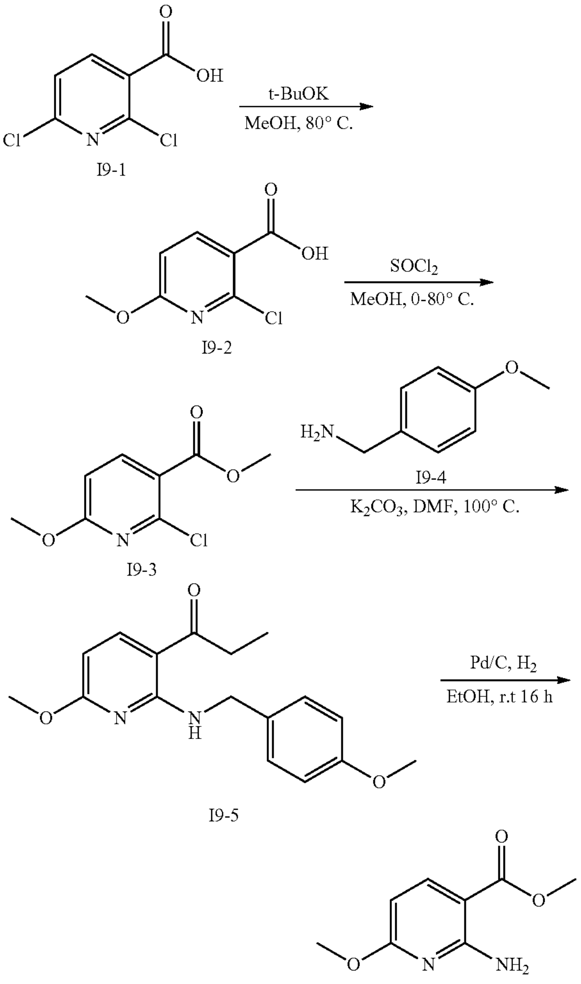

I9-1

I9-2

I9-3

I9-5

I9-6

Preparation of 2-chloro-6-methoxynicotinic acid (19-2). To a solution of 2,6-dichloronicotinic acid (I9-1, 5 g, 26.04 mmol) in MeOH was added potassium tert-butoxide (14.582 g, 130.2 mmol, 5 eq) at 27° C. The reaction mixture was heated to 80° C. for 16 h. The reaction mixture was concentrated and diluted with water and acidified with 6N HCl (to pH=2-3) until was obtained compound I9-2 (4.56 g, 94% yield) as white solid. LC/MS (ESI) m/z: 186.0$(M-H)^-$.

Preparation of methyl 2-chloro-6-methoxynicotinate (19-3). To a solution of 2-chloro-6-methoxynicotinic acid (I9-2, 4.56 g, 24.39 mmol) in MeOH was added thionyl chloride (18.569 g, 156.1 mmol, 6.4 eq) at 0° C. The reaction mixture was heated to 80° C. for 16 h. The reaction mixture was quenched with ice-cold water and concentrated. And extracted with ethyl acetate. The organic layer was washed with $NaHCO_3$ and concentrated to give I9-3 (4.3 g, 89% yield) as light-yellow oil. LC/MS (ESI) m/z: 201.9$(M+H)^+$.

Preparation of methyl 6-methoxy-2-((4-methoxybenzyl)amino)nicotinate (19-5). To a solution of methyl 2-chloro-6-methoxynicotinate (I9-3, 4.3 g, 21.39 mmol) in DMF (40 ml) was added (4-methoxyphenyl)methanamine (I9-4, 3.521 g, 25.67 mmol, 1.2 eq) and potassium carbonate(4.28 g, 32.085 mmol, 1.5 eq) at 0° C. The reaction mixture was heated to 100° C. for 16 h. The reaction mixture was added water and extracted with ethyl acetate. Concentrated and purified by silica gel column (PE/EA=40:1) to give I9-5 (3.8 g, 59% yield) as colorless oil. LC/MS (ESI) m/z: 303.1(M+H)+.

Preparation of methyl 2-amino-6-methoxynicotinate (I9-6). To a solution of methyl 6-methoxy-2-((4-methoxybenzyl)amino)nicotinate (I9-5, 3.794 g, 12.56 mmol, 1 eq) in MeOH was added palladium carbon (2.0 g, 6.28 mmol, 0.5 eq) and AcOH(1 ml) at 27° C. The reaction mixture was stirred under $H_2$ at 45° C. for 16 h. The reaction mixture was filtered and concentrated to give crude I9-6 (3 g, 100% yield) as off-white solid. LC/MS (ESI) m/z: 183.0(M+H)+.

Synthesis of Borolanes

10. Synthesis of 2-fluoro-6-methyl-3-(4,4,5,5-tetramethyl-1,3,2-dioxaborolan-2-yl)pyridine (I10-2)

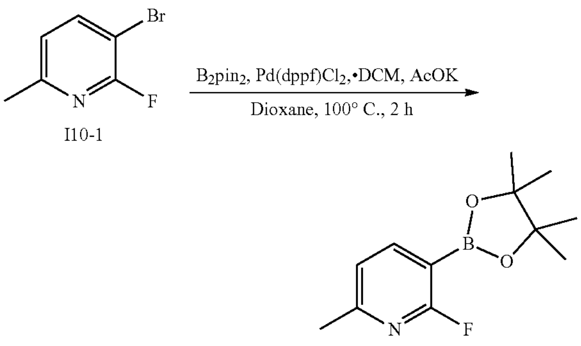

I10-1

I10-2

Preparation of 2-fluoro-6-methyl-3-(4,4,5,5-tetramethyl-1,3,2-dioxaborolan-2-yl)pyridine (compound I10-1). The mixture of I10-1 (500 mg, 2.6 mmol), AcOK (646 mg, 6.6 mmol), Pd(dppf)$Cl_2$-DCM (215 mg, 0.26 mmol) and $B_2pin_2$ (1.0 g, 3.9 mmol) was in 1,4-Dioxane (20 ml) stirred at 90° C. under Ar for 2 h. After completion, the mixture was quenched with $NaHCO_3$ extracted with EA, washed with water and brine, dried over $Na_2SO_4$ and concentrated. The crude product was purified by silica chromatography (DCM/MeOH=30/1). The product (I10-2) was obtained as yellow solid (124 mg, 0.52 mmol, 20%). LC/MS [M+H]:238.1

11. Synthesis of Methyl 3-(4-(4,4,5,5-tetramethyl-1,3,2-dioxaborolan-2-yl)-1H-pyrazol-1-yl)propanoate (I11-3)

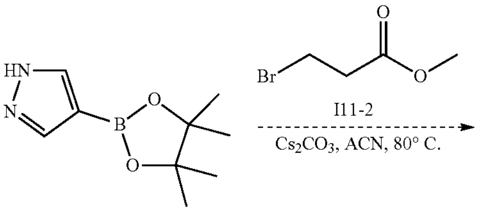

I11-1

-continued

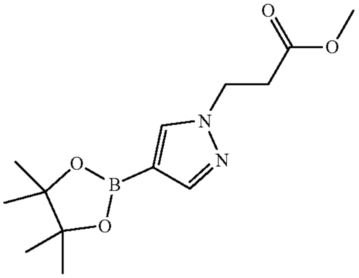

I11-3

Preparation of methyl 3-(4-(4,4,5,5-tetramethyl-1,3,2-dioxaborolan-2-yl)-1H-pyrazol-1-yl)propanoate (111-3). The mixture of I11-1 (500 mg, 2.6 mmol), I11-2 (646 mg, 3.9 mmol), and $Cs_2CO_3$ (1.7 g, 5.2 mmol) was in ACN (20 mL) stirred at 80° C. under $N_2$ for 12 h. After completion, the mixture was concentrated, extracted with EA, washed with water and brine, dried over $NaSO_4$ and concentrated. The product, I11-3-3, was obtained as colorless oil (515 mg, 1.8 mmol, 71%). LC/MS [M+H]:281.1

Synthesis of Phenols

12. Synthesis of methyl 4,5-dichloro-2-hydroxybenzoate (I12-3)

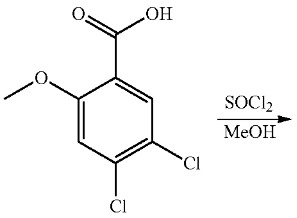

I12-1

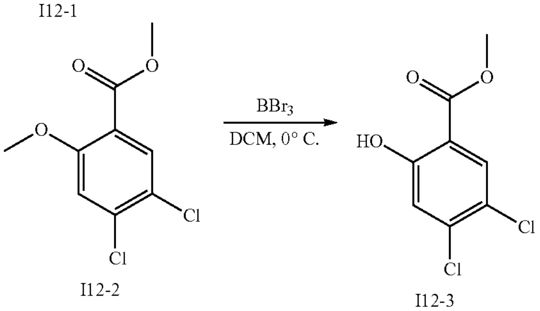

I12-2

I12-3

Preparation of methyl 4,5-dichloro-2-methoxybenzoate (112-2). To a solution of 4,5-dichloro-2-methoxybenzoic acid (I12-1, 900.0 mg, 4.1 mmol, 1.0 eq) in MeOH (13 mL) being cooled to 0° C. were added $SOCl_2$ (966.8 mg, 8.2 mmol, 2.0 eq) under $N_2$ protection. The reaction mixture was then stirred at 50° C. under $N_2$ for 16 hours. Once LC/MS showed the reaction finished, the mixture was then quenched with $H_2O$ (20 mL). The reaction mixture was concentrated to give 4,5-dichloro-2-methoxybenzoate (I12-2, 840.0 mg, 3.59 mmol, 87.6%).

Preparation of methyl 4,5-dichloro-2-hydroxybenzoate (112-3). To a solution of 4,5-dichloro-2-methoxybenzoate (I12-2, 840.0 mg, 3.59 mmol, 1.0 eq) in DCM (13 mL) being cooled to 0° C. was added $BBr_3$ (1.0 mol/L in DCM, 10.77 mL, 3.0 eq). The reaction mixture was stirred at room temperature for 2 hours. Once LC/MS showed the reaction finished, the reaction mixture was quenched by ice-water followed by the extraction with EA. All the organic phases were then washed with brine, dried by $Na_2SO_4$ and filtered. The filtration was then concentrated to give the crude, which was purified by silica gel column eluting with 0-20% EA in PE to give methyl 4,5-dichloro-2-hydroxybenzoate (I12-3, 458 mg, 2.08 mmol, 58.0%). LC/MS [M−H]: 219.0

13. Synthesis of methyl 2-(4-chloro-2-hydroxyphenyl) acetate (I13-3)

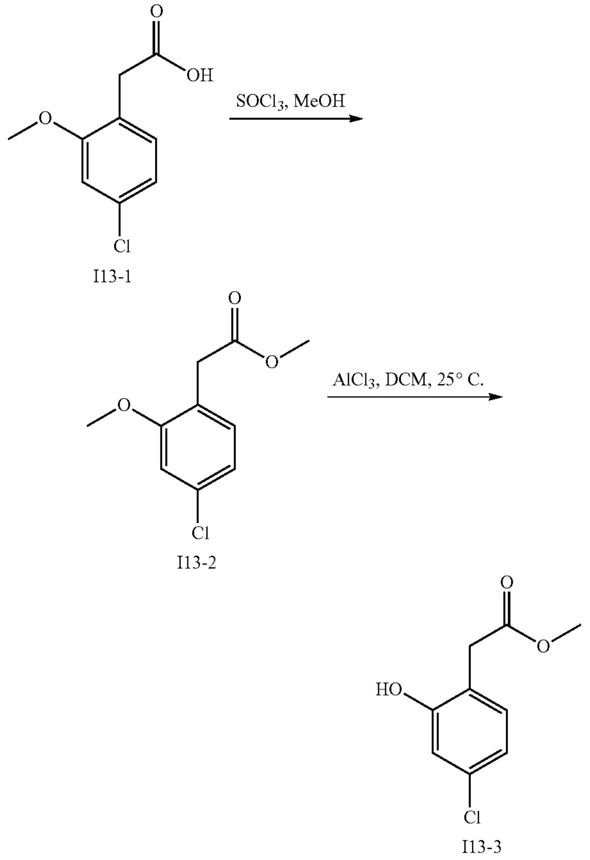

I13-1

I13-2

I13-3

Preparation of methyl 2-(4-chloro-2-methoxyphenyl) acetate (113-2). To a mixture of 2-(4-chloro-2-methoxyphenyl)acetic acid (I13-1, 2 g, 8.16 mmol) in MeOH (35 mL) was added $SOCl_2$(6 mL, 82.71 mmol) at 0° C. under Ar. The mixture was stirred at 55° C. for 16 h under Ar. LC/MS showed the reaction was completed. The mixture was concentrated on dryness directly. TLC showed a new spot. The mixture was extracted with EA, washed with $NaHCO_3$. The organic was dried over $Na_2SO_4$ and concentrated to get methyl 2-(4-chloro-2-methoxyphenyl) acetate (I13-2, 2.2 g) as a yellow oil. LC/MS: Rt: 1.697 min; Expected MS m/z (ESI) C10H11ClO3$[M+H]^+$: 215.04; Found: 215. $^1H$ NMR (400 MHz, DMSO-$d_6$) δ 7.21 (d, J=4.0 Hz, 1H), 7.06 (d, J=1.0 Hz, 1H), 6.98-6.95 (m, 1H), 3.78 (s, 3H), 3.59 (s, 5H).

Preparation of methyl 2-(4-chloro-2-hydroxyphenyl) acetate (113-3). To a mixture of methyl 2-(4-chloro-2-methoxyphenyl)acetate (I13-2, 500 mg, 2.336 mmol) in DCM (10 mL) was added $AlCl_3$(1.6 g, 11.682 mmol) at 25° C. under Ar. The mixture was stirred at 25° C. for 16 h under Ar. LC/MS showed the reaction was completed. The mixture was quenched with water, extracted with EA. The organic was dried over $Na_2SO_4$ and concentrated to get methyl 2-(4-chloro-2-hydroxyphenyl) acetate (I13-3, 460 mg) as a yellow oil. LC/MS: Rt: 1.373 min; Expected MS m/z (ESI) $C_9$H9ClO3$[M+H]^+$: 201.02; Found: 201.

General Synthetic Procedure 1

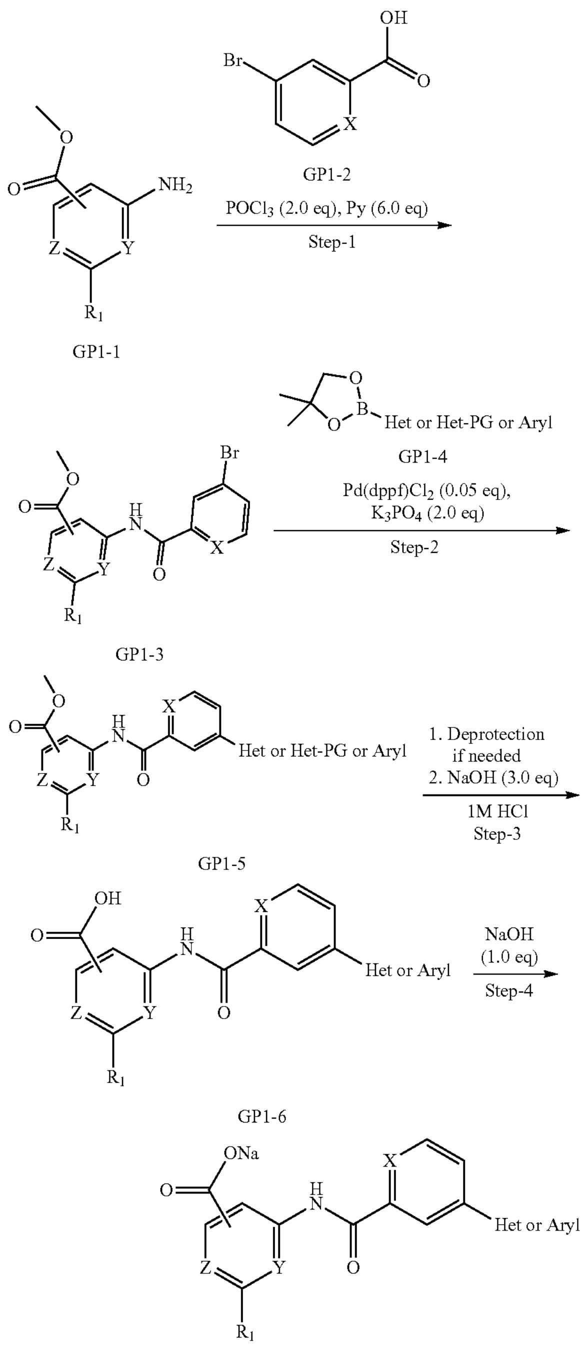

GP1-2

GP1-1

GP1-4

GP1-3

GP1-5

GP1-6

GP1-6-Na salt

X = C or N
Y = C or N
Z = N or C or C-$R_2$
$R_1$ = H, halogen, alkyl, alkoxy, $OCF_3$
$R_2$ = H, halogen, alkyl, alkoxy, $OCF_3$
$R_1$ and $R_2$ together can form a ring
Het = Hetrocycle or substituted heterocycle
Aryl = Phenyl or substituted phenyl
PG = protective group Step-1. To a solution of GP1-1 (1.0 eq) in DCM (200 mL), was added GP1-2 (1.0 eq), Py (6.0 eq), $POCl_3$ (2.0 eq) at 0° C. The mixture was stirred at room temperature for 16 hours. LC/MS showed finished. The mixture was poured into water, extracted with DCM (3×200 mL), the organic phase was dried over $Na_2SO_4$ and concentrated under vacuum. The crude compound was purified by column 0%-9% EA in PE to give a crude. The crude was triturated with hexane to afford GP1-3.

Step-2. GP1-3 (1.0 eq) in dioxane/$H_2O$=7:1, was added Het-4-(4,4,5,5-tetramethyl-1,3,2-dioxaborolane (GP1-4, 1.0 eq), Pd(dppf)$Cl_2$ (0.05 eq), $K_3PO_4$ (2.0 eq). The mixture was stirred at 90° C. for 16 hours LC/MS showed finished. The mixture was concentrated and purified by column 0% ~50% EA in PE to give GP1-5.

Step-3. To a solution of methyl compound GP1-5 (1.0 eq) in THF:MeOH:$H_2$ O=1:1:1 was added NaOH (3.0 eq). The reaction mixture was stirred at room temperature for 16 hours. TLC showed finished. The reaction solution was adjusted with 1M hydrochloric acid to pH 3-4 to give GP1-6.

Step-4. To a solution of GP1-6 (1.0 eq) in THF:MeOH:$H_2O$=1:1:1 was added NaOH (1.05 eq). The reaction mixture was stirred at room temperature for 12 hours. TLC showed finished. The reaction solution was concentrated in vacuum and lyophilized in vacuum to afford a crude product, which was triturated with $H_2O$ and dried in vacuum to afford GP1-6-Na salt.

The following compounds were prepared using general synthetic procedure 1. The examples and spectral data are shown in Table 2.

TABLE 2

| Example # | Name/Structure | Spectral data |
|---|---|---|
| 3 | 2-[[3-(1H-pyrazol-4-yl)benzoyl]amino]benzoic acid 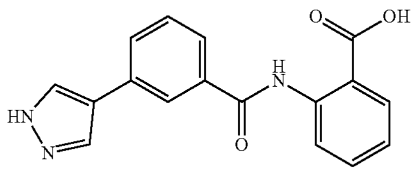 | $^1H$ NMR (400 MHz, DMSO-d6) δ 13.80-13.09 (m, 1H), 12.45 (s, 1H), 8.73 (d, J = 8.3 Hz, 1H), 8.19 (s, 3H), 8.08 (dd, J = 8.0, 1.5 Hz, 1H), 7.88 (d, J = 7.6 Hz, 1H), 7.77 (d, J = 7.9 Hz, 1H), 7.67 (t, J = 7.8 Hz, 1H), 7.57 (t, J = 7.7 Hz, 1H), 7.21 (t, J = 7.6 Hz, 1H). LC/MS (ESI) m/z: 308.1 $(M + H)^+$. |
| 4 | 2-[[3-(1-tetrahydropyran-4-ylpyrazol-3-yl)benzoyl]amino]benzoic acid 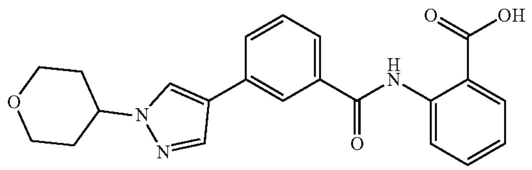 [SMILES: O=C(Nc1ccccc1C(=O)O)c1cccc(-c2cnn(C3CCOCC3)c2)c1] | LC/MS (ESI) m/z: 392.1 $(M + H)^+$. |
| 6 | 2-[[4-(1-tetrahydropyran-4-ylpyrazol-4-yl)pyridine-2-carbonyl]amino]benzoic acid 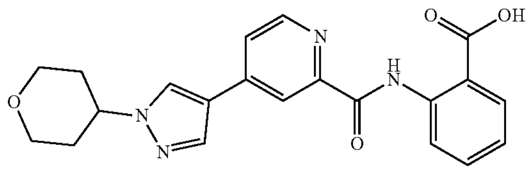 [SMILES: O=C(Nc1ccccc1C(=O)O)c1cc(-c2cnn(C3CCOCC3)c2)ccn1] | $^1H$ NMR (400 MHz, DMSO-d6) δ 13.59 (s, 1H), 13.07 (s, 1H), 8.88 (d, J = 7.6 Hz, 1H), 8.72 (s, 1H), 8.65 (d, J = 4.2 Hz, 1H), 8.37 (s, 1H), 8.23 (s, 1H), 8.06 (dd, J = 1.6 Hz, J = 8.0 Hz, 1H), 7.88 (dd, J = 1.6 Hz, J = 5.6 Hz, 1H), 7.69 (t, J-6.8 Hz, 1H), 7.23 (t, J = 7.2 Hz, 1H), 4.49-4.44 (m, 1H), 3.98 (d, J = 11.6 Hz, 2H), 3.53-3.46 (m, 2H), 2.07-1.97 (m, 4H). LC/MS (ESI) m/z: 392.1 $(M + H)^+$. |
| 8 | 2-[[3-(8-quinolyl)benzoyl]amino]benzoic acid 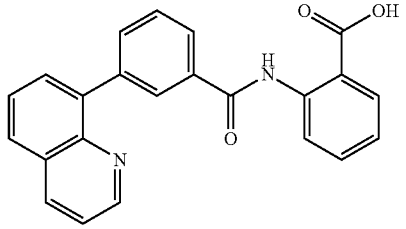 [SMILES: O=C(Nc1ccccc1C(=O)O)c1cccc(-c2cccc3cccnc23)c1] | $^1H$ NMR (400 MHz, DMSO-d6) δ 8.31 (s, 1H), 8.24 (s, 1H), 8.03 (s, 1H), 7.55-7.52 (m, 1H), 7.45 (s, 1H), 7.44-7.40 (m, 4H), 7.37-7.31 (m, 2H), 7.22 (s, 1H), 7.10 (s, 1H), 7.03 (s, 1H), 6.83 (s, 1H), 6.41 (s, 1H). LC/MS (ESI) m/z: 369.1 $(M + H)^+$. |

TABLE 2-continued

| Example # | Name/Structure | Spectral data |
|---|---|---|
| 9 | 4-methyl-2-[[3-(1H-pyrazol-4-yl)benzoyl]amino]benzoic acid 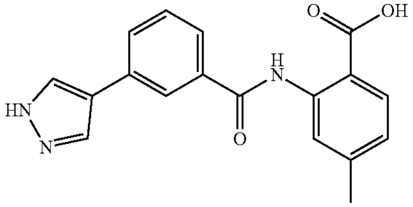 [SMILES: Cc1ccc(C(=O)O)c(NC(=O)c2cccc(-c3cn[nH]c3)c2)c1] | $^1$H NMR (400 MHz, DMSO-d6) δ 12.24 (s, 1H), 8.62 (s, 1H), 8.16 (d, J = 7.3 Hz, 3H), 7.96 (d, J = 8.1 Hz, 1H), 7.88 (d, J = 7.9 Hz, 1H), 7.75 (d, J = 7.8 Hz, 1H), 7.57 (t, J = 7.7 Hz, 1H), 7.04 (d, J = 8.0 Hz, 1H), 2.41 (s, 3H). LC/MS (ESI) m/z: 322.1 (M + H)$^+$. |
| 10 | 4-methyl-2-[[3-(1-tetrahydropyran-4-ylpyrazol-4-yl)benzoyl]amino]benzoic 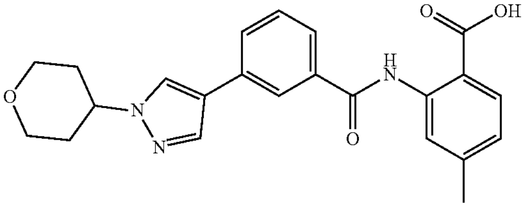 [SMILES: Cc1ccc(C(=O)O)c(NC(=O)c2cccc(-c3cnn(C4CCOCC4)c3)c2)c1] | $^1$H NMR (400 MHz, DMSO-d6) δ 14.08-13.24 (m, 1H), 12.55 (s, 1H), 8.60 (s, 1H), 8.38 (s, 1H), 8.16 (s, 1H), 8.01-7.94 (m, 2H), 7.84 (d, J = 7.9 Hz, 1H), 7.76 (d, J = 7.7 Hz, 1H), 7.57 (t, J = 7.7 Hz, 1H), 7.02 (d, J = 8.2 Hz, 1H), 4.43 (dt, J = 10.2, 5.3 Hz, 1H), 4.01 (dd, J = 18.2, 9.0 Hz, 2H), 3.49 (td, J = 11.3, 2.9 Hz, 2H), 2.40 (s, 3H), 2.10-1.87 (m, 4H). LC/MS (ESI) m/z: 406.0 (M + H)$^+$. |
| 12 | 4-methyl-2-[[4-(1-tetrahydropyran-4-ylpyrazol-4-yl)pyridine-2-carbonyl]amino]benzoic acid 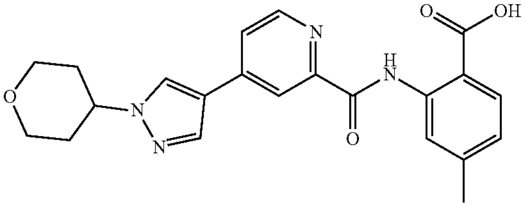 [SMILES: Cc1ccc(C(=O)O)c(NC(=O)c2cc(-c3cnn(C4CCOCC4)c3)ccn2)c1] | $^1$H NMR (400 MHz, DMSO-d6) δ 13.40 (s, 1H), 13.04 (s, 1H), 8.72 (d, J = 18.8 Hz, 2H), 8.64 (d, J = 5.1 Hz, 1H), 8.35 (s, 1H), 8.22 (s, 1H), 7.95 (d, J = 8.0 Hz, 1H), 7.87 (dd, J = 5.1, 1.7 Hz, 1H), 7.05 (d, J = 7.3 Hz, 1H), 4.57-4.37 (m, 1H), 4.00 (t, J = 13.0 Hz, 2H), 3.56-3.43 (m, 2H), 2.41 (s, 3H), 2.11-1.90 (m, 4H). LC/MS (ESI) m/z: 407.0 (M + H)$^+$. |
| 14 | 4-methyl-2-[[3-(8-quinolyl)benzoyl]amino]benzoic acid 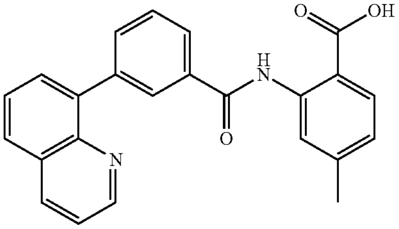 [SMILES: Cc1ccc(C(=O)O)c(NC(=O)c2cccc(-c3cccc4cccnc34)c2)c1] | $^1$H NMR (400 MHz, DMSO-d6) δ 13.77-13.35 (m, 1H), 12.33 (s, 1H), 8.94 (dd, J = 4.1, 1.8 Hz, 1H), 8.64 (s, 1H), 8.49 (d, J = 8.3 Hz, 1H), 8.26 (s, 1H), 8.08 (d, J = 8.2 Hz, 1H), 8.01 (d, J = 7.5 Hz, 1H), 7.96-7.90 (m, 2H), 7.87 (d, J = 5.7 Hz, 1H), 7.73 (dt, J = 15.4, 7.9 Hz, 2H), 7.62 (dd, J = 8.3, 4.2 Hz, 1H), 7.04 (d, J = 8.0 Hz, 1H), 2.41 (s, 3H). LC/MS (ESI) m/z: 383.0 (M + H)$^+$. |
| 15 | 2-[[3-(1H-pyrazol-4-yl)benzoyl]amino]-4-(trifluoromethyl)benzoic acid 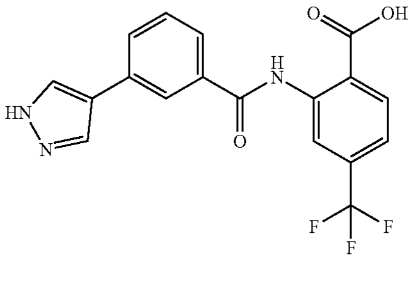 [SMILES: O=C(Nc1cc(C(F)(F)F)ccc1C(=O)O)c1cccc(-c2cn[nH]c2)c1] | $^1$H NMR (400 MHz, DMSO-d6) δ 9.09 (s, 1H), 8.22 (dd, J = 27.9, 14.3 Hz, 4H), 7.90 (d, J = 7.9 Hz, 1H), 7.78 (d, J = 8.0 Hz, 1H), 7.57 (dd, J = 16.9, 8.9 Hz, 2H). LC/MS (ESI) m/z: 374.0 (M − H)$^-$. |

TABLE 2-continued

| Example # | Name/Structure | Spectral data |
|---|---|---|
| 16 | 2-[[3-(1-tetrahydropyran-4-ylpyrazol-4-yl)benzoyl]amino]-4-(trifluoromethyl)benzoic acid 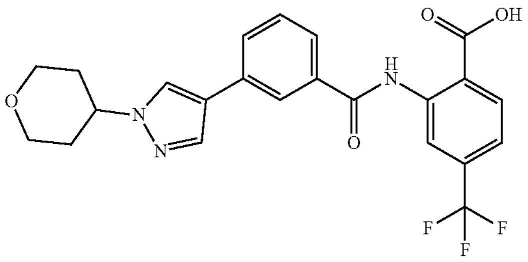 [SMILES: O=C(Nc1cc(C(F)(F)F)ccc1C(=O)O)c1cccc(-c2cnn(C3CCOCC3)c2)c1] | $^1$H NMR (400 MHz, DMSO-d6) δ 12.47 (s, 1H), 9.08 (s, 1H), 8.39 (s, 1H), 8.26 (d, J = 8.1 Hz, 1H), 8.19 (s, 1H), 7.99 (s, 1H), 7.88 (d, J = 7.8 Hz, 1H), 7.77 (d, J = 7.8 Hz, 1H), 7.62-7.54 (m, 2H), 4.44 (tt, J = 10.3, 5.1 Hz, 1H), 4.05-3.92 (m, 2H), 3.49 (td, J = 11.5, 2.9 Hz, 2H), 2.08-1.92 (m, 4H). LC/MS (ESI) m/z: 460.0 $(M + H)^+$. |
| 18 | 2-[[4-(1-tetrahydropyran-4-ylpyrazol-4-yl)pyridine-2-carbonyl]amino]-4-(trifluoromethyl)benzoic acid 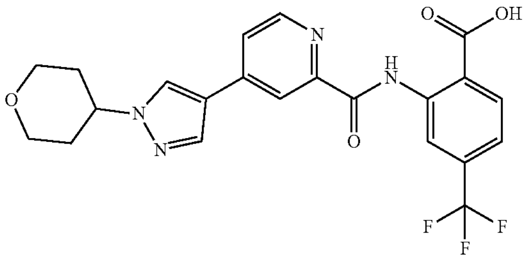 [SMILES: O=C(Nc1cc(C(F)(F)F)ccc1C(=O)O)c1cc(-c2cnn(C3CCOCC3)c2)ccn1] | 1H NMR (400 MHz, DMSO-d6) δ 14.10 (s, 1H), 13.21 (s, 1H), 9.30 (s, 1H), 8.71 (s, 1H), 8.67 (d, J = 5.1 Hz, 1H), 8.39 (s, 1H), 8.30-8.19 (m, 2H), 7.90 (dd, J = 5.1, 1.6 Hz, 1H), 7.58 (d, J = 7.4 Hz, 1H), 4.56-4.40 (m, 1H), 3.99 (d, J = 11.2 Hz, 2H), 3.49 (dt, J = 11.5, 5.8 Hz, 2H), 2.13-1.90 (m, 4H). LC/MS (ESI) m/z: 461.0 $(M + H)^+$. |
| 20 | 2-[[3-(8-quinolyl)benzoyl]amino]-4-(trifluoromethyl)benzoic acid 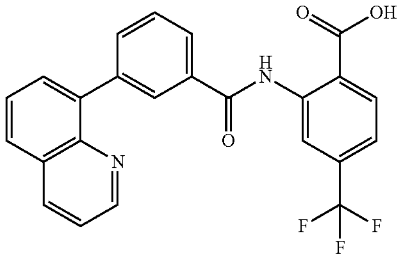 [SMILES: O=C(Nc1cc(C(F)(F)F)ccc1C(=O)O)c1cccc(-c2cccc3cccnc23)c1] | $^1$H NMR (400 MHz, DMSO-d6) δ 12.34 (s, 1H), 9.12 (s, 1H), 8.95 (dd, J = 4.1, 1.8 Hz, 1H), 8.49 (dd, J = 8.4, 1.8 Hz, 1H), 8.28 (s, 1H), 8.24 (d, J = 8.4 Hz, 1H), 8.08 (d, J = 8.2 Hz, 1H), 8.03 (d, J = 7.8 Hz, 1H), 7.96 (d, J = 7.7 Hz, 1H), 7.88 (d, J = 5.8 Hz, 1H), 7.74 (dd, J = 15.5, 7.8 Hz, 2H), 7.64-7.55 (m, 2H). LC/MS (ESI) m/z: 437.0 $(M + H)^+$. |
| 21 | 4-isopropyl-2-[[3-(1H-pyrazol-4-yl)benzoyl]amino]benzoic acid 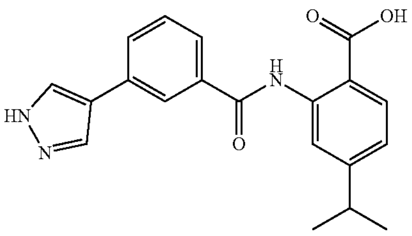 | $^1$H NMR (400 MHz, DMSO-d6) δ 13.28 (s, 1H), 12.72 (s, 1H), 8.70 (d, J = 1.6 Hz, 1H), 8.17 (d, J = 20.5 Hz, 3H), 7.99 (d, J = 8.1 Hz, 1H), 7.86 (d, J = 7.7 Hz, 1H), 7.77 (d, J = 8.1 Hz, 1H), 7.56 (t, J = 7.7 Hz, 1H), 7.08 (dd, J = 8.2, 1.6 Hz, 1H), 2.96 (dq, J = 13.8, 6.9 Hz, 1H), 1.25 (d, J = 6.9 Hz, 6H). LC/MS (ESI) m/z: 350.0 $(M + H)^+$. |

TABLE 2-continued

| Example # | Name/Structure | Spectral data |
|---|---|---|
| 22 | 4-isopropyl-2-[[3-(1-tetrahydropyran-4-ylpyrazol-4-yl)benzoyl]amino]benzoic acid 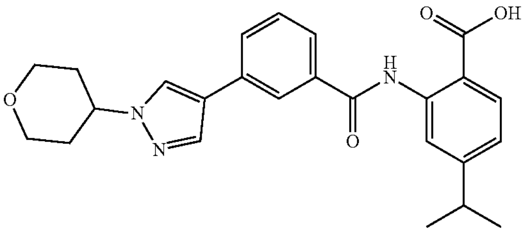 [SMILES: CC(C)c1ccc(C(=O)O)c(NC(=O)c2cccc(-c3cnn(C4CCOCC4)c3)c2)c1] | $^1H$ NMR (400 MHz, DMSO-d6) δ 12.59 (s, 1H), 8.69 (d, J = 1.5 Hz, 1H), 8.38 (s, 1H), 8.18 (s, 1H), 7.99 (d, J = 8.0 Hz, 2H), 7.84 (d, J = 7.8 Hz, 1H), 7.76 (d, J = 7.9 Hz, 1H), 7.56 (t, J = 7.7 Hz, 1H), 7.09 (dd, J = 8.2, 1.6 Hz, 1H), 4.44 (tt, J = 10.0, 4.9 Hz, 1H), 4.03-3.92 (m, 2H), 3.49 (td, J = 11.5, 3.0 Hz, 2H), 2.96 (dq, J = 13.7, 6.8 Hz, 1H), 2.12-1.92 (m, 4H), 1.25 (d, J = 6.9 Hz, 6H). LC/MS (ESI) m/z: 434.1 $(M + H)^+$. |
| 24 | 4-isopropyl-2-[[4-(1-tetrahydropyran-4-ylpyrazol-4-yl)pyridine-2-carbonyl]amino]benzoic acid 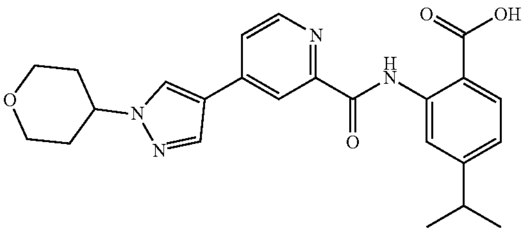 [SMILES: CC(C)c1ccc(C(=O)O)c(NC(=O)c2cc(-c3cnn(C4CCOCC4)c3)ccn2)c1] | $^1H$ NMR (400 MHz, DMSO-d6) δ 13.23 (s, 1H), 8.85 (d, J = 1.6 Hz, 1H), 8.69 (s, 1H), 8.63 (d, J = 5.1 Hz, 1H), 8.38 (d, J = 1.1 Hz, 1H), 8.21 (s, 1H), 7.98 (d, J = 8.1 Hz, 1H), 7.86 (dd, J = 5.1, 1.8 Hz, 1H), 7.10 (dd, J = 8.2, 1.6 Hz, 1H), 4.55-4.40 (m, 1H), 3.99 (d, J = 11.4 Hz, 2H), 3.50 (td, J = 11.5, 2.5 Hz, 2H), 2.97 (dt, J = 13.7, 6.9 Hz, 1H), 2.10-1.90 (m, 4H), 1.26 (d, J = 6.9 Hz, 6H). LC/MS (ESI) m/z: 435.2 $(M + H)^+$. |
| 26 | 4-isopropyl-2-[[3-(8-quinolyl)benzoyl]amino]benzoic acid 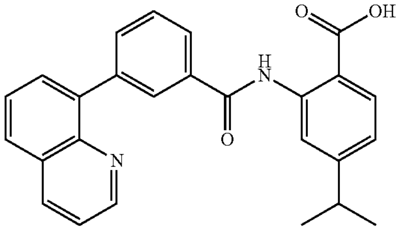 [SMILES: CC(C)c1ccc(C(=O)O)c(NC(=O)c2cccc(-c3cccc4cccnc34)c2)c1] | $^1H$ NMR (400 MHz, DMSO-d6) δ 12.32 (s, 1H), 8.96 (dd, J = 4.2, 1.7 Hz, 1H), 8.72 (d, J = 1.4 Hz, 1H), 8.53 (dd, J = 8.3, 1.4 Hz, 1H), 8.27 (s, 1H), 8.13-8.06 (m, 1H), 8.04-7.86 (m, 4H), 7.74 (dt, J = 18.4, 7.8 Hz, 2H), 7.64 (dd, J = 8.3, 4.2 Hz, 1H), 7.11 (dd, J = 8.2, 1.6 Hz, 1H), 2.98 (dt, J = 13.6, 6.8 Hz, 1H), 1.23 (t, J = 13.9 Hz, 6H). LC/MS (ESI) m/z: 411.2 $(M + H)^+$. |
| 27 | 4-tert-butyl-2-[[3-(1H-pyrazol-4-yl)benzoyl]amino]benzoic acid 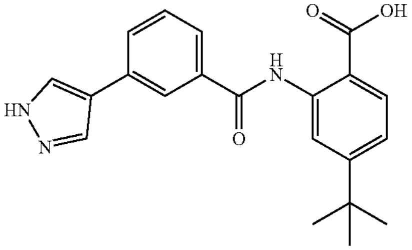 [SMILES: CC(C)(C)c1ccc(C(=O)O)c(NC(=O)c2cccc(-c3cn[nH]c3)c2)c1] | $^1H$ NMR (400 MHz, DMSO-d6) δ 13.32 (s, 1H), 12.75 (s, 1H), 8.89 (d, J = 1.8 Hz, 1H), 8.21 (s, 1H), 8.15 (s, 2H), 8.00 (d, J = 8.3 Hz, 1H), 7.86 (d, J = 7.8 Hz, 1H), 7.78 (d, J = 7.7 Hz, 1H), 7.56 (t, J = 7.7 Hz, 1H), 7.23 (dd, J = 8.3, 1.8 Hz, 1H), 1.33 (s, 9H). LC/MS (ESI) m/z: 364.1 $(M + H)^+$. |

TABLE 2-continued

| Example # | Name/Structure | Spectral data |
|---|---|---|
| 28 | 4-tert-butyl-2-[[3-(1-tetrahydropyran-4-ylpyrazol-3-yl)benzoyl]amino]benzoic acid 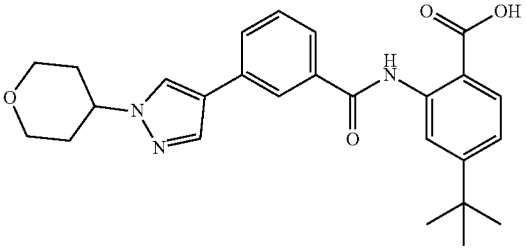 [SMILES: CC(C)(C)c1ccc(C(=O)O)c(NC(=O)c2cccc(-c3cnn(C4CCOCC4)c3)c2)c1] | $^1$H NMR (400 MHz, DMSO-d6) δ 12.69 (s, 1H), 8.88 (d, J = 1.9 Hz, 1H), 8.38 (s, 1H), 8.19 (s, 1H), 8.00 (d, J = 8.1 Hz, 2H), 7.84 (d, J = 7.8 Hz, 1H), 7.77 (d, J = 8.0 Hz, 1H), 7.56 (t, J = 7.7 Hz, 1H), 7.23 (dd, J = 8.4, 1.9 Hz, 1H), 4.44 (tt, J = 10.3, 5.0 Hz, 1H), 3.98 (d, J = 11.1 Hz, 2H), 3.49 (td, J = 11.5, 2.9 Hz, 3H), 2.08-1.90 (m, 4H), 1.33 (s, 9H). LC/MS (ESI) m/z: 448.1 (M + H)$^+$. |
| 30 | 4-tert-butyl-2-[[4-(1-tetrahydropyran-4-ylpyrazol-4-yl)pyridine-2-carbonyl]amino]benzoic acid 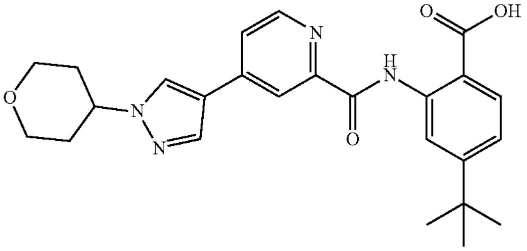 [SMILES: CC(C)(C)c1ccc(C(=O)O)c(NC(=O)c2cc(-c3cnn(C4CCOCC4)c3)ccn2)c1] | $^1$H NMR (400 MHz, DMSO-d6) δ 13.14 (s, 1H), 9.06 (d, J = 1.9 Hz, 1H), 8.70 (s, 1H), 8.64 (d, J = 5.1 Hz, 1H), 8.42 (d, J = 1.1 Hz, 1H), 8.22 (s, 1H), 7.99 (d, J = 8.3 Hz, 1H), 7.86 (dd, J = 5.1, 1.8 Hz, 1H), 7.26 (dd, J = 8.4, 1.9 Hz, 1H), 4.54-4.35 (m, 1H), 3.99 (dd, J = 11.0, 2.8 Hz, 2H), 3.50 (td, J = 11.5, 2.4 Hz, 2H), 2.13-1.88 (m, 4H), 1.33 (d, J = 9.4 Hz, 9H). LC/MS (ESI) m/z: 449.2 (M + H)$^+$. |
| 32 | 4-tert-butyl-2-[[3-(8-quinolyl)benzoyl]amino]benzoic acid 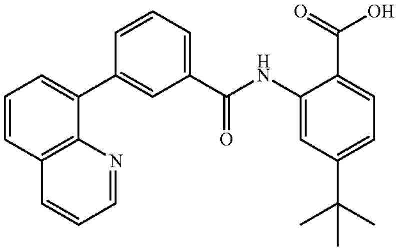 [SMILES: CC(C)(C)c1ccc(C(=O)O)c(NC(=O)c2cccc(-c3cccc4cccnc34)c2)c1] | $^1$H NMR (400 MHz, DMSO-d6) δ 12.30 (s, 1H), 8.95 (dd, J = 4.1, 1.8 Hz, 1H), 8.91 (d, J = 1.9 Hz, 1H), 8.50 (dd, J = 8.3, 1.7 Hz, 1H), 8.27 (s, 1H), 8.08 (dd, J = 8.2, 1.2 Hz, 1H), 8.08 (dd, J = 8.2, 1.2 Hz, 1H), 8.04-7.91 (m, 3H), 7.88 (dd, J = 7.1, 1.3 Hz, 1H), 7.73 (dt, J = 15.5, 7.8 Hz, 2H), 7.62 (dd, J = 8.3, 4.2 Hz, 1H), 7.26 (dd, J = 8.4, 1.9 Hz, 1H), 1.41-1.28 (m, 9H). LC/MS (ESI) m/z: 425.1 (M + H)$^+$. |
| 33 | 4-methoxy-2-[[3-(1H-pyrazol-4-yl)benzoyl]amino]benzoic acid 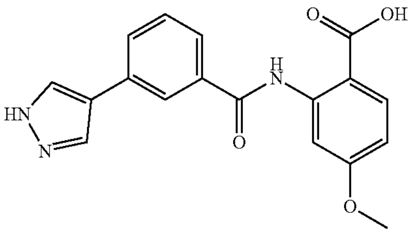 [SMILES: COc1ccc(C(=O)O)c(NC(=O)c2cccc(-c3cn[nH]c3)c2)c1] | $^1$H NMR (400 MHz, DMSO-d6) δ 13.22 (s, 1H), 13.02-12.55 (m, 1H), 8.44 (d, J = 2.6 Hz, 1H), 8.17 (d, J = 18.6 Hz, 3H), 8.02 (d, J = 8.9 Hz, 1H), 7.87 (d, J = 7.8 Hz, 1H), 7.77 (d, J = 7.9 Hz, 1H), 7.57 (t, J = 7.7 Hz, 1H), 6.76 (dd, J = 8.8, 2.6 Hz, 1H), 3.86 (s, 3H). LC/MS (ESI) m/z: 338.0 (M − H) . |

TABLE 2-continued

| Example # | Name/Structure | Spectral data |
|---|---|---|
| 34 | 4-methoxy-2-[3-(1-tetrahydropyran-4-ylpyrazol-4-yl)benzoyl]amino]benzoic acid 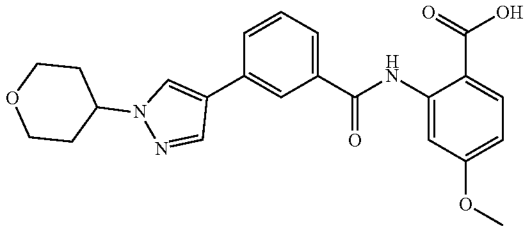 [SMILES: COc1ccc(C(=O)O)c(NC(=O)c2cccc(-c3cnn(C4CCOCC4)c3)c2)c1] | $^1H$ NMR (400 MHz, DMSO-d6) δ 13.48 (s, 1H), 12.70 (s, 1H), 8.43 (d, J = 2.6 Hz, 1H), 8.38 (s, 1H), 8.17 (s, 1H), 8.02 (d, J = 8.9 Hz, 1H), 7.98 (s, 1H), 7.85 (d, J = 7.8 Hz, 1H), 7.76 (d, J = 8.0 Hz, 1H), 7.57 (t, J = 7.8 Hz, 1H), 6.77 (dd, J = 8.9, 2.6 Hz, 1H), 4.44 (tt, J = 9.9, 5.0 Hz, 1H), 4.01 (dd, J = 19.0, 9.1 Hz, 2H), 3.86 (s, 3H), 3.49 (td, J = 11.4, 3.0 Hz, 2H), 1.98 (ddd, J = 17.4, 11.7, 5.2 Hz, 4H). LC/MS (ESI) m/z: 422.1 $(M + H)^+$. |
| 36 | 4-methoxy-2-[[4-(1-tetrahydropyran-4-ylpyrazol-4-yl)pyridine-2-carbonyl]amino]benzoic acid 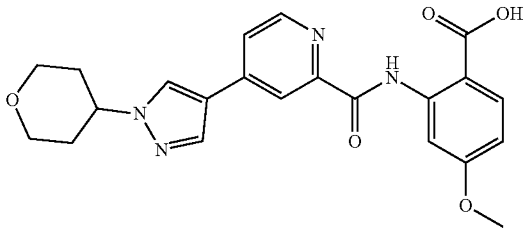 [SMILES: COc1ccc(C(=O)O)c(NC(=O)c2cc(-c3cnn(C4CCOCC4)c3)ccn2)c1] | $^1H$ NMR (400 MHz, DMSO-d6) δ 13.44 (s, 1H), 8.70 (s, 1H), 8.63 (d, J = 5.1 Hz, 1H), 8.56 (d, J = 2.5 Hz, 1H), 8.37 (s, 1H), 8.22 (s, 1H), 8.02 (d, J = 8.8 Hz, 1H), 7.86 (d, J = 3.5 Hz, 1H), 6.77 (dd, J = 8.8, 2.5 Hz, 1H), 4.50-4.38 (m, 1H), 3.98 (d, J = 11.1 Hz, 2H), 3.86 (s, 3H), 3.50 (dd, J = 11.4, 9.0 Hz, 2H), 2.12-1.90 (m, 4H). LC/MS (ESI) m/z: 423.1 $(M + H)^+$. |
| 38 | 4-methoxy-2-[3-(8-quinolyl)benzoyl]amino]benzoic acid 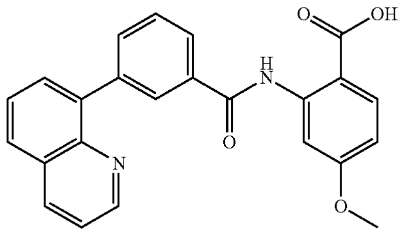 [SMILES: COc1ccc(C(=O)O)c(NC(=O)c2cccc(-c3cccc4cccnc34)c2)c1] | $^1H$ NMR (400 MHz, DMSO-d6) δ 13.66-13.08 (m, 1H), 12.56 (s, 1H), 8.94 (dd, J = 4.1, 1.7 Hz, 1H), 8.48 (dd, J = 13.2, 4.7 Hz, 2H), 8.27 (s, 1H), 8.08 (d, J = 8.2 Hz, 1H), 8.01 (dd, J = 8.4, 3.9 Hz, 2H), 7.94 (d, J = 7.8 Hz, 1H), 7.88 (d, J = 5.9 Hz, 1H), 7.73 (dt, J = 13.1, 7.8 Hz, 2H), 7.62 (dd, J = 8.3, 4.2 Hz, 1H), 6.78 (dd, J = 8.9, 2.6 Hz, 1H), 3.87 (s, 3H). LC/MS (ESI) m/z: 399.0 $(M + H)^+$. |
| 39 | 2-[[3-(1H-pyrazol-4-yl)benzoyl]amino]-4-(trifluoromethoxy)benzoic acid 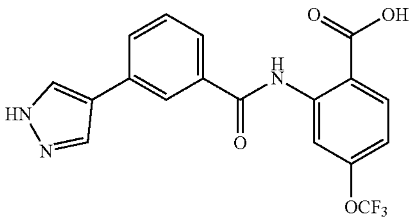 [SMILES: O=C(Nc1cc(OC(F)(F)F)ccc1C(=O)O)c1cccc(-c2cn[nH]c2)c1] | $^1H$ NMR (400 MHz, DMSO-d6) δ 12.39 (s, 1H), 8.80 (s, 1H), 8.19 (t, J = 9.0 Hz, 4H), 7.91 (d, J = 7.4 Hz, 1H), 7.76 (d, J = 7.7 Hz, 1H), 7.59 (t, J = 7.7 Hz, 1H), 7.21 (d, J = 8.6 Hz, 1H). LC/MS (ESI) m/z: 392.1 $(M + H)^+$. |
| 40 | 2-[3-(1-tetrahydropyran-4-ylpyrazol-4-yl)benzoyl]amino]-4-(trifluoromethoxy)benzoic acid 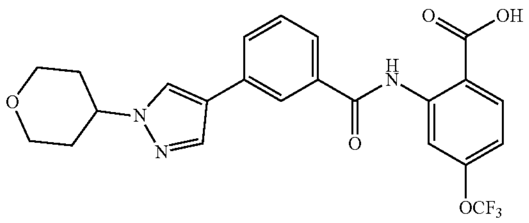 [SMILES: O=C(Nc1cc(OC(F)(F)F)ccc1C(=O)O)c1cccc(-c2cnn(C3CCOCC3)c2)c1] | $^1H$ NMR (400 MHz, DMSO-d6) δ 14.80-13.74 (m, 1H), 12.76 (s, 1H), 8.79 (d, J = 1.2 Hz, 1H), 8.39 (s, 1H), 8.20 (d, J = 8.8 Hz, 2H), 7.99 (s, 1H), 7.87 (d, J = 7.8 Hz, 1H), 7.76 (d, J = 8.0 Hz, 1H), 7.58 (t, J = 7.7 Hz, 1H), 7.18 (dd, J = 8.8, 1.5 Hz, 1H), 4.44 (tt, J = 10.0, 4.9 Hz, 1H), 4.05-3.89 (m, 2H), 3.49 (td, J = 11.4, 2.9 Hz, 2H), 1.97 (ddd, J = 22.3, 12.4, 7.9 Hz, 4H). LC/MS (ESI) m/z: 476.5 $(M + H)^+$. |

TABLE 2-continued

| Example # | Name/Structure | Spectral data |
|---|---|---|
| 42 | 2-[[4-(1-tetrahydropyran-4-ylpyrazol-4-yl)pyridine-2-carbonyl]amino]-4-(trifluoromethoxy)benzoic acid 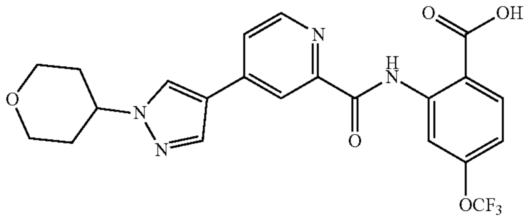 | $^1$H NMR (400 MHz, DMSO-d6) δ 14.21-13.45 (m, 1H), 13.26 (s, 1H), 8.96 (d, J = 1.3 Hz, 1H), 8.72 (s, 1H), 8.66 (d, J = 5.2 Hz, 1H), 8.40 (d, J = 1.1 Hz, 1H), 8.23 (s, 1H), 8.19 (d, J = 8.8 Hz, 1H), 7.89 (dd, J = 5.1, 1.8 Hz, 1H), 7.20 (d, J = 8.9 Hz, 1H), 4.46 (dt, J = 15.7, 5.5 Hz, 1H), 4.00 (t, J = 13.8 Hz, 2H), 3.50 (td, J = 11.6, 2.4 Hz, 2H), 2.12-1.91 (m, 4H). LC/MS (ESI) m/z: 477.1 (M + H)$^+$. |
| 44 | 2-[[3-(8-quinolyl)benzoyl]amino]-4-(trifluoromethoxy)benzoic acid 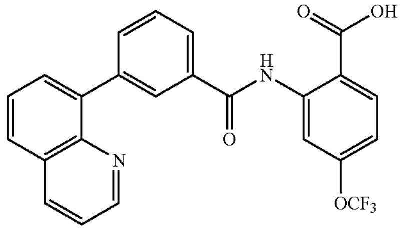 [SMILES: O=C(Nc1cc(OC(F)(F)F)ccc1C(=O)O)c1cccc(-c2cccc3cccnc23)c1] | $^1$H NMR (400 MHz, DMSO-d6) δ 12.46 (s, 1H), 8.95 (dd, J = 4.2, 1.6 Hz, 1H), 8.81 (d, J = 1.3 Hz, 1H), 8.51 (d, J = 8.4 Hz, 1H), 8.27 (s, 1H), 8.18 (d, J = 8.8 Hz, 1H), 8.09 (d, J = 8.1 Hz, 1H), 8.02 (d, J = 7.6 Hz, 1H), 7.96 (d, J = 7.7 Hz, 1H), 7.88 (d, J = 5.9 Hz, 1H), 7.74 (dd, J = 17.3, 7.8 Hz, 2H), 7.63 (dd, J = 8.0, 3.8 Hz, 1H), 7.20 (d, J = 8.7 Hz, 1H). LC/MS (ESI) m/z: 453.4 (M + H)$^+$. |
| 45 | 6-chloro-2-[[3-(1H-pyrazol-4-yl)benzoyl]amino]pyridine-3-carboxylic acid 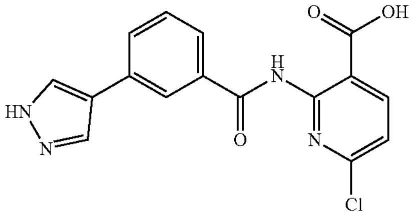 | $^1$H NMR (400 MHz, DMSO-d6) δ 11.75 (s, 1H), 8.26 (d, J = 8.2 Hz, 2H), 8.16 (s, 2H), 7.88 (d, J = 7.7 Hz, 1H), 7.79 (d, J = 7.8 Hz, 1H), 7.54 (t, J = 7.7 Hz, 1H), 7.41 (d, J = 8.1 Hz, 1H). LC/MS (ESI) m/z: 342.9 (M + H)$^+$. |
| 46 | 6-chloro-2-[[3-(1-tetrahydropyran-4-ylpyrazol-4-yl)benzoyl]amino]pyridine-3-carboxylic acid 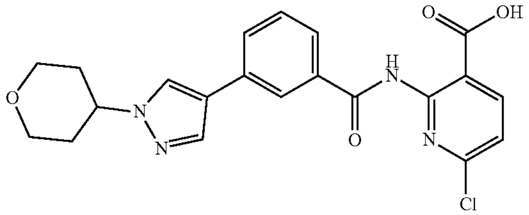 [SMILES: O=C(Nc1nc(Cl)ccc1C(=O)O)c1cccc(-c2cnn(C3CCOCC3)c2)c1] | $^1$H NMR (400 MHz, DMSO-d6) δ 11.46 (s, 1H), 8.37 (s, 1H), 8.26-8.21 (m, 2H), 8.00 (s, 1H), 7.85 (d, J = 7.9 Hz, 1H), 7.79 (d, J = 8.4 Hz, 1H), 7.54 (t, J = 7.8 Hz, 1H), 7.43 (d, J = 8.1 Hz, 1H), 4.43 (t, J = 7.8 Hz, 1H), 3.98 (d, J = 11.6 Hz, 2H), 3.49 (dd, J = 11.4, 8.9 Hz, 3H), 2.00 (dd, J = 13.5, 9.3 Hz, 4H). LC/MS (ESI) m/z: 427.0 (M + H)$^+$. |
| 48 | 6-chloro-2-[[3-(8-quinolyl)benzoyl]amino]pyridine-3-carboxylic acid 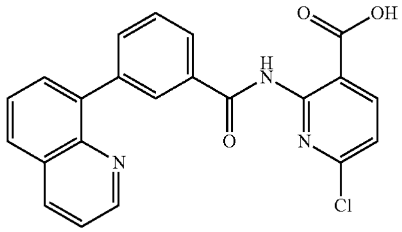 | $^1$H NMR (400 MHz, DMSO-d6) δ 11.63 (s, 1H), 8.50 (dd, J = 8.3, 1.7 Hz, 1H), 8.29-8.21 (m, 2H), 8.08 (d, J = 6.9 Hz, 1H), 8.02 (d, J = 8.2 Hz, 1H), 7.95 (d, J = 7.8 Hz, 1H), 7.90 (dd, J = 7.2, 1.4 Hz, 1H), 7.78-7.72 (m, 1H), 7.67 (t, J = 7.8 Hz, 1H), 7.62 (dd, J = 8.3, 4.2 Hz, 1H), 7.42 (d, J = 8.1 Hz, 1H). LC/MS (ESI) m/z: 404.0 (M + H)$^+$. |

TABLE 2-continued

| Example # | Name/Structure | Spectral data |
|---|---|---|
| 49 | 2-methyl-4-[[3-(1H-pyrazol-4-yl)benzoyl]amino]pyrimidine-5-carboxylic acid 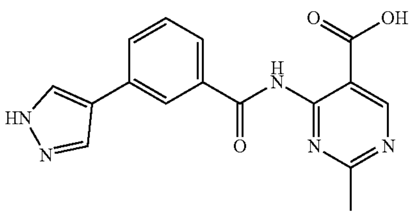 [SMILES: Cc1ncc(C(=O)O)c(NC(=O)c2cccc(-c3cn[nH]c3)c2)n1] | $^1H$ NMR (400 MHz, DMSO-d6) δ 15.42 (s, 1H), 13.07 (s, 1H), 8.91 (s, 1H), 8.26 (s, 1H), 7.83 (dd, J = 16.9, 7.9 Hz, 2H), 7.54 (t, J = 7.8 Hz, 1H), 2.53 (s, 3H). LC/MS (ESI) m/z: 324.0 $(M + H)^+$. |
| 50 | 2-methyl-4-[[3-(1-tetrahydropyran-4-ylpyrazol-4-yl)benzoyl]amino]pyrimidine-5-carboxylic acid 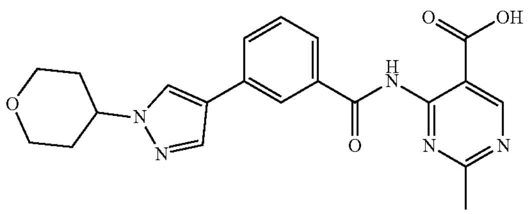 [SMILES: Cc1ncc(C(=O)O)c(NC(=O)c2cccc(-c3cnn(C4CCOCC4)c3)c2)n1] | $^1H$ NMR (400 MHz, DMSO-d6) δ 11.64 (s, 1H), 8.95 (s, 1H), 8.38 (s, 1H), 8.22 (s, 1H), 8.00 (s, 1H), 7.87 (d, J = 7.7 Hz, 1H), 7.78 (d, J = 8.0 Hz, 1H), 7.55 (t, J = 7.7 Hz, 1H), 4.48-4.38 (m, 1H), 3.98 (d, J = 11.1 Hz, 2H), 3.49 (s, 2H), 2.64 (s, 3H), 1.99 (dd, J = 13.6, 9.0 Hz, 4H). LC/MS (ESI) m/z: 408.1 $(M + H)^+$. |
| 52 | methyl-4-[[3-(8-quinolyl)benzoyl]amino]pyrimidine-5-carboxylic acid 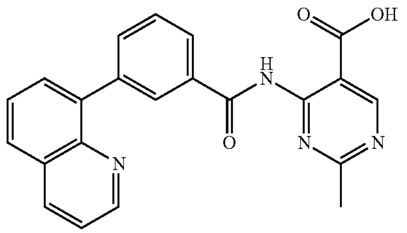 [SMILES: Cc1ncc(C(=O)O)c(NC(=O)c2cccc(-c3cccc4cccnc34)c2)n1] | $^1H$ NMR (400 MHz, DMSO-d6) δ 11.84 (s, 1H), 8.99-8.87 (m, 2H), 8.48 (dd, J = 8.3, 1.6 Hz, 1H), 8.27 (s, 1H), 8.07 (d, J = 7.7 Hz, 1H), 8.02 (d, J = 7.8 Hz, 1H), 7.97 (d, J = 7.7 Hz, 1H), 7.89 (d, J = 6.3 Hz, 1H), 7.74 (t, J = 7.6 Hz, 1H), 7.68 (t, J = 7.7 Hz, 1H), 7.61 (dd, J = 8.3, 4.1 Hz, 1H), 2.63 (s, 3H). LC/MS (ESI) m/z: 385.0$(M + H)^+$. |
| 53 | 6-methoxy-2-[[3-(1H-pyrazol-4-yl)benzoyl]amino]pyridine-3-carboxylic acid 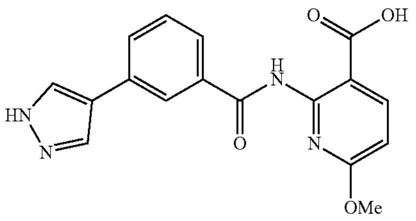 | $^1H$ NMR (400 MHz, DMSO-d6) δ 11.80 (s, 1H), 8.19 (dd, J = 16.5, 10.6 Hz, 4H), 7.87 (d, J = 7.7 Hz, 1H), 7.75 (d, J = 7.9 Hz, 1H), 7.55 (t, J = 7.7 Hz, 1H), 6.64 (d, J = 8.6 Hz, 1H), 3.94 (s, 3H). LC/MS (ESI) m/z: 339.0 $(M + H)^+$. |
| 54 | 6-methoxy-2-[[3-(1-tetrahydropyran-4-ylpyrazol-4-yl)benzoyl]amino]pyridine-3-carboxylic acid 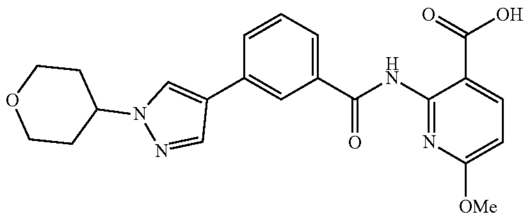 [SMILES: COc1ccc(C(=O)O)c(NC(=O)c2cccc(-c3cnn(C4CCOCC4)c3)c2)n1] | $^1H$ NMR (400 MHz, DMSO-d6) δ 13.46 (s, 1H), 11.76 (s, 1H), 8.39 (s, 1H), 8.26-8.15 (m, 2H), 7.99 (s, 1H), 7.85 (d, J = 7.9 Hz, 1H), 7.74 (d, J = 7.9 Hz, 1H), 7.56 (t, J = 7.7 Hz, 1H), 6.65 (d, J = 8.6 Hz, 1H), 4.43 (dt, J = 9.7, 5.4 Hz, 1H), 3.98 (d, J = 11.5 Hz, 2H), 3.94 (s, 3H), 3.49 (td, J = 11.5, 2.9 Hz, 2H), 1.98 (ddd, J = 24.2, 11.4, 4.2 Hz, 4H). LC/MS (ESI) m/z: 423.1$(M + H)^+$. |

TABLE 2-continued

| Example # | Name/Structure | Spectral data |
|---|---|---|
| 56 | 4,5-dichloro-2-[[3-(1-tetrahydropyran-4-ylpyrazol-4-yl)benzoyl]amino]benzoic acid 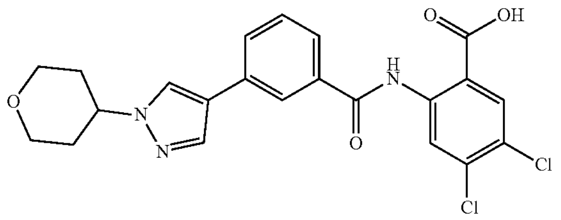 [SMILES: O=C(Nc1cc(Cl)c(Cl)cc1C(=O)O)c1cccc(-c2cnn(C3CCOCC3)c2)c1] | $^1$H NMR (400 MHz, MeOD) δ 9.01 (s, 1H), 8.34-8.12 (m, 3H), 7.95 (s, 1H), 7.89 (d, J = 8.4 Hz, 1H), 7.79 (d, J = 8.1 Hz, 1H), 7.52 (t, J = 7.8 Hz, 1H), 4.58-4.34 (m, 1H), 4.09 (dd, J = 11.1, 4.2 Hz, 2H), 3.60 (td, J = 11.8, 2.4 Hz, 2H), 2.24-2.04 (m, 4H). LC/MS (ESI) m/z: 460 $(M + H)^+$. |
| 58 | 4,5-dichloro-2-[[3-(1H-pyrazol-4-yl)benzoyl]amino]benzoic acid 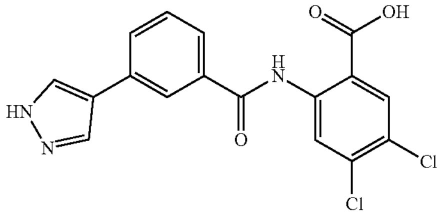 [SMILES: O=C(Nc1cc(Cl)c(Cl)cc1C(=O)O)c1cccc(-c2cn[nH]c2)c1] | $^1$H NMR (400 MHz, MeOD) δ 9.01 (s, 1H), 8.26-8.20 (m, 2H), 8.08 (s, 2H), 7.90 (d, J = 8.1 Hz, 1H), 7.81 (d, J = 7.9 Hz, 1H), 7.53 (t, J = 7.8 Hz, 1H). LC/MS (ESI) m/z: 376 $(M + H)^+$. |
| 59 | 3-[[3-(1-tetrahydropyran-4-ylpyrazol-4-yl)benzoyl]amino]naphthalene-2-carboxylic acid 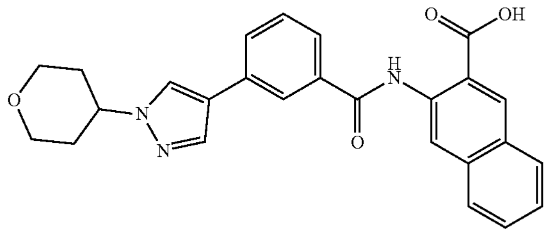 [SMILES: O=C(Nc1cc2ccccc2cc1C(=O)O)c1cccc(-c2cnn(C3CCOCC3)c2)c1] | $^1$H NMR (400 MHz, DMSO-d6) δ 13.98 (s, 1H), 12.46 (s, 1H), 9.16 (s, 1H), 8.77 (s, 1H), 8.38 (s, 1H), 8.21 (s, 1H), 8.06 (d, J = 8.2 Hz, 1H), 8.00 (s, 1H), 7.94 (d, J = 8.2 Hz, 1H), 7.83 (dd, J = 18.0, 7.8 Hz, 2H), 7.58 (tt, J = 29.7, 7.3 Hz, 3H), 4.45 (tt, J = 10.1, 5.1 Hz, 1H), 4.06-3.93 (m, 2H), 3.50 (td, J = 11.4, 3.0 Hz, 2H), 2.00 (ddd, J = 17.2, 11.4, 4.2 Hz, 4H). LC/MS (ESI) m/z: 442.2 $(M + H)^+$. |
| 61 | 3-[[3-(1H-pyrazol-4-yl)benzoyl]amino]naphthalene-2-carboxylic acid 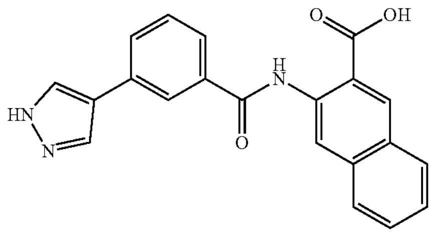 [SMILES: O=C(Nc1cc2ccccc2cc1C(=O)O)c1cccc(-c2cn[nH]c2)c1] | $^1$H NMR (400 MHz, DMSO-d6) δ 12.20 (s, 1H), 9.18 (s, 1H), 8.79 (s, 1H), 8.23 (s, 1H), 8.17 (s, 2H), 8.08 (d, J = 8.1 Hz, 1H), 7.95 (d, J = 8.2 Hz, 1H), 7.89 (d, J = 7.8 Hz, 1H), 7.81 (d, J = 7.9 Hz, 1H), 7.66 (t, J = 7.5 Hz, 1H), 7.59 (t, J = 7.7 Hz, 1H), 7.53 (t, J = 7.5 Hz, 1H). LC/MS (ESI) m/z: 358.1 $(M + H)^+$. |
| 62 | 2-[[3-(1-tetrahydropyran-4-ylpyrazol-4-yl)benzoyl]amino]quinoline-3-carboxylic acid 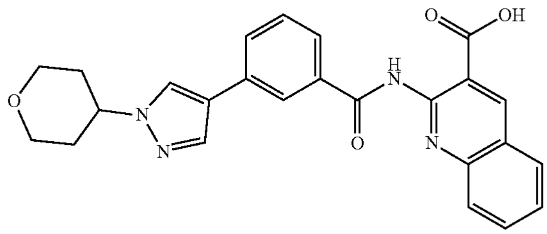 [SMILES: O=C(Nc1nc2ccccc2cc1C(=O)O)c1cccc(-c2cnn(C3CCOCC3)c2)c1] | $^1$H NMR (400 MHz, DMSO-d6) δ 11.78 (s, 1H), 8.93 (s, 1H), 8.38 (s, 1H), 8.30 (s, 1H), 8.15 (d, J = 7.9 Hz, 1H), 8.02 (s, 1H), 7.96 (d, J = 8.4 Hz, 1H), 7.89-7.81 (m, 3H), 7.63 (t, J = 7.1 Hz, 1H), 7.55 (t, J = 7.7 Hz, 1H), 4.51-4.36 (m, 1H), 3.99 (d, J = 11.0 Hz, 2H), 3.50 (td, J = 11.4, 2.6 Hz, 2H), 1.99 (ddd, J = 15.8, 11.4, 4.0 Hz, 4H). LC/MS (ESI) m/z: 443.2 $(M + H)^+$. |

TABLE 2-continued

| Example # | Name/Structure | Spectral data |
|---|---|---|
| 64 | 2-[3-(1H-pyrazol-4-yl)benzoyl]amino]quinoline-3-carboxylic acid 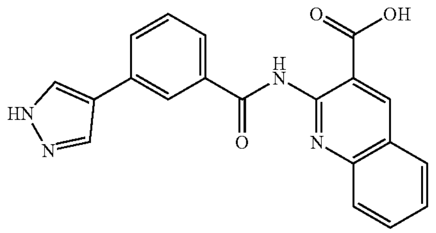 [SMILES: O=C(Nc1nc2ccccc2cc1C(=O)O)c1cccc(-c2cn[nH]c2)c1] | $^1H$ NMR (400 MHz, DMSO-d6) δ 13.08 (s, 1H), 8.90 (s, 1H), 8.33 (s, 1H), 8.22-8.05 (m, 3H), 7.95-7.77 (m, 4H), 7.56 (dt, J = 15.5, 7.6 Hz, 2H). LC/MS (ESI) m/z: 459.1 $(M + H)^+$. |
| 65 | 7-(3-(1-(tetrahydro-2H-pyran-4-yl)-1H-pyrazol-4-yl)benzamido)-2,3-dihydrobenzo[b][1,4]dioxine-6-carboxylic acid 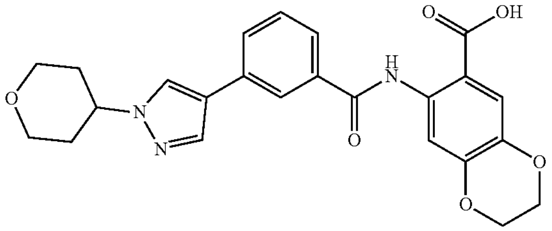 [SMILES: O=C(Nc1cc2c(cc1C(=O)O)OCCO2)c1cccc(-c2cnn(C3CCOCC3)c2)c1] | $^1H$ NMR (400 MHz, DMSO-d6) δ 13.56 (s, 1H), 12.14 (s, 1H), 8.38 (s, 1H), 8.30 (s, 1H), 8.13 (s, 1H), 7.98 (s, 1H), 7.84 (d, J = 7.7 Hz, 1H), 7.72 (d, J = 7.6 Hz, 1H), 7.56 (t, J = 7.8 Hz, 1H), 7.50 (s, 1H), 4.43 (dt, J = 15.9, 5.3 Hz, 1H), 4.33 (dd, J = 32.0, 3.0 Hz, 4H), 3.98 (d, J = 11.5 Hz, 2H), 3.49 (td, J = 11.5, 3.0 Hz, 2H), 2.08-1.91 (m, 4H). LC/MS (ESI) m/z: 450.2$(M + H)^+$. |
| 65a | [6-[[3-(1-tetrahydropyran-4-ylpyrazol-4-yl)benzoyl]amino]-2,3-dihydro-1,4-benzodioxine-7-carbonyl]oxysodium 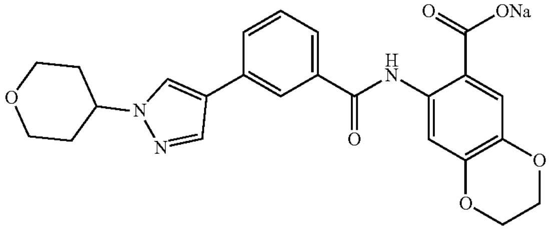 | $^1H$ NMR (400 MHz, DMSO-d6) δ 15.44 (s, 1H), 8.34 (s, 1H), 8.22 (d, J = 21.0 Hz, 2H), 7.96 (s, 1H), 7.88-7.72 (m, J = 19.2, 7.6 Hz, 2H), 7.56-7.44 (m, 2H), 4.54-4.38 (m, 1H), 4.24 (d, J = 14.8 Hz, 4H), 3.98 (d, J = 11.2 Hz, 2H), 3.56-3.42 (m, 2H), 2.10-1.94 (m, 4H). LC/MS [M − Na + H]: 450.0. |
| 67 | 6-[[3-(1H-pyrazol-3-yl)benzoyl]amino]-2,3-dihydro-1,4-benzodioxine-7-carboxylic acid 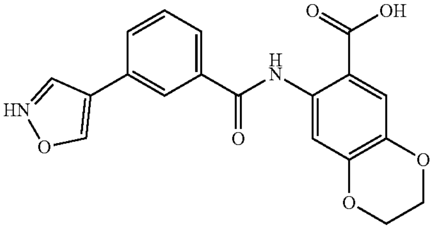 [SMILES: O=C(Nc1cc2c(cc1C(=O)O)OCCO2)c1cccc(-c2cnoc2)c1] | $^1H$ NMR (400 MHz, DMSO-d6) δ 13.90-12.98 (m, 1H), 12.16 (s, 1H), 8.31 (s, 1H), 8.14 (s, 3H), 7.86 (d, J = 7.6 Hz, 1H), 7.73 (d, J = 8.1 Hz, 1H), 7.56 (t, J = 7.7 Hz, 1H), 7.50 (s, 1H), 4.43-4.33 (m, 2H), 4.33-4.22 (m, 2H). LC/MS (ESI) m/z: 366.1 $(M + H)^+$. |

TABLE 2-continued

| Example # | Name/Structure | Spectral data |
|---|---|---|
| 68 | 6-[[3-(1-tetrahydropyran-4-ylpyrazol-4-yl)benzoyl]amino]-1,3-benzodioxole-5-carboxylic acid 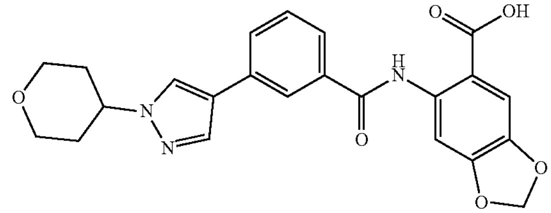 [SMILES: O=C(Nc1cc2c(cc1C(=O)O)OCO2)c1cccc(-c2cnn(C3CCOCC3)c2)c1] | $^1H$ NMR (400 MHz, DMSO-d6) δ 8.34 (d, J = 2.5 Hz, 2H), 8.20 (s, 1H), 7.96 (s, 1H), 7.80 (t, J = 9.1 Hz, 2H), 7.52 (dd, J = 15.9, 8.1 Hz, 2H), 6.03 (s, 2H), 4.44 (dq, J = 15.7, 5.3 Hz, 1H), 3.98 (d, J = 11.1 Hz, 2H), 3.49 (td, J = 11.3, 3.3 Hz, 2H), 1.99 (ddd, J = 17.1, 11.0, 4.0 Hz, 4H). LC/MS (ESI) m/z: 436 $(M + H)^+$. |
| 69 | 6-[[3-(1H-pyrazol-4-yl)benzoyl]amino]-1,3-benzodioxole-5-carboxylic acid 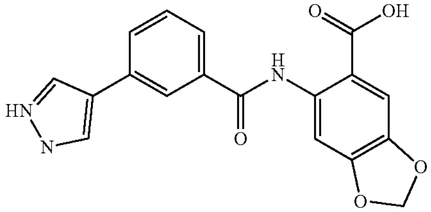 [SMILES: O=C(Nc1cc2c(cc1C(=O)O)OCO2)c1cccc(-c2cn[nH]c2)c1] | $^1H$ NMR (400 MHz, DMSO-d6) δ 12.47 (s, 1H), 8.37 (s, 1H), 8.16 (s, 3H), 7.87 (d, J = 7.3 Hz, 1H), 7.74 (d, J = 7.5 Hz, 1H), 7.56 (t, J = 7.7 Hz, 1H), 7.49 (s, 1H), 6.16 (s, 2H). LC/MS (ESI) m/z: 352 $(M + H)^+$. |
| 70 | 5-[[3-(1-tetrahydropyran-4-ylpyrazol-4-yl)benzoyl]amino]-1H-indazole-6-carboxylic acid 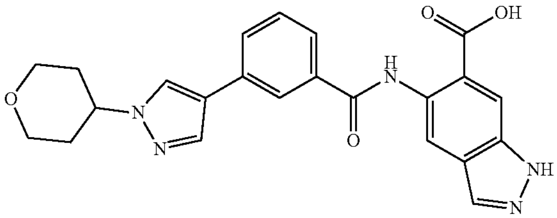 [SMILES: O=C(Nc1cc2cn[nH]c2cc1C(=O)O)c1cccc(-c2cnn(C3CCOCC3)c2)c1] | $^1H$ NMR (400 MHz, DMSO-d6) δ 11.97 (s, 1H), 9.00 (s, 1H), 8.38 (s, 1H), 8.32 (s, 1H), 8.22 (d, J = 0.9 Hz, 1H), 8.18 (s, 1H), 7.99 (s, 1H), 7.84 (d, J = 7.9 Hz, 1H), 7.77 (d, J = 8.2 Hz, 1H), 7.57 (t, J = 7.7 Hz, 1H), 4.44 (tt, J = 9.7, 4.9 Hz, 1H), 3.99 (d, J = 11.2 Hz, 2H), 3.51 (dd, J = 11.3, 2.8 Hz, 2H), 2.10-1.91 (m, 4H). LC/MS (ESI) m/z: 432.1 $(M + H)^+$. |
| 71 | 1-methyl-5-[[3-(1-tetrahydropyran-4-ylpyrazol-4-yl)benzoyl]amino]indazole-6-carboxylic acid 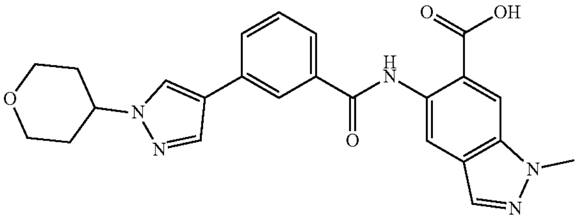 [SMILES: Cn1ncc2cc(NC(=O)c3cccc(-c4cnn(C5CCOCC5)c4)c3)c(C(=O)O)cc21] | $^1H$ NMR (400 MHz, DMSO-d6) δ 13.80 (s, 1H), 11.98 (s, 1H), 8.93 (s, 1H), 8.46 (d, J = 3.8 Hz, 2H), 8.38 (s, 1H), 8.16 (s, 1H), 7.99 (s, 1H), 7.83 (d, J = 7.8 Hz, 1H), 7.76 (d, J = 8.0 Hz, 1H), 7.56 (t, J = 7.7 Hz, 1H), 4.44 (ddd, J = 15.6, 10.4, 5.0 Hz, 1H), 4.23 (s, 3H), 3.99 (d, J = 11.0 Hz, 2H), 3.50 (td, J = 11.4, 3.0 Hz, 2H), 2.09-1.92 (m, 4H). LC/MS (ESI) m/z: 446.2 $(M + H)^+$. |
| 74 | 5-[[3-(1H-pyrazol-4-yl)benzoyl]amino]-1H-indazole-6-carboxylic acid 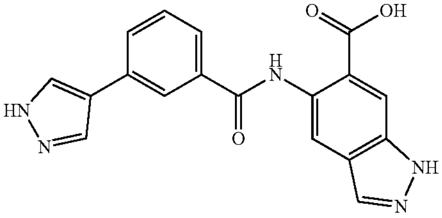 [SMILES: O=C(Nc1cc2cn[nH]c2cc1C(=O)O)c1cccc(-c2cn[nH]c2)c1] | $^1H$ NMR (400 MHz, DMSO-d6) δ 13.37 (s, 1H), 12.00 (s, 1H), 9.02 (s, 1H), 8.32 (s, 1H), 8.24-8.11 (m, 4H), 7.86 (d, J = 7.9 Hz, 1H), 7.78 (d, J = 7.4 Hz, 1H), 7.56 (t, J = 7.7 Hz, 1H). LC/MS (ESI) m/z: 348.1 $(M + H)^+$. |

TABLE 2-continued

| Example # | Name/Structure | Spectral data |
|---|---|---|
| 75 | 1-methyl-5-[3-(1H-pyrazol-4-yl)benzoyl]amino]indazole-6-carboxylic acid 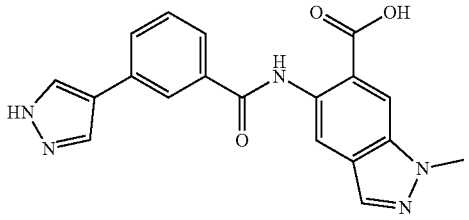 [SMILES: Cn1ncc2cc(NC(=O)c3cccc(-c4cn[nH]c4)c3)c(C(=O)O)cc21] | $^1$H NMR (400 MHz, DMSO-d6) δ 12.01 (s, 1H), 8.95 (s, 1H), 8.46 (d, J = 4.7 Hz, 2H), 8.17 (d, J = 10.7 Hz, 3H), 7.85 (d, J = 7.7 Hz, 1H), 7.77 (d, J = 7.7 Hz, 1H), 7.56 (t, J = 7.7 Hz, 1H), 4.23 (s, 3H). LC/MS (ESI) m/z: 362.1 (M + H)$^+$. |
| 76 | methyl 4-chloro-2-[[3-(1-tetrahydropyran-4-ylpyrazol-4-yl)benzoyl]amino]benzoate 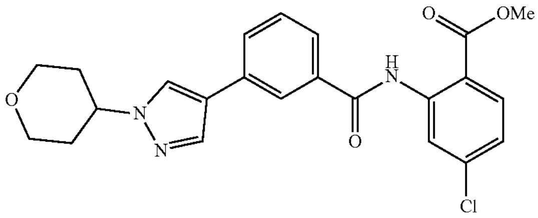 [SMILES: COC(=O)c1ccc(Cl)cc1NC(=O)c1cccc(-c2cnn(C3CCOCC3)c2)c1] | $^1$H NMR (400 MHz, DMSO-d6) δ11.66 (brs, 1H), 8.68 (d, J= 2.4 Hz, 1H), 8.39 (brs, 1H), 8.15 (t, J= 1.6 Hz, 1H), 8.02 (d, J= 8.8 Hz, 1H), 7.99 (brs, 1H), 7.88-7.86 (m, 1H), 7.75-7.73 (m, 1H), 7.59 (t, J= 8.0 Hz, 1H), 7.35-7.32 (m, 1H), 4.48-4.40 (m, 1H), 4.00-3.96 (m, 2H), 3.91 (brs, 3H), 3.54-3.46 (m, 2H), 2.07-1.93 (m, 4H). LC/MS [M + H]: 440.1 |
| 95 | 2-[[4-(1H-pyrazol-4-yl)pyridine-2-carbonyl]amino]benzoic acid 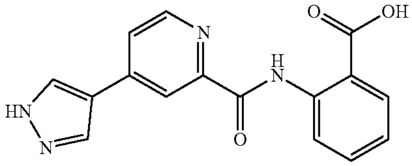 | )$^+$. $^1$H NMR (400 MHz, DMSO-d6) δ 13.04 (s, 1H), 8.88 (d, J = 8.5 Hz, 1H), 8.64 (d, J = 5.1 Hz, 1H), 8.40 (d, J = 22.2 Hz, 3H), 8.06 (d, J = 7.9 Hz, 1H), 7.90 (d, J = 4.9 Hz, 1H), 7.69 (t, J = 7.8 Hz, 1H), 7.23 (t, J = 7.5 Hz, 1H). LC/MS (ESI) m/z: 309.0 (M + H)$^+$. |
| 96 | 2-[[3-(1-tetrahydropyran-4-ylpyrazol-4-yl)benzoyl]amino]pyridine-3-carboxylic acid 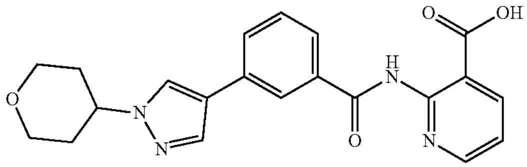 [SMILES: O=C(Nc1ncccc1C(=O)O)c1cccc(-c2cnn(C3CCOCC3)c2)c1] | $^1$H NMR (400 MHz, DMSO-d6) δ 11.42 (s, 1H), 8.60 (dd, J = 4.8, 1.9 Hz, 1H), 8.37 (s, 1H), 8.28-8.20 (m, 2H), 8.00 (s, 1H), 7.82 (dd, J = 17.8, 8.1 Hz, 2H), 7.53 (t, J = 7.7 Hz, 1H), 7.35 (dd, J = 7.7, 4.8 Hz, 1H), 4.43 (dt, J = 9.7, 5.4 Hz, 1H), 3.98 (d, J = 11.5 Hz, 2H), 3.49 (d, J = 2.6 Hz, 2H), 2.08-1.92 (m, 4H). LC/MS (ESI) m/z: 393.1(M + H)$^+$. |
| 97 | 1-methyl-3-[[4-(1H-pyrazol-4-yl)pyridine-2-carbonyl]amino]pyrazole-4-carboxylic acid 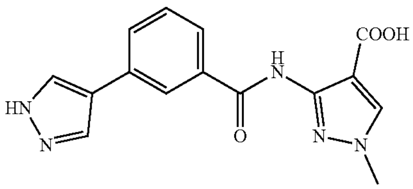 [SMILES: Cn1cc(C(=O)O)c(NC(=O)c2cccc(-c3cn[nH]c3)c2)n1] | $^1$H NMR (400 MHz, DMSO-d6) δ 12.65 (s, 1H), 10.15 (s, 1H), 8.21 (s, 1H), 8.14 (d, J = 11.5 Hz, 3H), 7.83 (d, J = 7.8 Hz, 1H), 7.72 (d, J = 7.9 Hz, 1H), 7.50 (t, J = 7.7 Hz, 1H), 3.84 (s, 3H). LC/MS (ESI) m/z: 312.00(M + H)$^+$. |

TABLE 2-continued

| Example # | Name/Structure | Spectral data |
|---|---|---|
| 98 | 1-methyl-3-[[3-(1-tetrahydropyran-4-ylpyrazol-4-yl)benzoyl]amino]pyrazole-4-carboxylic acid 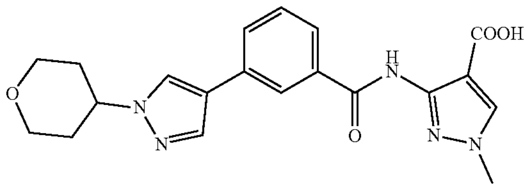 [SMILES: Cn1cc(C(=O)O)c(NC(=O)c2cccc(-c3cnn(C4CCOCC4)c3)c2)n1] | $^1H$ NMR (400 MHz, DMSO-d6) δ 12.34 (s, 1H), 10.13 (s, 1H), 8.34 (s, 1H), 8.21 (s, 1H), 8.14 (s, 1H), 7.97 (s, 1H), 7.81 (d, J = 7.9 Hz, 1H), 7.73 (d, J = 8.0 Hz, 1H), 7.50 (t, J = 7.7 Hz, 1H), 4.44-4.43 (m, 1H), 3.98 (d, J = 11.6 Hz, 2H), 3.85 (s, 3H), 3.49 (td, J = 11.5, 2.7 Hz, 2H), 2.07-1.91 (m, 4H). LC/MS (ESI) m/z: 396.05 $(M + H)^+$. |
| 99 | 2-[4-(1H-pyrazol-4-yl)pyridine-2-carbonyl]amino]pyridine-3-carboxylic acid 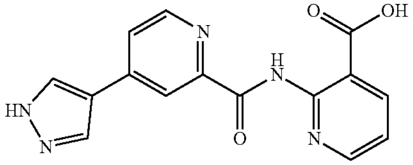 | $^1H$ NMR (400 MHz, DMSO-d6) δ 14.83 (s, 1H), 8.57 (t, J = 13.9 Hz, 1H), 8.34 (d, J = 18.0 Hz, 3H), 8.26 (s, 2H), 7.82 (d, J = 3.9 Hz, 1H), 7.09-7.00 (m, 1H). LC/MS (ESI) m/z: 310 $(M + H)^+$. |
| 100 | 2-[[4-(1-tetrahydropyran-4-ylpyrazol-4-yl)pyridine-2-carbonyl]amino]pyridine-3-carboxylic acid 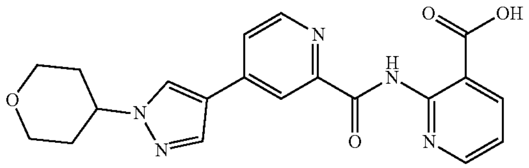 [SMILES: O=C(Nc1ncccc1C(=O)O)c1cc(-c2cnn(C3CCOCC3)c2)ccn1] | $^1H$ NMR (400 MHz, DMSO-d6) δ 12.59 (s, 1H), 8.71 (s, 1H), 8.66 (d, J = 5.6 Hz, 2H), 8.39-8.32 (m, 2H), 8.22 (s, 1H), 7.90 (s, 1H), 7.33 (d, J = 5.3 Hz, 1H), 4.47 (s, 1H), 3.99 (d, J = 10.0 Hz, 2H), 3.51 (s, 2H), 2.03 (s, 4H). LC/MS (ESI) m/z: 394 $(M + H)^+$. |
| 101 | 6-methoxy-2-[4-(1H-pyrazol-4-yl)pyridine-2-carbonyl]amino]pyridine-3-carboxylic acid 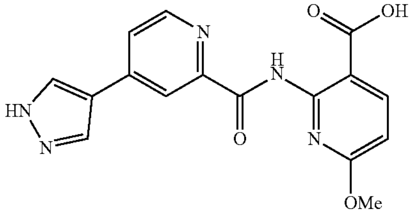 [SMILES: COc1ccc(C(=O)O)c(NC(=O)c2cc(-c3cn[nH]c3)ccn2)n1] | $^1H$ NMR (400 MHz, DMSO-d6) δ 12.95 (s, 1H), 8.64 (d, J = 5.1 Hz, 1H), 8.42 (d, J = 8.4 Hz, 3H), 8.24 (d, J = 8.6 Hz, 1H), 7.91 (dd, J = 5.1, 1.7 Hz, 1H), 6.63 (d, J = 8.6 Hz, 1H), 4.01 (s, 3H). LC/MS (ESI) m/z: 340.05 $(M + H)^+$. |
| 102 | 6-methoxy-2-[4-(1-tetrahydropyran-4-ylpyrazol-4-yl)pyridine-2-carbonyl]amino]pyridine-3-carboxylic acid 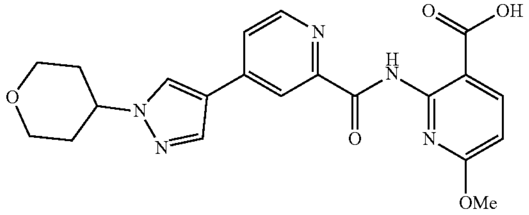 [SMILES: COc1ccc(C(=O)O)c(NC(=O)c2cc(-c3cnn(C4CCOCC4)c3)ccn2)n1] | $^1H$ NMR (400 MHz, DMSO-d6) δ 13.38 (s, 1H), 12.94 (s, 1H), 8.71 (s, 1H), 8.65 (d, J = 5.1 Hz, 1H), 8.41 (d, J = 1.1 Hz, 1H), 8.24 (d, J = 8.7 Hz, 2H), 7.88 (dd, J = 5.1, 1.8 Hz, 1H), 6.63 (d, J = 8.6 Hz, 1H), 4.53-4.39 (m, 1H), 3.99 (d, J = 14.7 Hz, 5H), 3.51 (dd, J = 11.7, 2.3 Hz, 2H), 2.10-1.92 (m, 4H). LC/MS (ESI) m/z: 424.15 $(M + H)^+$. |

TABLE 2-continued

| Example # | Name/Structure | Spectral data |
|---|---|---|
| 103 | 2-[[3-(1,3-dimethylpyrazol-4-yl)benzoyl]amino]benzoic acid 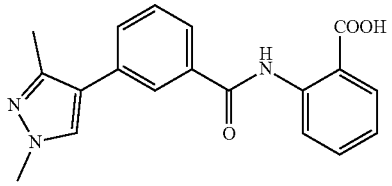 [SMILES: Cc1nn(C)cc1-c1cccc(C(=O)Nc2ccccc2C(=O)O)c1] | $^1$H NMR (400 MHz, DMSO-d6) δ 12.25 (brs, 1H), 7.24 (d, J = 8.0 Hz, 1H), 8.08 (d, J = 1.6 Hz, 1H), 8.00 (s, 2H), 7.81 (d, J = 8.0 Hz, 1H), 7.70-7.58 (m, 3H), 7.22 (t, J = 8.0 Hz, 1H), 3.81 (s, 3H), 2.33(s, 3H). LC/MS: (ESI) m/z: 336.1 (M + H)$^+$. |
| 104 | 2-[[3-(1,3,5-trimethylpyrazol-4-yl)benzoyl]amino]benzoic acid 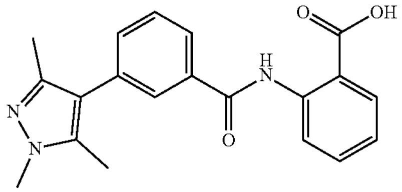 [SMILES: Cc1nn(C)c(C)c1-c1cccc(C(=O)Nc2ccccc2C(=O)O)c1] | $^1$H NMR (400 MHz, DMSO-d6) δ 12.23 (s, 1H), 8.75 (d, J = 8.4 Hz, 1H), 8.08 (dd, J = 1.2 Hz, 7.6Hz 1H), 7.88-7.83 (m, 2H), 7.70-7.53 (m, 3H), 7.22-7.20 (m, 1H), 3.73 (s, 3H), 2.28 (s, 3H), 2.20 (s, 3H). LC/MS: (ESI) m/z: 350.05 (M + H)$^+$. |
| 105 | 2-[[3-(1-methylpyrazol-4-yl)benzoyl]amino]benzoic acid 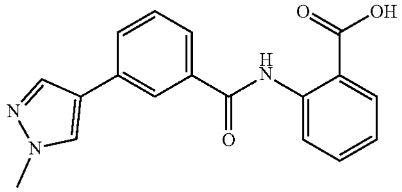 [SMILES: Cn1cc(-c2cccc(C(=O)Nc3ccccc3C(=O)O)c2)cn1] | $^1$H NMR (400 MHz, DMSO-d6) δ 12.18 (s, 1H), 8.72 (d, J = 8.0 Hz, 1H), 8.24 (s, 1H), 8.13 (s, 1H), 8.03 (dd, J = 1.2 Hz, 7.6Hz, 1H), 7.94 (s, 1H), 7.82 (d, J = 7.6 Hz, 1H), 7.75 (d, J = 7.6 Hz, 1H), 7.71-7.69 (m, 1H), 7.56 (t, J = 8.0 Hz, 1H), 7.22 (t, J = 7.6 Hz, 1H), 3.89 (s, 3H). LC/MS: (ESI) m/z: 321.95 (M + H)$^+$. |
| 106 | 2-[[3-(1-isopropylpyrazol-4-yl)benzoyl]amino]benzoic acid 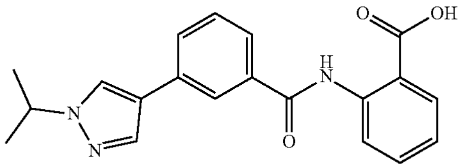 [SMILES: CC(C)n1cc(-c2cccc(C(=O)Nc3ccccc3C(=O)O)c2)cn1] | $^1$H NMR (400 MHz, DMSO-d6) δ 12.18 (s, 1H), 8.72 (d, J = 8.4 Hz, 1H), 8.34 (s, 1H), 8.15 (brs, 1H), 8.07 (dd, J = 1.6 Hz, 8.0 Hz, 1H), 7.95 (s, 1H), 7.84 (d, J = 7.6 Hz, 1H), 7.76-7.66 (m, 2H), 7.56 (t, J = 7.6 Hz, 1H), 7.24-7.20 (m, 1H), 4.55-4.51 (m, 1H), 1.46 (d, J = 6.8 Hz, 6H). LC/MS: 350.1 (M + H)$^+$. |
| 107 | 2-[[3-(1-cyclopropylpyrazol-4-yl)benzoyl]amino]benzoic acid 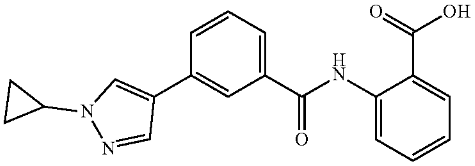 [SMILES: O=C(Nc1ccccc1C(=O)O)c1cccc(-c2cnn(C3CC3)c2)c1] | $^1$H NMR (400 MHz, DMSO-d6) δ 12.18 (s, 1H), 8.73 (d, J = 8.4 Hz, 1H), 8.36 (s, 1H), 8.15 (s, 1H), 8.08 (dd, J = 7.9, 1.5 Hz, 1H), 7.95 (d, J = 0.6 Hz, 1H), 7.85 (d, J = 7.7 Hz, 1H), 7.76 (d, J = 7.8 Hz, 1H), 7.73-7.65 (m, 1H), 7.57 (t, J = 7.7 Hz, 1H), 7.28-7.19 (m, 1H), 3.78 (dq, J = 11.2, 3.9 Hz, 1H), 1.11 (dq, J = 7.7, 4.0 Hz, 2H), 1.01 (td, J = 7.5, 5.5 Hz, 2H). LC/MS: (ESI) m/z: 346.05 (M + H)$^+$. |

TABLE 2-continued

| Example # | Name/Structure | Spectral data |
| --- | --- | --- |
| 109 | 2-[[3-[1-[2-(dimethylamino)ethyl]pyrazol-4-yl]benzoyl]amino]benzoic acid 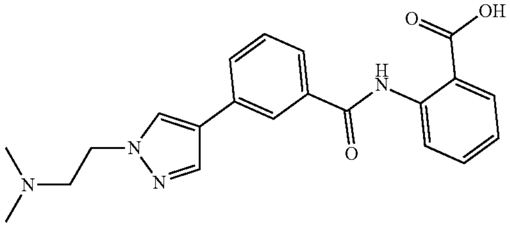 [SMILES: CN(C)CCn1cc(-c2cccc(C(=O)Nc3ccccc3C(=O)O)c2)cn1] | $^{1}H$ NMR (400 MHz, DMSO-d6) δ 12.21 (s, 1H), 8.71 (d, J = 8.4 Hz, 1H), 8.41 (s, 1H), 8.16 (s, 1H), 8.11(s, 1H), 8.08 (d, J = 1.6 Hz, 1H), 8.06 (d, J = 1.6 Hz, 1H), 7.86 (d, J = 7.6 Hz, 1H), 7.78(d, J = 8Hz,1H), 7.70-7.66 (m, 1H), 7.61 (t, J = 7.6 Hz, 1H), 7.25-7.21 (m, 1H), 4.58 (t, J = 8.0 Hz, 2H), 3.63(t, J = 6.0 Hz, 2H), 2.84 (s, 6H). LC/MS: (ESI) m/z: 379.2 $(M + H)^{+}$. |
| 110 | 2-[[3-[1-(4-piperidyl)pyrazol-4-yl]benzoyl]amino]benzoic acid 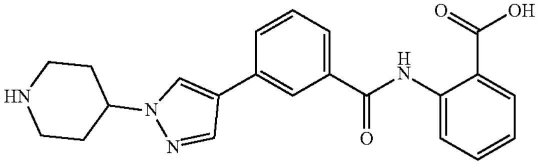 [SMILES: O=C(Nc1ccccc1C(=O)O)c1cccc(-c2cnn(C3CCNCC3)c2)c1] | $^{1}H$ NMR (400 MHz, DMSO-d6) δ 12.11 (brs, 1H), 8.71 (d, J = 8.0 Hz, 1H), 8.37 (s, 1H), 8.17(s, 1H), 8.08-8.04 (m, 2H), 7.87 (d, J = 8.4 Hz, 1H), 7.77 (d, J = 7.6 Hz, 1H), 7.68-7.66 (m, 1H), 7.58 (t, J = 7.6 Hz, 1H), 7.22 (t, J = 7.6 Hz, 1H), 4.53(s, 1H), 3.48-3.43 (m, 2H), 3.14-3.09 (m, 2H), 2.27-2.16 (m, 4H). LC/MS: (ESI) m/z: 391.1 $(M + H)^{+}$. |
| 111 | 2-[3-[1-(1-methyl-4-piperidyl)pyrazol-4-yl]benzoyl]amino]benzoic acid 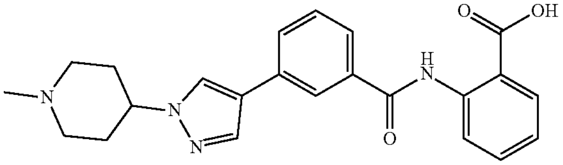 [SMILES: CN1CCC(n2cc(-c3cccc(C(=O)Nc4ccccc4C(=O)O)c3)cn2)CC1] | $^{1}H$ NMR (400 MHz, DMSO-d6) δ 12.6 (brs, 1H), 8.71 (d, J = 8.4 Hz, 1H), 8.39 (s, 1H), 8.18 (s, 1H), 8.08-8.06 (m, 1H), 8.04 (s, 1H), 7.81 (dd, J = 7.6, 22.4 Hz, 2H), 7.64-7.54 (m, 2H), 7.19(t, J = 7.6 Hz, 1H), 4.49-4.47(m, 1H), 3.21-3.18 (m, 4H), 2.82 (s, 3H), 2.30-2.29 (m,4H). LC/MS: (ESI) m/z: 405.1 $(M + H)^{+}$. |
| 112 | 2-[[3-(1,3-dimethylpyrazol-4-yl)benzoyl]amino]-6-methoxy-pyridine-3-carboxylic acid 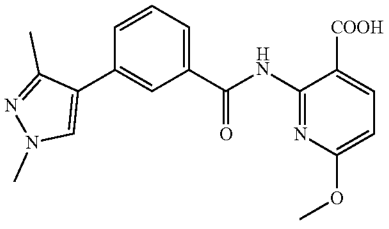 [SMILES: COc1ccc(C(=O)O)c(NC(=O)c2cccc(-c3cn(C)nc3C)c2)n1] | $^{1}H$ NMR (400 MHz, DMSO-d6) δ 13.8 (brs, 1H), 11.86 (s, 1H), 8.22 (d, J = 8.6 Hz, 1H), 8.00 (d, J = 3.1 Hz, 2H), 7.80 (d, J = 7.7 Hz, 1H), 7.69 (d, J = 7.8 Hz, 1H), 7.59 (t, J = 7.7 Hz, 1H), 6.64 (d, J = 8.6 Hz, 1H), 3.94 (s, 3H), 3.81 (d, J = 6.1 Hz, 3H), 2.36 (s, 3H). LC/MS: 367.05 $(M + H)^{+}$. |
| 113 | 6-methoxy-2-[[3-(1,3,5-trimethylpyrazol-4-yl)benzoyl]amino]pyridine-3-carboxylic acid 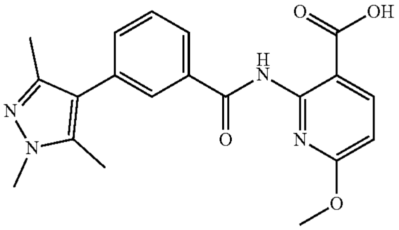 [SMILES: COc1ccc(C(=O)O)c(NC(=O)c2cccc(-c3c(C)nn(C)c3C)c2)n1] | $^{1}H$ NMR (400 MHz, DMSO-d6) δ 11.93 (brs, 1H), 8.21 (d, J = 8.6 Hz, 1H), 7.87-7.75 (m, 2H), 7.62 (t, J = 7.7 Hz, 1H), 7.52 (d, J = 7.6 Hz, 1H), 6.62 (d, J = 8.6 Hz, 1H), 3.93 (s, 3H), 3.72 (d, J = 5.1 Hz, 3H), 2.26 (s, 3H), 2.17 (s, 3H). LC/MS: 381.00 $(M + H)^{+}$. |

TABLE 2-continued

| Example # | Name/Structure | Spectral data |
|---|---|---|
| 114 | 6-methoxy-2-[3-(1-methylpyrazol-4-yl)benzoyl]amino]pyridine-3-carboxylic acid 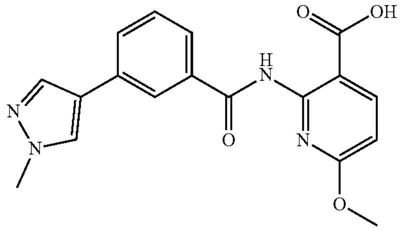 [SMILES: COc1ccc(C(=O)O)c(NC(=O)c2cccc(-c3cnn(C)c3)c2)n1] | $^1$H NMR (400 MHz, DMSO-d6) δ 11.77 (s, 1H), 8.26-8.18 (m, 2H), 8.14 (s, 1H), 7.95 (s, 1H), 7.82 (d, J = 7.8 Hz, 1H), 7.75 (d, J = 7.6 Hz, 1H), 7.55 (t, J = 7.7 Hz, 1H), 6.64 (d, J = 8.6 Hz, 1H), 3.94 (s, 3H), 3.88 (d, J = 7.5 Hz, 3H). LC/MS: 352.95 $(M + H)^+$. |
| 115 | 2-[[3-(1-isopropylpyrazol-4-yl)benzoyl]amino]-6-methoxy-pyridine-3-carboxylic acid 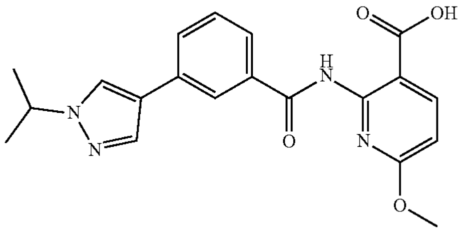 [SMILES: COc1ccc(C(=O)O)c(NC(=O)c2cccc(-c3cnn(C(C)C)c3)c2)n1] | $^1$H NMR (400 MHz, DMSO-d6) δ 11.75 (s, 1H), 8.34 (s, 1H), 8.21 (d, J = 8.6 Hz, 1H), 8.16 (s, 1H), 7.96 (s, 1H), 7.84 (d, J = 7.7 Hz, 1H), 7.74 (d, J = 7.7 Hz, 1H), 7.55 (t, J = 7.7 Hz, 1H), 6.65 (d, J = 8.6 Hz, 1H), 4.53 (dt, J = 13.2, 6.6 Hz, 1H), 3.94 (s, 3H), 1.47 (d, J = 6.7 Hz, 6H). LC/MS: 381.10 $(M + H)^+$. |
| 116 | 2-[3-(1-cyclopropylpyrazol-4-yl)benzoyl]amino]-6-methoxy-pyridine-3-carboxylic acid 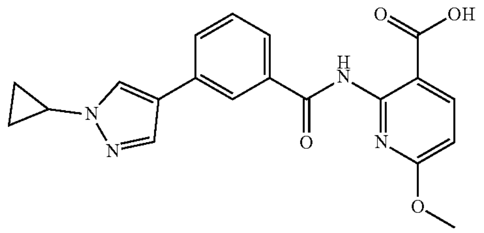 [SMILES: COc1ccc(C(=O)O)c(NC(=O)c2cccc(-c3cnn(C4CC4)c3)c2)n1] | $^1$H NMR (400 MHz, DMSO-d6) δ 8.34 (s.1H), 8.22-8.15 (m, 2H), 7.94 (s, 1H), 7.83 (d, J = 8 Hz, 1H), 7.74 (d, J = 7.6Hz, 1H), 7.54 (t, J = 3.6 Hz, 1H), 6.64 (d, J = 8.8 Hz, 1H), 3.93 (s.3H), 1.23 (s,1H), 1.11-0.99 (m,4H). LC/MS: (ESI) m/z: 379.1 $(M + H)^+$. |
| 117 | 2-[[3-[1-(2-hydroxyethyl)pyrazol-4-yl]benzoyl]amino]-6-methoxy-pyridine-3-carboxylic acid 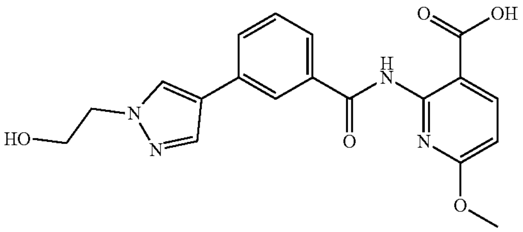 [SMILES: COc1ccc(C(=O)O)c(NC(=O)c2cccc(-c3cnn(CCO)c3)c2)n1] | $^1$H NMR (400 MHz, DMSO-d) & 11.76 (s, 1H), 8.25-8.15 (m, 4H), 7.97 (s, 1H), 7.83 (d, J = 7.6 Hz, 1H), 7.74 (d, J = 7.6 Hz, 1H), 7.56 (t, J = 7.8Hz, 1H), 4.18 (t, J = 6.4 Hz, 2H), 3.94 (s, 3H), 3.81-3.76 (m, 2H). LC/MS: (ESI) m/z: 383.2 $(M + H)^+$. |

TABLE 2-continued

| Example # | Name/Structure | Spectral data |
|---|---|---|
| 118 | 2-[[3-[1-[2-(dimethylamino)ethyl]pyrazol-4-yl]benzoyl]amino]-6-methoxy-pyridine-3-carboxylic acid 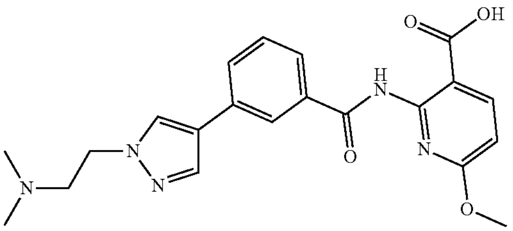 | $^{1}$H NMR (400 MHz, DMSO-d6) δ 11.78 (s, 1H), 8.40 (s, 1H), 8.23-8.11 (m, 3H), 7.85 (d, J = 8.0 Hz, 1H), 7.77 (d, J = 8.4 Hz, 1H), 7.61-7.55 (m, 1H), 6.64 (d, J = 8.4 Hz, 1H), 4.58-4.55 (m, 2H), 3.93 (s, 3H), 3.63-3.61 (m, 2H), 2.83 (s, 6H). LC/MS: (ESI) m/z: 410.1 $(M + H)^+$. |
| 119 | 6-methoxy-2-[3-[1-(1-methyl-4-piperidyl)pyrazol-4-yl]benzoyl]amino]pyridine-3-carboxylic acid 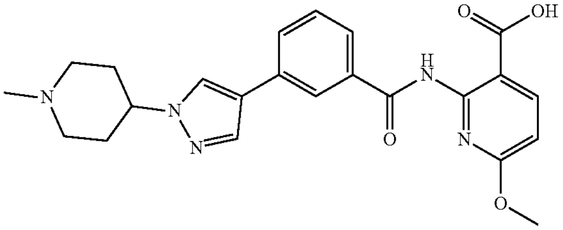 [SMILES: COc1ccc(C(=O)O)c(NC(=O)c2cccc(-c3cnn(C4CCN(C)CC4)c3)c2)n1] | $^{1}$H NMR (400 MHz, $CD_3OD$) δ 8.32 (d, J = 8.8 Hz, 1H), 8.20 (d, J = 2.0 Hz, 2H), 7.99 (s, 1H), 7.87-7.81 (m, 2H), 7.55 (t, J = 8.0 Hz, 1H), 6.58 (d, J = 8.8 Hz, 1H), 4.60-4.58 (m, 1H), 4.03 (s, 3H), 3.88-3.84 (m, 2H), 3.30-3.25 (m, 2H), 2.96 (s, 3H), 2.42-2.39 (m, 4H). LC/MS: (ESI) m/z: 436.1 $(M + H)^+$. |
| 229 | 6-methoxy-2-(3-(quinolin-8-yl)benzamido)nicotinic acid 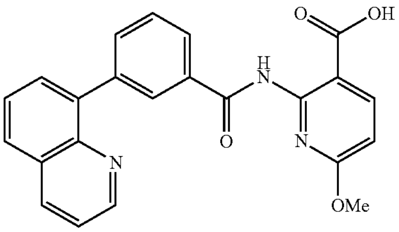 [SMILES: COc1ccc(C(=O)O)c(NC(=O)c2cccc(-c3cccc4cccnc34)c2)n1] | $^{1}$H NMR (400 MHz, DMSO-d6) δ 15.09 (s, 1H), 8.97-8.90 (m, 1H), 8.48 (d, J = 8.3 Hz, 1H), 8.26 (s, 1H), 8.20 (d, J = 8.3 Hz, 1H), 8.10-8.00 (m, 2H), 7.92-7.83 (m, 2H), 7.74 (t, J = 7.6 Hz, 1H), 7.65 (d, J = 7.7 Hz, 1H), 7.63-7.56 (m, 1H), 6.42 (d, J = 8.3 Hz, 1H), 3.90 (s, 3H). LC/MS (ESI) m/z: 400.0 $(M + H)^+$. |
| 232 | 2-(4-(1H-pyrazol-4-yl)picolinamido)-4,5-dichlorobenzoic acid 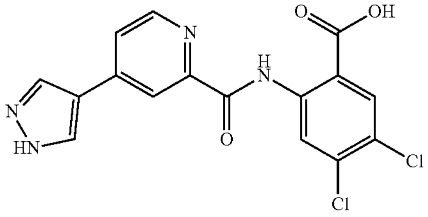 [SMILES: O=C(Nc1cc(Cl)c(Cl)cc1C(=O)O)c1cc(-c2cn[nH]c2)ccn1] | LC/MS (ESI) m/z: 377 $(M + H)^+$. |
| 232a | sodium 2-(4-(1H-pyrazol-4-yl)picolinamido)-4,5-dichlorobenzoate 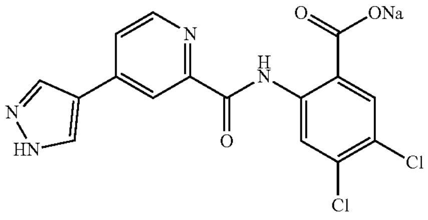 | $^{1}$H NMR (400 MHz, DMSO-d6) 815.29 (s, 1H), 13.13 (brs, 1H), 9.03 (s, 1H), 8.60 (d, J = 4.8 Hz, 1H), 8.37 (s, 2H), 8.30 (d, J = 1.2 Hz, 1H), 8.11 (s, 1H), 7.83-7.81 (m, 1H). LC/MS (ESI) m/z: 377 $(M + H - Na)^+$. |

TABLE 2-continued

| Example # | Name/Structure | Spectral data |
|---|---|---|
| 233 | 4,5-dichloro-2-(4-(1-(tetrahydro-2H-pyran-4-yl)-1H-pyrazol-4-yl)picolinamido)benzoic acid 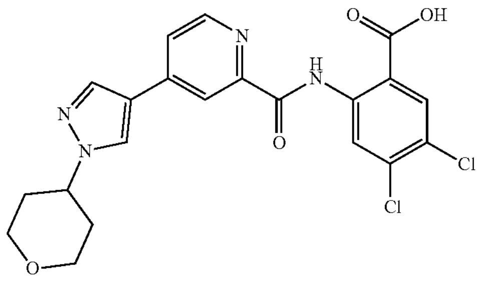 [SMILES: O=C(Nc1cc(Cl)c(Cl)cc1C(=O)O)c1cc(-c2cnn(C3CCOCC3)c2)ccn1] | LC/MS (ESI) m/z: 461(M + H)$^+$. |
| 233a | sodium 4,5-dichloro-2-(4-(1-(tetrahydro-2H-pyran-4-yl)-1H-pyrazol-4-yl)picolinamido)benzoate 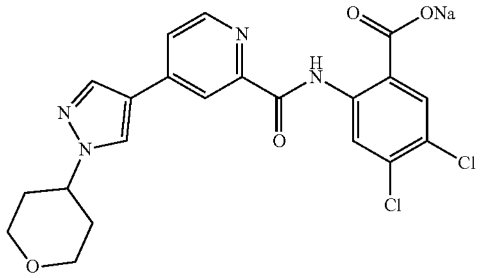 | $^1$H NMR (400 MHz, DMSO-d6) 15.05 (brs, 1H), 9.05 (s, 1H), 8.66 (s, 1H), 8.60 (s, 1H), 8.30 (s, 1H), 8.18-8.16 (m, 2H), 7.81 (s, 1H), 4.46 (s, 1H), 3.99-3.97 (m, 2H), 3.52-3.46 (m, 2H), 2.03-1.98 (m, 4H). LC/MS (ESI) m/z: 461 (M + H − Na)$^+$. |
| 234 | 4,5-dichloro-2-(4-(isoxazol-4-yl)picolinamido)benzoic acid 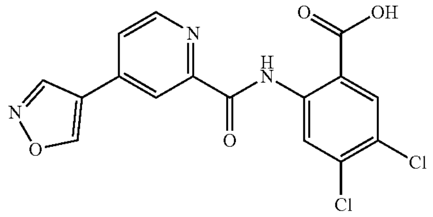 [SMILES: O=C(Nc1cc(Cl)c(Cl)cc1C(=O)O)c1cc(-c2cnoc2)ccn1] | LC/MS (ESI) m/z: 378.2 (M + H)$^+$. |
| 234a | sodium 4,5-dichloro-2-(4-(isoxazol-4-yl)picolinamido)benzoate 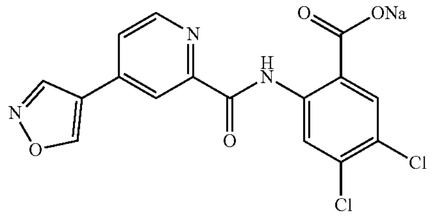 | $^1$H NMR (400 MHz, DMSO-d6) δ 14.83 (s, 1H), 9.52-7.12 (m, 8H). LC/MS (ESI) m/z: 378.2 (M + H − Na)$^+$. |
| 235 | 4,5-dichloro-2-(3-(isoxazol-4-yl)benzamido)benzoic acid 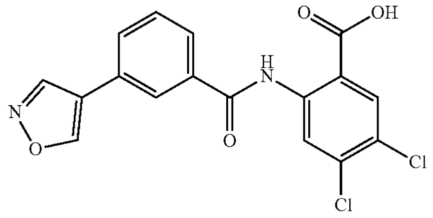 [SMILES: O=C(Nc1cc(Cl)c(Cl)cc1C(=O)O)c1cccc(-c2cnoc2)c1] | $^1$H NMR (400 MHz, DMSO-d6) δ 12.43 (brs, 1H), 8.95 (d, J = 6.4 Hz, 1H), 8.16-7.94 (m, 2H), 7.79-7.72 (m, 1H), 7.63-7.51 (m, 4H). LC/MS (ESI) m/z: 377 (M + H)$^+$. |

TABLE 2-continued

| Example # | Name/Structure | Spectral data |
|---|---|---|
| 236 | 4-chloro-2-(3-(isoxazol-4-yl)benzamido)benzoic acid 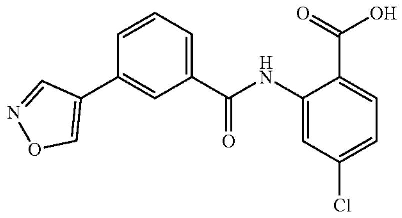 [SMILES: O=C(Nc1cc(Cl)ccc1C(=O)O)c1cccc(-c2cnoc2)c1] | LC/MS (ESI) m/z: 343 $(M + H)^+$. |
| 236a | sodium 4-chloro-2-(3-(isoxazol-4-yl)benzamido)benzoate 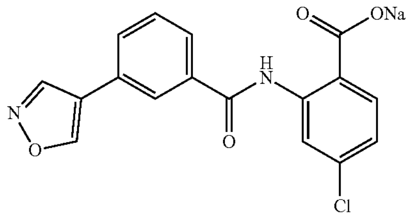 | $^1H$ NMR (400 MHz, CD3OD) δ 8.80 (s, 2H), 8.50 (d, 1H), 8.08-8.05 (m, 3H), 7.64-7.62 (m, 1H), 7.36-7.33 (m, 1H), 7.08-7.04 (m, 1H). LC/MS (ESI) m/z: 343 $(M + H - Na)^+$. |
| 237 | 7-(4-(1-(tetrahydro-2H-pyran-4-yl)-1H-pyrazol-4-yl)picolinamido)-2,3-dihydrobenzo[b][1,4]dioxine-6-carboxylic acid 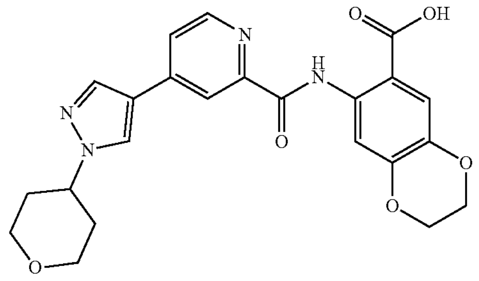 [SMILES: O=C(Nc1cc2c(cc1C(=O)O)OCCO2)c1cc(-c2cnn(C3CCOCC3)c2)ccn1] | LC/MS (ESI) m/z: 451.3 $(M + H)^+$. |
| 237a | sodium 7-(4-(1-(tetrahydro-2H-pyran-4-yl)-1H-pyrazol-4-yl)picolinamido)-2,3-dihydrobenzo[b][1,4]dioxine-6-carboxylate 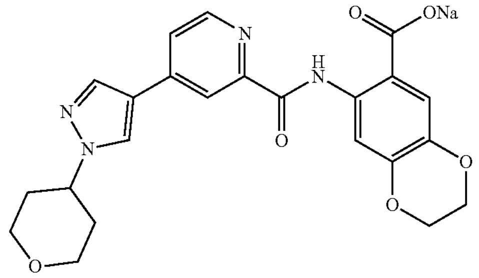 | $^1H$ NMR (400 MHz, DMSO-d6) δ 15.0 (s, 1H), 8.66 (S, 1H), 8.57 (d, J = 5.2 Hz, 1H), 8.35 (s, 1H), 8.28 (s, 1H), 8.17 (s, 1H), 7.77 (dd, J = 4, 1.2 Hz, 1H), 7.50 (s, 1H), 4.67-4.64 (m, 1H), 4.26 (dd, J = 16.4, 4.8 Hz, 4H), 4.0-3.97 (m, 1H), 3.49 (td, J = 11.2, 2.4 Hz, 2H), 2.06-1.98 (m, 4H). LC/MS (ESI) m/z: 451.3 $(M + H - Na)^+$. |

TABLE 2-continued

| Example # | Name/Structure | Spectral data |
|---|---|---|
| 238 | 7-(4-(1H-pyrazol-4-yl)picolinamido)-2,3-dihydrobenzo[b][1,4]dioxine-6-carboxylic acid 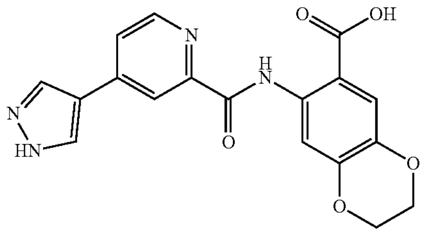 [SMILES: O=C(Nc1cc2c(cc1C(=O)O)OCCO2)c1cc(-c2cn[nH]c2)ccn1] | LC/MS (ESI) m/z: 367.2 (M + H − Na)$^+$. |
| 238a | sodium 7-(4-(1H-pyrazol-4-yl)picolinamido)-2,3-dihydrobenzo[b][1,4]dioxine-6-carboxylate 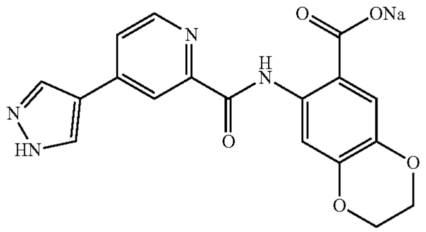 | $^1$H NMR (400 MHz, DMSO-d6) δ 14.92 (s, 1H), 13.29 (brs, 1H), 8.66 (S, 1H), 8.57 (d, J = 5.2 Hz, 1H), 8.38-8.36 (m, 3H), 8.29 (s, 1H), 7.79 (dd, J = 12.8, 1.2 Hz, 1H), 7.51 (s, 1H), 4.27-4.23 (m, 4H). LC/MS (ESI) m/z: 367.2 (M + H − Na)$^+$. |
| 239 | 7-(4-(isoxazol-4-yl)picolinamido)-2,3-dihydrobenzo[b][1,4]dioxine-6-carboxylic acid 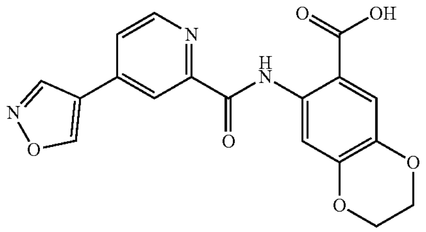 [SMILES: O=C(Nc1cc2c(cc1C(=O)O)OCCO2)c1cc(-c2cnoc2)ccn1] | LC/MS (ESI) m/z: 368.2 (M + H)$^+$. |
| 239a | sodium 7-(4-(isoxazol-4-yl)picolinamido)-2,3-dihydrobenzo[b][1,4]dioxine-6-carboxylate 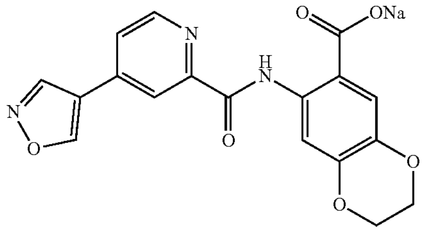 | $^1$H NMR (400 MHz, DMSO-d6) δ 14.63 (s, 1H), 9.59-6.97 (m, 8H), 4.22 (d, J = 11.5 Hz, 6H). LC/MS (ESI) m/z: 368.2 (M + H − Na)$^+$. |

TABLE 2-continued

| Example # | Name/Structure | Spectral data |
|---|---|---|
| 240 | 6-(4-(1H-pyrazol-4-yl)picolinamido)benzo[d][1,3]dioxole-5-carboxylic acid 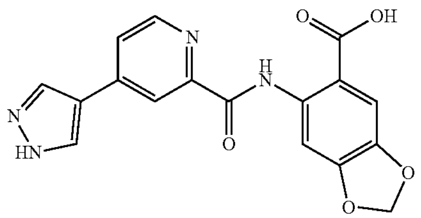 [SMILES: O=C(Nc1cc2c(cc1C(=O)O)OCO2)c1cc(-c2cn[nH]c2)ccn1] | LC/MS (ESI) m/z: 353.1 $(M + H)^+$. |
| 240a | sodium 6-(4-(1H-pyrazol-4-yl)picolinamido)benzo[d][1,3]dioxole-5-carboxylate 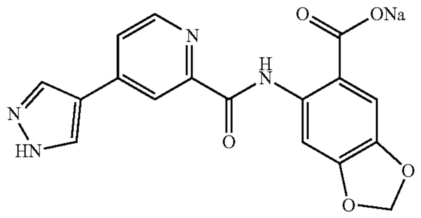 | $^1H$ NMR (400 MHz, DMSO-d6) δ 15.40 (s, 1H), 13.17 (s, 1H), 8.57 (d, J = 5.1 Hz, 1H), 8.47-8.23 (m, 4H), 7.78 (dd, J = 5.1, 1.8 Hz, 1H), 7.51 (s, 1H), 5.99 (s, 2H). LC/MS (ESI) m/z: 353.1 $(M + H)^+$. |
| 241 | 7-(3-(isoxazol-4-yl)benzamido)-2,3-dihydrobenzo[b][1,4]dioxine-6-carboxylic acid 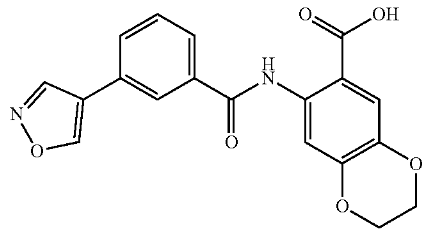 [SMILES: O=C(Nc1cc2c(cc1C(=O)O)OCCO2)c1cccc(-c2cnoc2)c1] | LC/MS (ESI) m/z: 367.3 $(M + H)^+$. |
| 241a | sodium 7-(3-(isoxazol-4-yl)benzamido)-2,3-dihydrobenzo[b][1,4]dioxine-6-carboxylate 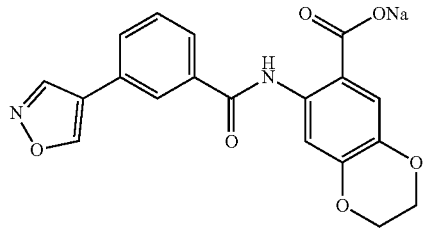 | $^1H$ NMR (400 MHz, DMSO-d6) δ 9.13 (s, 1H), 8.65-8.46 (m, 1H), 8.23 (s, 1H), 7.89-7.76 (m, 1H), 7.48-7.15 (m, 4H), 4.23 (d, J = 17.0 Hz, 4H). LC/MS (ESI) m/z: 367.3 $(M + H - Na)^+$. |
| 242 | 2-([1,1'-biphenyl]-3-carboxamido)-6-methoxynicotinic acid 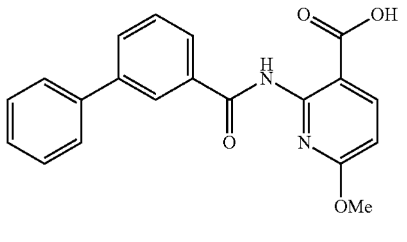 [SMILES: COc1ccc(C(=O)O)c(NC(=O)c2cccc(-c3ccccc3)c2)n1] | LC/MS (ESI) m/z: 349.2 $(M + H)^+$. |

TABLE 2-continued

| Example # | Name/Structure | Spectral data |
|---|---|---|
| 242a | sodium 2-([1,1'-biphenyl]-3-carboxamido)-6-methoxynicotinate 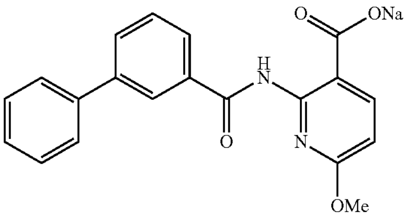 | $^1$H NMR (400 MHz, DMSO-d6) δ 15.59 (s, 1H), 8.31 (s, 1H), 8.19 (d, J = 8.0 Hz, 1H), 8.00 (d, J = 7.6 Hz, 1H), 7.88 (d, J = 8.0 Hz, 1H), 7.76 (d, J = 7.6 Hz, 2H), 7.65-7.61(m, 1H), 7.54-7.50 (m, 2H), 7.43 (d, J = 7.2 Hz, 1H), 6.40 (d, J = 8.4 Hz, 1H), 3.90 (s, 3H). LC/MS (ESI) m/z: 349.2 $(M + H - Na)^+$. |
| 243 | 2-(4'-fluoro-[1,1'-biphenyl]-3-carboxamido)-6-methoxynicotinic 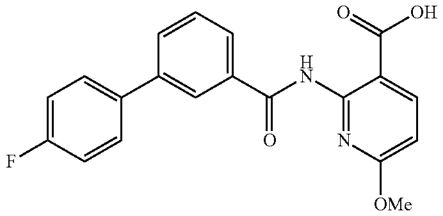 [SMILES: COc1ccc(C(=O)O)c(NC(=O)c2cccc(-c3ccc(F)cc3)c2)n1] | LC/MS (ESI) m/z: 367 $(M + H)^+$. |
| 243a | sodium 2-(4'-fluoro-[1,1'-biphenyl]-3-carboxamido)-6-methoxynicotinate 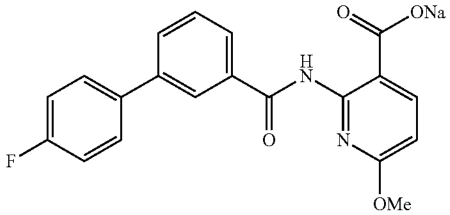 | $^1$H NMR (400 MHz, DMSO-d6) 11.96 (brs, 1H), 8.20 (d, J = 8.4 Hz, 1H), 7.94-7.91 (m, 2H), 7.82-7.79 (m, 2H), 7.68-7.64 (m, 1H), 7.37-7.33 (m, 2H), 6.64 (d, J = 8.4 Hz, 1H), 3.94 (s, 3H). LC/MS (ESI) m/z: 367 $(M + H - Na)^+$. |
| 244 | 2-(3'-fluoro-[1,1'-biphenyl]-3-carboxamido)-6-methoxynicotinic acid 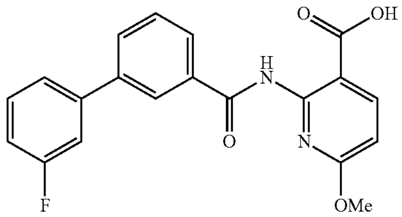 [SMILES: COc1ccc(C(=O)O)c(NC(=O)c2cccc(-c3cccc(F)c3)c2)n1] | LC/MS (ESI) m/z: 367.3 $(M + H)^+$. |
| 244a | sodium 2-(3'-fluoro-[1,1'-biphenyl]-3-carboxamido)-6-methoxynicotinate 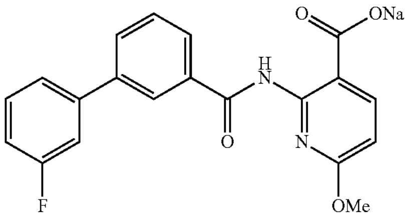 | $^1$H NMR (400 MHz, DMSO-d6) δ 15.64 (s, 1H), 8.32 (s, 1H), 8.21 (d, J = 8.4 Hz, 1H), 8.04 (d, J = 7.6 Hz, 1H), 7.94 (d, J = 7.6 Hz, 1H), 7.67-7.54 (m, 4H), 7.26 (t, J = 8.4 Hz, 1H), 6.41 (d, J = 8.4 Hz, 1H), 3.90 (s, 3H). LC/MS (ESI) m/z: 367.3 $(M + H - Na)^+$. |

TABLE 2-continued

| Example # | Name/Structure | Spectral data |
|---|---|---|
| 245 | 2-(2'-fluoro-[1,1'-biphenyl]-3-carboxamido)-6-methoxynicotinic acid 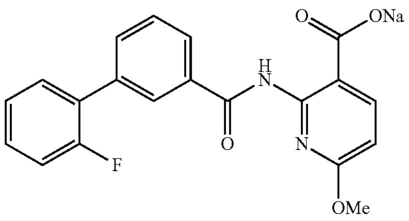 | LC/MS (ESI) m/z: 367.3 (M + H)+. |
| 245a | sodium 2-(2'-fluoro-[1,1'-biphenyl]-3-carboxamido)-6-methoxynicotinate 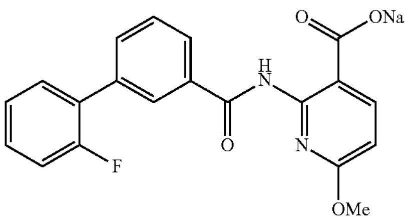 | $^{1}$H NMR (400 MHz, DMSO-d6) δ 15.53 (s, 1H), 8.20-8.17 (m, 2H), 8.06 (d, J = 7.6 Hz, 1H), 7.78 (d, J = 7.2 Hz, 1H), 7.67-7.60 (m, 2H), 7.49-7.46 (m, 2H), 7.39-7.34 (m, 2H), 6.42 (d, J = 8.0 Hz, 1H), 3.90 (s, 3H). LC/MS (ESI) m/z: 367.3 (M + H − Na)+. |
| 246 | 2-(3',4'-difluoro-[1,1'-biphenyl]-3-carboxamido)-6-methoxynicotinic 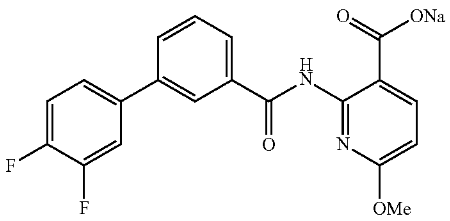 | LC/MS (ESI) m/z: 385.3 (M + H)+. |
| 246a | sodium 2-(3',4'-difluoro-[1,1'-biphenyl]-3-carboxamido)-6-methoxynicotinate 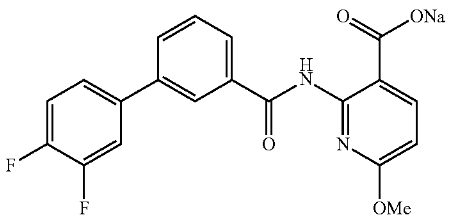 | $^{1}$H NMR (400 MHz, DMSO-d6) δ 15.55 (brs, 1H), 8.30 (brs, 1H), 8.22 (d, J = 8.4 Hz, 1H), 8.03 (d, J = 7.6 Hz, 1H), 7.92-7.84 (m, 2H), 7.49-7.46 (m, 2H), 7.66-7.57 (m, 3H), 6.42 (d, J = 8.0 Hz, 1H), 3.91 (s, 3H). LC/MS (ESI) m/z: 385.3 (M + H − Na)+. |
| 247 | 6-methoxy-2-(4'-(trifluoromethyl)-[1,1'-biphenyl]-3-carboxamido)nicotinic acid 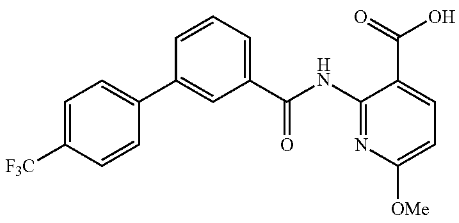 [SMILES: COc1ccc(C(=O)O)c(NC(=O)c2cccc(-c3ccc(C(F)(F)F)cc3)c2)n1] | LC/MS (ESI) m/z: 417.1 (M + H)+. |

TABLE 2-continued

| Example # | Name/Structure | Spectral data |
|---|---|---|
| 247a | sodium 6-methoxy-2-(4'-(trifluoromethyl)-[1,1'-biphenyl]-3-carboxamido)nicotinate 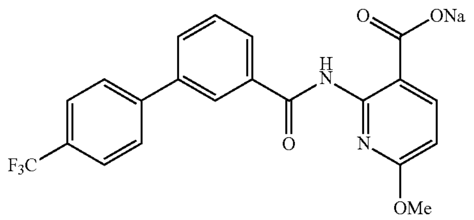 | $^1$H NMR (400 MHz, DMSO-d6) δ 15.85 (s, 1H), 8.37 (s, 1H), 8.19 (d, J = 8.0 Hz, 1H), 8.08 (d, J = 8.0 Hz, 1H), 8.00-7.98 (m, 3H), 7.89 (d, J = 8.0 Hz, 2H), 7.69 (t, J = 7.6 Hz, 1H), 6.40 (d, J = 8.0 Hz, 1H), 3.90 (s, 3H). LC/MS (ESI) m/z: 417.1 (M + H − Na)$^+$- |
| 248 | 2-(4'-chloro-[1,1'-biphenyl]-3-carboxamido)-6-methoxynicotinic acid 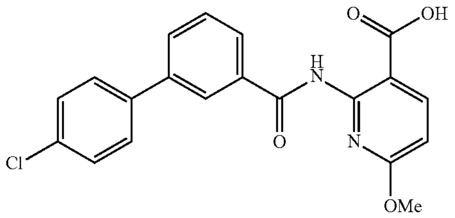 [SMILES: COc1ccc(C(=O)O)c(NC(=O)c2cccc(-c3ccc(Cl)cc3)c2)n1] | LC/MS (ESI) m/z: 383.2 (M + H)$^+$. |
| 248a | sodium 2-(4'-chloro-[1,1'-biphenyl]-3-carboxamido)-6-methoxynicotinate 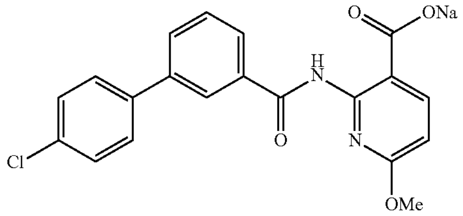 | $^1$H NMR (400 MHz, DMSO-d6) δ 15.68 (brs, 1H), 8.30 (brs, 1H), 8.20 (d, J = 8.4 Hz, 1H), 8.03 (d, J = 8.0 Hz, 1H), 7.90 (d, J = 8.4 Hz, 1H), 7.81-7.78 (m, 2H), 7.64 (t, J = 7.6 Hz, 3H), 7.59-7.57 (m, 1H), 6.41 (d, J = 8.4 Hz, 1H), 3.90 (s, 3H). LC/MS (ESI) m/z: 383.2 (M + H − Na)$^+$. |
| 249 | 7-(3',4'-difluoro-[1,1'-biphenyl]-3-carboxamido)-2,3-dihydrobenzo[b][1,4]dioxine-6-carboxylic acid 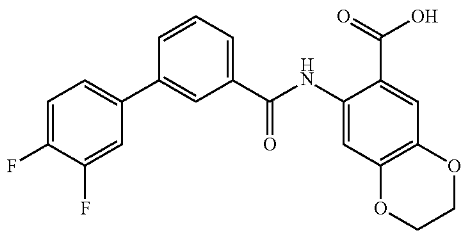 [SMILES: O=C(Nc1cc2c(cc1C(=O)O)OCCO2)c1cccc(-c2ccc(F)c(F)c2)c1] | LC/MS (ESI) m/z: 412. (M + H)$^+$. |
| 249a | sodium 7-(3',4'-difluoro-[1,1'-biphenyl]-3-carboxamido)-2,3-dihydrobenzo[b][1,4]dioxine-6-carboxylate 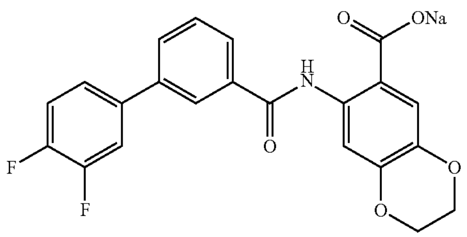 | $^1$H NMR (400 MHz, DMSO-d6) δ 15.85 (s, 1H), 8.28 (brs, 1H), 8.23(s, 1H), 8.35 (s, 1H), 8.02 (d, J = 7.6 Hz, 1H), 7.89-7.82 (m, 2H), 7.64-7.54 (m, 3H), 7.49 (s, 1H), 4.26-4.20 (m, 4H). LC/MS (ESI) m/z: 412. (M + H − Na)$^+$. |

TABLE 2-continued

| Example # | Name/Structure | Spectral data |
|---|---|---|
| 250 | 7-(4'-(trifluoromethyl)-[1,1'-biphenyl]-3-carboxamido)-2,3-dihydrobenzo[b][1,4]dioxine-6-carboxylic acid 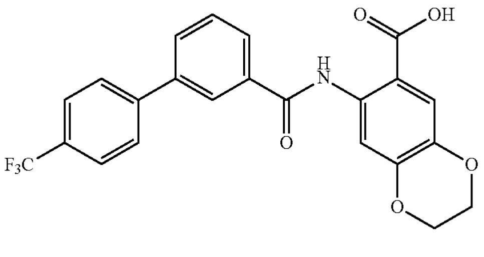 [SMILES: O=C(Nc1cc2c(cc1C(=O)O)OCCO2)c1cccc(-c2ccc(C(F)(F)F)cc2)c1] | LC/MS (ESI) m/z: 444.3 $(M + H)^+$. |
| 250a | sodium 7-(4'-(trifluoromethyl)-[1,1'-biphenyl]-3-carboxamido)-2,3-dihydrobenzo[b][1,4]dioxine-6-carboxylate 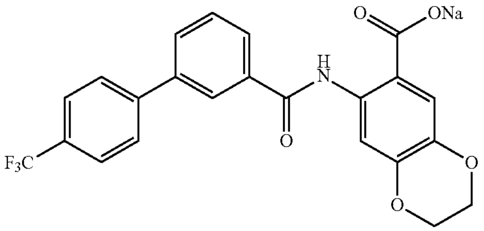 | $^1H$ NMR (400 MHz, DMSO-d6) δ 15.76 (s, 1H), 8.35 (brs, 1H), 8.25 (s, 1H), 8.08 (d, J = 8.0 Hz, 1H), 8.0 (d, J = 8.0 Hz, 1H), 7.95 (d, J = 7.6 Hz, 1H), 7.89 (d, J = 8.4 Hz, 1H), 7.67 (t, J = 7.6 Hz, 1H), 7.51 (s, 1H), 4.27-4.21 (m, 4H). LC/MS (ESI) m/z: 444.3 $(M + H - Na)^+$. |
| 251 | 7-(4'-chloro-[1,1'-biphenyl]-3-carboxamido)-2,3-dihydrobenzo[b][1,4]dioxine-6-carboxylic acid 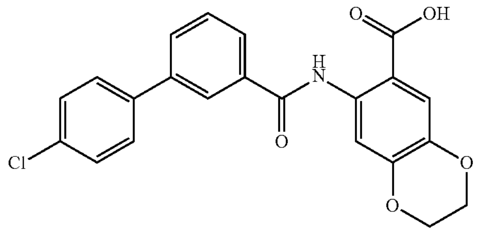 [SMILES: O=C(Nc1cc2c(cc1C(=O)O)OCCO2)c1cccc(-c2ccc(Cl)cc2)c1] | LC/MS (ESI) m/z: 410.0 $(M + H)^{+\cdot}$ |
| 251a | sodium 7-(4'-chloro-[1,1'-biphenyl]-3-carboxamido)-2,3-dihydrobenzo[b][1,4]dioxine-6-carboxylate 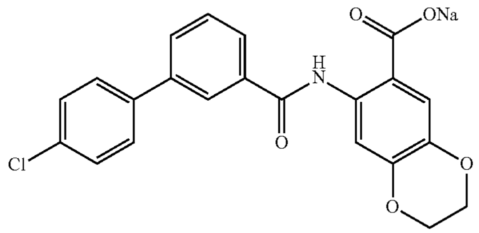 | $^1H$ NMR (400 MHz, DMSO-d6) δ 15.75 (s, 1H), 8.29 (brs, 1H), 8.24 (s, 1H), 8.02 (d, J = 7.6 Hz, 1H), 7.88 (d, J = 7.6 Hz, 1H), 7.80 (s, 1H), 7.77 (s, 1H), 7.62 (t, J = 7.6 Hz, 1H), 7.59 (s, 1H), 7.57 (s, 1H), 7.50 (s, 1H), 4.26 (dd, J = 17.2, 3.6 Hz, 4H). LC/MS (ESI) m/z: 410.0 $(M + H - Na)^{+\cdot}$ |

TABLE 2-continued

| Example # | Name/Structure | Spectral data |
|---|---|---|
| 252 | 7-(4'-fluoro-[1,1'-biphenyl]-3-carboxamido)-2,3-dihydrobenzo[b][1,4]dioxine-6-carboxylic acid 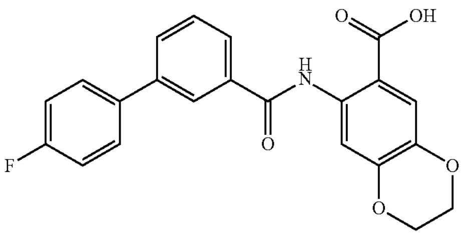 [SMILES: O=C(Nc1cc2c(cc1C(=O)O)OCCO2)c1cccc(-c2ccc(F)cc2)c1] | LC/MS (ESI) m/z: 394.1 $(M + H)^{+}$. |
| 252a | sodium 7-(4'-fluoro-[1,1'-biphenyl]-3-carboxamido)-2,3-dihydrobenzo[b][1,4]dioxine-6-carboxylate 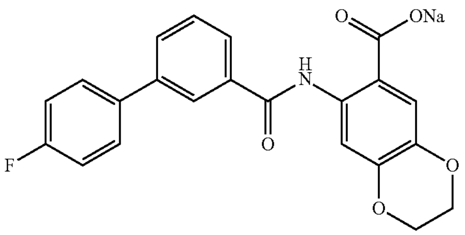 | $^{1}H$ NMR (400 MHz, DMSO-d6) δ 15.95-15.69 (m, 1H), 8.25 (d, J = 16.9 Hz, 2H), 7.99 (d, J = 7.9 Hz, 1H), 7.83-7.74 (m, 3H), 7.61 (t, J = 7.7 Hz, 1H), 7.48 (s, 1H), 7.35 (t, J = 8.8 Hz, 2H), 4.23 (dd, J = 16.6, 5.1 Hz, 4H). LC/MS (ESI) m/z: 394.1 $(M + H - Na)^{+}$. |
| 253 | 7-(3'-fluoro-[1,1'-biphenyl]-3-carboxamido)-2,3-dihydrobenzo[b][1,4]dioxine-6-carboxylic acid 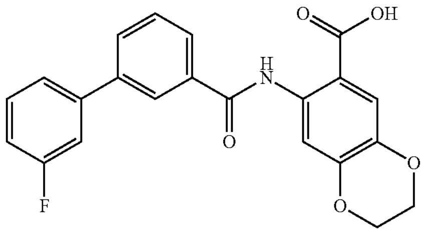 [SMILES: O=C(Nc1cc2c(cc1C(=O)O)OCCO2)c1cccc(-c2cccc(F)c2)c1] | LC/MS (ESI) m/z: 394 $(M + H)^{+}$. |
| 253a | sodium 7-(3'-fluoro-[1,1'-biphenyl]-3-carboxamido)-2,3-dihydrobenzo[b][1,4]dioxine-6-carboxylate 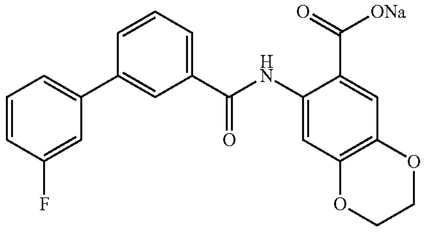 | $^{1}H$ NMR (400 MHz, DMSO-d6) δ 15.98 (s, 1H), 8.31 (s, 1H), 8.22 (s, 1H), 8.02 (d, J = 7.6 Hz, 1H), 7.90 (d, J = 7.6 Hz, 1H), 7.67-7.52 (m, 4H), 7.47 (s, 1H), 7.26 (t, J = 7.8 Hz, 1H), 4.30-4.16 (m, 4H). LC/MS (ESI) m/z: 416.0 $(M + Na)^{+}$. |

TABLE 2-continued

| Example # | Name/Structure | Spectral data |
|---|---|---|
| 254 | 7-([1,1'-biphenyl]-3-carboxamido)-2,3-dihydrobenzo[b][1,4]dioxine-6-carboxylic acid 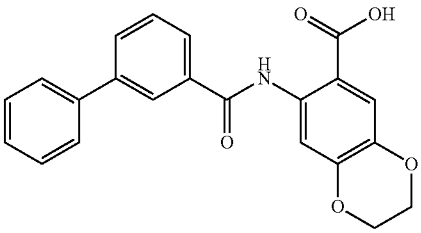 [SMILES: O=C(Nc1cc2c(cc1C(=O)O)OCCO2)c1cccc(-c2ccccc2)c1] | LC/MS [M + H]: 376.1. |
| 254a | sodium 7-([1,1'-biphenyl]-3-carboxamido)-2,3-dihydrobenzo[b][1,4]dioxine-6-carboxylate 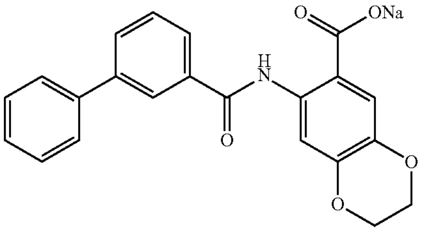 | $^1$H NMR (400 MHz, DMSO-d6) δ 15.74 (d, J = 4.7Hz, 1H), 8.29 (s, 1H), 8.25 (d, J = 2.6 Hz, 1H), 7.99 (d, J = 7.2 Hz, 1H), 7.86 (d, J = 7.7 Hz, 1H), 7.75 (d, J = 7.2 Hz, 2H), 7.61 (t, J = 7.7 Hz, 1H), 7.52 (dd, J = 14.3, 5.0 Hz, 3H), 7.42 (t, J = 7.3 Hz, 1H), 4.28-4.20 (m, 4H). LC/MS [M + H − Na]: 376.1. |
| 255 | 2-(3-(isoxazol-4-yl)benzamido)benzoic acid 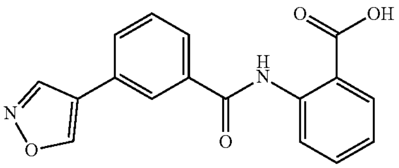 [SMILES: O=C(Nc1ccccc1C(=O)O)c1cccc(-c2cnoc2)c1] | LC/MS (ESI) m/z: 309.2 $(M + H)^+$. |
| 255a | sodium 2-(3-(isoxazol-4-yl)benzamido)benzoate 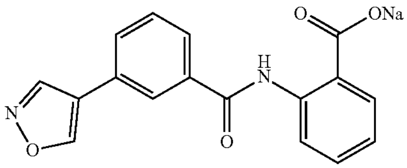 | $^1$H NMR (400 MHz, DMSO-d6) δ 15.13 (d, J = 96.4 Hz, 1H), 9.76-6.44 (m, 11H). LC/MS (ESI) m/z: 309.2 $(M + H)^+$. |
| 257 | 7-(2'-fluoro-[1,1'-biphenyl]-3-carboxamido)-2,3-dihydrobenzo[b][1,4]dioxine-6-carboxylic acid 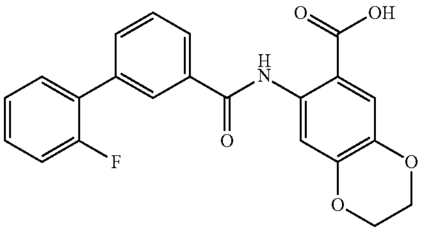 [SMILES: O=C(Nc1cc2c(cc1C(=O)O)OCCO2)c1cccc(-c2ccccc2F)c1] | LC/MS [M + H]: 394.1 |

TABLE 2-continued

| Example # | Name/Structure | Spectral data |
|---|---|---|
| 257a | sodium 7-(2'-fluoro-[1,1'-biphenyl]-3-carboxamido)-2,3-dihydrobenzo[b][1,4]dioxine-6-carboxylate 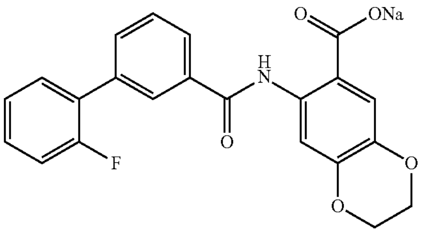 | $^1H$ NMR (400 MHz, DMSO-d6) δ 15.86 (s, 1H), 8.22 (s, 1H), 8.16 (s, 1H), 8.03 (s, 1H), 7.73 (d, J = 6.6 Hz, 1H), 7.63 (t, J = 7.8 Hz, 2H), 7.47 (s, 2H), 7.34 (d, J = 7.7 Hz, 2H), 4.23 (dd, J = 16.7, 5.1 Hz, 4H). LC/MS [M + H − Na]: 394.1 |
| 258 | 3-(3-(1-(tetrahydro-2H-pyran-4-yl)-1H-pyrazol-4-yl)benzamido)benzoic 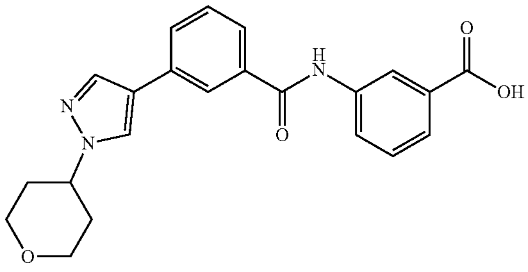 [SMILES: O=C(O)c1cccc(NC(=O)c2cccc(-c3cnn(C4CCOCC4)c3)c2)c1] | LC/MS (ESI) m/z: 392.1 $(M + H)^{+}$· |
| 258a | sodium 3-(3-(1-(tetrahydro-2H-pyran-4-yl)-1H-pyrazol-4-yl)benzamido)benzoate 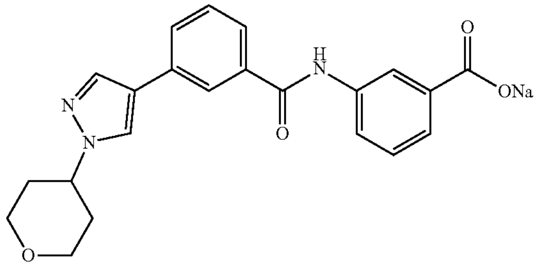 | $^1H$ NMR (400 MHz, DMSO-d6) δ 10.36-10.33 (m, 1H), 8.37-8.27 (m, 2H), 8.19-8.16 (m, 1H), 8.00-7.91 (m, 2H), 7.81-7.77 (m, 2H), 7.66-7.65 (m, 1H), 7.52-7.48 (m, 1H), 7.36-7.33 (m, 1H), 4.43-4.40 (m, 1H), 3.99-3.94 (m, 2H), 3.561-3.45 (m, 2H), 1.99-1.94 (m, 4H). LC/MS (ESI) m/z: 392.1 $(M + H - Na)^{+}$. |
| 259 | 3-chloro-5-(3-(1-(tetrahydro-2H-pyran-4-yl)-1H-pyrazol-4-yl)benzamido)benzoic acid 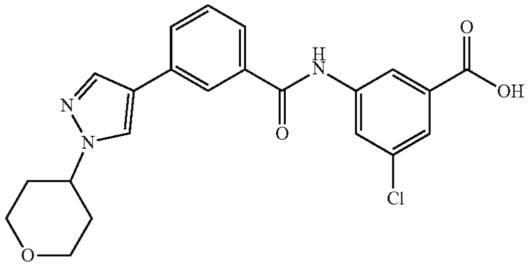 [SMILES: O=C(O)c1cc(Cl)cc(NC(=O)c2cccc(-c3cnn(C4CCOCC4)c3)c2)c1] | LC/MS (ESI) m/z: 426.1 $(M + H)^{+}$· |

TABLE 2-continued

| Example # | Name/Structure | Spectral data |
|---|---|---|
| 259a | sodium 3-chloro-5-(3-(1-(tetrahydro-2H-pyran-4-yl)-1H-pyrazol-4-yl)benzamido)benzoate 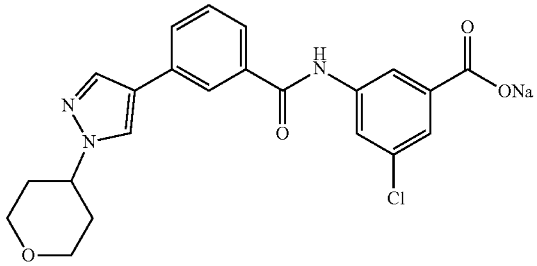 | $^1H$ NMR (400 MHz, DMSO-d6) δ 10.46 (s, 1H), 8.37 (s, 1H), 8.22 (s, 1H), 8.18 (s, 1H), 8.10 (s, 1H), 8.00 (s, 1H), 7.82-7.77 (m, 2H), 7.61 (s, 1H), 7.51 (t, J = 7.6 Hz, 1H), 4.47-4.40 (m, 1H), 3.99-3.97 (m, 2H), 3.52-3.46 (m, 2H), 2.02-1.97 (m, 4H). LC/MS (ESI) m/z: 426.1 $(M + H)^+$. |
| 261 | 2,3-dichloro-5-(3-(1-(tetrahydro-2H-pyran-4-yl)-1H-pyrazol-4-yl)benzamido)benzoic acid 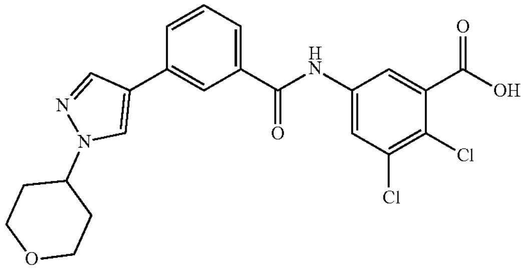 [SMILES: O=C(Nc1cc(Cl)c(Cl)c(C(=O)O)c1)c1cccc(-c2cnn(C3CCOCC3)c2)c1] | LC/MS (ESI) m/z: 460.0 $(M + H)^+$. |
| 261a | sodium 2,3-dichloro-5-(3-(1-(tetrahydro-2H-pyran-4-yl)-1H-pyrazol-4-yl)benzamido)benzoate 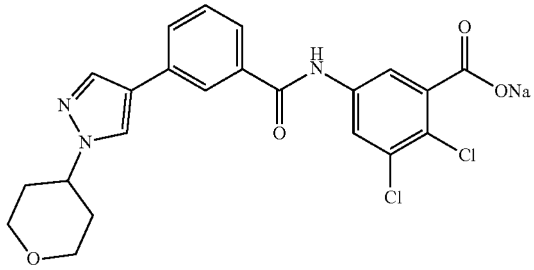 | $^1H$ NMR (400 MHz, DMSO-d6) δ 10.43 (s, 1H), 8.39 (s, 1H), 8.18 (s, 1H), 8.02 (d, J = 2.8 Hz, 1H), 8.00 (s, 1H), 7.78 (dd, J = 19.2, 8.0 Hz, 2H), 7.56 (d, J = 2.4 Hz, 1H), 7.50 (t, J = 8.0 Hz, 1H), 4.47-4.39 (m, 1H), 3.99-3.96 (m, 2H), 3.49 (td, J = 11.4, 3.2 Hz, 2H), 2.03-1.97 (m, 4H). LC/MS (ESI) m/z: 460.0 $(M + H)^+$. |
| 272 | 2-(3-(1H-pyrazol-4-yl)benzamido)nicotinic acid 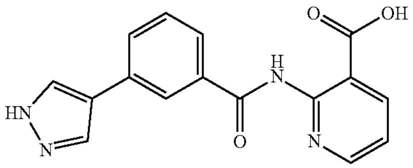 [SMILES: O=C(Nc1ncccc1C(=O)O)c1cccc(-c2cn[nH]c2)c1] | $^1H$ NMR (400 MHz, DMSO-d6) δ 11.44 (s, 1H), 8.60 (d, J = 3.0 Hz, 1H), 8.25 (s, 2H), 8.15 (s, 2H), 7.86 (d, J = 7.5 Hz, 1H), 7.79 (d, J = 7.6 Hz, 1H), 7.52 (t, J = 7.8 Hz, 1H), 7.34 (dd, J = 7.7, 4.9 Hz, 1H). LC/MS (ESI) m/z: 309.1 $(M + H)^+$. |

General Synthetic Procedure 2

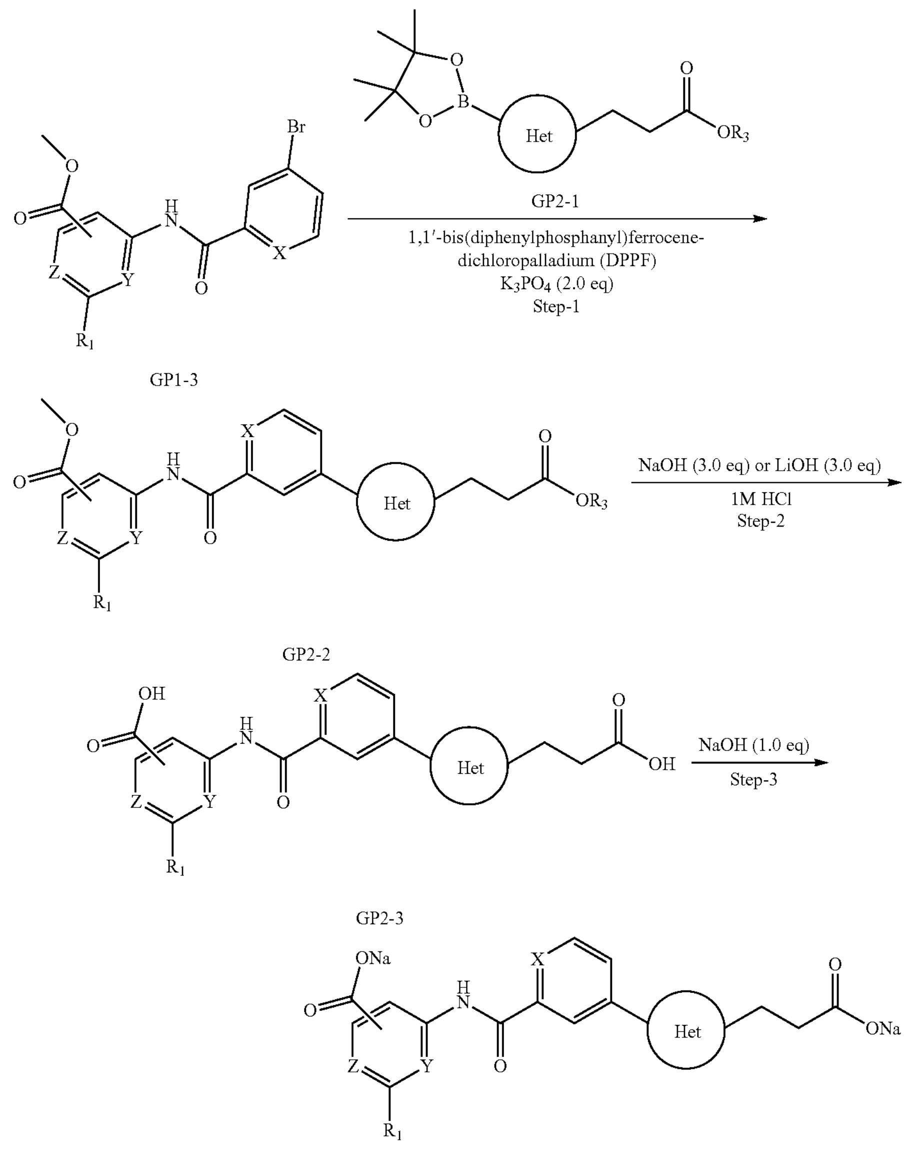

GP1-3

GP2-1

GP2-2

GP2-3

GP2-4-di Na salt

X = C or N
Y = C or N
Z = N or C or C-$R_2$
$R_1$ = H, halogen, alkyl, alkoxy, $OCF_3$
$R_2$ = H, halogen, alkyl, alkoxy, $OCF_3$
$R_1$ and $R_2$ can form a ring
Het = Heterocycle or substituted heterocycle Step-1. To a solution of GP1-3 (2.71 mmol) in 1,4-Dioxane (14 mL) was added (4,4,5,5-tetramethyl-1,3,2-dioxaborolane containing carboxylic acid ester (GP2-1, 2.98 mmol) and tripotassium phosphate (6.78 mmol). The mixture was degassed under a flow of nitrogen for 5 mins then 1,1'-bis(diphenylphosphanyl)ferrocene-dichloropalladium (DPPF) (0.27 mmol) was added and the mixture was heated at 80° C. overnight. The reaction was cooled to RT and diluted with ethyl acetate then filtered through celite, rinsing the celite pad with ethyl acetate. The filtrate was concentrated and the crude residue was absorbed onto silica and purified by biotage automated chromatography (100 g, Sfar Duo) eluting with 50-100% ethyl acetate in heptanes to give GP2-2.

Step-2. To a solution of GP2-2 (2.42 mmol) in a mixture of THF (4 mL)/Methanol (4 mL)/Water (4 mL) was added lithium hydroxide hydrate (7.26 mmol) and the mixture stirred at RT for 3 h. The reaction mixture was acidified to pH 1 using 1M HCl solution, which caused a precipitate to form. The precipitate was filtered, washed with water and dried in a vacuum oven at 40° C. overnight to give GP2-3.

Step-3. To a solution of GP2-3 in methanol (10 mL) was added 1 M sodium hydroxide (4.06 mmol) and the mixture stirred at RT for 1 h. The mixture was then concentrated under reduced pressure and the residue azeotropically dried with acetonitrile before being dried further in a vacuum oven at 40° C. overnight to give disodium salt (GP2-4-di Na salt.

Synthesis of 2-[[3-[1-(2-carboxylatoethyl)pyrazol-4-yl]benzoyl]amino]-4-chloro-benzoic acid (Example 2) and its disodium salt (Example 2 di-Na salt)

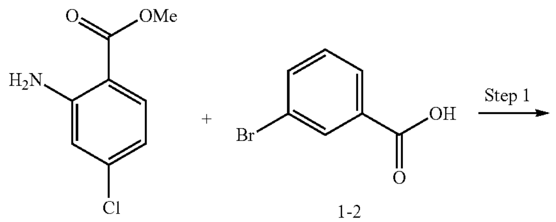

1-1 1-2

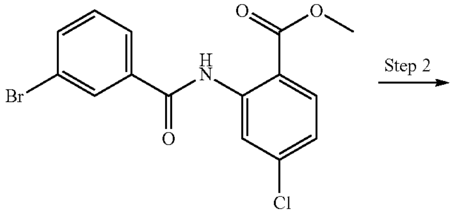

1-3

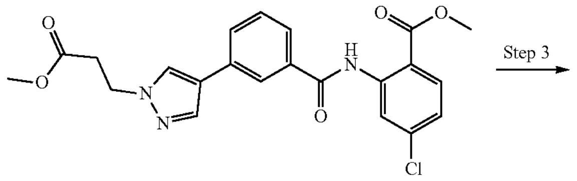

2-2

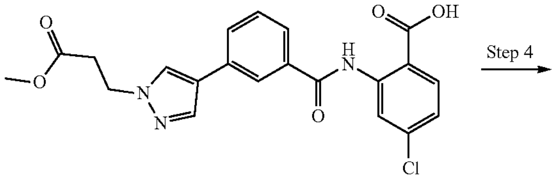

2-3

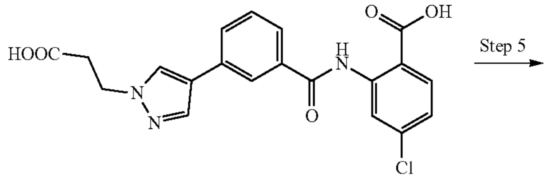

compound 2

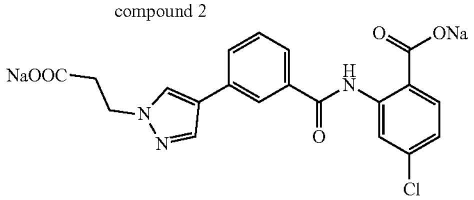

compound 2-Na salt

Preparation of methyl 2-[(3-bromobenzoyl)amino]-4-chloro-benzoate (compound 1-3). Step 1 was performed as shown in Example 1.

Preparation of methyl 4-chloro-2-[[3-(1-tetrahydropyran-4-ylpyrazol-4-yl)benzoyl]amino]benzoate (Step 2). To a solution of methyl 2-[(3-bromobenzoyl)amino]-4-chloro-benzoate (1.00 g, 2.71 mmol) in 1,4-Dioxane (14 mL) was added 1-(tetrahydro-2H-pyran-4-yl)-4-(4,4,5,5-tetramethyl-1,3,2-dioxaborolan-2-yl)-1H-pyrazole (830 mg, 2.98 mmol) and tripotassium phosphate (1440 mg, 6.78 mmol). The mixture was degassed under a flow of nitrogen for 5 mins then 1,1'-bis(diphenylphosphanyl)ferrocene-dichloropalladium (DPPF) (199 mg, 0.27 mmol) was added and the mixture was heated at 80° C. overnight. The reaction was cooled to RT and diluted with ethyl acetate then filtered through celite, rinsing the celite pad with ethyl acetate. The filtrate was concentrated and the crude residue was absorbed onto silica and purified by biotage automated chromatography (100 g, Sfar Duo) eluting with 50-100% ethyl acetate in heptanes to give methyl 4-chloro-2-[[3-(1-tetrahydropyran-4-ylpyrazol-4-yl)benzoyl]amino]benzoate (2-2, 1.02 g, 85%) as a colorless solid. LC/MS (method A); RT 1.1 mins (99%), m/z 440.3/442.3 $(M+H)^+$. $^1$H-NMR (400 MHz, DMSO-$d_6$): 11.66 (s, 1H), 8.68 (d, J=2.1 Hz, 1H), 8.39 (s, 1H), 8.17-8.14 (m, 1H), 8.03 (d, J=8.6 Hz, 1H), 7.99 (s, 1H), 7.89-7.85 (m, 1H), 7.76-7.72 (m, 1H), 7.59 (t, J=7.7 Hz, 1H), 7.33 (dd, J=8.6, 2.2 Hz, 1H), 4.48-4.40 (m, 1H), 4.01-3.96 (m, 2H), 3.91 (s, 3H), 3.49 (td, J=11.5, 2.8 Hz, 2H), 2.07-1.97 (m, 4H).

Preparation of 2-[[3-[1-(2-carboxyethyl)pyrazol-4-yl]benzoyl]amino]-4-chloro-benzoic acid (Step 3). To a solution of methyl 4-chloro-2-[[3-[1-(3-methoxy-3-oxo-propyl)pyrazol-4-yl]benzoyl]amino]benzoate (2-2, 1.08 g, 2.42 mmol) in a mixture of THF (4 mL)/Methanol (4 mL)/Water (4 mL) was added lithium hydroxide hydrate (305 mg, 7.26 mmol) and the mixture stirred at RT for 3 h. The reaction mixture was acidified to pH 1 using 1M HCl solution, which caused a precipitate to form. The precipitate was filtered, washed with water and dried in a vacuum oven at 40° C. overnight to give 2-[[3-[1-(2-carboxyethyl)pyrazol-4-yl]benzoyl]amino]-4-chloro-benzoic acid (Example 2, 819 mg, 82%) as a colorless powder. LC/MS (method B); RT 3.20 mins (100%), m/z 414.2/416.2 $(M+H)^+$. $^1$H-NMR (400 MHz, DMSO-$d_6$) 12.28 (s, 1H), 8.82 (s, 1H), 8.27 (s, 1H), 8.12 (s, 1H), 8.07 (d, J=8.5 Hz, 1H), 7.97 (s, 1H), 7.84 (d, J=7.4 Hz, 1H), 7.75 (d, J=7.4 Hz, 1H), 7.58 (t, J=7.6 Hz, 1H), 7.31-7.26 (m, 1H), 4.36 (t, J=6.7 Hz, 2H), 2.85 (t, J=6.6 Hz, 2H).

Preparation of disodium;2-[[3-[1-(2-carboxylatoethyl)pyrazol-4-yl]benzoyl]amino]-4-chloro-benzoate (Steps 4 and 5). To a solution of 2-[[3-[1-(2-carboxyethyl)pyrazol-4-yl]benzoyl]amino]-4-chloro-benzoic acid (Example 2, 819 mg, 1.98 mmol) in Methanol (10 mL) was added 1 M sodium hydroxide (4.1 mL, 4.06 mmol) and the mixture stirred at RT for 1 h. The mixture was then concentrated under reduced pressure and the residue azeotropically dried with acetonitrile before being dried further in a vacuum oven at 40° C. overnight to give disodium;2-[[3-[1-(2-carboxylatoethyl)pyrazol-4-yl]benzoyl]amino]-4-chloro-benzoate (Example 2-Na salt, 892 mg, 98%) as a colorless powder. LC/MS (method A); RT 3.17 mins (100%), m/z 414.2/416.2 $(M+H)^+$ $^1$H NMR: (500 MHz, DMSO-$d_6$) 15.56 (s, 1H), 8.80 (d, J=2.2 Hz, 1H), 8.28 (s, 1H), 8.23 (s, 1H), 8.09 (d, J=8.3 Hz, 1H), 7.88 (d, J=0.5 Hz, 1H), 7.85-7.80 (m, 1H), 7.80-7.77 (m, 1H), 7.51 (t, J=7.7 Hz, 1H), 7.07 (dd, J=8.3, 2.2 Hz, 1H), 4.34 (t, J=6.1 Hz, 2H), 2.43 (t, J=6.1 Hz, 2H).

The following compounds were prepared using general synthetic procedure 2. The examples and spectral data are shown in Table 3.

TABLE 3

| Example # | Name/Structure | Spectral data |
|---|---|---|
| 5 | 2-[[3-[1-(2-carboxyethyl)pyrazol-4-yl]benzoyl]amino]benzoic acid 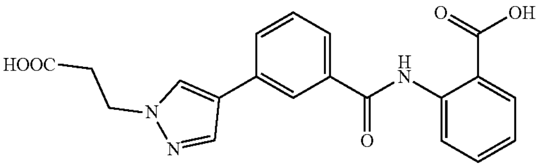 [SMILES: O=C(O)CCn1cc(-c2cccc(C(=O)Nc3ccccc3C(=O)O)c2)cn1] | $^1$H NMR (400 MHz, DMSO-d6) δ 13.10 (s, 1H), 8.88 (d, J = 7.6 Hz, 1H), 8.64 (d, J = 5.2 Hz, 1H), 8.61 (s, 1H), 8.32 (s, 1H), 8.21 (s, 1H), 8.06 (dd, J = 1.6 Hz, J = 8.0 Hz, 1H), 7.85 (dd, J = 1.6 Hz, J = 5.2 Hz, 1H), 7.68 (t, J = 7.2 Hz, 1H), 7.22 (t, J = 8.0 Hz, 1H), 4.38 (t, J = 6.8 Hz, 2H), 2.88 (t, J = 6.8 Hz, 2H). LC/MS (ESI) m/z: 380.0 (M + H)$^+$. |
| 7 | 2-[[4-[1-(2-carboxyethyl)pyrazol-4-yl]pyridine-2-carbonyl]amino]benzoic acid 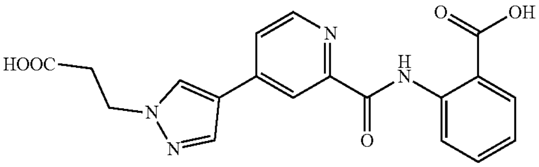 [SMILES: O=C(O)CCn1cc(-c2ccnc(C(=O)Nc3ccccc3C(=O)O)c2)cn1] | $^1$H NMR (400 MHz, DMSO-d6) δ 12.68 (s, 1H), 8.71 (d, J = 7.6 Hz, 1H), 8.28 (s, 1H), 8.15 (s, 1H), 8.07 (dd, J = 1.6 Hz, J = 8.0 Hz, 1H), 7.97 (s, 1H), 7.80 (t, J = 8.8 Hz, 1H), 7.76 (s, 1H), 7.63 (t, J = 8.4 Hz, 1H), 7.56 (t, J = 7.6 Hz, 1H), 7.19 (t, J = 6.8 Hz, 1H), 4.36 (t, J = 6.8 Hz, 2H), 2.85 (t, J = 6.4 Hz, 2H). LC/MS (ESI) m/z: 381.0 (M + H)$^+$. |
| 11 | 2-[[3-[1-(2-carboxyethyl)pyrazol-4-yl]benzoyl]amino]-4-methyl-benzoic acid 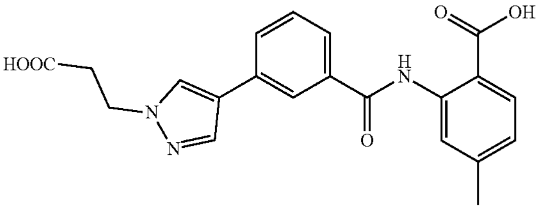 | $^1$H NMR (400 MHz, DMSO-d6) δ 12.25 (s, 1H), 8.60 (s, 1H), 8.28 (s, 1H), 8.13 (s, 1H), 7.96 (d, J = 8.1 Hz, 2H), 7.83 (d, J = 7.8 Hz, 1H), 7.76 (d, J = 7.9 Hz, 1H), 7.58 (t, J = 7.8 Hz, 1H), 7.05 (d, J = 8.0 Hz, 1H), 4.36 (t, J = 6.9 Hz, 2H), 2.86 (t, J = 6.7 Hz, 2H), 2.41 (s, 3H). LC/MS (ESI) m/z: 394.0 (M + H)$^+$. |
| 13 | 2-[[4-[1-(2-carboxyethyl)pyrazol-4-yl]pyridine-2-carbonyl]amino]-4-methyl-benzoic acid 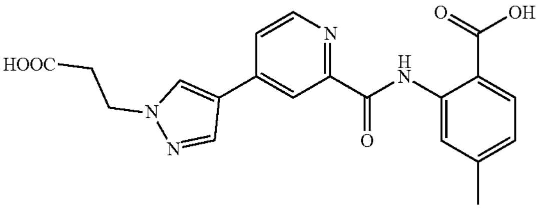 | $^1$H NMR (400 MHz, DMSO-d6) δ 13.38-12.88 (m, 1H), 12.51-12.12 (m, 1H), 8.74 (s, 1H), 8.64 (d, J = 5.1 Hz, 1H), 8.59 (s, 1H), 8.30 (s, 1H), 8.20 (s, 1H), 7.95 (d, J = 8.1 Hz, 1H), 7.84 (dd, J = 5.1, 1.8 Hz, 1H), 7.04 (d, J = 8.6 Hz, 1H), 4.38 (t, J = 6.7 Hz, 2H), 2.87 (t, J = 6.8 Hz, 2H), 2.41 (s, 3H). LC/MS (ESI) m/z: 395.0 (M + H)$^+$. |
| 17 | 2-[[3-[1-(2-carboxyethyl)pyrazol-4-yl]benzoyl]amino]-4-(trifluoromethyl)benzoic acid 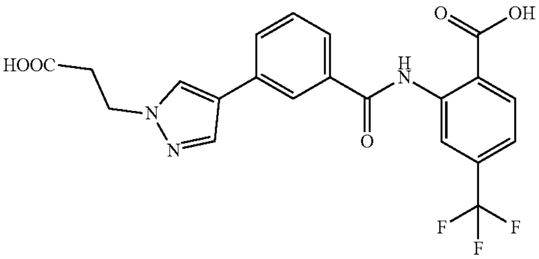 [SMILES: O=C(O)CCn1cc(-c2cccc(C(=O)Nc3cc(C(F)(F)F)ccc3C(=O)O)c2)cn1] | 1H NMR (400 MHz, DMSO-d6) δ 9.08 (s, 1H), 8.29-8.21 (m, 2H), 8.17 (s, 1H), 7.98 (s, 1H), 7.84 (d, J = 8.2 Hz, 1H), 7.78 (s, 1H), 7.62-7.50 (m, 2H), 4.36 (t, J = 6.7 Hz, 2H), 2.86 (t, J = 6.7 Hz, 2H). LC/MS (ESI) m/z: 448.0 (M + H)$^+$. |

TABLE 3-continued

| Example # | Name/Structure | Spectral data |
|---|---|---|
| 19 | 2-[[4-[1-(2-carboxyethyl)pyrazol-4-yl]pyridine-2-carbonyl]amino]-4-(trifluoromethyl)benzoic acid 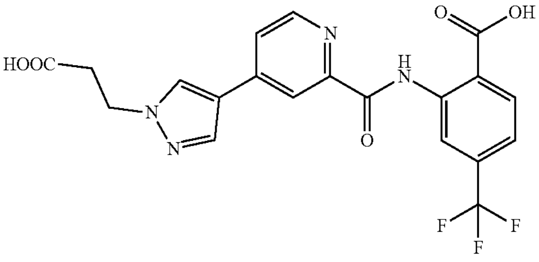 [SMILES: O=C(O)CCn1cc(-c2ccnc(C(=O)Nc3cc(C(F)(F)F)ccc3C(=O)O)c2)cn1] | $^{1}$H NMR (400 MHz, DMSO-d6) δ 13.45 (s, 1H), 12.45 (s, 1H), 9.28 (s, 1H), 8.66 (d, J = 5.1 Hz, 1H), 8.60 (s, 1H), 8.34 (s, 1H), 8.27-8.18 (m, 2H), 7.87 (dd, J = 5.1, 1.7 Hz, 1H), 7.55 (d, J = 8.1 Hz, 1H), 4.38 (t, J = 6.7 Hz, 2H), 2.87 (t, J = 6.7 Hz, 2H). LC/MS (ESI) m/z: 449.0 (M + H)$^{+}$. |
| 23 | 2-[[3-[1-(2-carboxyethyl)pyrazol-4-yl]benzoyl]amino]-4-isopropyl-benzoic acid 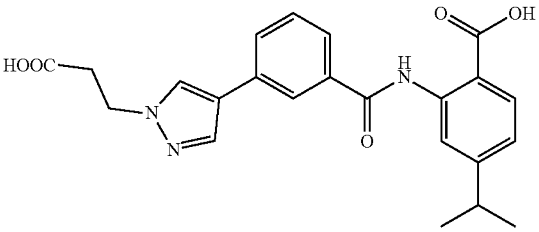 [SMILES: CC(C)c1ccc(C(=O)O)c(NC(=O)c2cccc(-c3cnn(CCC(=O)O)c3)c2)c1] | $^{1}$H NMR (400 MHz, DMSO-d6) δ 12.68 (s, 1H), 8.68 (d, J = 1.5 Hz, 1H), 8.27 (s, 1H), 8.15 (s, 1H), 8.02-7.94 (m, 2H), 7.79 (dd, J = 17.5, 7.9 Hz, 2H), 7.56 (t, J = 7.7 Hz, 1H), 7.08 (dd, J = 8.2, 1.5 Hz, 1H), 4.36 (t, J = 6.7 Hz, 2H), 2.96 (dt, J = 13.7, 6.9 Hz, 1H), 2.85 (t, J = 6.7 Hz, 2H), 1.25 (d, J = 6.9 Hz, 6H). LC/MS (ESI) m/z: 422.2 (M + H)$^{+}$. |
| 25 | 2-[4-[1-(2-carboxyethyl)pyrazol-4-yl]pyridine-2-carbonyl]amino]-4-isopropyl-benzoic acid 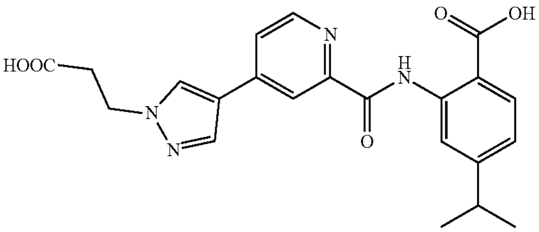 [SMILES: CC(C)c1ccc(C(=O)O)c(NC(=O)c2cc(-c3cnn(CCC(=O)O)c3)ccn2)c1] | $^{1}$H NMR (400 MHz, DMSO-d6) δ 13.06 (s, 1H), 8.86 (s, 1H), 8.64 (d, J = 5.1 Hz, 1H), 8.58 (s, 1H), 8.34 (s, 1H), 8.20 (s, 1H), 7.98 (d, J = 8.1 Hz, 1H), 7.87-7.81 (m, 1H), 7.11 (d, J = 8.0 Hz, 1H), 4.38 (t, J = 6.7 Hz, 2H), 2.98 (dt, J = 13.8, 6.9 Hz, 1H), 2.88 (t, J = 6.7 Hz, 2H), 1.26 (d, J = 6.9 Hz, 6H). LC/MS (ESI) m/z: 423.1 (M + H)$^{+}$. |
| 29 | 4-tert-butyl-2-[3-[1-(2-carboxyethyl)pyrazol-4-yl]benzoyl]amino]benzoic acid 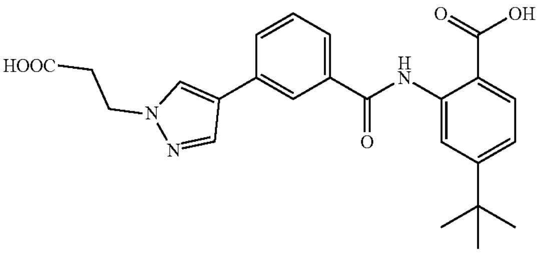 | 1H NMR (400 MHz, DMSO-d6) δ 8.87 (d, J = 1.8 Hz, 1H), 8.27 (s, 1H), 8.19 (s, 1H), 8.02-7.95 (m, 2H), 7.80 (t, J = 6.8 Hz, 2H), 7.54 (t, J = 7.8 Hz, 1H), 7.17 (d, J = 8.3 Hz, 1H), 4.36 (t, J = 6.7 Hz, 2H), 2.84 (t, J = 6.6 Hz, 2H), 1.32 (s, 9H). LC/MS (ESI) m/z: 422.2 (M + H)$^{+}$. |

TABLE 3-continued

| Example # | Name/Structure | Spectral data |
|---|---|---|
| 31 | 4-tert-butyl-2-[[4-[1-(2-carboxyethyl)pyrazol-4-yl]pyridine-2-carbonyl]amino]benzoic acid 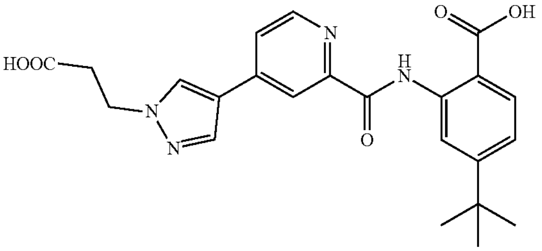 [SMILES: CC(C)(C)c1ccc(C(=O)O)c(NC(=O)c2cc(-c3cnn(CCC(=O)O)c3)ccn2)c1] | $^1$H NMR (400 MHz, DMSO-d6) δ 13.40 (s, 1H), 13.03 (s, 1H), 12.43 (s, 1H), 9.06 (d, J = 1.5 Hz, 1H), 8.64 (d, J = 5.1 Hz, 1H), 8.59 (s, 1H), 8.37 (s, 1H), 8.21 (s, 1H), 7.99 (d, J = 8.4 Hz, 1H), 7.84 (d, J = 3.6 Hz, 1H), 7.27 (dd, J = 8.4, 1.6 Hz, 1H), 4.38 (t, J = 6.6 Hz, 2H), 2.88 (t, J = 6.7 Hz, 2H), 1.34 (s, 9H). LC/MS (ESI) m/z: 437.1 (M + H)$^+$. |
| 35 | 2-[[3-[1-(2-carboxyethyl)pyrazol-4-yl]benzoyl]amino]-4-methoxy-benzoic acid 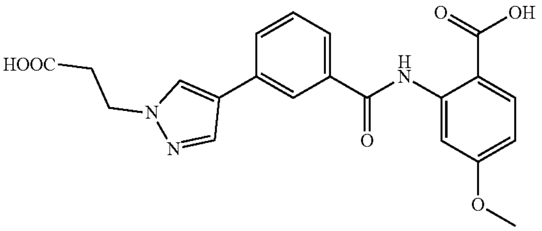 [SMILES: COc1ccc(C(=O)O)c(NC(=O)c2cccc(-c3cnn(CCC(=O)O)c3)c2)c1] | $^1$H NMR (400 MHz, DMSO-d6) δ 13.80-13.16 (m, 1H), 12.51 (s, 1H), 8.43 (d, J = 2.6 Hz, 1H), 8.27 (s, 1H), 8.14 (s, 1H), 8.02 (d, J = 8.9 Hz, 1H), 7.97 (s, 1H), 7.83 (d, J = 7.8 Hz, 1H), 7.76 (d, J = 7.8 Hz, 1H), 7.57 (t, J = 7.7 Hz, 1H), 6.79 (dd, J = 8.9, 2.6 Hz, 1H), 4.36 (t, J = 6.7 Hz, 2H), 3.87 (s, 3H), 2.85 (t, J = 6.7 Hz, 2H). LC/MS (ESI) m/z: 410.1 (M + H)$^+$. |
| 37 | 2-[[4-[1-(2-carboxyethyl)pyrazol-4-yl]pyridine-2-carbonyl]amino]-4-methoxy-benzoic acid 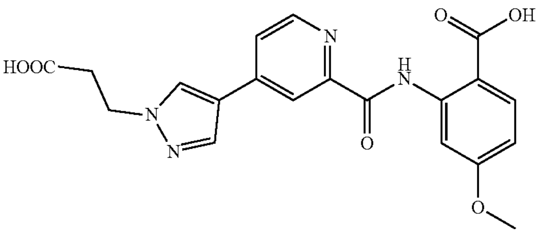 [SMILES: COc1ccc(C(=O)O)c(NC(=O)c2cc(-c3cnn(CCC(=O)O)c3)ccn2)c1] | $^1$H NMR (400 MHz, DMSO-d6) δ 8.63 (d, J = 4.9 Hz, 1H), 8.59 (s, 1H), 8.55 (d, J = 2.5 Hz, 1H), 8.32 (s, 1H), 8.20 (s, 1H), 8.01 (d, J = 8.8 Hz, 1H), 7.83 (d, J = 3.5 Hz, 1H), 6.77 (d, J = 6.3 Hz, 1H), 4.38 (t, J = 6.7 Hz, 2H), 3.86 (s, 3H), 2.87 (t, J = 6.7 Hz, 2H). LC/MS (ESI) m/z: 411.1 (M + H)$^+$. |
| 41 | 2-[[3-[1-(2-carboxyethyl)pyrazol-4-yl]benzoyl]amino]-4-(trifluoromethoxy)benzoic acid 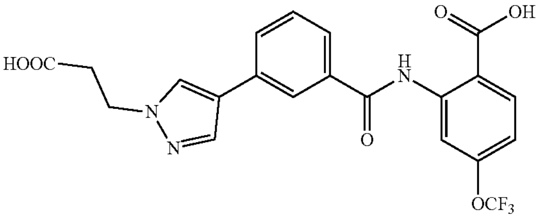 [SMILES: O=C(O)CCn1cc(-c2cccc(C(=O)Nc3cc(OC(F)(F)F)ccc3C(=O)O)c2)cn1] | 1H NMR (400 MHz, DMSO-d6) δ 8.78 (s, 1H), 8.29 (s, 1H), 8.21-8.13 (m, 2H), 7.98 (s, 1H), 7.84 (d, J = 7.5 Hz, 1H), 7.77 (d, J = 7.7 Hz, 1H), 7.58 (t, J = 7.6 Hz, 1H), 7.17 (s, 1H), 4.36 (t, J = 6.7 Hz, 2H), 2.86 (t, J = 6.6 Hz, 2H). LC/MS (ESI) m/z: 464.4 (M + H)$^+$. |

TABLE 3-continued

| Example # | Name/Structure | Spectral data |
|---|---|---|
| 43 | 2-[[4-[1-(2-carboxyethyl)pyrazol-4-yl]pyridine-2-carbonyl]amino]-4-(trifluoromethoxy)benzoic acid 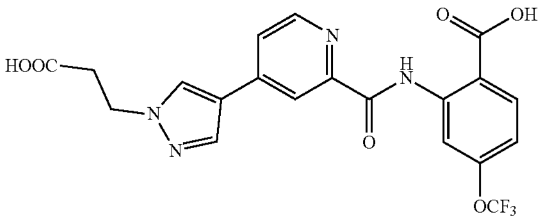 [SMILES: O=C(O)CCn1cc(-c2ccnc(C(=O)Nc3cc(OC(F)(F)F)ccc3C(=O)O)c2)cn1] | $^1H$ NMR (400 MHz, DMSO-d6) δ 13.28 (s, 1H), 12.41 (s, 1H), 8.95 (d, J = 1.3 Hz, 1H), 8.65 (d, J = 5.1 Hz, 1H), 8.61 (s, 1H), 8.35 (d, J = 1.3 Hz, 1H), 8.28-8.14 (m, 2H), 7.87 (dd, J = 5.1, 1.8 Hz, 1H), 7.20 (d, J = 8.9 Hz, 1H), 4.38 (t, J = 6.7 Hz, 2H), 2.87 (t, J = 6.7 Hz, 2H). LC/MS (ESI) m/z: 465.1 $(M + H)^+$. |
| 47 | 2-[[3-[1-(2-carboxyethyl)pyrazol-4-yl]benzoyl]amino]-6-chloro-pyridine-3-carboxylic acid 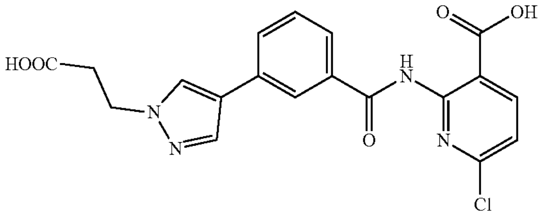 [SMILES: O=C(O)CCn1cc(-c2cccc(C(=O)Nc3nc(Cl)ccc3C(=O)O)c2)cn1] | $^1H$ NMR (400 MHz, DMSO-d6) δ 12.64-12.22 (m, 1H), 11.79-11.27 (m, 1H), 8.24 (dd, J = 16.1, 8.0 Hz, 3H), 7.98 (s, 1H), 7.81 (dd, J = 14.9, 7.8 Hz, 2H), 7.53 (t, J = 7.7 Hz, 1H), 7.42 (d, J = 8.1 Hz, 1H), 4.36 (t, J = 6.7 Hz, 2H), 2.85 (t, J = 6.7 Hz, 2H). LC/MS (ESI) m/z: 415.0 $(M + H)^+$. |
| 51 | 4-[3-[1-(2-carboxyethyl)pyrazol-4-yl]benzoyl]amino]-2-methyl-pyrimidine-5-carboxylic acid 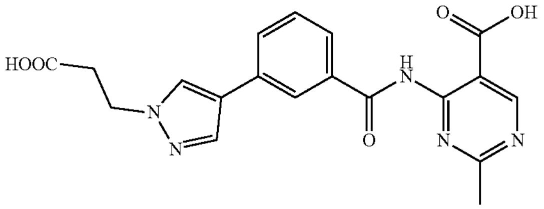 [SMILES: Cc1ncc(C(=O)O)c(NC(=O)c2cccc(-c3cnn(CCC(=O)O)c3)c2)n1] | $^1H$ NMR (400 MHz, DMSO-d6) δ 11.81 (s, 1H), 8.95 (s, 1H), 8.28 (s, 1H), 8.20 (s, 1H), 7.99 (s, 1H), 7.84 (d, J = 8.0 Hz, 1H), 7.78 (d, J = 7.8 Hz, 1H), 7.55 (t, J = 7.7 Hz, 1H), 4.36 (t, J = 6.6 Hz, 2H), 2.85 (t, J = 6.7 Hz, 2H), 2.64 (s, 3H). LC/MS (ESI) m/z: 396.0 $(M + H)^+$. |
| 55 | 2-[3-[1-(2-carboxyethyl)pyrazol-4-yl]benzoyl]amino]-6-methoxy-pyridine-3-carboxylic acid 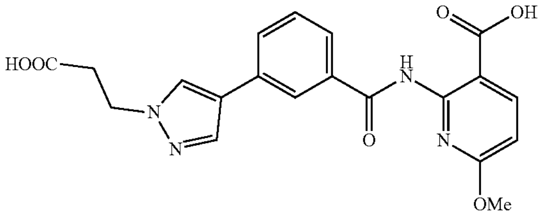 [SMILES: COc1ccc(C(=O)O)c(NC(=O)c2cccc(-c3cnn(CCC(=O)O)c3)c2)n1] | $^1H$ NMR (400 MHz, DMSO-d6) δ 11.83 (s, 1H), 8.28 (s, 1H), 8.21 (d, J = 8.6 Hz, 1H), 8.15 (s, 1H), 7.98 (s, 1H), 7.82 (d, J = 8.0 Hz, 1H), 7.75 (d, J = 8.2 Hz, 1H), 7.55 (t, J = 7.8 Hz, 1H), 6.64 (d, J = 8.6 Hz, 1H), 4.35 (t, J = 6.7 Hz, 2H), 3.94 (s, 3H), 2.85 (t, J = 6.8 Hz, 2H). LC/MS (ESI) m/z: 411.1 $(M + H)^+$. |
| 57 | 2-[[3-[1-(2-carboxyethyl)pyrazol-4-yl]benzoyl]amino]-4,5-dichloro-benzoic acid 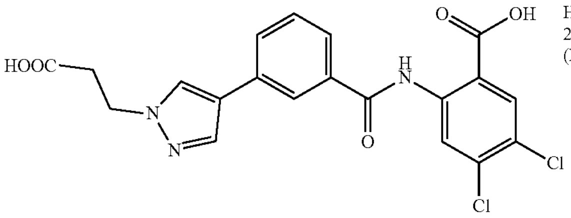 | 1H NMR (400 MHz, DMSO-d6) δ 15.61 (s, 1H), 8.95 (s, 1H), 8.30-8.09 (m, 3H), 7.90 (s, 1H), 7.80 (dd, J = 13.0, 7.8 Hz, 2H), 7.52 (t, J = 7.7 Hz, 1H), 4.34 (t, J = 6.4 Hz, 2H), 2.59 (t, J = 6.4 Hz, 2H). LC/MS (ESI) m/z: 448 $(M + H)^+$. |

TABLE 3-continued

| Example # | Name/Structure | Spectral data |
|---|---|---|
| 60 | 3-[[3-[1-(2-carboxyethyl)pyrazol-4-yl]benzoyl]amino]naphthalene-2-carboxylic acid 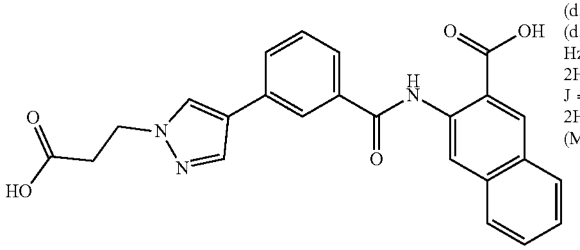 | $^1$H NMR (400 MHz, DMSO-d6) δ 12.60 (s, 1H), 9.16 (s, 1H), 8.77 (s, 1H), 8.28 (s, 1H), 8.19 (s, 1H), 8.06 (d, J = 8.1 Hz, 1H), 7.99 (s, 1H), 7.93 (d, J = 8.3 Hz, 1H), 7.82 (d, J = 7.4 Hz, 2H), 7.61 (dt, J = 15.5, 7.5 Hz, 2H), 7.51 (t, J = 7.6 Hz, 1H), 4.37 (t, J = 6.8 Hz, 2H), 2.86 (t, J = 6.8 Hz, 2H). LC/MS (ESI) m/z: 430.2 $(M + H)^+$. |
| 63 | 2-[3-[1-(2-carboxyethyl)pyrazol-4-yl]benzoyl]amino]quinoline-3-carboxylic acid 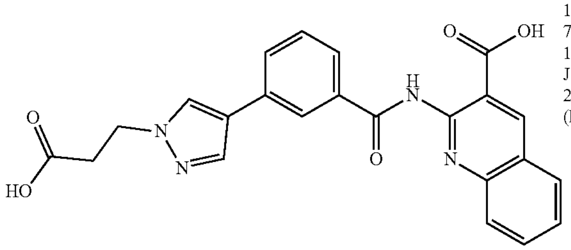 | $^1$H NMR (400 MHz, DMSO-d6) δ 11.55 (s, 1H), 8.91 (s, 1H), 8.28 (s, 2H), 8.15 (d, J = 8.1 Hz, 1H), 8.00 (s, 1H), 7.96 (d, J = 8.1 Hz, 1H), 7.89-7.80 (m, 3H), 7.63 (t, J = 7.5 Hz, 1H), 7.54 (t, J = 7.8 Hz, 1H), 4.37 (t, J = 6.7 Hz, 2H), 2.86 (t, J = 6.7 Hz, 2H). LC/MS (ESI) m/z: 431.0 $(M + H)^+$. |
| 66 | 6-[[3-[1-(2-carboxyethyl)pyrazol-4-yl]benzoyl]amino]-2,3-dihydro-1,4-benzodioxine-7-carboxylic acid 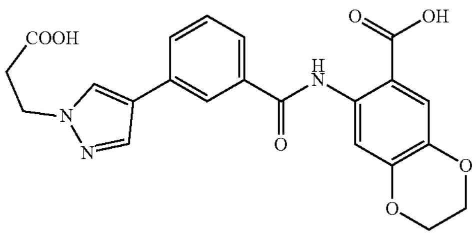 [SMILES: O=C(O)CCn1cc(-c2cccc(C(=O)Nc3cc4c(cc3C(=O)O)OCCO4)c2)cn1] | $^1$H NMR (400 MHz, DMSO-d6) δ 12.13 (s, 1H), 8.30 (s, 1H), 8.27 (s, 1H), 8.10 (s, 1H), 7.96 (s, 1H), 7.81 (d, J = 7.9 Hz, 1H), 7.72 (d, J = 7.8 Hz, 1H), 7.56 (t, J = 7.7 Hz, 1H), 7.50 (s, 1H), 4.35 (t, J = 6.7 Hz, 4H), 4.28 (d, J = 3.1 Hz, 2H), 2.85 (t, J = 6.8 Hz, 2H). LC/MS (ESI) m/z: 438.1 $(M + H)^+$. |
| 72 | 5-[[3-[1-(2-carboxyethyl)pyrazol-4-yl]benzoyl]amino]-1H-indazole-6-carboxylic acid 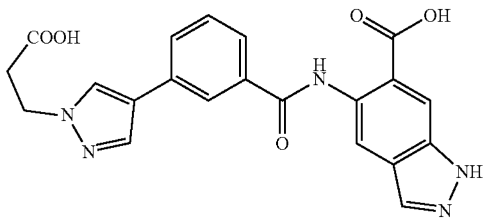 [SMILES: O=C(O)CCn1cc(-c2cccc(C(=O)Nc3cc4cn[nH]c4cc3C(=O)O)c2)cn1] | 1H NMR (400 MHz, DMSO-d6) δ 13.37 (s, 1H), 11.98 (s, 1H), 9.00 (s, 1H), 8.35-8.19 (m, 3H), 8.15 (s, 1H), 7.98 (s, 1H), 7.84-7.73 (m, 2H), 7.57 (t, J = 7.7 Hz, 1H), 4.36 (t, J = 6.6 Hz, 2H), 2.86 (t, J = 6.6 Hz, 2H). LC/MS (ESI) m/z: 420.0 $(M + H)^+$. |
| 73 | 5-[[3-[1-(2-carboxyethyl)pyrazol-4-yl]benzoyl]amino]-1-methyl-indazole-6-carboxylic acid 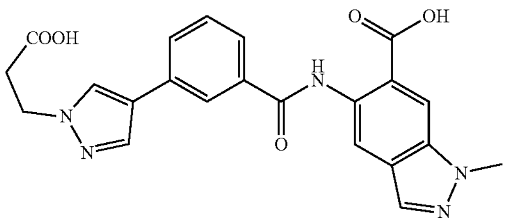 [SMILES: Cn1ncc2cc(NC(=O)c3cccc(-c4cnn(CCC(=O)O)c4)c3)c(C(=O)O)cc21] | $^1$H NMR (400 MHz, DMSO-d6) δ 11.98 (s, 1H), 8.92 (s, 1H), 8.46 (d, J = 1.2 Hz, 2H), 8.27 (s, 1H), 8.14 (s, 1H), 7.97 (s, 1H), 7.78 (dd, J = 14.9, 7.8 Hz, 2H), 7.56 (t, J = 7.8 Hz, 1H), 4.36 (t, J = 6.7 Hz, 2H), 4.23 (s, 3H), 2.86 (t, J = 6.8 Hz, 2H). LC/MS (ESI) m/z: 434.1$(M + H)^+$. |

TABLE 3-continued
| Example # | Name/Structure | Spectral data |
| --- | --- | --- |
| 108 | 2-[[3-[1-(2-hydroxyethyl)pyrazol-4-yl]benzoyl]amino]benzoic acid 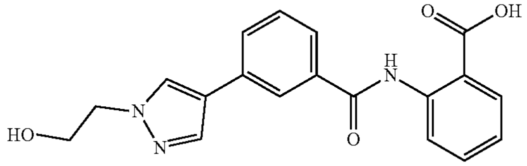 [SMILES: O=C(Nc1ccccc1C(=O)O)c1cccc(-c2cnn(CCO)c2)c1] | $^{1}H$ NMR (400 MHz, DMSO-d6) δ 12.38 (s, 1H), 8.72 (d, J = 8.4 Hz, 1H), 8.25 (s, 1H), 8.14 (s, 1H), 8.07 (dd, J = 1.2 Hz, 1.6 Hz, 1H), 7.96 (d, J = 4 Hz, 1H), 7.83 (d, J = 7.6 Hz, 1H), 7.76 (d, J = 7.6 Hz, 1H), 7.68-7.64 (m, 1H), 7.55 (t, J = 7.6 Hz, 1H), 7.23-7.19 (m, 1H), 4.94 (d, J = 7.6 Hz, 1H), 4.20-4.16 (m, 2H), 3.78 (s, 2H). LC/MS: 350.1 $(M + H)^{+}$. |
General Synthetic Procedure 3
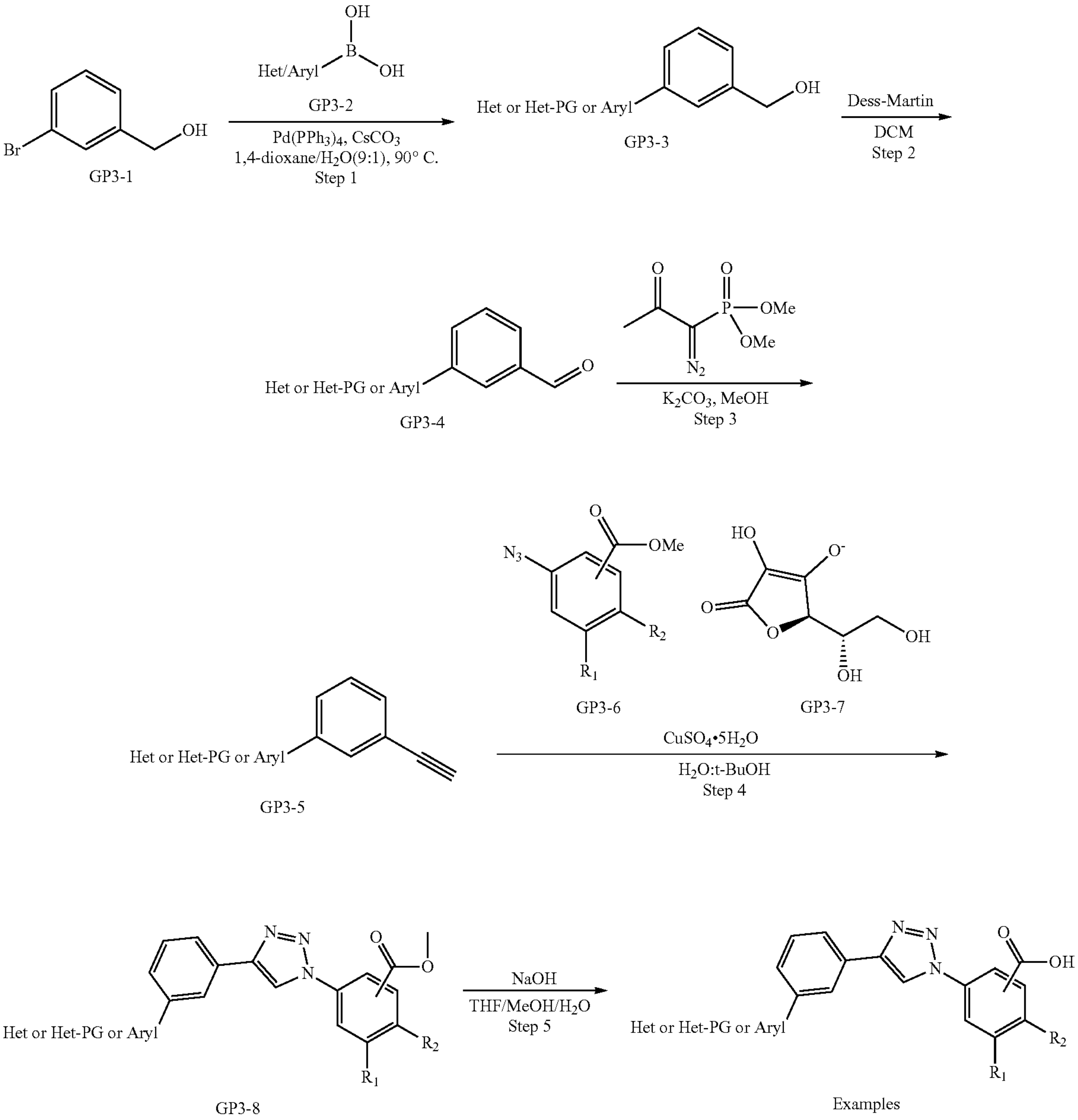

-continued

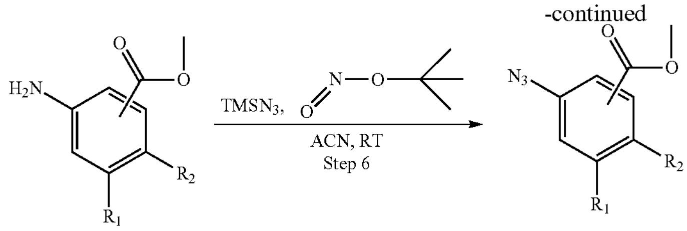

GP3-6A GP3-6

$R_1$ = H, halide, alkoxy, $OCF_3$
$R_2$ = H, halide, alkoxy, $OCF_3$
$R_1$ and $R_2$ together can form a ring
Aryl = phenyl or substituted phenyl
Het = Heterocycle or substituted heterocycle
PG = protective group Step 1. To a solution of (3-bromophenyl)methanol (GP3-1, 2.0 g, 10.7 mmol, 1.0 eq), aryl or heterocyclic boronic acid (GP3-2, 9.6 mmol, 0.9 eq) and $Cs_2CO_3$ (9.42 g, 28.89 mmol, 2.7 eq) in 1, 4-dioxane/$H_2O$ (90 mL/10 mL) was added $Pd(PPh_3)_4$(560 mg, 0.48 mmol, 0.045 eq) under $N_2$ protection. The reaction mixture was then heated to 100° C. under $N_2$ protection for 1 hour. Once LC/MS showed the reaction finished, the mixture was cooled down to rt, filtered, the precipitate was washed with THF (30 mL*2), The filtrate was evaporated, the residue was then purified $SiO_2$ manual column (DCM:MeOH=10:1) to give GP3-3.

Step2. To a solution of GP3-3, (0.98 mmol, 1.0 eq) in DCM (10.0 mL) was added Dess-Martin (828 mg, 1.95 mmol, 2.0 eq), and the reaction mixture was stirred at rt for 2 hour. Once TLC showed the reaction finished, the reaction mixture was filtered, the precipitate was washed with DCM (10.0 mL*2). The filtrate was washed with Sat. $NaHCO_3$ solution (10.0 mL) and Sat. $Na_2S_2O_3$ solution (10.0 mL), dried by $Na_2SO_4$ and filtered. The filtration was then concentrated to give the crude, which was purified by Chem-flash to give GP3-4.

Step 3. To a solution of GP3-4, (0.58 mmol, 1.0 eq) in MeOH (5.0 mL) was added $K_2CO_3$ (161 mg, 1.162 mmol, 2.0 eq) and dimethyl (1-diazo-2-oxopropyl)phosphonate (157 mg, 0.813 mmol, 1.4 eq). The reaction mixture was stirred at RT for 16 hours. Then, the reaction mixture was evaporated, the residue was taken up by EtOAc (20.0 mL), and washed with brine (5.0 mL), dried over $Na_2SO_4$, filtered. The filtrate was evaporated, the residue was then purified $SiO_2$ manual column (EA:PE=1:2) to give GP3-5 (100 mg, obtained) as a white solid.

Step 6. To a solution of GP3-6A, (1.2 mmol, 1.0 eq) in ACN (8 ml) was added $TMSN_3$ (207 mg, 1.8 mmol, 1.5 eq) and tert-butyl nitrite (186 mg, 1.8 mmol, 1.5 eq) at 0° C. It was stirred at RT for 2 h. It was concentrated in vacuum. No further purification was needed, the residue was used directly.

Step 4. To a solution of GP3-5, (0.595 mmol, 1.0 eq) in 4 mL t-BuOH/$H_2O$ (2:1) was added GP3-6, (252.0 mg, 1.189 mmol, 2.0 eq) in 2 mL t-BuOH/$H_2O$ (2:1). Followed by $CuSO_4{\cdot}5H_2O$ (45.0 mg, 0.18 mmol, 0.3 eq) and sodium (R)-2-((S)-1,2-dihydroxyethyl)-4-hydroxy-5-oxo-2,5-dihydrofuran-3-olate (GP3-7, 71.0 mg, 0.357 mmol, 0.6 eq). The reaction mixture was stirred at rt for 16 hours. Then, 40 mL of EtOAc and 20 mL of water was added, the organic layer was washed with brine, dried over $Na_2SO_4$, filtered. The filtrate was evaporated to give compound GP3-8 (150 mg, crude) as a white solid.

Step 5. To a solution of methyl 2-(4-(3-(1H-pyrazol-4-yl)phenyl)-1H-1,2,3-triazol-1-yl)-4-chlorobenzoate (GP3-8, 150 mg, crude) in 6 mL THF/MeOH/$H_2O$ (1:1:1) was added NaOH (58.0 mg, 1.37 mmol, 4.0 eq). The reaction mixture was stirred at rt for 2 h, and then adjusted with 2M hydrochloric acid to pH=3-4. The mixture was extracted with DCM and concentrated. The crude then purified by prep-HPLC (0.1% TFA) to give Examples.

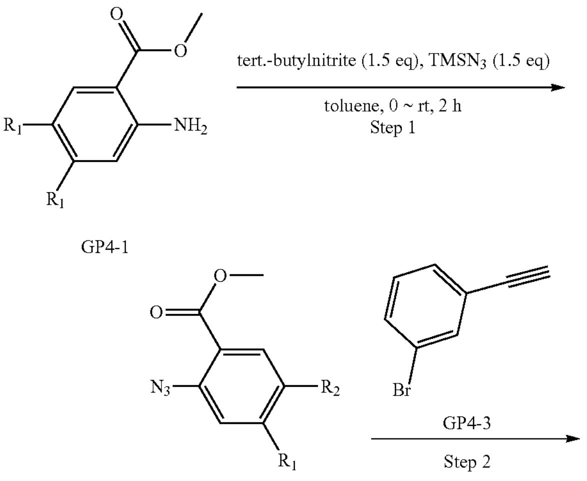

GP4-1

GP4-3

GP4-2

-continued

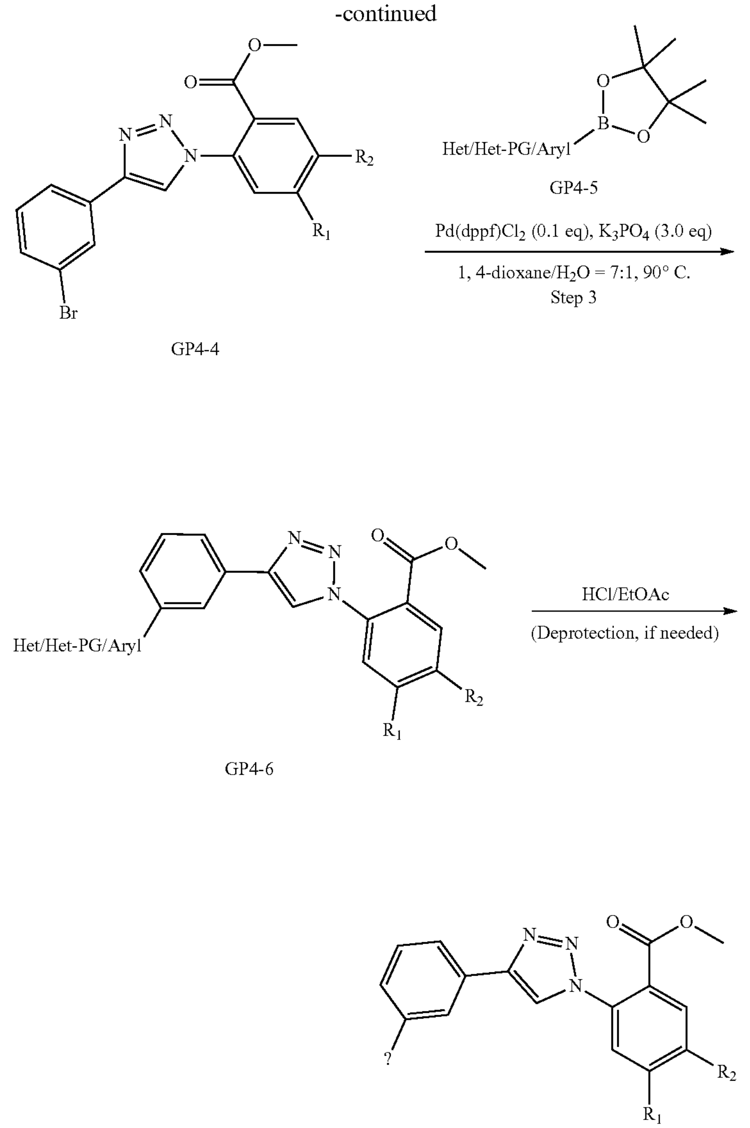

GP4-4

GP4-6

Step 1. a: To a solution of GP4-1, (19.87 mmol, 1.0 eq) in toluene (30 mL), was slowly dropwise added t-$BuNO_2$ (3.07 g, 29.8 mmol, 1.5 eq), $TMSN_3$ (3.4 g, 29.8 mmol, 1.5 eq) at 0° C., then stirred at 0° C. for 30 min, stirred at room temperature for 2 h. to obtain GP4-2.

Step 2. The slurry (GP4-2) from step a was added toluene (20 mL), 1-bromo-3-ethynylbenzene (GP4-3, 10.7 g, 59.61 mmol 3.0 eq), the mixture was stirred at 90° C. for overnight. LC/MS showed finished. The mixture was concentrated, added $H_2O$ (20 mL), extracted with EtOAc (3x30 mL), dried over $Na_2SO_4$ and concentrated. The residue was purified by silica gel chromatography eluting with 1% ~10% EtOAc in PE to afford GP4-4, (8.65 mmol, 43.5%) as a yellow solid.

Step 3. To a solution of GP4-4, (0.838 mmol, 1.0 eq.) in dioxane (7 mL) and $H_2O$ (1 mL), was added Aryl or heterocyclic or heterocycle with protective group with 4-(4, 4,5,5-tetramethyl-1,3,2-dioxaborolane (GP4-5, 1.676 mmol, 2.0 eq.), Pd(dppf)$Cl_2$ (61 mg, 0.0838 mmol, 0.1 eq), $K_3PO_4$ (533 mg, 2.514 mmol, 3.0 eq), the mixture was stirred at 90° C. for 16 h. LC/MS showed finished. The reaction mixture was added $H_2O$ (10 mL), extracted with EtOAc (3x20 mL), dried over $Na_2SO_4$ and concentrated. The residue was purified by silica gel chromatography eluting with 0% ~2% MeOH in DCM to afford GP4-6.

Step 4. To a solution of GP4-6, (0.76 mmol, 1.0 eq) in EtOAc (5 mL), was added HCl/EA (3.0 M) (5 mL). The reaction mixture was stirred at room temperature for 16 h. LC/MS showed finished. The mixture was concentrated and added $NH_3$. $H_2O$ adjust pH>10, extracted with DCM (3x20 mL), dried over $Na_2SO_4$ and concentrated. The residue was purified by silica gel chromatography eluting with 0% ~5% MeOH in DCM to afford GP4-7.

Step 5. To a solution of GP4-7, (0.49 mmol, 1.0 eq) was added NaOH (59 mg, 1.47 mmol, 3.0 eq) in THF/MeOH/$H_2O$ (2 mL/2 mL/2 mL). The reaction mixture was stirred at room temperature for 16 hours. The reaction mixture was purified by prep-HPLC (0.1% $NH_4HCO_3$) to give example compounds.

The following compounds were prepared using general synthetic procedures 3 and 4. The examples and spectral data are shown in Table 4.

TABLE 4

| Example # | Name/Structure | Spectral data |
|---|---|---|
| 89 | 4-chloro-2-[4-[3-(1H-pyrazol-4-yl)phenyl]triazol-1-yl]benzoic acid 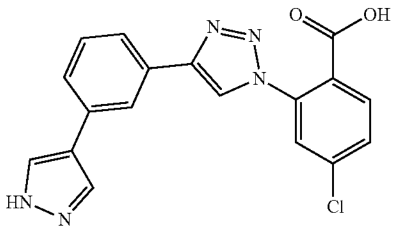 [SMILES: O=C(O)c1ccc(Cl)cc1-n1cc(-c2cccc(-c3cn[nH]c3)c2)nn1] | $^{1}H$ NMR (400 MHz, MeOD) δ 8.63 (s, 1H), 8.09 (d, J = 29.7 Hz, 3H), 7.79-7.67 (m, 3H), 7.61-7.53 (m, 2H), 7.45 (t, J = 7.8 Hz, 1H). LC/MS [M + H]: 366.0. |
| 90 | 4-chloro-2-(4-(3-(1-(tetrahydro-2H-pyran-4-yl)-1H-pyrazol-4-yl)phenyl)-1H-1,2,3-triazol-1-yl)benzoic acid 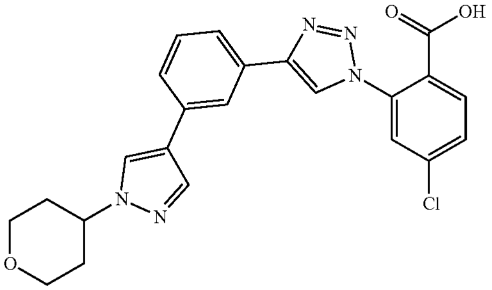 [SMILES: O=C(O)c1ccc(Cl)cc1-n1cc(-c2cccc(-c3cnn(C4CCOCC4)c3)c2)nn1] | $^{1}H$ NMR (400 MHz, DMSO-d6) δ13.39 (brs, 1H), 9.05 (brs, 1H), 8.36 (brs, 1H), 8.15-8.14 (m, 1H), 7.97-7.91 (m, 3H), 7.78-7.73 (m, 2H), 7.60-7.58 (m, 1H), 7.47 (t, J = 7.6 Hz, 1H), 4.47-4.39 (m, 1H), 4.00-3.96 (m, 2H), 3.52-3.46 (m, 2H), 2.07-1.93 (m, 4H). LC/MS [M + H]: 450.0. |
| 91 | 2-[4-[3-[1-(2-carboxyethyl)pyrazol-4-yl]phenyl]triazol-1-yl]-4-chloro-benzoic acid 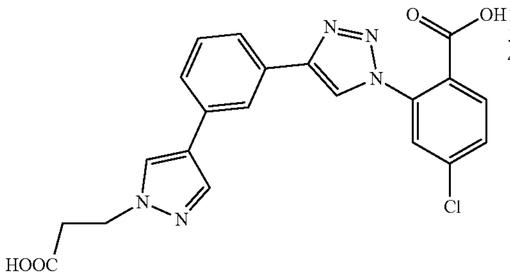 | $^{1}H$ NMR (400 MHz, MeOD) δ 8.63 (s, 1H), 8.09 (d, J = 2.4 Hz, 2H), 7.92 (s, 1H), 7.76-7.69 (m, 3H), 7.58-7.52 (m, 2H), 7.44 (t, J = 7.7 Hz, 1H), 4.46 (t, J = 6.8 Hz, 2H), 2.87 (t, J = 6.8 Hz, 2H). LC/MS [M + H]: 438.1. |
| 92 | 4-chloro-2-[1-[3-(1H-pyrazol-4-yl)phenyl]triazol-4-yl]benzoic acid 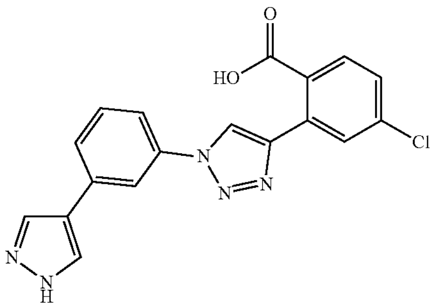 [SMILES: O=C(O)c1ccc(Cl)cc1-c1cn(-c2cccc(-c3cn[nH]c3)c2)nn1] | $^{1}H$ NMR (400 MHz, DMSO-d6) δ = 9.20 (s, 1H), 8.23-8.17 (m, 3H), 7.83-7.75 (m, 4H), 7.62-7.58 (m, 2H). LC/MS: 366 $[M + H]^{+}$. |

TABLE 4-continued

| Example # | Name/Structure | Spectral data |
| --- | --- | --- |
| 93 | 2-[1-[3-[1-(2-carboxyethyl)pyrazol-4-yl]phenyl]triazol-4-yl]-4-chloro-benzoic acid 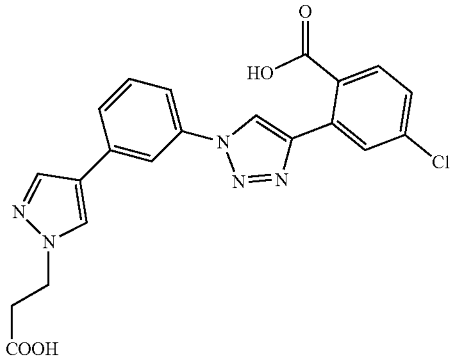 [SMILES: O=C(O)CCn1cc(-c2cccc(-n3cc(-c4cc(Cl)ccc4C(=O)O)nn3)c2)cn1] | $^1H$ NMR (400 MHz, DMSO-d6) δ12.83 (brs, 2H), 9.18 (brs, 1H), 8.34 (brs, 1H), 8.13 (brs, 1H), 8.04 (brs, 1H), 7.83 (d, J = 2.0 Hz, 1H), 7.78-7.75 (m, 2H), 7.70 (d, J = 7.6 Hz, 1H), 7.60-7.58 (m, 2H), 4.35 (t, J = 6.4 Hz, 2H), 2.85 (t, J = 6.4 Hz, 2H). LC/MS [M + H]: 437.95. |
| 260 | 2-(4-(3-(1H-pyrazol-4-yl)phenyl)-1H-1,2,3-triazol-1-yl)benzoic acid 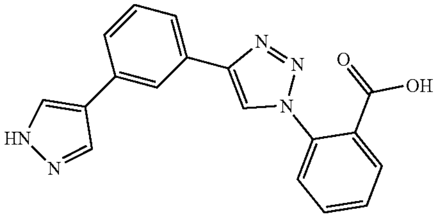 [SMILES: O=C(O)c1ccccc1-n1cc(-c2cccc(-c3cn[nH]c3)c2)nn1] | LC/MS (ESI) m/z: 323.2 $(M + H)^+$. |
| 260a | sodium 2-(4-(3-(1H-pyrazol-4-yl)phenyl)-1H-1,2,3-triazol-1-yl)benzoate 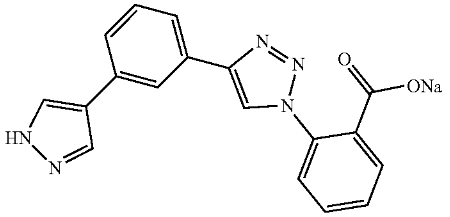 | $^1H$ NMR (400 MHz, DMSO-d6) δ 8.73 (s, 1H), 7.88 (s, 1H), 7.71 (s, 2H), 7.63-7.61 (m, 1H), 7.50-7.39 (m, 4H), 7.34 (d, J = 8.0 Hz, 1H), 7.27-7.23 (m, 1H). LC/MS (ESI) m/z: 323.2 $(M + H - Na)^+$. |
| 262 | 2-(1-(3-(1H-pyrazol-4-yl)phenyl)-1H-1,2,3-triazol-4-yl)benzoic acid 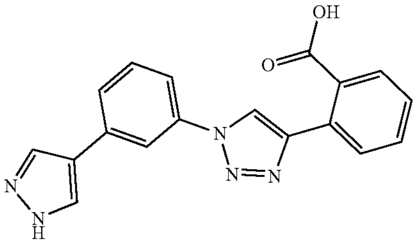 [SMILES: O=C(O)c1ccccc1-c1cn(-c2cccc(-c3cn[nH]c3)c2)nn1] | LC/MS (ESI) m/z: 323.2 $(M + H)^+$. |

TABLE 4-continued

| Example # | Name/Structure | Spectral data |
|---|---|---|
| 262a | sodium 2-(1-(3-(1H-pyrazol-4-yl)phenyl)-1H-1,2,3-triazol-4-yl)benzoate 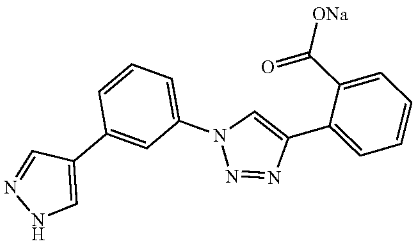 | $^{1}H$ NMR (400 MHz, DMSO-d6) δ 13.19 (s, 1H), 8.94 (s, 1H), 8.21 (s, 2H), 8.06-8.05 (m, 1H), 7.92-7.90 (m, 1H), 7.73 (d, J = 7.6 Hz, 1H), 7.65 (d, J = 7.2 Hz, 1H), 7.58-7.54 (m, 3H), 7.33-7.31 (m, 1H), 7.28-7.25 (m, 2H). LC/MS (ESI) m/z: 323.2 $(M + H - Na)^{+}$. |
| 263 | 2-(4-(3-(1H-pyrazol-4-yl)phenyl)-1H-1,2,3-triazol-1-yl)-4,5-dichlorobenzoic acid 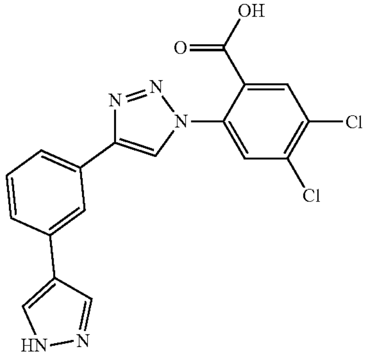 [SMILES: O=C(O)c1cc(Cl)c(Cl)cc1-n1cc(-c2cccc(-c3cn[nH]c3)c2)nn1] | LC/MS (ESI) m/z: 400.2 $(M + H)^{+}$. |
| 263a | sodium 2-(4-(3-(1H-pyrazol-4-yl)phenyl)-1H-1,2,3-triazol-1-yl)-4,5-dichlorobenzoate 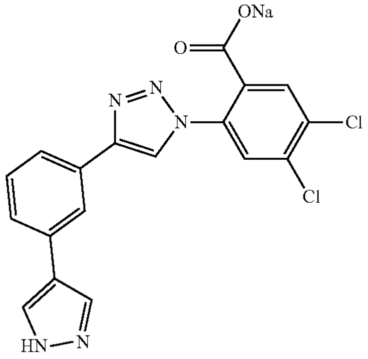 | $^{1}H$ NMR (400 MHz, DMSO-d6) δ 12.97 (brs, 1H), 8.86 (s, 1H), 8.11 (d, J = 9.6 Hz, 3H), 7.81-7.77 (m, 2H), 7.71 (d, J = 7.6 Hz, 1H), 7.58 (d, J = 7.6 Hz, 1H), 7.46-7.42 (m, 1H). LC/MS (ESI) m/z: 400.2 $(M + H - Na)^{+}$. |
| 264 | 7-(4-(3-(1H-pyrazol-4-yl)phenyl)-1H-1,2,3-triazol-1-yl)-2,3-dihydrobenzo[b][1,4]dioxine-6-carboxylic acid 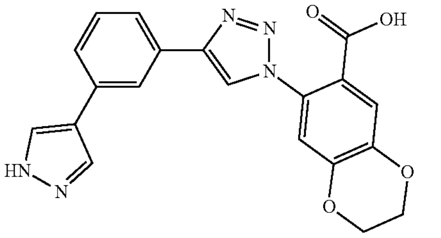 | LC/MS (ESI) m/z: 390.3 $(M + H)^{+}$. |

TABLE 4-continued

| Example # | Name/Structure | Spectral data |
|---|---|---|
| 264a | sodium 7-(4-(3-(1H-pyrazol-4-yl)phenyl)-1H-1,2,3-triazol-1-yl)-2,3-dihydrobenzo[b][1,4]dioxine-6-carboxylate 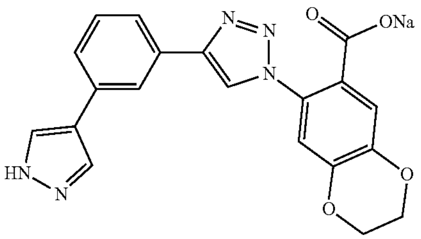 | $^1$H NMR (400 MHz, DMSO-d6) δ 8.69 (s, 1H), 8.09-8.07 (m, 3H), 7.69 (d, J = 7.6 Hz, 1H), 7.54 (d, J = 7.6 Hz, 1H), 7.42-7.38 (m, 1H), 7.21 (s, 1H), 6.92 (s, 1H), 4.30 (s, 4H). LC/MS (ESI) m/z: 390.3 $(M + H)^+$. |
| 265 | 2-(4-(3-(1H-pyrazol-4-yl)phenyl)-1H-1,2,3-triazol-1-yl)-5-chlorobenzoic 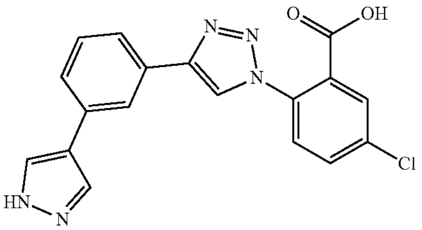 [SMILES: O=C(O)c1cc(Cl)ccc1-n1cc(-c2cccc(-c3cn[nH]c3)c2)nn1] | LC/MS (ESI) m/z: 367 $(M + H)^+$. |
| 265a | sodium 2-(4-(3-(1H-pyrazol-4-yl)phenyl)-1H-1,2,3-triazol-1-yl)-5-chlorobenzoate 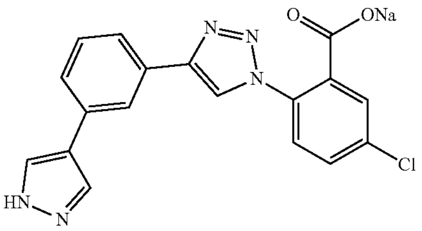 | $^1$H NMR (400 MHz, DMSO-d6) δ 8.81 (s, 1H), 8.09 (d, J = 2.0 Hz, 3H), 7.68 (d, J = 7.2 Hz, 1H), 7.56-7.55 (m, 2H), 7.53-7.50 (m, 1H), 7.47.45-7.42 (m, 2H). LC/MS (ESI) m/z: 407.2 $(M + ACN)^+$. |

General Synthetic Procedure 5

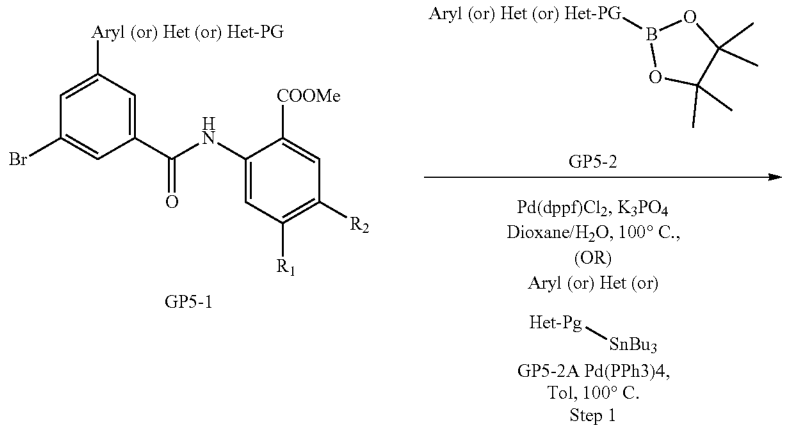

-continued

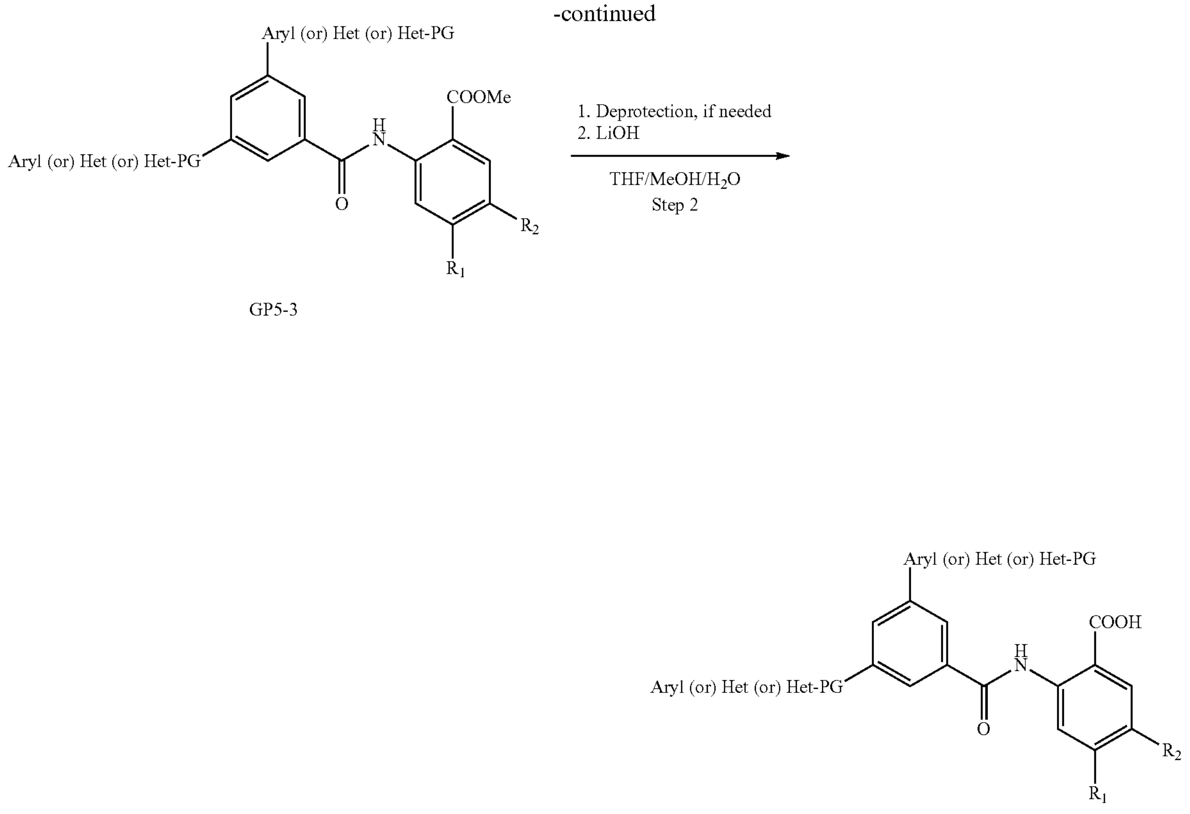

GP5-3

Examples $R_1$ = H, halide, alkyl, alkoxy, $OCF_3$
$R_2$ = H, halide, alkyl, alkoxy, $OCF_3$
$R_1$ and $R_2$ together can form a ring
Aryl = phenyl or substituted phenyl
Het = Heterocycle or substituted heterocycle
PG = protective group Step 1. The mixture of compound GP5-1 (0.4 mmol), compound GP5-2 (80 mg, 0.4 mmol), $K_3PO_4$ (164 mg, 0.8 mmol) and Pd(pddf)$Cl_2$ (30 mg, 0.04 mmol) [OR] GP5-2A and $Pd(Ph_3)_4$ in dioxane/$H_2O$ (5 ml/1 ml) was stirred at 100° C. under $N_2$ for 6 h. After completion, the mixture was extracted with EA, washed with water and brine, dried over $Na_2SO_4$ and concentrated. The crude product was purified by silica gel chromatography to give product, GP5-3.

Step 2. The mixture of compound GP5-3 (50 mg, 0.1 mmol) and LiOH (10 mg, 0.4 mmol) was in THF/MeOH/$H_2O$ (1 ml/1 ml/1 ml) stirred at 30° C. under $N_2$ for 4 h. After the reaction finished, the mixture was diluted with water and adjusted with 2M hydrochloric acid to PH=2-3, a large amount of precipitate formed, filtered, washed with water and dried in vacuum to afford example compounds.

Synthesis of 4-chloro-2-[[3-phenyl-5-(1-tetrahydro-pyran-4-ylpyrazol-4-yl)benzoyl]amino]benzoic acid (Example 120)

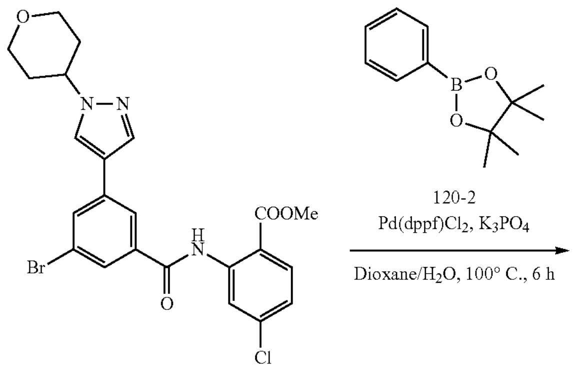

120-1

-continued

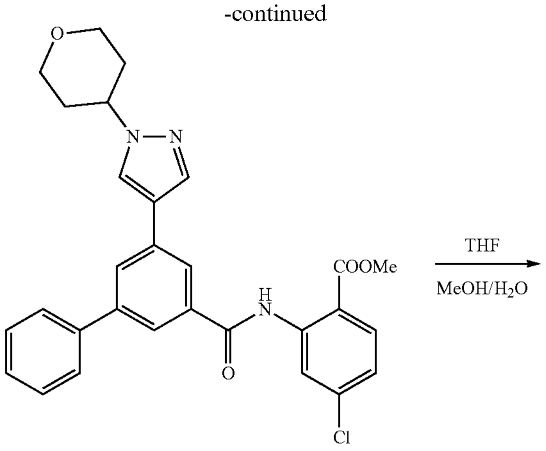

120-3

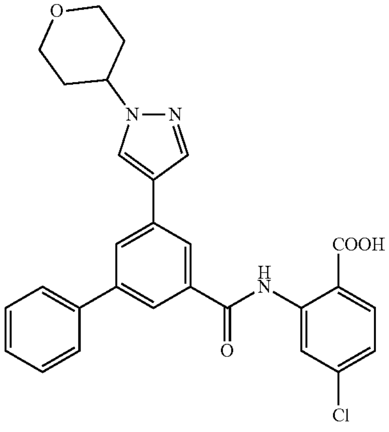

Example 120

Preparation of methyl 4-chloro-2-(5-(1-(tetrahydro-2H-pyran-4-yl)-1H-pyrazol-4-yl)-[1,1'-biphenyl]-3-carboxamido)benzoate (compound 120-3). The mixture of 120-1 (200 mg, 0.4 mmol), 120-2 (50 mg, 0.4 mmol), $K_3PO_4$ (164 mg, 0.8 mmol) and Pd(dppf)$Cl_2$ (30 mg, 0.04 mmol) was in dioxane/$H_2O$ (5 ml/1 ml) stirred at 100° C. under $N_2$ for 6 h. Once LC/MS showed finished, the mixture was extracted with EA, washed with water and brine, dried over $Na_2SO_4$ and concentrated. The crude product was purified by silica gel chromatography. The product was obtained as yellow solid (120-3, 52 mg, 0.1 mmol, Yield 25%). LC/MS [M+H]: 516.7

Preparation of 4-chloro-2-[[3-phenyl-5-(I-tetrahydropyran-4-ylpyrazol-4-yl)benzoyl)amino]benzoic acid (Example 20). The mixture of 120-3 (52 mg, 0.1 mmol) and LiOH (10 mg, 0.4 mmol) was in THF/MeOH/$H_2O$ (1 ml/1 ml/1 ml) stirred at 30° C. under $N_2$ for 4 h. After the reaction finished, the mixture solution was adjusted with 1M hydrochloric acid to pH=2-3, a large amount of precipitate formed, filtered, washed with water and dried in vacuum to afford Example 120 (45 mg, 0.1 mmol, Yield 90%) as yellow solid. LC/MS [M+H]:502.1. $^1$H NMR (400 MHz, DMSO-$d_6$) δ 13.05 (s, 1H), 8.85 (d, J=2.0 Hz, 1H), 8.53 (s, 1H), 8.16 (s, 2H), 8.08 (d, J 8.4 Hz, 2H), 8.03 (s, 1H), 7.83 (d, J 7.6 Hz, 2H), 7.53 (t, J 7.6 Hz, 2H), 7.46 (d, J 43.6 Hz, 1H), 7.28-7.26 (m, 1H), 4.47-4.44 (m, 1H), 4.00 (d, J 10.0 Hz, 2H), 3.52 (d, J 11.6 Hz, 2H), 2.08-1.99 (m, 4H).

The following compounds were prepared using general synthetic procedure 5. The examples and spectral data are shown in Table 5.

TABLE 5

| Example # | Name/Structure | Spectral data |
|---|---|---|
| 121 | 4-chloro-2-[[3-(2-pyridyl)-5-(1-tetrahydropyran-4-ylpyrazol-4-yl)benzoyl]amino]benzoic acid 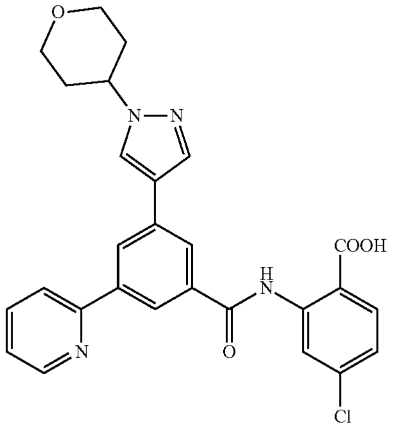 [SMILES: O=C(Nc1cc(Cl)ccc1C(=O)O)c1cc(-c2cnn(C3CCOCC3)c2)cc(-c2ccccn2)c1] | $^1$H NMR (400 MHz, DMSO-d6) δ 8.84 (s, 1H), 8.78-8.72 (m, 1H), 8.37 (d, J = 7.6 Hz, 3H), 8.16 (s, 1H), 8.14-8.07 (m, 1H), 8.00-7.98 (m, 2H), 7.96 (t, J = 4.0 Hz, 1H), 4.51-4.43 (m, 1H), 4.02-3.60 (m, 2H), 3.75-3.74 (m, 2H), 2.24-1.90 (m, 4H). LC/MS [M + H]: 503.1. |

TABLE 5-continued

| Example # | Name/Structure | Spectral data |
|---|---|---|
| 122 | 4-chloro-2-[[3-(3-pyridyl)-5-(1-tetrahydropyran-4-ylpyrazol-4-yl)benzoyl]amino]benzoic acid 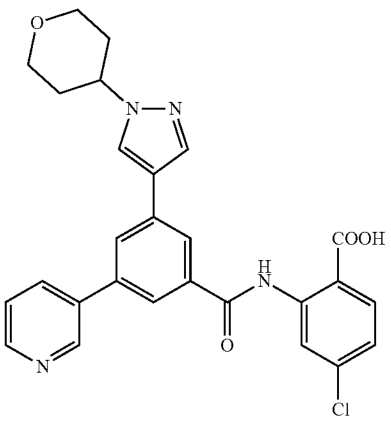 [SMILES: O=C(Nc1cc(Cl)ccc1C(=O)O)c1cc(-c2cccnc2)cc(-c2cnn(C3CCOCC3)c2)c1] | $^{1}$H NMR (400 MHz, DMSO-d6) δ = 12.40 (s, 1H), 9.07 (d, J = 2.0 Hz, 1H), 8.83 (d, J = 2.0 Hz, 1H), 8.66 (d, J = 4.6 Hz, 1H), 8.56 (s, 1H), 8.29-8.17 (m, 3H), 8.13-8.02 (m, 3H), 7.58 (dd, J = 8.0 Hz, 4.8 Hz, 1H), 7.31 (dd, J = 8.6 Hz, 2.0 Hz, 1H), 4.48-4.42 (m, 1H), 4.01-3.98 (m, 2H), 3.54-3.48 (m, 2H), 2.08-1.96 (m, 4H). LC/MS [M + H]: 503.1 |
| 125 | 4-chloro-2-[[3-(6-methyl-2-pyridyl)-5-(1-tetrahydropyran-4-ylpyrazol-4-yl)benzoyl]amino]benzoic acid 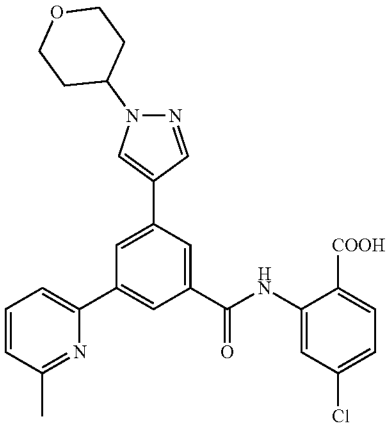 [SMILES: Cc1cccc(-c2cc(C(=O)Nc3cc(Cl)ccc3C(=O)O)cc(-c3cnn(C4CCOCC4)c3)c2)n1] | $^{1}$H NMR (400 MHz, DMSO-d6) δ 12.35 (s, 1H), 8.85 (d, J = 2.0 Hz, 1H), 8.53 (s, 1H), 8.48 (d, J = 1.6 Hz, 2H), 8.21 (s, 1H), 8.11-8.06 (m, 2H), 7.97 (d, J = 7.6 Hz, 1H), 7.90 (t, J = 7.6 Hz, 1H), 7.38-7.30 (m, 2H), 4.57-4.44 (m, 1H), 4.00 (d, J = 11.2 Hz, 2H), 3.50 (dt, J = 11.2, 6.0 Hz, 2H), 2.62 (s, 3H), 2.09-1.99 (m, 4H). LC/MS [M + H]: 517.1. |
| 126 | 4-chloro-2-[[3-(2-fluoro-6-methyl-3-pyridyl)-5-(1-tetrahydropyran-4-ylpyrazol-4-yl)benzoyl]amino]benzoic acid 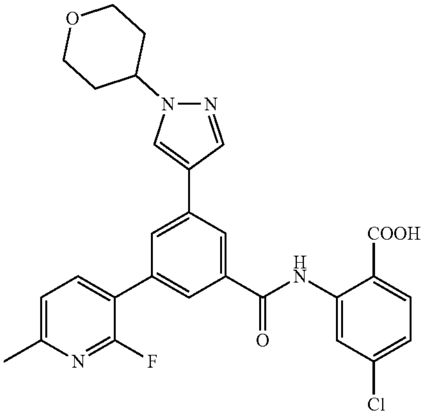 [SMILES: Cc1ccc(-c2cc(C(=O)Nc3cc(Cl)ccc3C(=O)O)cc(-c3cnn(C4CCOCC4)c3)c2)c(F)n1] | $^{1}$H NMR (400 MHz, DMSO-d6) δ 12.58 (s, 1H), 8.83 (s, 1H), 8.49 (s, 1H), 8.20 (s, 1H), 8.17-8.12 (m, 1H), 8.07 (d, J = 8.4 Hz, 3H), 7.94 (s, 1H), 7.40 (d, J = 7.6 Hz, 1H), 7.32-7.28 (m, 1H), 4.49-4.41 (m, 1H), 3.99 (d, J = 10.8 Hz, 2H), 3.52 (d, J = 5.2 Hz, 2H), 3.17 (s, 3H), 2.05-1.96 (m, 4H). LC/MS [M + H]: 535.2. |

TABLE 5-continued

| Example # | Name/Structure | Spectral data |
|---|---|---|
| 127 | 4-chloro-2-[[3-(6-methylpyrazin-2-yl)-5-(1-tetrahydropyran-4-ylpyrazol-4-yl)benzoyl]amino]benzoic acid 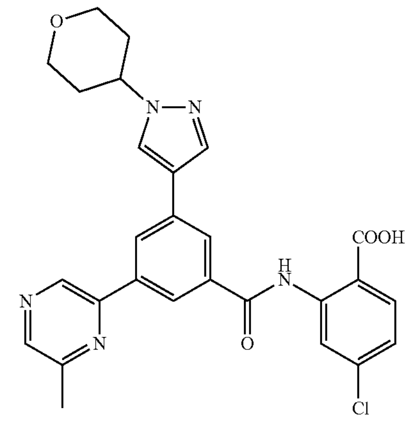 [SMILES: Cc1cncc(-c2cc(C(=O)Nc3cc(Cl)ccc3C(=O)O)cc(-c3cnn(C4CCOCC4)c3)c2)n1] | $^1$H NMR (400 MHz, DMSO-d6) δ 12.35 (s, 1H), 9.23 (s, 1H), 8.82 (s, 1H), 8.60 (s, 1H), 8.55 (s, 2H), 8.51 (s, 1H), 8.25 (s, 1H), 8.11-8.05 (m, 2H), 7.32 (d, J = 8.6 Hz, 1H), 4.46 (dt, J = 15.5, 5.4 Hz, 1H), 4.00 (d, J = 11.1 Hz, 2H), 3.55-3.51 (m, 2H), 2.63 (s, 3H), 2.03 (dt, J = 11.6, 8.0 Hz, 4H). LC/MS [M + H]: 518.1. |
| 128 | 4-chloro-2-[[3-(6-methyl-3-pyridyl)-5-(1-tetrahydropyran-4-ylpyrazol-4-yl)benzoyl]amino]benzoic acid 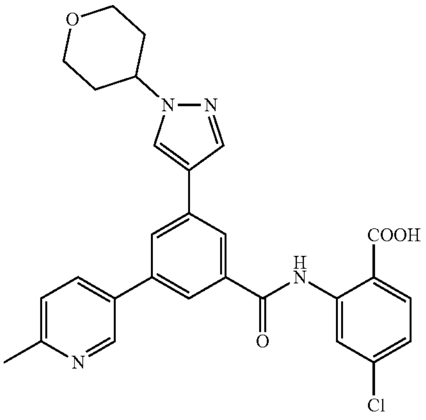 [SMILES: Cc1ccc(-c2cc(C(=O)Nc3cc(Cl)ccc3C(=O)O)cc(-c3cnn(C4CCOCC4)c3)c2)cn1] | $^1$H NMR (400 MHz, DMSO-d6) δ 12.32 (s, 1H), 9.10 (s, 1H), 8.81 (d, J = 2.0 Hz, 1H), 8.52 (d, J = 12.0 Hz, 2H), 8.43 (s, 1H), 8.28 (s, 1H), 8.12-8.07 (m, 3H), 7.73 (d, J = 7.2 Hz, 1H), 7.34-7.31 (m, 1H), 4.50-4.42 (m, 1H), 3.99 (t, J = 6.0 Hz, 2H), 3.66 (t, J = 4.4 Hz, 2H), 2.66 (d, J = 13.2 Hz, 3H), 2.08-1.94 (m, 4H). LC/MS [M + H]: 517.1. |
| 129 | 4-chloro-2-[[3-pyrimidin-5-yl-5-(1-tetrahydropyran-4-ylpyrazol-4-yl)benzoyl]amino]benzoic acid 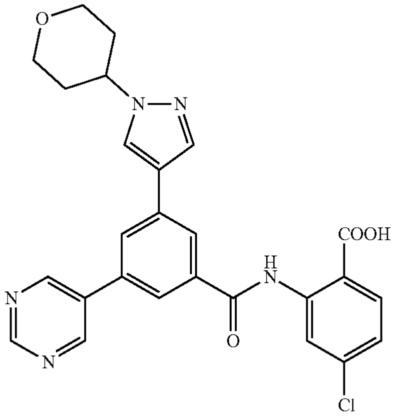 [SMILES: O=C(Nc1cc(Cl)ccc1C(=O)O)c1cc(-c2cncnc2)cc(-c2cnn(C3CCOCC3)c2)c1] | $^1$H NMR (400 MHz, DMSO-d6) δ 14.14 (s, 1H), 12.35 (s, 1H), 9.27 (t, J = 6.0 Hz, 3H), 8.81 (d, J = 2.0 Hz, 1H), 8.55 (s, 1H), 8.43 (s, 1H), 8.33 (s, 1H), 8.04 (t, J = 7.6 Hz, 3H), 7.32-7.29 (m, 1H), 4.48-4.42 (m, 1H), 4.00 (d, J = 9.2 Hz, 2H), 3.49 (t, J = 10.8 Hz, 2H), 2.03 (t, J = 9.6 Hz, 2H), 2.01-1.97 (m, 2H). LC/MS [M + H]: 504.1. |

TABLE 5-continued

| Example # | Name/Structure | Spectral data |
|---|---|---|
| 130 | 4-chloro-2-[[3-(2,4-dioxo-1H-pyrimidin-5-yl)-5-(1-tetrahydropyran-4-ylpyrazol-4-yl)benzoyl]amino]benzoic acid 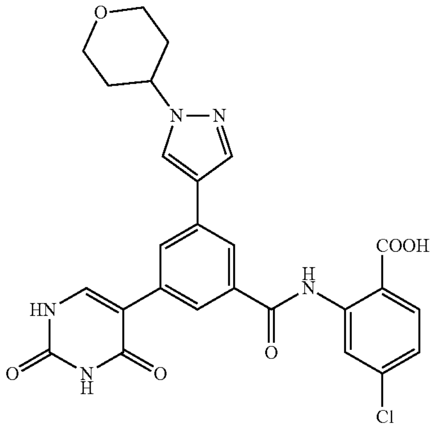 [SMILES: O=C(Nc1cc(Cl)ccc1C(=O)O)c1cc(-c2cnn(C3CCOCC3)c2)cc(-c2c[nH]c(=O)[nH]c2=O)c1] | $^1$H NMR (400 MHz, DMSO-d6) δ 11.45-11.16 (m, 2H), 8.77 (s, 1H), 8.35 (s, 1H), 8.15-7.89 (m, 5H), 7.79 (d, J = 5.8 Hz, 1H), 7.11 (d, J = 8.0 Hz, 1H), 4.46 (s, 1H), 3.98 (d, J = 10.5 Hz, 2H), 3.49 (t, J = 10.3 Hz, 2H), 2.00 (d, J = 21.5 Hz, 4H). LC/MS [M − H]: 536.1. |
| 131 | 4-chloro-2-[[3-(4-fluorophenyl)-5-(1-tetrahydropyran-4-ylpyrazol-4-yl)benzoyl]amino]benzoic acid 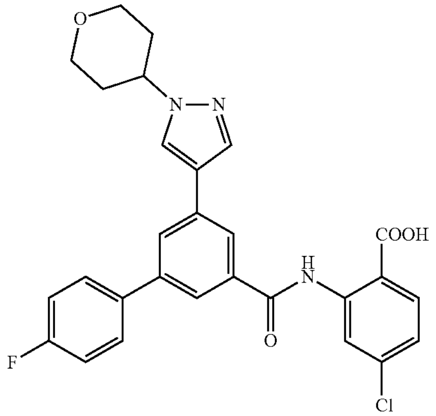 [SMILES: O=C(Nc1cc(Cl)ccc1C(=O)O)c1cc(-c2ccc(F)cc2)cc(-c2cnn(C3CCOCC3)c2)c1] | $^1$H NMR (400 MHz, DMSO-d6) δ 12.53 (s, 1H), 8.84 (d, J = 2.0 Hz, 1H), 8.53 (s, 1H), 8.15 (d, J = 1.6 Hz, 2H), 8.08 (d, J = 8.0 Hz, 2H), 7.98 (s, 1H), 7.88-7.85 (m, 2H), 7.35 (t, J = 8.8 Hz, 2H), 7.32-7.30 (m, 1H), 4.47-4.42 (m, 1H), 3.98 (t, J = 5.6 Hz, 2H), 3.53-3.48 (m, 2H), 2.07-1.96 (m, 4H). LC/MS [M + H]: 520.1. |
| 132 | 4-chloro-2-[[3-(3,4-difluorophenyl)-5-(1-tetrahydropyran-4-ylpyrazol-4-yl)benzoyl]amino]benzoic acid 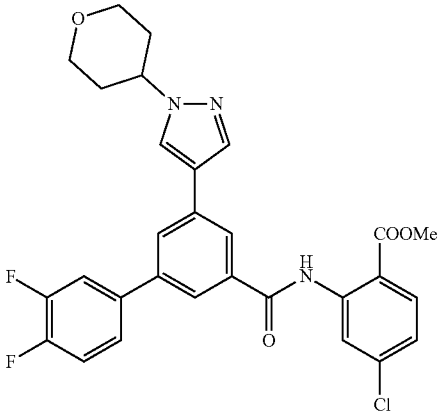 [SMILES: COC(=O)c1ccc(Cl)cc1NC(=O)c1cc(-c2ccc(F)c(F)c2)cc(-c2cnn(C3CCOCC3)c2)c1] | $^1$H NMR (400 MHz, DMSO-d6) δ 12.30 (s, 1H), 8.82 (d, J = 2.0 Hz, 1H), 8.54 (s, 1H), 8.17 (d, J = 10.0 Hz, 2H), 8.07 (t, J = 6.8 Hz, 2H), 8.01-7.97 (m, 1H), 7.96-7.93 (m, 1H), 7.69 (t, J = 3.2 Hz, 1H), 7.64-7.57 (m, 1H), 7.33-7.30 (m, 1H), 4.45 (d, J = 24.4 Hz, 1H), 3.88 (t, J = 27.0 Hz, 2H), 3.53-3.48 (m, 2H), 2.07-1.94 (m, 4H). LC/MS [M + H]: 538.1 |

TABLE 5-continued

| Example # | Name/Structure | Spectral data |
|---|---|---|
| 133 | 4-chloro-2-[[3-(1,5-dihydroimidazo[1,2-a]pyridin-6-yl)-5-(1-tetrahydropyran-4-ylpyrazol-4-yl)benzoyl]amino]benzoic acid 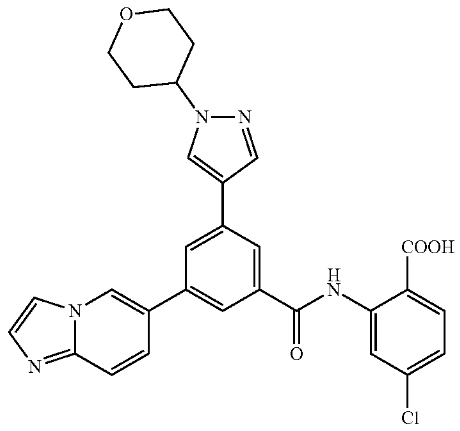 [SMILES: O=C(Nc1cc(Cl)ccc1C(=O)O)c1cc(-c2cnn(C3CCOCC3)c2)cc(-c2ccc3nccn3c2)c1] | $^{1}H$ NMR (400 MHz, DMSO-d6) δ 9.13 (s, 1H), 8.82 (d, J = 2.2 Hz, 1H), 8.52 (s, 1H), 8.20 (d, J = 14.9 Hz, 2H), 8.11-8.06 (m, 3H), 8.04 (s, 1H), 7.81-7.73 (m, 2H), 7.71 (d, J = 1.1 Hz, 1H), 7.31-7.24 (m, 1H), 4.50-4.42 (m, 1H), 3.99 (d, J = 11.5 Hz, 2H), 3.55-3.49 (m, 2H), 2.02 (dt, J = 11.5, 8.8 Hz, 4H). LC/MS [M + H]: 542.4. |
| 134 | 4-chloro-2-[[3-(1H-pyrrolo[2,3-b]pyridin-6-yl)-5-(1-tetrahydropyran-4-ylpyrazol-4-yl)benzoyl]amino]benzoic acid 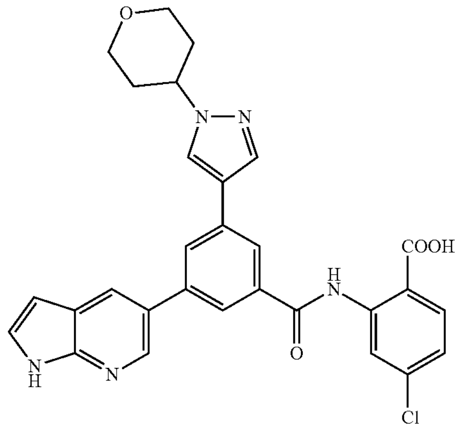 [SMILES: O=C(Nc1cc(Cl)ccc1C(=O)O)c1cc(-c2cnc3[nH]ccc3c2)cc(-c2cnn(C3CCOCC3)c2)c1] | $^{1}H$ NMR (400 MHz, DMSO-d6) δ 12.40 (s, 1H), 11.81 (s, 1H), 8.86 (d, J = 1.6 Hz, 1H), 8.69 (d, J = 1.6 Hz, 1H), 8.56 (s, 1H), 8.39 (s, 1H), 8.25 (s, 1H), 8.13-8.07 (m, 4H), 7.57 (d, J = 2.8 Hz, 1H), 7.32-7.30 (m, 1H), 6.55 (d, J = 1.2 Hz, 1H), 4.44 (t, J = 4.4 Hz, 1H), 4.00 (d, J = 10.4 Hz, 2H), 3.48 (t, J = 10.8 Hz, 2H), 2.09-1.99 (m, 4H). LC/MS [M + H]: 542.2. |

TABLE 5-continued

| Example # | Name/Structure | Spectral data |
|---|---|---|
| 135 | 2-[[3,5-bis(1-tetrahydropyran-4-ylpyrazol-4-yl)benzoyl]amino]-4-chloro-benzoic acid 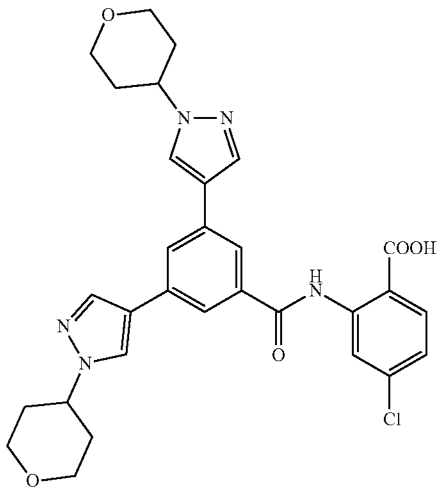 [SMILES: O=C(Nc1cc(Cl)ccc1C(=O)O)c1cc(-c2cnn(C3CCOCC3)c2)cc(-c2cnn(C3CCOCC3)c2)c1] | $^1H$ NMR (400 MHz, DMSO-d6) δ 14.09 (s, 1H), 12.31 (s, 1H), 8.83 (d, J = 2.0 Hz, 1H), 8.43 (s, 2H), 8.09 (d, J = 2.4 Hz, 2H), 8.06 (d, J = 10.4 Hz, 2H), 7.95 (d, J = 1.2 Hz, 2H), 7.32-7.19 (m, 1H), 4.49-4.41 (m, 2H), 4.02-3.98 (m, 4H), 3.54-3.48 (m, 4H), 2.08-1.95 (m, 8H). LC/MS [M + H]: 576.2. |
| 136 | 2-[[3-[1-(2-carboxyethyl)pyrazol-4-yl]-5-(1-tetrahydropyran-4-ylpyrazol-4-yl)benzoyl]amino]-4-chloro-benzoic acid 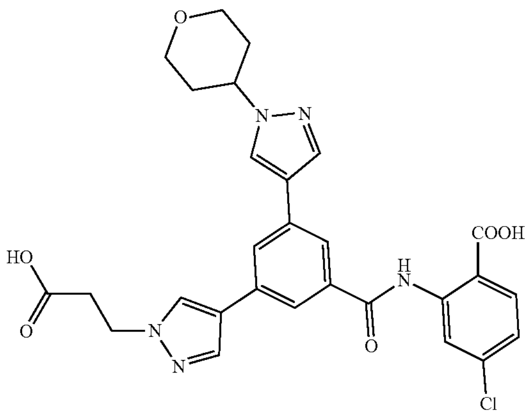 [SMILES: O=C(O)CCn1cc(-c2cc(C(=O)Nc3cc(Cl)ccc3C(=O)O)cc(-c3cnn(C4CCOCC4)c3)c2)cn1] | $^1H$ NMR (400 MHz, DMSO-d6) δ 12.34 (s, 1H), 8.82 (d, J = 2.4 Hz, 1H), 8.45 (s, 1H), 8.32 (s, 1H), 8.07 (t, J = 4.4 Hz, 2H), 8.04 (d, J = 2.8 Hz, 2H), 7.95 (d, J = 8.4 Hz, 2H), 7.32-7.29 (m, 1H), 4.46-4.42 (m, 1H), 4.36 (t, J = 6.6 Hz, 2H), 4.02-3.98 (m, 2H), 3.54-3.48 (m, 2H), 2.86 (t, J = 6.8 Hz, 2H), 2.08-1.98 (m, 4H). LC/MS [M + H]: 564.1 |
| 137 | 4-chloro-2-[[3-(1H-pyrazol-4-yl)-5-(1-tetrahydropyran-4-ylpyrazol-4-yl)benzoyl]amino]benzoic acid 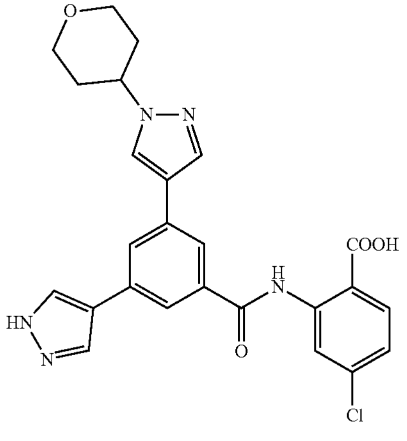 [SMILES: O=C(Nc1cc(Cl)ccc1C(=O)O)c1cc(-c2cn[nH]c2)cc(-c2cnn(C3CCOCC3)c2)c1] | $^1H$ NMR (400 MHz, DMSO-d6) δ 12.34 (s, 1H), 8.90 (d, J = 2.0 Hz, 1H), 8.52 (s, 1H), 8.27 (s, 2H), 8.17 (d, J = 12.4 Hz, 2H), 8.12 (d, J = 8.8 Hz, 1H), 8.03 (d, J = 6.8 Hz, 2H), 7.38-7.36 (m, 1H), 4.52-4.48 (m, 1H), 4.04 (t, J = 6.8 Hz, 2H), 3.60-3.54 (m, 2H), 2.14-2.04 (m, 4H). LC/MS [M + H]: 492.1. |

TABLE 5-continued

| Example # | Name/Structure | Spectral data |
|---|---|---|
| 138 | 6-methoxy-2-[3-phenyl-5-(1H-pyrazol-4-yl)benzoyl]amino]pyridine-3-carboxylic acid 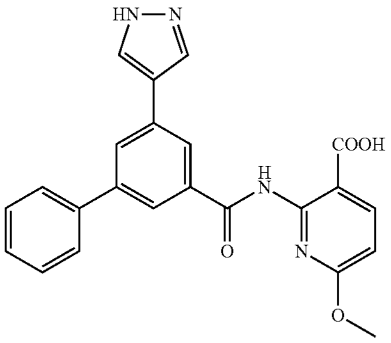 [SMILES: COc1ccc(C(=O)O)c(NC(=O)c2cc(-c3ccccc3)cc(-c3cn[nH]c3)c2)n1] | $^1$H NMR (400 MHz, DMSO-d6) δ 15.83 (s, 1H), 13.06 (s, 1H), 8.38 (s, 1H), 8.26 (s, 1H), 8.19 (d, J = 8.3 Hz, 1H), 8.11 (d, J = 11.1 Hz, 2H), 7.83 (d, J = 7.3 Hz, 2H), 7.54 (t, J = 7.6 Hz, 2H), 7.44 (t, J = 7.3 Hz, 1H), 6.39 (d, J = 8.3 Hz, 1H), 3.91 (s, 3H). LC/MS [M − H]: 415.1. |
| 139 | 6-methoxy-2-[[3-(1H-pyrazol-4-yl)-5-(2-pyridyl)benzoyl]amino]pyridine-3-carboxylic acid 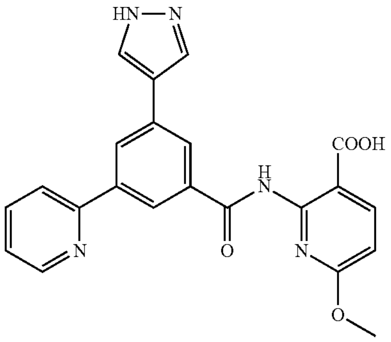 [SMILES: COc1ccc(C(=O)O)c(NC(=O)c2cc(-c3cn[nH]c3)cc(-c3ccccn3)c2)n1] | $^1$H NMR (400 MHz, DMSO-d6) δ 11.89 (s, 1H), 8.75 (d, J = 4.6 Hz, 1H), 8.50 (d, J = 8.6 Hz, 2H), 8.27 (d, J = 6.4 Hz, 3H), 8.22 (d, J = 8.6 Hz, 1H), 8.18 (d, J = 8.1 Hz, 1H), 7.99 (t, J = 7.6 Hz, 1H), 7.48-7.42 (m, 1H), 6.66 (d, J = 8.6 Hz, 1H), 3.96 (s, 3H). LC/MS [M + H]: 416.1. |
| 140 | 6-methoxy-2-[3-(1H-pyrazol-3-yl)-5-(3-pyridyl)benzoyl]amino]pyridine-3-carboxylic acid 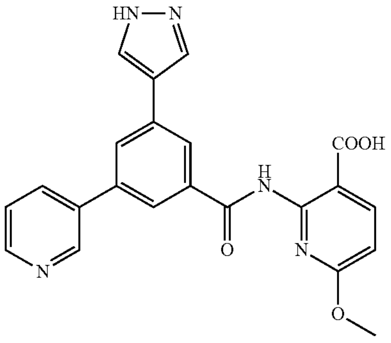 [SMILES: COc1ccc(C(=O)O)c(NC(=O)c2cc(-c3cccnc3)cc(-c3cn[nH]c3)c2)n1] | $^1$H NMR (400 MHz, DMSO-d6) δ 9.07 (d, J = 2.1 Hz, 1H), 8.66-8.62 (m, 1H), 8.30-8.19 (m, 5H), 8.11 (s, 1H), 7.59-7.53 (m, 1H), 6.56 (d, J = 8.4 Hz, 1H), 3.94 (s, 3H). LC/MS [M − H]: 414.1 |

TABLE 5-continued

| Example # | Name/Structure | Spectral data |
|---|---|---|
| 141 | 6-methoxy-2-[3-pyrazin-2-yl-5-(1H-pyrazol-4-yl)benzoyl]amino]pyridine-3-carboxylic acid 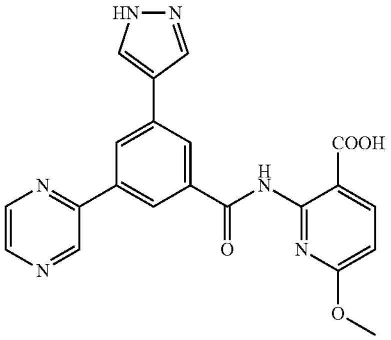 [SMILES: COc1ccc(C(=O)O)c(NC(=O)c2cc(-c3cn[nH]c3)cc(-c3cnccn3)c2)n1] | $^{1}H$ NMR (400 MHz, DMSO-d6) δ 9.42 (d, J = 1.4 Hz, 1H), 8.81 (dd, J = 2.4, 1.6 Hz, 1H), 8.70 (d, J = 2.5 Hz, 1H), 8.58 (s, 1H), 8.53 (s, 1H), 8.39 (s, 2H), 8.20 (d, J = 8.3 Hz, 2H), 6.41 (d, J = 8.3 Hz, 1H), 3.91 (s, 3H). LC/MS [M + H]: 417.0 |
| 142 | 6-methoxy-2-[[3-(1H-pyrazol-4-yl)-5-pyridazin-3-yl-benzoyl]amino]pyridine-3-carboxylic acid 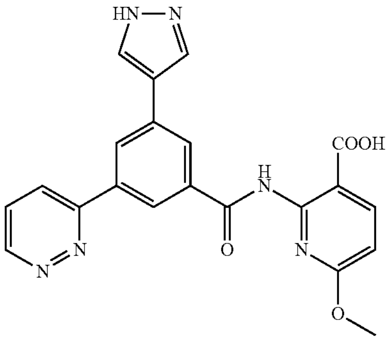 [SMILES: COc1ccc(C(=O)O)c(NC(=O)c2cc(-c3cn[nH]c3)cc(-c3cccnn3)c2)n1] | $^{1}H$ NMR (400 MHz, DMSO-d6) δ 9.30 (d, J = 3.8 Hz, 1H), 8.58 (s, 2H), 8.43 (d, J = 8.5 Hz, 1H), 8.35 (s, 1H), 8.23 (d, J = 8.5 Hz, 1H), 7.88 (dd, J = 8.6, 4.9 Hz, 1H), 6.65 (d, J = 8.6 Hz, 1H), 3.96 (s, 3H). LC/MS [M + H]: 417.0. |
| 143 | 6-methoxy-2-[[3-(6-methyl-2-pyridyl)-5-(1H-pyrazol-4-yl)benzoyl]amino]pyridine-3-carboxylic acid 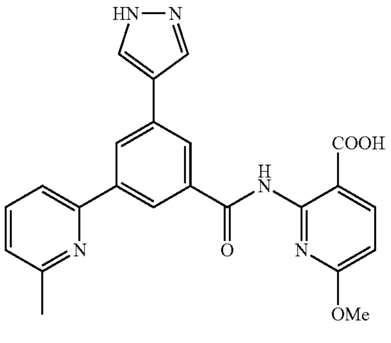 [SMILES: COc1ccc(C(=O)O)c(NC(=O)c2cc(-c3cn[nH]c3)cc(-c3cccc(C)n3)c2)n1] | $^{1}H$ NMR (400 MHz, DMSO-d6) δ 11.85 (s, 1H), 8.47 (d, J = 1.2 Hz, 2H), 8.26 (s, 3H), 8.22 (d, J = 8.6 Hz, 1H), 8.02-7.89 (m, 2H), 7.38 (d, J = 7.3 Hz, 1H), 6.67 (d, J = 8.6 Hz, 1H), 3.96 (s, 3H), 2.63 (s, 3H). LC/MS [M + H]: 430.1. |

TABLE 5-continued

| Example # | Name/Structure | Spectral data |
|---|---|---|
| 144 | 2-[[3-(2-fluoro-6-methyl-3-pyridyl)-5-(1H-pyrazol-4-yl)benzoyl]amino]-6-methoxy-pyridine-3-carboxylic acid 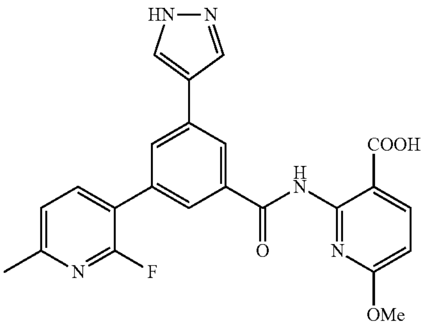 [SMILES: COc1ccc(C(=O)O)c(NC(=O)c2cc(-c3cn[nH]c3)cc(-c3ccc(C)nc3F)c2)n1] | $^1$H NMR (400 MHz, DMSO-d6) δ 13.10 (s, 1H), 8.29 (s, 1H), 8.19 (d, J = 8.4 Hz, 1H), 8.17-8.10 (m, 1H), 8.02 (d, J = 1.2 Hz, 1H), 7.98 (d, J = 1.3 Hz, 1H), 7.42-7.37 (m, 1H), 7.11 (s, 2H), 6.46 (d, J = 8.3 Hz, 1H), 3.91 (s, 3H), 2.51 (s, 3H). LC/MS [M + H]: 448.1 |
| 145 | 6-methoxy-2-[[3-(6-methylpyrazin-2-yl)-5-(1H-pyrazol-4-yl)benzoyl]amino]pyridine-3-carboxylic acid 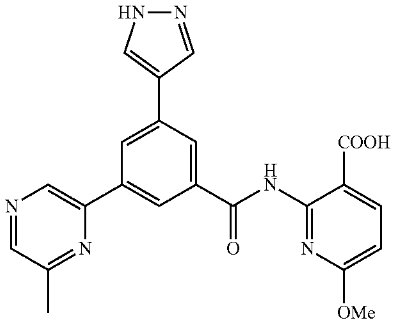 [SMILES: COc1ccc(C(=O)O)c(NC(=O)c2cc(-c3cn[nH]c3)cc(-c3cncc(C)n3)c2)n1] | $^1$H NMR (400 MHz, DMSO-d6) δ 9.22 (s, 1H), 8.58 (s, 1H), 8.53 (d, J = 10.1 Hz, 2H), 8.35 (s, 1H), 8.21 (d, J = 8.4 Hz, 1H), 7.12 (s, 2H), 6.50 (d, J = 8.5 Hz, 1H), 3.93 (s, 3H), 2.63 (s, 3H). LC/MS [M + H]: 431.1 |
| 146 | 6-methoxy-2-[[3-(6-methyl-3-pyridyl)-5-(1H-pyrazol-4-yl)benzoyl]amino]pyridine-3-carboxylic acid 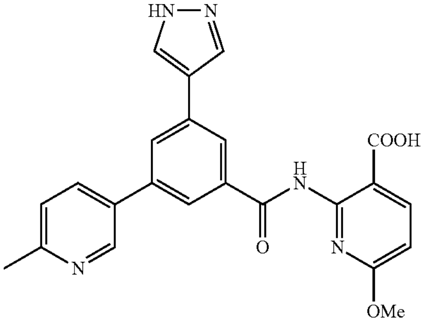 [SMILES: COc1ccc(C(=O)O)c(NC(=O)c2cc(-c3ccc(C)nc3)cc(-c3cn[nH]c3)c2)n1] | $^1$H NMR (400 MHz, DMSO-d6) δ 13.09 (s, 1H), 8.92 (d, J = 2.2 Hz, 1H), 8.27-8.19 (m, 3H), 8.17 (s, 1H), 8.12 (dt, J = 6.9, 3.4 Hz, 1H), 8.09 (s, 1H), 7.41 (d, J = 8.1 Hz, 1H), 7.12 (s, 1H), 6.52 (d, J = 8.4 Hz, 1H), 3.94 (s, 3H), 2.55 (s, 3H). LC/MS [M + H]: 430.1. |

TABLE 5-continued

| Example # | Name/Structure | Spectral data |
|---|---|---|
| 147 | 6-methoxy-2-[3-(1H-pyrazol-4-yl)-5-pyrimidin-5-yl-benzoyl]amino]pyridine-3-carboxylic acid 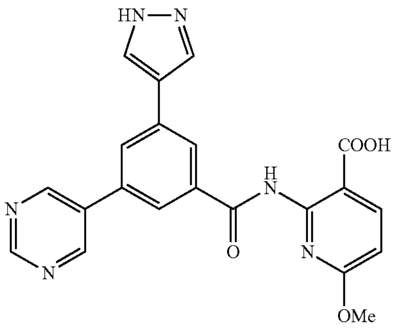 [SMILES: COc1ccc(C(=O)O)c(NC(=O)c2cc(-c3cncnc3)cc(-c3cn[nH]c3)c2)n1] | $^1$H NMR (400 MHz, DMSO-d6) δ 13.14 (s, 1H), 9.31 (s, 2H), 9.26 (s, 1H), 8.31 (s, 4H), 8.22-8.18 (m, 2H), 7.14 (s, 2H), 6.53 (d, J = 8.4 Hz, 1H), 3.93 (s, 3H). LC/MS [M + H]: 417.1. |
| 148 | 2-[[3-(2,4-dioxo-1H-pyrimidin-5-yl)-5-(1H-pyrazol-4-yl)benzoyl]amino]-6-methoxy-pyridine-3-carboxylic acid 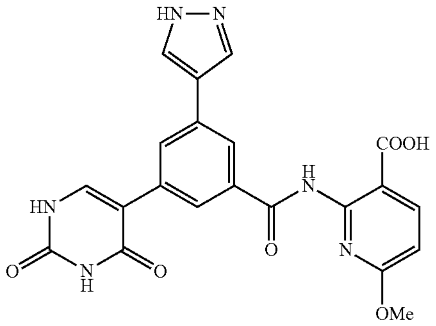 [SMILES: COc1ccc(C(=O)O)c(NC(=O)c2cc(-c3cn[nH]c3)cc(-c3c[nH]c(=O)[nH]c3=O)c2)n1] | $^1$H NMR (400 MHz, DMSO-d6) δ 13.36-12.87 (m, 1H), 11.32 (s, 1H), 8.20 (d, J = 8.4 Hz, 1H), 8.12 (s, 1H), 7.97 (d, J = 12.8 Hz, 2H), 7.81 (s, 1H), 7.09 (s, 1H), 6.54 (d, J = 8.2 Hz, 1H), 3.91 (d, J = 13.5 Hz, 3H). LC/MS [M + H]: 449.0 |
| 149 | 2-[[3-(4-fluorophenyl)-5-(1H-pyrazol-4-yl)benzoyl]amino]-6-methoxy-pyridine-3-carboxylic acid 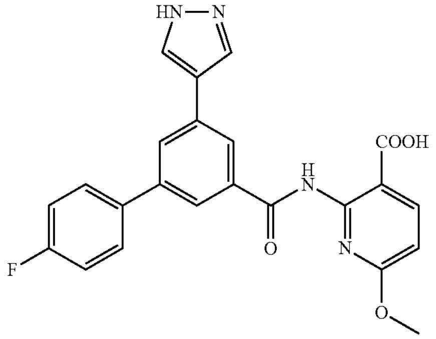 [SMILES: COc1ccc(C(=O)O)c(NC(=O)c2cc(-c3ccc(F)cc3)cc(-c3cn[nH]c3)c2)n1] | $^1$H NMR (400 MHz, DMSO-d6) δ 15.83 (s, 1H), 13.05 (s, 1H), 8.25 (s, 1H), 8.19 (d, J = 8.3 Hz, 1H), 8.11-8.07 (m, 2H), 7.91-7.84 (m, 2H), 7.37 (t, J = 8.8 Hz, 2H), 6.39 (d, J = 8.3 Hz, 1H), 3.91 (s, 3H). LC/MS [M + H]: 433.0. |

TABLE 5-continued

| Example # | Name/Structure | Spectral data |
|---|---|---|
| 150 | 2-[[3-(3,4-difluorophenyl)-5-(1H-pyrazol-3-yl)benzoyl]amino]-6-methoxy-pyridine-3-carboxylic acid 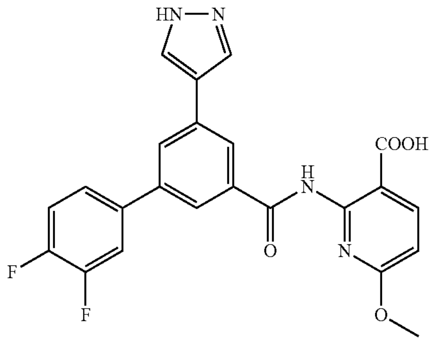 [SMILES: COc1ccc(C(=O)O)c(NC(=O)c2cc(-c3cn[nH]c3)cc(-c3ccc(F)c(F)c3)c2)n1] | $^1$H NMR (400 MHz, DMSO-d6) δ 15.62 (s, 1H), 13.08 (s, 1H), 8.37 (s, 1H), 8.27 (s, 1H), 8.19 (d, J = 8.3 Hz, 1H), 8.12 (d, J = 8.9 Hz, 2H), 7.98-7.91 (m, 1H), 7.69 (s, 1H), 7.64-7.55 (m, 1H), 6.41 (d, J = 8.3 Hz, 1H), 3.91 (s, 3H). LC/MS [M + H]: 451.1. |
| 151 | 2-[[3-(1,5-dihydroimidazo[1,2-alpyridin-6-yl)-5-(1H-pyrazol-4-yl)benzoyl]amino]-6-methoxy-pyridine-3-carboxylic acid 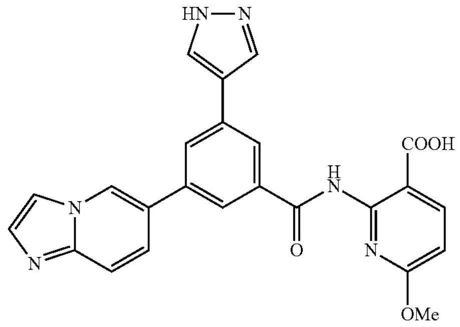 [SMILES: COc1ccc(C(=O)O)c(NC(=O)c2cc(-c3cn[nH]c3)cc(-c3ccc4nccn4c3)c2)n1] | $^1$H NMR (400 MHz, DMSO-d6) δ 15.81 (s, 1H), 13.09 (s, 1H), 9.09 (s, 1H), 8.37 (s, 1H), 8.29 (s, 1H), 8.20 (d, J = 8.3 Hz, 1H), 8.16 (d, J = 7.8 Hz, 3H), 8.01 (s, 1H), 7.76-7.69 (m, 2H), 7.64 (d, J = 1.0 Hz, 1H), 6.40 (d, J = 8.3 Hz, 1H), 3.89 (d, J = 18.9 Hz, 3H). LC/MS [M + H]: 455.1 |
| 152 | 6-methoxy-2-[[3-(1H-pyrazol-3-yl)-5-(1H-pyrrolo[2,3-b]pyridin-5-yl)benzoyl]amino]pyridine-3-carboxylic acid 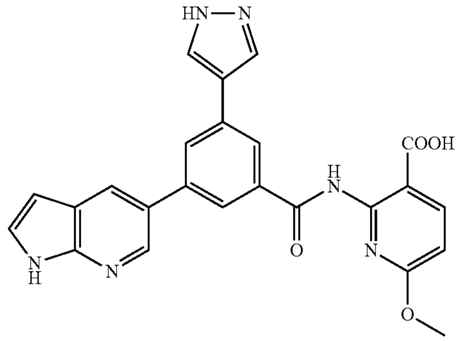 [SMILES: COc1ccc(C(=O)O)c(NC(=O)c2cc(-c3cn[nH]c3)cc(-c3cnc4[nH]ccc4c3)c2)n1] | $^1$H NMR (400 MHz, DMSO-d6) δ 11.79 (s, 1H), 8.68 (d, J = 2.1 Hz, 1H), 8.38 (d, J = 2.0 Hz, 1H), 8.21 (d, J = 8.4 Hz, 3H), 8.12 (s, 1H), 7.57-7.52 (m, 1H), 6.57-6.51 (m, 2H), 3.93 (d, J = 15.5 Hz, 3H). LC/MS [M + H]: 455.1. |

TABLE 5-continued

| Example # | Name/Structure | Spectral data |
|---|---|---|
| 153 | 6-methoxy-2-[[3-(1H-pyrazol-4-yl)-5-(1-tetrahydropyran-4-ylpyrazol-4-yl)benzoyl]amino]pyridine-3-carboxylic acid 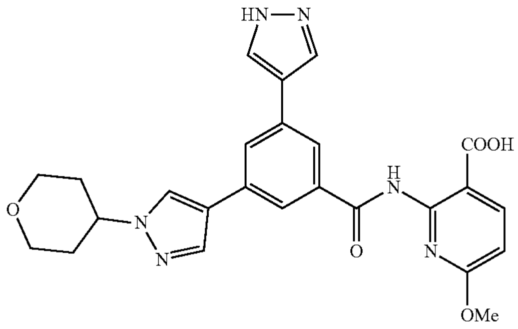 [SMILES: COc1ccc(C(=O)O)c(NC(=O)c2cc(-c3cn[nH]c3)cc(-c3cnn(C4CCOCC4)c3)c2)n1] | $^1H$ NMR (400 MHz, DMSO-d6) δ 13.07 (s, 1H), 8.41 (s, 1H), 8.20 (d, J = 8.4 Hz, 1H), 8.06 (s, 2H), 8.04 (s, 1H), 8.02 (s, 1H), 7.12 (s, 2H), 6.47 (d, J = 8.4 Hz, 1H), 4.52-4.39 (m, 1H), 3.99 (d, J = 11.6 Hz, 2H), 3.92 (s, 3H), 3.50 (td, J = 11.5, 2.4 Hz, 2H), 2.02 (dt, J = 11.4, 8.1 Hz, 4H). LC/MS [M + H]: 489.1 |
| 154 | 2-[[3-[1-(2-carboxyethyl)pyrazol-4-yl]-5-(1H-pyrazol-4-yl)benzoyl]amino]-6-methoxy-pyridine-3-carboxylic acid 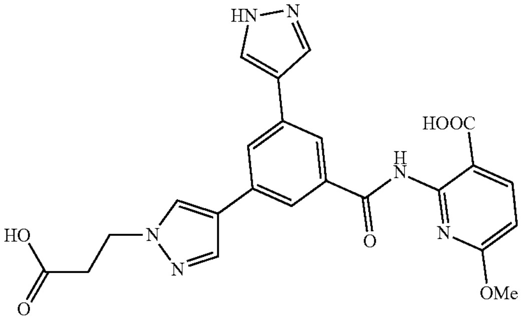 [SMILES: COc1ccc(C(=O)O)c(NC(=O)c2cc(-c3cn[nH]c3)cc(-c3cnn(CCC(=O)O)c3)c2)n1] | $^1H$ NMR (400 MHz, DMSO-d6) δ 8.34 (s, 1H), 8.22 (d, J = 8.6 Hz, 2H), 8.08 (s, 1H), 8.05 (s, 1H), 8.00 (s, 1H), 7.95 (s, 1H), 6.64 (d, J = 8.6 Hz, 1H), 4.37 (t, J = 6.7 Hz, 2H), 3.95 (s, 3H), 2.87 (t, J = 6.7 Hz, 2H). LC/MS [M − H]: 475.2. |
| 155 | 2-[[3,5-bis(1H-pyrazol-4-yl)benzoyl]amino]-6-methoxy-pyridine-3-carboxylic acid 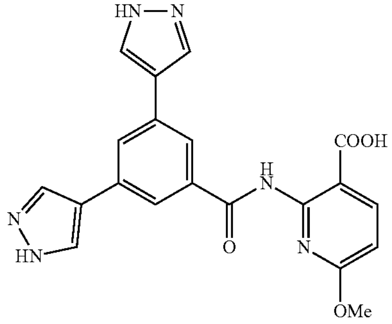 [SMILES: COc1ccc(C(=O)O)c(NC(=O)c2cc(-c3cn[nH]c3)cc(-c3cn[nH]c3)c2)n1] | $^1H$ NMR (400 MHz, DMSO-d6) δ 13.12 (s, 2H), 8.27-8.06 (m, 6H), 8.03 (s, 2H), 7.12 (s, 1H), 6.54 (d, J = 8.3 Hz, 1H), 3.94 (s, 3H). LC/MS [M + H]: 405.0. |

TABLE 5-continued

| Example # | Name/Structure | Spectral data |
|---|---|---|
| 156 | 6-[3-phenyl-5-(1-tetrahydropyran-4-ylpyrazol-4-yl)benzoyl]amino]-2,3-dihydro-1,4-benzodioxine-7-carboxylic acid 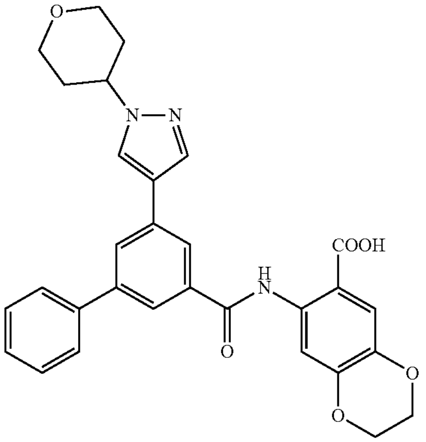 [SMILES: O=C(Nc1cc2c(cc1C(=O)O)OCCO2)c1cc(-c2ccccc2)cc(-c2cnn(C3CCOCC3)c2)c1] | $^1$H NMR (400 MHz, DMSO-d6) δ 12.67 (s, 1H), 8.53 (s, 1H), 8.32 (s, 1H), 8.13 (s, 2H), 8.08 (s, 1H), 8.00 (s, 1H), 7.81 (d, J = 7.4 Hz, 2H), 7.57-7.50 (m, 3H), 7.45 (t, J = 7.4 Hz, 1H), 4.44 (dt, J = 15.8, 5.5 Hz, 1H), 4.36 (d, J = 3.3 Hz, 2H), 4.28 (d, J = 3.4 Hz, 2H), 3.99 (d, J = 10.8 Hz, 2H), 3.56-3.47 (m, 2H), 2.09-1.96 (m, 4H). LC/MS [M + H]: 526.1. |
| 157 | 6-[3-(2-pyridyl)-5-(1-tetrahydropyran-4-ylpyrazol-4-yl)benzoyl]amino]-2,3-dihydro-1,4-benzodioxine-7-carboxylic acid 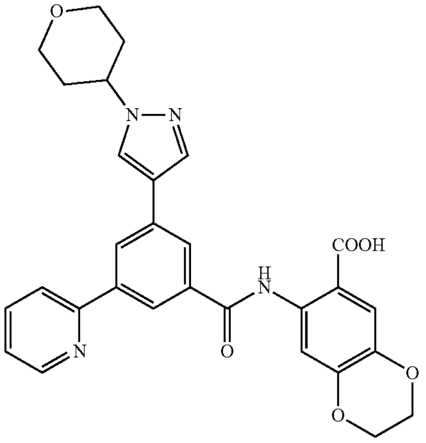 [SMILES: O=C(Nc1cc2c(cc1C(=O)O)OCCO2)c1cc(-c2cnn(C3CCOCC3)c2)cc(-c2ccccn2)c1] | $^1$H NMR (400 MHz, DMSO-d6) δ 13.66 (s, 1H), 12.27 (s, 1H), 8.74 (d, J = 4.2 Hz, 1H), 8.53 (s, 1H), 8.48 (d, J = 4.5 Hz, 2H), 8.34 (s, 1H), 8.18 (d, J = 13.1 Hz, 1H), 8.15 (d, J = 8.0 Hz, 1H), 8.08 (s, 1H), 7.97 (t, J = 7.0 Hz, 1H), 7.51 (s, 1H), 7.46-7.40 (m, 1H), 4.51-4.42 (m, 1H), 4.38 (d, J = 2.8 Hz, 2H), 4.30 (s, 2H), 4.00 (d, J = 10.9 Hz, 2H), 3.55-3.47 (m, 2H), 2.09-1.97 (m, 4H). LC/MS [M + H]: 527.1 |

TABLE 5-continued

| Example # | Name/Structure | Spectral data |
|---|---|---|
| 158 | 6-[[3-(3-pyridyl)-5-(1-tetrahydropyran-4-ylpyrazol-4-yl)benzoyl]amino]-2,3-dihydro-1,4-benzodioxine-7-carboxylic acid 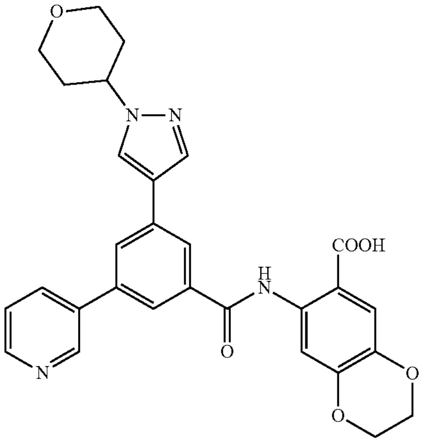 [SMILES: O=C(Nc1cc2c(cc1C(=O)O)OCCO2)c1cc(-c2cccnc2)cc(-c2cnn(C3CCOCC3)c2)c1] | $^1H$ NMR (400 MHz, DMSO-d6) δ 13.69 (s, 1H), 12.25 (s, 1H), 9.06 (s, 1H), 8.66 (d, J = 4.3 Hz, 1H), 8.56 (s, 1H), 8.31 (s, 1H), 8.24 (d, J = 8.8 Hz, 2H), 8.18 (s, 1H), 8.11 (s, 1H), 8.03 (s, 1H), 7.59-7.53 (m, 1H), 7.51 (s, 1H), 4.51-4.40 (m, 1H), 4.37 (d, J = 2.7 Hz, 2H), 4.30 (s, 2H), 3.99 (d, J = 11.0 Hz, 2H), 3.55-3.47 (m, 2H), 2.08-1.97 (m, 4H). LC/MS [M + H]: 527.1. |
| 161 | 6-[[3-(6-methyl-2-pyridyl)-5-(1-tetrahydropyran-4-ylpyrazol-3-yl)benzoyl]amino]-2,3-dihydro-1,4-benzodioxine-7-carboxylic acid 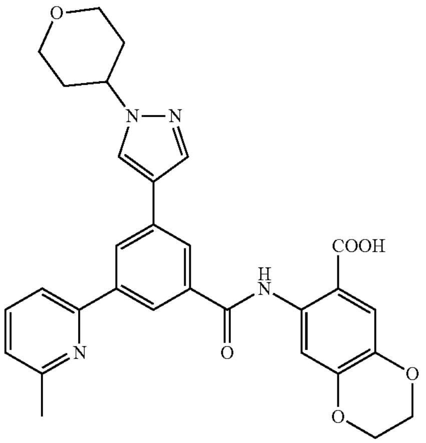 [SMILES: Cc1cccc(-c2cc(C(=O)Nc3cc4c(cc3C(=O)O)OCCO4)cc(-c3cnn(C4CCOCC4)c3)c2)n1] | $^1H$ NMR (400 MHz, DMSO-d6) δ 8.51-8.41 (m, 3H), 8.31 (s, 1H), 8.19 (s, 1H), 8.05 (d, J = 5.4 Hz, 1H), 7.92 (d, J = 7.8 Hz, 1H), 7.84 (t, J = 7.7 Hz, 1H), 7.51 (s, 1H), 7.30 (d, J = 7.5 Hz, 1H), 4.46 (tt, J = 9.8, 4.8 Hz, 1H), 4.35 (d, J = 3.4 Hz, 2H), 4.27 (d, J = 3.1 Hz, 2H), 3.99 (d, J = 11.1 Hz, 2H), 3.50 (td, J = 11.1, 2.5 Hz, 2H), 2.60 (s, 3H), 2.08-1.97 (m, 4H). LC/MS [M + H]: 541.2 |

TABLE 5-continued

| Example # | Name/Structure | Spectral data |
|---|---|---|
| 162 | 6-[[3-(2-fluoro-6-methyl-3-pyridyl)-5-(1-tetrahydropyran-4-ylpyrazol-4-yl)benzoyl]amino]-2,3-dihydro-1,4-benzodioxine-7-carboxylic acid 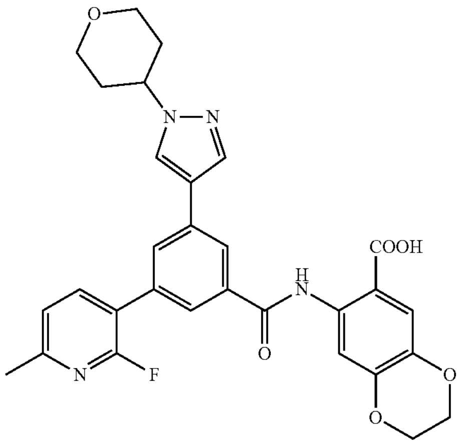 [SMILES: Cc1ccc(-c2cc(C(=O)Nc3cc4c(cc3C(=O)O)OCCO4)cc(-c3cnn(C4CCOCC4)c3)c2)c(F)n1] | $^1H$ NMR (400 MHz, DMSO-d6) δ 8.47 (s, 1H), 8.29 (s, 1H), 8.18 (s, 1H), 8.16-8.10 (m, 1H), 8.04 (d, J = 4.7 Hz, 2H), 7.92 (s, 1H), 7.50 (s, 1H), 7.38 (d, J = 7.7 Hz, 1H), 4.43 (td, J = 10.7, 5.2 Hz, 1H), 4.35 (d, J = 3.4 Hz, 2H), 4.28 (d, J = 4.6 Hz, 2H), 4.02-3.94 (m, 2H), 3.49 (td, J = 11.5, 2.4 Hz, 2H), 2.11-1.94 (m, 4H). LC/MS [M + H]: 559.2 |
| 163 | 6-[[3-(6-methylpyrazin-2-yl)-5-(1-tetrahydropyran-4-ylpyrazol-4-yl)benzoyl]amino]-2,3-dihydro-1,4-benzodioxine-7-carboxylic acid 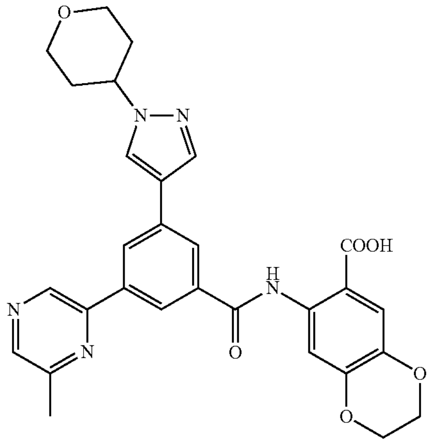 [SMILES: Cc1cncc(-c2cc(C(=O)Nc3cc4c(cc3C(=O)O)OCCO4)cc(-c3cnn(C4CCOCC4)c3)c2)n1] | $^1H$ NMR (400 MHz, DMSO-d6) δ 12.23 (s, 1H), 9.23 (s, 1H), 8.59 (s, 1H), 8.55 (d, J = 6.4 Hz, 2H), 8.49 (s, 1H), 8.31 (s, 1H), 8.23 (s, 1H), 8.10 (s, 1H), 7.52 (s, 1H), 4.51-4.42 (m, 1H), 4.38 (d, J = 2.9 Hz, 2H), 4.30 (s, 2H), 4.00 (d, J = 8.0 Hz, 2H), 3.52 (d, J = 9.4 Hz, 2H), 2.63 (s, 3H), 2.09-1.96 (m, 4H). LC/MS [M + H]: 542.2 |

TABLE 5-continued

| Example # | Name/Structure | Spectral data |
|---|---|---|
| 164 | 6-[[3-(6-methyl-3-pyridyl)-5-(1-tetrahydropyran-4-ylpyrazol-4-yl)benzoyl]amino]-2,3-dihydro-1,4-benzodioxine-7-carboxylic acid 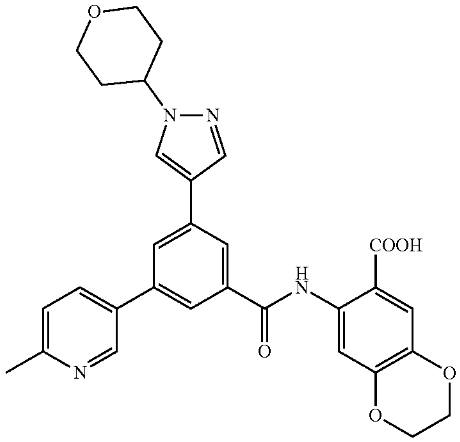 [SMILES: Cc1ccc(-c2cc(C(=O)Nc3cc4c(cc3C(=O)O)OCCO4)cc(-c3cnn(C4CCOCC4)c3)c2)cn1] | $^1$H NMR (400 MHz, DMSO-d6) δ 12.22 (s, 1H), 9.02 (s, 1H), 8.54 (s, 1H), 8.34 (s, 1H), 8.30 (s, 1H), 8.22 (s, 1H), 8.17 (s, 1H), 8.10 (s, 1H), 8.05 (s, 1H), 7.59 (d, J = 7.9 Hz, 1H), 7.51 (s, 1H), 4.51-4.40 (m, 1H), 4.37 (d, J = 2.5 Hz, 2H), 4.30 (s, 2H), 3.99 (d, J = 10.9 Hz, 2H), 3.52 (d, J = 10.4 Hz, 2H), 2.62 (s, 3H), 2.09-1.95 (m, 4H). LC/MS [M + H]: 541.3 |
| 165 | 6-[[3-pyrimidin-5-yl-5-(1-tetrahydropyran-4-ylpyrazol-4-yl)benzoyl]amino]-2,3-dihydro-1,4-benzodioxine-7-carboxylic acid 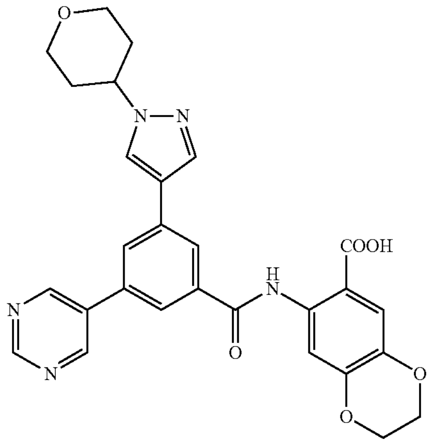 | $^1$H NMR (400 MHz, DMSO-d6) δ 12.23 (s, 1H), 9.29 (d, J = 7.8 Hz, 2H), 9.27 (s, 1H), 8.56 (s, 1H), 8.30 (d, J = 10.6 Hz, 2H), 8.22 (s, 1H), 8.12 (d, J = 8.5 Hz, 2H), 7.51 (s, 1H), 4.50-4.41 (m, 1H), 4.37 (d, J = 2.6 Hz, 2H), 4.30 (s, 2H), 3.99 (d, J = 8.9 Hz, 2H), 3.51 (t, J = 10.7 Hz, 2H), 2.13-1.90 (m, 4H). LC/MS [M-H]: 526.2 |

TABLE 5-continued

| Example # | Name/Structure | Spectral data |
|---|---|---|
| 166 | 6-[[3-(2,4-dioxo-1H-pyrimidin-5-yl)-5-(1-tetrahydropyran-4-ylpyrazol-3-yl)benzoyl]amino]-2,3-dihydro-1,4-benzodioxine-7-carboxylic acid 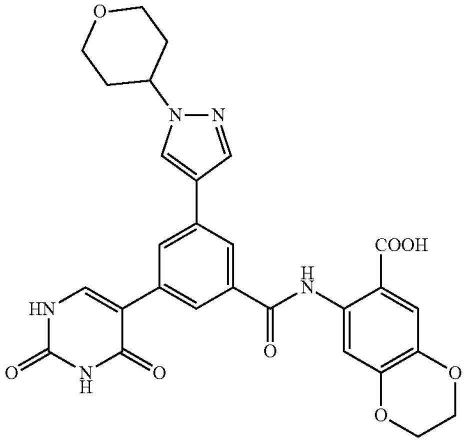 [SMILES: O=C(Nc1cc2c(cc1C(=O)O)OCCO2)c1cc(-c2cnn(C3CCOCC3)c2)cc(-c2c[nH]c(=O)[nH]c2=O)c1] | $^{1}$H NMR (400 MHz, DMSO-d6) δ 11.32 (s, 2H), 8.36 (s, 1H), 8.28 (s, 1H), 8.06 (s, 1H), 7.97 (s, 2H), 7.91 (s, 1H), 7.80 (s, 1H), 7.50 (s, 1H), 4.50-4.40 (m, 1H), 4.32 (s, 2H), 4.26 (s, 2H), 3.98 (d, J = 10.5 Hz, 2H), 3.52-3.47 (m, 2H), 2.07-1.92 (m, 4H). LC/MS [M + H]: 560.2 |
| 167 | 6-[[3-(4-fluorophenyl)-5-(1-tetrahydropyran-4-ylpyrazol-4-yl)benzoyl]amino]-2,3-dihydro-1,4-benzodioxine-7-carboxylic acid 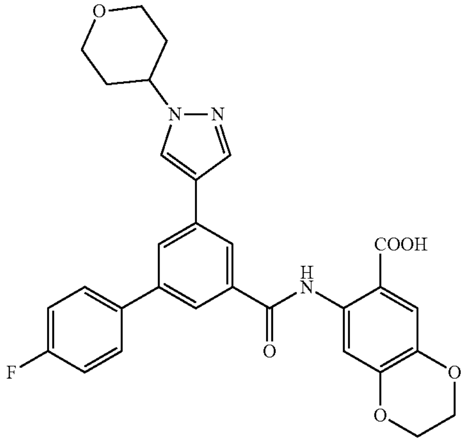 [SMILES: O=C(Nc1cc2c(cc1C(=O)O)OCCO2)c1cc(-c2ccc(F)cc2)cc(-c2cnn(C3CCOCC3)c2)c1] | $^{1}$H NMR (400 MHz, DMSO-d6) δ 12.23 (s, 1H), 8.52 (s, 1H), 8.31 (s, 1H), 8.12 (s, 2H), 8.08 (s, 1H), 7.95 (s, 1H), 7.89-7.82 (m, 2H), 7.51 (s, 1H), 7.37 (t, J = 8.8 Hz, 2H), 4.50-4.41 (m, 1H), 4.37 (d, J = 2.8 Hz, 2H), 4.29 (s, 2H), 3.99 (d, J = 10.9 Hz, 2H), 3.50 (t, J = 10.5 Hz, 2H), 2.10-1.95 (m, 4H). LC/MS [M + H]: 544.1 |

TABLE 5-continued

| Example # | Name/Structure | Spectral data |
|---|---|---|
| 168 | 6-[[3-(3,4-difluorophenyl)-5-(1-tetrahydropyran-4-ylpyrazol-4-yl)benzoyl]amino]-2,3-dihydro-1,4-benzodioxine-7-carboxylic acid 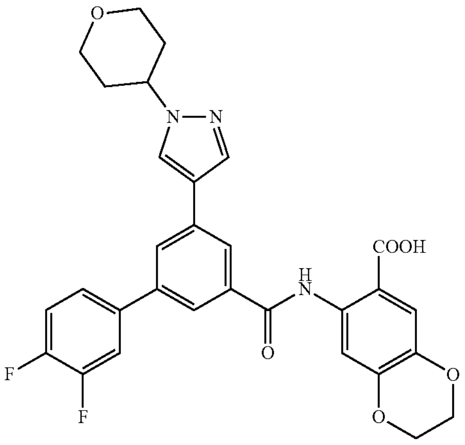 [SMILES: O=C(Nc1cc2c(cc1C(=O)O)OCCO2)c1cc(-c2ccc(F)c(F)c2)cc(-c2cnn(C3CCOCC3)c2)c1] | $^1H$ NMR (400 MHz, DMSO-d6) δ 8.48 (s, 1H), 8.22 (d, J = 11.6 Hz, 2H), 8.08 (d, J = 6.8 Hz, 3H), 7.98-7.88 (m, 1H), 7.68 (s, 1H), 7.65-7.54 (m, 1H), 7.49 (s, 1H), 4.50-4.40 (m, 1H), 4.29-4.18 (m, 4H), 3.99 (d, J = 11.5 Hz, 2H), 3.57-3.46 (m, 2H), 2.11-1.92 (m, 4H). LC/MS [M + H]: 562.1 |
| 169 | 6-[[3-(1,5-dihydroimidazo[1,2-alpyridin-6-yl)-5-(1-tetrahydropyran-4-ylpyrazol-4-yl)benzoyl]amino]-2,3-dihydro-1,4-benzodioxine-7-carboxylic acid 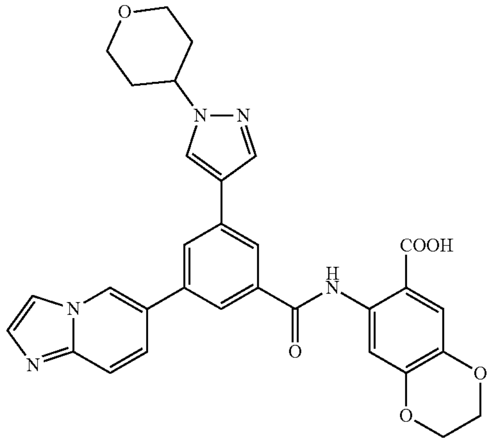 [SMILES: O=C(Nc1cc2c(cc1C(=O)O)OCCO2)c1cc(-c2cnn(C3CCOCC3)c2)cc(-c2ccc3nccn3c2)c1] | $^1H$ NMR (400 MHz, DMSO-d6) δ 12.17 (s, 1H), 9.56 (s, 1H), 8.56 (s, 1H), 8.44 (d, J = 9.6Hz, 1H), 8.38 (s, 1H), 8.30-8.27 (m, 3H), 8.21 (s, 1H), 8.14-8.10 (m, 2H), 7.60-7.51 (m, 3H), 4.47-4.44 (m, 1H), 4.38-4.29 (m, 4H), 4.01-3.98 (m, 2H), 3.57-3.51 (m, 2H), 2.09-1.98 (m, 4H). $C_{31}H_{27}N_5O_6$ $[M + H]^+$: 566.4 |

TABLE 5-continued

| Example # | Name/Structure | Spectral data |
|---|---|---|
| 170 | 6-[3-(1H-pyrrolo[2,3-b]pyridin-5-yl)-5-(1-tetrahydropyran-4-ylpyrazol-4-yl)benzoyl]amino]-2,3-dihydro-1,4-benzodioxine-7-carboxylic acid 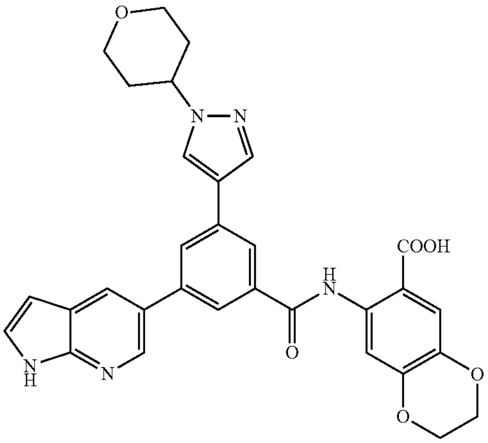 [SMILES: O=C(Nc1cc2c(cc1C(=O)O)OCCO2)c1cc(-c2cnc3[nH]ccc3c2)cc(-c2cnn(C3CCOCC3)c2)c1] | $^1$H NMR (400 MHz, DMSO-d6) δ 13.68 (s, 1H), 12.34 (s, 1H), 11.79 (s, 1H), 8.68 (d, J = 1.9 Hz, 1H), 8.55 (s, 1H), 8.38 (s, 1H), 8.33 (s, 1H), 8.21 (s, 1H), 8.11 (d, J = 5.0 Hz, 2H), 8.05 (s, 1H), 7.59-7.53 (m, 1H), 7.51 (s, 1H), 6.55 (s, 1H), 4.52-4.41 (m, 1H), 4.37 (s, 2H), 4.30 (s, 2H), 3.99 (d, J = 11.1 Hz, 2H), 3.51 (t, J = 10.6 Hz, 2H), 2.10-1.98 (m, 4H). LC/MS [M + H]: 566.5 |
| 171 | 6-[[3,5-bis(1-tetrahydropyran-4-ylpyrazol-4-yl)benzoyl]amino]-2,3-dihydro-1,4-benzodioxine-7-carboxylic acid 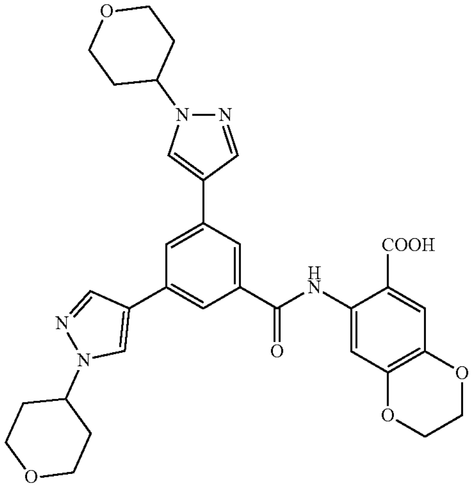 [SMILES: O=C(Nc1cc2c(cc1C(=O)O)OCCO2)c1cc(-c2cnn(C3CCOCC3)c2)cc(-c2cnn(C3CCOCC3)c2)c1] | $^1$H NMR (400 MHz, DMSO-d6) δ 13.62 (s, 1H), 12.12 (s, 1H), 8.43 (s, 2H), 8.30 (s, 1H), 8.07 (s, 1H), 8.04 (s, 2H), 7.93 (d, J = 1.1 Hz, 2H), 7.51 (s, 1H), 4.44 (dt, J = 15.7, 5.5 Hz, 2H), 4.37 (d, J = 2.7 Hz, 2H), 4.29 (s, 2H), 3.99 (d, J = 11.4 Hz, 4H), 3.55-3.46 (m, 4H), 2.02 (dt, J = 11.7, 8.1 Hz, 8H). LC/MS [M + H]: 600.4 |

TABLE 5-continued

| Example # | Name/Structure | Spectral data |
| --- | --- | --- |
| 172 | 6-[3-[1-(2-carboxyethyl)pyrazol-4-yl]-5-(1-tetrahydropyran-4-ylpyrazol-3-yl)benzoyl]amino]-2,3-dihydro-1,4-benzodioxine-7-carboxylic acid 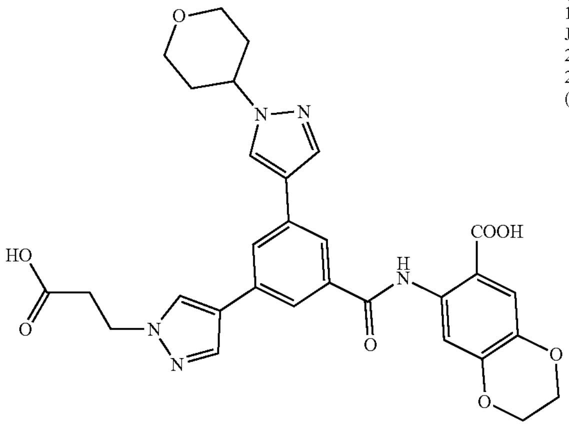 | $^1$H NMR (400 MHz, DMSO-d6) δ 12.18 (s, 1H), 8.44 (s, 1H), 8.32 (s, 1H), 8.30 (s, 1H), 8.05 (s, 1H), 8.03 (d, J = 2.8 Hz, 2H), 7.93 (s, 1H), 7.90 (s, 1H), 7.51 (s, 1H), 4.50-4.41 (m, 1H), 4.37 (t, J = 6.4 Hz, 4H), 4.29 (d, J = 3.0 Hz, 2H), 3.99 (d, J = 12.0 Hz, 2H), 3.50 (dt, J = 11.5, 6.0 Hz, 2H), 2.87 (t, J = 6.7 Hz, 2H), 2.09-1.93 (m, 4H). LC/MS [M − H]: 586.2 |
| 173 | 6-[[3-(1H-pyrazol-4-yl)-5-(1-tetrahydropyran-4-ylpyrazol-4-yl)benzoyl]amino]-2,3-dihydro-1,4-benzodioxine-7-carboxylic acid 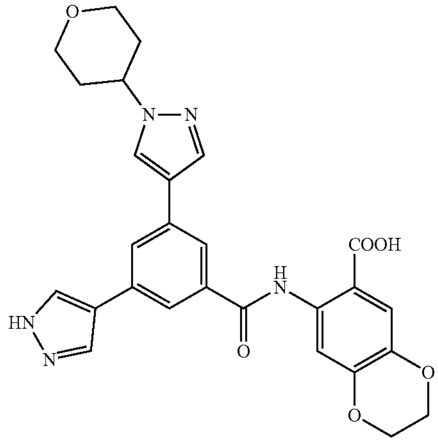 [SMILES: O=C(Nc1cc2c(cc1C(=O)O)OCCO2)c1cc(-c2cn[nH]c2)cc(-c2cnn(C3CCOCC3)c2)c1] | $^1$H NMR (400 MHz, DMSO-d6) δ 12.16 (s, 1H), 8.45 (s, 1H), 8.31 (s, 1H), 8.20 (s, 2H), 8.09 (s, 1H), 8.04 (s, 1H), 7.96-7.91 (m, 2H), 7.51 (s, 1H), 4.44 (dt, J = 15.5, 5.5 Hz, 1H), 4.37 (d, J = 5.0 Hz, 2H), 4.29 (d, J = 3.1 Hz, 2H), 3.99 (d, J = 11.7 Hz, 2H), 3.50 (dt, J = 11.5, 5.8 Hz, 2H), 2.09-1.95 (m, 4H). LC/MS [M + H]: 516.3 |
| 174 | 4,5-dichloro-2-[[3-phenyl-5-(1-tetrahydropyran-4-ylpyrazol-4-yl)benzoyl]amino]benzoic acid 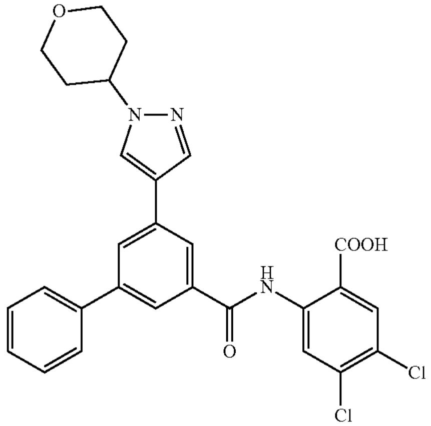 | $^1$H NMR (400 MHz, DMSO-d6) δ 8.96 (s, 1H), 8.50 (s, 1H), 8.19 (s, 1H), 8.15-8.05 (m, 4H), 7.83 (d, J = 7.2 Hz, 2H), 7.55 (t, J = 7.6 Hz, 2H), 7.45 (t, J = 7.3 Hz, 1H), 7.22 (s, 1H), 7.09 (s, 1H), 6.97 (s, 1H), 4.45 (d, J = 11.0 Hz, 1H), 3.99 (d, J = 11.3 Hz, 2H), 3.50 (t, J = 10.2 Hz, 2H), 2.08-1.95 (m, 4H). LC/MS [M − H]: 534.1 |

TABLE 5-continued

| Example # | Name/Structure | Spectral data |
|---|---|---|
| 175 | 4,5-dichloro-2-(3-(pyridin-2-yl)-5-(1-(tetrahydro-2H-pyran-4-yl)-1H-pyrazol-4-yl)benzamido)benzoic acid 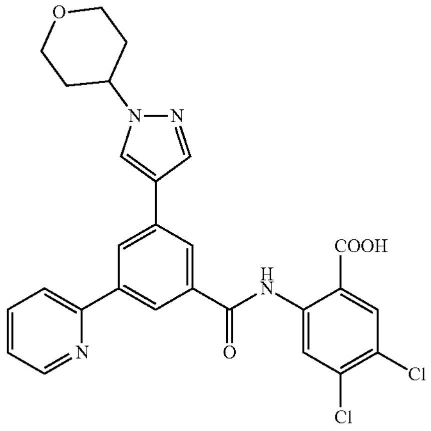 [SMILES: O=C(Nc1cc(Cl)c(Cl)cc1C(=O)O)c1cc(-c2cnn(C3CCOCC3)c2)cc(-c2ccccn2)c1] | $^1$H NMR (400 MHz, DMSO-d6) δ 8.99 (s, 1H), 8.76-8.72 (m, 1H), 8.51 (d, J = 4.0 Hz, 3H), 8.24 (s, 1H), 8.18-8.12 (m, 2H), 8.07 (s, 1H), 8.02-7.95 (m, 1H), 7.48-7.41 (m, 1H), 4.53-4.43 (m, 1H), 4.04-3.96 (m, 2H), 3.51 (dt, J = 10.2, 5.0 Hz, 2H), 2.08-1.96 (m, 4H). LC/MS [M + H]: 537.0 |
| 176 | 4,5-dichloro-2-[[3-(3-pyridyl)-5-(1-tetrahydropyran-4-ylpyrazol-4-yl)benzoyl]amino]benzoic acid 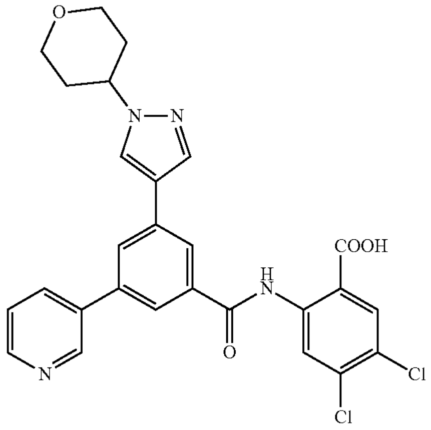 [SMILES: O=C(Nc1cc(Cl)c(Cl)cc1C(=O)O)c1cc(-c2cccnc2)cc(-c2cnn(C3CCOCC3)c2)c1] | $^1$H NMR (400 MHz, DMSO-d6) δ 12.19 (s, 1H), 9.19 (d, J = 1.9 Hz, 1H), 8.95 (d, J = 3.4 Hz, 1H), 8.77 (d, J = 3.9 Hz, 1H), 8.54 (d, J = 10.9 Hz, 1H), 8.51 (d, J = 8.5 Hz, 1H), 8.30 (s, 1H), 8.22 (s, 1H), 8.18 (s, 1H), 8.11 (d, J = 6.6 Hz, 2H), 7.82-7.77 (m, 1H), 4.51-4.40 (m, 2H), 4.03-3.96 (m, 2H), 3.54-3.47 (m, 2H), 2.08-1.94 (m, 4H). LC/MS [M − H]: 535.1. |
| 179 | 4,5-dichloro-2-[[3-(6-methyl-2-pyridyl)-5-(1-tetrahydropyran-4-ylpyrazol-4-yl)benzoyl]amino]benzoic acid 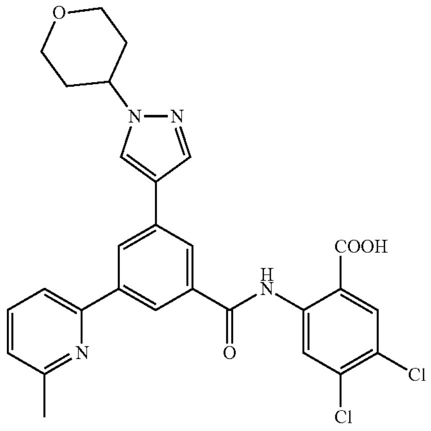 [SMILES: Cc1cccc(-c2cc(C(=O)Nc3cc(Cl)c(Cl)cc3C(=O)O)cc(-c3cnn(C4CCOCC4)c3)c2)n1] | $^1$H NMR (400 MHz, DMSO-d6) δ 8.98 (s, 1H), 8.49 (s, 2H), 8.46 (s, 1H), 8.20 (s, 1H), 8.17 (s, 1H), 8.06 (s, 1H), 7.93 (d, J = 7.7 Hz, 1H), 7.85 (t, J = 7.7 Hz, 1H), 7.30 (d, J = 7.4 Hz, 1H), 4.52-4.42 (m, 1H), 4.00 (d, J = 11.4 Hz, 2H), 3.55-3.49 (m, 2H), 2.60 (s, 3H), 2.09-1.98 (m, 4H). LC/MS [M + H]: 551.1 |

TABLE 5-continued

| Example # | Name/Structure | Spectral data |
|---|---|---|
| 180 | 4,5-dichloro-2-[[3-(2-fluoro-6-methyl-3-pyridyl)-5-(1-tetrahydropyran-4-ylpyrazol-4-yl)benzoyl]amino]benzoic acid 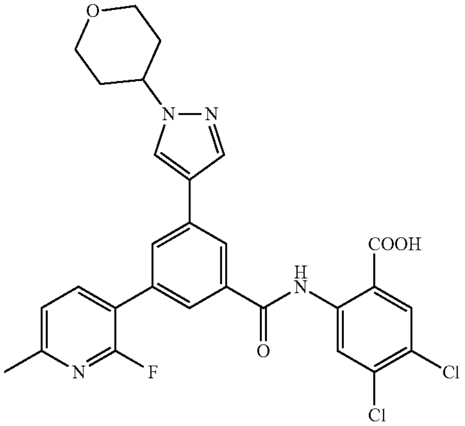 [SMILES: Cc1ccc(-c2cc(C(=O)Nc3cc(Cl)c(Cl)cc3C(=O)O)cc(-c3cnn(C4CCOCC4)c3)c2)c(F)n1] | $^1$H NMR (400 MHz, DMSO-d6) δ 12.39 (s, 1H), 8.97 (s, 1H), 8.48 (s, 1H), 8.21-8.11 (m, 3H), 8.08 (s, 1H), 8.05 (s, 1H), 7.93 (s, 1H), 7.39 (d, J = 7.2 Hz, 1H), 4.50-4.39 (m, 1H), 3.99 (d, J = 10.4 Hz, 2H), 3.54-3.45 (m, 2H), 2.09-1.94 (m, 4H). LC/MS [M + H]: 569.1. |
| 181 | 4,5-dichloro-2-[[3-(6-methylpyrazin-2-yl)-5-(1-tetrahydropyran-4-ylpyrazol-4-yl)benzoyl]amino]benzoic acid 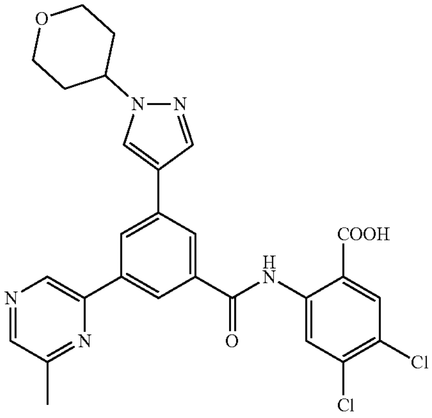 [SMILES: Cc1cncc(-c2cc(C(=O)Nc3cc(Cl)c(Cl)cc3C(=O)O)cc(-c3cnn(C4CCOCC4)c3)c2)n1] | $^1$H NMR (400 MHz, DMSO-d6) δ 9.20 (s, 1H), 8.96 (s, 1H), 8.59 (s, 1H), 8.54 (s, 1H), 8.50 (d, J = 1.6 Hz, 2H), 8.31 (s, 1H), 8.17 (s, 1H), 8.08 (s, 1H), 4.48 (tt, J = 9.5, 4.7 Hz, 1H), 4.00 (d, J = 11.6 Hz, 2H), 3.54-3.48 (m, 2H), 2.64 (d, J = 6.2 Hz, 3H), 2.08-1.98 (m, 4H). LC/MS [M + H]: 552.1 |
| 182 | 4,5-dichloro-2-[[3-(6-methyl-3-pyridyl)-5-(1-tetrahydropyran-4-ylpyrazol-4-yl)benzoyl]amino]benzoic acid 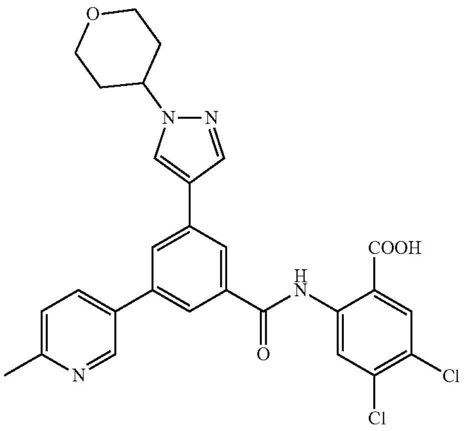 [SMILES: Cc1ccc(-c2cc(C(=O)Nc3cc(Cl)c(Cl)cc3C(=O)O)cc(-c3cnn(C4CCOCC4)c3)c2)cn1] | $^1$H NMR (400 MHz, DMSO-d6) δ 8.97 (s, 1H), 8.92 (d, J = 2.2 Hz, 1H), 8.53 (s, 1H), 8.20 (d, J = 1.6 Hz, 1H), 8.17 (d, J = 4.0 Hz, 1H), 8.16 (s, 1H), 8.15-8.10 (m, 1H), 8.09 (s, 1H), 8.06 (s, 1H), 7.42 (d, J = 8.1 Hz, 1H), 4.45 (dt, J = 15.8, 5.5 Hz, 1H), 3.99 (d, J = 11.9 Hz, 2H), 3.55-3.49 (m, 2H), 2.55 (s, 3H), 2.10-1.93 (m, 4H). LC/MS [M − H]: 551.0 |

TABLE 5-continued

| Example # | Name/Structure | Spectral data |
|---|---|---|
| 183 | 4,5-dichloro-2-[[3-pyrimidin-5-yl-5-(1-tetrahydropyran-4-ylpyrazol-4-yl)benzoyl]amino]benzoic acid 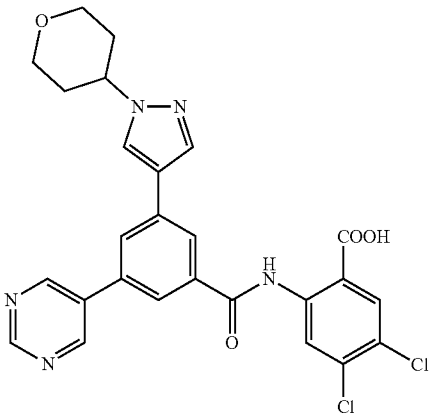 [SMILES: O=C(Nc1cc(Cl)c(Cl)cc1C(=O)O)c1cc(-c2cncnc2)cc(-c2cnn(C3CCOCC3)c2)c1] | $^1H$ NMR (400 MHz, DMSO-d6) δ 9.29 (d, J = 11.5 Hz, 3H), 8.95 (s, 1H), 8.54 (s, 1H), 8.29 (d, J = 26.5 Hz, 2H), 8.15 (t, J = 8.8 Hz, 3H), 4.50-4.42 (m, 1H), 3.99 (d, J = 11.7 Hz, 2H), 3.55-3.48 (m, 2H), 2.08-1.93 (m, 4H). LC/MS [M + H]: 538.0. |
| 184 | 4,5-dichloro-2-[[3-[1-(methylcarbamoylcarbamoyl)vinyl]-5-(1-tetrahydropyran-4-ylpyrazol-3-yl)benzoyl]amino]benzoic acid 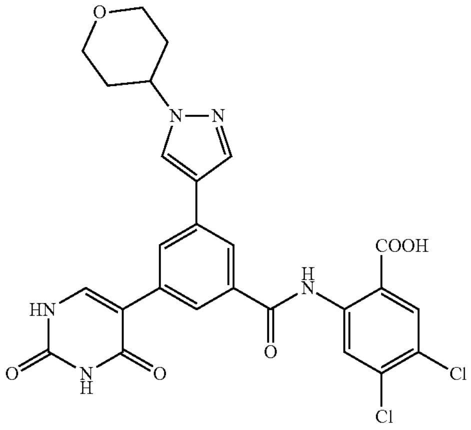 [SMILES: O=C(Nc1cc(Cl)c(Cl)cc1C(=O)O)c1cc(-c2cnn(C3CCOCC3)c2)cc(-c2c[nH]c(=O)[nH]c2=O)c1] | $^1H$ NMR (400 MHz, DMSO-d6) δ 12.60 (s, 1H), 11.34 (s, 2H), 8.98 (s, 1H), 8.39 (s, 1H), 8.16 (s, 1H), 8.06 (s, 1H), 8.03-7.94 (m, 3H), 7.83 (d, J = 5.6 Hz, 1H), 4.47-4.34 (m, 1H), 3.98 (d, J = 10.7 Hz, 2H), 3.49 (t, J = 10.4 Hz, 2H), 2.05-1.89 (m, 4H). LC/MS [M + H]: 570.1. |
| 185 | 4,5-dichloro-2-[3-(4-fluorophenyl)-5-(1-tetrahydropyran-4-ylpyrazol-4-yl)benzoyl]amino]benzoic acid 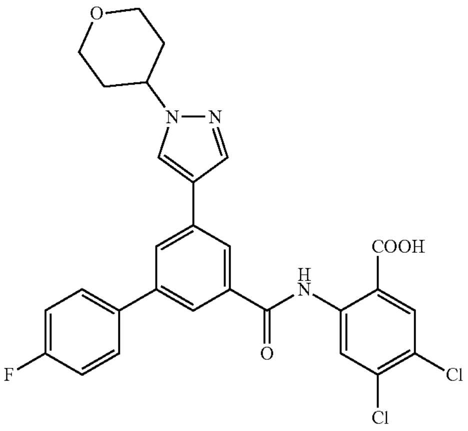 [SMILES: O=C(Nc1cc(Cl)c(Cl)cc1C(=O)O)c1cc(-c2ccc(F)cc2)cc(-c2cnn(C3CCOCC3)c2)c1] | $^1H$ NMR (400 MHz, DMSO-d6) δ 16.00 (s, 1H), 8.95 (s, 1H), 8.48 (s, 1H), 8.18 (s, 1H), 8.14 (s, 1H), 8.10 (s, 1H), 8.07 (d, J = 3.1 Hz, 2H), 7.90-7.83 (m, 2H), 7.38 (t, J = 8.8 Hz, 2H), 6.06 (s, 3H), 4.49-4.43 (m, 1H), 3.99 (d, J = 10.5 Hz, 2H), 3.50 (d, J = 2.4 Hz, 2H), 2.08-1.98 (m, 4H). LC/MS [M − H]: 552.1 |

TABLE 5-continued

| Example # | Name/Structure | Spectral data |
|---|---|---|
| 186 | 4,5-dichloro-2-[[3-(3,4-difluorophenyl)-5-(1-tetrahydropyran-4-ylpyrazol-4-yl)benzoyl]amino]benzoic acid 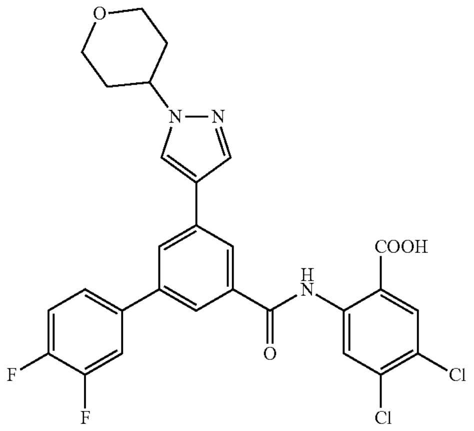 [SMILES: O=C(Nc1cc(Cl)c(Cl)cc1C(=O)O)c1cc(-c2ccc(F)c(F)c2)cc(-c2cnn(C3CCOCC3)c2)c1] | $^1$H NMR (400 MHz, DMSO-d6) δ 12.19 (d, J = 28.8 Hz, 1H), 8.96 (s, 1H), 8.52 (s, 1H), 8.16 (d, J = 3.2 Hz, 2H), 8.15-8.12 (m, 1H), 8.08 (s, 1H), 7.98 (s, 1H), 7.96-7.90 (m, 1H), 7.67 (s, 1H), 7.64-7.57 (m, 1H), 4.50-4.40 (m, 1H), 4.03-3.96 (m, 2H), 3.56-3.47 (m, 2H), 2.09-1.95 (m, 4H). LC/MS [M + H]: 572.0. |
| 187 | 4,5-dichloro-2-[[3-(1,5-dihydroimidazo[1,2-a]pyridin-6-yl)-5-(1-tetrahydropyran-4-ylpyrazol-4-yl)benzoyl]amino]benzoic acid 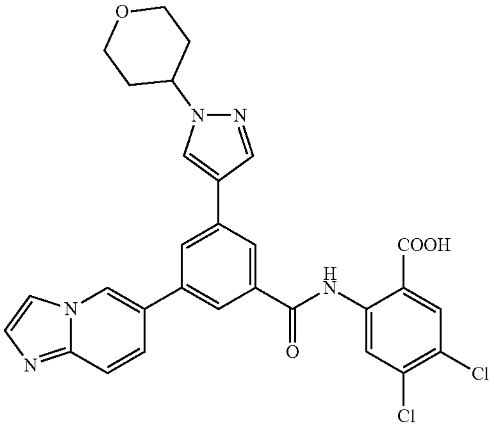 [SMILES: O=C(Nc1cc(Cl)c(Cl)cc1C(=O)O)c1cc(-c2cnn(C3CCOCC3)c2)cc(-c2ccc3nccn3c2)c1] | $^1$H NMR (400 MHz, DMSO-d6) δ 12.22 (s, 1H), 9.72 (s, 1H), 8.85 (s, 1H), 8.58 (s, 1H), 8.44 (d, J = 13.6Hz, 3H), 8.34 (s, 1H), 8.29 (s, 1H), 8.18 (s, 1H), 8.12-8.08 (m, 2H), 7.65-7.60 (m, 1H), 7.55-7.53 (m, 1H), 4.46-4.38 (m, 1H), 4.00-3.98 (m, 2H), 3.57-3.49 (m, 2H), 2.07-1.96 (m, 4H). LC/MS[M + H]+: 576.1 |
| 188 | 4,5-dichloro-2-[[3-(1H-pyrrolo[2,3-b]pyridin-5-yl)-5-(1-tetrahydropyran-4-ylpyrazol-4-yl)benzoyl]amino]benzoic acid 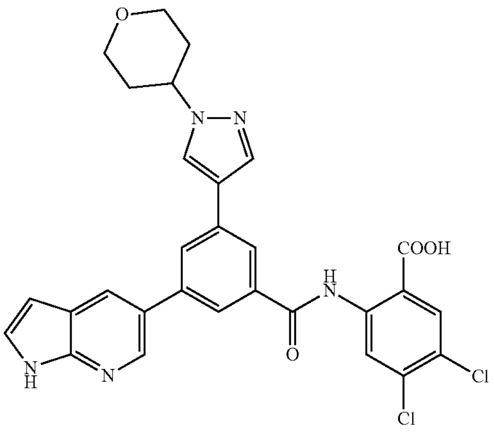 [SMILES: O=C(Nc1cc(Cl)c(Cl)cc1C(=O)O)c1cc(-c2cnc3[nH]ccc3c2)cc(-c2cnn(C3CCOCC3)c2)c1] | $^1$H NMR (400 MHz, DMSO-d6) δ 16.07 (s, 1H), 8.96 (s, 1H), 8.68 (d, J = 2.2 Hz, 1H), 8.52 (s, 1H), 8.37 (d, J = 2.2 Hz, 1H), 8.21-8.16 (m, 2H), 8.14 (d, J = 3.9 Hz, 2H), 8.09 (s, 1H), 7.55 (d, J = 3.4 Hz, 1H), 6.56 (d, J = 3.4 Hz, 1H), 4.54-4.40 (m, 1H), 3.99 (d, J = 11.2 Hz, 2H), 3.58-3.45 (m, 2H), 2.09-1.98 (m, 4H). LC/MS [M + H]: 576.0. |

TABLE 5-continued

| Example # | Name/Structure | Spectral data |
|---|---|---|
| 189 | 2-(3,5-bis(1-(tetrahydro-2H-pyran-4-yl)-1H-pyrazol-4-yl)benzamido)-4,5-dichlorobenzoic acid 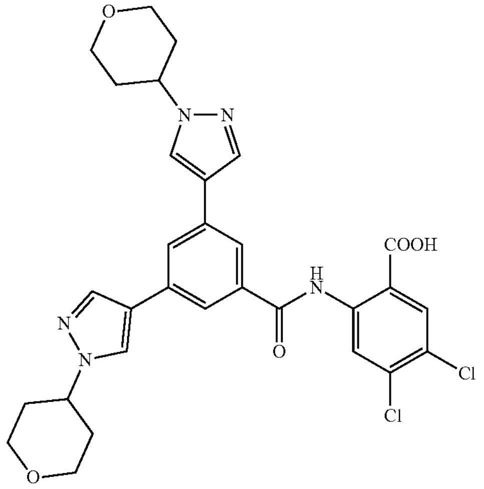 [SMILES: O=C(Nc1cc(Cl)c(Cl)cc1C(=O)O)c1cc(-c2cnn(C3CCOCC3)c2)cc(-c2cnn(C3CCOCC3)c2)c1] | $^1H$ NMR (400 MHz, DMSO-d6) δ 12.17 (s, 1H), 8.97 (s, 1H), 8.43 (s, 2H), 8.18 (s, 1H), 8.10 (s, 1H), 8.04 (s, 2H), 7.94 (d, J = 1.5 Hz, 2H), 4.50-4.40 (m, 2H), 3.99 (d, J = 11.7 Hz, 4H), 3.51 (td, J = 11.5, 2.3 Hz, 4H), 2.02 (dt, J = 11.6, 8.3 Hz, 8H). LC/MS [M + H]: 610.2 |
| 190 | 2-[[3-[1-(2-carboxyethyl)pyrazol-4-yl]-5-(1-tetrahydropyran-4-ylpyrazol-4-yl)benzoyl]amino]-4,5-dichloro-benzoic acid 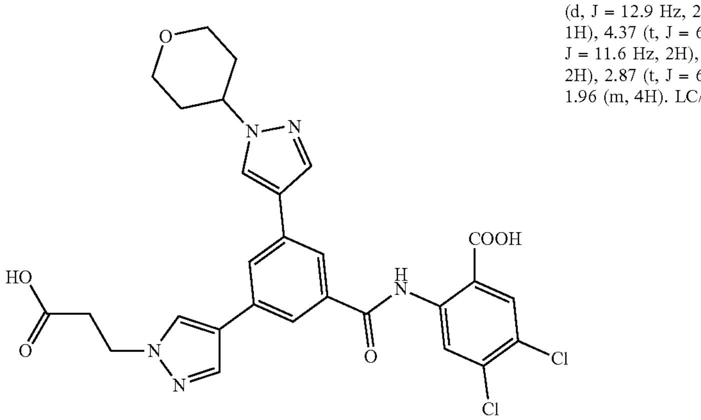 | $^1H$ NMR (400 MHz, DMSO-d6) δ 12.16 (s, 1H), 8.97 (s, 1H), 8.45 (s, 1H), 8.32 (s, 1H), 8.17 (s, 1H), 8.09 (s, 1H), 8.04 (d, J = 2.3 Hz, 2H), 7.93 (d, J = 12.9 Hz, 2H), 4.51-4.41 (m, 1H), 4.37 (t, J = 6.7 Hz, 2H), 3.99 (d, J = 11.6 Hz, 2H), 3.55-3.48 (m, 2H), 2.87 (t, J = 6.7 Hz, 2H), 2.10-1.96 (m, 4H). LC/MS [M − H]: 597.1 |

TABLE 5-continued
| Example # | Name/Structure | Spectral data |
|---|---|---|
| 191 | 4,5-dichloro-2-[[3-(1H-pyrazol-4-yl)-5-(1-tetrahydropyran-4-ylpyrazol-4-yl)benzoyl]amino]benzoic acid 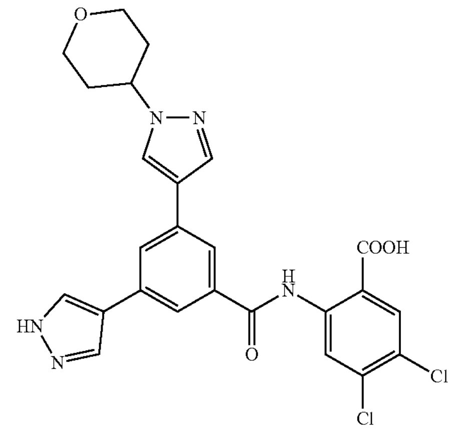 [SMILES: O=C(Nc1cc(Cl)c(Cl)cc1C(=O)O)c1cc(-c2cn[nH]c2)cc(-c2cnn(C3CCOCC3)c2)c1] | $^1$H NMR (400 MHz, DMSO-d6) δ 8.97 (s, 1H), 8.43 (s, 1H), 8.18 (d, J = 11.5 Hz, 3H), 8.09 (d, J = 1.4 Hz, 1H), 8.04 (s, 1H), 8.01 (s, 1H), 7.98 (d, J = 1.4 Hz, 1H), 4.45 (dt, J = 15.5, 5.5 Hz, 1H), 4.05-3.95 (m, 2H), 3.56-3.47 (m, 2H), 2.10-1.94 (m, 4H). LC/MS [M + H]: 526.1. |
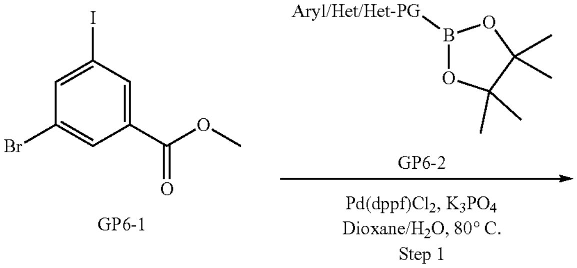
GP6-1
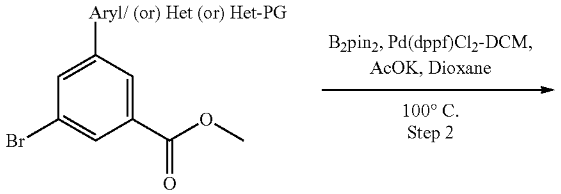
GP6-3
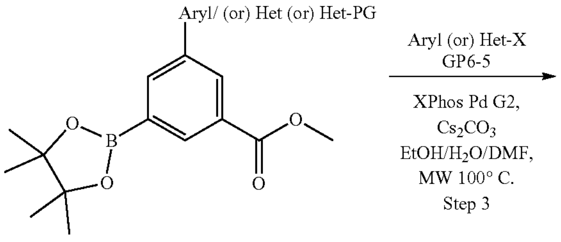
GP6-4
-continued
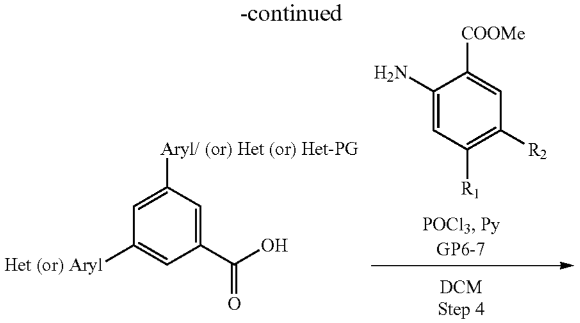
GP6-6
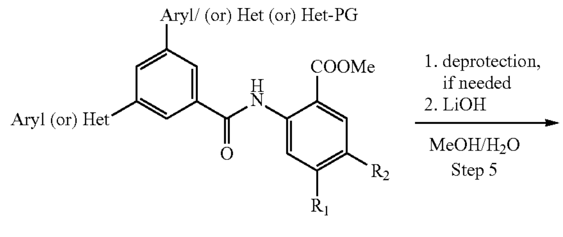
GP6-8

-continued

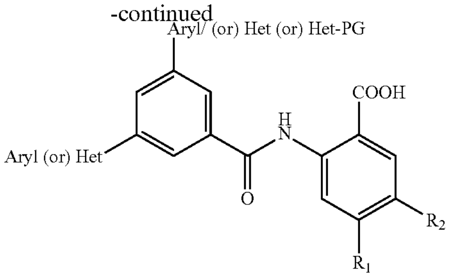

Examples $R_1$ = H, halide, alkyl, alkoxy, $OCF_3$ $R_2$ = H, halide, alkyl, alkoxy, $OCF_3$ $R_1$ and $R_2$ together can form a ring Aryl = phenyl or substituted phenyl Het = Heterocycle or substituted heterocycle PG = protective group Step 1. The mixture of compound GP6-1 (2.93 mmol), compound GP6-2 (2.93 mmol), $K_3PO_4$ (1245 mg, 5.87 mmol) and $Pd(dppf)Cl_2$ (430 mg, 0.59 mmol) was in 1,4-Dioxane/$H_2O$ (5/1 ml) stirred at 80° C. under Ar for 3 h. After completion, the mixture was extracted with LA, washed with water and brine, dried over $Na_2SO_4$ and concentrated. The crude product was purified by silica gel chromatography. The product, GP6-3 was obtained as white solid (2.29 mmol).

Step 2. The mixture of compound GP6-3 (600 mg, 1.65 mmol), $B_2pin_2$ (502 mg, 1.98 mmol), AcOK (323 mg, 3.30 mmol) and $Pd(dppf)Cl_2$-DCM (67 mg, 0.08 mmol) was in 1,4-Dioxane (15 ml) stirred at 100° C. under Ar for 1 h. After completion, the mixture was extracted with EA, washed with water and brine, dried over $Na_2SO_4$ and concentrated. The crude product was purified by silica gel chromatography to give GP6-4, Step 3. The mixture of compound GP6-5 (500 mg, 1.21 mmol), compound GP6-4 (1.21 mmol), $K_3PO_4$ (710 mg, 3.63 mmol) and $Pd(dppf)Cl_2$ (90 mg, 0.12 mmol) was in 1,4-Dioxane/$H_2O$ (5/1 ml) stirred at 80° C. under Ar for 1 h under microwave radiation. After completion, the mixture was extracted with EA, washed with water and brine, dried over $Na_2SO_4$ and concentrated. The crude product was purified by flash chromatography. To give GP6-6.

Step 4. The mixture of compound GP6-6 (0.29 mmol), compound GP6-7 (63 mg, 0.29 mmol) in Py(5 ml) was added $POCl_3$ (88 mg, 0.57 mmol) at 0° C., then stirred at 25° C. under Ar for 2 h. After completion, the mixture was extracted with EA, washed with HCl(1 mol/L) and brine, dried over $Na_2SO_4$ and concentrated. The crude product was purified by pre-TLC to give GP6-8.

Step 5. The mixture of compound GP6-8 (0.15 mmol) and LiOH (7 mg, 0.30 mmol) was in THF/MeOH/$H_2O$ (1 ml/1 ml/1 ml) stirred at 25° C. for 2 h. After the reaction finished, the mixture was diluted with water and acidified by 1 mol/L HCl, then filtered. The product was purified by either silica gel chromatography of prep-HPLC to give example compounds.

Synthesis of 4,5-dichloro-2-[[3-pyrazin-2-yl-5-(1-tetrahydropyran-4-ylpyrazol-4-yl)benzoyl]amino]benzoic acid (Example 177)

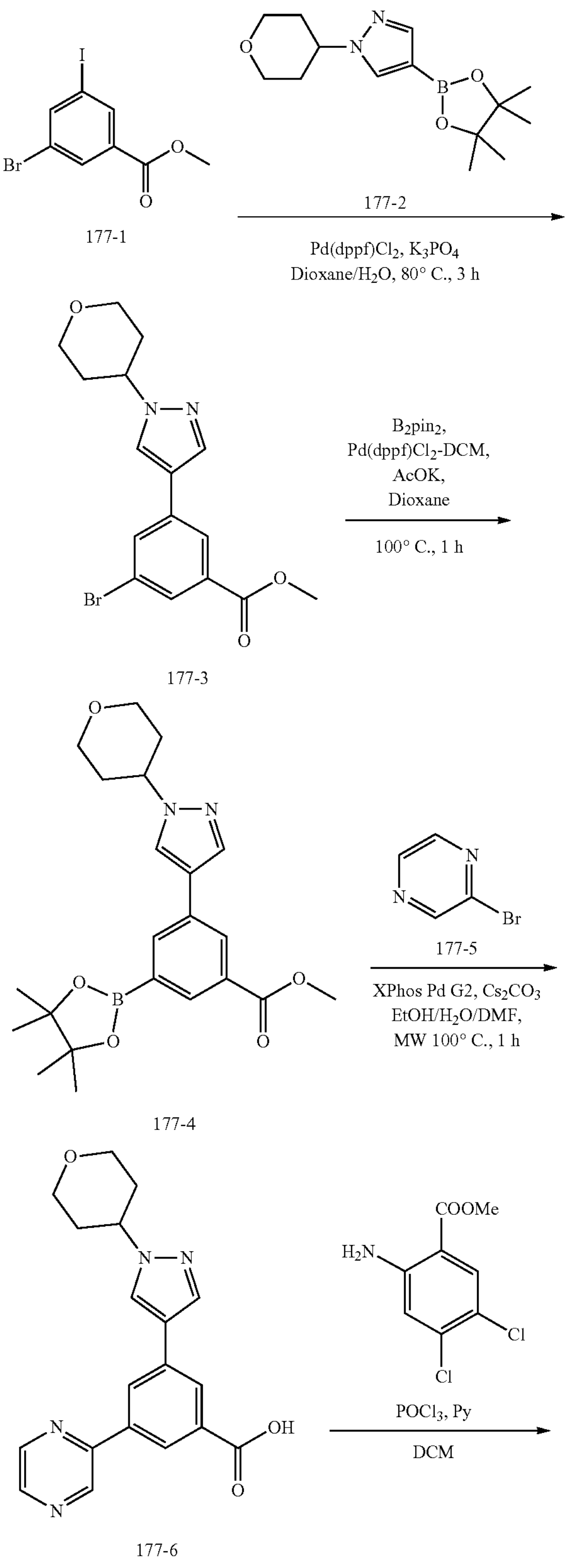

-continued

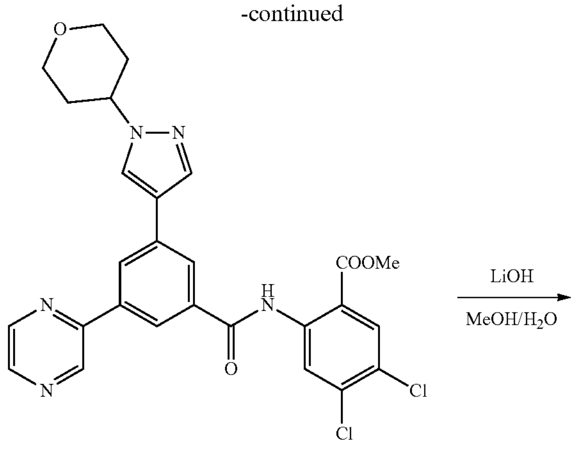

177-8

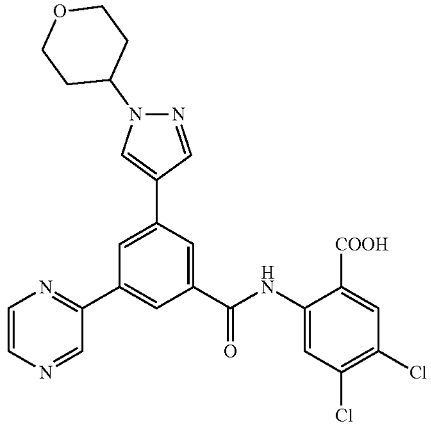

Example 177

Preparation of methyl 3-bromo-5-(1-(tetrahydro-2H-pyran-4-yl)-1H-pyrazol-4-yl)benzoate (compound 177-3). The mixture of 177-1 (1000 mg, 2.93 mmol), compound 177-2 (815 mg, 2.93 mmol), $K_3PO_4$ (1245 mg, 5.87 mmol) and Pd(dppf)$Cl_2$ (430 mg, 0.59 mmol) was in 1,4-Dioxane/$H_2O$ (5/1 ml) stirred at 80° C. under Ar for 3 h. After completion, the mixture was extracted with EA, washed with water and brine, dried over $Na_2SO_4$ and concentrated. The crude product was purified by silica gel chromatography. The product, 177-3, was obtained as white solid (833 mg, 2.29 mmol, 78%). LC/MS [M+H]:365.0

Preparation of methyl 3-(1-(tetrahydro-2H-pyran-4-yl)-H-pyrazol-4-yl)-5-(4,4,5,5-tetramethyl-1,3,2-dioxaborolan-2-yl)benzoate (177-4). The mixture of compound 177-3 (600 mg, 1.65 mmol), $B_2pin_2$ (502 mg, 1.98 mmol), AcOK (323 mg, 3.30 mmol) and Pd(dppf)$Cl_2$-DCM (67 mg, 0.08 mmol) was in 1,4-Dioxane (15 ml) stirred at 100° C. under Ar for 1 h. After completion, the mixture was extracted with EA, washed with water and brine, dried over $Na_2SO_4$ and concentrated. The crude product was purified by silica gel chromatography. The product, 177-4, was obtained as white solid (646 mg, 1.57 mmol, 95%). LC/MS [M+H]:413.2

Preparation of 3-(pyridazin-3-yl)-5-(1-(tetrahydro-2H-pyran-4-yl)-1H-pyrazol-4-yl)benzoic acid (177-6). The mixture of compound 177-5 (400 mg, 0.97 mmol), compound 177-4 (154 mg, 0.97 mmol), XPhos-Pd-G2 (38 mg, 0.05 mmol) and $Cs_2CO_3$ (975 mg, 2.99 mmol) was in EtOH/$H_2O$/DMF (3/3/3 ml) stirred at 100° C. under Ar for 1 h under microwave radiation. After completion, the mixture was extracted with EA, washed with water and brine, dried over $Na_2SO_4$ and concentrated. The crude product was purified by flash chromatography. The product, 177-6, was obtained as white solid (195 mg, 0.56 mmol, 57%). LC/MS [M+H]:351.2

Preparation of methyl 4,5-dichloro-2-(3-(pyrazin-2-yl)-5-(1-(tetrahydro-2H-pyran-4-yl)-1H-pyrazol-4-yl)benzamido) benzoate (177-8). The mixture of compound 177-6 (175 mg, 0.50 mmol), compound 177-7 (131 mg, 0.60 mmol) in Py(5 ml) was added $POCl_3$ (153 mg, 1.00 mmol) at 0° C., then stirred at 25° C. under Ar for 2 h. After completion, the mixture was extracted with EA, washed with HCl(1 mol/L) and brine, dried over $Na_2SO_4$ and concentrated. The crude product was purified by pre-TLC. The product, 177-8, was obtained as white solid (238 mg, 0.43 mmol, 86%). LC/MS [M+H]:552.1

Preparation of 4,5-dichloro-2-[[3-pyrazin-2-yl-5-(1-tetrahydropyran-4-ylpyrazol-4-yl)benzoyl]amino]benzoic acid (Example 177). The mixture of compound 177-8 (238 mg, 0.43 mmol) and LiOH (21 mg, 0.86 mmol) was in THF/MeOH/$H_2O$ (1 ml/1 ml/1 ml) stirred at 25° C. for 2 h. After the reaction finished, the mixture was diluted with water and acidified by 1 mol/L HCl, then filtered. The product, Example 177, was formed as white solid (175 mg, 0.33 mmol, 76%). LOMS [M−H]:536.1. $^1$H NMR (400 MHz, DMSO-$d_6$) δ 12.36 (s, 1H), 9.44 (d, J=1.3 Hz, 1H), 8.97 (s, 1H), 8.81-8.76 (s, 1H), 8.70 (d, J=2.5 Hz, 1H), 8.58 (s, 1H), 8.55 (s, 1H), 8.51 (s, 1H), 8.24 (s, 1H), 8.15 (s, 1H), 8.10 (s, 1H), 4.50-4.39 (i, 1H), 4.00 (d, J=11.6 Hz, 2H), 3.57-3.49 (m, 2H), 2.09-1.98 (m, 4H).

The following compounds were prepared using general synthetic procedure 6. The examples and spectral data are shown in Table 6.

TABLE 6

| Example # | Name/Structure | Spectral data |
|---|---|---|
| 123 | 4-chloro-2-[3-pyrazin-2-yl-5-(1-tetrahydropyran-4-ylpyrazol-4-yl)benzoyl]amino]benzoic acid 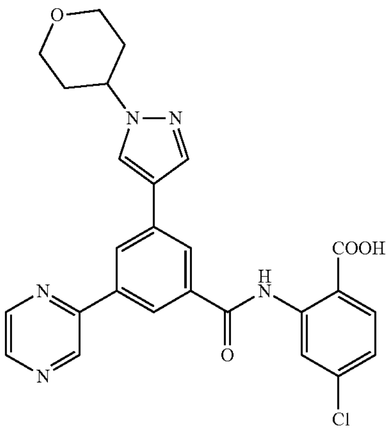 [SMILES: O=C(Nc1cc(Cl)ccc1C(=O)O)c1cc(-c2cnn(C3CCOCC3)c2)cc(-c2cnccn2)c1] | $^1$H NMR (400 MHz, MeOD) δ 9.28 (s, 1H), 8.93 (d, J = 2.1 Hz, 1H), 8.74 (s, 1H), 8.60 (d, J = 2.5 Hz, 1H), 8.56 (s, 1H), 8.51 (s, 1H), 8.31 (d, J = 5.6 Hz, 2H), 8.14 (d, J = 8.5 Hz, 1H), 8.05 (s, 1H), 7.22-7.17 (m, 1H), 4.53-4.44 (m, 1H), 4.11 (d, J = 11.5 Hz, 2H), 3.61 (td, J = 11.6, 3.0 Hz, 2H), 2.19-2.07 (m, 4H). LC/MS [M + H]: 504.1 |
| 124 | 4-chloro-2-[[3-pyridazin-3-yl-5-(1-tetrahydropyran-4-ylpyrazol-4-yl)benzoyl]amino]benzoic acid 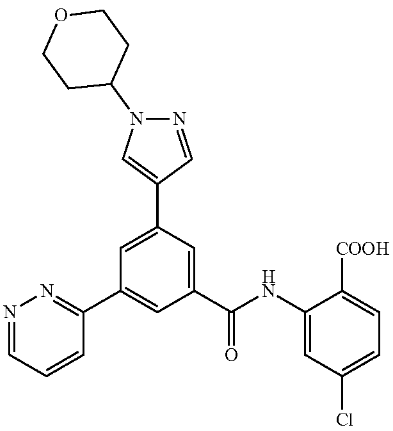 [SMILES: O=C(Nc1cc(Cl)ccc1C(=O)O)c1cc(-c2cnn(C3CCOCC3)c2)cc(-c2cccnn2)c1] | $^1$H NMR (400 MHz, DMSO-d6) δ 12.46 (s, 1H), 9.36-9.26 (m, 1H), 8.85 (d, J = 2.1 Hz, 1H), 8.63-8.53 (m, 3H), 8.42 (d, J = 8.6 Hz, 1H), 8.31 (s, 1H), 8.12 (s, 1H), 8.08 (d, J = 8.5 Hz, 1H), 7.96-7.85 (m, 1H), 7.36-7.27 (m, 1H), 4.46 (dt, J = 15.5, 5.4 Hz, 1H), 4.00 (d, J = 11.5 Hz, 2H), 3.56-3.48 (m, 2H), 2.10-1.93 (m, 4H). LC/MS [M + H]: 504.1. |
| 159 | 6-[[3-pyrazin-2-yl-5-(1-tetrahydropyran-4-ylpyrazol-4-yl)benzoyl]amino]-2,3-dihydro-1,4-benzodioxine-7-carboxylic acid 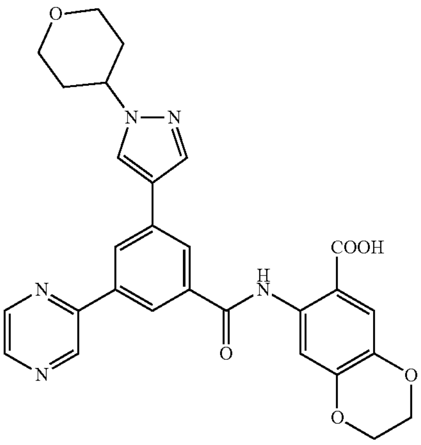 [SMILES: O=C(Nc1cc2c(cc1C(=O)O)OCCO2)c1cc(-c2cnn(C3CCOCC3)c2)cc(-c2cnccn2)c1] | $^1$H NMR (400 MHz, DMSO-d6) δ 12.46 (s, 1H), 9.45 (d, J = 1.4 Hz, 1H), 8.82-8.78 (m, 1H), 8.70 (d, J = 2.5 Hz, 1H), 8.57 (d, J = 3.9 Hz, 2H), 8.52 (s, 1H), 8.32 (s, 1H), 8.26 (s, 1H), 8.11 (s, 1H), 7.51 (s, 1H), 4.47 (td, J = 11.0, 5.4 Hz, 1H), 4.37 (d, J = 3.0 Hz, 2H), 4.29 (d, J = 3.2 Hz, 2H), 4.00 (d, J = 11.6 Hz, 2H), 3.50 (dt, J = 11.6, 5.9 Hz, 2H), 2.10-1.96 (m, 4H). LC/MS [M + H]: 528.2 |

TABLE 6-continued

| Example # | Name/Structure | Spectral data |
|---|---|---|
| 160 | 6-[[3-pyridazin-3-yl-5-(1-tetrahydropyran-4-ylpyrazol-4-yl)benzoyl]amino]-2,3-dihydro-1,4-benzodioxine-7-carboxylic acid 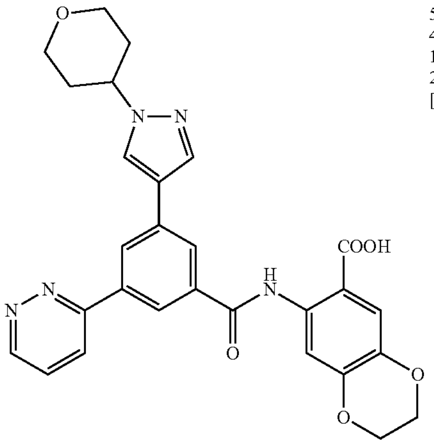 | $^1$H NMR (400 MHz, DMSO-d6) δ 9.32-9.26 (m, 1H), 8.55 (d, J = 6.3 Hz, 3H), 8.42-8.36 (m, 1H), 8.31 (s, 2H), 8.11 (s, 1H), 7.92-7.85 (m, 1H), 7.51 (s, 1H), 4.46 (dt, J = 10.2, 5.6 Hz, 1H), 4.35 (d, J = 3.2 Hz, 2H), 4.28 (d, J = 3.2 Hz, 2H), 3.99 (d, J = 11.4 Hz, 2H), 3.56-3.47 (m, 2H), 2.09-1.97 (m, 4H). LC/MS [M + H]: 528.1 |
| 178 | 4,5-dichloro-2-[[3-pyridazin-3-yl-5-(1-tetrahydropyran-4-ylpyrazol-4-yl)benzoyl]amino]benzoic acid 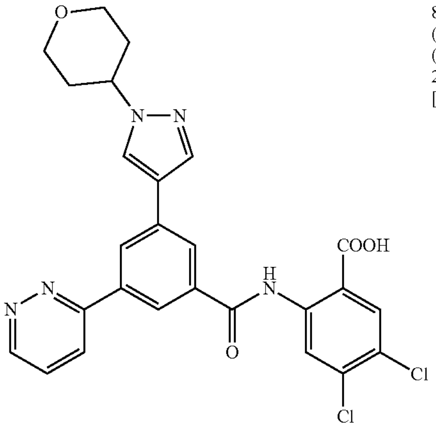 | $^1$H NMR (400 MHz, DMSO-d6) δ 12.52 (s, 1H), 9.32-9.28 (m, 1H), 8.98 (s, 1H), 8.58 (d, J = 6.9 Hz, 3H), 8.43 (d, J = 8.7 Hz, 1H), 8.31 (s, 1H), 8.18 (s, 1H), 8.12 (s, 1H), 7.91-7.87 (m, 1H), 4.51-4.42 (m, 1H), 4.00 (d, J = 10.1 Hz, 2H), 3.54-3.50 (m, 2H), 2.08-1.99 (m, 4H). LC/MS [M + H]: 538.1 |

General Synthesis Procedure 7

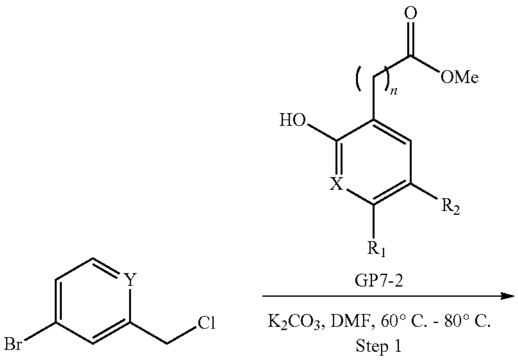

GP7-1

-continued

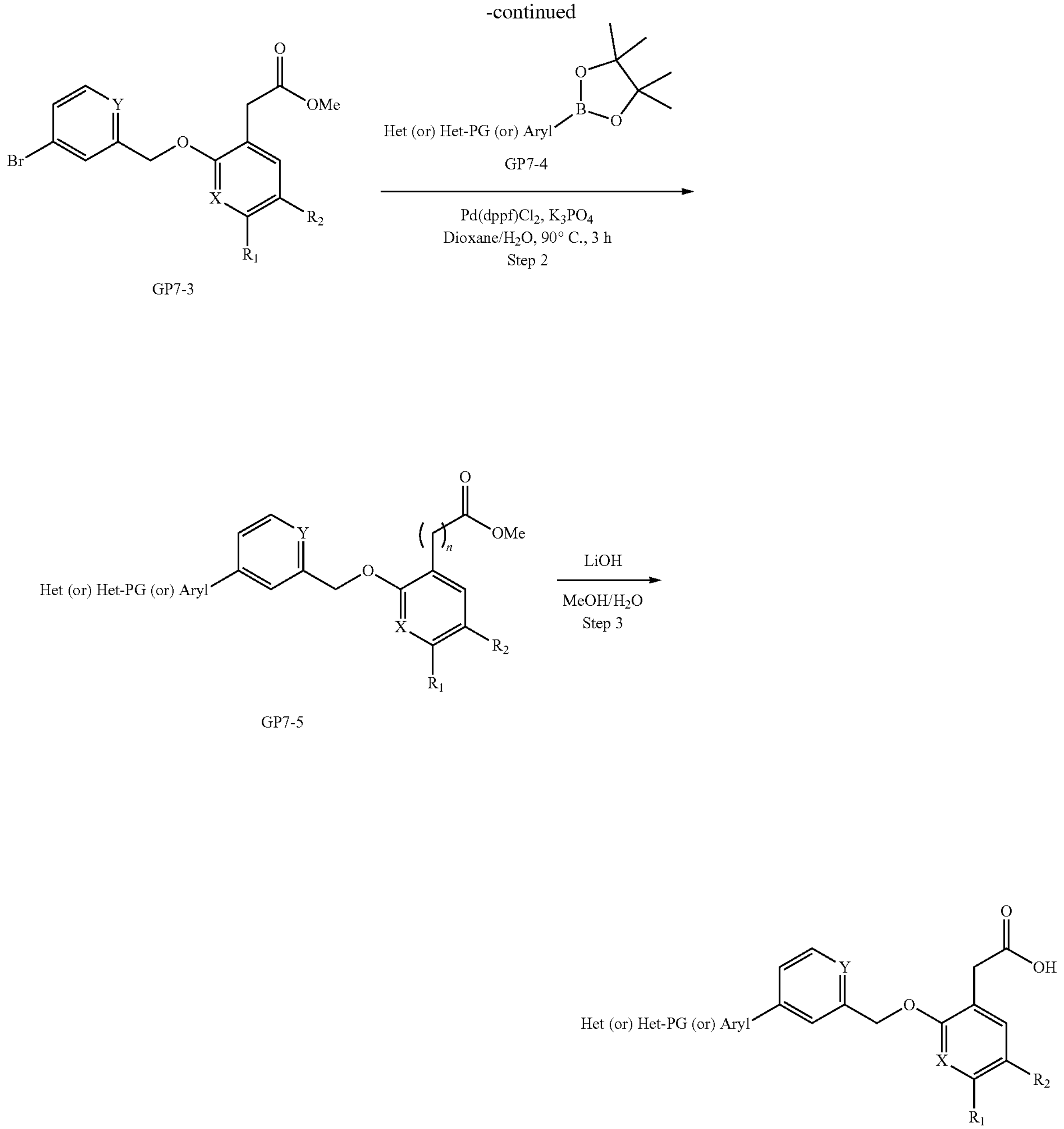

GP7-3

GP7-4

GP7-5

Examples $R_1$ = halogen, alkyl, alkoxy, $OCF_3$
$R_2$ = halogen, alkyl, alkoxy, $OCF_3$
$R_1$ and $R_2$ can together form a ring
X = C, N
Y = C, N
n = 0 to 2

Step 1. To a solution of compound GP7-1 (1.0 eq) and compound GP7-2 (1.0 eq) in DMF (15 mL) was $K_2CO_3$ (1.4 g, 2.0 eq) and stirred at 90° C. for 12 h. The mixture was poured into water, a large of amount of solid formed, filtered, washed with water and dried to afford GP7-3, Step 2. A mixture of compound GP7-3 (1.0 eq), compound GP7-4 (1.1 eq), $K_3PO_4$ (598 mg, 2.0 eq) and Pd(dppf) $Cl_2$ (52 mg, 0.05 eq) in Dioxane/$H_2O$ (10 mL/2 mL) was stirred at 90° C. for 4 h. After the reaction finished, the mixture was diluted with LA, washed with water, NaCl (aq), and dried over $Na_2SO_4$. Filtered, concentrated and purified by silica gel chromatography to afford GP7-5.

Step 3. To a stirred solution of compound GP7-5 (1.1 mmol) in MeOH/THF/$H_2O$ (3 mL/3 mL/3 mL) was added LiOH (277 mg, 6.6 mmol). The result solution was stirred at 25° C. for 3 h. The mixture was poured into water and acidified with 1N HCl to pH 3-4, a large amount of solid formed, filtered and dried to give Examples.

Synthesis of 4-chloro-2-[[3-(1-tetrahydropyran-4-ylpyrazol-4-yl)phenyl]methoxy]benzoic acid (Example 204)

Preparation of methyl 4-chloro-2-((3-(1-(tetrahydro-2H-pyran-4-yl)-1H-pyrazol-4-yl)benzyl)oxy)benzoate (204-5). A mixture of compound 204-3 (500 mg, 1.0 eq), compound

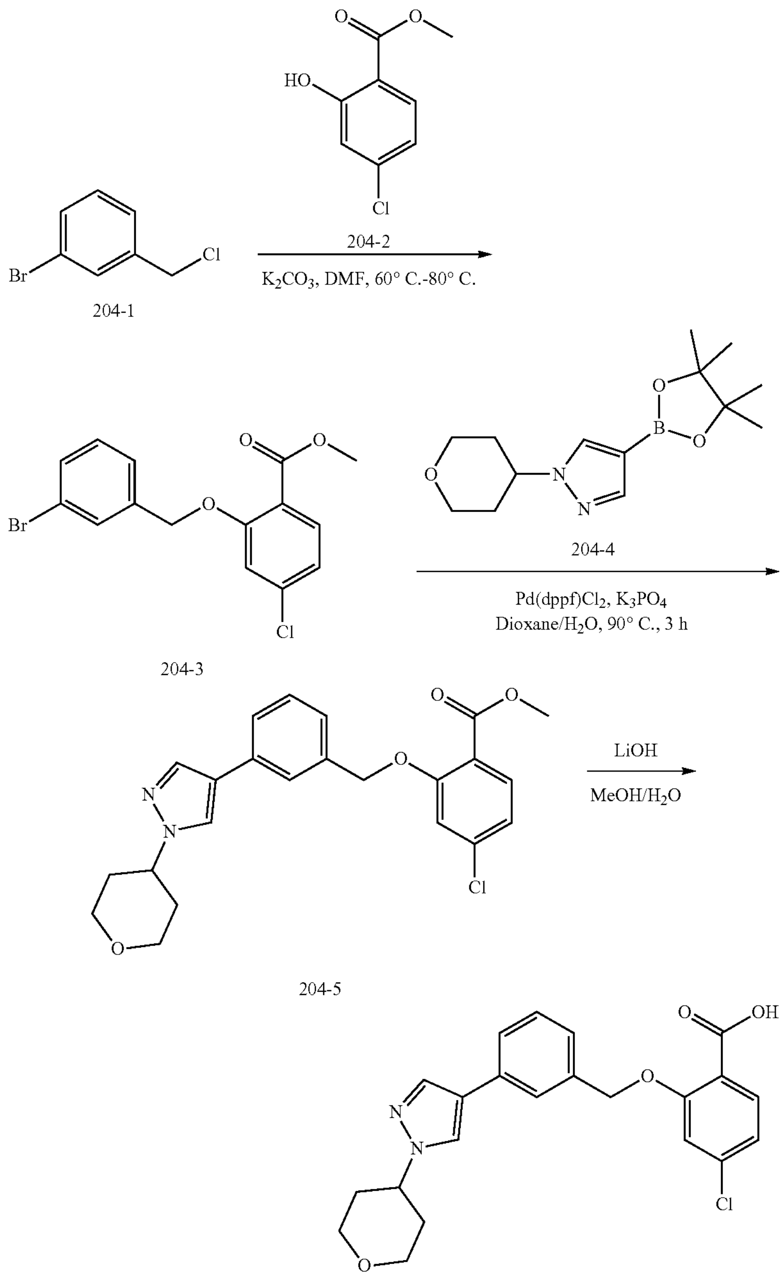

Example 204

Preparation of methyl 2-((3-bromobenzyl)oxy)-4-chlorobenzoate (204-3). To a solution of compound 204-1 (1.0 g, 1.0 eq) and compound 204-2 (911 mg, 1.0 eq) in DMF (15 mL) was $K_2CO_3$ (1.4 g, 2.0 eq) and stirred at 90° C. for 12 h. The mixture was poured into water, a large of amount of solid formed, filtered, washed with water and dried to afford a white solid (204-3, 1.6 g, yield 94%). $^1$H NMR (400 MHz, DMSO-$d_6$) δ 7.75 (d, J=8.8 Hz, 1H), 7.74 (s, 1H), 7.54 (d, J=7.6 Hz, 1H), 7.48 (d, J=7.6 Hz, 1H), 7.40-7.35 (m, 2H), 7.13 (dd, J=8.4 Hz, 2.0 Hz, 1H), 5.27 (s, 2H), 3.38 (s, 3H).

204-4 (431 mg, 1.1 eq), $K_3PO_4$ (598 mg, 2.0 eq) and $Pd(dppf)Cl_2$ (52 mg, 0.05 eq) in Dioxane/$H_2O$ (10 mL/2 mL) was stirred at 90° C. for 4 h. After the reaction finished, the mixture was diluted with EA, washed with water, NaCl (aq), and dried over $Na_2SO_4$. Filtered, concentrated and purified by silica gel chromatography to afford a white solid (204-5, 470 mg, 78%). LC/MS: Rt: 1.56 min; [M+H]$^+$: 427.0

Preparation of 4-chloro-2-[[3-(1-tetrahydropyran-4-ylpyrazol-4-yl)phenyl]methoxy]benzoic acid (Example 204). To a stirred solution of compound 204-5 (470 mg, 1.1 mmol) in MeOH/THF/$H_2O$ (3 mL/3 mL/3 mL) was added LiOH (277 mg, 6.6 mmol). The result solution was stirred at 25° C. for 3 h. The mixture was poured into water and acidified with 1N HCl to pH 3-4, a large of amount solid formed, filtered and dried to give a white solid (Example 204, 377.02 mg, yield 83%). LC/MS: Rt: 1.58 min; $[M+H]^+$: 413.0. $^1H$ NMR (400 MHz, DMSO-$d_6$) δ 12.91 (s, 1H), 8.23 (s, 1H), 7.90 (s, 1H), 7.78 (s, 1H), 7.71 (d, J=8.4 Hz, 1H), 7.54 (d, J=7.6 Hz, 1H), 7 39-7.28 (m, 3H), 7.09 (dd, J=8.4 Hz, 2.0 Hz, 1H), 5.25 (s, 2H), 4.46-4.38 (m, 1H), 4.04-3.97 (m, 2H), 3.52-3.45 (m, 2H), 2.02-1.93 (m, 4H).

The following compounds were prepared using general synthetic procedure 7. The examples and spectral data are shown in Table 7.

TABLE 7

| Example # | Name/Structure | Spectral data |
|---|---|---|
| 205 | 4,5-dichloro-2-[[3-(1-tetrahydropyran-4-ylpyrazol-4-yl)phenyl]methoxy]benzoic acid 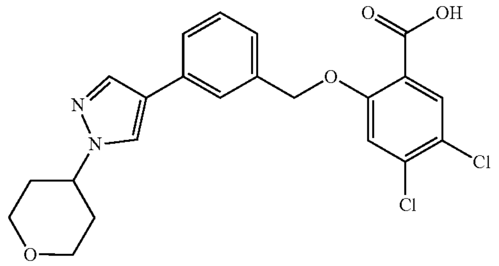 | $^1H$ NMR (400 MHz, DMSO-d6) δ 13.24 (s, 1H), 8.23 (s, 1H), 7.89 (s, 1H), 7.86 (s, 1H), 7.75 (s, 1H), 7.56 (s, 1H), 7.55-7.53 (d, 8.0 Hz, 1H), 7.39-7.35 (t, 8.0 Hz, 1H), 7.28-7.26 (d, 8.0 Hz, 1H), 5.26 (s, 2H), 4.45-4.38 (m, 1H), 3.99-3.96 (d, 12.0 Hz, 2H), 3.51-3.45 (m, 1H), 2.01-1.93 (m, 1H). LC/MS [M + H]: 447.1. |
| 207 | 4-methoxy-2-[[3-(1-tetrahydropyran-4-ylpyrazol-4-yl)phenyl]methoxy]benzoic acid 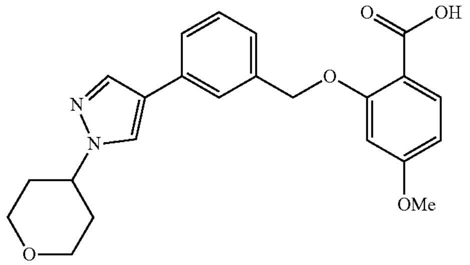 | 1H NMR (400 MHz, DMSO-d6) δ 12.32 (s, 1H), 8.23 (s, 1H), 7.90 (s, 1H), 7.82 (s, 1H), 7.75 (d, J = 8.8 Hz, 1H), 7.53 (d, J = 7.6 Hz, 1H), 7 38-7.30 (m, 3H), 6.73 (d, J = 2.0 Hz, 1H), 6.60 (dd, J = 8.8 Hz, 2.0 Hz, 1H), 5.21 (s, 2H), 4.44-4.39 (m, 1H), 3.99-3.96 (m, 2H), 3.81 (s, 1H), 3.52-3.45 (m, 2H), 2.02-1.96 (m, 4H). LC/MS: Rt: 1.58 min; $[M + H]^+$: 409.1 |
| 208 | 4-chloro-2-[1-[3-(1-tetrahydropyran-4-ylpyrazol-4-yl)phenyl]ethoxy]benzoic acid 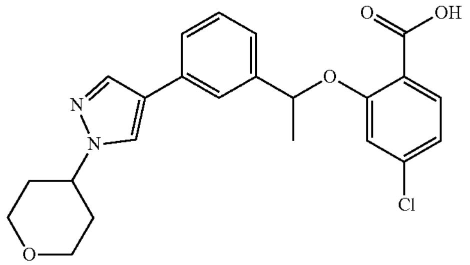 [SMILES: CC(Oc1cc(Cl)ccc1C(=O)O)c1cccc(-c2cnn(C3CCOCC3)c2)c1] | $^1H$ NMR (400 MHz, DMSO-d6) δ 12.94 (s, 1H), 8.20 (s, 1H), 7.86 (s, 1H), 7.74 (s, 1H), 7.63 (d, J = 8.0Hz, 1H), 7.47 (d, J = 7.6Hz, 1H), 7.33 (t, J = 7.6Hz, 1H), 7.25 (d, J = 7.6Hz, 1H), 7.16 (d, J = 2.0Hz, 1H), 7.00 (dd, J = 8.4Hz, 1H), 5.71 (dd, J = 12.4Hz, 1H), 4.43-4.38 (m, 1H), 3.98 (dd, J = 9.6Hz, 2H), 3.51-3.45 (m, 2H), 2.01-1.95 (m, 4H), 1.56 (d, J = 6.4Hz, 3H). LC/MS $[M + H]^+$: 427.4 |

TABLE 7-continued

| Example # | Name/Structure | Spectral data |
|---|---|---|
| 209 | 4-chloro-2-[[4-(1-tetrahydropyran-4-ylpyrazol-4-yl)-2-pyridyl]methoxy]benzoic acid 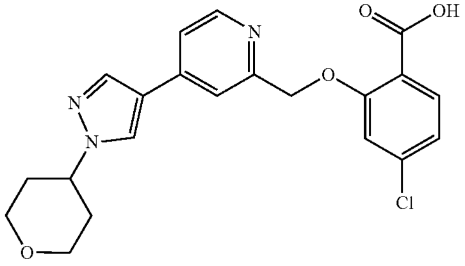 | $^1$H NMR (400 MHz, DMSO-d6) δ 12.22 (s, 1H), 8.48 (d, J = 4.8 Hz, 1H), 8.45 (s, 1H), 8.08 (s, 1H), 7.96 (s, 1H), 7.76 (d, J = 8.0 Hz, 1H), 7.55 (d, J = 5.2 Hz, 1H), 7.41 (d, J = 1.2 Hz, 1H), 7.12 (dd, J = 8.0 Hz, 2.0 Hz, 1H), 5.31 (s, 2H), 4.49-4.42 (m, 1H), 4.00-3.97 (m, 2H), 3.52-3.46 (m, 2H), 2.02-1.93 (m, 4H). LC/MS: Rt: 1.58 min; $[M + H]^+$: 414.1 |
| 210 | 4-chloro-2-[[3-(1H-pyrazol-4-yl)phenyl]methoxy]benzoic acid 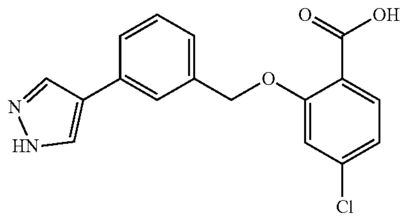 | $^1$H NMR (400 MHz, DMSO-d6) δ 13.03 (s, 1H), 8.03 (s, 1H), 7.81 (s, 1H), 7.70 (d, J = 8.3 Hz, 1H), 7.55 (d, J = 7.6 Hz, 1H), 7.39-7.31 (m, 1H), 7.26 (d, J = 7.5 Hz, 1H), 7.09 (d, J = 8.3 Hz, 1H), 5.24 (s, 1H). LC/MS (ESI) m/z: 329 $(M + H)^+$. |
| 211 | 4,5-dichloro-2-[[3-(1H-pyrazol-4-yl)phenyl]methoxy]benzoic acid 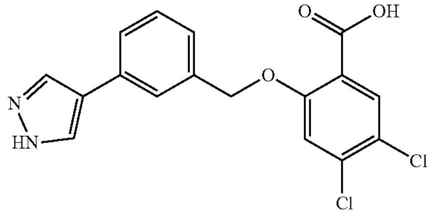 [SMILES: O=C(O)c1cc(Cl)c(Cl)cc1OCc1cccc(-c2cn[nH]c2)c1] | $^1$H NMR (400 MHz, DMSO-d6) δ 8.05 (s, 2H), 7.81 (s, 1H), 7.54-7.52 (d, 4.0Hz, 1H), 7.35-7.32 (m, 2H), 7.27-7.25 (d, 7.0 Hz, 1H), 5.19 (s, 2H). LC/MS [M + H]: 363.0. |
| 212 | 4,5-dichloro-2-[[4-(1-tetrahydropyran-4-ylpyrazol-4-yl)-2-pyridyl]methoxy]benzoic acid 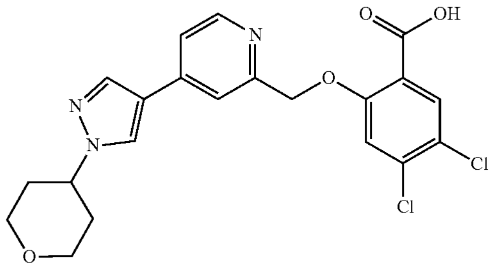 [SMILES: O=C(O)c1cc(Cl)c(Cl)cc1OCc1cc(-c2cnn(C3CCOCC3)c2)ccn1] | $^1$H NMR (400 MHz, DMSO-d6) δ 8.55 (d, J = 5.6 Hz, 1H), 8.52 (s, 1H), 8.13 (s, 1H), 8.02 (s, 1H), 7.92 (s, 1H), 7.67 (d, J = 5.6 Hz, 1H), 7.65 (s, 1H), 5.36 (s, 2H), 4.53-4.42 (m, 1H), 3.53-3.46 (m, 2H), 3.47 (s, 2H), 2.07-1.89 (m, 4H). LC/MS [M + H]: 448.1 |
| 214 | 2-[[4-(1H-pyrazol-4-yl)-2-pyridyl]methoxy]benzoic acid 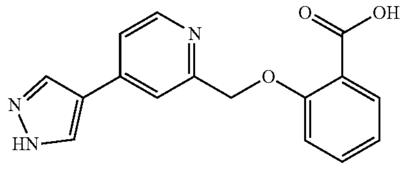 [SMILES: O=C(O)c1ccccc1OCc1cc(-c2cn[nH]c2)ccn1] | $^1$H NMR (400 MHz, DMSO-d6) δ 8.60 (d, J = 5.6 Hz, 1H), 8.37 (s, 2H), 8.19 (s, 1H), 7.80 (d, J = 4.6 Hz, 1H), 7.8-7.5 (m, 1H), 7.59-7.53 (m, 1H), 7.28 (d, J = 8.0 Hz, 1H), 7.09 (t, J = 7.6 Hz, 1H), 5.36 (s, 2H). LC/MS [M + H]: 296.1. |

TABLE 7-continued

| Example # | Name/Structure | Spectral data |
| --- | --- | --- |
| 216 | methyl 2-[4-chloro-2-[[4-(1-tetrahydropyran-4-ylpyrazol-4-yl)-2-pyridyl]methoxy]phenyl]acetate 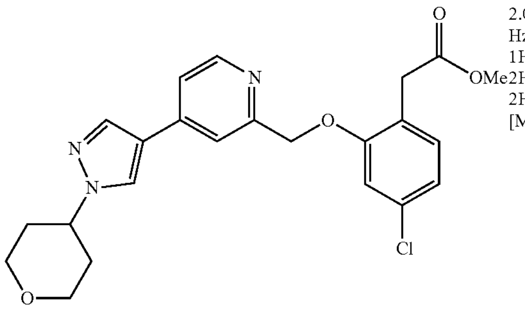 | $^1$H NMR (400 MHz, DMSO-d6) δ 8.64-8.56 (m, 2H), 8.20 (s, 1H), 7.83 (s, 1H), 7.73 (d, J = 4.8 Hz, 1H), 7.30 (d, J = 8.0 Hz, 1H), 7.18 (d, J = 2.0 Hz, 1H), 7.03 (dd, J = 8.0, 2.0 Hz, 1H), 5.27 (s, 2H), 4.51-4.45 (m, 1H), 4.00-3.94 (m, 2H), 3.76 (s, 2H), 3.53 (s, 3H), 3.52-3.45 (m, 2H), 2.11-1.90 (m, 4H). LC/MS [M + H]: 442.1. |
| 217 | 2-[4-chloro-2-[[4-(1-tetrahydropyran-4-ylpyrazol-4-yl)-2-pyridyl]methoxy phenyl]acetic acid 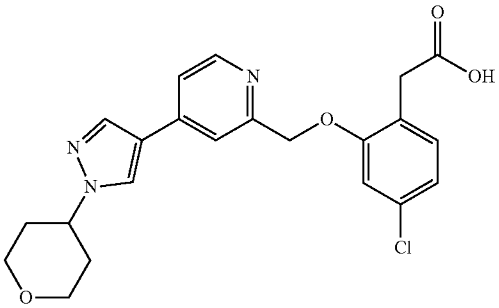 [SMILES: O=C(O)Cc1ccc(Cl)cc1OCc1cc(-c2cnn(C3CCOCC3)c2)ccn1] | $^1$H NMR (400 MHz, DMSO-d6) δ 8.53-8.43 (m, 2H), 8.12 (s, 1H), 7.73 (s, 1H), 7.54 (d, J = 5.2 Hz, 1H), 7.26 (d, J = 8.0 Hz, 1H), 7.11 (d, J = 1.8 Hz, 1H), 6.98 (dd, J = 8.0, 2.0 Hz, 1H), 5.20 (s, 2H), 4.52-4.35 (m, 1H), 4.01-3.91 (m, 2H), 3.65 (s, 2H), 3.55-3.41 (m, 2H), 2.08-1.88 (m, 4H). LC/MS [M + H]: 428.2. |
| 218 | methyl 2-[4-chloro-2-[3-(1-tetrahydropyran-4-ylpyrazol-4-yl)phenyl]methoxyphenyl]acetate 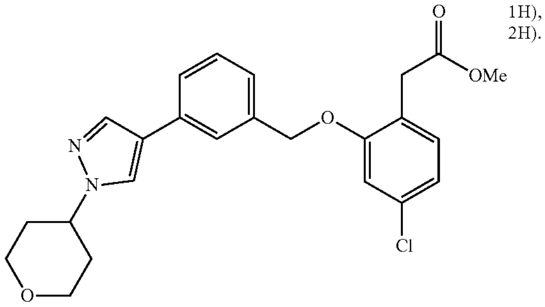 | $^1$H NMR (400 MHz, DMSO-d6) δ 13.26 (s, 1H), 8.51 (s, 1H), 7.82 (s, 1H), 7.03 (s, 1H), 6.66 (s, 1H), 4.43(d, J = 3.0Hz, 2H), 2.39-2.33 (m, 1H), 1.11-1.06 (m, 2H),0.93-0.89 (m, 2H). LC/MS $[M + H]^+$: 441.15. |
| 219 | 2-[4-chloro-2-[[3-(1-tetrahydropyran-4-ylpyrazol-4-yl)phenyl]methoxy]phenyl]acetic acid 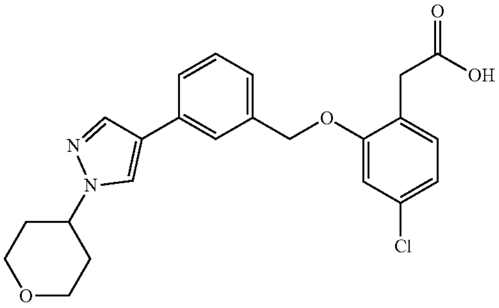 | $^1$H NMR (400 MHz, DMSO-d6) δ 8.26 (s, 1H), 7.92 (s, 1H), 7.66 (s, 1H), 7.54 (d, J = 7.7 Hz, 1H), 7.36 (t, J = 7.7 Hz, 1H), 7.24 (t, J = 7.6 Hz, 2H), 7.12 (d, J = 1.9 Hz, 1H), 6.98 (dd, J = 8.0, 1.9 Hz, 1H), 5.17 (s, 2H), 4.41 (tt, J = 10.0, 5.0 Hz, 1H), 3.97 (d, J = 11.1 Hz, 2H), 3.60 (s, 2H), 3.52-3.46 (m, 2H), 2.04-1.94 (m, 4H). LC/MS [M + H]: 427.0. |

TABLE 7-continued

| Example # | Name/Structure | Spectral data |
|---|---|---|
| 220 | 2-[[3-(1-isopropylpyrazol-4-yl)phenyl]methoxy]-6-methoxy-pyridine-3-carboxylic acid 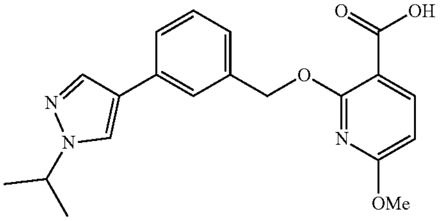 [SMILES: COc1ccc(C(=O)O)c(OCc2cccc(-c3cnn(C(C)C)c3)c2)n1] | $^1$H NMR (400 MHz, DMSO-d6) δ 8.23 (s, 1H), 8.12 (d, J = 8.4, 1H), 7.87 (s, 1H), 7.69 (s, 1H), 7.56 (d, J = 7.6, 1H), 7.37 (t, J = 7.6, 1H), 7.27 (d, J = 7.6, 1H), 6.38 (d, J = 8.0, 1H), 5.33 (s, 2H), 4.54-4.47 (m, 1H), 3.88 (s, 3H), 1.46 (s, 3H), 1.44 (s, 3H). LC/MS [M + H]$^+$: 368.2. |
| 230 | 4-chloro-2-[(3-isoxazol-4-ylphenyl)methoxy]benzoic acid 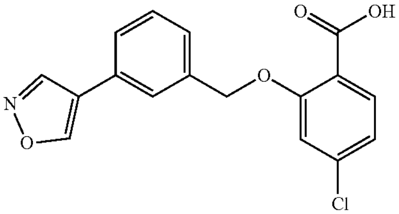 [SMILES: O=C(O)c1ccc(Cl)cc1OCc1cccc(-c2cnoc2)c1] | $^1$H NMR (400 MHz, DMSO-d6) δ 13.26 (s, 1H), 8.02 (s, 1H), 7.74-7.62 (m, 2H), 7.53 (s, 1H), 7.38-7.33 (m, 4H), 7.09 (s, 1H), 5.24 (s, 2H). LC/MS [M + Na]$^+$: 352.05. |
| 256 | 4-chloro-2-((3-(1-(tetrahydro-2H-pyran-4-yl)-1H-pyrazol-4-yl)benzyl)oxy)benzoic acid 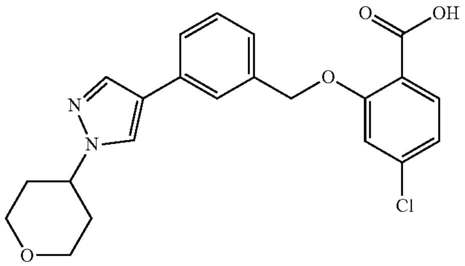 [SMILES: O=C(O)c1ccc(Cl)cc1OCc1cccc(-c2cnn(C3CCOCC3)c2)c1] | LC/MS (ESI) m/z: 413.1 (M + H)$^+$· |
| 256a | sodium 4-chloro-2-((3-(1-(tetrahydro-2H-pyran-4-yl)-1H-pyrazol-4-yl)benzyl)oxy)benzoate 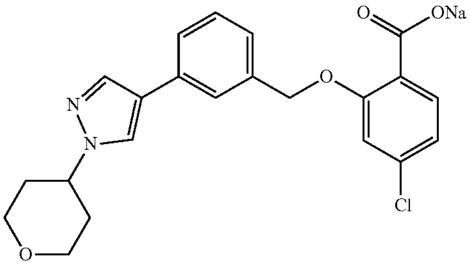 | $^1$H NMR (400 MHz, DMSO-d6) δ 8.31 (s, 1H), 7.92 (s, 1H), 7.85 (s, 1H), 7.50 (d, J = 7.2 Hz, 1H), 7.34-7.26 (m, 1H), 7.18 (d, J = 7.6 Hz, 1H), 6.95 (d, J = 1.6 Hz, 1H), 6.84 (dd, J = 8.0, 1.6Hz, 1H), 5.12 (s, 2H), 4.44-4.36 (m, 1H), 3.99-3.96 (m, 2H), 3.51-3.45 (m, 2H), 2.01-1.95 (m, 4H). LC/MS (ESI) m/z: 413.1 (M + H − Na)$^+$ |
| 277 | 2-((3-(isoxazol-4-yl)benzyl)oxy)benzoic acid 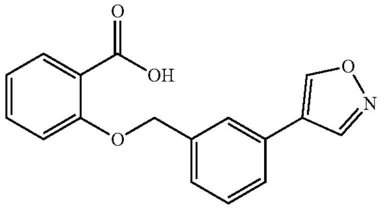 [SMILES: O=C(O)c1ccccc1OCc1cccc(-c2cnoc2)c1] | $^1$H NMR (400 MHz, DMSO-d6) δ 13.0 (brs, 1H), 8.02 (s, 1H), 7.76 (s, 1H), 7.71 (s, 1H), 7.54 (s, 1H), 7.49-7.48 (m, 1H), 7.41-7.36 (m, 3H), 7.19 (d, J-7.2 Hz, 1H), 7.01 (t, J = 7.2 Hz, 1H), 5.20 (s, 2H). LC/MS [M − H]$^-$: 294.1 |

TABLE 7-continued
| Example # | Name/Structure | Spectral data |
|---|---|---|
| 278 | 6-methoxy-2-((3-(1-(tetrahydro-2H-pyran-4-yl)-1H-pyrazol-4-yl)benzyl)oxy)nicotinic acid 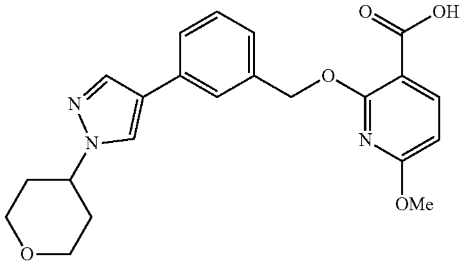 [SMILES: COc1ccc(C(=O)O)c(OCc2cccc(-c3cnn(C4CCOCC4)c3)c2)n1] | $^{1}H$ NMR (400 MHz, $CDCl_3$) δ 8.05 (d, J = 8.4, 1H), 7.89 (s, 1H), 7.75 (s, 1H), 7.52-7.47 (m, 2H), 7.42 (t, J = 7.6, 1H), 7.33 (d, J = 7.2, 1H), 6.33 (d, J = 8.4, 1H), 5.39 (s, 2H), 4.56-4.55 (m, 1H), 4.14 (dd, J = 11.2, 2H), 3.99 (s, 3H), 3.59 (dt, J = 12.0, 2H), 2.16-2.06 (m, 4H). LC/MS [M + H]+: 410.2. |
General Synthetic Procedure 8
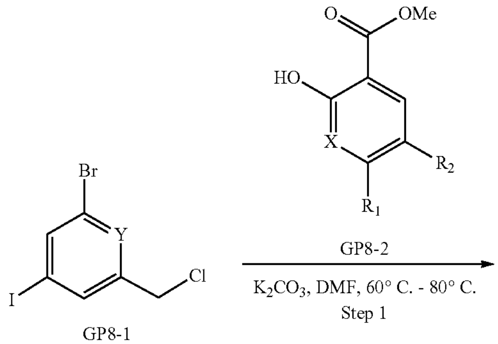
GP8-1
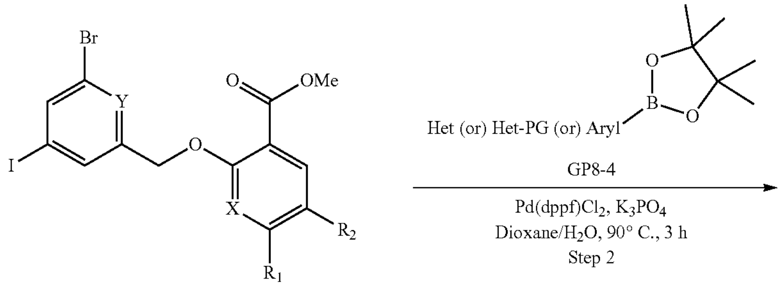
GP8-3
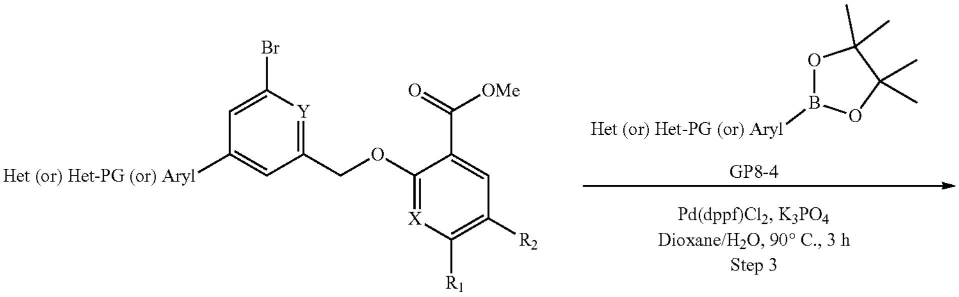
GP8-5

-continued

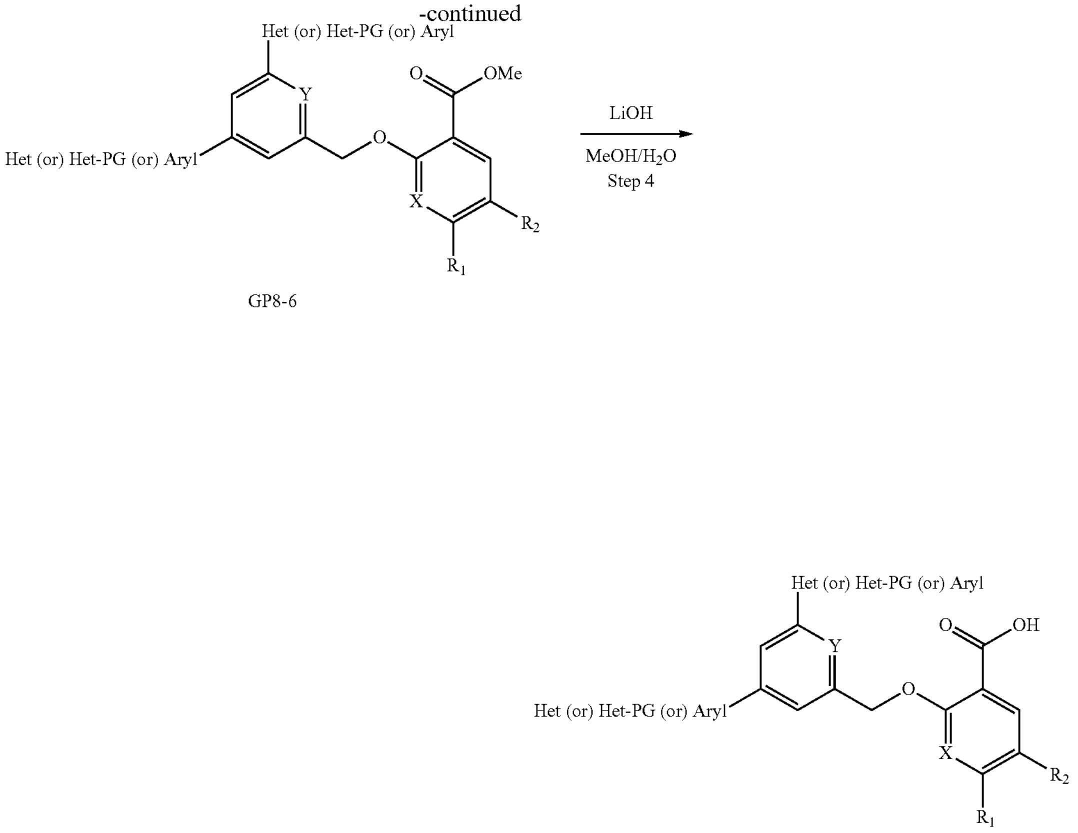

GP8-6

Examples $R_1$ = halogen, alkyl, alkoxy, $OCF_3$
$R_2$ = halogen, alkyl, alkoxy, $OCF_3$
$R_1$ and $R_2$ can together form a ring
X = C, N
Y = C, N Step 1. To a solution of compound GP8-1 (1.0 eq) and compound GP8-2 (1.0 eq) in DMF (15 mL) was $K_2CO_3$ (1.4 g, 2.0 eq) and stirred at 90° C. for 12 h. The mixture was poured into water, a large amount of solid formed, filtered, washed with water and dried to afford GP8-3.

Step 2. A mixture of compound GP8-3 (1.0 eq), compound GP8-4 (1.1 eq), $K_3PO_4$ (598 mg, 2.0 eq) and Pd(dppf)$Cl_2$ (52 mg, 0.05 eq) in Dioxane/$H_2O$ (10 mL/2 mL) was stirred at 90° C. for 4 h. After the reaction finished, the mixture was diluted with EA, washed with water, NaCl (aq), and dried over $Na_2SO_4$. Filtered, concentrated and purified by silica gel chromatography to afford GP8-5.

Step 3. A mixture of compound GP8-5 (1.0 eq), compound GP8-4 (1.1 eq), $K_3PO_4$ (598 mg, 2.0 eq) and Pd(dppf)$Cl_2$ (52 mg, 0.05 eq) in Dioxane/$H_2O$ (10 mL/2 mL) was stirred at 90° C. for 4 h. After the reaction finished, the mixture was diluted with EA, washed with water, NaCl (aq), and dried over $Na_2SO_4$. Filtered, concentrated and purified by silica gel chromatography to afford GP8-6. Also note that sometimes using excess amount of compound GP8-4 also would lead to GP8-6.

Step 4. To a stirred solution of compound GP8-6 (1.1 mmol) in MeOH/THF/$H_2O$ (3 mL/3 mL/3 mL) was added LiOH (277 mg, 6.6 mmol). The result solution was stirred at 25° C. for 3 h. The mixture was poured into water and acidified with 1N HCl to pH 3-4, a large of amount solid formed, filtered and dried to give example compounds.

Synthesis of 4,5-dichloro-2-((3-(pyridin-3-yl)-5-(1-(tetrahydro-2H-pyran-4-yl)-1H-pyrazol-4-yl)benzyl)oxy)benzoic acid (Example 280)

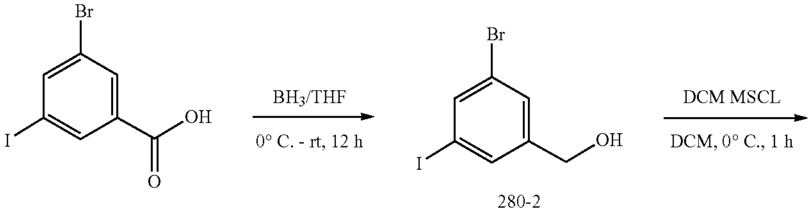

280-1

280-2

-continued
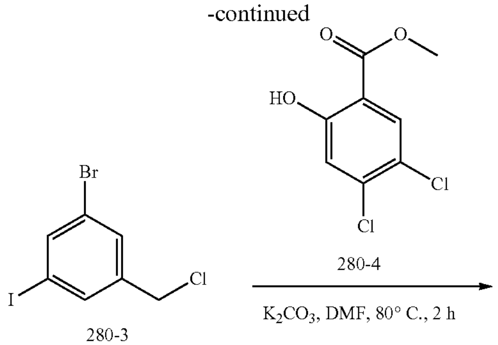
280-3
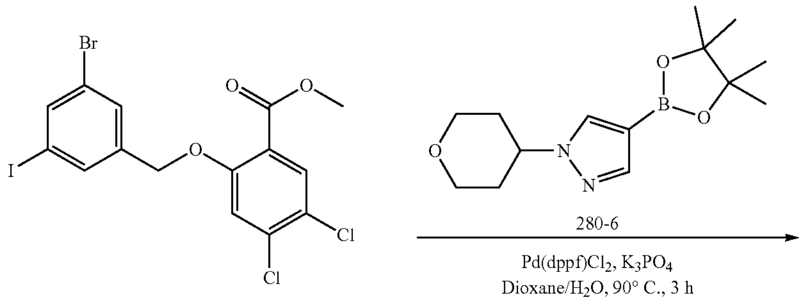
280-5
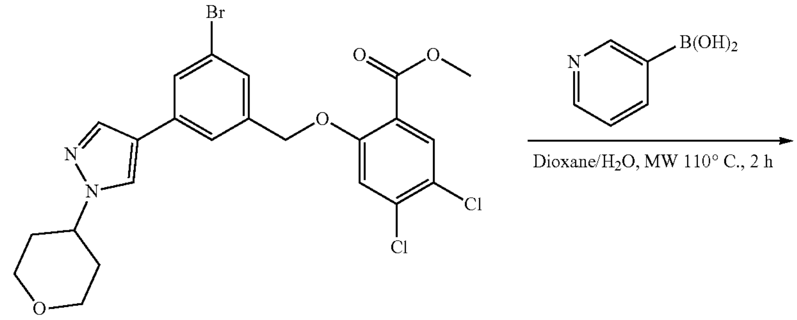
280-7
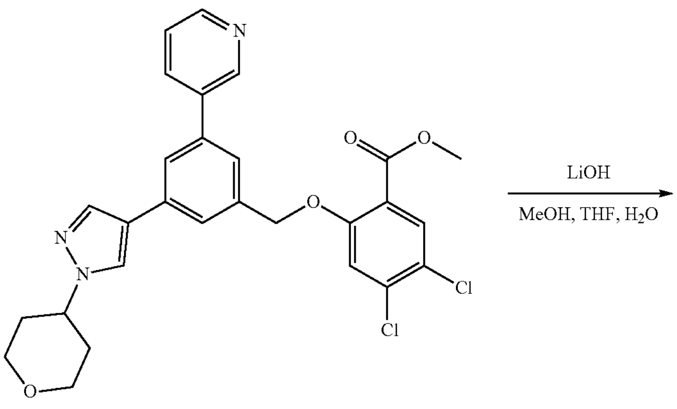
280-8

-continued

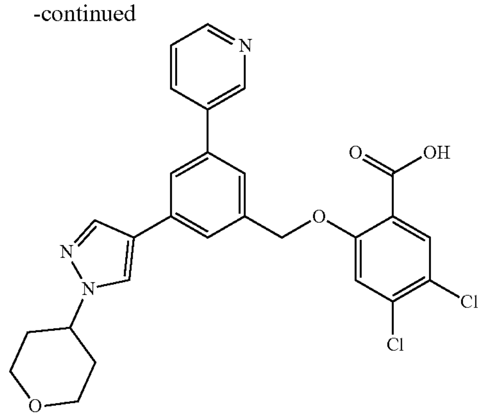

Compound 280

Preparation of (3-bromo-5-iodophenyl)methanol (280-2). To a solution of 3-bromo-5-iodobenzoic acid (5.0 g, 15.3 mmol, 1.0 eq) in dry THF (25 mL) being cooled to 0° C. was added $BH_3$ (1.0 mol/L in THF, 4.6 mL, 3.0 eq). The reaction mixture was stirred at room temperature for 72 hours. Once LC/MS showed the reaction finished, the reaction mixture was quenched by saturated sodium bicarbonate aqueous solution dropwise. The mixture was extracted with EA. The organic lay was concentrated. Purification by column chromatography through silica gel afford (3-bromo-5-iodophenyl)methanol (280-2, 4.9 g, 100%) as a yellow solid. $^1$H NMR (400 MHz, $CDCl_3$) δ 7.82 (d, J=1.2 Hz, 1H), 7.67 (s, 1H), 7.51 (s, 1H), 4.47 (d, J=4.0 Hz, 2H).

Preparation of 1-bromo-3-(chloromethyl)-5-iodobenzene (280-3). To a solution of (3-bromo-5-iodophenyl)methanol (280-2, 300 mg, 1.0 mmol, 1.0 eq) in dry DCM (5 mL) being cooled to 0° C. were added TEA (194 mg, 1.9 mmol, 2.0 eq), MsCl (220 mg, 1.9 mmol, 2.0 eq) under $N_2$ protection. The reaction mixture was then stirred at RT under $N_2$ for 2 hours. Once LC/MS showed the reaction finished, the mixture was then quenched with $H_2O$ (20 mL). The mixture was extracted with DCM, dried over $Na_2SO_4$, concentrated. The crude product was purified by silica gel chromatography to give 1-bromo-3-(chloromethyl)-5-iodobenzene (280-3, 198 mg, 62%) as a white solid. $^1$H NMR (400 MHz, $CDCl_3$) δ 7.77 (t, J=1.6 Hz, 1H), 7.64 (s, 1H), 7.48 (s, 1H), 4.66 (d, J=17.2 Hz, 2H).

Preparation of methyl 2-((3-bromo-5-iodobenzyl)oxy)-4,5-dichlorobenzoate (280-5). To a solution of 1-bromo-3-(chloromethyl)-5-iodobenzene (280-3, 200 mg, 0.6 mmol, 1.0 eq) in dry DMF (4 mL) was added methyl 4,5-dichloro-2-hydroxybenzoate (280-4, 133 mg, 0.6 mmol, 1.0 eq) and $K_2CO_3$ (168 mg, 1.2 mmol, 2.0 eq). The reaction mixture was stirred at 80° C. for 3 hours under $N_2$. The mixture was extracted with DCM, the organic lay was concentrated. Purification by column chromatography through silica gel afford methyl 2-((3-bromo-5-iodobenzyl)oxy)-4,5-dichlorobenzoate (280-5, 255 mg, 82%) as a white solid. $^1$H NMR (400 MHz, $CDCl_3$) δ 7.98 (s, 1H), 7.83 (s, 1H), 7.79 (s, 1H), 7.64 (s, 1H), 7.07 (s, 1H), 5.05 (s, 2H), 3.96 (s, 3H).

Preparation of methyl 2-((3-bromo-5-(1-(tetrahydro-2H-pyran-4-yl)-1H-pyrazol-4-yl)benzyl)oxy)-4,5-dichlorobenzoate (280-7). To a solution of methyl 2-((3-bromo-5-iodobenzyl)oxy)-4,5-dichlorobenzoate (280-5, 900 mg, 1.8 mmol, 1.0 eq) in Dioxane/$H_2O$ (15/3 mL) was added 1-(tetrahydro-2H-pyran-4-yl)-4-(4,4,5,5-tetramethyl-1,3,2-dioxaborolan-2-yl)-1H-pyrazole (280-6, 488 mg, 1.8 mmol, 1.0 eq), $K_3PO_4$ (745 mg, 3.5 mmol, 2.0 eq) and Pd(dppf)$Cl_2$ (64 mg, 0.1 mmol, 0.05 eq). The reaction mixture was stirred at 100° C. for 1 hours under microwave radiation. The mixture was extracted with DCM, the organic lay was concentrated. Purification by column chromatography through silica gel afford methyl 2-((3-bromo-5-(1-(tetrahydro-2H-pyran-4-yl)-1H-pyrazol-4-yl)benzyl)oxy)-4,5-dichlorobenzoate (280-7, 717 mg, 76%) as a white solid. LC/MS [M+H]: 540.9

Preparation of methyl 2-((3-bromo-5-(1-(tetrahydro-2H-pyran-4-yl)-1H-pyrazol-4-yl)benzyl)oxy)-4,5-dichlorobenzoate (280-8). To a solution of methyl 2-((3-bromo-5-(1-(tetrahydro-2H-pyran-4-yl)-1H-pyrazol-4-yl)benzyl)oxy)-4,5-dichlorobenzoate (280-7, 250 mg, 0.5 mmol, 1.0 eq) in Dioxane/$H_2O$ (10/2 mL), was added pyridin-3-ylboronic acid (57 mg, 0.5 mmol, 1.0 eq), $K_3PO_4$ (197 mg, 0.9 mmol, 2.0 eq) and Pd(dppf)$Cl_2$ (17 mg, 0.02 mmol, 0.05 eq). The reaction mixture was stirred at 110° C. for 2 hours under microwave radiation. The mixture was extracted with DCM, the organic lay was concentrated.

Purification by column chromatography through silica gel afford methyl 4,5-dichloro-2-((3-(pyridin-3-yl)-5-(1-(tetrahydro-2H-pyran-4-yl)-1H-pyrazol-4-yl)benzyl)oxy)benzoate (280-8, 130 mg, 52%) as a grey solid. LC/MS [M+H]: 538.1 Preparation of 4,5-dichloro-2-((3-(pyridin-3-yl)-5-(1-(tetrahydro-2H-pyran-4-yl)-1H-pyrazol-4-yl)benzyl)oxy) benzoic acid (Example 280). To a solution of methyl 4,5-dichloro-2-((3-(pyridin-3-yl)-5-(1-(tetrahydro-2H-pyran-4-yl)-1H-pyrazol-4-yl)benzyl)oxy)benzoate (280-8, 50 mg, 0.1 mmol, 1.0 eq) in MeOH/$H_2O$/THF (0.5/0.5/0.5 mL) was added LiOH (9 mg, 0.4 mmol). The reaction mixture was stirred at room temperature for 2 hours. After the reaction finished, the mixture was diluted with water and acidified by 1 mol/L HCl, then filtered. The crude product was triturated in MeOH:ACN=(1:9) and filtered. The product was formed as white solid (Example 280, 36 mg, 73%). LC/MS [M+H]: 524.2. $^1$H NMR (400 MHz, DMSO-$d_6$) δ 9.12 (d, J=1.6 Hz, 1H), 8.75-8.73 (m, 1H), 8.45 (d, J=8.8 Hz, 1H), 8.41 (s, 1H), 8.02 (s, 1H), 8.01 (s, 1H), 7.90 (s, 1H), 7.84 (s, 1H), 7.80-7.75 (m, 1H), 7.73 (s, 1H), 7.62 (s, 1H), 5.35 (s, 2H), 4.48-4.40 (m, 1H), 3.98 (d, J=11.6 Hz, 2H), 3.53-3.47 (m, 2H), 2.07-1.96 (m, 4H).

The following compounds were prepared using general synthetic procedure 8. The examples and spectral data are shown in Table 8.

TABLE 8

| Example # | Name/Structure | Spectral data |
|---|---|---|
| 225 | 2-[[3,5-bis(1-tetrahydropyran-4-ylpyrazol-4-yl)phenyl]methoxy]-4,5-dichloro-benzoic acid 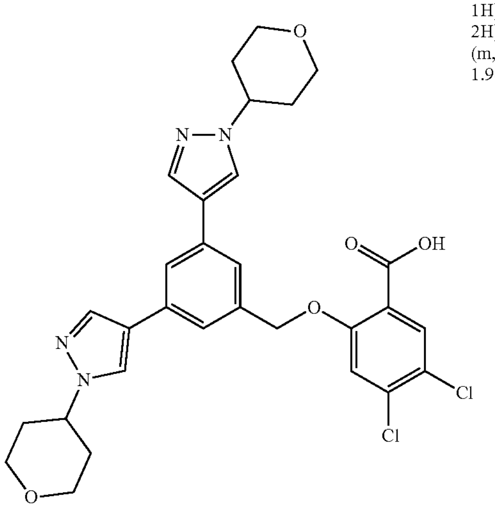 | $^1$H NMR (400 MHz, DMSO-d6) δ 8.29 (s, 2H), 7.95 (d, J = 0.8 Hz, 2H), 7.88 (s, 1H), 7.79 (s, 1H), 7.59 (s, 1H), 7.54 (d, J-1.6 Hz, 2H), 5.26 (s, 2H), 4.47-4.39 (m, 2H), 4.01-3.97 (m, 4H), 3.53-3.47 (m, 4H), 2.06-1.96 (m, 8H). LC/MS [M + H]: 597.1 |
| 226 | 2-((3,5-bis(1-(tetrahydro-2H-pyran-4-yl)-1H-pyrazol-4-yl)benzyl)oxy)-6-methoxynicotinic acid 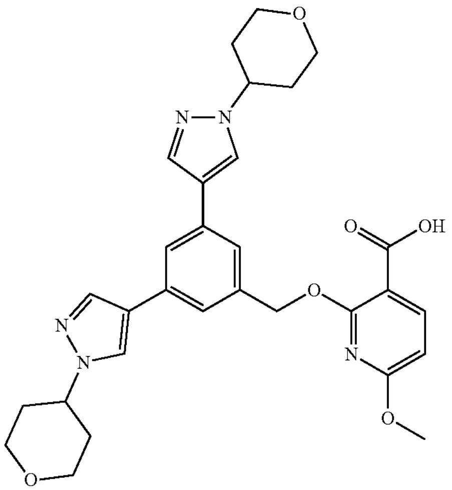 [SMILES: COc1ccc(C(=O)O)c(OCc2cc(-c3cnn(C4CCOCC4)c3)cc(-c3cnn(C4CCOCC4)c3)c2)n1] | $^1$H NMR (400 MHz, DMSO-d6) δ 8.33 (s, 2H), 8.14 (d, J = 8.5 Hz, 1H), 7.98 (s, 2H), 7.82 (s, 1H), 7.52 (s, 2H), 6.39 (s, 1H), 5.33 (s, 2H), 4.41 (dt, J = 15.7, 5.4 Hz, 2H), 3.98 (d, J = 11.3 Hz, 4H), 3.88 (s, 3H), 3.49 (td, J = 11.4, 2.4 Hz, 4H), 2.06-1.93 (m, 8H). LC/MS [M + H]: 560.1 |
| 228 | 2-[[3,5-bis(1H-pyrazol-4-yl)phenyl]methoxy]benzoic acid 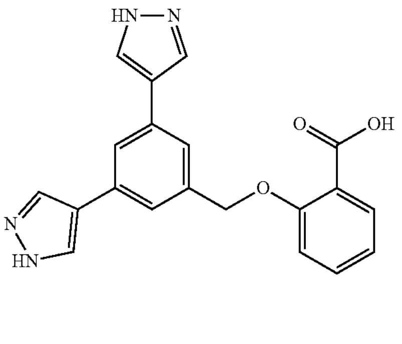 [SMILES: O=C(O)c1ccccc1OCc1cc(-c2cn[nH]c2)cc(-c2cn[nH]c2)c1] | $^1$H NMR (400 MHz, DMSO-d6) δ 12.89 (s, 2H), 8.11 (s, 4H), 7.81 (s, 1H), 7.71-7.66 (m, 1H), 7.60 (s, 2H), 7.55-7.49 (m, 1H), 7.25 (d, J = 8.2 Hz, 1H), 7.03 (t, J = 7.5 Hz, 1H), 5.22 (s, 2H). LC/MS [M + H]: 360.0 |

TABLE 8-continued
| Example # | Name/Structure | Spectral data |
|---|---|---|
| 282 | 4,5-dichloro-2-((3-(6-methylpyridin-3-yl)-5-(1-(tetrahydro-2H-pyran-4-yl)-1H-pyrazol-4-yl)benzyl)oxy)benzoic acid 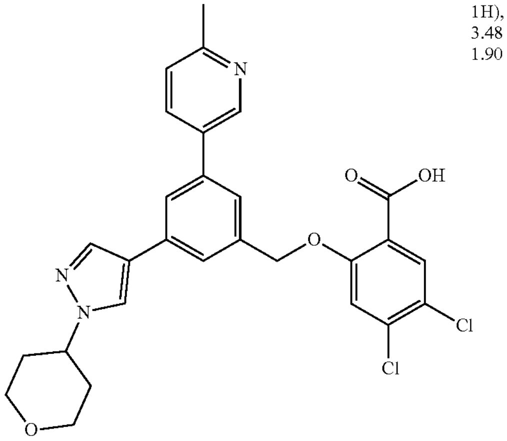 | $^1$H NMR (400 MHz, DMSO-d6) δ 9.10 (s, 1H), 8.65 (s, 1H), 8.40 (s, 1H), 8.04 (d, J = 3.6 Hz, 2H), 7.89 (t, J = 7.6 Hz, 3H), 7.77 (s, 1H), 7.62 (s, 1H), 5.34 (s, 2H), 4.54-4.33 (m, 1H), 3.99 (d, J = 2.8 Hz, 2H), 3.53-3.48 (m, 2H), 2.74 (s, 3H), 2.11-1.90 (m, 4H). LC/MS [M + H]: 538.2 |
General Synthetic Procedure 9
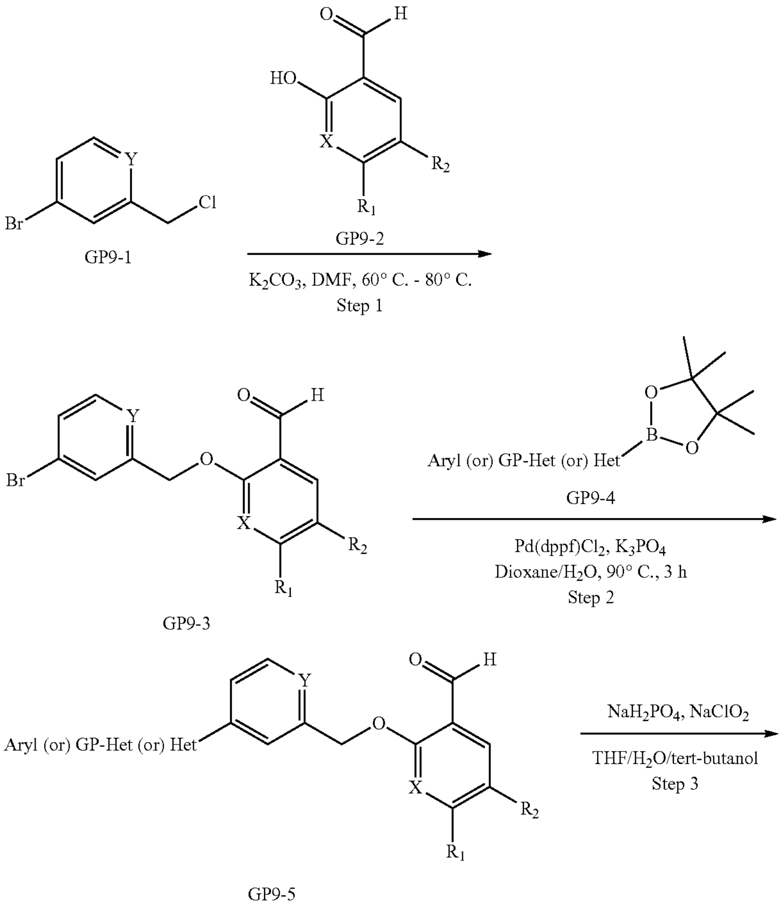

-continued

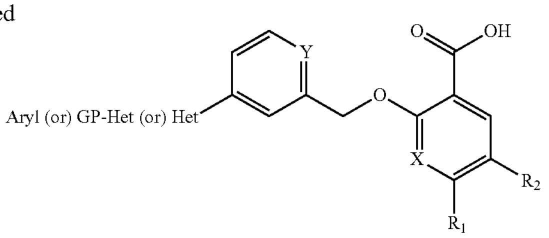

Examples $R_1$ = halogen, alkyl, alkoxy, $OCF_3$
$R_2$ = halogen, alkyl, alkoxy, $OCF_3$
$R_1$ and $R_2$ can together form a ring
X = C, N
Y = C, N Step 1. To a solution of compound GP9-1 (1.0 eq) and compound GP9-2 (1.0 eq) in DMF (15 mL) was $K_2CO_3$ (1.4 g, 2.0 eq) and stirred at 90° C. for 12 h. The mixture was poured into water, a large amount of solid formed, filtered, washed with water and dried to afford GP9-3.

Step 2. A mixture of compound GP9-3 (1.0 eq), compound GP9-4 (1.1 eq), $K_3PO_4$ (598 mg, 2.0 eq) and Pd(dppf)$Cl_2$ (52 mg, 0.05 eq) in Dioxane/$H_2O$ (10 mL/2 mL) was stirred at 90° C. for 4 h. After the reaction finished, the mixture was diluted with EA, washed with water, NaCl (aq), and dried over $Na_2SO_4$. Filtered, concentrated and purified by silica gel chromatography to afford GP9-5.

Step 3. To a mixture of (GP9-5, 0.14 mmol), 2-Methyl-2-butene (1.4 mmol), $NaH_2PO_4$—$H_2O$ (0.55 mmol) and $NaClO_2$ (0.55 mmol) in THF/$H_2O$/tert-Butanol (3 mL/1.5 mL/3 mL) was stirred at room temperature for 2 h. LC/MS showed the reaction was completed. The mixture was purified by prep-HPLC to give example compounds.

Synthesis of 7-[[3-(1-tetrahydropyran-4-ylpyrazol-4-yl)phenyl]methoxy]-2,3-dihydro-1,4-benzodioxine-5-carboxylic acid (Example 206)

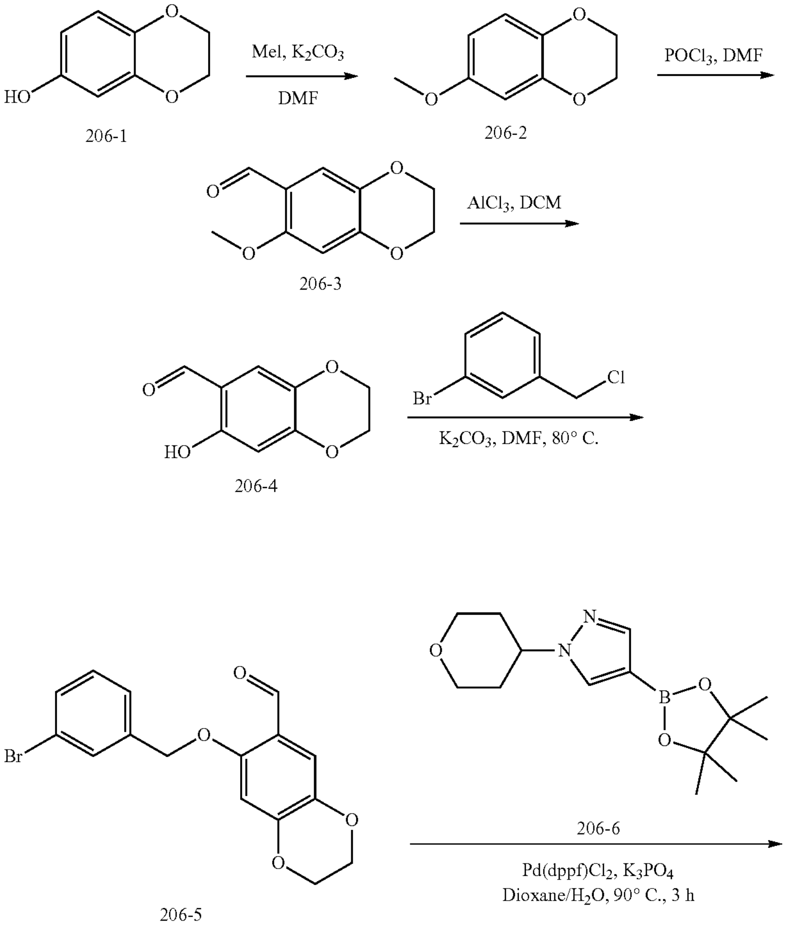

206-1

206-2

206-3

206-4

206-5

206-6

-continued

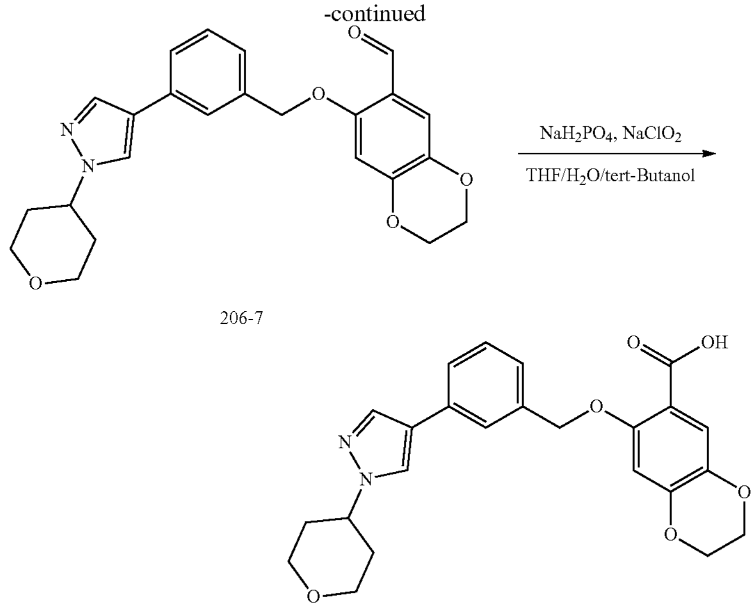

206-7

Example 206

Preparation of 6-methoxy-2,3-dihydrobenzo[b][1,4]dioxine (206-2). To a mixture of 2,3-dihydrobenzo[b][1,4]dioxin-6-ol (206-1, 1 g, 6.57 mmol), MeI (818 μL, 13.14 mmol) and $K_2CO_3$ (2.73 g, 19.72 mmol) in DMF (10 mL) was stirred at room temperature for 24 h. TLC showed the reaction was completed. The mixture was purified by C-18 reverse column chromatography eluting with 10-95% ACN in water to get 6-methoxy-2,3-dihydrobenzo[b][1,4]dioxine (206-2, 380 mg) as a clear syrup. $^1H$ NMR (400 MHz, DMSO-$d_6$) δ 6.75 (d, J=8.8 Hz, 1H), 6.44-6.38 (m, 2H), 4.22-4.15 (m, 4H), 3.66 (s, 3H).

Preparation of 7-methoxy-2,3-dihydrobenzo[b][1,4]dioxine-6-carbaldehyde (206-3). To a solution of 6-methoxy-2,3-dihydrobenzo[b][1,4]dioxane (206-2, 380 mg, 2.29 mmol) in DMF (5 mL) was added $POCl_3$ (260 μl, 2.75 mmol) at 0° C. stirred for 2 h under Argon, then stirred at 100° C. for 1 h. LC/MS showed the reaction was completed. The mixture was purified by C-18 reverse column chromatography eluting with 10-95% ACN in water to get 7-methoxy-2,3-dihydrobenzo[b][1,4]dioxine-6-carbaldehyde (206-3, 250 mg) as a white solid. LC/MS: Rt: 1.63 min; Expected MS m/z (ESI) for Chemical Formula: $C_{10}H_{10}O_4$[M+H]$^+$: 167.2; Found: 167.2.

Preparation of 7-hydroxy-2,3-dihydrobenzo[b][1,4]dioxine-6-carbaldehyde (206-4). To a mixture of 7-methoxy-2,3-dihydrobenzo[b][1,4]dioxine-6-carbaldehyde (206-3, 250 mg, 1.29 mmol) and $AlCl_3$ (618 mg, 4.64 mmol) in anhydrous DCM (30 mL) was stirred at room temperature for 2 h. TLC showed the reaction was completed. The mixture was quenched with EtOAc and washed by $NaHCO_3$ solution of water, the organic layer was concentrated to get 7-hydroxy-2,3-dihydrobenzo[b][1,4]dioxine-6-carbaldehyde (206-4, 200 mg) as a white solid. $^1H$ NMR (400 MHz, DMSO-$d_6$) δ 10.52 (s, 1H), 10.02 (s, 1H), 7.11 (s, 1H), 6.49 (s, 1H), 4.32-4.19 (m, 4H).

Preparation of 7-((3-bromobenzyl)oxy)-2,3-dihydrobenzo[b][1,4]dioxine-6-carbaldehyde (206-5). To a mixture of 7-hydroxy-2,3-dihydrobenzo[b][1,4]dioxine-6-carbaldehyde (206-4, 50 mg, 0.28 mmol), 1-bromo-3-(chloromethyl)benzene (40 μl, 0.31 mmol) and $K_2CO_3$ (77 mg, 0.56 mmol) in DMF (3 mL) was stirred at 80° C. under Argon for 16 h.

LC/MS showed the reaction was completed. The mixture was purified by silica gel chromatography eluting with PE:EA (2:1) to get 7-((3-bromobenzyl)oxy)-2,3-dihydrobenzo[b][1,4]dioxine-6-carbaldehyde (206-5, 30 mg) as a white solid. LC/MS: Rt: 1.78 min; Expected MS m/z (ESI) for Chemical Formula: $C_{16}H_{13}BrO_4$ [M+H]$^+$: 351.2; Found: 351.2.

Preparation of 7-((3-(1-(tetrahydro-2H-pyran-4-yl)-1H-pyrazol-4-yl)benzyl)oxy)-2,3-dihydrobenzo[b][1,4]dioxine-6-carbaldehyde (206-7). To a mixture of 7-((3-bromobenzyl)oxy)-2,3-dihydrobenzo[b][1,4]dioxine-6-carbaldehyde (206-5, 30 mg, 0.086 mmol), 1-(tetrahydro-2H-pyran-4-yl)-4-(4,4,5,5-tetramethyl-1,3,2-dioxaborolan-2-yl)-1H-pyrazole (206-6, 26.36 mg, 0.095 mmol), $K_3PO_4$ (36.55 mg, 0.172 mmol) and Pd(dppf)$Cl_2$ (3.16 mg, 0.004 mmol) in 1,4-Dioxane/$H_2O$ (2 mL/0.5 mL) was stirred at 90° C. under Argon for 16 h. TLC showed the reaction was completed. The mixture was washed by water and quenched with EtOAc, the organic layer was concentrated to get a crude product 7-((3-(1-(tetrahydro-2H-pyran-4-yl)-1H-pyrazol-4-yl)benzyl)oxy)-2,3-dihydrobenzo[b][1,4]dioxine-6-carbaldehyde (206-7, 60 mg) as a yellow oil. LC/MS: Rt: 1.615 min; Expected MS m/z (ESI) for Chemical Formula: $C_{24}H_{24}N_2O_5$ [M+H]$^+$: 421.2; Found: 421.2.

Preparation of 7-[[3-(1-tetrahydropyran-4-ylpyrazol-4-yl)phenyl]methoxy]-2,3-dihydro-1,4-benzodioxine-5-carboxylic acid (Example 206). To a mixture of 7-((3-(1-(tetrahydro-2H-pyran-4-yl)-1H-pyrazol-4-yl)benzyl)oxy)-2,3-dihydrobenzo[b][1,4]dioxine-6-carbaldehyde (206-7, 60 mg, 0.14 mmol), 2-Methyl-2-butene (152 μl, 1.4 mmol), $NaH_2PO_4$—$H_2O$ (81 mg, 0.55 mmol) and $NaClO_2$ (53 mg, 0.55 mmol) in THF/H2O/tert-Butanol (3 mL/1.5 mL/3 mL) was stirred at room temperature for 2 h. LC/MS showed the reaction was completed. The mixture was purified by prep-HPLC to get 7-((3-(1-(tetrahydro-2H-pyran-4-yl)-1H-pyrazol-4-yl)benzyl)oxy)-2,3-dihydrobenzo[b][1,4]dioxine-6- carboxylic acid (Example 206, 50 mg) as a white solid. LC/MS: Rt: 7.507 min; Expected MS m/z (ESI) for Chemical Formula: $C_{24}H_{24}N_2O_6$ $[M+H]^+$: 437.3; Found: 437.3. $^1H$ NMR (400 MHz, DMSO-$d_6$) δ 12.43 (s, 1H), 8.23 (s, 1H), 7.89 (s, 1H), 7.77 (s, 1H), 7.52 (d, J=7.6 Hz, 1H), 7.35 (t, J=7.6 Hz, 1H), 7.27 (d, J=7.6 Hz, 1H), 7.24 (s, 1H), 6.72 (s, 1H), 5.11 (s, 2H), 4.44-4.39 (m, 1H), 4.30-4.20 (m, 4H), 3.99-3.96 (m, 2H), 3.52-3.45 (m, 2H), 2.02-1.96 (m, 4H).

The following compounds were prepared using general synthetic procedure 9. The examples and spectral data are shown in Table 9.

TABLE 9

| Example # | Name/Structure | Spectral data |
|---|---|---|
| 213 | 6-[[4-(1-tetrahydropyran-4-ylpyrazol-4-yl)-2-pyridyl]methoxy]-2,3-dihydro-1,4-benzodioxine-7-carboxylic acid 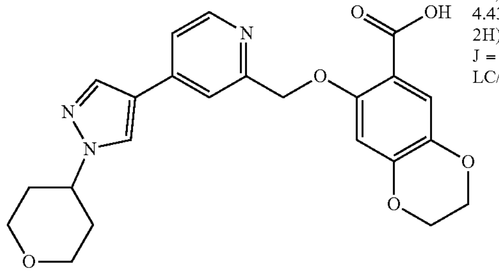 | $^1H$ NMR (400 MHz, DMSO-d6) δ 8.45 (s, 2H), 8.08 (s, 1H), 7.98 (s, 1H), 7.53 (d, J = 4.00, 1H), 7.26 (s, 1H), 6.78 (s, 1H), 5.18 (s, 1H), 4.47-4.43 (m, 1H), 4.28 (s, 2H), 4.21 (s, 2H), 3.98 (d, J = 10.80, 2H), 3.48 (t, J = 10.00, 2H), 2.01-1.97 (m, 4H). LC/MS: $[M + H]^+$: 438.4 |
| 215 | 4-isopropyl-2-[4-(1-tetrahydropyran-4-ylpyrazol-4-yl)-2-pyridyl]methoxy]benzoic acid 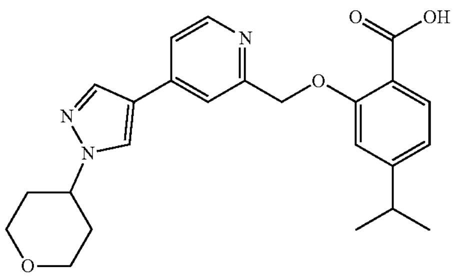 [SMILES: CC(C)c1ccc(C(=O)O)c(OCc2cc(-c3cnn(C4CCOCC4)c3)ccn2)c1] | $^1H$ NMR (400 MHz, DMSO-d6) δ 8.61 (d, J = 5.6 Hz, 1H), 8.59 (s, 1H), 8.19 (d, J = 5.2 Hz, 2H), 7.77 (d, J = 4.8 Hz, 1H), 7.72 (d, J = 8.0 Hz, 1H), 7.14 (d, J = 1.2 Hz, 1H), 7.00-6.99 (m, 1H), 5.37 (s, 2H), 4.52-4.44(m, 1H), 4.03-4.00 (m, 2H), 3.53-3.47 (m, 2H), 3.00-2.91 (m, 1H), 2.09-1.91 (m, 4H), 1.23 (s, 3H), 1.21 (s, 3H). LC/MS [M + H]: 422.2 |
| 231 | 6-[(3-isoxazol-4-ylphenyl)methoxy]-2,3-dihydro-1,4-benzodioxine-7-carboxylic acid 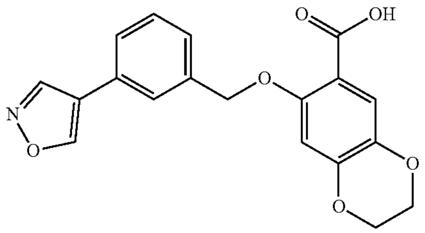 [SMILES: O=C(O)c1cc2c(cc1OCc1cccc(-c3cnoc3)c1)OCCO2] | $^1H$ NMR (400 MHz, DMSO-d6) δ 9.43 (s, 1H), 9.13 (s, 1H), 7.90 (s, 1H), 7.66-7.63 (m, 1H), 7.47-7.43 (m, 2H), 7.25 (s, 1H), 6.73 (s, 1H), 5.13 (s, 2H), 4.30-4.20 (m, 4H). LC/MS: $[M + H]^+$: 354.1 |
| 275 | 7-((3-(1H-pyrazol-4-yl)benzyl)oxy)-2,3-dihydrobenzo[b][1,4]dioxine-6-carboxylic acid 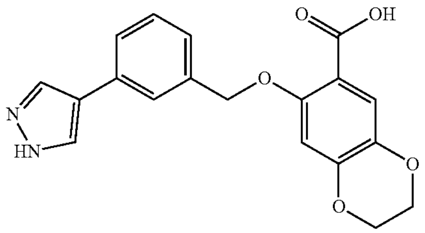 [SMILES: O=C(O)c1cc2c(cc1OCc1cccc(-c3cn[nH]c3)c1)OCCO2] | $^1H$ NMR (400 MHz, DMSO-d6) δ 8.04 (s, 2H), 7.81 (s, 1H), 7.53 (d, J-7.6 Hz, 1H), 7.34 (t, J = 7.6 Hz, 1H), 7.26 (d, J-7.6 Hz, 1H), 7.21 (s, 1H), 6.70 (s, 1H), 5.11 (s, 2H), 4.33-4.24 (m, 2H), 4.24-4.12 (m, 2H). LC/MS [M + H]: 353.1 |

Synthesis of 4-chloro-2-[[3-(1-tetrahydropyran-4-ylpyrazol-4-yl)benzoyl]amino]benzamide (Example 77)

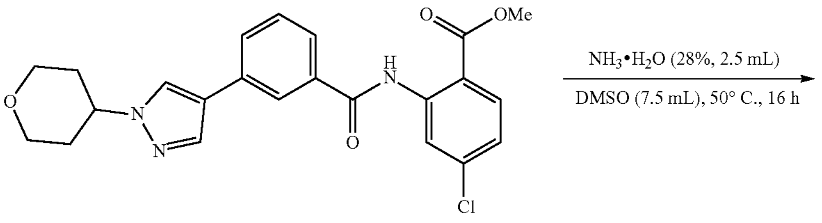

76

Example 77

Preparation of N-(2-carbamoyl-5-chlorophenyl)-3-(1-(tetrahydro-2H-pyran-4-yl)-1H-pyrazol-4-yl)benzamide (Example 77). A mixture of methyl 4-chloro-2-(3-(1-(tetrahydro-2H-pyran-4-yl)-1H-pyrazol-4-yl)benzamido)benzoate (Example 76, 241 mg, 0.55 mmol, 1.0 eq) and ammonia hydrate in water (28%, 2.5 mL) in DMSO (7.5 mL) in a sealed-tube was heated to 50° C. for 16 h. The reaction mixture was cooled down to RT, and then purified by prep-HPLC to give Example 77 (45.0 mg, 0.106 mmol, 19.3%) as a white solid. LC/MS [M+H]: 425.0. $^1$H NMR (400 MHz, DMSO-$d_6$) δ13.16 (brs, 1H), 8.82 (d, J=2.0 Hz, 1H), 8.50 (brs, 1H), 8.37 (brs, 1H), 8.13 (brs, 1H), 7.98-7.94 (m, 3H), 7.84 (d, J=7.6 Hz, 1H), 7.72 (d, J=7.6 Hz, 1H), 7.57 (t, J=7.6 Hz, 1H), 7.30-7.27 (m, 1H), 4.45-4.41 (m, 1H), 3.99-3.96 (m, 2H), 3.52-3.45 (m, 2H), 2.02-1.97 (m, 4H).

Synthesis of N-[5-chloro-2-(hydrazinecarbonyl)phenyl]-3-(1-tetrahydropyran-4-ylpyrazol-4-yl)benzamide (Example 78)

Preparation of N-[5-chloro-2-(hydrazinecarbonyl)phenyl]-3-(1-tetrahydropyran-4-ylpyrazol-4-yl)benzamide (Example 78). A mixture of methyl 4-chloro-2-(3-(1-(tetrahydro-2H-pyran-4-yl)-1H-pyrazol-4-yl)benzamido) benzoate (76, 160 mg, 0.364 mmol, 1.0 eq) and hydrazine hydrate in water (84%, 2.5 mL) in DMSO (7.5 mL) in a sealed-tube was heated to 80° C. for 5 h. The reaction mixture was cooled down to RT, and then purified by Prep-HPLC to give Example 78 (66.0 mg, 0.15 mmol, 41.3%) as a white solid. LC/MS [M+H]: 440.1. $^1$H NMR (400 MHz, DMSO-$d_6$) δ12.72 (brs, 1H), 10.25 (brs, 1H), 8.76 (d, J=2.0 Hz, 1H), 8.39 (brs, 1H), 8.14 (brs, 1H), 7.99 (brs, 1H), 7.86-7.81 (m, 2H), 7.73 (d, J=8.0 Hz, 1H), 7.57 (t, J=7.6 Hz, 1H), 7.29-7.26 (m, 1H), 4.72 (brs, 2H), 4.48-4.40 (m, 1H), 3.99-3.96 (m, 2H), 3.52-3.46 (m, 2H), 2.02-1.94 (m, 4H).

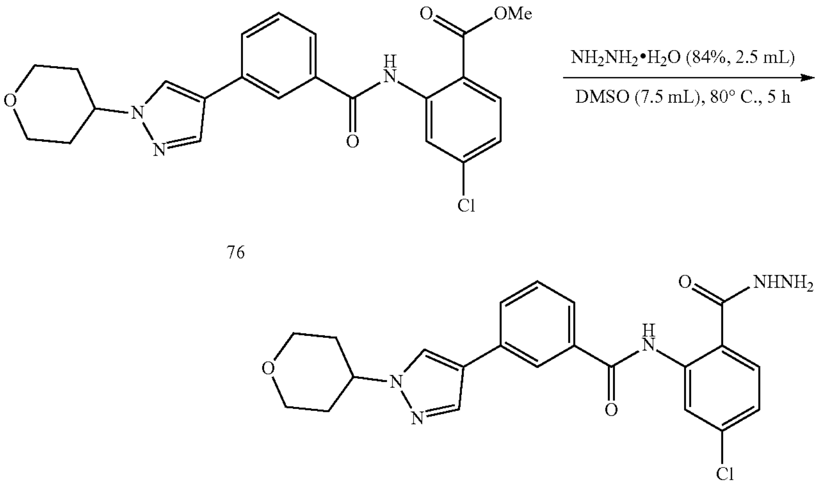

76

Example 78

Synthesis of 4-chloro-N-methoxy-2-[[3-(1-tetrahydropyran-4-ylpyrazol-3-yl)benzoyl]amino]benzamide (Example 79)

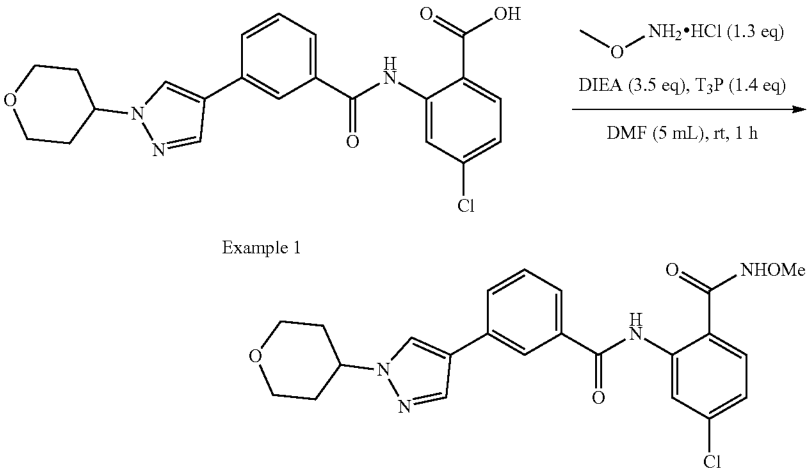

Example 1

Example 79

Preparation of 4-chloro-N-methoxy-2-[[3-(1-tetrahydropyran-4-ylpyrazol-3-yl)benzoyl]amino]benzamide (Example 79). To a solution of 4-chloro-2-(3-(1-(tetrahydro-2H-pyran-4-yl)-1H-pyrazol-4-yl)benzamido)benzoic acid (79-2, 194 mg, 0.456 mmol, 1.0 eq), O-methylhydroxylamine hydrochloride (50.0 mg, 0.60 mmol, 1.3 eq) in DMF (5.0 mL) at 0° C. was added DIEA (206 mg, 1.6 mmol, 3.5 eq), followed by T3P (202 mg, 0.638 mmol, 1.4 eq). The reaction mixture was stirred at rt for 1 h, the mixture purified by Prep-HPLC to give Example 79 (67.3 mg, 0.148 mmol, 32.5%) as a white solid. LC/MS [M+H]:455.1. $^1H$ NMR (400 MHz, DMSO-$d_6$) δ12.16 (brs, 1H), 12.08 (brs, 1H), 8.65 (d, J=1.2 Hz, 1H), 8.38 (brs, 1H), 8.14 (brs, 1H), 7.98 (brs, 1H), 7.85 (d, J=7.6 Hz, 1H), 7.71 (d, J=7.6 Hz, 2H), 7.58 (t, J=7.6 Hz, 1H), 7.32-7.30 (m, 1H), 4.48-4.40 (m, 1H), 4.00-3.96 (m, 2H), 3.75 (brs, 3H), 3.52-3.46 (m, 2H), 2.07-1.93 (m, 4H).

Synthesis of N-[5-chloro-2-(hydroxycarbamoyl)phenyl]-3-(1-tetrahydropyran-4-ylpyrazol-3-yl)benzamide (Example 80)

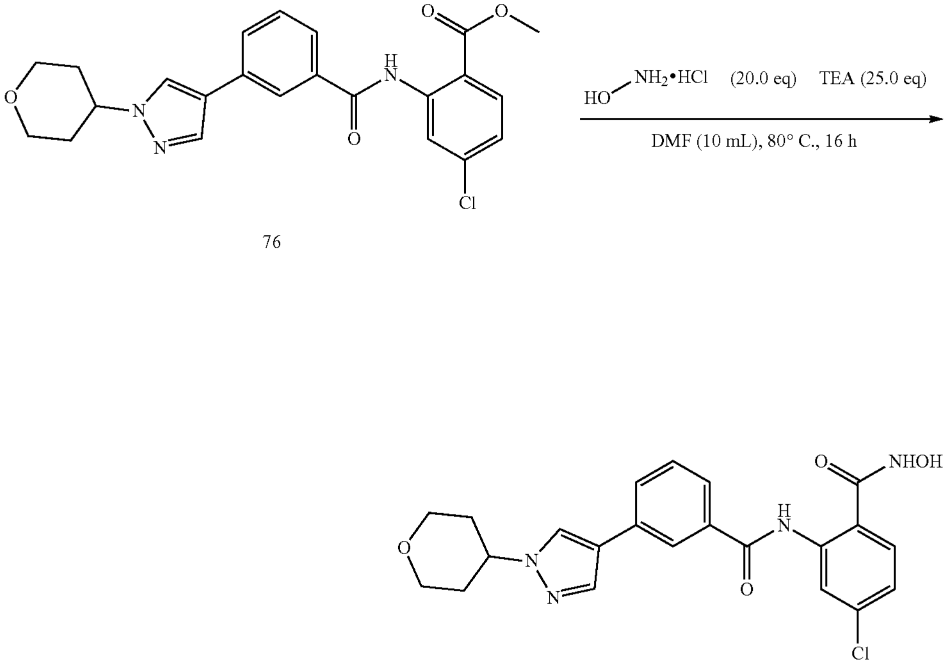

76

Example 80

Preparation of N-[5-chloro-2-(hydroxycarbamoyl)phenyl]-3-(1-tetrahydropyran-4-ylpyrazol-3-yl)benzamide (Example 80). A mixture of methyl 4-chloro-2-(3-(1-(tetrahydro-2H-pyran-4-yl)-1H-pyrazol-4-yl)benzamido) benzoate (76, 132 mg, 0.30 mmol, 1.0 eq), hydroxylamine hydrochloride (420 mg, 3.0 mmol, 20.0 eq). and TEA (756 mg, 7.5 mmol, 25.0 eq) in DMF (10 mL) in a sealed-tube was heated to 80° C. for 16 h. The reaction mixture was cooled down to RT, and then purified by Prep-HPLC to give Example 80 (19.6 mg, 0.045 mmol, 14.8%) as a white solid. LC/MS [M+H]: 441.1. $^1$H NMR (400 MHz, DMSO-$d_6$) δ12.45 (brs, 1H), 11.74 (brs, 1H), 9.47 (brs, 1H), 8.73 (d, J=2.0 Hz, 1H), 8.39 (brs, 1H), 8.13 (brs, 1H), 7.99 (brs, 1H), 7.85 (d, J=7.6 Hz, 1H), 7.74-7.71 (m, 2H), 7.58 (t, J=7.6 Hz, 1H), 7.30-7.28 (m, 1H), 4.49-4.41 (m, 1H), 4.00-3.97 (m, 2H), 3.53-3.46 (m, 2H), 2.08-1.95 (m, 4H).

Synthesis of N-[5-chloro-2-(hydroxymethyl)phenyl]-3-(1-tetrahydropyran-4-ylpyrazol-4-yl)benzamide (Example 81)

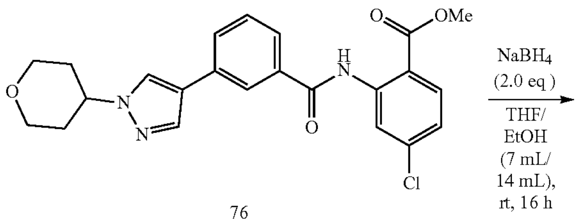

76

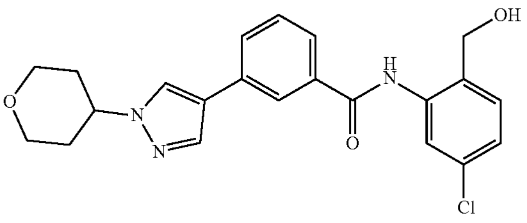

Example 81

Preparation of N-[5-chloro-2-(hydroxymethyl)phenyl]-3-(1-tetrahydropyran-4-ylpyrazol-4-yl)benzamide (Example 81). To a solution of $NaBH_4$ (31.0 mg, 0.82 mmol, 2.0 eq) in EtOH (14 mL) was added methyl 4-chloro-2-(3-(1-(tetrahydro-2H-pyran-4-yl)-1H-pyrazol-4-yl)benzamido)benzoate (76, 180 mg, 0.41 mmol, 1.0 eq) in THF (7.0 mL). The reaction mixture was stirred at RT for 16 h. 1 mL of Sat. $NH_4Cl$ solution was added. The reaction mixture was evaporated, and then purified by Prep-HPLC to give Example 81 (37.5 mg, 0.091 mmol, 22.2%) as a white solid. LC/MS [M+H]: 412.1. $^1$H NMR (400 MHz, MeOD-$d_4$) δ8.15 (brs, 1H), 8.13 (d, J=1.6 Hz, 1H), 8.08 (d, J=2.0 Hz, 1H), 7.92 (brs, 1H), 7.80-7.75 (m, 2H), 7.51 (t, J=7.6 Hz, 1H), 7.32 (t, J=8.4 Hz, 1H), 7.18-7.16 (m, 1H), 4.74 (s, 2H), 4.46-4.41 (m, 1H), 4.09-4.05 (m, 2H), 3.61-3.55 (m, 2H), 2.14-2.06 (m, 4H).

Synthesis of 2-[4-chloro-2-[[3-(1-tetrahydropyran-4-ylpyrazol-4-yl)benzoyl]amino]phenyl]acetic acid (Example 82)

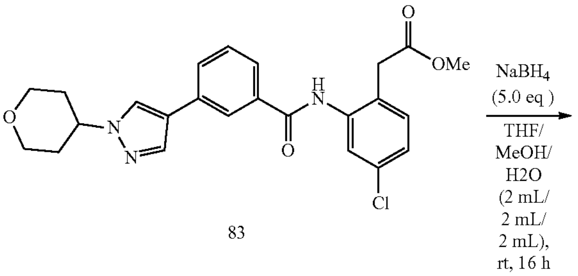

83

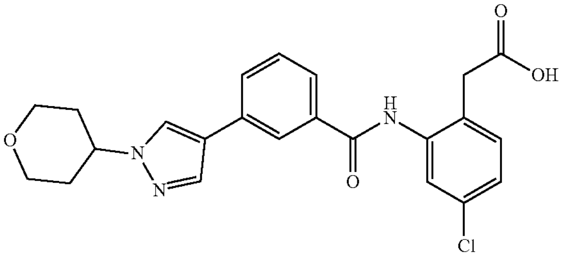

Example 82

Preparation of 2-[4-chloro-2-[[3-(1-tetrahydropyran-4-ylpyrazol-4-yl)benzoyl]amino]phenyl]acetic acid (Example 82). To a solution of methyl 2-(4-chloro-2-(3-(1-(tetrahydro-2H-pyran-4-yl)-1H-pyrazol-4-yl)benzamido)phenyl)acetate (83, 50.0 mg, 0.11 mmol, 1.0 eq) was added NaOH (22 mg, 0.55 mmol, 5.0 eq). The reaction mixture was stirred at rt for 16 h, and then adjusted with 2M hydrochloric acid to pH=3-4. The mixture was extracted with DCM and concentrated. The crude then purified by Prep-HPLC (0.1% TFA) to give Example 82 (45.1 mg, 0.103 mmol, 93.3%) as a white solid. LC/MS [M+H]: 440.1. $^1$H NMR (400 MHz, DMSO-$d_6$) δ11.74 (brs, 1H), 8.34 (brs, 1H), 8.25 (brs, 1H), 7.98 (brs, 1H), 7.83-7.78 (m, 3H), 7.49 (t, J=7.6 Hz, 1H), 7.28 (d, J=8.0 Hz, 1H), 7.20-7.17 (m, 1H), 7.07 (brs, 1H), 4.47-4.40 (m, 1H), 3.99-3.96 (m, 2H), 3.58 (brs, 2H), 3.52-3.45 (m, 2H), 2.04-1.93 (m, 4H).

Synthesis of methyl 2-[4-chloro-2-[[3-(1-tetrahydropyran-4-ylpyrazol-4-yl)benzoyl]amino]phenyl]acetate (Example 83)

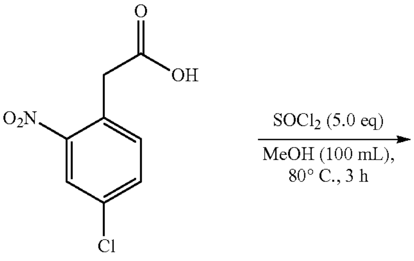

83-1

-continued

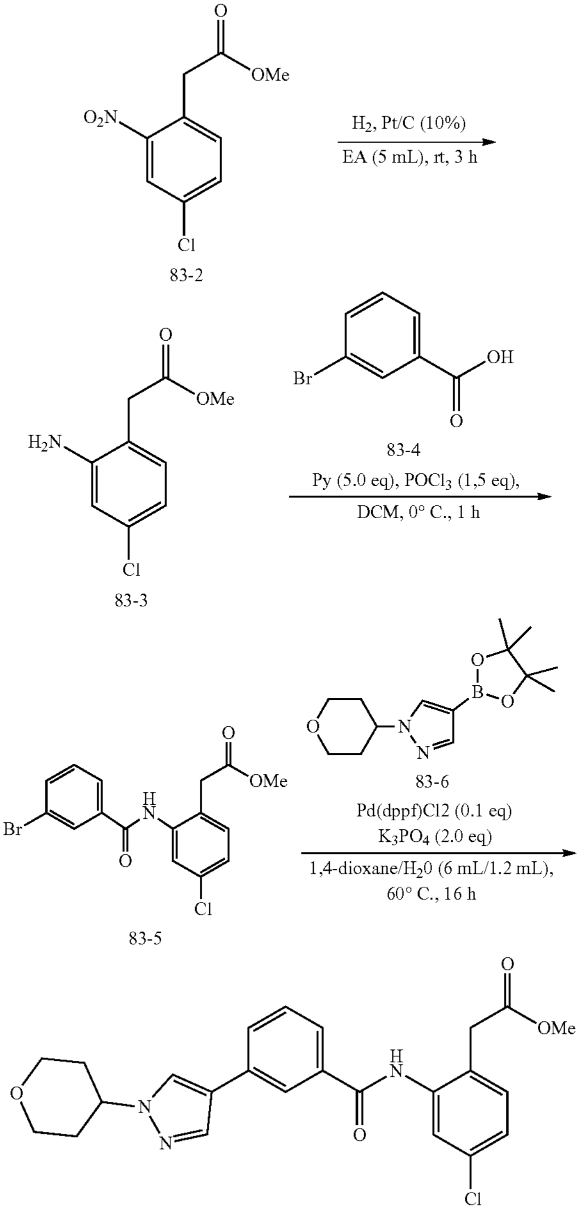

83-2

83-3

83-4

83-5

83-6

Example 83

Preparation of methyl 2-(4-chloro-2-nitrophenyl)acetate (83-2). To a solution of 2-(4-chloro-2-nitrophenyl)acetic acid (83-1, 10.8 g, 50.0 mmol, 1.0 eq) in MeOH (100 mL) at 0° C. was added $SOCl_2$ (29.8 g, 250 mmol, 5.0 eq) slowly. The reaction mixture was heated to 80° C. for 3 h. Then the reaction mixture was cooled down to rt, evaporated, 400 mL of EtOAc was added. washed with water (100 mL) and brine (100 mL), dried over $Na_2SO_4$, evaporated to give 83-2 (10.89 g, 47.6 mmol, 95.2%) as a white solid. $^1$H NMR (400 MHz, $CDCl_3$) δ 8.11 (d, J=2.4 Hz, 1H), 7.56 (dd, J=8.4 Hz, 2.0 Hz, 1H), 7.30 (d, J=8.4 Hz, 1H), 4.00 (brs, 2H), 3.71 (brs, 3H).

Preparation of methyl 2-(2-amino-4-chlorophenyl)acetate (83-3). A mixture of methyl 2-(4-chloro-2-nitrophenyl)acetate (83-2, 229 mg, 1.0 mmol, 1.0 eq), Pd/C (22.9 mg, 10%) in EtOAc (5.0 mL) under hydrogen atmosphere. The reaction mixture was then stirred at rt for 3 hours, filtered. The filtrate was evaporated to give 83-3 (168 mg, 0.844 mmol, 84.4%) as a white solid LC/MS [M+H]:200.0 Preparation of methyl 2-(2-(3-bromobenzamido)-4-chlorophenyl)acetate (83-5). To a solution of methyl 2-(2-amino-4-chlorophenyl) acetate (83-3, 168 mg, 0.844 mmol, 1.05 eq) , 3-bromobenzoic acid (83-4, 160 mg, 0.80 mmol, 1.0 eq) in DCM (5.0 mL) at 0° C. was added Pyridine (316 mg, 4.0 mmol, 5.0 eq), followed by $POCl_3$ (190 mg, 1.2 mmol, 1.5 eq). The reaction mixture was then stirred at 0° C. for 1 hours. 10 mL of water was added, adjusted with 1M HCl solution to pH=4, Extracted with DCM (15 mL*3), The combined organic layers was washed with brine (10 mL*2), dried over $Na_2SO_4$, filtered, the filtrate was evaporated, the residue was purification by SiO2 manual column (EtOAc:PE=1:10) to give compound 83-5 (131 mg, 0.343 mmol, 40.7%) as a white solid. LC/MS [M+H]:383.9.

Preparation of methyl 2-[4-chloro-2-[[3-(1-tetrahydropyran-4-ylpyrazol-4-yl)benzoyl]amino]phenyl]acetate (Example 83). A mixture of methyl 2-(2-(3-bromobenzamido)-4-chlorophenyl)acetate (83-5, 100 mg, 0.26 mmol, 1.0 eq), 1-(tetrahydro-2H-pyran-4-yl)-4-(4,4,5,5-tetramethyl-1,3,2-dioxaborolan-2-yl)-1H-pyrazole (83-6, 108 mg, 0.29 mmol, 1.5 eq), $K_3PO_4$ (110 mg, 0.52 mmol, 2.0 eq) in 1,4-dioxane/$H_2O$ (5.0 mL/1 mL) under $N_2$ atmosphere was heated to 90° C. for 1 h. The reaction mixture was cooled down to rt, filtered. The filtrate was evaporated, the residue was purified by Prep-HPLC to give Example 83 (26.1 mg, 0.057 mmol, 22.1%) as a white solid. LC/MS [M+H]:454.1. $^1$H NMR (400 MHz, DMSO-$d_6$) δ10.05 (brs, 1H), 8.34 (brs, 1H), 8.10 (brs, 1H), 7.97 (brs, 1H), 7.82-7.80 (m, 1H), 7.72-7.70 (m, 1H), 7.58 (d, J=2.4 Hz, 1H), 7.51 (t, J=8.0 Hz, 1H), 7.38 (d, J=8.0 Hz, 1H), 7.33-7.30 (m, 1H), 4.48-4.40 (m, 1H), 3.99-3.96 (m, 2H), 3.80 (brs, 2H), 3.51 (brs, 3H), 3.49-3.45 (m, 2H), 2.07-1.93 (m, 4H).

Synthesis of N-[2-(2-amino-2-oxo-ethyl)-5-chloro-phenyl]-3-(1-tetrahydropyran-4-ylpyrazol-4-yl)benzamide (Example 84)

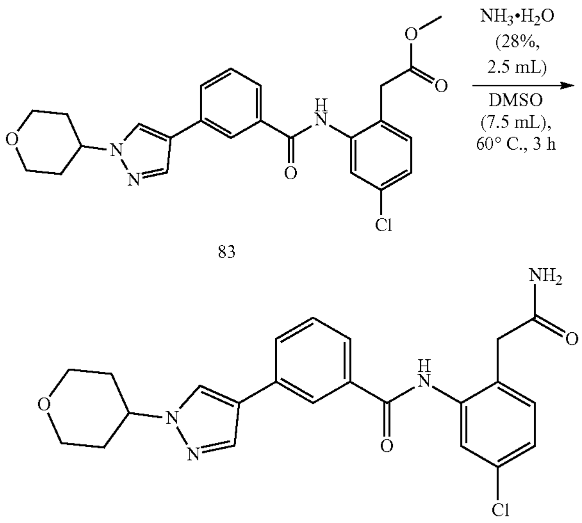

83

Example 84

Preparation of N-[2-(2-amino-2-oxo-ethyl)-5-chloro-phenyl]-3-(1-tetrahydropyran-4-ylpyrazol-4-yl)benzamide (Example 84). A mixture of methyl 2-(4-chloro-2-(3-(1-(tetrahydro-2H-pyran-4-yl)-1H-pyrazol-4-yl)benzamido)phenyl) acetatee (83, 160 mg, 0.353 mmol, 1.0 eq) and ammonia hydrate in water (28%, 2.5 mL) in DMSO (7.5 mL) in a sealed-tube was heated to 60° C. for 3 h. The reaction mixture was cooled down to RT, and then purified by Prep-HPLC to give Example 84 (64.5 mg, 0.147 mmol, 41.7%) as a white solid. LC/MS [M+H]: 439.1. $^1$H NMR (400 MHz, DMSO-$d_6$) δ11.16 (brs, 1H), 8.34 (brs, 1H), 8.25 (t, J=1.6 Hz, 1H), 8.04 (d, J=2.0 Hz, 1H), 7.99-7.98 (m, 2H), 7.83-7.81 (m, 2H), 7.53 (t, J=8.0 Hz, 1H), 7.42 (brs, 1H), 7.31 (d, J=8.0 Hz, 1H), 7.23-7.21 (m, 1H), 4.47-4.39 (m, 1H), 4.00-3.96 (m, 2H), 3.60 (brs, 2H), 3.52-3.45 (m, 2H), 2.05-1.93 (m, 4H).

Synthesis of N-[5-chloro-2-(2-hydrazino-2-oxo-ethyl)phenyl]-3-(1-tetrahydropyran-4-ylpyrazol-4-yl) benzamide (Example 85)

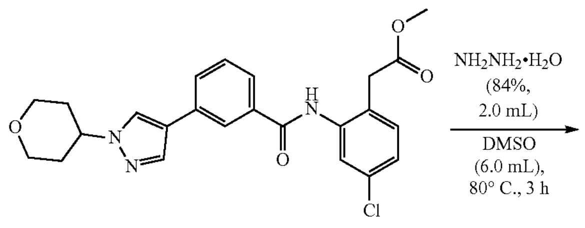

83

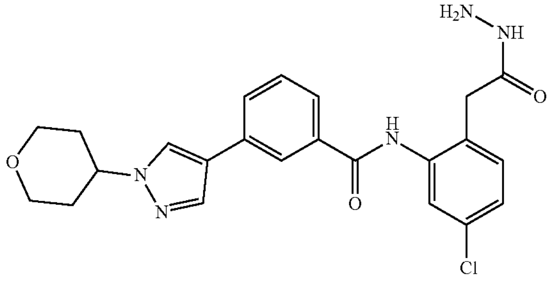

Example 86

Preparation of N-[5-chloro-2-(2-hydrazino-2-oxo-ethyl) phenyl]-3-(1-tetrahydropyran-4-ylpyrazol-4-yl)benzamide (Example 85). A mixture of methyl 2-(4-chloro-2-(3-(1-(tetrahydro-2H-pyran-4-yl)-1H-pyrazol-4-yl)benzamido) phenyl)acetate (83, 180 mg, 0.397 mmol, 1.0 eq) and hydrazine hydrate in water (84%, 2.0 mL) in DMSO (6.0 mL) in a sealed-tube was heated to 80° C. for 3 h. The reaction mixture was cooled down to RT, and then purified by Prep-HPLC to give Example 85 (133.3 mg, 0.294 mmol, 74.0%) as a white solid. LC/MS [M+H]: 454.1. $^1$H NMR (400 MHz, MeOD-$d_4$) δ 8.33 (t, J=1.6 Hz, 1H), 8.20 (brs, 1H), 7.99 (d, J=2.0 Hz, 1H), 7.98 (brs, 1H), 7.91 (d, J=8.0 Hz, 1H), 7.79 (d, J=8.0 Hz, 1H), 7.51 (t, J=7.6 Hz, 1H), 7.27 (d, J=8.4 Hz, 1H), 7.18-7.16 (m, 1H), 4.48-4.43 (m, 1H), 4.09-4.06 (m, 2H), 3.62-3.56 (m, 4H), 2.15-2.07 (m, 4H).

Synthesis of N-[5-chloro-2-[2-(methoxyamino)-2-oxo-ethyl]phenyl]-3-(1-tetrahydropyran-4-ylpyrazol-4-yl)benzamide (Example 86)

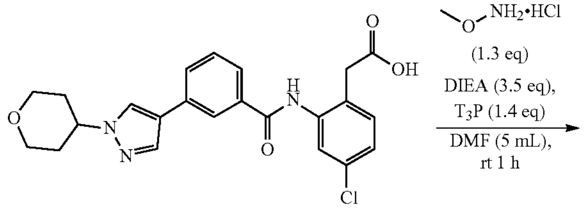

Example 82

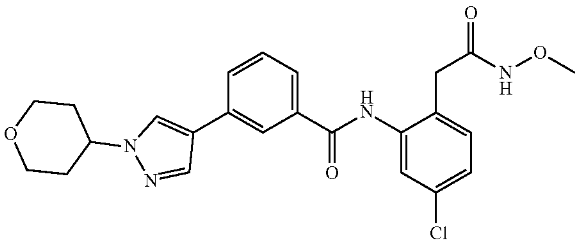

Example 86

Preparation of N-[5-chloro-2-[2-(methoxyamino)-2-oxo-ethyl]phenyl]-3-(1-tetrahydropyran-4-ylpyrazol-4-yl)benzamide (Example 86). To a solution of 2-(4-chloro-2-(3-(1-(tetrahydro-2H-pyran-4-yl)-1H-pyrazol-4-yl)benzamido) phenyl)acetic acid (82, 132 mg, 0.30 mmol, 1.0 eq), O-methylhydroxylamine hydrochloride (32.4 mg, 0.39 mmol, 1.3 eq) in DMF (5.0 mL) at 0° C. was added DIEA (134 mg, 1.05 mmol, 3.5 eq), followed by T3P (136 mg, 0.42 mmol, 1.4 eq). The reaction mixture was stirred at RT for 1 h, the mixture purified by Prep-HPLC to give Example 86 (58.7 mg, 0.125 mmol, 41.8%) as a white solid. LC/MS [M+H]:469.1. $^1$H NMR (400 MHz, DMSO-$d_6$) δ11.60 (brs, 1H), 10.87 (brs, 1H), 8.35 (brs, 1H), 8.24 (brs, 1H), 7.99 (brs, 1H), 7.92 (d, J=1.6 Hz, 1H), 7.82 (t, J=8.4 Hz, 2H), 7.54 (t, J=7.6 Hz, 1H), 7.31-7.24 (m, 2H), 4.47-4.39 (m, 1H), 3.99-3.94 (m, 2H), 3.59 (brs, 3H), 3.51 (brs, 2H), 3.49-3.40 (m, 2H), 2.07-1.92 (m, 4H).

Synthesis of N-[5-chloro-2-[2-(hydroxyamino)-2-oxo-ethyl]phenyl]-3-(1-tetrahydropyran-4-ylpyrazol-4-yl)benzamide (Example 87)

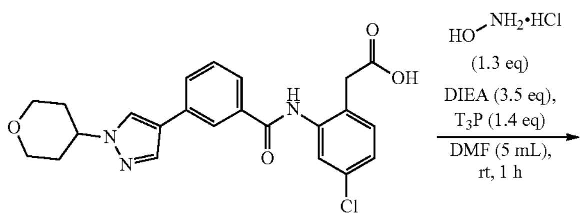

82

-continued

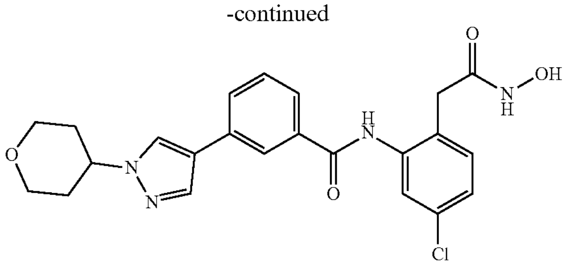

Example 87

Preparation of N-[5-chloro-2-[2-(hydroxyamino)-2-oxo-ethyl]phenyl]-3-(1-tetrahydropyran-4-ylpyrazol-4-yl)benzamide (Example 87). To a solution of 2-(4-chloro-2-(3-(1-(tetrahydro-2H-pyran-4-yl)-1H-pyrazol-4-yl)benzamido)phenyl)acetic acid (82, 132 mg, 0.30 mmol, 1.0 eq), hydroxylamine hydrochloride (27.3 mg, 0.39 mmol, 1.3 eq) in DMF (5.0 mL) at 0° C. was added DIEA (134 mg, 1.05 mmol, 3.5 eq), followed by $T_3P$ (136 mg, 0.42 mmol, 1.4 eq). The reaction mixture was stirred at RT for 1 h, the mixture purified by Prep-HPLC to give Example 87 (62.5 mg, 0.138 mmol, 45.9%) as a white solid. LC/MS [M+H]: 455.1. $^1$H NMR (400 MHz, DMSO-$d_6$) δ11.36 (brs, 1H), 11.12 (brs, 1H), 8.37 (brs, 1H), 8.27 (brs, 1H), 8.05 (d, J=2.4 Hz, 1H), 7.99 (brs, 1H), 7.85-7.82 (m, 2H), 7.54 (t, J=8.0 Hz, 1H), 7.29-7.21 (m, 2H), 4.45-4.40 (m, 1H), 3.99-3.96 (m, 2H), 3.70 (brs, 1H), 3.53 (brs, 2H), 3.51-3.45 (m, 2H), 2.07-1.96 (m, 4H).

Synthesis of N-[5-chloro-2-(2-hydroxyethyl)phenyl]-3-(1-tetrahydropyran-4-ylpyrazol-3-yl)benzamide (Example 88)

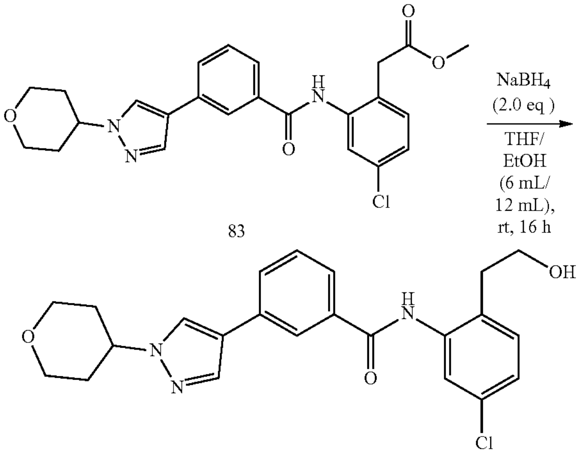

83

Example 88

Preparation of N-[5-chloro-2-(2-hydroxyethyl)phenyl]-3-(1-tetrahydropyran-4-ylpyrazol-3-yl)benzamide (Example 88). To a solution of NaBH4 (83, 30.4 mg, 0.80 mmol, 2.0 eq) in EtOH (12.0 mL) was added methyl 2-(4-chloro-2-(3-(1-(tetrahydro-2H-pyran-4-yl)-1H-pyrazol-4-yl)benzamido)phenyl)acetate (181.2 mg, 0.40 mmol, 1.0 eq) in THF (6 mL). The reaction mixture was stirred at RT for 16 h. 1 mL of Sat. $NH_4Cl$ solution was added. The reaction mixture was evaporated, and then purified by Prep-HPLC to give Example 88 (28.6 mg, 0.067 mmol, 16.8%) as a white solid. LC/MS [M+H]: 426.1. $^1$H NMR (400 MHz, DMSO-$d_6$) δ10.41 (brs, 1H), 8.34 (brs, 1H), 8.13 (brs, 1H), 7.97 (brs, 1H), 7.81 (d, J=7.6 Hz, 1H), 7.78-7.73 (m, 2H), 7.52 (t, J=8.0 Hz, 1H), 7.33 (d, J=8.0 Hz, 1H), 7.26-7.22 (m, 1H), 5.52 (t, J=4.0 Hz, 1H), 4.47-4.39 (m, 1H), 3.99-3.94 (m, 2H), 3.72-3.68 (m, 2H), 3.52-3.45 (m, 2H), 2.83 (t, J=4.0 Hz, 2H), 2.04-1.93 (m, 4H).

Synthesis of 2-[5-[3-(1H-pyrazol-4-yl)phenyl]-1,2,4-oxadiazol-3-yl]benzoic acid Example 94

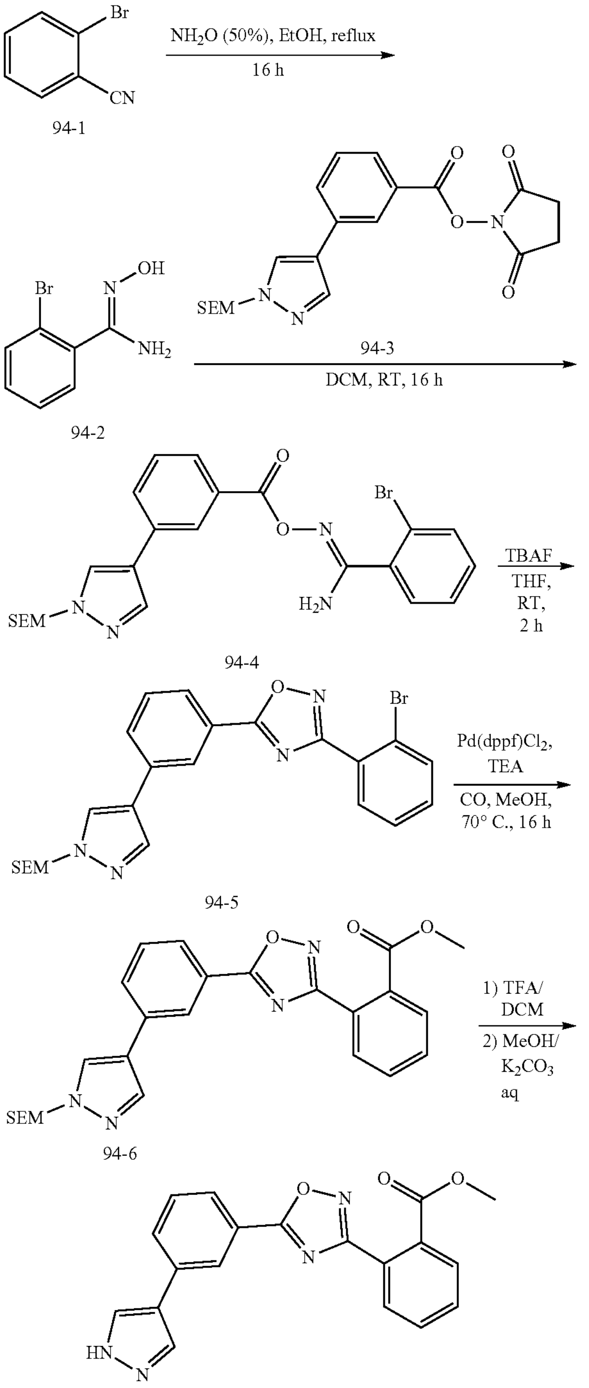

94-1, 94-2, 94-4, 94-5, 94-6, 94-7

-continued

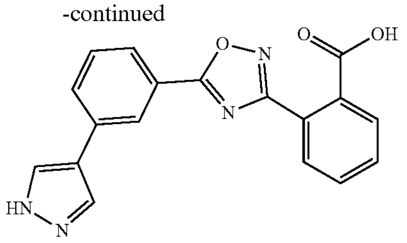

Example 94

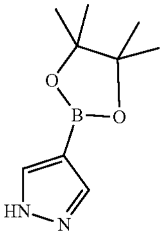

94-3A

SEM—Cl, $K_2CO_3$

NMP, RT, 16 h

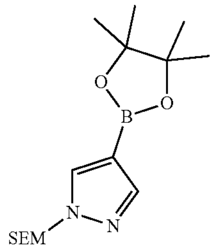

94-3B

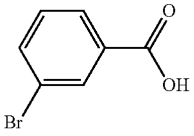

94-3C $Pd(dppf)Cl_2$, $K_3PO_4$, dioxane

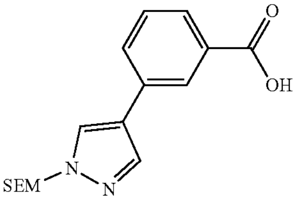

94-3D

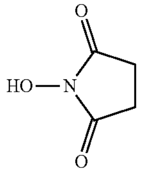

94-3E

DCC, THF, 0° C.-RT, 16h

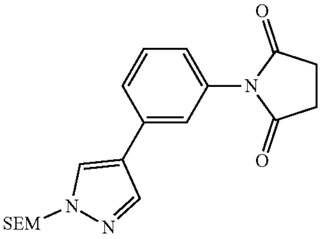

94-3

Preparation of 4-(4,4,5,5-tetramethyl-1,3,2-dioxaborolan-2-yl)-1-((2-(trimethylsilyl)ethoxy)methyl)-1H-pyrazole (94-3B). To a solution of 4-(4,4,5,5-tetramethyl-1,3,2-dioxaborolan-2-yl)-1H-pyrazole (94-3A, 4.5 g, 23.2 mmol, 1.0 eq) in NMP (50 mL) was added $K_2CO_3$ (6.403 g, 46.4 mmol, 2 eq), SEM-Cl (4.061 g, 24.36 mmol, 1.05 eq). The reaction mixture was stirred at room temperature under $N_2$ for 16 h. The resulting mixture was dilute and filtered, and then the filtrate was diluted with EA. The resulting solution was washed with sat. $NaHCO_3$ (3×100 mL), $H_2O$(4×100 mL), brine(1×100 mL), dried over $Na_2SO_4$, filtered,concentrated to give 94-3B (3.66 g, 49% yield) as a yellow oil.

Preparation of 3-(1-((2-(trimethylsilyl)ethoxy)methyl)-1H-pyrazol-4-yl)benzoic acid (94-3D). To a solution of 4-(4,4,5,5-tetramethyl-1,3,2-dioxaborolan-2-yl)-1-((2-(trimethylsilyl)ethoxy)methyl)-1H-pyrazole (94-3B, 3.66 g, 11.3 mmol, 1.0 eq), 3-bromobenzoic acid (94-3C, 2.272 g, 11.3 mmol, 1.0 eq), $Pd(dppf)Cl_2$ (826 mg, 1.13 mmol, 0.1 eq) and $K_3PO_4$ (4.791 g, 22.6 mmol, 2.0 eq) in 1,4-dioxane/$H_2O$ (60 mL/10 mL) was stirred at 90° C. for 3 hours under $N_2$. Concentrated and purified by silica gel column (PE/DCM/EA=1/1/2) to give 94-3D (1 g, 28% yield) as yellow solid. LC/MS: LC/MS (ESI) m/z: 319.1 $(M+H)^+$.

Preparation of 2,5-dioxopyrrolidin-1-yl 3-(1-((2-(trimethylsilyl)ethoxy)methyl)-1H-pyrazol-4-yl)benzoate (94-3). To a solution of 3-(1-((2-(trimethylsilyl)ethoxy)methyl)-1H-pyrazol-4-yl)benzoic acid (94-3D, 200 mg, 0.63 mmol, 1.0 eq) and 1-hydroxypyrrolidine-2,5-dione (94-3E, 73 mg, 0.63 mmol, 1.0 eq) in THF(3 mL) was stirred at 0° C. for 15 min, and then added a solution of DCC(132 mg, 0.64 mmol, 1.01 eq) in THF(2 mL). After addition, the mixture was stirred at room temperature for 16 h. The mixture was filtered, filtrate was purified by column on silica gel with PE;EA=2:1 to give 94-3 (150 mg, 57% yield) as yellow solid. LC/MS: LC/MS (ESI) m/z: 416.1 $(M+H)^+$.

Preparation of (Z)-2-bromo-N'-hydroxybenzimidamide (94-2). To a solution of 2-bromobenzonitrile (94-1, 500 mg, 2.31 mmol, 1.0 eq) in EtOH (5 mL) was added $NH_2OH$ (50%) (229 mg, 3.47 mmol, 1.5 eq), DIEA (478 mg, 3.70 mmol, 1.6 eq). The reaction mixture was stirred at 95° C. for 16 h. The resulting mixture was concentrated and diluted with water. And then the mixture was extracted with DCM (20 mL×3). The organic phase was dried over anhydrous sodium sulfate, filtered and evaporated. The residue was purified by column on silica-gel with PE:EA=5:1 to give 94-2(500 mg, 87% yield) as a white solid. LC/MS (ESI) m/z: 217.0$(M+H)^+$.

Preparation of (Z)-2-bromo-N'-((3-(1-((2-(trimethylsilyl)ethoxy)methyl)-1H-pyrazol-4-yl)benzoyl)oxy)benzimidamide (94-4). To a solution of (Z)-2-bromo-N'-hydroxybenzimidamide (94-2, 63 mg, 0.29 mmol, 1.0 eq) in DCM (2 mL) was added 2,5-dioxopyrrolidin-1-yl 3-(1-((2-(trimethylsilyl)ethoxy)methyl)-1H-pyrazol-4-yl)benzoate (120 mg, 0.29 mmol, 1.0 eq) at room temperature and the reaction mixture was stirred at room temperature for 16 h. The resulting mixture was concentrated and purified by silica gel column chromatography, eluted with PE/EA=2:1 to afford 94-4 (100 mg, 67% yield) as a yellow solid. LC/MS (ESI) m/z: 517.0$(M+H)^+$.

Preparation of 3-(2-bromophenyl)-5-(3-(1-((2-(trimethylsilyl)ethoxy)methyl)-1H-pyrazol-4-yl)phenyl)-1,2,4-oxadiazole (94-5). To a solution of (Z)-2-bromo-N'-((3-(1-((2-(trimethylsilyl)ethoxy)methyl)-1H-pyrazol-4-yl)benzoyl)oxy)benzimidamide (94-4, 100 mg, 0.19 mmol, 1.0 eq) in THF (2 mL) was added TBAF (0.32 mL). The reaction was stirred for 16 h at room temperature. The resulting solution was washed with Sat. $NH_4Cl$ solution. The organic layer was dried, concentrated and purified by column on silica gel, eluted with PE/EA=3:1 to afford 94-5 (80 mg, 85% yield) as a colorless oil. LC/MS (ESI) m/z: 499.1$(M+H)^+$.

Preparation of methyl 2-(5-(3-(1H-pyrazol-4-yl)phenyl)-1,2,4-oxadiazol-3-yl)benzoate (94-6). To a solution of 3-(2-bromophenyl)-5-(3-(1-((2-(trimethylsilyl)ethoxy)methyl)-1H-pyrazol-4-yl)phenyl)-1,2,4-oxadiazole (94-5, 90 mg, 0.18 mmol, 1.0 eq) in MeOH (5 mL) was added TEA (55 mg, 0.54 mmol, 3 eq) and $Pd(dppf)Cl_2$ (8 mg, 0.011 mmol, 0.06 eq) at room temperature. The reaction mixture was stirred at 70° C. under CO for 16 h. The material of compound 4 didn't consumed completed, and it was recycled until it was consumed completely. The mixture was purified by TLC with PE/EA=4:1 to afford 94-6 (75 mg 88% yield) of as a white solid. LC/MS (ESI) m/z: 477.1$(M+H)^+$.

Preparation of methyl 2-(1-(3-(1H-pyrazol-4-yl)phenyl)-1H-1,2,3-triazol-4-yl)-4-chlorobenzoate (94-7). To a solution of methyl 2-(5-(3-(1-((2-(trimethylsilyl)ethoxy) methyl)-1H-pyrazol-4-yl)phenyl)-1,2,4-oxadiazol-3-yl) benzoate (94-6, 75 mg, 0.16 mmol, 1.0 eq) in TFA/DCM(0.5 mL/1.5 mL) was stirred for 3 h at room temperature. The reaction mixture was concentrated and acidified with Sat.$K_2CO_3$ solution to pH=9. And then it was extracted with EA. The organic phase was dried over anhydrous sodium sulfate, filtered and evaporated to give 94-7 (50 mg, 90% yield) as white solid. LC/MS (ESI) m/z:347.1$(M+H)^+$.

Preparation of 2-[5-[3-(1H-pyrazol-4-yl)phenyl]-1,2,4-oxadiazol-3-yl]benzoic acid (Example 94). To a solution of methyl 2-(5-(3-(1H-pyrazol-4-yl)phenyl)-1,2,4-oxadiazol-3-yl)benzoate (94-7, 50 mg, 0.11 mmol, 1.0 eq) in THF/MeOH/water (1.5 mL/1.5 mL/1.5 mL) was added NaOH (13 mg, 0.33 mmol, 3.0 eq). The mixture was stirred for 16 h at room temperature. The solvent was evaporated. The residue was dissolved in DMF and purified by prep-HPLC (0.1% TFA) to give Example 94 (17 mg, 47% yield). LC/MS (ESI) m/z: 333.00 $(M+H)^+$. $^1H$ NMR (400 MHz, DMSO-$d_6$) δ 8.34 (s, 1H), 8.25 (s, 2H), 7.97 (t, J=7.0 Hz, 2H), 7.94-7.89 (m, 1H), 7.80 (d, J=6.2 Hz, 1H), 7.76-7.72 (m, 2H), 7.64 (t, J=7.7 Hz, 1H).

Synthesis of [4-ethynyl-2-[[3-(1-tetrahydropyran-4-ylpyrazol-3-yl)benzoyl]amino]benzoyl]oxysodium (Example 192)

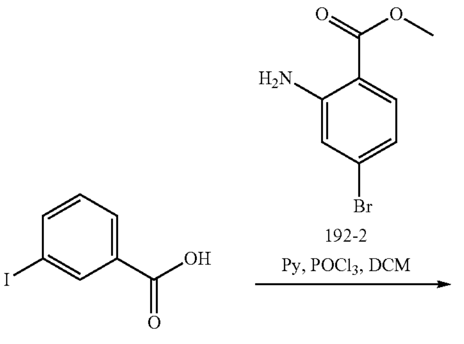

192-2

192-1

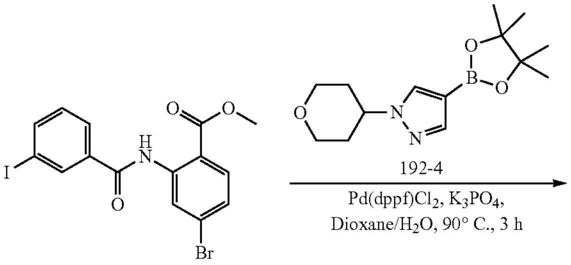

192-4

192-3

-continued

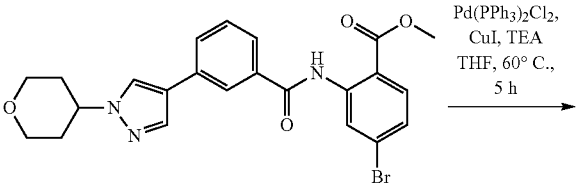

192-5

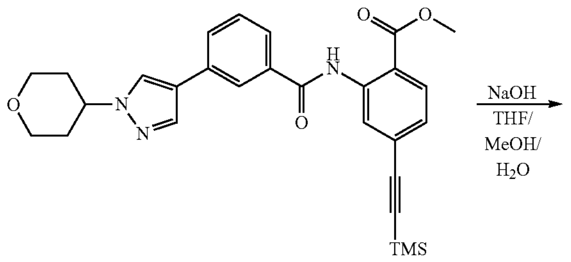

192-6

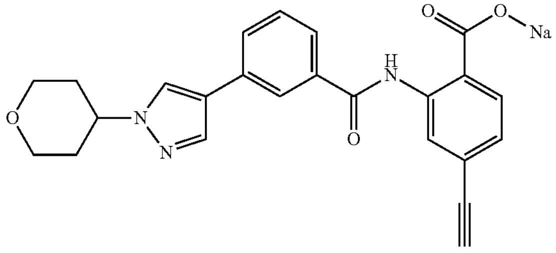

Example 192

Preparation of methyl 4-bromo-2-(3-iodobenzamido)benzoate (192-3). To a solution of 3-iodobenzoic acid (192-1, 3 g, 12.1 mmol, 1.0 eq) in DCM (50 mL) was added methyl 2-amino-4-bromobenzoate (192-2, 2.9 g, 12.7 mmol, 1.05 eq) and Py (5.8 mL, 72.9 mmol, 6.0 eq) at 0° C. under $N_2$. The mixture was stirred at 0° C. for 30 min was added $POCl_3$(3.7 mL, 24.3 mmol, 2.0 eq), then 25° C. for 3 h. The mixture was extracted with DCM, dried over $Na_2SO_4$, concentrated. The crude product was triturated in EA and filtered to give methyl 4-bromo-2-(3-iodobenzamido)benzoate (192-3, 2.1 g, 38%). LC/MS [M+H]:459.9

Preparation of methyl 4-bromo-2-(3-(1-(tetrahydro-2H-pyran-4-yl)-1H-pyrazol-4-yl)benzamido)benzoate (192-5). To a solution of methyl 4-bromo-2-(3-iodobenzamido)benzoate (192-3, 500 mg, 1.1 mmol, 1.0 eq) in dioxane (10 mL) and $H_2O$ (2 mL) at 25° C. were added 1-(tetrahydro-2H-pyran-4-yl)-4-(4,4,5,5-tetramethyl-1,3,2-dioxaborolan-2-yl)-1H-pyrazole (192-4, 364 mg, 1.3 mmol, 1.2 eq), $K_3PO_4$ (462 mg, 2.2 mmol, 2.0 eq) and $Pd(dppf)Cl_2$ (89 mg, 0.1 mmol, 0.1 eq) at 90° C. The mixture was stirred at 90° C. for 3 h under $N_2$. The mixture was extracted with DCM, dried over $Na_2SO_4$, concentrated. The crude product was purified by silica gel chromatography (PE:EA=1:1) to give methyl 4-bromo-2-(3-(1-(tetrahydro-2H-pyran-4-yl)-1H-pyrazol-4-yl)benzamido)benzoate (192-5, 304 mg, 57%)LC/MS [M+H]:484.0

Preparation of methyl 2-(3-(1-(tetrahydro-2H-pyran-4-yl)-1H-pyrazol-4-yl)benzamido)-4-((trimethylsilyl)ethynyl) benzoate (192-6). To a solution of methyl 4-bromo-2-(3-(1-(tetrahydro-2H-pyran-4-yl)-1H-pyrazol-4-yl)benzamido) benzoate (192-5, 240 mg, 0.5 mmol, 1.0 eq) in THF (5 mL) was added CuI (10 mg, 0.05 mmol, 0.1 eq), $Pd(pph_3)_2Cl_2$ (35 mg, 0.05 mmol, 0.1 eq), TEA (300 mg, 3.0 mmol, 6.0 eq) and ethynyltrimethylsilane (54 mg, 0.6 mmol, 1.1 eq) at 60°

C. The mixture was stirred at 60° C. for 18 h under $N_2$. The mixture was extracted with DCM, dried over $Na_2SO_4$, concentrated. The crude product was purified by silica gel chromatography (PE:EA=1:1) to give methyl 4-chloro-2-(3-(1-(prop-2-yn-1-yl)-1H-pyrazol-4-yl)benzamido)benzoate. (192-6, 449 mg, 179%)LC/MS [M+H]:502.2

Preparation of [4-ethynyl-2-[[3-(1-tetrahydropyran-4-ylpyrazol-3-yl)benzoyl]amino]benzoyl]oxysodium (Example 192). To a solution of methyl 2-(3-(1-(tetrahydro-2H-pyran-4-yl)-1H-pyrazol-4-yl)benzamido)-4-((trimethylsilyl)ethynyl)benzoate (192-6, 535 mg,1.07 mmol, 1.0 eq) and NaOH (170 mg, 4.27 mmol, 4.0 eq) in THF (3 mL), MeOH (3 mL) and $H_2O$ (3 mL) at 25° C. The mixture was stirred at 25° C. for 3 h. The crude product was purified by silica Prep-HPLC to give sodium 4-ethynyl-2-(3-(1-(tetrahydro-2H-pyran-4-yl)-1H-pyrazol-4-yl)benzamido)benzoate (Example 192, 112.75 mg, 25%). LC/MS [M−Na+H]:416.0. $^1H$ NMR (400 MHz, DMSO-$d_6$) δ 8.78 (d, J=1.6 Hz, 1H), 8.32 (s, 1H), 8.22 (s, 1H), 8.04-7.94 (m, 2H), 7.82 (dd, J=13.8, 7.8 Hz, 2H), 7.52 (t, J=7.6 Hz, 1H), 7.10 (d, J=7.8 Hz, 1H), 4.52-4.40 (m, 1H), 4.22 (s, 1H), 3.98 (d, J=11.4 Hz, 2H), 3.48 (td, J=11.4, 3.2 Hz, 2H), 3.32 (s, 15H), 2.50 (dd, J=12.0, 10.4 Hz, 60H), 2.18-1.92 (m, 4H), −0.00 (s, 1H).

Synthesis of [4-chloro-2-[[3-ethynyl-5-(1-tetrahydropyran-4-ylpyrazol-4-yl)benzoyl]amino]benzoyl]oxysodium (Example 193)

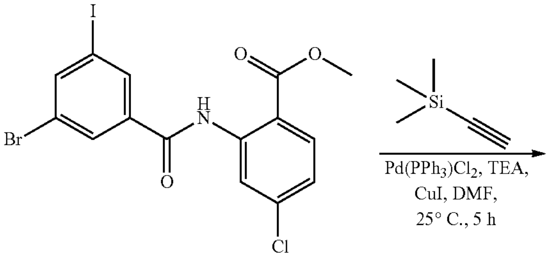

193-1

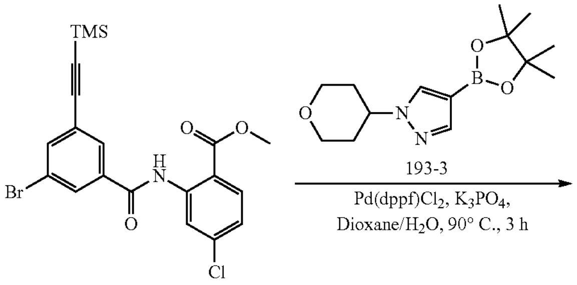

193-2

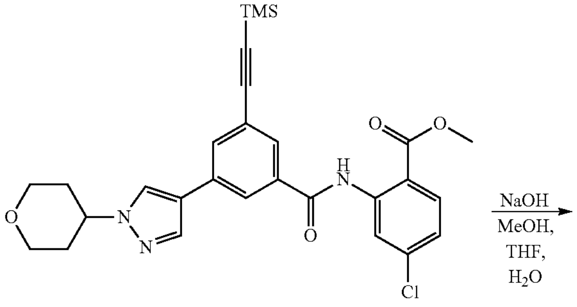

193-4

-continued

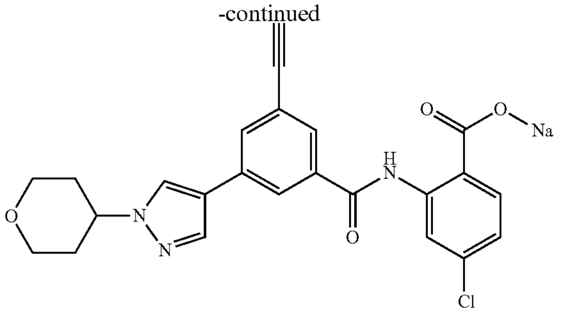

Example 193

Preparation of methyl 2-(3-bromo-5-((trimethylsilyl)ethynyl)benzamido)-4-chlorobenzoate (193-2). To a solution of methyl 2-(3-bromo-5-iodobenzamido)-4-chlorobenzoate (193-1, 500 mg, 1.71 mmol, 1.0 eq) in TEA (10 mL) was added CuI(32.5 mg, 0.17 mmol, 0.1 eq), $Pd(pph_3)_2Cl_2$ (119.3 mg, 0.17 mmol, 0.1 eq) and ethynyltrimethylsilane (184.6 mg, 1.88 mmol, 1.1 eq) at 25° C. The mixture was stirred at 25° C. for 18 h under $N_2$. The mixture was extracted with DCM, dried over $Na_2SO_4$, concentrated. The crude product was purified by silica gel chromatography (PE:EA=10:1) to give methyl 2-(3-bromo-5-((trimethylsilyl)ethynyl)benzamido)-4-chlorobenzoate. (193-2, 397 mg, 50.1%)LC/MS [M+H]:464.0

Preparation of methyl 4-chloro-2-(3-(1-(tetrahydro-2H-pyran-4-yl)-1H-pyrazol-4-yl)-5-((trimethylsilyl)ethynyl)benzamido)benzoate (193-4). To a solution of methyl 2-(3-bromo-5-((trimethylsilyl)ethynyl)benzamido)-4-chlorobenzoate (193-2, 200 mg, 0.43 mmol, 1.0 eq) in dioxane(10 mL)and $H_2O$(2 mL) at 25° C. were added 1-(tetrahydro-2H-pyran-4-yl)-4-(4,4,5,5-tetramethyl-1,3,2-dioxaborolan-2-yl)-1H-pyrazole (193-3, 144 mg, 0.52 mmol, 1.2 eq), $K_3PO_4$ (182 mg, 0.86 mmol, 2.0 eq) and $Pd(dppf)Cl_2$ (28 mg, 0.04 mmol, 0.1 eq) at 90° C. The mixture was stirred at 90° C. for 3 h under $N_2$. The mixture was extracted with DCM, dried over $Na_2SO_4$, concentrated. The crude product was purified by silica gel chromatography (PE:EA=1:1) to give methyl 4-chloro-2-(3-(1-(tetrahydro-2H-pyran-4-yl)-1H-pyrazol-4-yl)-5-((trimethylsilyl)ethynyl)benzamido)benzoate (193-4, 97 mg, 42.2%)LC/MS [M+H]:536.0

Preparation of [4-chloro-2-[[3-ethynyl-5-(1-tetrahydropyran-4-ylpyrazol-4-yl)benzoyl]amino]benzoyl]oxysodium (Example 193). To a solution of methyl 4-chloro-2-(3-(1-(tetrahydro-2H-pyran-4-yl)-1H-pyrazol-4-yl)-5-((trimethylsilyl)ethynyl)benzamido)benzoate (193-4, 97 mg, 0.18 mmol, 1.0 eq) and NaOH (29 mg, 0.72 mmol, 4.0 eq) in MeOH (1 mL), THF (1 mL) and $H_2O$ (1 mL) at 25° C. The mixture was stirred at 25° C. for 5 h. The crude product was purified by Prep-HPLC to give sodium 4-chloro-2-(3-ethynyl-5-(1-(tetrahydro-2H-pyran-4-yl)-1H-pyrazol-4-yl)benzamido)benzoate (Example 193, 74.7 mg, 92.4%)LC/MS [M−Na+H]:450.0. $^1H$ NMR (400 MHz, DMSO-$d_6$) δ 8.28 (s, 1H), 8.14 (s, 1H), 7.88 (s, 2H), 7.58 (s, 1H), 7.30 (s, 1H), 7.02 (d, J=8.0 Hz, 1H), 6.54 (dd, J=8.0, 2.2 Hz, 1H), 4.44-4.36 (m, 1H), 3.96 (d, J=11.4 Hz, 2H), 3.48 (td, J=11.6, 3.4 Hz, 2H), 2.00 (dd, J=9.8, 4.2 Hz, 4H).

Synthesis of [6-[[3-ethynyl-5-(1-tetrahydropyran-4-ylpyrazol-4-yl)benzoyl]amino]-2,3-dihydro-1,4-benzodioxine-7-carbonyl]oxysodium (Example 194)

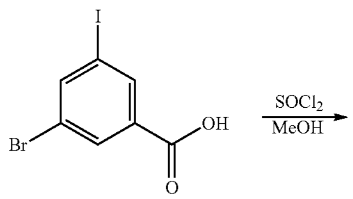

194-1

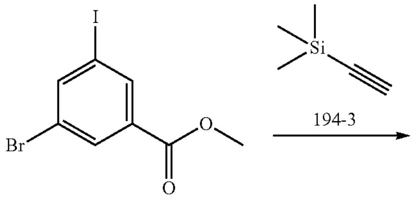

194-2

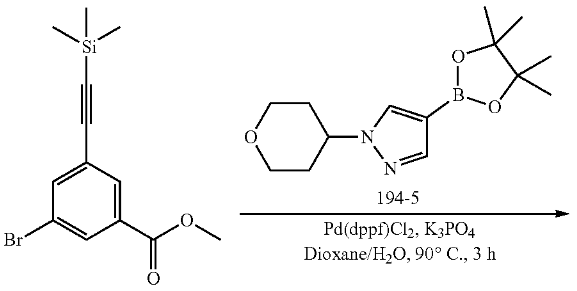

194-4

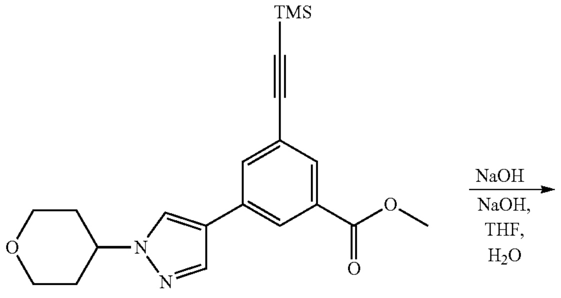

194-6

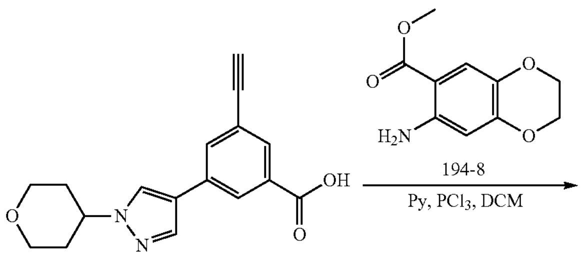

194-7

-continued

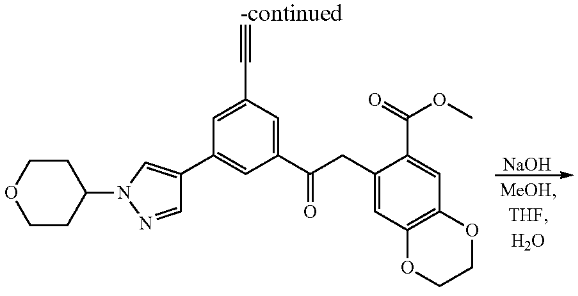

194-9

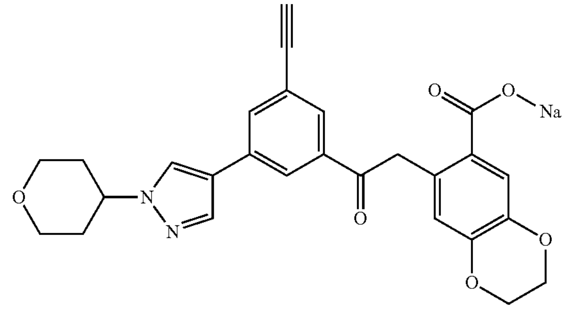

Example 194

Preparation of methyl 3-bromo-5-iodobenzoate (194-2). To a solution of 194-1(5 g,15.3 mmol,1 eq) in MeOH (50 ml) was added $SOCl_2$ (2.2 g,18.4 mmol,1.2 eq) at 0° C. The mixture was stirred at 60° C. for 12 h. The mixture was extracted with EA(100 ml×3),washed with $NaHCO_3$,dried over $Na_2SO_4$,concentrated to afford 2 g white solid (194-2). LC/MS [M−H]: 339.2

Preparation of methyl 3-bromo-5-((trimethylsilyl)ethynyl)benzoate (194-4). A mixture of 194-2, (2 g,5.8 mmol,1 eq), 194-3 (0.9 g,8.8 mmol,1.5 eq), CuI(0.1 g,0.6 mmol,0.1 eq) and $Pd(pph_3)Cl_2$(800 mg) in Et3N/DMF(10 ml/10 ml) was stirred at 25° C. for 5 h under $Ar_2$. The mixture was extracted with EA (20 ml×3),washed with $H_2O$,purified by silica gel chromatography. The mixture was monitored by TLC and (194-4, 2.5 g) was obtained as yellow oil.

Preparation of methyl 3-(1-(tetrahydro-2H-pyran-4-yl)-H-pyrazol-4-yl)-5-((trimethylsilyl)ethynyl)benzoate (194-6). The mixture of 194-4 (2.5 g,8 mmol,1 eq), 194-5 (2.5 g,8.8 mmol,1.1 eq), $K_3PO_4$(5 g,24 mmol,3 eq) and pd(dppf) $Cl_2$(250 mg) in Dioxane/$H_2O$(45 ml/5 ml) was stirred at 90° C. for 4 h under Ar. The mixture was extracted with EA (60 ml×3), purified by silica gel chromatography to afford 2.7 g of 194-6, as a yellow oil. LC/MS [M+H]:383.1

Preparation of 3-ethynyl-5-(1-(tetrahydro-2H-pyran-4-yl)-1H-pyrazol-4-yl)benzoic acid (compound 194-7). The compound 194-6 (2.7 g,7 mmol,1 eq) was added in THF/MeOH/$H_2O$(14 ml/14 ml/14 ml), then NaOH (845 mg,21 mmol,3 eq) was added at 0° C. The reaction mixture was stirred at 25° C. for 12 h. The mixture was acidified with HCl(1M)to pH=3, extracted with EA (50 ml×5), concentrated to afford, 194-7, 1.8 g as a yellow solid. LC/MS [M+H]:297.0

Preparation of methyl 7-(3-ethynyl-5-(1-(tetrahydro-2H-pyran-4-yl)-1H-pyrazol-4-yl)benzamido)-2,3-dihydrobenzo[b][1,4]dioxine-6-carboxylate (194-9). The mixture of 194-7 (500 mg,1.7 mmol,1 eq), 194-8 (388 mg,0.8 mmol,1.1 eq), $POCl_3$(517 mg,3.4 mmol,2 eq) and Py(801 mg,10.2 mmol,6 eq) in DCM(10 ml) was stirred at 25° C. for 2 h. The mixture was extracted with DCM (10 ml×3), purified by silica gel chromatography to afford 300 mg of 194-9 as a yellow solid. LC/MS [M+H]:488.1

Preparation of [6-[[3-ethynyl-5-(1-tetrahydropyran-4-ylpyrazol-4-yl)benzoyl]amino]-2,3-dihydro-1,4-benzodioxine-7-carbonyl]oxysodium (Example 194). The mixture of 194-9 (250 mg,0.5 mmol,1 eq) and NaOH (63.5 mg,1.5 mmol,3 eq) in MeOH/THF/$H_2O$(2.5 mL/2.5 mL/2.5 mL) was stirred at 25° C. for 2 h. The mixture was purified by Prep-HPLC to afford 58 mg of Example 194 as a white solid. LC/MS [M+H]:474.1. $^1$H NMR (400 MHz, DMSO-$d_6$) δ=8.48 (s, 1H), 8.24 (s, 1H), 8.16 (s, 1H), 8.04 (s, 1H), 7.97 (s, 1H), 7.78 (s, 1H), 7.50 (s, 1H), 4.42 (dd, J=10.2, 5.5, 1H), 4.35 (s, 3H), 4.28 (s, 2H), 3.98 (d, J=11.2, 2H), 3.49 (d, J=2.4, 2H), 2.02 (s, 4H).

Synthesis of [4-chloro-2-[[3-(1-prop-2-ynylpyrazol-4-yl)benzoyl]amino]benzoyl]oxysodium (Example 195)

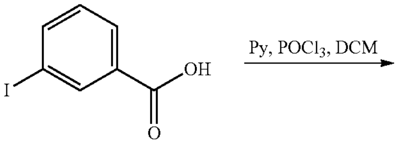

195-1

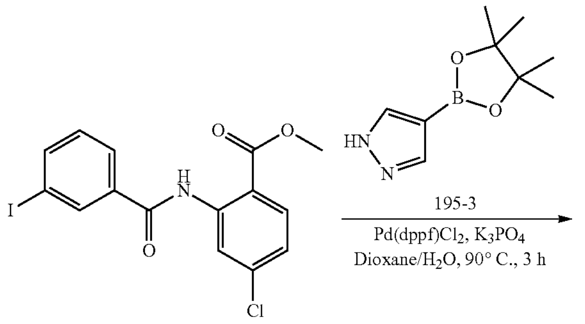

195-2

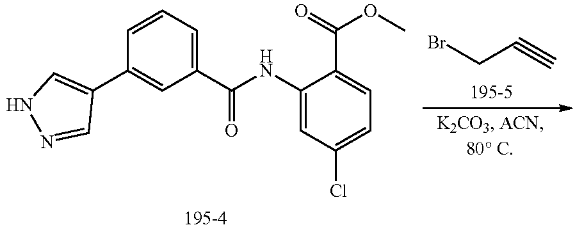

195-4

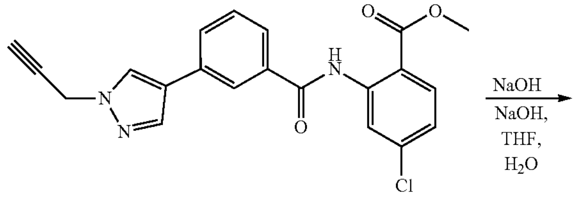

195-6

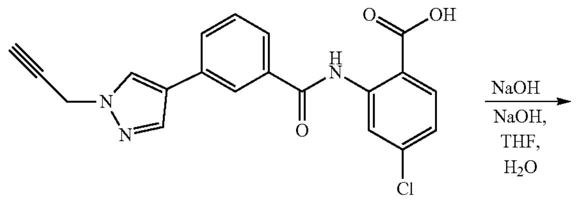

195-6

-continued

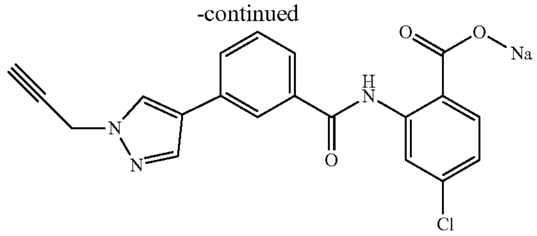

Example 195-Na slat

Preparation of methyl 4-chloro-2-(3-iodobenzamido)benzoate (195-2). To a solution of 3-iodobenzoic acid (195-1, 2 g, 8.1 mmol, 1.0 eq) in DCM (50 mL) was added methyl 2-amino-4-chlorobenzoate (1.6 g, 8.5 mmol, 1.05 eq) and Py (3.9 mL, 48.6 mmol, 6.0 eq) at 0° C. under $N_2$.The mixture was stirred at 0° C. for 30 min was added $POCl_3$(1.5 mL, 16.2 mmol, 2.0 eq), then 25° C. for 3 h. The mixture was extracted with DCM, dried over $Na_2SO_4$, concentrated. The crude product was triturated in EA and filtered to give methyl 4-chloro-2-(3-iodobenzamido)benzoate (195-2, 1.9 g, 56.5%). LC/MS [M−H]:413.9

Preparation of methyl 2-(3-(H-pyrazol-4-yl)benzamido)-4-chlorobenzoate (195-4). To a solution of methyl 4-chloro-2-(3-iodobenzamido)benzoate (195-2, 500 mg, 1.2 mmol, 1.0 eq) in dioxane (10 mL) and $H_2O$ (2 mL) at 25° C. were added 4-(4,4,5,5-tetramethyl-1,3,2-dioxaborolan-2-yl)-1H-pyrazole (195-3, 280 mg, 1.4 mmol, 1.2 eq), $K_3PO_4$ (509 mg, 2.4 mmol, 2.0 eq) and $Pd(dppf)Cl_2$ (97 mg, 0.12 mmol, 0.1 eq) at 90° C. The mixture was stirred at 90° C. for 3 h under $N_2$. The mixture was extracted with DCM, dried over $Na_2SO_4$, concentrated. The crude product was purified by silica gel chromatography (PE:EA=1:1) to give methyl 2-(3-(1H-pyrazol-4-yl)benzamido)-4-chlorobenzoate (195-4, 260 mg, 61.0%)LC/MS [M+H]:356.0

Preparation of methyl 4-chloro-2-(3-(1-(prop-2-yn-1-yl)-1H-pyrazol-4-yl)benzamido)benzoate (195-6). To a solution of methyl 2-(3-(1H-pyrazol-4-yl)benzamido)-4-chlorobenzoate (195-4, 260 mg, 0.73 mmol, 1.0 eq) in ACN (5 mL) was added $K_2CO_3$ (201 mg, 1.46 mmol, 2.0 eq) and 3-bromoprop-1-yne (195-5, 130 mg, 1.09 mmol, 1.5 eq) at 80° C. The mixture was stirred at 80° C. for 18 h under $N_2$. The mixture was extracted with DCM, dried over $Na_2SO_4$, concentrated. The crude product was purified by silica gel chromatography (PE:EA=1:1) to give methyl 4-chloro-2-(3-(1-(prop-2-yn-1-yl)-1H-pyrazol-4-yl)benzamido)benzoate (195-6, 80 mg, 27.9%)LC/MS [M+H]:394.0

Preparation of 7-(3-(1-(prop-2-yn-1-yl)-1H-pyrazol-4-yl)benzamido)-2,3-dihydrobenzo[b][1,4]dioxine-6-carboxylic acid (Example 195). To a solution of methyl 4-chloro-2-(3-(1-(prop-2-yn-1-yl)-1H-pyrazol-4-yl)benzamido)benzoate (195-6, 80 mg, 0.20 mmol, 1.0 eq) and NaOH (33 mg, 0.8 mmol, 4.0 eq) in THF (1 mL), MeOH (1 mL) and $H_2O$ (1 mL) at 25° C. The mixture was stirred at 25° C. for 3 h. The mixture was acidified with HCl (1M) to $p^H$=3, filtered. The crude product was purified by silica Prep-HPLC to give 4-chloro-2-(3-(1-(prop-2-yn-1-yl)-1H-pyrazol-4-yl)benzamido)benzoic acid (Example 195, 18 mg, 23.7%)LC/MS [M+H]:380.0

Preparation of [4-chloro-2-[[3-(1-prop-2-ynylpyrazol-4-yl)benzoyl]amino]benzoyl]oxysodium (Example 195-Na salt). To a solution of 4-chloro-2-(3-(1-(prop-2-yn-1-yl)-1H-pyrazol-4-yl)benzamido)benzoic acid (195, 18 mg, 0.04 mmol, 1.0 eq) and NaOH (1.6 mg, 0.04 mmol, 1.0 eq) in MeOH (1 mL) and $H_2O$ (1 mL) at 25° C. The mixture was stirred at 25° C. for 5 h to give sodium 4-chloro-2-(3-(1-

(prop-2-yn-1-yl)-1H-pyrazol-4-yl)benzamido)benzoate (Example 195-sodium salt 15.75 mg, 98.1%)LC/MS [M-Na+H]:380.0. $^1$H NMR (400 MHz, DMSO-$d_6$) δ 8.76 (d, J=2.2 Hz, 1H), 8.30 (s, 1H), 8.22 (s, 1H), 8.06-7.96 (m, 2H), 7.84 (dd, J=19.4, 7.8 Hz, 2H), 7.54 (t, J=7.8 Hz, 1H), 7.02 (dd, J=8.2, 2.2 Hz, 1H), 5.10 (d, J=2.6 Hz, 2H), 3.54 (t, J=2.4 Hz, 1H).

Synthesis of [6-[[3-(1-prop-2-ynylpyrazol-4-yl)benzoyl]amino]-2,3-dihydro-1,4-benzodioxine-7-carbonyl]oxysodium (Example 196)

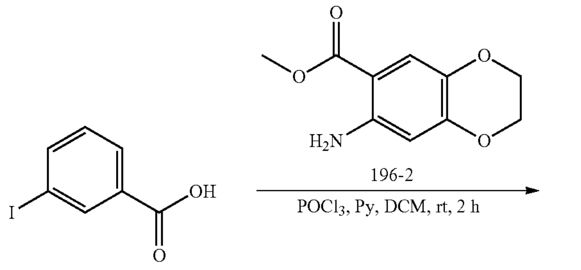

196-1

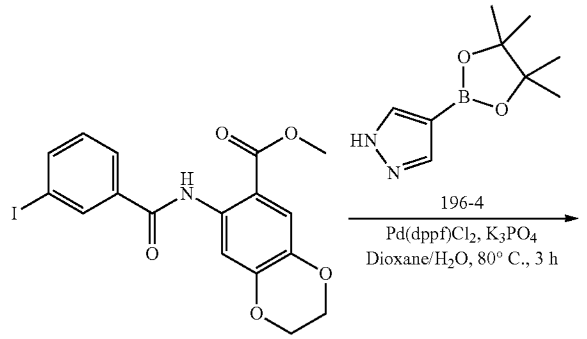

196-3

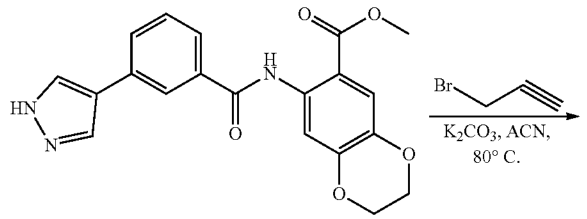

196-5

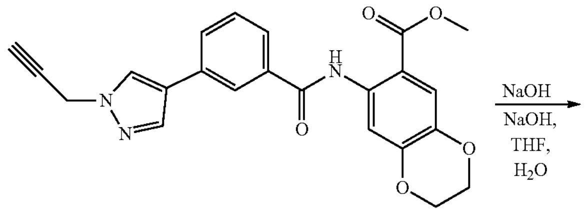

195-6

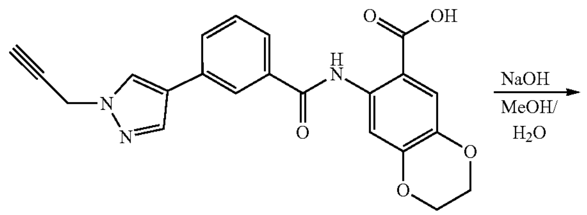

Example 196

-continued

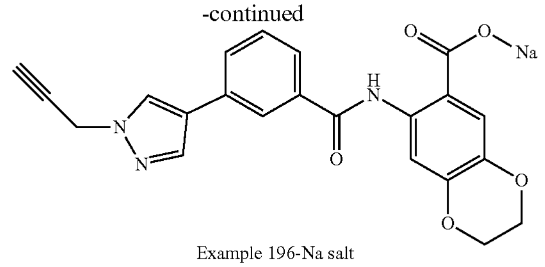

Example 196-Na salt

Preparation of methyl 7-(3-iodobenzamido)-2,3-dihydrobenzo[b][1,4]dioxine-6-carboxylate (196-3). To a solution of 3-iodobenzoic acid (196-1, 2 g, 8.06 mmol, 1.0 eq) in DCM (50 mL) was added methyl 7-amino-2,3-dihydrobenzo[b][1,4]dioxine-6-carboxylate (196-2, 1.8 g, 8.47 mmol, 1.05 eq) and Py (3.9 mL, 48.36 mmol, 6.0 eq) at 0° C. under $N_2$.The mixture was stirred at 0° C. for 30 min was added $POCl_3$(1.5 mL, 16.12 mmol, 2.0 eq), then 25° C. for 3 h. The mixture was extracted with DCM, dried over $Na_2SO_4$, concentrated. The crude product was triturated in EA and filtered to give methyl 7-(3-iodobenzamido)-2,3-dihydrobenzo[b][1,4]dioxine-6-carboxylate (196-3, 2.12 g, 59.9%). LC/MS [M−H]:438.0

Preparation of methyl 7-(3-(1H-pyrazol-4-yl)benzamido)-2,3-dihydrobenzo[b][1,4]dioxine-6-carboxylate (196-5). To a solution of methyl 7-(3-iodobenzamido)-2,3-dihydrobenzo[b][1,4]dioxine-6-carboxylate (196-3, 1.2 g, 2.73 mmol, 1.0 eq) in dioxane(30 mL)and $H_2O$(6 mL) at 25° C. were added 4-(4,4,5,5-tetramethyl-1,3,2-dioxaborolan-2-yl)-1H-pyrazole (196-4, 636 mg, 3.28 mmol, 1.2 eq), $K_3PO_4$ (1.2 g, 5.46 mmol, 2.0 eq) and Pd(dppf)$Cl_2$ (221 mg, 0.27 mmol, 0.1 eq) at 80° C. The mixture was stirred at 80° C. for 3 h under $N_2$. The mixture was extracted with DCM, dried over $Na_2SO_4$, concentrated. The crude product was purified by silica gel chromatography (PE:EA=1:1) to give methyl 7-(3-(1H-pyrazol-4-yl)benzamido)-2,3-dihydrobenzo[b][1,4]dioxine-6-carboxylate (196-5, 438 mg, 42.3%)LC/MS [M+H]:380.0

Preparation of methyl 7-(3-(1-(prop-2-yn-1-yl)-1H-pyrazol-4-yl)benzamido)-2,3-dihydrobenzo[b][1,4]dioxine-6-carboxylate (196-6). To a solution of methyl 7-(3-(1H-pyrazol-4-yl)benzamido)-2,3-dihydrobenzo[b][1,4]dioxine-6-carboxylate (196-5, 150 mg, 0.40 mmol, 1.0 eq) in ACN (10 mL) was added $K_2CO_3$ (110 mg, 0.80 mmol, 2.0 eq) and 3-bromoprop-1-yne (71 mg, 0.59 mmol, 1.5 eq) at 80° C. The mixture was stirred at 80° C. for 18 h under $N_2$. The mixture was extracted with DCM, dried over $Na_2SO_4$, concentrated. The crude product was purified by silica gel chromatography (PE:EA=1:2) to give methyl 7-(3-(1-(prop-2-yn-1-yl)-1H-pyrazol-4-yl)benzamido)-2,3-dihydrobenzo[b][1,4]dioxine-6-carboxylate. (196-6, 113 mg, 67.7%)LC/MS [M+H]:418.0

Preparation of 7-(3-(1-(prop-2-yn-1-yl)-1H-pyrazol-4-yl)benzamido)-2,3-dihydrobenzo[b][1,4]dioxine-6-carboxylic acid (Example 196). To a solution of methyl 7-(3-(1-(prop-2-yn-1-yl)-1H-pyrazol-4-yl)benzamido)-2,3-dihydrobenzo[b][1,4]dioxine-6-carboxylate (196-6, 113 mg, 0.26 mmol, 1.0 eq) and NaOH (42 mg, 1.06 mmol, 4.0 eq) in THF (1 mL), MeOH (1 mL) and $H_2O$ (1 mL) at 25° C. The mixture was stirred at 25° C. for 3 h. The mixture was acidified with HCl (1M) to pH=3, filtered to give 7-(3-(1-(prop-2-yn-1-yl)-1H-pyrazol-4-yl)benzamido)-2,3-dihydrobenzo[b][1,4]dioxine-6-carboxylic acid (Example 196, 59 mg, 56.3%)LC/MS [M+H]:404.0

Preparation of [6-[[3-(1-prop-2-ynylpyrazol-4-yl)benzoyl]amino]-2,3-dihydro-1,4-benzodioxine-7-carbonyl]oxysodium (Example 196-sodium salt). To a solution of 7-(3-(1-(prop-2-yn-1-yl)-1H-pyrazol-4-yl)benzamido)-2,3-dihydrobenzo[b][1,4]dioxine-6-carboxylic acid (196, 59 g, 0.14 mmol, 1.0 eq) and NaOH (5.8 mg, 0.14 mmol, 1.0 eq) in MeOH (1 mL) and $H_2O$ (1 mL) at 25° C. The mixture was stirred at 25° C. for 5 h to give sodium 7-(3-(1-(prop-2-yn-1-yl)-1H-pyrazol-4-yl)benzamido)-2,3-dihydrobenzo[b][1,4]dioxine-6-carboxylate (196-sodium salt, 11.3 mg, 19%) LC/MS [M−Na+H]:404.0. $^1H$ NMR (400 MHz, DMSO-$d_6$) δ 8.38 (s, 1H), 8.24 (s, 1H), 8.18 (s, 1H), 8.16 (s, 1H), 7.86-7.82 (m, 2H), 7.58-7.52 (m, 3H), 5.78 (d, J=6.4 Hz, 2H), 4.28 (d, J=3.4 Hz, 2H), 4.22 (d, J=5.2 Hz, 2H).

Synthesis of N-[6-methoxy-3-(1H-tetrazol-5-yl)-2-pyridyl]-3-(1H-pyrazol-4-yl)benzamide (Example 197)

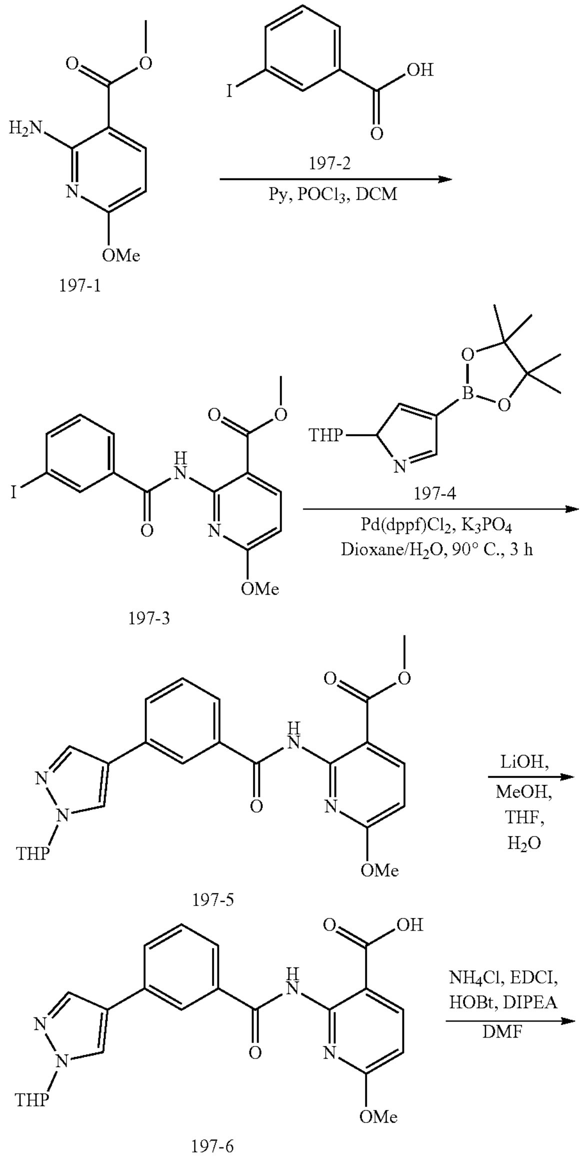

-continued

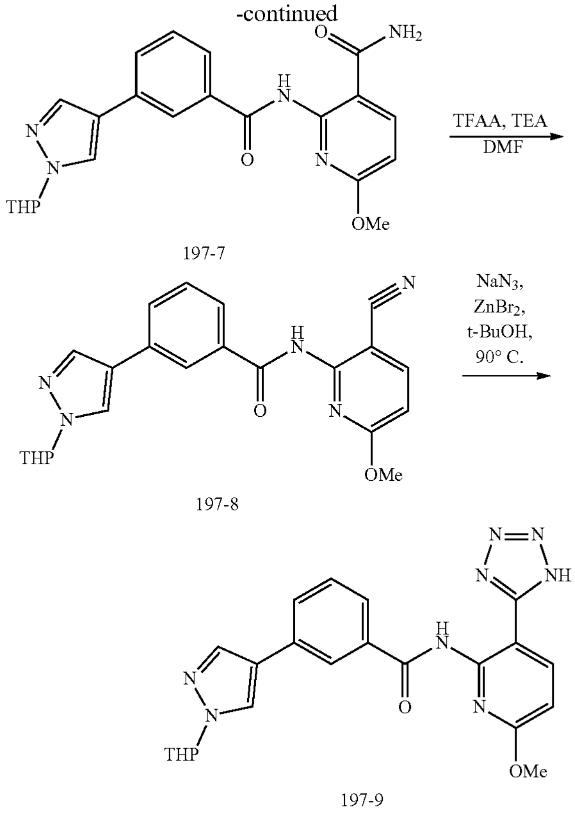

Preparation of methyl 2-(3-iodobenzamido)-6-methoxynicotinate (197-3). To a solution of methyl 2-amino-6-methoxynicotinate (197-1, 1.0 g, 5.49 mmol, 1.0 eq) in DCM (50 mL) was added 3-iodobenzoic acid (197-2, 1.4 g, 5.49 mmol, 1.0 eq) and Py (2.6 mL, 32.94 mmol, 6.0 eq) at 0° C. under $N_2$.The mixture was stirred at 0° C. for 30 min was added $POCl_3$ (1.7 mL, 10.98 mmol, 2.0 eq), then 25° C. for 18 h. The mixture was extracted with DCM, dried over $Na_2SO_4$, concentrated. The crude product was purified by silica gel chromatography (PE:EA=5:1) to give methyl 2-(3-iodobenzamido)-6-methoxynicotinate (197-3, 895 mg, 39.5%). LC/MS [M+H]:412.0

Preparation of methyl 6-methoxy-2-(3-(1-(tetrahydro-2H-pyran-2-yl)-1H-pyrazol-4-yl)benzamido)nicotinate (197-5). To a solution of compound 197-3 (700 mg, 1.71 mmol, 1.0 eq) in dioxane (10 mL) and $H_2O$ (2 mL) at 25° C. were added 1-(tetrahydro-2H-pyran-2-yl)-4-(4,4,5,5-tetramethyl-1,3,2-dioxaborolan-2-yl)-1H-pyrazole (197-4, 567 mg, 2.04 mmol, 1.2 eq), $K_3PO_4$ (720 mg, 3.40 mmol, 2.0 eq) and $Pd(dppf)Cl_2$ (62 mg, 0.09 mmol, 0.05 eq) at 90° C. The mixture was stirred at 90° C. for 3 h under $N_2$. The mixture was extracted with DCM, dried over $Na_2SO_4$, concentrated. The crude product was purified by silica gel chromatography (PE:EA=1:1) to give methyl 6-methoxy-2-(3-(1-(tetrahydro-2H-pyran-2-yl)-1H-pyrazol-4-yl)benzamido)nicotinate (197-5, 632 mg, 85.3%). LC/MS [M+H]:436.0

Preparation of 6-methoxy-2-(3-(1-(tetrahydro-2H-pyran-2-yl)-1H-pyrazol-4-yl)benzamido)nicotinic acid (197-6). To a solution of compound 197-5 (630 mg,1.45 mmol, 1.0 eq) and LiOH (139 mg, 5.78 mmol, 4.0 eq) in THF (3 mL), MeOH (3 mL) and $H_2O$ (3 mL) at 25° C. The mixture was stirred at 25° C. for 3 h. The mixture was acidified with HCl (1M) to pH=3, filtered to give 6-methoxy-2-(3-(1-(tetrahydro-2H-pyran-2-yl)-1H-pyrazol-4-yl)benzamido)nicotinic acid (197-6, 605 mg, 98.8%). LC/MS [M−H]:422.0

Preparation of 6-methoxy-2-(3-(1-(tetrahydro-2H-pyran-2-yl)-1H-pyrazol-4-yl)benzamido)nicotinamide (197-7). To a solution of compound 197-6 (550 mg, 1.30 mmol, 1.0 eq) in DMF (15 mL) was added $NH_4Cl$ (697 mg, 13.0 mmol, 10.0 eq), EDCI (300 mg, 1.56 mmol, 1.2 eq) and HOBt (210 mg, 1.56 mmol, 1.2 eq) at 0° C. under $N_2$.The mixture was stirred at 0° C. for 10 min, then 25° C. for 18 h. The mixture was extracted with DCM, dried over $Na_2SO_4$, concentrated. The crude product was triturated in EA and filtered to give 6-methoxy-2-(3-(1-(tetrahydro-2H-pyran-2-yl)-1H-pyrazol-4-yl)benzamido)nicotinamide (197-7, 204 mg, 37.3%). LC/MS [M+H]:421.0

Preparation of N-(3-cyano-6-methoxypyridin-2-yl)-3-(1-(tetrahydro-2H-pyran-2-yl)-1H-pyrazol-4-yl)benzamide (197-8). To a solution of compound 197-7 (200 mg, 0.4 mmol, 1.0 eq) in THF (5 mL) was added TEA (102 mg, 1.01 mmol, 2.5 eq) at 0° C. under $N_2$.The mixture was stirred at 0° C. for 10 min, was added TFAA (212 mg, 1.01 mmol, 2.5 eq) at 0° C., then 25° C. for 18 h. The mixture was extracted with DCM, dried over $Na_2SO_4$, concentrated. The crude product was purified by silica gel chromatography (PE: EA=1:1) to give N-(3-cyano-6-methoxypyridin-2-yl)-3-(1-(tetrahydro-2H-pyran-2-yl)-1H-pyrazol-4-yl)benzamide (197-8, 102 mg, 63.3%)LC/MS [M−H]:403.0

Preparation of N-(6-methoxy-3-(1H-tetrazol-5-yl)pyridin-2-yl)-3-(1-(tetrahydro-2H-pyran-2-yl)-1H-pyrazol-4-yl) benzamide (197-9). To a solution of compound 197-8 (100 mg, 0.25 mmol, 1.0 eq) in t-BuOH (4 mL) and $H_2O$ (2 mL) was added $ZnBr_2$ (112 mg, 0.50 mmol, 2.0 eq) and $NaN_3$ (32 mg, 0.50 mmol, 2.0 eq) at 25° C. The mixture was stirred at 90° C. for 18 h under $N_2$. The crude product was triturated in PE (10 mL) and filtered to give N-(6-methoxy-3-(1H-tetrazol-5-yl)pyridin-2-yl)-3-(1-(tetrahydro-2H-pyran-2-yl)-1H-pyrazol-4-yl)benzamide. (197-9, 78 mg, 69.9%)LC/MS [M+H]:446.0

Preparation of N-[6-methoxy-3-(1H-tetrazol-5-yl)-2-pyridyl]-3-(1H-pyrazol-4-yl)benzamide (Example 197). To a solution of compound 197-9 (78 mg, 0.17 mmol, 1.0 eq) in MeOH (5 mL) was added PPTS (22 mg, 0.26 mmol, 1.5 eq) at 70° C. The mixture was stirred at 70° C. for 18 h under $N_2$. The crude product was purified by Prep-HPLC (1% FA) to give N-(6-methoxy-3-(1H-tetrazol-5-yl)pyridin-2-yl)-3-(1H-pyrazol-4-yl)benzamide (Example 197, 4.77 mg, 7.8%) LC/MS [M+H]:362.0. $^1H$ NMR (400 MHz, DMSO-$d_6$) δ 8.46 (s, 1H), 8.33 (d, J=8.5 Hz, 1H), 7.92-7.80 (m, 2H), 7.55 (t, J=7.8 Hz, 1H), 6.75 (d, J=8.5 Hz, 1H), 3.95 (s, 3H).

Synthesis of N-[5-chloro-2-(5-oxo-4H-1,2,4-oxadiazol-3-yl)phenyl]-3-(1-tetrahydropyran-4-ylpyrazol-4-yl)benzamide (Example 198)

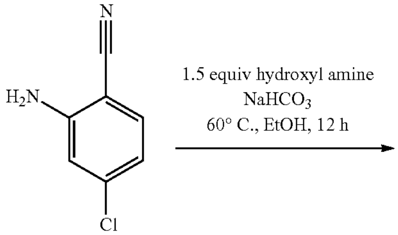

198-1

-continued

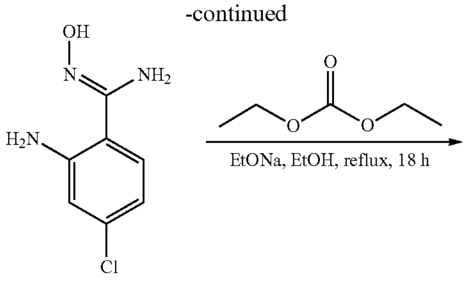

198-2

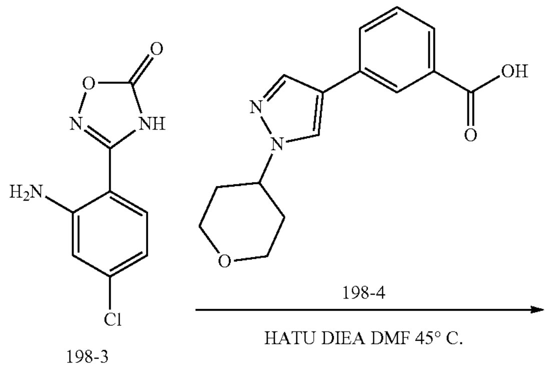

198-3

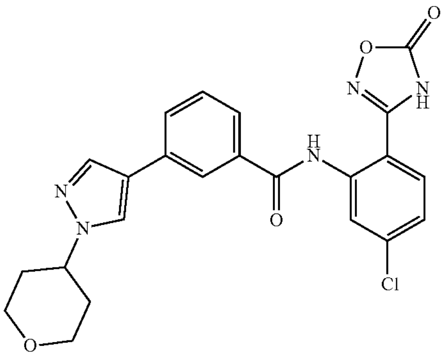

Example 198

Preparation of (Z)-2-amino-4-chloro-N'-hydroxybenzimidamide (198-2). To a solution of 2-amino-4-chlorobenzonitrile (198-1, 1.0 g, 6.57 mmol, 1.0 eq) in EtOH (30 mL) was added hydroxyl amine (2.3 g, 32.89 mmol, 5.0 eq) $NaHCO_3$ (2.76 g, 32.89 mmol, 5.0 eq). The mixture was stirred at 60° C. for 18 h under $N_2$. The mixture was concentrated. The crude product was diluted with EtOAc and filtered to give (Z)-2-amino-4-chloro-N'-hydroxybenzimidamide (198-2, 850 g, 70.8% as white solid). LC/MS [M−H]:186.1

Preparation of 3-(2-amino-4-chlorophenyl)-1,2,4-oxadiazol-5(4H)-one (compound 198-3). To a solution of (Z)-2-amino-4-chloro-N'-hydroxybenzimidamide (198-2, 650 mg, 3.15 mmol, 1.0 eq) in EtOH (30 mL) was added diethyl carbonate (1.66 g, 14.0 mmol, 4.0 eq) EtONa (447 mg, 7.02 mmol, 2.0 eq). The mixture was stirred at 90° C. for 18 h under $N_2$. The mixture was quenched with $H_2O$ and extracted with EA, dried over $Na_2SO_4$, concentrated. The crude product was triturated in DCM and filtered to give 3-(2-amino-4-chlorophenyl)-1,2,4-oxadiazol-5(4H)-one (198-3, 680 mg, 91.9% as white solid). LC/MS [M−H]: 212.0

Preparation of N-[5-chloro-2-(5-oxo-4H-1,2,4-oxadiazol-3-yl)phenyl]-3-(1-tetrahydropyran-4-ylpyrazol-4-yl)benzamide (Example 198). To a solution of 3-(1-(tetrahydro-2H- pyran-4-yl)-1H-pyrazol-4-yl)benzoic acid (130 mg, 0.46 mmol, 1.0 eq) in DMF (5 mL) was added DIAE (61 mg, 0.94 mmol, 2.0 eq) HATU (216 mg, 0.56 mmol, 1.2 eq) at 0° C. The mixture was stirred at 0° C. for 15 min. Then was added 3-(2-amino-4-chlorophenyl)-1,2,4-oxadiazol-5(4H)-one (198-3, 100 mg, 0.46 mmol, 1.0 eq). The mixture was stirred at 45° C. for 18 h under $N_2$. The mixture quenched with $H_2O$ and extracted with DCM/MeOH(10:1), dried over $Na_2SO_4$, concentrated. The crude product was purified by Prep-HPLC (0.1% FA) to give N-(5-chloro-2-(5-oxo-4,5-dihydro-1,2,4-oxadiazol-3-yl)phenyl)-3-(1-(tetrahydro-2H-pyran-4-yl)-1H-pyrazol-4-yl)benzamide (Example 198, 17.49 mg, 7.95% as white solid). LC/MS [M+H]:466.2. $^1H$ NMR (400 MHz, DMSO-$d_6$) δ 13.03 (s, 1H), 10.66 (s, 1H), 8.40 (d, J=2.0 Hz, 1H), 8.37 (s, 1H), 8.16 (s, 1H), 7.99 (s, 1H), 7.86 (d, J=7.8 Hz, 1H), 7.75 (d, J=8.6 Hz, 2H), 7.56 (t, J=7.6 Hz, 1H), 7.49 (dd, J=8.6, 2.0 Hz, 1H), 4.53-4.35 (m, 1H), 4.04-3.89 (m, 2H), 3.55-3.46 (m, 2H), 2.10-1.95 (m, 4H).

Synthesis of N-[5-chloro-2-(1H-tetrazol-5-yl)phenyl]-3-(1-tetrahydropyran-4-ylpyrazol-4-yl)benzamide (Example 199)

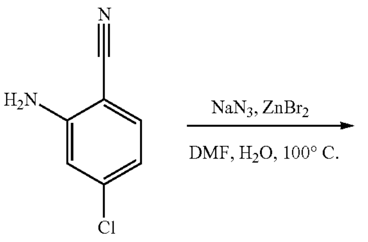

199-1

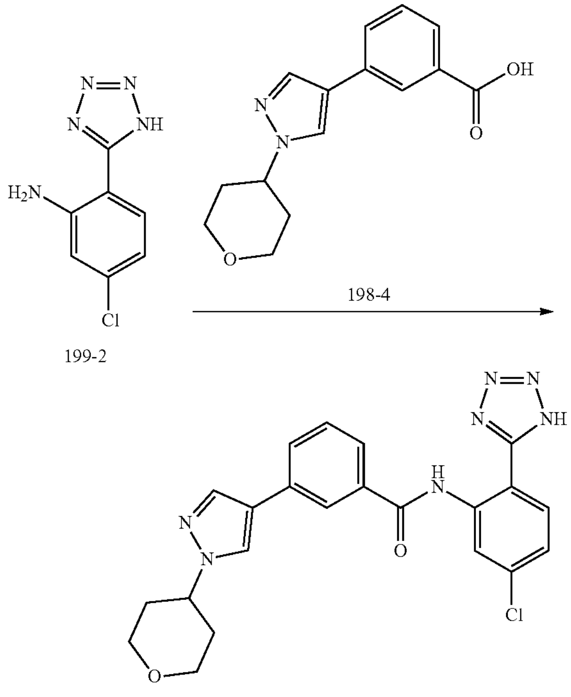

199-2

Example 199

Preparation of 5-chloro-2-(1H-tetrazol-5-yl)aniline (compound 199-2). To a solution of 2-amino-4-chlorobenzonitrile (199-1, 1.0 g, 6.58 mmol, 1.0 eq) in t-BuOH (20 mL) and $H_2O$ (10 mL) was added $ZnBr_2$ (2.2 g, 9.87 mmol, 1.5 eq) and $NaN_3$ (641 mg, 9.87 mmol, 1.5 eq) at 25° C. The mixture was stirred at 90° C. for 18 h under $N_2$. The crude product was triturated in PE (10 mL) and filtered to give 5-chloro-2-(1H-tetrazol-5-yl)aniline (199-2, 943 mg, 73.5%)LC/MS [M+H]:195.0

Preparation of N-[5-chloro-2-(1H-tetrazol-5-yl)phenyl]-3-(1-tetrahydropyran-4-ylpyrazol-4-yl)benzamide (Example 199). To a solution of 3-(1-(tetrahydro-2H-pyran-4-yl)-1H-pyrazol-4-yl)benzoic acid (198-4, 418 mg, 1.54 mmol, 1.0 eq) in DMF (10 mL) was added DIEA (0.57 mL, 3.08 mmol, 2.0 eq) and HATU (702 mg, 1.85 mmol, 1.2 eq) at 0° C. under $N_2$. The mixture was stirred at 0° C. for 30 min was added 5-chloro-2-(1H-tetrazol-5-yl)aniline (199-2, 300 mg, 1.54 mmol, 1.0 eq), then 25° C. for 18 h. The mixture was extracted with DCM, dried over $Na_2SO_4$, concentrated. The crude product was purified by Prep-HPLC to give N-(5-chloro-2-(1H-tetrazol-5-yl)phenyl)-3-(1-(tetrahydro-2H-pyran-4-yl)-1H-pyrazol-4-yl)benzamide (Example 199, 36.5 mg, 5.2%)LC/MS [M+H]:450.0. $^1H$ NMR (400 MHz, DMSO-$d_6$) δ 13.74 (s, 1H), 8.90 (d, J=2.0 Hz, 1H), 8.68 (s, 1H), 8.54 (s, 1H), 8.28 (d, J=8.4 Hz, 1H), 8.18 (s, 1H), 7.96 (d, J=7.8 Hz, 1H), 7.88 (d, J=7.8 Hz, 1H), 7.60 (t, J=7.6 Hz, 1H), 7.24 (dd, J=8.4, 2.2 Hz, 1H), 6.08 (s, 1H), 4.46 (dt, J=15.8, 5.2 Hz, 1H), 3.98 (s, 2H), 3.56-3.48 (m, 2H), 2.18-1.96 (m, 4H).

Synthesis of N-[7-(5-oxo-4H-1,2,4-oxadiazol-3-yl)-2,3-dihydro-1,4-benzodioxin-6-yl]-3-(1-tetrahydropyran-4-ylpyrazol-4-yl)benzamide (Example 200)

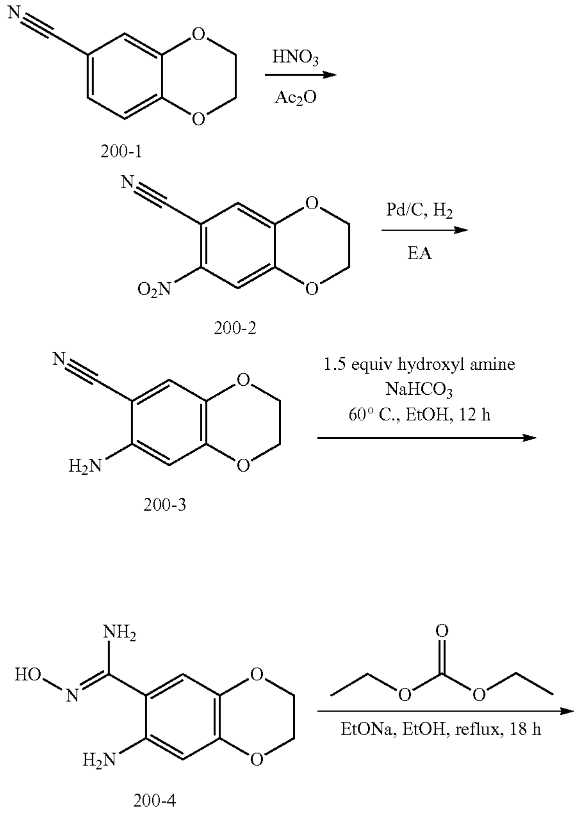

-continued

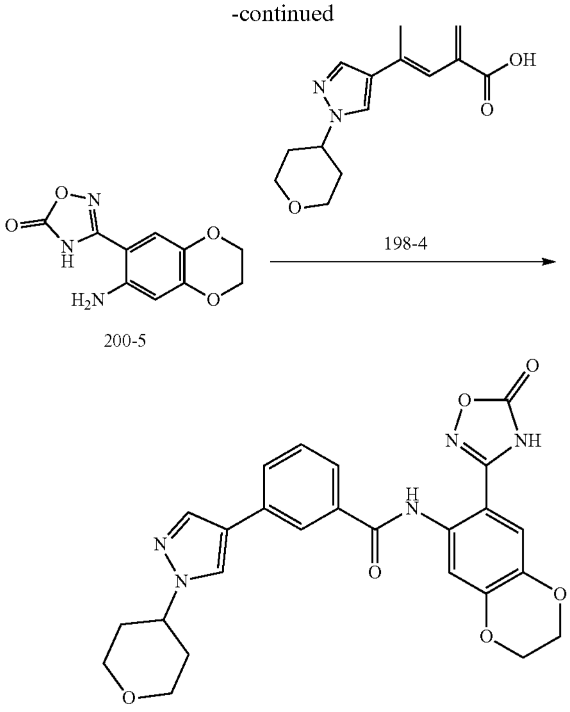

200-5

Example 200

Preparation of 7-nitro-2,3-dihydrobenzo[b][1,4]dioxine-6-carbonitrile (200-2). To a solution of 2,3-dihydrobenzo[b][1,4]dioxine-6-carbonitrile (200-1, 4.5 g, 27.95 mmol, 1.0 eq) in $AC_2O$ (45 mL) being cooled 0° C. was added $HNO_3$ (4.5 mL). The mixture was stirred at Rt for 18 h under $N_2$. The mixture was poured into $NaHCO_3$ solution, extracted with EA, and dried over $Na_2SO_4$. The crude product was purified by silica gel column eluting with 0-10% EA in PE to give 7-nitro-2,3-dihydrobenzo[b][1,4]dioxine-6-carbonitrile (200-2, 2.4 g, 11.65 mmol, 41.7%) as a white solid. LC/MS [M+H]:207.0

Preparation of 7-amino-2,3-dihydrobenzo[b][1,4]dioxine-6-carbonitrile (200-3). To a solution of 7-nitro-2,3-dihydrobenzo[b][1,4]dioxine-6-carbonitrile (200-2, 2.4 g, 11.65 mmol, 1.0 eq) in EA (30 mL) was added Pd/C (0.32 g). The mixture was stirred at Rt for 18 h under $H_2$. The mixture was filtered and concentrated. The crude product was purified by silica gel column eluting with 0-20% EA in PE to give 7-amino-2,3-dihydrobenzo[b][1,4]dioxine-6-carbonitrile (200-3, 1.3 g, 7.39 mmol, 63.4%). LC/MS [M+H]:177.1

Preparation of (Z)-7-amino-N'-hydroxy-2,3-dihydrobenzo[b][1,4]dioxine-6-carboximidamide (200-4). To a solution of 7-amino-2,3-dihydrobenzo[b][1,4]dioxine-6-carbonitrile (200-3, 1.3 g, 7.39 mmol, 1.0 eq) in EtOH (12 mL) was added hydroxyl amine (1.2 g, 17.04 mmol, 3.0 eq) and $NaHCO_3$ (1.432 g, 17.04 mmol, 3.0 eq). The mixture was stirred at 70° C. for 12 h under $N_2$. Once LC/MS showed no starting material left, the mixture was concentrated and dissolved in DCM, then filtered. The organic was concentrated to afford (Z)-7-amino-N'-hydroxy-2,3-dihydrobenzo[b][1,4]dioxine-6-carboximidamide (200-4, 1.06 g, 5.08 mmol, 68.7%). LC/MS [M+H]:210.1

Preparation of 3-(7-amino-2,3-dihydrobenzo[b][1,4]dioxin-6-yl)-1,2,4-oxadiazol-5(4H)-one (200-5). To a solution of (Z)-7-amino-N'-hydroxy-2,3-dihydrobenzo[b][1,4]dioxine-6-carboximidamide (200-4, 1.06 g, 5.08 mmol, 1.0 eq) in EtOH (20 mL) was added EtONa (0.691 g, 10.16 mmol, 2.0 eq) and diethyl carbonate (3.6 g, 30.48 mmol, 6.0 eq). The mixture was stirred at 90° C. for 18 h under $N_2$. The mixture was poured into saturated salt water, extracted with EA. The water phase was extracted with THF. The organic was concentrated to afford 3-(7-amino-2,3-dihydrobenzo[b][1,4]dioxin-6-yl)-1,2,4-oxadiazol-5(4H)-one (200-5, 680 mg, 2.9 mmol, 57.1%)LC/MS [M+H]:236.0

Preparation of N-[7-(5-oxo-4H-1,2,4-oxadiazol-3-yl)-2,3-dihydro-1,4-benzodioxin-6-yl]-3-(1-tetrahydropyran-4-ylpyrazol-4-yl)benzamide (Example 200). To a solution of 3-(7-amino-2,3-dihydrobenzo[b][1,4]dioxin-6-yl)-1,2,4-oxadiazol-5(4H)-one (200-5, 150 mg, 0.638 mmol, 1 eq) in DMF (3 mL) was added 3-(1-(tetrahydro-2H-pyran-4-yl)-1H-pyrazol-4-yl)benzoic acid (198-4, 173.36 mg, 0.638 mmol, 1 eq), HTTU (300.24 mg, 0.766 mmol, 1.2 eq), and DIEA (165.04 mg, 1.276 mmol, 2 eq). The mixture was stirred at 50° C. for 18 h. The crude product was purified by Prep-HPLC to give N-(7-(5-oxo-4,5-dihydro-1,2,4-oxadiazol-3-yl)-2,3-dihydrobenzo[b][1,4]dioxin-6-yl)-3-(1-(tetrahydro-2H-pyran-4-yl)-1H-pyrazol-4-yl)benzamide (Example 200, 71.36 mg, 0.163 mmol, 25.5%)LC/MS [M+H]: 490.2. $^1$H NMR (400 MHz, DMSO-$d_6$) δ 12.822 (s, 1H), 10.300 (s, 1H), 8.350 (s, 1H), 8.146 (s, 1H), 7.978 (s, 1H), 7.836-7.809 (t, J=8 Hz, 2H), 7.738-7.717 (d, J=8.4 Hz, 1H), 7.556-7.518 (t, J=8.4 Hz, 1H), 7.276 (s, 1H), 4.63-4.608 (m, 1H), 4.373-4.360 (t, J=3.6 Hz, 2H), 4.327-4.314 (t, J=1.6 Hz, 2H), 3.999-3.964 (m, 2H), 3.526-3.398 (m, 2H), 2.074-1.968 (m, 4H).

Synthesis of 3-(1-tetrahydropyran-4-ylpyrazol-4-yl)-N-[7-(1H-tetrazol-5-yl)-2,3-dihydro-1,4-benzodioxin-6-yl]benzamide (Example 201)

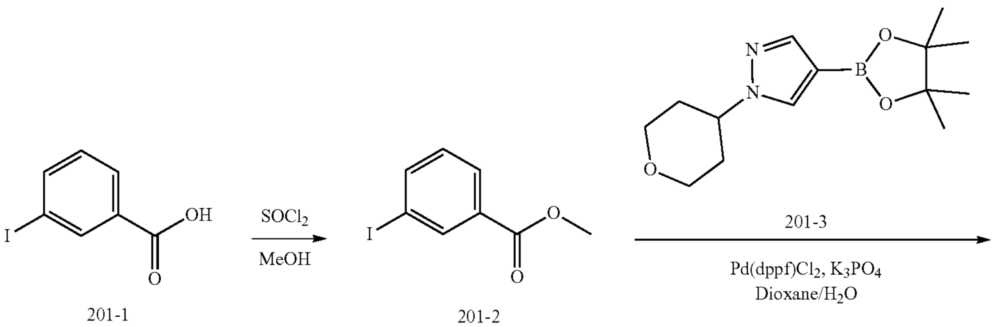

201-1

201-2

-continued

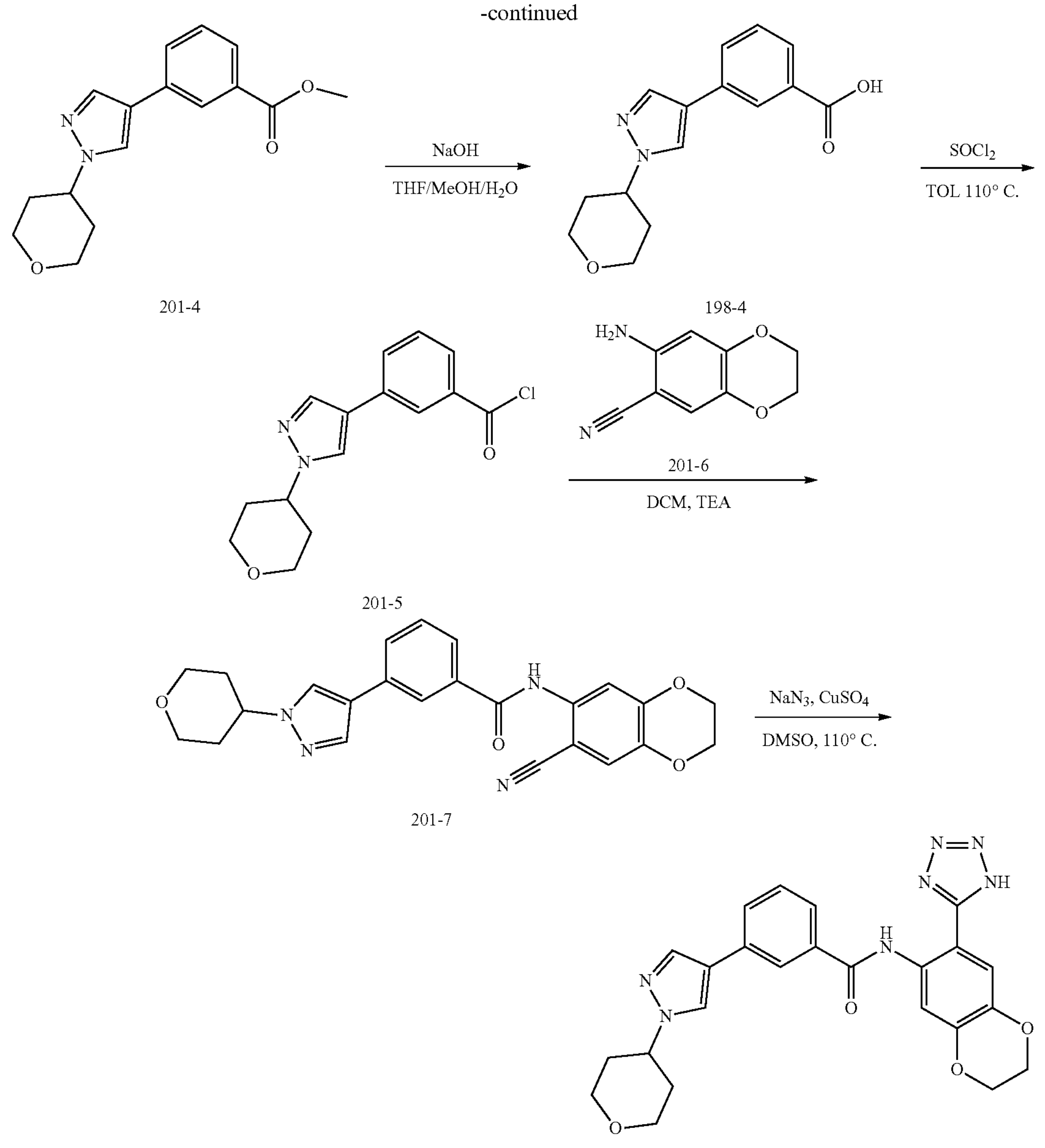

201-4

198-4

201-6

201-5

201-7

Example 201

Preparation of methyl 3-iodobenzoate (201-2). To a solution of 3-iodobenzoic acid (201-1, 1.0 g, 4.03 mmol, 1.0 eq) in MeOH (12 mL) being cooled 0° C. was added $SOCl_2$ (0.6 mL, 8.06 mmol, 2.0 eq). The mixture was stirred at Rt for 18 h under $N_2$. The mixture was concentrated to give crude 3-iodobenzoate (201-2, 2.5 g). LC/MS [M+H]:263.0

Preparation of methyl 3-(1-(tetrahydro-2H-pyran-4-yl)-1H-pyrazol-4-yl)benzoate (201-4). To a solution of crude 3-iodobenzoate (201-2, 2.5 g) in Dioxane/$H_2O$ (40/8 mL) was added 1-(tetrahydro-2H-pyran-4-yl)-4-(4,4,5,5-tetramethyl-1,3,2-dioxaborolan-2-yl)-1H-pyrazole (201-3, 2.7 g, 9.7 mmol, 1.2 eq), $K_3PO_4$ (3.4 g, 12.9 mmol, 2.0 eq) and Pd(dppf)$Cl_2$ (656.0 mg, 0.81 mmol, 0.10 eq) at 90° C. for 18 h under $N_2$. The mixture was poured into water, extracted with EA, and dried over $Na_2SO_4$. The crude product was purified by silica gel column eluting with 0-50% EA in PE to give methyl 3-(1-(tetrahydro-2H-pyran-4-yl)-1H-pyrazol-4-yl)benzoate (201-4, 1.1 g, 3.8 mmol, 48.1%).

Preparation of 3-(1-(tetrahydro-2H-pyran-4-yl)-1H-pyrazol-4-yl)benzoic acid (198-4). To a solution of methyl 3-(1-(tetrahydro-2H-pyran-4-yl)-1H-pyrazol-4-yl)benzoate (201-4, 1.1 g, 3.8 mmol, 1.0 eq) in MeOH/THF/$H_2O$ (4.0/4.0/2.0 mL) was added NaOH (800.0 mg, 20.0 mmol, 5.2 eq). The mixture was stirred at Rt for 2 h. The mixture was filtered to give 3-(1-(tetrahydro-2H-pyran-4-yl)-1H-pyrazol-4-yl)benzoic acid (198-4, 800.0 mg, 2.9 mmol, 76.4%). $^1$H NMR (400 MHz, DMSO-$d_6$) δ 12.96 (s, 1H), 8.38 (s, 1H), 8.12 (s, 1H), 7.95 (s, 1H), 7.84-7.82 (d, J=8 Hz, 1H), 7.77-7.75 (d, J=8 Hz, 1H), 7.50-7.46 (t, J=8 Hz, 1H), 4.42-4.39 (m, 1H), 3.98-3.95 (m, 2H), 3.51-3.45 (m, 2H), 2.02-1.93 (m, 2H).

Preparation of 3-(1-(tetrahydro-2H-pyran-4-yl)-1H-pyrazol-4-yl)benzoyl chloride (201-5). To a solution of 3-(1-(tetrahydro-2H-pyran-4-yl)-1H-pyrazol-4-yl)benzoic acid (198-4, 500.0 mg, 1.84 mmol, 1.0 eq) in TOI (7 mL) was added $SOCl_2$ (437.8 mg, 3.68 mmol, 2.0 eq). The mixture was stirred at 110° C. for 18 h under $N_2$. The mixture was concentrated to give crude 3-(1-(tetrahydro-2H-pyran-4-yl)-1H-pyrazol-4-yl)benzoyl chloride (201-5, 720 mg). LC/MS [M+H]:291.1

Preparation of N-(7-cyano-2,3-dihydrobenzo[b][1,4]dioxin-6-yl)-3-(1-(tetrahydro-2H-pyran-4-yl)-1H-pyrazol-4-yl)benzamide (201-7). To a solution of 3-(1-(tetrahydro-2H-pyran-4-yl)-1H-pyrazol-4-yl)benzoyl chloride (201-5, 720 mg) in DCM (10 mL) being cooled to 0° C. was added 7-amino-2,3-dihydrobenzo[b][1,4]dioxine-6-carbonitrile (201-6, 439.0 mg, 2.48 mmol, 1.0 eq) and TEA (752.9 mg, 7.44 mmol, 3.0 eq) at Rt for 18 h under $N_2$. The mixture was concentrated to give crude compound 8. The crude product was purified by silica gel column eluting with 0-20% EA in PE to give N-(7-cyano-2,3-dihydrobenzo[b][1,4]dioxin-6-yl)-3-(1-(tetrahydro-2H-pyran-4-yl)-1H-pyrazol-4-yl)benzamide (201-7, 158 mg, 0.367 mmol, 14.8%). LC/MS [M−H]: 429.0

Preparation of 3-(1-tetrahydropyran-4-ylpyrazol-4-yl)-N-[7-(1H-tetrazol-5-yl)-2,3-dihydro-1,4-benzodioxin-6-yl] benzamide (Example 201). To a solution of N-(7-cyano-2,3-dihydrobenzo[b][1,4]dioxin-6-yl)-3-(1-(tetrahydro-2H-pyran-4-yl)-1H-pyrazol-4-yl)benzamide (201-7, 148 mg, 0.344 mmol, 1.0 eq) in DMSO (3 mL) was added $NaN_3$ (67.1 mg, 1.032 mmol, 3 eq) and $CuSO_4$ (11.0 mg, 0.0688 mmol, 0.3 eq). The mixture was stirred at 110° C. for 18 h under $N_2$. The mixture product was purified by Prep-HPLC to give N-(7-(1H-tetrazol-5-yl)-2,3-dihydrobenzo[b][1,4]dioxin-6-yl)-3-(1-(tetrahydro-2H-pyran-4-yl)-1H-pyrazol-4-yl)benzamide (Example 201, 42.7 mg, 0.09 mmol, 26.2%) LC/MS [M+H]:474.2. $^1$H NMR (400 MHz, DMSO-$d_6$) δ 11.63 (s, 1H), 8.41 (s, 1H), 8.33 (s, 1H), 8.23 (s, 1H), 8.06 (s, 1H), 7.87-7.83 (t, J=8.0 Hz, 2H), 7.60-7.56 (t, J=8.0 Hz, 2H), 4.47-4.42 (m, 1H), 4.38-4.33 (m, 4H), 4.00-3.97 (m, 2H), 3.54-3.47 (m, 2H), 2.07-1.99 (m, 4H).

Synthesis of 5-[2-[4-[3-(1H-pyrazol-4-yl)phenyl] triazol-1-yl]phenyl]-1H-tetrazole (Example 202)

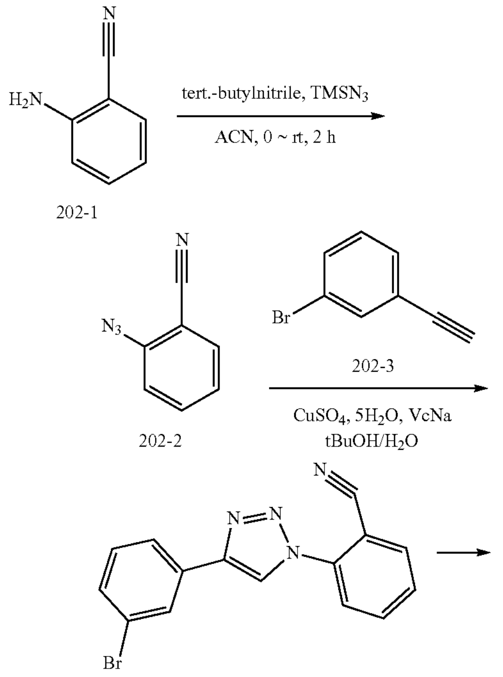

202-1

202-2

202-3

202-4

-continued

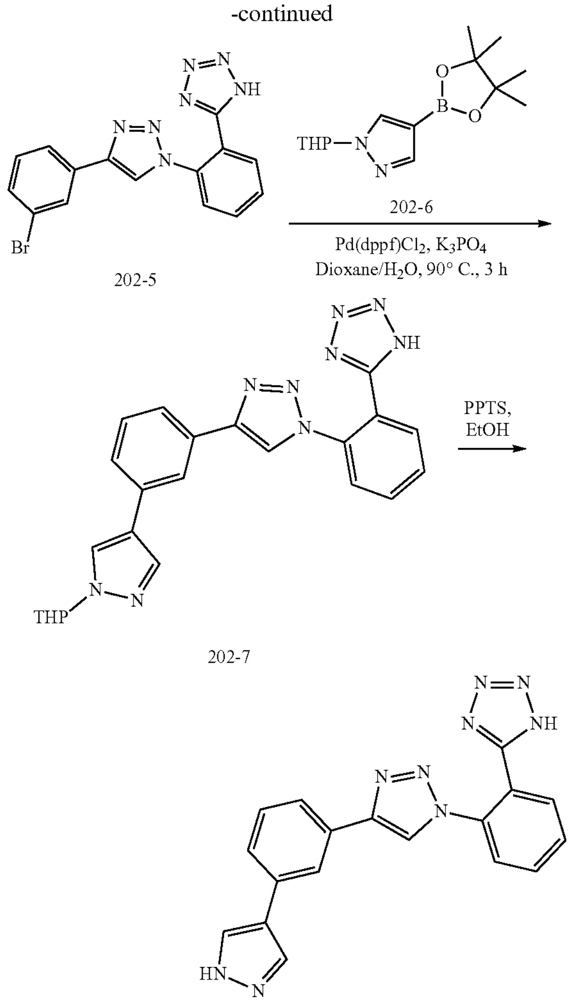

202-5

202-6

202-7

Example 202

Preparation of 2-azidobenzonitrile (202-2). To a solution of compound 202-1 (1.0 g, 8.5 mmol, 1.0 eq) in ACN (30 mL) was added tert-butylnitrite (1.3 g, 12.7 mmol, 1.5 eq) and $TMSN_3$ (1.5 g, 12.7 mmol, 1.5 eq) at 0° C. under $N_2$. The mixture was stirred at 0° C. for 30 min, then, r.t for 2 h. The mixture was extracted with EA, dried over $Na_2SO_4$, concentrated to give 2-azidobenzonitrile (202-2, 980 mg, 80.0%)LC/MS [M+H]:144.0

Preparation of 2-(4-(3-bromophenyl)-1H-1,2,3-triazol-1-yl)benzonitrile (202-4). To a solution of compound 202-2 (980 mg, 6.94 mmol, 1.0 eq) in t-BuOH/$H_2O$ (10:5 mL) was added $CuSO_4 \cdot 5H_2O$ (521 mg, 2.08 mmol, 0.3 eq), VcNa (825 mg, 4.16 mmol, 0.6 eq) at 25° C. under $N_2$, then, compound 202-3 was added at 25° C. for 18 h under $N_2$. The crude product was triturated in PE and filtered to give 2-(4-(3-bromophenyl)-1H-1,2,3-triazol-1-yl)benzonitrile. (202-4, 1.32 g, 58.7%)LC/MS [M+H]:324.0

Preparation of 5-(2-(4-(3-bromophenyl)-1H-1,2,3-triazol-1-yl)phenyl)-1H-tetrazole (202-5). To a solution of compound 202-4 (300 mg, 0.93 mmol, 1.0 eq) in t-BuOH (10 mL) and $H_2O$ (5 mL) was added $ZnBr_2$ (416 mg, 1.85 mmol, 2.0 eq) and $NaN_3$ (120 mg, 1.85 mmol, 2.0 eq) at 25° C. The mixture was stirred at 90° C. for 18 h under $N_2$. The crude product was triturated in PE (10 mL) and filtered to give 5-(2-(4-(3-bromophenyl)-1H-1,2,3-triazol-1-yl)phenyl)-1H-tetrazole (202-5, 305 mg, 89.4%)LC/MS [M−H]:367.0

Preparation of 5-(2-(4-(3-(1-(tetrahydro-2H-pyran-2-yl)-1H-pyrazol-4-yl)phenyl)-1H-1,2,3-triazol-1-yl)phenyl)-1H-tetrazole (202-7). To a solution of compound 202-5 (240 mg, 0.65 mmol, 1.0 eq) in dioxane/$H_2O$ (5:1 mL) was added compound 202-6 (218 mg, 0.78 mmol, 1.2 eq), $K_3PO_4$ (276 mg, 1.3 mmol, 2.0 eq) and Pd(dppf)$Cl_2$ (53 mg, 0.07 mmol, 0.1 eq) at 90° C. for 18 h under $N_2$. The crude product was purified by gel chromatography (PE:EA=1:1) to give 5-(2-(4-(3-(1-(tetrahydro-2H-pyran-2-yl)-1H-pyrazol-4-yl)phenyl)-1H-1,2,3-triazol-1-yl)phenyl)-1H-tetrazole. (202-7, 130 mg, 45.6%)LC/MS [M−H]:439.0

Preparation of 5-[2-[4-[3-(1H-pyrazol-4-yl)phenyl]triazol-1-yl]phenyl]-1H-tetrazole (Example 202). To a solution of compound 202-7 (130 mg, 0.3 mmol, 1.0 eq) in MeOH (5 mL) was added PPTS (30 mg, 0.12 mmol, 0.4 eq) at 70° C. under $N_2$. The mixture was stirred at 70° C. for 18 h. The mixture was extracted with DCM, dried over $Na_2SO_4$, concentrated. The crude product was purified by Prep-HPLC to give 5-(2-(4-(3-(1H-pyrazol-4-yl)phenyl)-1H-1,2,3-triazol-1-yl)phenyl)-1H-tetrazole (Example 202, 19.14 mg, 18.1%)LC/MS [M+H]:355.0. $^1H$ NMR (400 MHz, DMSO-$d_6$) δ 9.01 (s, 1H), 8.13 (d, J=1.7 Hz, 3H), 8.03 (s, 1H), 7.90-7.81 (m, 3H), 7.72 (d, J=7.6 Hz, 1H), 7.61 (d, J=7.9 Hz, 1H), 7.46 (t, J=7.8 Hz, 1H).

Synthesis of 3-[6-[4-[3-(1H-pyrazol-4-yl)phenyl]triazol-1-yl]-2,3-dihydro-1,4-benzodioxin-7-yl]-4H-1,2,4-oxadiazol-5-one (Example 203)

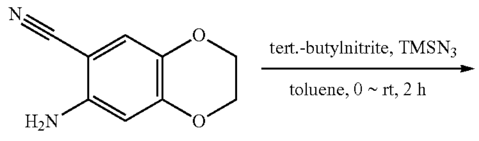

203-1

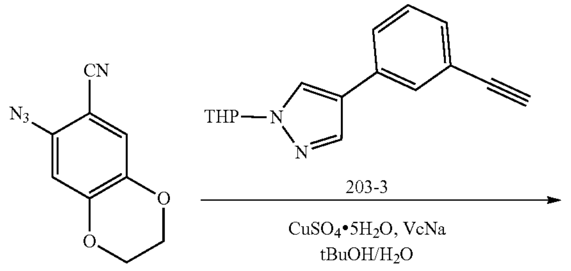

203-2

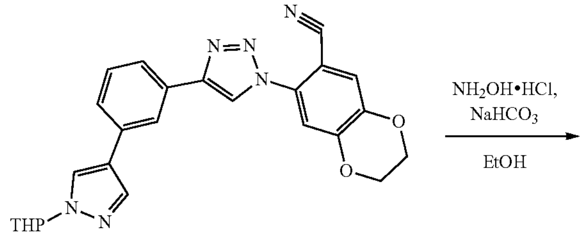

203-4

-continued

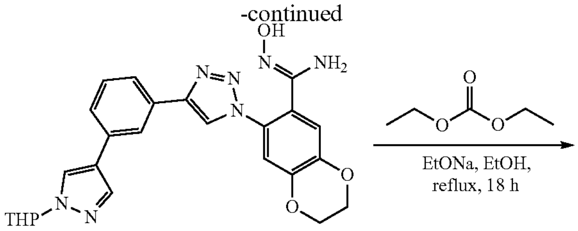

203-5

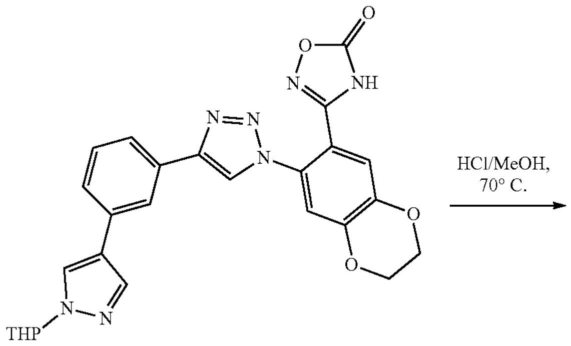

203-6

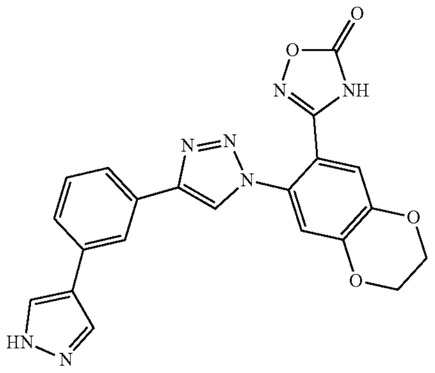

Example 203

Preparation of 7-azido-2,3-dihydrobenzo[b][1,4]dioxine-6-carbonitrile (203-2). To a solution of 7-amino-2,3-dihydrobenzo[b][1,4]dioxine-6-carbonitrile (203-1, 2.0 g, 11.36 mmol, 1.0 eq) in ACN (40 mL) being cooled 0° C. was added tert-butylnitrite (1.76 g, 17.04 mmol, 1.5 eq), and $TMSN_3$ (1.97 g, 17.04 mmol, 1.5 eq). The crude product, 203-2, was used directly for the next step.

Preparation of 7-(4-(3-(1-(tetrahydro-2H-pyran-2-yl)-1H-pyrazol-4-yl)phenyl)-1H-1,2,3-triazol-1-yl)-2,3-dihydrobenzo[b][1,4]dioxine-6-carbonitrile (203-4). To a solution of 7-azido-2,3-dihydrobenzo[b][1,4]dioxine-6-carbonitrile (203-2, 2.3 g, 11.36 mmol, 1.0 eq) in t-BuOH/$H_2O$ (40/20 mL) was added 4-(3-ethynylphenyl)-1-(tetrahydro-2H-pyran-2-yl)-1H-pyrazole (203-3, 2.9 g, 11.36 mmol, 1.0 eq), $CuSO_4.5H_2O$ (0.851 g, 3.41 mmol, 0.3 eq) and VcNa (1.4 g, 6.82 mmol, 0.6 eq). The mixture was stirred at Rt for 18 h under $N_2$. The mixture was poured into water, extracted with EA, and dried over $Na_2SO_4$. The crude product was purified by silica gel column eluting with 0-50% EA in PE to give 7-(4-(3-(1-(tetrahydro-2H-pyran-2-yl)-1H-pyrazol-4-yl)phenyl)-1H-1,2,3-triazol-1-yl)-2,3-dihydrobenzo[b][1,4]dioxine-6-carbonitrile (203-4, 1.6 g, 3.52 mmol, 31.0%). LC/MS [M+H]:445.3

Preparation of 3-(1-(tetrahydro-2H-pyran-4-yl)-1H-pyrazol-4-yl)benzoyl chloride (203-5). To a solution of 7-(4-(3-

(1-(tetrahydro-2H-pyran-2-yl)-1H-pyrazol-4-yl)phenyl)-1H-1,2,3-triazol-1-yl)-2,3-dihydrobenzo[b][1,4]dioxine-6-carbonitrile (203-4, 0.8 g, 1.76 mmol, 1.0 eq) in EtOH (15 mL) was added $NH_2OH \cdot HCl$ (367.0 mg, 5.28 mmol, 3.0 eq), $NaHCO_3$ (443.6 mg, 5.28 mmol, 3.0 eq). The mixture was stirred at 70° C. for 18 h under $N_2$. The mixture was concentrated, followed by dissolved in $CH_2Cl_2$ and filtered to give crude product 203-5 in the amount of 857.1 mg.

Preparation of 3-(7-(4-(3-(1-(tetrahydro-2H-pyran-2-yl)-1H-pyrazol-4-yl)phenyl)-1H-1,2,3-triazol-1-yl)-2,3-dihydrobenzo[b][1,4]dioxin-6-yl)-1,2,4-oxadiazol-5(4H)-one (203-6). To a solution of compound 203-5, (857.1 mg, 1.76 mmol, 1.0 eq) in EtOH (25 mL) was added diethyl carbonate (1.25 g, 10.56 mmol, 6.0 eq) and EtONa (480.0 mg, 7.04 mmol, 4.0 eq) at 90° C. for 18 h under $N_2$. The mixture was concentrated to give crude compound 8. The crude product was purified by silica gel column eluting with 0-20% EA in PE to give 3-(7-(4-(3-(1-(tetrahydro-2H-pyran-2-yl)-1H-pyrazol-4-yl)phenyl)-1H-1,2,3-triazol-1-yl)-2,3-dihydrobenzo[b][1,4]dioxin-6-yl)-1,2,4-oxadiazol-5(4H)-one (203-6, 107.0 mg, 0.209 mmol, 11.9%). LC/MS [M+H]: 514.3

Preparation of 3-[6-[4-[3-(1H-pyrazol-4-yl)phenyl]triazol-1-yl]-2,3-dihydro-1,4-benzodioxin-7-yl]-4H-1,2,4-oxadiazol-5-one (Example 203). To a solution of 3-(7-(4-(3-(1-(tetrahydro-2H-pyran-2-yl)-1H-pyrazol-4-yl)phenyl)-1H-1,2,3-triazol-1-yl)-2,3-dihydrobenzo[b][1,4]dioxin-6-yl)-1,2,4-oxadiazol-5(4H)-one (203-6, 107.0 mg, 0.209 mmol, 1.0 eq) in HCl/MeOH (2 mL). The mixture was stirred at for 18 h under $N_2$. The mixture product was purified by Prep-HPLC to give N-(7-(1H-tetrazol-5-yl)-2,3-dihydrobenzo[b][1,4]dioxin-6-yl)-3-(1-(tetrahydro-2H-pyran-4-yl)-1H-pyrazol-4-yl)benzamide (Example 203, 42.7 mg, 0.09 mmol, 26.2%)LC/MS [M+H]:430.1. $^1H$ NMR (400 MHz, DMSO-$d_6$) δ 12.69 (s, 1H), 8.99 (s, 1H), 8.16 (s, 3H), 7.75-7.73 (d, J=8.0 Hz, 1H), 7.62-7.60 (d, J=8.0 Hz, 1H), 7.48-7.46 (d, J=8.0 Hz, 1H), 7.44 (s, 1H), 7.42 (s, 1H), 4.43 (s, 4H).

Synthesis of 3-[4-chloro-2-[[3-(1-tetrahydropyran-4-ylpyrazol-4-yl)phenyl]methoxy]phenyl]-4H-1,2,4-oxadiazol-5-one (Example 221)

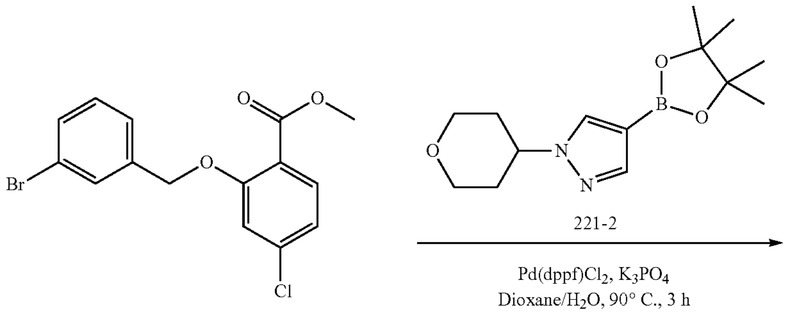

221-1

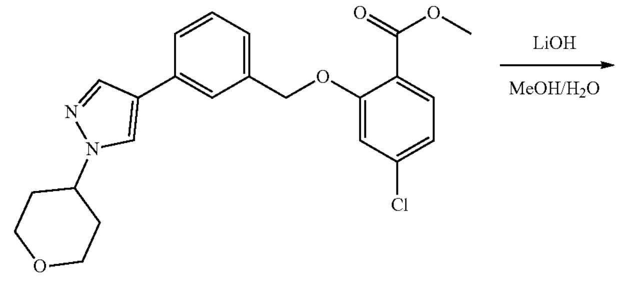

221-3

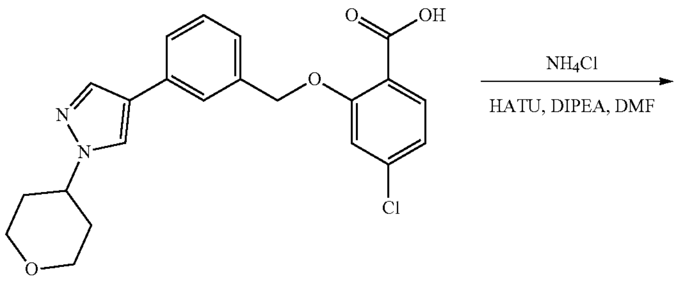

221-4

-continued

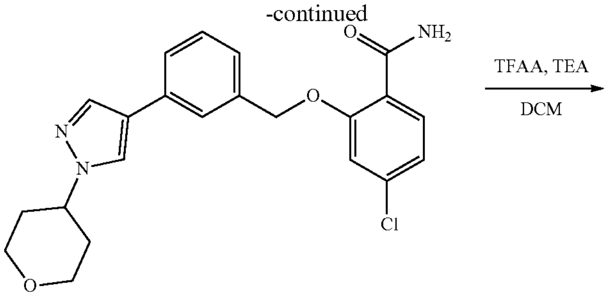

221-5

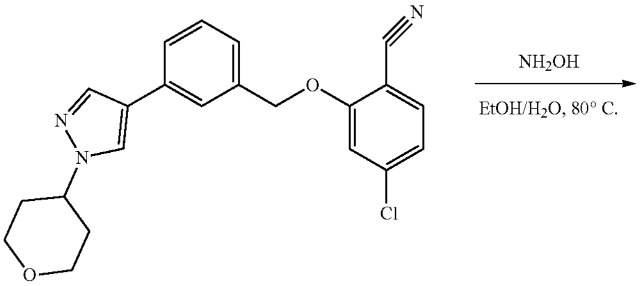

221-6

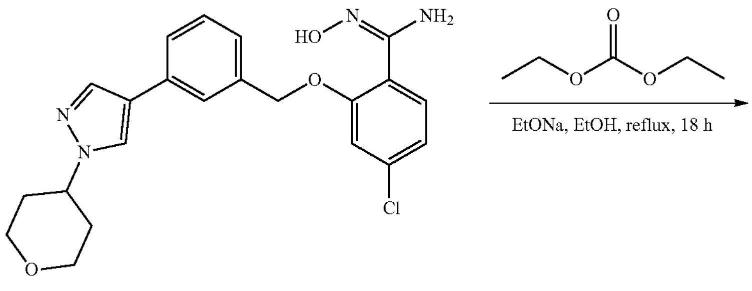

221-7

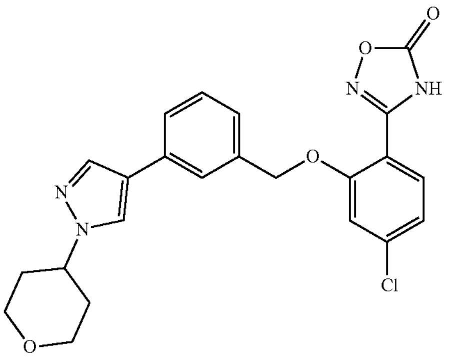

Example 221

Preparation of methyl 4-chloro-2-((3-(1-(tetrahydro-2H-pyran-4-yl)-1H-pyrazol-4-yl)benzyl)oxy)benzoate (221-3). To a solution of compound 221-1 (1.0 g, 2.82 mmol, 1.0 eq) in dioxane (30 mL) and $H_2O$ (6 mL) at 25° C. were added compound 221-2 (942 mg, 3.39 mmol, 1.2 eq), $K_3PO_4$ (1.2 g, 5.64 mmol, 2.0 eq) and Pd(dppf)$Cl_2$ (205 mg, 0.28 mmol, 0.1 eq) at 90° C. The mixture was stirred at 90° C. for 3 h under $N_2$. The mixture was extracted with DCM, dried over $Na_2SO_4$, concentrated. The crude product was purified by silica gel chromatography (PE:EA=10:1) to give methyl 4-chloro-2-((3-(1-(tetrahydro-2H-pyran-4-yl)-1H-pyrazol-4-yl)benzyl)oxy)benzoate (221-3, 988 mg, 82.3%)LC/MS [M+H]:426.0

Preparation of 6-methoxy-2-(3-(1-(tetrahydro-2H-pyran-2-yl)-1H-pyrazol-4-yl)benzamido)nicotinic acid (221-4). To a solution of compound 221-3 (988 mg, 2.32 mmol, 1.0 eq) and LiOH (223 mg, 9.29 mmol, 4.0 eq) in THF (5 mL), MeOH (5 mL) and $H_2O$ (5 mL) at 25° C. The mixture was stirred at 25° C. for 3 h. The mixture was acidified with HCl (1M) to pH=3, filtered to give 4-chloro-2-((3-(1-(tetrahydro-2H-pyran-4-yl)-1H-pyrazol-4-yl)benzyl)oxy)benzoic acid (221-4, 950 mg, 99.4%)LC/MS [M−H]:412.0

Preparation of 4-chloro-2-((3-(1-(tetrahydro-2H-pyran-4-yl)-1H-pyrazol-4-yl)benzyl)oxy)benzamide (221-5). To a solution of compound 221-4 (950 mg, 2.30 mmol, 1.0 eq) in DMF (15 mL) was added $NH_4Cl$ (1.2 g, 23.0 mmol, 10.0 eq), HATU (961 mg, 2.53 mmol, 1.2 eq) and DIEA (593 mg, 4.60 mmol, 2.0 eq) at 0° C. under $N_2$. The mixture was stirred at 0° C. for 10 min, then 25° C. for 18 h. The mixture was extracted with DCM, dried over $Na_2SO_4$, concentrated. The crude product was purified by silica gel chromatography (100% EA) to give 4-chloro-2-((3-(1-(tetrahydro-2H-pyran-4-yl)-1H-pyrazol-4-yl)benzyl)oxy)benzamide (221-5, 580 mg, 61.4%). LC/MS [M+H]:411.0

Preparation of 4-chloro-2-((3-(1-(tetrahydro-2H-pyran-4-yl)-1H-pyrazol-4-yl)benzyl)oxy)benzonitrile (221-6). To a solution of compound 221-5 (580 mg, 1.41 mmol, 1.0 eq) in THF (15 mL) was added TEA (357 mg, 3.51 mmol, 2.5 eq) at 0° C. under $N_2$. The mixture was stirred at 0° C. for 10 min, was added TFAA (741 mg, 3.53 mmol, 2.5 eq) at 0° C., then 25° C. for 18 h. The mixture was extracted with DCM, dried over $Na_2SO_4$, concentrated. The crude product was purified by silica gel chromatography (PE:EA=5:1) to give 4-chloro-2-((3-(1-(tetrahydro-2H-pyran-4-yl)-1H-pyrazol-4-yl)benzyl)oxy)benzonitrile (221-6, 331 mg, 59.7%)LC/MS [M−H]:393.0

Preparation of (E)-4-chloro-N'-hydroxy-2-((3-(1-(tetrahydro-2H-pyran-4-yl)-1H-pyrazol-4-yl)benzyl)oxy)benzimidamide (221-7). To a solution of compound 221-6 (300 mg, 0.76 mmol, 1.0 eq) in EtOH (10 mL) was added $H_2N$—OH HCl(267 mg, 3.82 mmol, 5.0 eq) and $NaHCO_3$ (321 mg, 3.82 mmol, 5.0 eq) at 80° C. The mixture was stirred at 80° C. for 18 h under $N_2$. The crude product was filtered to give (E)-4-chloro-N'-hydroxy-2-((3-(1-(tetrahydro-2H-pyran-4-yl)-1H-pyrazol-4-yl)benzyl)oxy)benzimidamide (221-7, 323 g, 99.7%)LC/MS [M+H]:426.0

Preparation of 3-[4-chloro-2-[[3-(1-tetrahydropyran-4-ylpyrazol-4-yl)phenyl]methoxy]phenyl]-4H-1,2,4-oxadiazol-5-one (Example 221). To a solution of compound 221-7 (300 g, 0.70 mmol, 1.0 eq) in EtOH (10 mL) was added EtONa (191 mg, 2.82 mmol, 4.0 eq) and diethyl carbonate (661 mg, 5.6 mmol, 8.0 eq) at 80° C. The mixture was stirred at 80° C. for 18 h under $N_2$. The crude product was purified by Prep-HPLC (1% FA) to give 3-[4-chloro-2-[[3-(1-tetrahydropyran-4-ylpyrazol-4-yl)phenyl]methoxy]phenyl]-4H-1,2,4-oxadiazol-5-one (Example 221, 148.89 mg, 47.1%) LC/MS [M+H]:452.0. $^1H$ NMR (400 MHz, DMSO-$d_6$) δ 12.60 (s, 1H), 8.22 (s, 1H), 7.88 (d, J=0.6 Hz, 1H), 7.76 (s, 1H), 7.66 (d, J=8.2 Hz, 1H), 7.56 (d, J=7.8 Hz, 1H), 7.44 (d, J=1.8 Hz, 1H), 7.36 (t, J=7.7 Hz, 1H), 7.28-7.17 (m, 2H), 5.32 (s, 2H), 4.47-4.34 (m, 1H), 4.05-3.88 (m, 2H), 3.49 (td, J=11.5, 3.0 Hz, 2H), 2.09-1.89 (m, 4H).

Synthesis of 3-[4,5-dichloro-2-[[3-(1-tetrahydropyran-4-ylpyrazol-4-yl)phenyl]methoxy]phenyl]-4H-1,2,4-oxadiazol-5-one (Example 222)

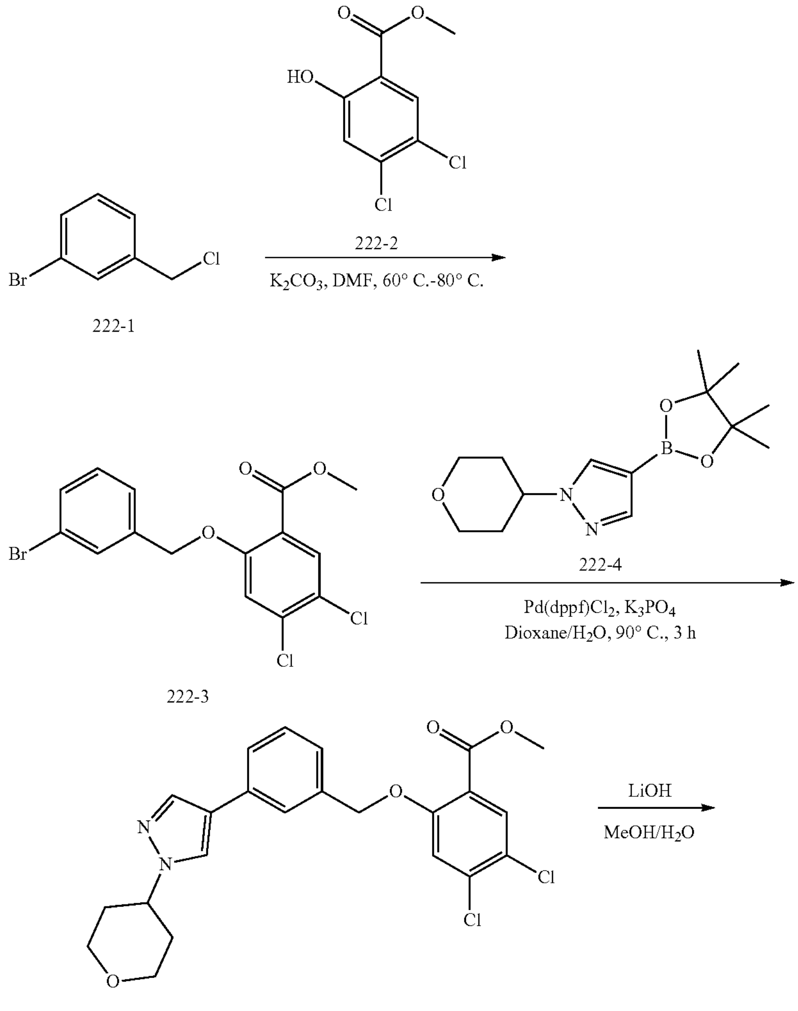

222-2

222-1

222-4

222-3

222-5

-continued
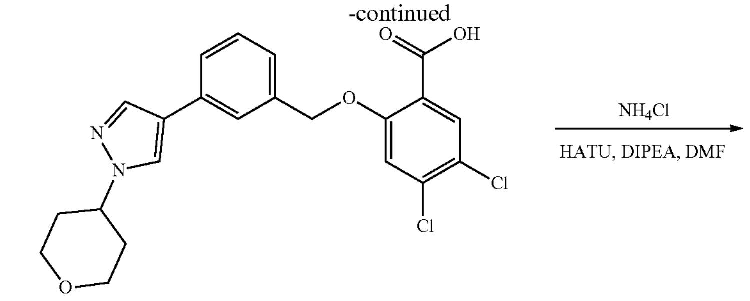
222-6
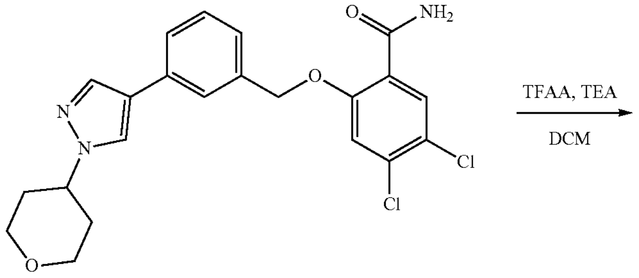
222-7
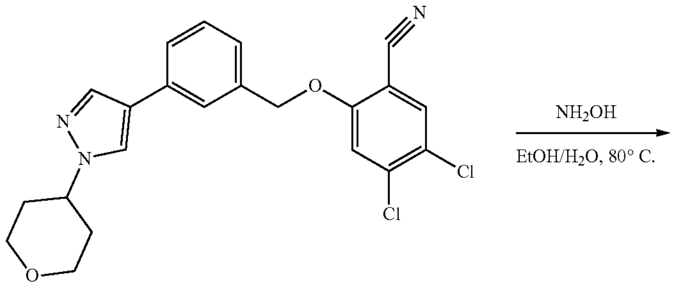
222-8
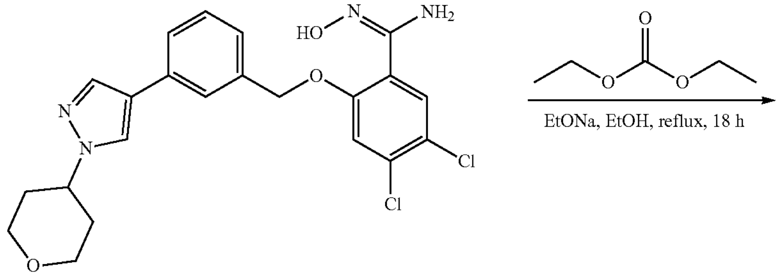
222-9
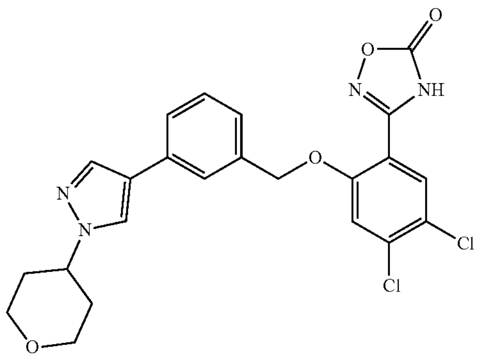
Example 222

Preparation of methyl 2-((3-bromobenzyl)oxy)-4,5-dichlorobenzoate (222-3). To a mixture of 1-bromo-3-(chloromethyl)benzene (222-1, 1.00 g, 4.90 mmol), methyl 4,5-dichloro-2-hydroxybenzoate (222-2, 1.13 g, 5.15 mmol) and $K_2CO_3$ (1.36 g, 9.80 mmol) in DMF (10 mL) was stirred at 80° C. for 3 h. TLC showed the reaction was completed. The mixture was purified by silica gel column chromatography eluting with 5-95% EA in PE to get methyl 2-((3-bromobenzyl)oxy)-4,5-dichlorobenzoate (222-3, 1.4 g) as a white solid. LC/MS: Rt: 1.741 min; Expected MS m/z (ESI) for Chemical Formula: $C_{15}H_{11}BrCl_2O_3$[M−H]$^+$: 386.8; Found: 386.8.

Preparation of methyl 4,5-dichloro-2-((3-(1-(tetrahydro-2H-pyran-4-yl)-1H-pyrazol-4-yl)benzyl)oxy)benzoate (222-5). To a mixture of methyl 2-((3-bromobenzyl)oxy)-4,5-dichlorobenzoate (222-3, 1.1 g, 2.84 mmol), 1-(tetrahydro-2H-pyran-4-yl)-4-(4,4,5,5-tetramethyl-1,3,2-dioxaborolan-2-yl)-1H-pyrazole (222-4, 829 mg, 3.12 mmol), $K_3PO_4$ (1.20 g, 5.67 mmol) and Pd(dppf)$Cl_2$ (105 mg, 0.14 mmol) in 1,4-Dioxane/$H_2O$ (10 mL/2.5 mL) was stirred at 90° C. under Argon for 3 h. TLC showed the reaction was completed. The mixture was washed by water and quenched with EtOAc, the organic layer was concentrated and purified by silica gel column chromatography eluting with 5-95% EA in PE to get methyl 4,5-dichloro-2-((3-(1-(tetrahydro-2H-pyran-4-yl)-1H-pyrazol-4-yl)benzyl)oxy)benzoate (222-5, 1.218 g) as a white solid. LC/MS: Rt: 0.95 min; Expected MS m/z (ESI) for Chemical Formula: $C_{23}H_{22}Cl_2N_2O_4$ [M+H]$^+$: 461.3; Found: 461.3.

Preparation of 4,5-dichloro-2-((3-(1-(tetrahydro-2H-pyran-4-yl)-1H-pyrazol-4-yl)benzyl)oxy)benzoic acid (222-6). To a mixture of methyl 4,5-dichloro-2-((3-(1-(tetrahydro-2H-pyran-4-yl)-1H-pyrazol-4-yl)benzyl)oxy)benzoate (222-5, 1.218 g, 2.65 mmol) and LiOH (254 mg, 10.59 mmol) in MeOH/$H_2O$/THF (6 mL/3 mL/6 mL) was stirred at room temperature for 3 h. TLC showed the reaction was completed. The mixture was purified by silica gel column chromatography eluting with 5-95% EA in PE to get 4,5-dichloro-2-((3-(1-(tetrahydro-2H-pyran-4-yl)-1H-pyrazol-4-yl)benzyl)oxy)benzoic acid (222-6, 1.1 g) as a white solid. LC/MS: Rt: 1.65 min; Expected MS m/z (ESI) for Chemical Formula: $C_{22}H_{20}Cl_2N_2O_4$ [M+H]$^+$: 447.3; Found: 447.3.

Preparation of 4,5-dichloro-2-((3-(1-(tetrahydro-2H-pyran-4-yl)-1H-pyrazol-4-yl)benzyl)oxy)benzamide (222-7). To a mixture of 4,5-dichloro-2-((3-(1-(tetrahydro-2H-pyran-4-yl)-1H-pyrazol-4-yl)benzyl)oxy)benzoic acid (1.1 g, 2.46 mmol), $NH_4Cl$ (1.32 g, 24.60 mmol), HATU (956 mg, 2.52 mmol) and DIPEA (857 μL, 4.93 mmol) in DMF (5 mL) was stirred at room temperature for 3 h. TLC showed the reaction was completed. The mixture was purified by silica gel column chromatography eluting with 5-95% EA in PE to get 4,5-dichloro-2-((3-(1-(tetrahydro-2H-pyran-4-yl)-1H-pyrazol-4-yl)benzyl)oxy)benzamide (222-7, 1.05 g) as a white solid. LC/MS: Rt: 1.82 min; Expected MS m/z (ESI) for Chemical Formula: $C_{22}H_{21}Cl_2N_3O_3$ [M+H]$^+$: 446.3; Found: 446.3

Preparation of 4,5-dichloro-2-((3-(1-(tetrahydro-2H-pyran-4-yl)-1H-pyrazol-4-yl)benzyl)oxy)benzonitrile (222-8). To a mixture of 4,5-dichloro-2-((3-(1-(tetrahydro-2H-pyran-4-yl)-1H-pyrazol-4-yl)benzyl)oxy)benzamide (222-7, 1 g, 2.25 mmol), TFAH (781 μL, 5.62 mmol) and TEA (779 μl, 5.62 mmol) in DCM (10 mL) was stirred at room temperature under Argon for 16 h. TLC showed the reaction was completed. The mixture was purified by silica gel column chromatography eluting with 5-95% EA in PE to get 4,5-dichloro-2-((3-(1-(tetrahydro-2H-pyran-4-yl)-1H-pyrazol-4-yl)benzyl)oxy)benzonitrile (222-8, 950 mg) as a yellow solid. LC/MS: Rt: 1.85 min; Expected MS m/z (ESI) for Chemical Formula: $C_{22}H_{19}Cl_2N_3O_2$ [M+H]$^+$: 428.3; Found: 428.3

Preparation of (E)-4,5-dichloro-N'-hydroxy-2-((3-(1-(tetrahydro-2H-pyran-4-yl)-1H-pyrazol-4-yl)benzyl)oxy)benzimidamide (222-9). To a solution of 4,5-dichloro-2-((3-(1-(tetrahydro-2H-pyran-4-yl)-1H-pyrazol-4-yl)benzyl)oxy)benzonitrile (222-8, 950 mg, 2.30 mmol) in EtOH (10 mL) was added $NH_2OH$ (3 mL,50% wt. in water) stirred at 80° C. under Argon for 16 h. TLC showed the reaction was completed. The mixture was purified by silica gel column chromatography eluting with 5-95% EA in PE to get (E)-4,5-dichloro-N'-hydroxy-2-((3-(1-(tetrahydro-2H-pyran-4-yl)-1H-pyrazol-4-yl)benzyl)oxy)benzimidamide (222-9, 790 mg) as a white solid. LC/MS: Rt: 1.09 min; Expected MS m/z (ESI) for Chemical Formula: $C_{22}H_{22}Cl_2N_4O_3$ [M+H]$^+$: 461.4; Found: 461.4

Preparation of 3-[4,5-dichloro-2-[[3-(1-tetrahydropyran-4-ylpyrazol-4-yl)phenyl]methoxy]phenyl]-4H-1,2,4-oxadiazol-5-one (Example 222). To a mixture of (E)-4,5-dichloro-N'-hydroxy-2-((3-(1-(tetrahydro-2H-pyran-4-yl)-1H-pyrazol-4-yl)benzyl)oxy)benzimidamide (222-9, 380 mg, 0.83 mmol) and EtONa (114 mg, 1.65 mmol) in EtOH (10 mL) was added diethyl carbonate (400 μl, 3.30 mmol) stirred at 80° C. for 18 h. TLC showed the reaction was completed. The mixture was purified by prep-HPLC to get 33-[4,5-dichloro-2-[[3-(1-tetrahydropyran-4-ylpyrazol-4-yl)phenyl]methoxy]phenyl]-4H-1,2,4-oxadiazol-5-one (Example 222, 52.50 mg) as a white solid. LC/MS: Rt: 9.397 min; Expected MS m/z (ESI) for Chemical Formula: $C_{23}H_{20}Cl_2N_4O_4$ [M+H]$^+$: 487.2; Found: 487.2. $^1$H NMR (400 MHz, DMSO-$d_6$) δ 12.72 (s, 1H), 8.22 (s, 1H), 7.90 (s, 1H), 7.89 (s, 1H), 7.76 (s, 1H), 7.67 (s, 1H), 7.55 (d, J=8.0, 1H), 7.38 (t, J=7.6, 1H), 7.25 (d, J=7.6, 1H), 5.33 (m, 2H), 4.44-4.39 (m, 1H), 3.99-3.96 (m, 2H), 3.52-3.42 (m, 2H), 2.04-1.94 (m, 4H).

Synthesis of 3-[4-chloro-2-[[4-(1-tetrahydropyran-4-ylpyrazol-4-yl)-2-pyridyl]methoxy]phenyl]-4H-1,2,4-oxadiazol-5-one (Example 223)

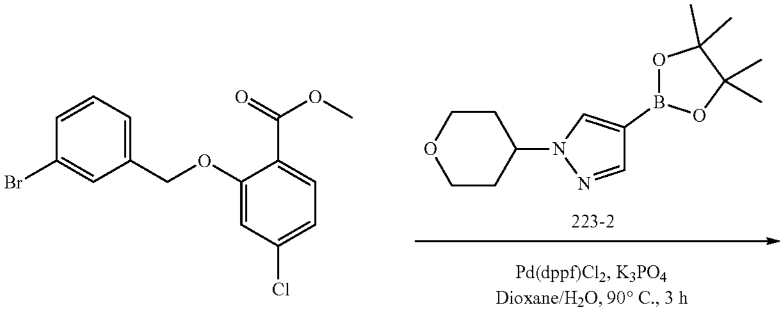

223-1

223-2

-continued
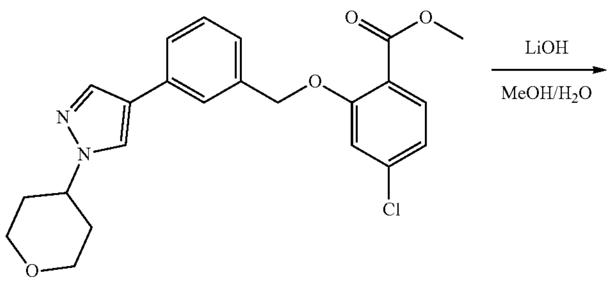
223-3
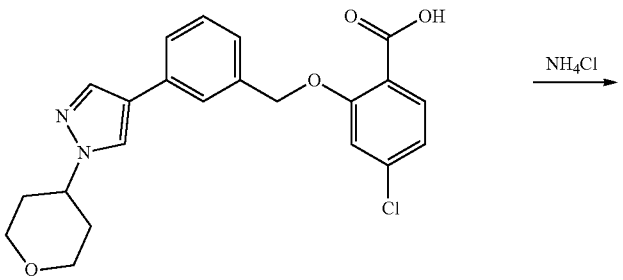
223-4
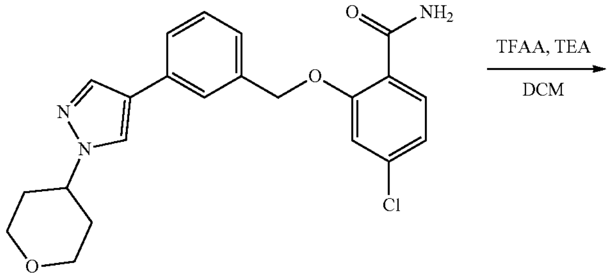
223-5
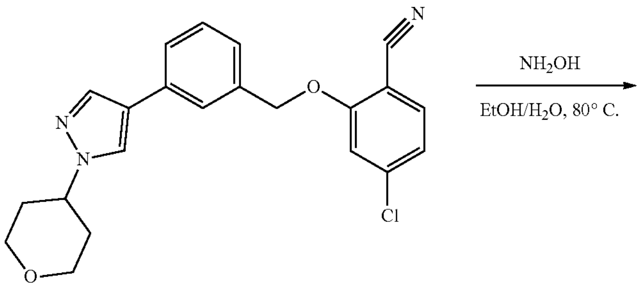
223-6
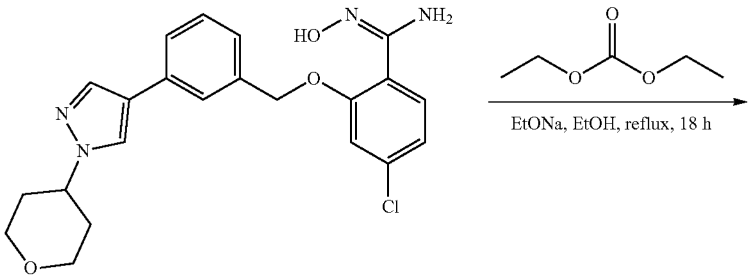
223-7

-continued

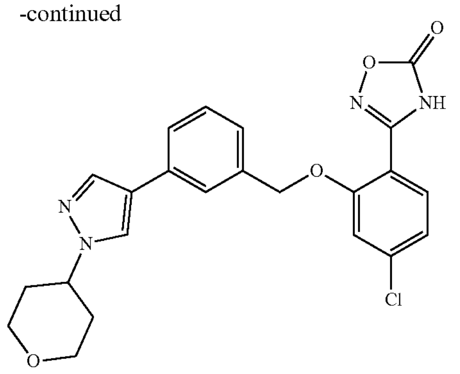

Example 223

Preparation of methyl 4-chloro-2-((4-(1-(tetrahydro-2H-pyran-4-yl)-1H-pyrazol-4-yl)pyridin-2-yl)methoxy)benzoate (223-3). To a solution of compound 223-1 (900 mg, 2.54 mmol, 1.0 eq) in dioxane (15 mL) and $H_2O$ (3 mL) at 25° C. were added compound 223-2 (846 mg, 3.04 mmol, 1.2 eq), $K_3PO_4$(1.08 g, 5.08 mmol, 2.0 eq) and Pd(dppf)$Cl_2$ (93 mg, 0.13 mmol, 0.05 eq) at 90° C. The mixture was stirred at 90° C. for 3 h under $N_2$. The mixture was extracted with DCM, dried over $Na_2SO_4$, concentrated. The crude product was purified by silica gel chromatography (PE:EA=11:1) to give methyl 4-chloro-2-((4-(1-(tetrahydro-2H-pyran-4-yl)-1H-pyrazol-4-yl)pyridin-2-yl)methoxy)benzoate. (223-3, 903 mg, 83.3%)LC/MS [M+H]:428.0

Preparation of 4-chloro-2-((4-(1-(tetrahydro-2H-pyran-4-yl)-1H-pyrazol-4-yl)pyridin-2-yl)methoxy)benzoic acid (223-4). To a solution of compound 223-3 (850 mg, 1.99 mmol, 1.0 eq) in MeOH (3 mL) and $H_2O$ (3 mL) was added LiOH (191 mg, 7.96 mmol, 4.0 eq) at 25° C. The mixture was stirred at 25° C. for 3 h. The mixture was acidified with HCl (1M) to pH=3, filtered to give 4-chloro-2-((4-(1-(tetrahydro-2H-pyran-4-yl)-1H-pyrazol-4-yl)pyridin-2-yl) methoxy)benzoic acid (223-4, 805 mg, 98.0%)LC/MS [M+H]:414.0

Preparation of 4-chloro-2-((4-(1-(tetrahydro-2H-pyran-4-yl)-1H-pyrazol-4-yl)pyridin-2-yl)methoxy)benzamide (223-5). To a solution of compound 223-4 (500 mg, 1.21 mmol, 1.0 eq) in DMF (10 mL) was added $NH_4Cl$ (647 mg, 12.1 mmol, 10.0 eq), HATU (483 mg, 1.27 mmol, 1.05 eq) and DIEA (312 mg, 2.42 mmol, 2.0 eq) at 0° C. under $N_2$.The mixture was stirred at 0° C. for 10 min, then 25° C. for 18 h. The mixture was extracted with DCM, dried over $Na_2SO_4$, concentrated. The crude product was purified by silica gel chromatography (100% EA) to give 4-chloro-2-((4-(1-(tetrahydro-2H-pyran-4-yl)-1H-pyrazol-4-yl)pyridin-2-yl)methoxy)benzamide (223-5, 363 mg, 68.9%). LC/MS [M+H]:413.0

Preparation of 4-chloro-2-((4-(1-(tetrahydro-2H-pyran-4-yl)-1H-pyrazol-4-yl)pyridin-2-yl)methoxy)benzamide (223-6). To a solution of compound 223-5 (360 mg, 0.89 mmol, 1.0 eq) in THF (10 mL) was added TEA (224 mg, 2.21 mmol, 2.5 eq) at 0° C. under $N_2$.The mixture was stirred at 0° C. for 10 min, was added TFAA (464 mg, 2.21 mmol, 2.5 eq) at 0° C., then 25° C. for 18 h. The mixture was extracted with DCM, dried over $Na_2SO_4$, concentrated. The crude product was purified by silica gel chromatography (100% EA) to give 4-chloro-2-((4-(1-(tetrahydro-2H-pyran-4-yl)-1H-pyrazol-4-yl)pyridin-2-yl)methoxy)benzamide (223-6, 280 mg, 79.8%)LC/MS [M−H]:395.0

Preparation of (E)-4-chloro-N'-hydroxy-2-((4-(1-(tetrahydro-2H-pyran-4-yl)-1H-pyrazol-4-yl)pyridin-2-yl) methoxy)benzimidamide (223-7). To a solution of compound 223-6 (230 mg, 0.58 mmol, 1.0 eq) in EtOH (5 mL) was added $H_2NOH$ (385 mg, 5.84 mmol, 10.0 eq) at 80° C. The mixture was stirred at 80° C. for 18 h under $N_2$. The crude product was filtered to give (E)-4-chloro-N'-hydroxy-2-((4-(1-(tetrahydro-2H-pyran-4-yl)-1H-pyrazol-4-yl)pyridin-2-yl)methoxy)benzimidamide (223-7, 243 g, 97.9%)LC/MS [M+H]:428.0

Preparation of 3-[4-chloro-2-[[4-(1-tetrahydropyran-4-ylpyrazol-4-yl)-2-pyridyl]methoxy]phenyl]-4H-1,2,4-oxadiazol-5-one (Example 223). To a solution of compound 223-7 (230 g, 0.54 mmol, 1.0 eq) in EtOH (10 mL) was added EtONa (148 mg, 2.16 mmol, 4.0 eq) and diethyl carbonate (508 mg, 4.31 mmol, 8.0 eq) at 80° C. The mixture was stirred at 80° C. for 18 h under $N_2$. The crude product was purified by Prep-HPLC (1% FA) to give 3-[4-chloro-2-[[4-(1-tetrahydropyran-4-ylpyrazol-4-yl)-2-pyridyl] methoxy]phenyl]-4H-1,2,4-oxadiazol-5-one (Example 223, 77.43 mg, 31.7%)LC/MS [M+H]:454.0

Synthesis of 3-[6-[[4-(1-tetrahydropyran-4-ylpyrazol-4-yl)-2-pyridyl]methoxy]-2,3-dihydro-1,4-benzodioxin-7-yl]-4H-1,2,4-oxadiazol-5- one (Example 224)

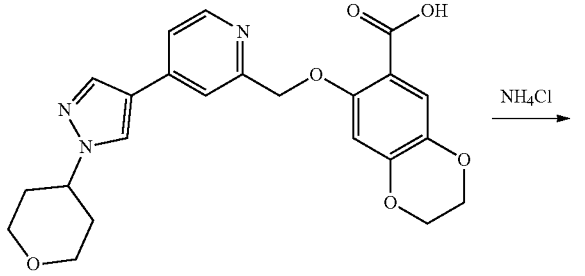

224-1

-continued

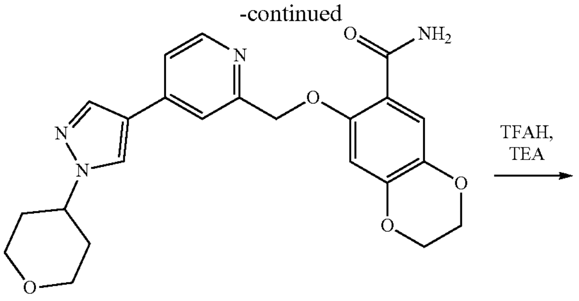

224-2

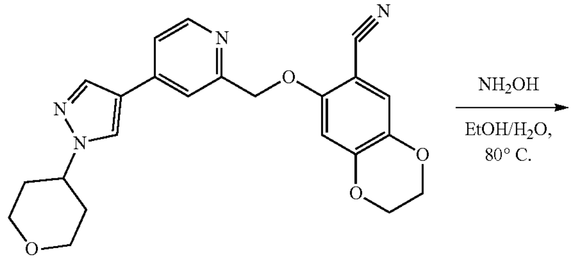

224-3

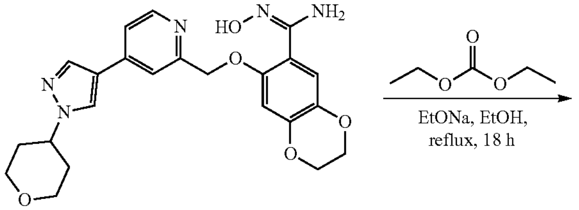

224-4

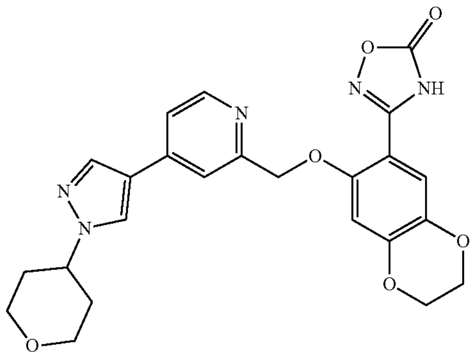

Example 224

Preparation of 7-((4-(1-(tetrahydro-2H-pyran-4-yl)-1H-pyrazol-4-yl)pyridin-2-yl)methoxy)-2,3-dihydrobenzo[b][1,4]dioxine-6-carboxamide (224-2). To a mixture of 7-((4-(1-(tetrahydro-2H-pyran-4-yl)-1H-pyrazol-4-yl)pyridin-2-yl)methoxy)-2,3-dihydrobenzo[b][1,4]dioxine-6-carboxylic acid (224-1, 600 mg, 1.40 mmol), $NH_4Cl$ (734 mg, 14.00 mmol), HATU (532 mg, 1.02 mmol) and DIPEA (480 μl, 2.80 mmol) in DMF (10 mL) was stirred at room temperature for 3 h. TLC showed the reaction was completed. The mixture was purified by silica gel column chromatography eluting with 5-95% EA in PE to get 7-((4-(1-(tetrahydro-2H-pyran-4-yl)-1H-pyrazol-4-yl)pyridin-2-yl)methoxy)-2, 3-dihydrobenzo[b][1,4]dioxine-6-carboxamide (224-2, 330 mg) as a yellow solid. LC/MS: Rt: 1.17 min; Expected MS m/z (ESI) for Chemical Formula: $C_{23}H_{24}N_4O_5$ $[M+H]^+$: 437.3; Found: 437.3.

Preparation of 7-((4-(1-(tetrahydro-2H-pyran-4-yl)-1H-pyrazol-4-yl)pyridin-2-yl)methoxy)-2,3-dihydrobenzo[b][1,4]dioxine-6-carbonitrile (224-3). To a mixture of 7-((4-(1-(tetrahydro-2H-pyran-4-yl)-1H-pyrazol-4-yl)pyridin-2-yl)methoxy)-2,3-dihydrobenzo[b][1,4]dioxine-6-carboxamide (224-2, 280 mg, 0.62 mmol), TFAH (224 μl, 1.54 mmol) and TEA (224 μl, 1.54 mmol) in DCM (5 mL) was stirred at room temperature under Argon for 16 h. TLC showed the reaction was completed. The mixture was purified by silica gel column chromatography eluting with 5-95% EA in PE to get 7-((4-(1-(tetrahydro-2H-pyran-4-yl)-1H-pyrazol-4-yl)pyridin-2-yl)methoxy)-2,3-dihydrobenzo[b][1,4]dioxine-6-carbonitrile (224-3, 270 mg) as a yellow solid. LC/MS: Rt: 1.43 min; Expected MS m/z (ESI) for Chemical Formula: $C_{23}H_{22}N_4O_4$ $[M+H]^+$: 419.4; Found: 419.4

Preparation of (E)-N'-hydroxy-7-((4-(1-(tetrahydro-2H-pyran-4-yl)-1H-pyrazol-4-yl)pyridin-2-yl)methoxy)-2,3-dihydrobenzo[b][1,4]dioxine-6-carboximidamide (224-4). To a solution of 7-((4-(1-(tetrahydro-2H-pyran-4-yl)-1H-pyrazol-4-yl)pyridin-2-yl)methoxy)-2,3-dihydrobenzo[b][1,4]dioxine-6-carbonitrile (224-3, 270 mg, 0.62 mmol) in EtOH (10 mL) was added $NH_2OH$ (2 mL,50% wt. in water) stirred at 80° C. under Argon for 16 h. TLC showed the reaction was completed. The mixture was purified by silica gel column chromatography eluting with 5-95% EA in PE to get (E)-N'-hydroxy-7-((4-(1-(tetrahydro-2H-pyran-4-yl)-1H-pyrazol-4-yl)pyridin-2-yl)methoxy)-2,3-dihydrobenzo[b][1,4]dioxine-6-carboximidamide (224-4, 200 mg) as a yellow solid. LC/MS: Rt: 1.02 min; Expected MS m/z (ESI) for Chemical Formula: $C_{23}H_{25}N_5O_5$ $[M+H]^+$: 452.4; Found: 452.4

Preparation of 3-[6-[[4-(1-tetrahydropyran-4-ylpyrazol-4-yl)-2-pyridyl]methoxy]-2,3-dihydro-1,4-benzodioxin-7-yl]-4H-1,2,4-oxadiazol-5-one (Example 224). To a mixture of (E)-N'-hydroxy-7-((4-(1-(tetrahydro-2H-pyran-4-yl)-1H-pyrazol-4-yl)pyridin-2-yl)methoxy)-2,3-dihydrobenzo[b][1,4]dioxine-6-carboximidamide (224-3, 200 mg, 0.44 mmol) and EtONa (60 mg, 0.88 mmol) in EtOH (10 mL) was added diethyl carbonate (212 mg, 1.76 mmol) stirred at 80° C. for 18 h. TLC showed the reaction was completed. The mixture was purified by prep-HPLC to get 3-[6-[[4-(1-tetrahydropyran-4-ylpyrazol-4-yl)-2-pyridyl]methoxy]-2,3-dihydro-1,4-benzodioxin-7-yl]-4H-1,2,4-oxadiazol-5-one (Example 224, 8.42 mg) as a white solid. LC/MS: Rt: 7.097 min; Expected MS m/z (ESI) for Chemical Formula: $C_{24}H_{23}N_5O_6$ $[M+H]^+$: 478.3; Found: 478.3. $^1H$ NMR (400 MHz, DMSO-$d_6$) δ 8.52 (t, J=3.20, 2H), 8.11 (s, 1H), 7.91 (s, 1H), 7.61 (dd, J=5.20, 1H), 7.23 (s, 1H), 6.90 (s, 1H), 5.29 (s, 2H), 4.47-4.43 (m, 1H), 4.33-4.24 (m, 4H), 4.00-3.97 (m, 2H), 3.53-3.46 (m, 2H), 2.07-1.96 (m, 4H).

Synthesis of 7-((3,5-bis(1-(tetrahydro-2H-pyran-4-yl)-1H-pyrazol-4-yl)benzyl)oxy)-2,3-dihydrobenzo[b][1,4]dioxine-6-carboxylic acid (Example 227)
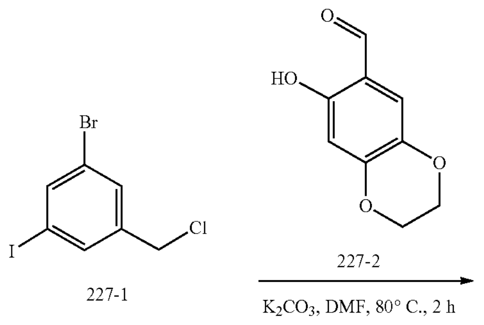
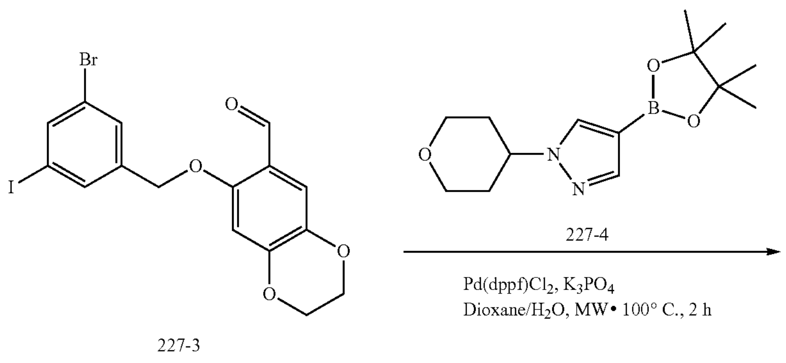
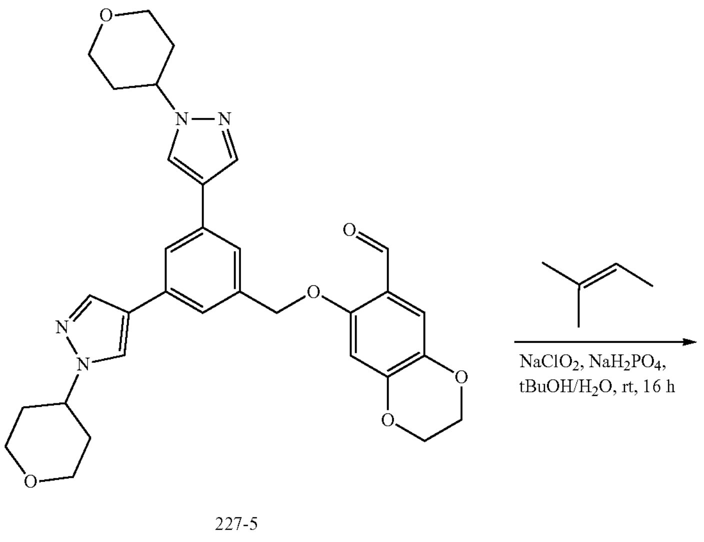

-continued

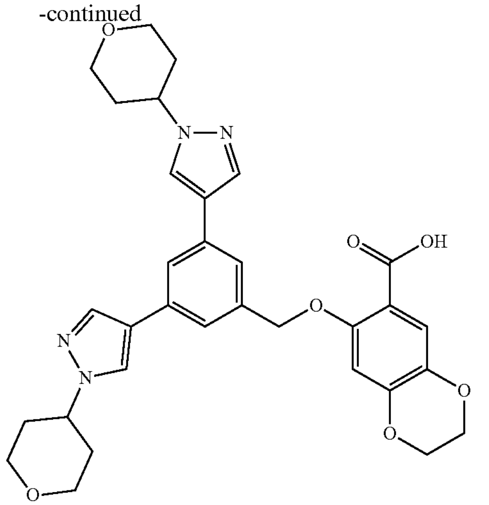

Example 227

Preparation of 7-((3-bromo-5-iodobenzyl)oxy)-2,3-dihydrobenzo[b][1,4]dioxine-6-carbaldehyde (227-3). To a solution of 1-bromo-3-(chloromethyl)-5-iodobenzene (227-1, 200 g, 0.61 mmol, 1.0 eq) in DMF (5 mL) was added $K_2CO_3$ (168 mg, 1.22 mmol, 2.0 eq) and 7-hydroxy-2,3-dihydrobenzo[b][1,4]dioxine-6-carbaldehyde (227-2, 131 mg, 0.73 mmol, 1.2 eq) at 80° C. The mixture was stirred at 80° C. for 2 h under $N_2$. The mixture was extracted with EA, dried over $Na_2SO_4$, concentrated. The crude product was purified by silica gel chromatography (PE:EA=10:1) to give 7-((3-bromo-5-iodobenzyl)oxy)-2,3-dihydrobenzo[b][1,4]dioxine-6-carbaldehyde (227-3, 246 mg, 85.1%). LC/MS [M+H]:475.0

Preparation of 7-((3,5-bis(1-(tetrahydro-2H-pyran-4-yl)-1H-pyrazol-4-yl)benzyl)oxy)-2,3-dihydrobenzo[b][1,4]dioxine-6-carbaldehyde (227-5). To a solution of compound 227-3 (250 mg, 0.63 mmol, 1.0 eq) in dioxane (10 mL) and $H_2O$ (2 mL) at 25° C. were added compound 227-4 (369 mg, 1.33 mmol, 1.2 eq), $K_3PO_4$ (267 mg, 1.26 mmol, 2.0 eq) and Pd(dppf)$Cl_2$ (46 mg, 0.06 mmol, 0.1 eq) at 100° C. The mixture was stirred at 100° C. for 2 h under microwave radiation. The mixture was extracted with DCM, dried over $Na_2SO_4$, concentrated. The crude product was purified by silica gel chromatography (DCM:MeOH=10:1) to give 7-((3,5-bis(1-(tetrahydro-2H-pyran-4-yl)-1H-pyrazol-4-yl)benzyl)oxy)-2,3-dihydrobenzo[b][1,4]dioxine-6-carbaldehyde (227-5, 255 mg, 71.0%)LC/MS [M+H]:571.0

Preparation of 7-((3,5-bis(1-(tetrahydro-2H-pyran-4-yl)-1H-pyrazol-4-yl)benzyl)oxy)-2,3-dihydrobenzo[b][1,4]dioxine-6-carboxylic acid (Example 227). To a solution of compound 227-5 (250 mg, 0.44 mmol, 1.0 eq) in tBuOH (8 mL) and $H_2O$ (2 mL) was added $NaH_2PO_4$ (472 mg, 3.42 mmol, 7.8 eq), $NaClO_2$ (198 mg, 2.20 mmol, 5.0 eq) and 2-methylbut-2-ene (239 mg, 3.42 mmol, 7.8 eq) at 25° C. The mixture was stirred at 25° C. for 3 h. The mixture was extracted with EA, dried over $Na_2SO_4$, concentrated. The crude product was purified by Prep-HPLC to give 7-((3,5-bis(1-(tetrahydro-2H-pyran-4-yl)-1H-pyrazol-4-yl)benzyl)oxy)-2,3-dihydrobenzo[b][1,4]dioxine-6-carboxylic acid (Example 227,107.34 mg, 41.5%). LC/MS [M+H]:587.0. $^1H$ NMR (400 MHz, DMSO-$d_6$) δ 8.28 (s, 2H), 7.95 (s, 2H), 7.77 (s, 1H), 7.56 (s, 2H), 7.26 (s, 1H), 6.74 (s, 1H), 5.11 (s, 2H), 4.46-4.38 (m, 2H), 4.29 (d, J=4.3 Hz, 2H), 4.21 (d, J=2.9 Hz, 2H), 3.99 (d, J=11.5 Hz, 4H), 3.47 (d, J=2.5 Hz, 4H), 2.07-1.94 (m, 8H).

Synthesis of 3-(2-(4-(3-(1H-pyrazol-4-yl)phenyl)-1H-1,2,3-triazol-1-yl)phenyl)-1,2,4-oxadiazol-5(4H)-one (Example 276)

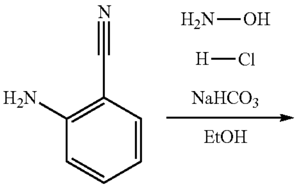

276-1

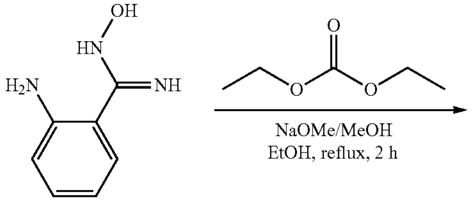

276-2

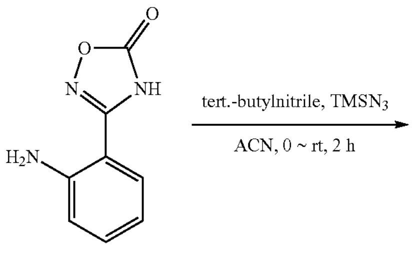

276-3

-continued

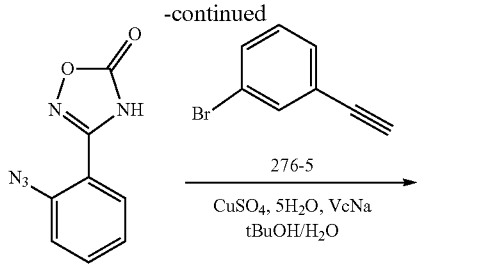

276-4

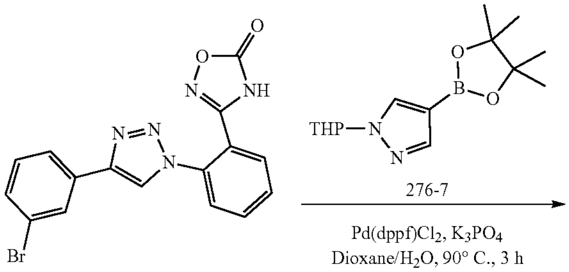

276-6

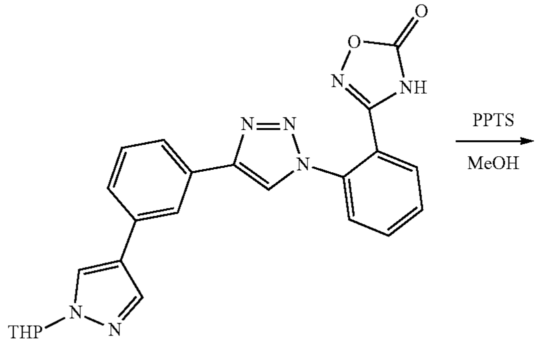

276-8

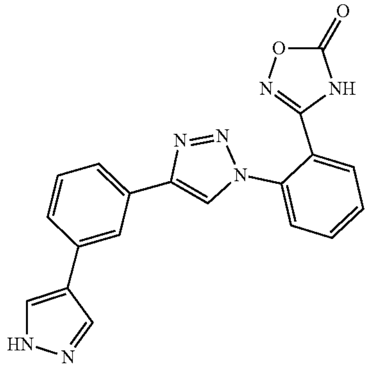

Example 276

Preparation of 2-amino-N-hydroxybenzimidamide (276-2). To a solution of 2-aminobenzonitrile (276-1, 1.0 g, 8.5 mmol, 1.0 eq) in EtOH (70 mL) was added $H_2N$—OH HCl (3.0 g, 42.4 mmol, 5.0 eq) and $NaHCO_3$ (3.6 g, 42.4 mmol, 5.0 eq) at 60° C. The mixture was stirred at 60° C. for 18 h under $N_2$. The crude product was filtered to give 2-amino-N-hydroxybenzimidamide (276-2, 1.1 g, 85.7%)LC/MS [M+H]:152.0

Preparation of 3-(2-aminophenyl)-1,2,4-oxadiazol-5(4H)-one (276-3). To a solution of 2-amino-N-hydroxybenzimidamide (276-2, 1.0 g, 6.6 mmol, 1.0 eq) in EtOH (70 mL) was added EtONa (0.9 g, 13.2 mmol, 2.0 eq) and diethyl carbonate (3.3 mL, 26.5 mmol, 4.0 eq) at 60° C. The mixture was stirred at 60° C. for 18 h under $N_2$. The crude product was purified by flash chromatography (5% FA). The mixture was extracted with EA, dried over $Na_2SO_4$, concentrated to give 3-(2-aminophenyl)-1,2,4-oxadiazol-5(4H)-one. (276-3, 825 mg, 70.4%)LC/MS [M+H]:178.0

Preparation of 3-(2-azidophenyl)-1,2,4-oxadiazol-5(4H)-one (276-4). To a solution of 3-(2-aminophenyl)-1,2,4-oxadiazol-5(4H)-one (276-3, 700 mg, 3.9 mmol, 1.0 eq) in ACN (10 mL) was added tert-butylnitrite (2 mL, 15.8 mmol, 4.0 eq) and $TMSN_3$ (2 mL, 15.8 mmol, 4.0 eq) at 0° C. The mixture was stirred at 0° C. for 30 min, then r.t for 2 h under $N_2$ to give 3-(2-azidophenyl)-1,2,4-oxadiazol-5(4H)-one (276-4). The crude product was used directly for the next step. LC/MS [M−H]:202.0

Preparation of 3-(2-(4-(3-bromophenyl)-1H-1,2,3-triazol-1-yl)phenyl)-1,2,4-oxadiazol-5(4H)-one (276-6). To a solution of 1-bromo-3-ethynylbenzene (276-5, 1.2 g, 6.9 mmol, 2.0 eq) in t-BuOH/$H_2O$ (10:5 mL) was added $CuSO_4.5H_2O$ (259 mg, 1.0 mmol, 0.3 eq), VcNa (410 mg, 2.1 mmol, 0.6 eq) at 25° C. under $N_2$, then, 3-(2-azidophenyl)-1,2,4-oxadiazol-5(4H)-one (276-4) was added at 25° C. for 18 h under $N_2$. The crude product was triturated in PE and filtered to give 3-(2-(4-(3-bromophenyl)-1H-1,2,3-triazol-1-yl)phenyl)-1,2,4-oxadiazol-5(4H)-one (276-6, 615 mg, 46.6%)LC/MS [M+H]:386.0

Preparation of 3-(2-(4-(3-(1-(tetrahydro-2H-pyran-2-yl)-1H-pyrazol-4-yl)phenyl)-1H-1,2,3-triazol-1-yl)phenyl)-1,2,4-oxadiazol-5(4H)-one (276-8). To a solution of 3-(2-(4-(3-bromophenyl)-1H-1,2,3-triazol-1-yl)phenyl)-1,2,4-oxadiazol-5(4H)-one (276-6, 300 mg, 0.8 mmol, 1.0 eq) in dioxane/$H_2O$ (5:1 mL) was added 1-(tetrahydro-2H-pyran-2-yl)-4-(4,4,5,5-tetramethyl-1,3,2-dioxaborolan-2-yl)-1H-pyrazole (276-7, 261 mg, 0.94 mmol, 1.2 eq), $K_3PO_4$ (331 mg, 1.6 mmol, 2.0 eq) and Pd(dppf)$Cl_2$ (63 mg, 0.08 mmol, 0.1 eq) at 90° C. for 18 h under $N_2$. The crude product was purified by flash chromatography (5% FA) to give 3-(2-(4-(3-(1-(tetrahydro-2H-pyran-2-yl)-1H-pyrazol-4-yl)phenyl)-1H-1,2,3-triazol-1-yl)phenyl)-1,2,4-oxadiazol-5(4H)-one. (276-8, 90 mg, 24.7%)LC/MS [M−H]:454.0

Preparation of 3-(2-(4-(3-(1H-pyrazol-4-yl)phenyl)-1H-1,2,3-triazol-1-yl)phenyl)-1,2,4-oxadiazol-5(4H)-one (Example 276). To a solution of 3-(2-(4-(3-(1-(tetrahydro-2H-pyran-2-yl)-1H-pyrazol-4-yl)phenyl)-1H-1,2,3-triazol-1-yl)phenyl)-1,2,4-oxadiazol-5(4H)-one (276-8, 90 mg, 0.2 mmol, 1.0 eq) in MeOH (5 mL) was added PPTS (20 mg, 0.08 mmol, 0.4 eq) at 70° C. under $N_2$. The mixture was stirred at 70° C. for 18 h. The mixture was extracted with DCM, dried over $Na_2SO_4$, concentrated. The crude product was purified by Prep-HPLC to give 3-(2-(4-(3-(1H-pyrazol-4-yl)phenyl)-1H-1,2,3-triazol-1-yl)phenyl)-1,2,4-oxadiazol-5(4H)-one (Example 276, 5.37 mg, 7.2%)LC/MS [M+H]: 371.0. $^1$H NMR (400 MHz, DMSO-$d_6$) δ 12.76 (s, 1H), 9.14 (s, 1H), 8.16 (d, J=15.6 Hz, 3H), 7.92 (t, J=8.4 Hz, 3H), 7.82 (dd, J=10.2, 4.2 Hz, 1H), 7.76 (d, J=7.8 Hz, 1H), 7.64 (d, J=8.2 Hz, 1H), 7.48 (t, J=7.6 Hz, 1H).

Synthesis of 3-(4,5-dichloro-2-((4-(1-(tetrahydro-2H-pyran-4-yl)-1H-pyrazol-4-yl)pyridin-2-yl)methoxy)phenyl)-1,2,4-oxadiazol-5(4H)-one (Example 279)
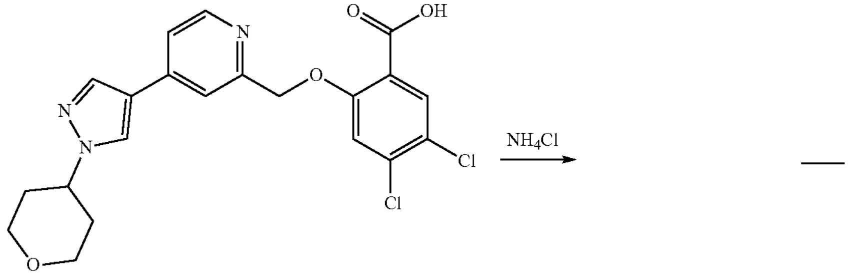
74
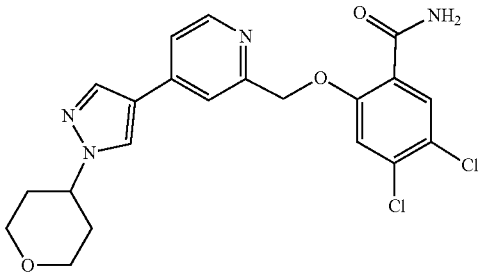
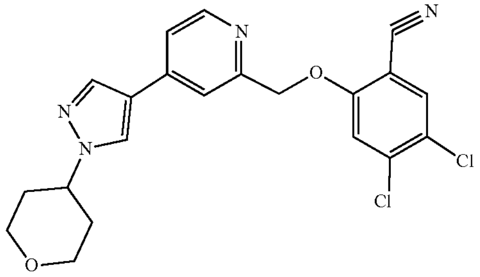
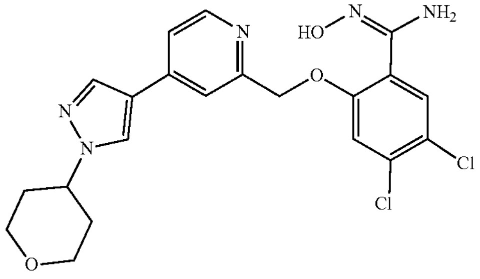
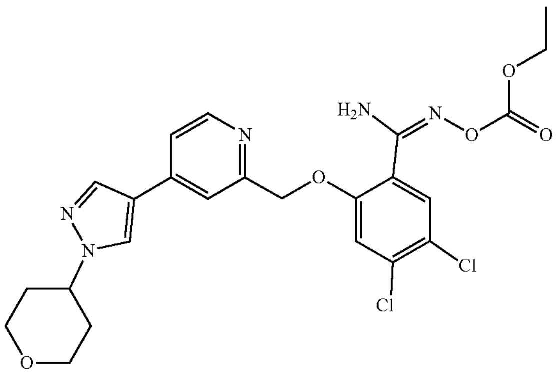

-continued

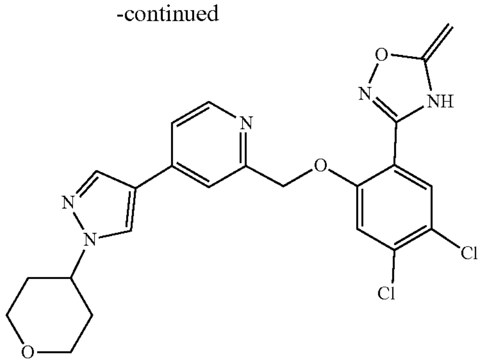

Preparation of 4,5-dichloro-2-((4-(1-(tetrahydro-2H-pyran-4-yl)-1H-pyrazol-4-yl)pyridin-2-yl)methoxy)benzamide (279-1). To a solution of 4,5-dichloro-2-((4-(1-(tetrahydro-2H-pyran-4-yl)-1H-pyrazol-4-yl)pyridin-2-yl)methoxy)benzoic acid (74, 1.4 g, 3.1 mmol, 1.0 eq) in dry DMF (15 mL), was added $NH_4Cl$ (1.7 g, 31 mmol, 10.0 eq), DIEA (804 mg, 602 mmol, 2.0 eq) and HATU (1.2 g, 3.2 mmol, 1.02 eq) at 0° C. under $N_2$. The mixture was stirred at 25° C. for 3 h. The mixture was extracted with DCM, dried over $Na_2SO_4$, concentrated. The crude product was purified by silica gel chromatography to give 4,5-dichloro-2-((4-(1-(tetrahydro-2H-pyran-4-yl)-1H-pyrazol-4-yl)pyridin-2-yl)methoxy)benzamide (279-1, 1.06 g, 76%) as a white solid. LC/MS [M+H]:447.1

Preparation of 4,5-dichloro-2-((4-(1-(tetrahydro-2H-pyran-4-yl)-1H-pyrazol-4-yl)pyridin-2-yl)methoxy)benzonitrile (279-2). To a solution of 4,5-dichloro-2-((4-(1-(tetrahydro-2H-pyran-4-yl)-1H-pyrazol-4-yl)pyridin-2-yl)methoxy)benzamide (279-1, 1.1 g, 2.4 mmol, 1.0 eq) in dry DCM (10 mL), was added TEA (600 mg, 5.9 mmol, 2.5 eq) at 0° C. under $N_2$.The mixture was stirred at 0° C. for 10 min, was added TFAA (1.2 g, 5.9 mmol, 2.5 eq) at 0° C., then 25° C. for 5 h. The mixture was extracted with DCM, dried over $Na_2SO_4$, concentrated. The crude product was purified by silica gel chromatography to give 4,5-dichloro-2-((4-(1-(tetrahydro-2H-pyran-4-yl)-1H-pyrazol-4-yl)pyridin-2-yl)methoxy)benzonitrile (279-2, 1.01 g, 99%) as a white solid. LC/MS [M−H]:429.0

Preparation of (E)-4,5-dichloro-N'-hydroxy-2-((4-(1-(tetrahydro-2H-pyran-4-yl)-1H-pyrazol-4-yl)pyridin-2-yl)methoxy)benzimidamide (279-3). To a solution of 4,5-dichloro-2-((4-(1-(tetrahydro-2H-pyran-4-yl)-1H-pyrazol-4-yl)pyridin-2-yl)methoxy)benzonitrile (279-2, 1.0 g, 2.4 mmol, 1.0 eq) in EtOH (10 mL) was added Hydroxylamine aqueous solution (1.5 mL, 23.6 mmol, 10.0 eq). The mixture was stirred at 80° C. for 4 h under $N_2$. The crude product was filtered to give (E)-4,5-dichloro-N'-hydroxy-2-((4-(1-(tetrahydro-2H-pyran-4-yl)-1H-pyrazol-4-yl)pyridin-2-yl)methoxy)benzimidamide (279-3, 800 mg, 74%) as a white solid. LC/MS [M+H]:462.2

Preparation of (E)-4,5-dichloro-N'-((ethoxycarbonyl)oxy)-2-((4-(1-(tetrahydro-2H-pyran-4-yl)-1H-pyrazol-4-yl)pyridin-2-yl)methoxy)benzimidamide (279-4). To a stirred solution of (E)-4,5-dichloro-N'-hydroxy-2-((4-(1-(tetrahydro-2H-pyran-4-yl)-1H-pyrazol-4-yl)pyridin-2-yl)methoxy)benzimidamide (279-3, 800 mg, 1.8 mmol, 1.0 eq) and TEA (526 mg, 5.2 mmol, 3.0 eq) in DCM (10 mL), were added $EtCO_2Cl$ (282 mg, 2.6 mmol, 1.5 eq) in one portion at 0° C. under nitrogen atmosphere. The reaction mixture was stirred at RT for 48 hour. Once LC/MS showed no starting material left, The mixture was extracted with DCM, dried over $Na_2SO_4$, concentrated. The crude product was purified by silica gel chromatography to give (E)-4,5-dichloro-N'-((ethoxycarbonyl)oxy)-2-((4-(1-(tetrahydro-2H-pyran-4-yl)-1H-pyrazol-4-yl)pyridin-2-yl)methoxy)benzimidamide (279-4, 855 mg, 92%) as a white solid. LC/MS [M+H]:534.2

Preparation of 3-(4,5-dichloro-2-((4-(1-(tetrahydro-2H-pyran-4-yl)-1H-pyrazol-4-yl)pyridin-2-yl)methoxy)phenyl)-1,2,4-oxadiazol-5(4H)-one (Example 279). To a stirred solution of (E)-4,5-dichloro-N'-((ethoxycarbonyl)oxy)-2-((4-(1-(tetrahydro-2H-pyran-4-yl)-1H-pyrazol-4-yl)pyridin-2-yl)methoxy)benzimidamide (279-4, 100 mg, 0.2 mmol, 1.0 eq) in dry DMSO (2 mL), was add $K_2CO_3$ (5 mg, 0.04 mmol, 0.2 eq). The reaction mixture was stirred at 80° C. for 8 hour. The mixture was purified by Prep-HPLC to give 3-(4,5-dichloro-2-((4-(1-(tetrahydro-2H-pyran-4-yl)-1H-pyrazol-4-yl)pyridin-2-yl)methoxy)phenyl)-1,2,4-oxadiazol-5(4H)-one (Example 279, 29 mg, 36%) as a white solid. LC/MS [M+H]:488.0. $^1H$ NMR (400 MHz, DMSO-$d_6$) δ 8.55 (s, 1H), 8.50 (d, J=5.2 Hz, 1H), 8.12 (s, 1H), 8.10 (s, 1H), 7.95 (s, 1H), 7.70 (s, 1H), 7.60-7.58 (m, 1H), 5.38 (s, 2H), 4.52-4.43 (m, 1H), 3.40-3.97 (m, 2H), 3.53-3.42 (m, 2H), 2.04-1.95 (m, 4H).

Synthesis of 5-(2-(4-(3-(1H-pyrazol-4-yl)phenyl)-1H-1,2,3-triazol-1-yl)-4,5-dichlorophenyl)-1H-tetrazole (Example 281)

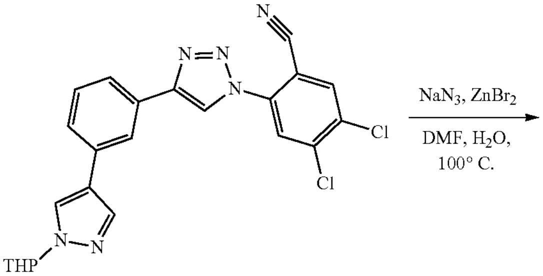

281-1

-continued

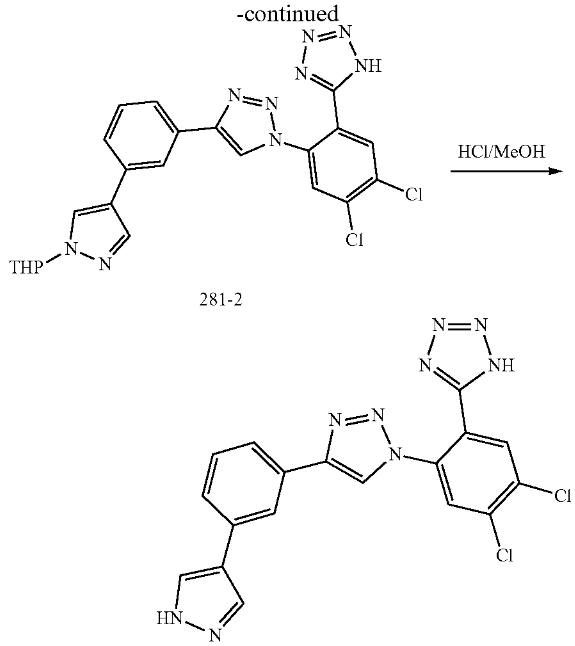

281-2

Example 281

Preparation of 5-(4,5-dichloro-2-(4-(3-(1-(tetrahydro-2H-pyran-2-yl)-1H-pyrazol-4-yl)phenyl)-1H-1,2,3-triazol-1-yl)phenyl)-1H-tetrazole (281-2). To a solution of 4,5-dichloro-2-(4-(3-(1-(tetrahydro-2H-pyran-2-yl)-1H-pyrazol-4-yl)phenyl)-1H-1,2,3-triazol-1-yl)benzonitrile (281-1, 600.0 mg, 1.30 mmol, 1.0 eq) in DMF/$H_2O$ (10/5 mL) was added $NaN_3$ (169.0 mg, 2.6 mmol, 2.0 eq) and $ZnBr_2$ (585.5 mg, 2.6 mmol, 2.0 eq)) The mixture was stirred at 100° C. for 12 h under Ar. The mixture was filtered to give 5-(4,5-dichloro-2-(4-(3-(1-(tetrahydro-2H-pyran-2-yl)-1H-pyrazol-4-yl)phenyl)-1H-1,2,3-triazol-1-yl)phenyl)-1H-tetrazole (281-2, 500.0 mg, 1.0 mmol, 77.4%). LC/MS [M+H]:508.1

Preparation of 5-(2-(4-(3-(1H-pyrazol-4-yl)phenyl)-1H-1,2,3-triazol-1-yl)-4,5-dichlorophenyl)-1H-tetrazole (Example 281). To a solution of 5-(4,5-dichloro-2-(4-(3-(1-(tetrahydro-2H-pyran-2-yl)-1H-pyrazol-4-yl)phenyl)-1H-1,2,3-triazol-1-yl)phenyl)-1H-tetrazole (281-2, 500.0 mg, 1.0 mmol, 1.0 eq) in HCl/MeOH (10 mL). The mixture was stirred at Rt for 1 h under Ar. The mixture was filtered to give crude. The crude product was triturated in MeOH and filtered to afford 5-(2-(4-(3-(1H-pyrazol-4-yl)phenyl)-1H-1,2,3-triazol-1-yl)-4,5-dichlorophenyl)-1H-tetrazole (Example 281, 271.28 mg, 0.64 mmol, 64.0%). LC/MS [M+H]: 424.1. $^1$H NMR (400 MHz, DMSO-$d_6$) δ 9.06 (s, 1H), 8.37-8.36 (d, J=4 Hz, 2H), 8.13 (s, 3H), 7.72-7.70 (d, J=8.0 Hz, 2H), 7.63-7.61 (d, J=8.0 Hz, 2H), 7.48-7.44 (t, J=8.0 Hz, 1H).

Synthesis of 3-(2-(4-(3-(1H-pyrazol-4-yl)phenyl)-1H-1,2,3-triazol-1-yl)-4,5-dichlorophenyl)-1,2,4-oxadiazol-5(4H)-one (Example 283)

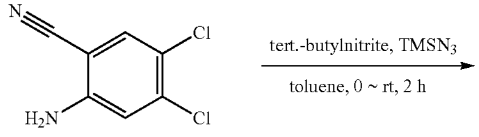

283-1

-continued

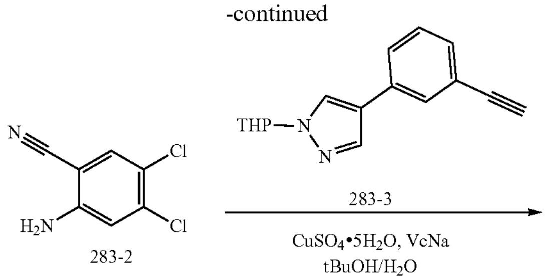

283-2

283-3

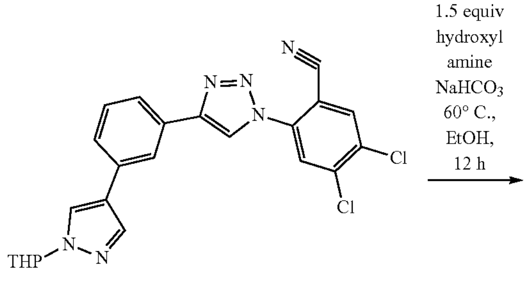

283-4

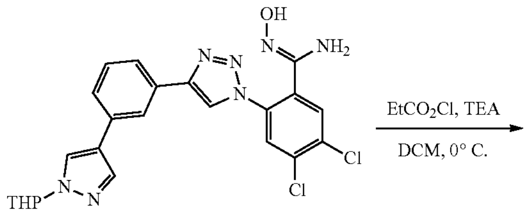

283-5

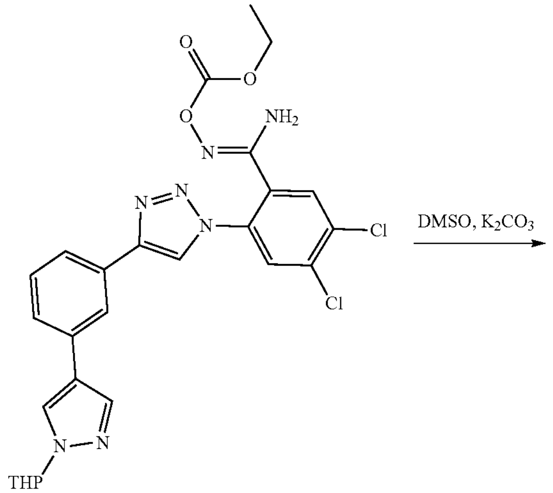

283-6

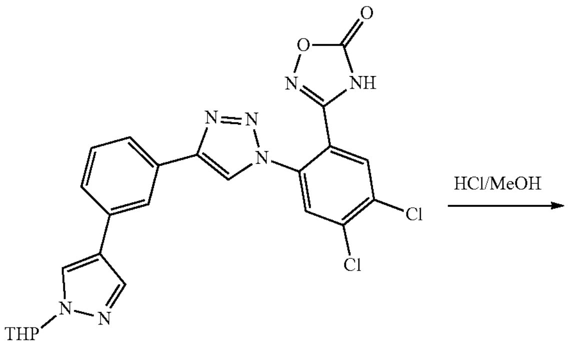

283-7

-continued

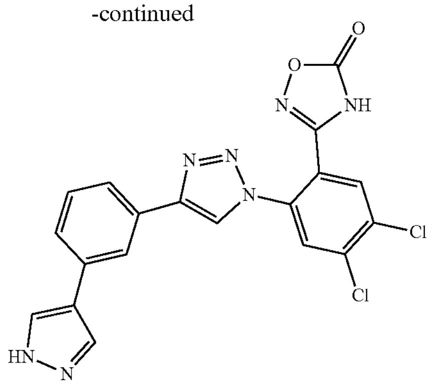

283

Preparation of 2-azido-4,5-dichlorobenzonitrile (Compound 283-2). To a solution of 2-amino-4,5-dichlorobenzonitrile (283-1, 1.9 g, 10.22 mmol, 1.0 eq) in water (15 mL) at 0° C. was added HCl (2.0 M, 25.5 mL, 51.1 mmol), followed by a solution of $NaNO_2$ (1.4 g, 20.44 mmol, 2.0 eq) in water (7 mL). The reaction mixture was stirred at 0° C. for 15 min. To this mixture was added a solution of $NaN_3$ (1.33 g, 20.44 mmol, 2.0 eq). in water (12 mL). The reaction mixture was stirred at 0° C. for 30 min. Once LC/MS showed the reaction finished, the mixture was filtered to give 2-azido-4,5-dichlorobenzonitrile (283-2, 1.9 g, 8.96 mmol, 87.7%).

Preparation of 4,5-dichloro-2-(4-(3-(1-(tetrahydro-2H-pyran-2-yl)-1H-pyrazol-4-yl)phenyl)-1H-1,2,3-triazol-1-yl) benzonitrile (Compound 283-4). To a solution of 2-azido-4,5-dichlorobenzonitrile (283-2, 1.9 g, 8.96 mmol, 1.0 eq) in t-BuOH/$H_2O$ (20/10 mL) was added 4-(3-ethynylphenyl)-1-(tetrahydro-2H-pyran-2-yl)-1H-pyrazole (283-3, 2.2 g, 8.96 mmol, 1.0 eq), $CuSO_4.5H_2O$ (0.671 g, 2.69 mmol 0.3 eq) and VcNa (1.1 g, 5.38 mmol, 0.6 eq). The reaction mixture was stirred at room temperature for 12 hours. The mixture was poured into water, extracted with EA, and dried over $Na_2SO_4$. The crude product was purified by silica gel column eluting with 0-50% EA in PE to give 4,5-dichloro-2-(4-(3-(1-(tetrahydro-2H-pyran-2-yl)-1H-pyrazol-4-yl) phenyl)-1H-1,2,3-triazol-1-yl)benzonitrile (283-4, 1.6 g, 3.45 mmol, 38.5%). LC/MS [M+H]: 465.1

Preparation of (Z)-4,5-dichloro-N'-hydroxy-2-(4-(3-(1-(tetrahydro-2H-pyran-2-yl)-1H-pyrazol-4-yl)phenyl)-1H-1,2,3-triazol-1-yl)benzimidamide (283-5). To a solution of 4,5-dichloro-2-(4-(3-(1-(tetrahydro-2H-pyran-2-yl)-1H-pyrazol-4-yl)phenyl)-1H-1,2,3-triazol-1-yl)benzonitrile (283-4, 0.6 g, 1.29 mmol, 1.0 eq) in EtOH (10 mL) was added hydroxy amine (0.426 g, 3.87 mmol, 3.0 eq). The mixture was stirred at 70° C. for 18 h under $N_2$. The mixture was concentrated, followed by dissolved in $CH_2Cl_2$ and filtered to give (Z)-4,5-dichloro-N'-hydroxy-2-(4-(3-(1-(tetrahydro-2H-pyran-2-yl)-1H-pyrazol-4-yl)phenyl)-1H-1,2,3-triazol-1-yl)benzimidamide (283-5, 0.5 g, 0.6 mmol). LC/MS [M+H]: 498.2

Preparation of compound (Z)-4,5-dichloro-N'-((ethoxycarbonyl)oxy)-2-(4-(3-(1-(tetrahydro-2H-pyran-2-yl)-1H-pyrazol-4-yl)phenyl)-1H-1,2,3-triazol-1-yl)benzimidamide (283-6). To a stirred solution of (Z)-4,5-dichloro-N'-hydroxy-2-(4-(3-(1-(tetrahydro-2H-pyran-2-yl)-1H-pyrazol-4-yl)phenyl)-1H-1,2,3-triazol-1-yl)benzimidamide (283-5, 0.5 g, 0.6 mmol, 1.0 eq) and TEA (0.3 g, 0.3 mmol, 3.0 eq) in DCM (15 mL) were added Ethyl chloroformate (0.32 g, 0.3 mmol, 3.0 eq) in one portion at 0° C. under nitrogen atmosphere. The reaction mixture was stirred at 0° C. for 2 hour. Once LC/MS showed no starting material left, the mixture was poured into sat.$NH_4Cl$ and stirred for 10 minutes. The residue was then extracted with EtOAc, washed with sat. sodium bicarbonate, dried over $Na_2SO_4$, and filtered. The filtration was concentrated under vacuum to give the crude, which was then purified by silica gel chromatography eluting with PE/EA (v/v:2/1) to afford (Z)-4,5-dichloro-N'-((ethoxycarbonyl)oxy)-2-(4-(3-(1-(tetrahydro-2H-pyran-2-yl)-1H-pyrazol-4-yl)phenyl)-1H-1,2,3-triazol-1-yl)benzimidamide (283-6, 0.18 g, 0.316 mmol, 52.7%).

Preparation of compound 3-(4,5-dichloro-2-(4-(3-(1-(tetrahydro-2H-pyran-2-yl)-1H-pyrazol-4-yl)phenyl)-1H-1,2,3-triazol-1-yl)phenyl)-1,2,4-oxadiazol-5(4H)-one (283-7). To a stirred solution of (Z)-4,5-dichloro-N'-((ethoxycarbonyl)oxy)-2-(4-(3-(1-(tetrahydro-2H-pyran-2-yl)-1H-pyrazol-4-yl)phenyl)-1H-1,2,3-triazol-1-yl)benzimidamide (283-6, 0.18 g, 0.316 mmol, 1.0 eq) in dry DMSO (3 mL) was added $K_2CO_3$ (0.017 g, 0.126 mmol, 0.4 eq).

The reaction mixture was stirred at 80° C. for 12 hour. Once LC/MS showed no starting material left, the mixture was poured into satd. NaCl and stirred for 10 minutes. The residue was then extracted with EtOAc, washed with water, dried over $Na_2SO_4$, and filtered. The filtration was concentrated under vacuum to give the crude, which was then purified by silica gel chromatography eluting with PE/EA (v/v:1/1) afford 3-(4,5-dichloro-2-(4-(3-(1-(tetrahydro-2H-pyran-2-yl)-1H-pyrazol-4-yl)phenyl)-1H-1,2,3-triazol-1-yl) phenyl)-1,2,4-oxadiazol-5(4H)-one (283-7, 120.0 mg, 0.229 mmol, 72.6%). LC/MS [M−H]: 522.1

Preparation of 3-(2-(4-(3-(1H-pyrazol-4-yl)phenyl)-1H-1,2,3-triazol-1-yl)-4,5-dichlorophenyl)-1,2,4-oxadiazol-5 (4H)-one (Example 283). To a solution of 3-(4,5-dichloro-2-(4-(3-(1-(tetrahydro-2H-pyran-2-yl)-1H-pyrazol-4-yl) phenyl)-1H-1,2,3-triazol-1-yl)phenyl)-1,2,4-oxadiazol-5 (4H)-one (283-7, 120.0 mg, 0.229 mmol, 1.0 eq) in HCl/MeOH (2 mL). The mixture was stirred at for 1 h under $N_2$. The mixture product was purified by Prep-HPLC to give 3-(2-(4-(3-(1H-pyrazol-4-yl)phenyl)-1H-1,2,3-triazol-1-yl)-4,5-dichlorophenyl)-1,2,4-oxadiazol-5(4H)-one (Example 283, 13.76 mg, 0.0025 mmol, 1.0%)LC/MS [M+H]:440. $^1H$ NMR (400 MHz, DMSO-$d_6$) δ 9.21 (s, 1H), 8.36 (s, 1H), 8.27 (s, 1H), 8.19-8.18 (d, 4.0 Hz, 3H), 7.76-7.74 (d, J=8.0 Hz, 1H), 7.65-7.63 (d, J=8.0 Hz, 1H), 7.50-7.47 (d, J=8.0 Hz, 1H).

Measuring PAI-1 Inhibition

SensoLyte AMC tPA Activity Assay Kit (AnaSpec AS-72160) has been modified to screen small molecules for inhibition of Recombinant Human Serpin E1/PAI-1 (R&D Systems 1786-PI) resulting in the collection of tPA fluorimetric activity.

Assay Preparation. Kit reagents were thawed and kept on wet ice: tPA substrate (Component A), tPA enzyme (Component D), tPA inhibitor (Leupeptin Component E). 2× Assay Buffer (Component C) was thawed at room temperature and diluted to 1× with deionized water. Working dilution of tPA enzyme and substrate is 1:100 in 1× Assay Buffer. Small molecule inhibitors are diluted from 10 mM in DMSO to 500 μM in D-PBS, thawed at 37° C. for 10 minutes and cooled to room temperature. Concentration utilized for all small molecules is 25 μM.

Determining optimal concentration of Recombinant Human PAI-1 for small molecule screening. Recombinant Human PAI-1 (R&D Systems 1786-PI) was serial diluted 8 points 1:2 dilution series starting at 20 μg/mL to 0.156

μg/mL in the SensoLyte AMC tPA Activity Assay to find 50% of tPA enzymatic activity at 25 minutes as compared to the positive control having 100% activity. The concentration of Recombinant Human PAI-1 utilized in small molecule screening assay is 1.25 μg/mL.

Non-treated, black with clear flat bottom plates (Corning 3631) are placed on wet ice prior to running PAI-1/tPA modified activity assay.

Assay components were added to 96 well plate in the following order on wet ice, in duplicates: PAI-1 small molecule inhibitors (25 μM), recombinant human PAI-1 (1.25 μg/mL), tPA enzyme (1:100), tPA substrate (1:100). Volumes were adjusted with 1× Assay Buffer to a final volume 100p L as recommended by kit manufacturer.

Eight controls were utilized per plate:

1) Positive control vehicle DMSO (0.3%), tPA enzyme and substrate.
2) Recombinant PAI-1 50% inhibition contains 1.25 μg/mL (R&D 1786-PI), tPA enzyme and substrate.
3) Inhibitor control contains Leupeptin (1 mM), tPA enzyme and substrate.
4) CCF benchmark positive control contains 25 μM Example 1 (Cleveland Clinic Foundation), tPA enzyme and substrate.
5) Example 1 control for tPA activity contains 25 μM Example 1, tPA enzyme, substrate and 1× Assay Buffer.
6) Commercial PAI-1 inhibitor utilized was 25 μM Tiplaxtinin (Tocris Bioscience 5565) containing 1.25 μg/mL PAI-1, tPA enzyme and substrate.
7) Tiplaxtinin control for tPA activity contains 25 μM Tiplaxtinin, tPA enzyme, substrate and 1× Assay Buffer.
8) Background control contains substrate and 1× Assay Buffer. Fluorimeter was set to 37C° C. and fluorescence intensity Ex/Em=354/442 nm was collected every 5 minutes for 1 hour.

Calculations % tPA activity:

(Result−Background)/(Positive control−Background)*100

TABLE 10

PAI-1 Inhibition Data

| Example # | % PAI-1 inhibition at 25 μM |
|---|---|
| 1 | 85 |
| 2 | 50 |
| 3 | 75 |
| 4 | 60 |
| 5 | 60 |
| 6 | — |
| 7 | 54 |
| 8 | 70 |
| 9 | — |
| 10 | 74 |
| 11 | 56 |
| 12 | 56 |
| 13 | 58 |
| 14 | 60 |
| 15 | 81 |
| 16 | 89 |
| 17 | 73 |
| 18 | 43 |
| 19 | 50 |
| 20 | 55 |
| 21 | 49 |
| 22 | 73 |
| 23 | 58 |
| 24 | 58 |
| 25 | 60 |
| 26 | — |
| 27 | 62 |
| 28 | 65 |
| 29 | 73 |
| 30 | 54 |
| 31 | 51 |
| 32 | 45 |
| 33 | 60 |
| 34 | 38 |
| 35 | 60 |
| 36 | 34 |
| 37 | 41 |
| 38 | 51 |
| 39 | 90 |
| 40 | 87 |
| 41 | 90 |
| 42 | 53 |
| 43 | 56 |
| 44 | 53 |
| 45 | 52 |
| 46 | 45 |
| 47 | 42 |
| 48 | 53 |
| 49 | 48 |
| 50 | 63 |
| 51 | — |
| 52 | 45 |
| 53 | 78 |
| 54 | 66 |
| 55 | 64 |
| 56 | 43 |
| 57 | 74 |
| 58 | 56 |
| 59 | 47 |
| 60 | 68 |
| 61 | 70 |
| 62 | 36 |
| 63 | 29 |
| 64 | 41 |
| 65 | 41 |
| 65 | 41 |
| 66 | 27 |
| 67 | 60 |
| 68 | 50 |
| 69 | 69 |
| 70 | 63 |
| 71 | 42 |
| 72 | 47 |
| 73 | 40 |
| 74 | 61 |
| 75 | 77 |
| 76 | 40 |
| 77 | 41 |
| 78 | 28 |
| 79 | 39 |
| 80 | 49 |
| 81 | 42 |
| 82 | — |
| 83 | — |
| 84 | 41 |
| 85 | 42 |
| 86 | 49 |
| 87 | 56 |
| 88 | 47 |
| 89 | 31 |
| 91 | 27 |
| 92 | 29 |
| 93 | 27 |
| 94 | 41 |
| 95 | 30 |
| 96 | 29 |
| 97 | — |
| 98 | 29 |
| 99 | 30 |
| 100 | 27 |
| 101 | 53 |
| 102 | 25 |

TABLE 10-continued

PAI-1 Inhibition Data

| Example # | % PAI-1 inhibition at 25 μM |
|---|---|
| 103 | 37 |
| 104 | 36 |
| 105 | 30 |
| 106 | 35 |
| 106 | 51 |
| 108 | 44 |
| 109 | 29 |
| 110 | 50 |
| 111 | 53 |
| 112 | 55 |
| 113 | 62 |
| 114 | 53 |
| 115 | 56 |
| 116 | 48 |
| 117 | 30 |
| 118 | — |
| 119 | — |
| 120 | 48 |
| 121 | 63 |
| 122 | 35 |
| 123 | 52 |
| 124 | 43 |
| 125 | 68 |
| 126 | 68 |
| 127 | 61 |
| 128 | 44 |
| 129 | 39 |
| 130 | 37 |
| 131 | 38 |
| 132 | 44 |
| 133 | 33 |
| 134 | 69 |
| 135 | 43 |
| 136 | 61 |
| 137 | 46 |
| 138 | 53 |
| 139 | 34 |
| 140 | 42 |
| 141 | 27 |
| 142 | 55 |
| 143 | 36 |
| 144 | 98 |
| 145 | 101 |
| 146 | 32 |
| 147 | 36 |
| 148 | 44 |
| 149 | 37 |
| 150 | 42 |
| 151 | 37 |
| 152 | 33 |
| 153 | 21 |
| 154 | 101 |
| 155 | 104 |
| 156 | 89 |
| 157 | 96 |
| 158 | 81 |
| 159 | 93 |
| 160 | — |
| 161 | 32 |
| 162 | 35 |
| 163 | 35 |
| 164 | 28 |
| 165 | 37 |
| 166 | 4 |
| 167 | 56 |
| 168 | 33 |
| 169 | — |
| 170 | — |
| 171 | 49 |
| 172 | 31 |
| 173 | 52 |
| 174 | 60 |
| 176 | 29 |
| 177 | 20 |
| 178 | 56 |
| 179 | 52 |

TABLE 10-continued

PAI-1 Inhibition Data

| Example # | % PAI-1 inhibition at 25 μM |
|---|---|
| 180 | — |
| 181 | — |
| 182 | 63 |
| 183 | 67 |
| 184 | 22 |
| 185 | — |
| 186 | 37 |
| 187 | 34 |
| 188 | 52 |
| 189 | 34 |
| 190 | 73 |
| 191 | 44 |
| 192 | 69 |
| 193 | 25 |
| 194 | 53 |
| 195 | 31 |
| 196 | 58 |
| 197 | 28 |
| 198 | 29 |
| 199 | 74 |
| 200 | 67 |
| 201 | 72 |
| 202 | 71 |
| 203 | 67 |
| 204 | 83 |
| 205 | 82 |
| 206 | 74 |
| 207 | 75 |
| 208 | 82 |
| 209 | 72 |
| 210 | 81 |
| 211 | 75 |
| 212 | 74 |
| 213 | 83 |
| 214 | 82 |
| 215 | 85 |
| 216 | 84 |
| 217 | 77 |
| 218 | 68 |
| 219 | — |
| 220 | 72 |
| 221 | 74 |
| 222 | 79 |
| 223 | 77 |
| 224 | 85 |
| 225 | — |
| 228 | 77 |
| 230 | 82 |
| 231 | 79 |
| 233 | 30 |
| 234 | 39 |
| 235 | 85 |
| 236 | 38 |
| 237 | 23 |
| 238 | 27 |
| 239 | — |
| 240 | — |
| 241 | 37 |
| 242 | 25 |
| 243 | 37 |
| 244 | 34 |
| 245 | 29 |
| 246 | 26 |
| 247 | 42 |
| 248 | 19 |
| 249 | 36 |
| 250 | — |
| 251 | 32 |
| 252 | 35 |
| 253 | 36 |
| 254 | 51 |
| 255 | 36 |
| 256 | — |
| 257 | 57 |
| 258 | 41 |
| 259 | 49 |

TABLE 10-continued

| PAI-1 Inhibition Data | |
|---|---|
| Example # | % PAI-1 inhibition at 25 μM |
| 260 | 39 |
| 261 | 43 |
| 262 | 47 |
| 263 | — |
| 264 | 47 |
| 265 | 39 |
| 272 | 29 |
| 275 | — |
| 276 | — |
| 277 | 81 |
| 278 | 72 |
| 279 | 77 |
| 280 | 78 |
| 281 | 67 |
| 282 | 68 |
| 283 | 59 |

Figure 1B:
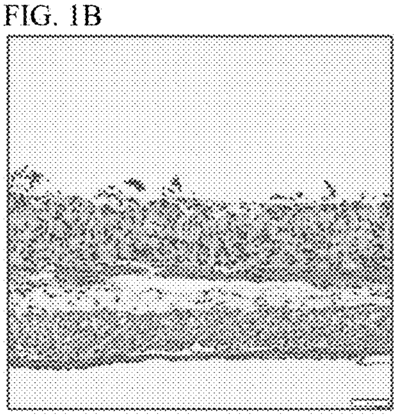
Figure 1C:
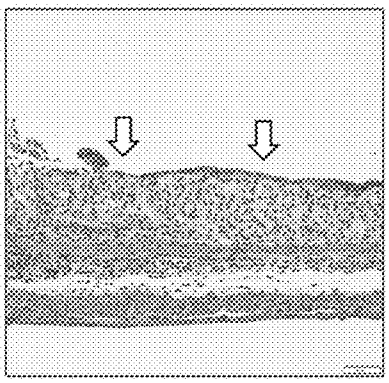
Figure 1D:
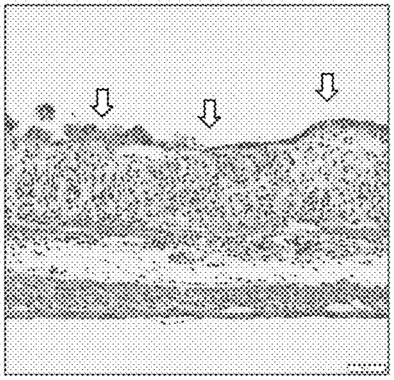
Figure 1E:
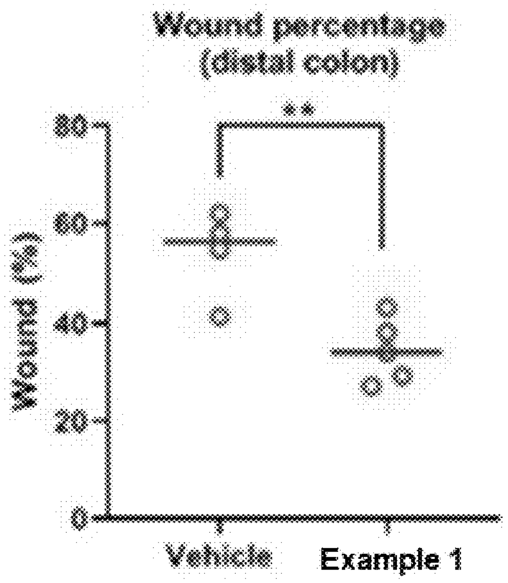
Figure 1F:
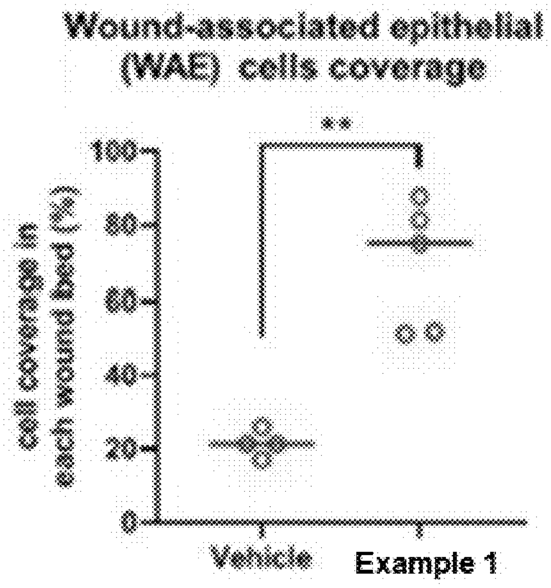
Figure 1G:
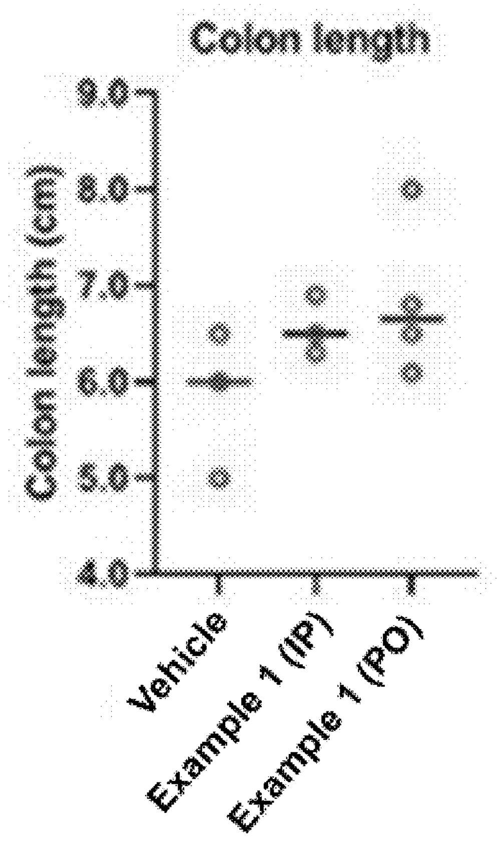
Figure 1H:
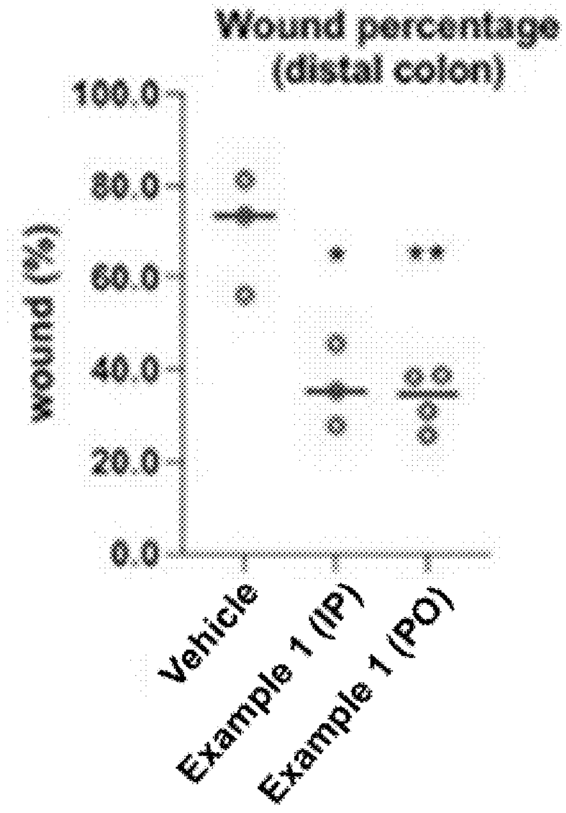

In vivo efficacy in DSS-induced mouse model of IBD In dextran sodium sulfate (DSS)-colitis models, mice orally receive DSS, which causes focal death of colonic epithelial cells, compromising barrier function and causing subsequent inflammation. Example 1, vehicle, and in some experiments an additional negative control (Example 1-NC, a structurally close analogue to Example 1, not shown, $IC_{50}$ >500 μM). Wild type (WT) C57BL/6 conventionally-raised mice were administered 2.5% dextran sodium sulfate (DSS) for 12 days to induce colonic injury and inflammation that models features of damage that occurs in IBD. From day 6 through day 12, mice received daily intraperitoneal injections of vehicle, Example 1 (FIG. 1A). After treatment, mucosal damage was reduced, as measured by distal colon wound size, in the Example 1 treated mice compared to the vehicle (FIG. 1B vs 1C). Furthermore, Example 1 treatment led to increased coverage of WAE cells in the wound bed compared to the vehicle treatment despite the persistent injury stimulus (FIG. 1E-F). This implies this compound can stimulate the first phase of wound repair even with a continued injury stimulus. In a separate experiment, Example 1 was administered orally (PO) at 5 mg/kg using the same dosing schedule (FIG. 1A). Example 1 was similarly efficacious as evidenced by effects on colon length (FIG. 1G) and WAE coverage (FIG. 1H). Example 1 was able to stimulate WAE coverage of wounds during injury which secondarily inhibits inflammation and cytokine expression.

In Vivo Efficacy in TNBS-Induced Mouse Model of IBD

Figures 2A, 2B, 2C, 2D:
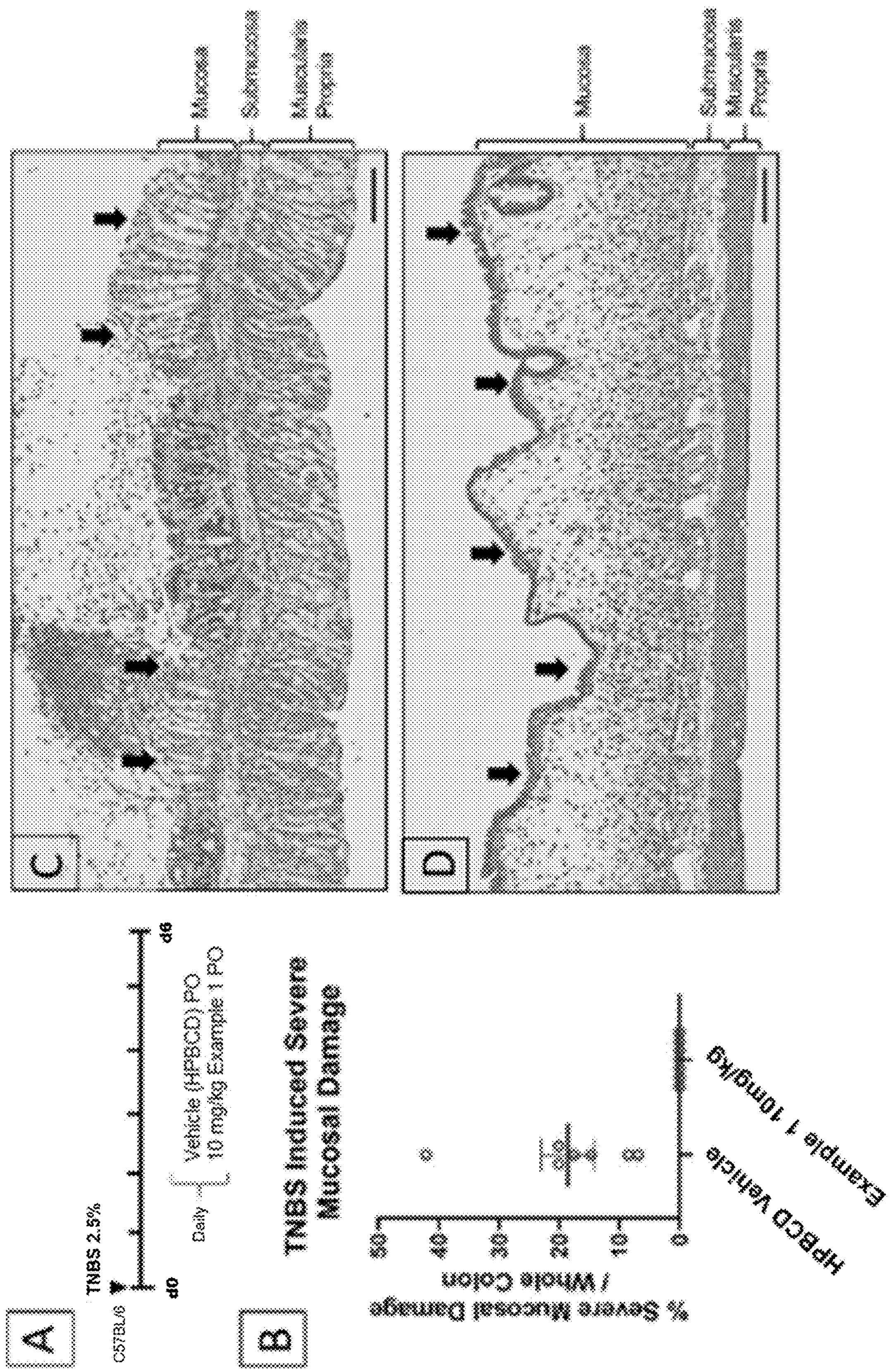
FIGS. 2A-2D show in vivo efficacy data in a TNBS-induced mouse model of IBD.

In dextran 2,4,6-trinitro-benzene sulfonic acid (TNBS)-colitis models, topical administration of hapten reagents results in T-cell-mediated immunity against haptenized proteins and luminal antigens leading to colonic damage. Wild type (WT) C57BL/6 conventionally-raised mice were administered 2.5% TNBS intra rectal along with a hapten substance in 50% ethanol to induce colonic damage/inflammation. From day 2 to 6, mice were received either vehicle (hydroxyl propyl-beta-cyclodextrin) or Example 1 (5 mg/k) orally (FIG. 2A, note the ethanol alone is not shown). We assayed for repair after day 6 of recovery. The TNBS-damaged, vehicle-treated mice showed areas of severe ulceration at this time point. In contrast, TNBS-damaged Example 1-treated mice showed injured areas were covered with WAE cells and contained much less inflammation (FIG. 2). The muscularis propria also appeared to contain much less damage and inflammation in the Example 1 treated mice as compared to controls.

The invention claimed is:

1. A compound of formula (Ia):

(Ia)

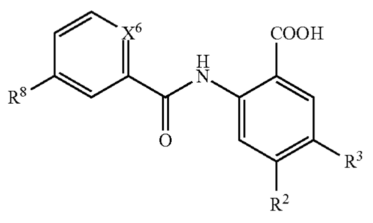

or a pharmaceutically acceptable salt thereof, wherein:

$R^2$ is H, halo, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, or $C_1$-$C_4$ haloalkoxy;

$R^3$ is H, halo, or $C_1$-$C_4$ alkyl;

wherein $R^2$ and $R^3$ are optionally taken together with the carbon atoms to which they are attached to form a 5-or 6-membered ring optionally substituted with 1 or 2 substituents independently selected from $C_1$-$C_4$ alkyl, halo, and oxo;

$X^6$ is $CR^6$ or N;

$R^6$ is H, halo, or $C_1$-$C_4$ alkyl; and $R^8$ is a group of formula:

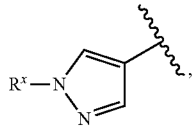, wherein $R^x$ is —$(CH_2)_n$—Y or a monocyclic heterocyclyl having 1 or 2 heteroatoms independently selected from O and N, wherein the monocyclic heterocyclyl is unsubstituted or substituted with 1 $C_1$-$C_4$ alkyl group, wherein n is 1 or 2, and Y is selected from —$COOR^g$ and —$NR^hR^i$, wherein $R^g$, $R^h$, and $R^i$ are each independently selected from H and $C_1$-$C_4$ alkyl.

2. The compound of claim 1, or a pharmaceutically acceptable salt thereof, wherein:

$R^2$ is H, halo, $C_1$-$C_4$ alkyl, $C_2$-$C_4$ alkenyl, $C_2$-$C_4$ alkynyl, $C_1$-$C_4$ alkoxy, $C_1$-$C_4$ haloalkyl, or $C_1$-$C_4$ haloalkoxy; and $R^3$ is H, halo, or $C_1$-$C_4$ alkyl.

3. The compound of claim 1, or a pharmaceutically acceptable salt thereof, wherein $X^6$ is $CR^6$ and $R^6$ is H.

4. The compound of claim 1, wherein the compound is selected from:

4-chloro-2-[[3-(1-tetrahydropyran-4-ylpyrazol-4-yl)benzoyl]amino]benzoic acid,

2-[[3-[1-(2-carboxyethyl)pyrazol-4-yl]benzoyl]amino]-4-chloro-benzoic acid,

2-[[3-(1-tetrahydropyran-4-ylpyrazol-3-yl)benzoyl]amino]benzoic acid,

2-[[3-[1-(2-carboxyethyl)pyrazol-4-yl]benzoyl]amino]benzoic acid,

2-[[4-(1-tetrahydropyran-4-ylpyrazol-4-yl)pyridine-2-carbonyl]amino]benzoic acid, 2-[[4-[1-(2-carboxyethyl)pyrazol-4-yl]pyridine-2-carbonyl]amino]benzoic acid, 2-[[3-[1-(2-carboxyethyl)pyrazol-4-yl]benzoyl]amino]-4-methyl-benzoic acid, 4-methyl-2-[[4-(1-tetrahydropyran-4-ylpyrazol-4-yl)pyridine-2-carbonyl]amino]benzoic acid, 2-[[4-[1-(2-carboxyethyl)pyrazol-4-yl]pyridine-2-carbonyl]amino]-4-methyl-benzoic acid, 2-[[3-(1-tetrahydropyran-4-ylpyrazol-4-yl)benzoyl]amino]-4-(trifluoromethyl)benzoic acid, 2-[[3-[1-(2-carboxyethyl)pyrazol-4-yl]benzoyl]amino]-4-(trifluoromethyl)benzoic acid, 2-[[4-(1-tetrahydropyran-4-ylpyrazol-4-yl)pyridine-2-carbonyl]amino]-4-(trifluoromethyl)benzoic acid, 2-[[4-[1-(2-carboxyethyl)pyrazol-4-yl]pyridine-2-carbonyl]amino]-4-(trifluoromethyl)benzoic acid, 4-isopropyl-2-[[3-(1-tetrahydropyran-4-ylpyrazol-4-yl)benzoyl]amino]benzoic acid, 2-[[3-[1-(2-carboxyethyl)pyrazol-4-yl]benzoyl]amino]-4-isopropyl-benzoic acid, 4-isopropyl-2-[[4-(1-tetrahydropyran-4-ylpyrazol-4-yl)pyridine-2-carbonyl]amino]benzoic acid, 2-[[4-[1-(2-carboxyethyl)pyrazol-4-yl]pyridine-2-carbonyl]amino]-4-isopropyl-benzoic acid, 4-tert-butyl-2-[[3-(1-tetrahydropyran-4-ylpyrazol-3-yl)benzoyl]amino]benzoic acid, 4-tert-butyl-2-[[3-[1-(2-carboxyethyl)pyrazol-4-yl]benzoyl]amino]benzoic acid, 4-tert-butyl-2-[[4-(1-tetrahydropyran-4-ylpyrazol-4-yl)pyridine-2-carbonyl]amino]benzoic acid, 4-tert-butyl-2-[[4-[1-(2-carboxyethyl)pyrazol-4-yl]pyridine-2-carbonyl]amino]benzoic acid, 4-methoxy-2-[[3-(1-tetrahydropyran-4-ylpyrazol-4-yl)benzoyl]amino]benzoic acid, 2-[[3-[1-(2-carboxyethyl)pyrazol-4-yl]benzoyl]amino]-4-methoxy-benzoic acid, 4-methoxy-2-[[4-(1-tetrahydropyran-4-ylpyrazol-4-yl)pyridine-2-carbonyl]amino]benzoic acid, 2-[[4-[1-(2-carboxyethyl)pyrazol-4-yl]pyridine-2-carbonyl]amino]-4-methoxy-benzoic acid, 2-[[3-(1-tetrahydropyran-4-ylpyrazol-4-yl)benzoyl]amino]-4-(trifluoromethoxy)benzoic acid, 2-[[3-[1-(2-carboxyethyl)pyrazol-4-yl]benzoyl]amino]-4-(trifluoromethoxy)benzoic acid, 2-[[4-(1-tetrahydropyran-4-ylpyrazol-4-yl)pyridine-2-carbonyl]amino]-4-(trifluoromethoxy)benzoic acid, 2-[[4-[1-(2-carboxyethyl)pyrazol-4-yl]pyridine-2-carbonyl]amino]-4-(trifluoromethoxy)benzoic acid, 4,5-dichloro-2-[[3-(1-tetrahydropyran-4-ylpyrazol-4-yl)benzoyl]amino]benzoic acid, 2-[[3-[1-(2-carboxyethyl)pyrazol-4-yl]benzoyl]amino]-4,5-dichloro-benzoic acid, 3-[[3-(1-tetrahydropyran-4-ylpyrazol-4-yl)benzoyl]amino]naphthalene-2-carboxylic acid, 3-[[3-[1-(2-carboxyethyl)pyrazol-4-yl]benzoyl]amino]naphthalene-2-carboxylic acid, 6-[[3-(1-tetrahydropyran-4-ylpyrazol-4-yl)benzoyl]amino]-2,3-dihydro-1,4-benzodioxine-7-carboxylic acid,

[6-[[3-(1-tetrahydropyran-4-ylpyrazol-4-yl)benzoyl]amino]-2,3-dihydro-1,4-benzodioxine-7-carbonyl]oxy-sodium, 6-[[3-[1-(2-carboxyethyl)pyrazol-4-yl]benzoyl]amino]-2,3-dihydro-1,4-benzodioxine-7-carboxylic acid, 6-[[3-(1-tetrahydropyran-4-ylpyrazol-4-yl)benzoyl]amino]-1,3-benzodioxole-5-carboxylic acid, 5-[[3-(1-tetrahydropyran-4-ylpyrazol-4-yl)benzoyl]amino]-1H-indazole-6-carboxylic acid, 1-methyl-5-[[3-(1-tetrahydropyran-4-ylpyrazol-4-yl)benzoyl]amino]indazole-6-carboxylic acid, 5-[[3-[1-(2-carboxyethyl)pyrazol-4-yl]benzoyl]amino]-1H-indazole-6-carboxylic acid, 5-[[3-[1-(2-carboxyethyl)pyrazol-4-yl]benzoyl]amino]-1-methyl-indazole-6-carboxylic acid, 2-[[3-[1-[2-(dimethylamino)ethyl]pyrazol-4-yl]benzoyl]amino]benzoic acid, 2-[[3-[1-(4-piperidyl)pyrazol-4-yl]benzoyl]amino]benzoic acid, 2-[[3-[1-(1-methyl-4-piperidyl)pyrazol-4-yl]benzoyl]amino]benzoic acid, sodium 4,5-dichloro-2-(4-(1-(tetrahydro-2H-pyran-4-yl)-1H-pyrazol-4-yl)picolinamido)benzoate, and sodium 7-(4-(1-(tetrahydro-2H-pyran-4-yl)-1H-pyrazol-4-yl)picolinamido)-2,3-dihydrobenzo[b][1,4]dioxine-6-carboxylate, and pharmaceutically acceptable salts thereof.

5. A pharmaceutical composition comprising a compound of claim 1, or a pharmaceutically acceptable salt thereof, and a pharmaceutically acceptable carrier.

6. A pharmaceutical composition comprising a compound of claim 4, or a pharmaceutically acceptable salt thereof, and a pharmaceutically acceptable carrier.

7. A compound:

4-chloro-2-[[3-(1-tetrahydropyran-4-ylpyrazol-4-yl)benzoyl]amino]benzoic acid, or a pharmaceutically acceptable salt thereof.

8. A pharmaceutical composition comprising the compound of claim 7, or a pharmaceutically acceptable salt thereof, and a pharmaceutically acceptable carrier.

* * * * *